United States Patent
Yoshikawa et al.

(10) Patent No.: US 7,772,226 B2
(45) Date of Patent: Aug. 10, 2010

(54) CONDENSED IMIDAZOLE DERIVATIVES

(75) Inventors: Seiji Yoshikawa, Kashima-gun (JP); Eita Emori, Tsuchiura (JP); Fumiyoshi Matsuura, Tsukuba (JP); Richard Clark, Tsuchiura (JP); Hironori Ikuta, Ushiku (JP); Kazunobu Kira, Tsukuba (JP); Nobuyuki Yasuda, Ushiku (JP); Tadashi Nagakura, Tsukuba (JP); Kazuto Yamazaki, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 12/199,982

(22) Filed: Aug. 28, 2008

(65) Prior Publication Data

US 2009/0018331 A1 Jan. 15, 2009

Related U.S. Application Data

(60) Division of application No. 11/212,407, filed on Aug. 26, 2005, now abandoned, which is a continuation of application No. 10/457,002, filed on Jun. 6, 2003, now abandoned.

(30) Foreign Application Priority Data

| Jun. 6, 2002 | (JP) | 2002-166069 |
| Jul. 18, 2002 | (JP) | 2002-209373 |
| Oct. 23, 2002 | (JP) | 2002-307750 |

(51) Int. Cl.
*A61K 31/437* (2006.01)
*A61K 31/496* (2006.01)
*C07D 487/04* (2006.01)
*C07D 471/04* (2006.01)
*C07D 473/06* (2006.01)
*C07D 473/18* (2006.01)
*C07D 473/22* (2006.01)
*C07D 473/30* (2006.01)
*C07D 473/40* (2006.01)
*C07D 498/14* (2006.01)
*A61K 31/5025* (2006.01)
*A61K 31/522* (2006.01)

(52) U.S. Cl. ............ 514/218; 514/253.04; 514/228.5; 514/234.2; 514/248; 514/263.2; 514/263.21; 514/263.22; 514/263.23; 540/575; 544/362; 544/61; 544/118; 544/236; 544/265; 544/266; 544/267; 544/268; 544/269; 544/270; 544/271; 544/272; 546/118

(58) Field of Classification Search ................. None
See application file for complete search history.

(56) References Cited

U.S. PATENT DOCUMENTS

| 5,041,448 A | 8/1991 | Janssens et al. |
| 7,109,192 B2 * | 9/2006 | Hauel et al. ............. 514/218 |
| 7,169,926 B1 * | 1/2007 | Burgess et al. ............. 546/82 |
| 2002/0161001 A1 | 10/2002 | Kanstrup et al. |
| 2002/0198205 A1 | 12/2002 | Himmelsbach et al. |
| 2004/0082570 A1 | 4/2004 | Yoshikawa et al. |
| 2004/0116328 A1 | 6/2004 | Yoshikawa et al. |
| 2004/0122228 A1 | 6/2004 | Maier et al. |
| 2005/0020574 A1 | 1/2005 | Hauel et al. |
| 2006/0063787 A1 | 3/2006 | Yoshikawa et al. |
| 2006/0094722 A1 | 5/2006 | Yasuda et al. |
| 2006/0100199 A1 | 5/2006 | Yoshikawa et al. |
| 2007/0219178 A1 | 9/2007 | Muramoto |
| 2009/0018331 A1 | 1/2009 | Yoshikawa et al. |

FOREIGN PATENT DOCUMENTS

| EP | 0 206 415 A2 | 12/1986 |
| EP | 1 338 595 A2 | 8/2003 |
| EP | 1 338 595 A3 | 8/2003 |
| WO | WO 00/56296 A1 | 9/2000 |
| WO | WO 02/02560 A2 | 1/2002 |
| WO | WO 02/068420 A1 | 9/2002 |

(Continued)

OTHER PUBLICATIONS

Ahren, Bo et al.; "Inhibition of dipeptidyl peptidase IV improves metabolic control over a 4-week study period in type 2 diabetes"; *Diabetes Care*; May 2002; pp. 869-875; vol. 25, No. 5.

(Continued)

*Primary Examiner*—Emily Bernhardt
(74) *Attorney, Agent, or Firm*—Townsend and Townsend and Crew LLP

(57) ABSTRACT

The present invention is related to compounds represented by the following formula, or salts or hydrates thereof

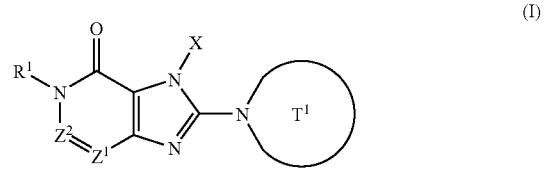

(I)

wherein,
$T^1$ represents a 4- to 12-membered heterocyclic group containing one or two nitrogen atoms in the ring, which is a monocyclic or bicyclic structure that may have one or more substituents;
X represents a $C_{1-6}$ alkyl group which may have one or more substituents, or such;
$Z^1$ and $Z^2$ each independently represent a nitrogen atom or a group represented by the formula —$CR^2$—;
$R^1$ and $R^2$ independently represent a hydrogen atom, a $C_{1-6}$ alkyl group which may have one or more substituents, or a $C_{1-6}$ alkoxy group which may have one or more substituents, or such.

These are novel compounds that exhibit an excellent DPPIV-inhibiting activity.

7 Claims, No Drawings

FOREIGN PATENT DOCUMENTS

| WO | WO 03/004496 A1 | 1/2003 |
|---|---|---|
| WO | WO 03/104229 A1 | 12/2003 |
| WO | WO 2004/028524 A1 | 4/2004 |
| WO | WO 2004/050656 A1 | 6/2004 |
| WO | WO 2004/096806 A1 | 11/2004 |
| WO | WO 2005/053695 A1 | 6/2005 |

OTHER PUBLICATIONS

Balkan et al.; "Inhibition of Dipeptidyl Peptidase IV with NVP-DPP728 Increases Plasma GLP-1 (7-36 Amide) Concentrations and Improves Oral Glucose Tolerance in Obese Zucker Rats" *Diabetologia* (1999) vol. 42, pp. 1324-1331.

Bauvois et al.; "Constitutive Expression of CD26/dipeptidylpeptidase IV on Peripheral Blood B Lymphocytes of Patients with B Chronic Lymphocytic Leukaemia" *British Journal of Cancer* (1999) vol. 79, 7/8, pp. 1042-1048.

Beljean-Leymarie et al., "Hydrazines et hydrazones hétérocycliques. IV. Synthèses de dérivés de l'hydrazine dans la série des imidazo[4,5-*d*] pyridazinones-4" *Canadian Journal of Chemistry* (1983), vol. 61, pp. 2563-2566.

Berry, et al., "Synthesis of 8-Amino-3-deazaguanine via Imidazole Precursors. Antitumor Activity and Inhibition of Purine Nucleoside Phosphorylase" *Journal of Medicinal Chemistry* (1986), vol. 29, No. 10, pp. 2034-2037.

Callebaut et al.; "T Cell Activation Antigen, CD26, as a Cofactor for Entry of HIV in CD4 Cells" *Science* (Dec. 24, 1993) vol. 2, pp. 2045-2050.

Clark, Richard S. J. et al.; "Novel piperazine-substituted, heterocyclic compounds as selective, competitive DPP-IV inhibitors"; *National Meeting & Exposition Program: 228th ACS National Meeting*, Philadelphia, PA; Aug. 22-26, 2004; Abstract. 265; American Medical Society; Abstract.

Clark, Richard S. J. et al.; *Yakugaku Zasshi: Journal of the Pharmaceutical Society of Japan*, The 23rd Medicinal Chemistry Symposium, The 12th Annual Meeting of Division of Medicinal Chemistry (Tsukuba); Nov. 24, 2004; Abstract 2P-11; vol. 124, Suppl. 3.

Evans, D. Michael; "Dipeptidyl peptidase IV inhibitors"; *IDrugs*; Jun. 2002; pp. 577-585; vol. 5, No. 6.

Gotoh et al.; "Activity of Dipeptidyl Peptidase IV and Post-Proline Cleaving Enzyme in Sera from Osteoporotic Patients" *Clinical Chemistry* (1988) vol. 34, No. 12, pp. 2499-2501.

Hartmann et al.; "Dipeptidyl Peptidase IV Inhibition Enhances the Intestinotrophic Effect of Glucagon-Like Peptide-2 in Rats and Mice" *Endocrinology* (2000) vol. 141, No. 11, pp. 4013-4020.

Holst et al.; "Perspectives in Diabetes: Inhibition of the Activity of Dipeptidyl-Peptidase IV as a Treatment for Type 2 Diabetes" *Diabetes* (Nov. 1998) vol. 47, pp. 1663-1670.

Kohl et al.; "The Role of Dipeptidylpeptidase IV Positive T Cells in Wound Healing and Angiogenesis" *Agents and Actions* (1991) vol. 32, 1/2, pp. 125-127.

Martin, J. C.; "'Frozen' Transition States: Pentavalent Carbon et al."; *Science*; Aug. 5, 1983; pp. 509-514; vol. 221, No. 4610.

U.S. Appl. 60/437,438, filed Dec. 30, 2002 (Hauel et al.).

U.S. Appl. 60/456,598, filed Mar. 21, 2003 (Hauel et al.).

Reimer, M. Kvist et al.; "Long-term inhibition of dipeptidyl peptidase IV improves glucose tolerance and preserves islet function in mice"; *European Journal of Endocrinology*; 2002; pp. 717-727; vol. 146.

Steinbrecher et al.; "Targeting Dipeptidyl Peptidase IV (CD26) Suppresses Autoimmune Encephalomyelitis and Up-Regulates TGF-β1 Secretion In Vivo" *The Journal of Immunology* (2001) vol. 166, pp. 2041-2048.

Sudre, Beatrice et al.; "Chronic inhibition of circulating dipeptidyl peptidase IV by FE 999011 delays the occurrence of diabetes in male Zucker diabetic fatty rats"; *Diabetes*; May 2002; pp. 1461-1469; vol. 51, No. 5.

Wilson et al.; "Dipeptidylpeptidase IV Activities are Elevated in Prostate Cancers and Adjacent Benign Hyperplastic Glands" *Journal of Andrology* (Mar./Apr. 2000) vol. 21, No. 2, pp. 220-226.

Yip et al.; "Minireview: GIP Biology and Fat Metabolism" *Life Sciences* (2000) vol. 66, No. 2, pp. 91-103.

Morris, Kenneth R., "Chapter 4: Structural Aspects of Hydrates and Solvates and Hydrates; Section I: Pharmaceutical Importance of Crystalline Hydrates." *Polymorphism in Pharmaceutical Solids*. Ed. Harry G. Brittain. USA: Taylor & Francis, Inc. 1999. 126-127.

\* cited by examiner

CONDENSED IMIDAZOLE DERIVATIVES

CROSS REFERENCE TO RELATED APPLICATIONS

This application is a division of U.S. application Ser. No. 11/212,407, filed Aug. 26, 2005, which is a continuation of U.S. application Ser. No. 10/457,002, filed Jun. 6, 2003, which claims priority to Japanese Patent Application No. 2002-307750 filed Oct. 23, 2002, which claims priority to Japanese Patent Application No. 2002-209373 filed Jul. 18, 2002, which claims priority to Japanese Patent Application No. 2002-166069 filed Jun. 6, 2002, whereby the disclosures of each are herein incorporated by reference in their entirety.

TECHNICAL FIELD

The present invention relates to novel condensed imidazole derivatives useful as dipeptidyl peptidase-IV (DPPIV) inhibitors and uses thereof.

BACKGROUND ART

Dipeptidyl peptidase IV (DPPIV) is a serine protease which specifically hydrolyzes dipeptide —X-Pro (X=arbitrary amino acid) from the free N terminus of a polypeptide chain.

Glucose-dependent, insulin secretion-stimulating hormones, known as incretins (GLP-1: Glucagon-Like Peptide-1 and GIP: Glucose-dependent Insulinotropic Polypeptide) secreted in the digestive tract following meals are rapidly hydrolyzed and inactivated by DPPIV. When the hydrolysis by DPPIV is suppressed, the action of incretin (GLP-1 an GIP) is enhanced, which in turn increases the glucose-stimulated secretion of insulin from the β cells of the pancreas. This has been shown to improve hyperglycemia in the oral glucose tolerance test (see Diabetologia 1999 November, 42(11), 1324-31). In addition, GLP-1 is known to be involved in the suppression of appetite and food intake. GLP-1 has also been reported to have the effect of protecting the β cells of the pancreas by enhancing β cell differentiation and proliferation.

Thus, a DPPIV inhibitor can be a useful therapeutic or preventive agent for diseases with which GLP-1 and/or GIP are associated, such as obesity and diabetes mellitus.

Furthermore, there are many reports suggesting a relationship between dipeptidyl peptidase IV and various diseases as described below. Thus, a DPPIV inhibitor can be a therapeutic agent for diseases such as:

(1) preventive and therapeutic agents for AIDS (see Science 1993, 262, 2045-2050), (2) preventive and therapeutic agents for osteoporosis (see Clinical chemistry 1988, 34, 2499-2501), (3) preventive and therapeutic agents for intestinal disorders (see Endocrinology 2000, 141, 4013-4020), (4) preventive and therapeutic agents for diabetes mellitus, obesity, and hyperlipidemia (see Diabetes 1998, 47, 1663-1670; and Life Sci 2000, 66(2), 91-103), (5) preventive and therapeutic agents for angiogenesis (see Agents and Actions 1991, 32, 125-127), (6) preventive and therapeutic agents for infertility (see International Publication WO 00/56296), (7) preventive and therapeutic agents for inflammatory diseases, autoimmune diseases, and chronic rheumatoid arthritis (see The Journal of Immunology 2001, 166, 2041-2048), and (8) preventive and therapeutic agents for cancer (see Br J Cancer 1999 March, 79(7-8), 1042-8; and J Androl 2000 March-April, 21(2), 220-6).

Some DPPIV inhibitors are disclosed in the Publication of US patent No. 2002/0161001; International Publication WO 03/004496; and Publication of US patent No. 2002/0198205. However, there is no known DPPIV inhibitor having a hypoxanthine or imidazopyridazinone structure backbone.

A compound having DPPIV-inhibiting activity that can be used as a pharmaceutical agent is being anxiously sought as described above. However, a compound with excellent DPPIV-inhibiting activity, which is also highly useful as a clinically effective pharmaceutical is yet to be discovered. Specifically, an objective of the present invention is to provide compounds having DPPIV-inhibiting activity, which can be used as preventive, therapeutic, or alleviating agents for diabetes mellitus or such diseases.

DISCLOSURE OF THE INVENTION

The present inventors conducted extensive studies in view of the above background. As a result, they succeeded in synthesizing novel condensed imidazole derivatives, including hypoxanthine and imidazopyridazinone derivatives. To complete the present invention they also found that these compounds had excellent DPPIV-inhibiting activity. Specifically, the present invention comprises:

[1] a compound represented by the following formula, or a salt or hydrate thereof,

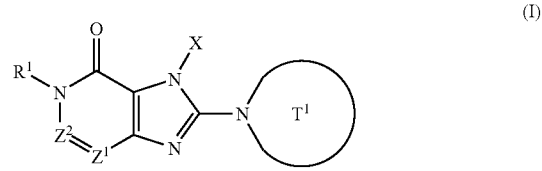

(I)

wherein, $T^1$ represents a monocyclic or bicyclic 4- to 12-membered heterocyclic group containing one or two nitrogen atoms in the ring, that may have one or more substituents;

X represents a $C_{1-6}$ alkyl group which may have one or more substituents, a $C_{2-6}$ alkenyl group which may have one or more substituents, a $C_{2-6}$ alkynyl group which may have one or more substituents, a $C_{6-10}$ aryl group which may have one or more substituents, a 5 to 10-membered heteroaryl group which may have one or more substituents, a $C_{6-10}$ aryl $C_{1-6}$ alkyl group which may have one or more substituents, or a 5 to 10-membered heteroaryl $C_{1-6}$ alkyl group which may have one or more substituents;

$Z^1$ and $Z^2$ each independently represent a nitrogen atom or a group represented by the formula —$CR^2$=;

$R^1$ and $R^2$ each independently represent a group according to the formula -$A^0$-$A^1$-$A^2$ (wherein $A^0$ represents a single bond or a $C_{1-6}$ alkylene group, which may have 1 to 3 substituents selected from group B consisting of the substituents described below;

$A^1$ represents a single bond, an oxygen atom, a sulfur atom, a sulfinyl group, a sulfonyl group, a carbonyl group, a group represented by the formula —O—CO—, a group represented by the formula —CO—O—, a group represented by the formula —NR$^A$—, a group represented by the formula —CO—NR$^A$—, a group represented by the formula —NR$^A$—CO—, a group represented by the formula —SO$_2$—NR$^A$—, or a group represented by the formula —NR$^A$—SO$_2$—;

A$^2$ and R$^A$ each independently represent a hydrogen atom, a halogen atom, a cyano group, a C$_{1-6}$ alkyl group, a C$_{3-8}$ cycloalkyl group, a C$_{2-6}$ alkenyl group, a C$_{2-6}$ alkynyl group, C$_{6-10}$ aryl group, a 5 to 10-membered heteroaryl group, a 4 to 8-membered heterocyclic group, a 5 to 10-membered heteroaryl C$_{1-6}$ alkyl group, a C$_{6-10}$ aryl C$_{1-6}$ alkyl group, or a C$_{2-7}$ alkylcarbonyl group;

however, A$^2$ and R$^A$ each independently may have 1 to 3 substituents selected from the substituent group B described below:

when Z$^2$ is a group represented by the formula —CR$^2$=, R$^1$, and R$^2$ may in combination form a 5 to 7-membered ring;

except in cases where: [1] R$^1$ is a hydrogen atom; Z$^1$ is a nitrogen atom; and Z$^2$ is —CH=; and [2] Z$^1$ is a nitrogen atom; and Z$^2$ is —C(OH)=;

<Substituent group B>

Substituent group B represents the group consisting of: a hydroxyl group, a mercapto group, a cyano group, a nitro group, a halogen atom, a trifluoromethyl group, a C$_{1-6}$ alkyl group which may have one or more substituents, a C$_{3-8}$ cycloalkyl group, a C$_{2-6}$ alkenyl group, a C$_{2-6}$ alkynyl group, a C$_{6-10}$ aryl group, a 5 to 10-membered heteroaryl group, a 4 to 8-membered heterocyclic group, a C$_{1-6}$ alkoxy group, a C$_{1-6}$ alkylthio group, a group represented by the formula —SO$_2$—NR$^{B1}$—R$^{B2}$, a group represented by the formula —NR$^{B1}$—CO—R$^{B2}$, a group represented by the formula —NR$^{B1}$—R$^{B2}$ (where R$^{B1}$ and R$^{B2}$ each independently represent a hydrogen atom or a C$_{1-6}$ alkyl group), a group represented by the formula —CO—R$^{B3}$ (where R$^{B3}$ represents a 4 to 8-membered heterocyclic group) a group represented by the formula —CO—R$^{B4}$—R$^{B5}$ and a group represented by the formula —CH$_2$—CO—R$^{B4}$—R$^{B5}$ (where R$^{B4}$ represents a single bond, an oxygen atom, or a group represented by the formula —NR$^{B6}$—; R$^{B5}$ and R$^{B6}$ each independently represent a hydrogen atom, a C$_{1-6}$ alkyl group, a C$_{3-8}$ cycloalkyl group, a C$_{2-6}$ alkenyl group, a C$_{2-6}$ alkynyl group, a C$_{6-10}$ aryl group, a 5 to 10-membered heteroaryl group, a 4 to 8-membered heterocyclic C$_{1-6}$ alkyl group, a C$_{6-10}$ aryl C$_{1-6}$ alkyl group, or a 5 to 10-membered heteroaryl C$_{1-6}$ alkyl group)), and

[2] the compound according to [1], or a salt or hydrate thereof, wherein T$^1$ is, a group represented by the following formula:

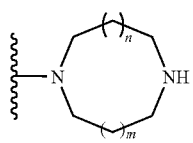

(wherein, n and m each independently represent 0 or 1) which may have one or more substituents;

an azetidin-1-yl group which may have one or more substituents;

a pyrrolidin-1-yl group which may have one or more substituents;

a piperidin-1-yl group which may have one or more substituents; or an azepan-1-yl group which may have one or more substituents;

[3] the compound according to [1], or a salt or hydrate thereof, wherein T$^1$ is, a group represented by the following formula:

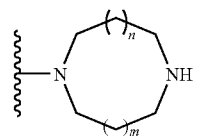

(where n and m each independently represent 0 or 1);

an azetidin-1-yl group which may have an amino group;

a pyrrolidin-1-yl group which may have an amino group;

a piperidin-1-yl group which may have an amino group; or an azepan-1-yl group which may have an amino group;

[4] the compound according to [1], or a salt or hydrate thereof, wherein T$^1$ is a piperazin-1-yl group or a 3-aminopiperidin-1-yl group;

[5] the compound according to [1], or a salt or hydrate thereof, wherein T$^1$ is a piperazin-1-yl group;

[6] the compound according to any one of [1] to [5], or a salt or hydrate thereof, wherein X is a group represented by the formula —X$^1$—X$^2$ (where X$^1$ represents a single bond or a methylene group which may have one or more substituents; X$^2$ represents a C$_{2-6}$ alkenyl group which may have one or more substituents, a C$_{2-6}$ alkynyl group may have one or more substituents, or a phenyl group which may have one or more substituents);

[7] the compound according to any one of [1] to [5], or a salt or hydrate thereof, wherein X is a group represented by the formula —X$^{11}$—X$^{12}$ (where X$^{11}$ represents a single bond or a methylene group; X$^{12}$ represents a C$_{2-6}$ alkenyl group, a C$_{2-6}$ alkynyl group, or a phenyl group which may have one or more substituents);

[8] the compound according to [6] or [7], or a salt or hydrate thereof, wherein the phenyl group that may have one or more substituents is a phenyl group which may have at the 2-position a substituent selected from the group consisting of a hydroxyl group, a fluorine atom, a chlorine atom, a methyl group, an ethyl group, a fluoromethyl group, a vinyl group, a methoxy group, an ethoxy group, an acetyl group, a cyano group, a formyl group, and a C$_{2-7}$ alkoxycarbonyl group;

[9] the compound according to any one of [1] to [5], or a salt or hydrate thereof, wherein X is a 3-methyl-2-buten-1-yl group, a 2-butyn-1-yl group, a benzyl group, or a 2-chlorophenyl group;

[10] the compound according to any one of [1] to [5], or a salt or hydrate thereof, wherein X is a 2-butyn-1-yl group;

[11] the compound according to any one of [1] to [10], or a salt or hydrate thereof, wherein either the Z$^1$ or Z$^2$ is a nitrogen atom;

[12] the compound according to any one of [1] to [10], or a salt or hydrate thereof, wherein, $Z^1$ is a nitrogen atom; and
$Z^2$ is a group represented by the formula —$CR^2$=
(where $R^2$ is as defined above in [1]);

[13] the compound according to any one of [1] to [10], or a salt or a hydrate thereof, wherein,
$Z^2$ is a nitrogen atom; and
$Z^1$ is a group represented by the formula —$CR^2$=
(where $R^2$ is as defined above in [1]);

[14] the compound according to any one of [1] to [13], or a salt or hydrate thereof, wherein $R^1$ represents a hydrogen atom, or a group represented by the formula -$A^{10}$-$A^{11}$-$A^{12}$
(where $A^{10}$ represents a $C_{1-6}$ alkylene group which may have 1 to 3 substituents selected from the substituent group C described below;
$A^{11}$ represents a single bond, an oxygen atom, a sulfur atom or a carbonyl group;
$A^{12}$ represents a hydrogen atom, a $C_{6-10}$ aryl group which may have 1 to 3 substituents selected from the substituent group C described below, a 5 to 10-membered heteroaryl group which may have 1 to 3 substituents selected from the substituent group C described below, a 5 to 10-membered heteroaryl $C_{1-6}$ alkyl group which may have 1 to 3 substituents selected from the substituent group C described below, or a $C_{6-10}$ aryl $C_{1-6}$ alkyl group which may have 1 to 3 substituents selected from the substituent group C described below:
<Substituent group C>
Substituent group C represents the group consisting of: a hydroxyl group, a nitro group, a cyano group, a halogen atom, a $C_{1-6}$ alkyl group, a $C_{1-6}$ alkoxy group, a $C_{1-6}$ alkylthio group, a trifluoromethyl group, a group represented by the formula —$NR^{C1}$—$R^{C2}$ (where each of $R^{C1}$ and $R^{C2}$ independently represent a hydrogen atom or $C_{1-6}$ alkyl group), a group represented by the formula —CO—$R^{C3}$—$R^{C4}$ and a group represented by the formula $CH_2$—CO—$R^{C3}$—$R^{C4}$ (where $R^{C3}$ represents a single bond, an oxygen atom, or a group represented by the formula —$NR^{C5}$—; $R^{C4}$ and $R^{C5}$ each independently represent a hydrogen atom or a $C_{1-6}$ alkyl group));

[15] the compound according to any one of [1] to [13], or a salt or hydrate thereof, wherein $R^1$ is a hydrogen atom, a $C_{1-6}$ alkyl group which may have 1 to 3 substituents selected from the substituent group C described below, a 5 to 10-membered heteroaryl $C_{1-6}$ alkyl group which may have 1 to 3 substituents selected from the substituent group C described below, or a $C_{6-10}$ aryl $C_{1-6}$ alkyl group which may have 1 to 3 substituents selected from the substituent group C described below:
<Substituent group C>
Substituent group C represents the group consisting of: a hydroxyl group, a nitro group, a cyano group, a halogen atom, a $C_{1-6}$ alkyl group, a $C_{1-6}$ alkoxy group, a $C_{1-6}$ alkylthio group, a trifluoromethyl group, a group represented by the formula —$NR^{C1}$—$R^{C2}$ (where each of $R^{C1}$ and $R^{C2}$ independently represents a hydrogen atom or a $C_{1-6}$ alkyl group), a group represented by the formula —$COR^{C3}$—$R^{C4}$ and a group represented by the formula —$CH_2$—CO—$R^{C3}$—$R^{C4}$ (where $R^{C3}$ represents a single bond, an oxygen atom, or a group represented by the formula —$NR^{C5}$—; $R^{C4}$ and $R^{C5}$ each independently represent a hydrogen atom or a $C_{1-6}$ alkyl group);

[16] the compound according to [14] or [15], or a salt or hydrate thereof, wherein the substituent group C is a group consisting of a cyano group, a $C_{1-6}$ alkoxy group, a $C_{2-7}$ alkoxycarbonyl group, and a halogen atom;

[17] the compound according to any one of [1] to [13], or a salt or hydrate thereof, wherein $R^1$ is a methyl group, a cyanobenzyl group, a fluorocyanobenzyl group, a phenethyl group, a 2-methoxyethyl group, or a 4-methoxycarbonylpyridin-2-yl group;

[18] the compound according to any one of [1] to [13], or a salt or hydrate thereof, wherein $R^1$ is a methyl group or a 2-cyanobenzyl group;

[19] the compound according to any one of [1] to [18], or a salt or hydrate thereof, wherein $R^2$ is a hydrogen atom, a cyano group, or a group represented by the formula -$A^{21}$-$A^{22}$
(where $A^{21}$ represents a single bond, an oxygen atom, a sulfur atom, a sulfinyl group, a sulfonyl group, a carbonyl group, a group represented by the formula —O—CO—, a group represented by the formula —CO—O—, a group represented by the formula —$NR^{A2}$—, a group represented by the formula —CO—$NR^{A2}$—, or a group represented by the formula —$NR^{A2}$—CO—;
$A^{22}$ and $R^{A2}$ each independently represent a hydrogen atom, a cyano group, a $C_{1-6}$ alkyl group, a $C_{3-8}$ cycloalkyl group, a $C_{2-6}$ alkenyl group, a $C_{2-6}$ alkynyl group, a $C_{6-10}$ aryl group, a 5- to 10-membered heteroaryl group, a 4- to 8-membered heterocyclic group, a 5- to 10-membered heteroaryl $C_{1-6}$ alkyl group, or a $C_{6-10}$ aryl $C_{1-6}$ alkyl group;
however, $A^{22}$ and $R^{A2}$ each may independently have 1 to 3 substituents selected from the substituent group D described below:
<Substituent group D>
Substituent group D represents the group consisting of: a hydroxyl group, a cyano group, a nitro group, a halogen atom, a $C_{1-6}$ alkyl group, a $C_{1-6}$ alkoxy group, a $C_{1-6}$ alkylthio group, a trifluoromethyl group, a group represented by the formula —$NR^{D1}$—$R^{D2}$ (where $R^{D1}$ and $R^{D2}$ each independently represent a hydrogen atom or a $C_{1-6}$ alkyl group), a group represented by the formula —CO—$R^{D3}$ (where $R^{D3}$ represents a 4 to 8-membered heterocyclic group), and a group represented by the formula —CO—$R^{D4}$—$R^{D5}$ (where $R^{D4}$ represents a single bond, an oxygen atom, or a group represented by the formula —$NR^{D6}$; $R^{D5}$ and $R^{D6}$ each independently represent a hydrogen atom, a $C_{3-8}$ cycloalkyl group, or a $C_{1-6}$ alkyl group));

[20] the compound according to any one of [1] to [18], or a salt or hydrate thereof, wherein $R^2$ represents a hydrogen atom, a cyano group, a carboxy group, a $C_{2-7}$ alkoxycarbonyl group, a $C_{1-6}$ alkyl group, a group represented by the formula —$CONR^{D7}R^{D8}$ (where $R^{D7}$ and $R^{D8}$ each independently represent a hydrogen atom or a $C_{1-6}$ alkyl group), or a group represented by the formula -$A^{23}$-$A^{24}$
(where $A^{23}$ represents an oxygen atom, a sulfur atom or a group represented by the formula —$NR^{A3}$;
$A^{24}$ and $R^{A3}$ each independently represent a hydrogen atom, a $C_{1-6}$ alkyl group which may have a substituent selected from the substituent group D1 described below, a $C_{3-8}$ cycloalkyl group which may have a substituent selected from the substituent group D1 described below, a $C_{2-6}$ alkenyl group which may have a substituent selected from the substituent group D1 described below, a $C_{2-6}$ alkynyl group which may have a substituent selected from the substituent group D1 described below, a phenyl group which may have a substituent selected from the substituent group D1 described below, or a 5 to 10-membered heteroaryl group which may have a substituent selected from the substituent group D1 described below:

<Substituent group D1>

Substituent group D1 represents the group consisting of: a carboxy group, a $C_{2-7}$ alkoxycarbonyl group, a $C_{1-6}$ alkyl group, a group represented by the formula —$CONR^{D7}R^{D8}$ (where $R^{D7}$ and $R^{D8}$ each independently represent a hydrogen atom or $C_{1-6}$ alkyl group), a pyrrolidin-1-ylcarbonyl group, a $C_{1-6}$ alkyl group, and a $C_{1-6}$ alkoxy group);

[21] the compound according to any one of [1] to [18], or a salt or hydrate thereof, wherein $R^2$ represents a hydrogen atom, a cyano group, a $C_{1-6}$ alkoxy group, or a group represented by the formula -$A^{25}$-$A^{26}$ (where $A^{25}$ represents an oxygen atom, a sulfur atom, or a group represented by the formula —$NR^{44}$—;

$A^{26}$ and $R^{44}$ each independently represent a hydrogen atom, a $C_{1-6}$ alkyl group having a substituent selected from the substituent group D1 described below, a $C_{3-8}$ cycloalkyl group having a substituent selected from the substituent group D1 described below, or a phenyl group having a substituent selected from the substituent group D1 described below:

<Substituent group D1>

Substituent group D1 represents the group consisting of: a carboxy group, a $C_{2-7}$ alkoxycarbonyl group, a $C_{1-6}$ alkyl group, a group represented by the formula —$CONR^{D7}R^{D8}$ (where $R^{D7}$ and $R^{D8}$ each independently represent a hydrogen atom or a $C_{1-6}$ alkyl group), pyrrolidin-1-ylcarbonyl group, a $C_{1-6}$ alkyl group, and a $C_{1-6}$ alkoxy group);

[22] the compound according to any one of [1] to [18], or a salt or hydrate thereof, wherein $R^2$ is a hydrogen atom, a cyano group, a methoxy group, a carbamoylphenyloxy group, or a group represented by the following formula:

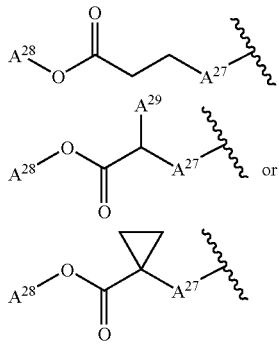

(where $A^{27}$ represents an oxygen atom, a sulfur atom, or —NH—; $A^{28}$ and $A^{29}$ each independently represent a hydrogen atom or a $C_{1-6}$ alkyl group);

[23] the compound according to any one of [1] to [18], or a salt or hydrate thereof, wherein $R^2$ is a hydrogen atom, a cyano group, or a 2-carbamoylphenyloxy group;

[24] the compound according to [1], or a salt or hydrate thereof, wherein the compound of formula (I) indicated above is any one selected from the group consisting of:

7-(2-butynyl)-2-cyano-1-methyl-8-(piperazin-1-yl)-1,7-dihydropurin-6-one, 3-(2-butynyl)-5-methyl-2-(piperazin-1-yl)-3,5-dihydroimidazo[4,5-d]pyridazin-4-one, 2-(3-aminopiperidin-1-yl)-3-(2-butynyl)-5-methyl-3,5-dihydroimidazo[4,5-d]pyridazin-4-one, 2-[7-(2-butynyl)-1-methyl-6-oxo-8-(piperazin-1-yl)-6,7-dihydro-1H-purin-2-yloxy]benzamide, 7-(2-butynyl)-1-(2-cyanobenzyl)-6-oxo-8-(piperazin-1-yl)-6,7-dihydro-1H-purine-2-carbonitrile, and 2-[3-(2-butynyl)-4-oxo-2-(piperazin-1-yl)-3,4-dihydroimidazo[4,5-d]pyridazin-5-ylmethyl]benzonitrile;

[25] a pharmaceutical agent comprising a compound of any one of [1] to [24];

[26] a dipeptidyl peptidase IV inhibitor comprising a compound of any one of [1] to [24];

[27] a pharmaceutical composition comprising a compound of any one of [1] to [24] and an adjuvant useful for formulation;

[28] a preventive or a therapeutic agent for diabetes mellitus, which comprises a compound of any one of [1] to [24];

[29] a preventive or therapeutic agent, which comprises a compound of any one of [1] to [24], for diabetes mellitus, obesity, hyperlipidemia, AIDS, osteoporosis, a gastrointestinal disorder, angiogenesis, infertility, an inflammatory disease, an allergic disease, or cancer;

[30] an immunomodulator, a hormone modulator, or an antirheumatic drug, which comprises a compound of any one of [1] to [24];

[31] a therapeutic or preventive method for a disease in which the inhibition of dipeptidyl peptidase IV is effective, wherein the method comprises administering to a patient a compound of any one of [1] to [24], or a salt or hydrate thereof, in a pharmaceutically effective amount;

[32] the use of a compound of any one of [1] to [24], or a salt or hydrate thereof, in producing a pharmaceutical agent;

[33] the use of a compound of any one of [1] to [24], or a salt or hydrate thereof, in producing a therapeutic or preventive agent for a disease in which the inhibition of dipeptidyl peptidase IV is effective;

[34] a compound represented by the following formula, or a salt or hydrate thereof

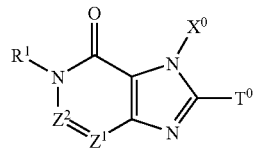

wherein, $T^0$ represents, a group represented by $T^1$ described above in [1], a pyridyl group which may have one or more substituents, a pyridinium group which may have one or more substituents, a group represented by the following formula:

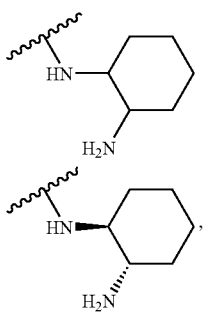
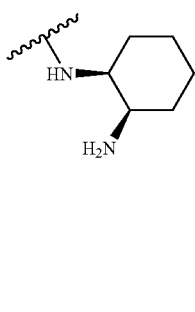
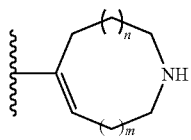

a group, which may have one or more substituents, represented by the following formula:

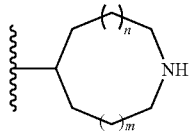

(where n and m each independently represent 0 or 1), or a group, which may have one or more substituents, represented by the following formula:

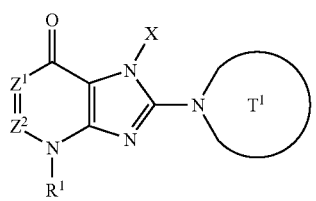

(where n and m each independently represent 0 or 1);

$X^0$ represents a $C_{3-8}$ cycloalkyl group which may have one or more substituents, a $C_{1-6}$ alkyl group which may have one or more substituents, a $C_{2-6}$ alkenyl group which may have one or more substituents, a $C_{2-6}$ alkynyl group which may have one or more substituents, a $C_{6-10}$ aryl group which may have one or more substituents, a 5 to 10-membered heteroaryl group which may have one or more substituents, a $C_{6-10}$ aryl $C_{1-6}$ alkyl group which may have one or more substituents, or a 5 to 10-membered heteroaryl $C_{1-6}$ alkyl group which may have one or more substituents; and $R^1$, $Z^1$ and $Z^2$ are, as defined above in [1];

[35] a compound represented by the following formula, or a salt or hydrate thereof,

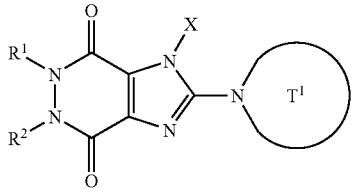

wherein $R^1$, $R^2$, $T^1$, $Z^1$ and $Z^2$ are, as defined above in [1];

[36] a compound represented by the following formula, or a salt or hydrate thereof,

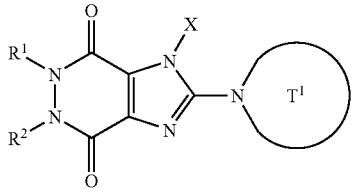

wherein $R^1$, $R^2$, $T^1$, $Z^1$ and $Z^2$ are, as defined above in [1];

[37] a compound represented by the following formula, or a salt or hydrate thereof,

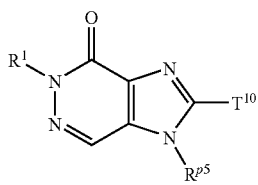

wherein, $R^1$ is as defined above in [1];

$R^{p5}$ represents a t-butoxycarbonyloxy group, a trityl group or a group represented by the formula —$SO_2NH_2$; and $T^{10}$ represents a halogen atom or a hydrogen atom;

[38] a compound represented by the following formula, or a salt or hydrate thereof,

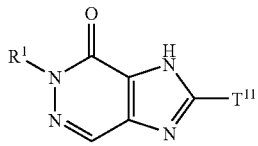

wherein, $R^1$ is as defined above in [1]; and $T^{11}$ represents a halogen atom or a group represented by the following formula:

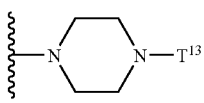

(where $T^{13}$ represents a t-butoxycarbonyl group, a benzyloxycarbonyl group, or a formyl group));

[39] a compound represented by the following formula, or a salt or hydrate thereof,

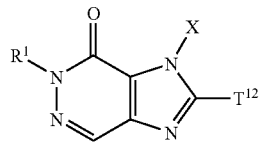

wherein, $R^1$ and X are as defined above in [1], respectively; and $T^{12}$ represents a halogen atom;

[40] a compound represented by the following formula, or a salt or hydrate thereof,

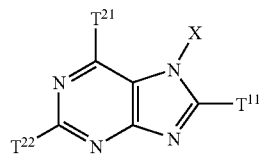

wherein,

X is as defined above in [1], except when X is a benzyl group;

T21 and T22 each independently represent a halogen atom; and $T^{11}$ represents a halogen atom or a group represented by the following formula:

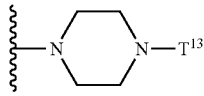

(where $T^{13}$ represents a t-butoxycarbonyl group, a benzyloxycarbonyl group, or a formyl group));

[41] a compound represented by the following formula, or a salt or hydrate thereof

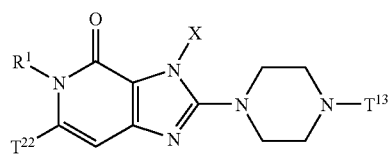

wherein,

X and $R^1$ are as defined above in [1], respectively;

$T^{22}$ represents a halogen atom; and $T^{13}$ represents a t-butoxycarbonyl group, a benzyloxycarbonyl group, or a formyl group;

[42] a compound represented by the following formula, or a salt or hydrate thereof

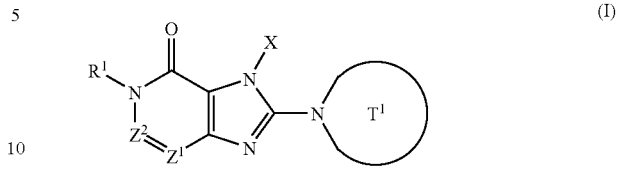

(I)

wherein, the ring of $T^1$ represents a monocyclic or bicyclic 6- to 12-membered heterocyclic group containing two nitrogen atoms in the ring, which may have one or more substituents;

X represents a $C_{1-6}$ alkyl group which may have one or more substituents, a $C_{2-6}$ alkenyl group which may have one or more substituents, a $C_{2-6}$ alkynyl group which may have one or more substituents, a $C_{6-10}$ aryl group which may have one or more substituents, a 5 to 10-membered heteroaryl group which may have one or more substituents, a $C_{6-10}$ aryl $C_{1-6}$ alkyl group which may have one or more substituents, or a 5 to 10-membered heteroaryl $C_{1-6}$ alkyl group which may have one or more substituents;

X may form a bond with an atom constituting the ring of $T^1$;

$Z^1$ and $Z^2$ each independently represent a nitrogen atom or a group represented by the formula —$CR^2$=, $R^1$ and $R^2$ independently represent a hydrogen atom, a 4- to 8-membered heterocyclic group which may have one or more substituents, or a group represented by the formula $-A^0-A^1-A^2$ (where $A^0$ represents a single bond or a $C_{1-6}$ alkylene group that may have 1 to 3 substituents selected from the substituent group B described below; A1 represents a single bond, an oxygen atom, a sulfur atom, a sulfinyl group, a sulfonyl group, a carbonyl group, a group represented by the formula —O—CO—, a group represented by the formula —CO—O—, a group represented by the formula —$NR^4$—, a group represented by the formula —CO—$NR^4$—, a group represented by the formula —$NR^4$—CO—, a group represented by the formula —$SO_2$—$NR^4$—, or a group represented by the formula —$NR^4$—$SO_2$—;

$A^2$ and $R^4$ each independently represent a hydrogen atom, a $C_{1-6}$ alkyl group, a $C_{3-8}$ cycloalkyl group, a $C_{2-6}$ alkenyl group, a $C_{2-6}$ alkynyl group, a $C_{6-10}$ aryl group, a 5 to 10-membered heteroaryl group, or a 4 to 8-membered heterocyclic group. However, $A^2$ and $R^4$ each may independently have 1 to 3 substituents selected from the substituent group B described below:

except in cases where: (i) both $R^1$ and $R^2$ are hydrogen atoms, and (ii) $R^2$ is a hydroxyl group.

<Substituent B group>

Substituent group B represents the group consisting of: a hydroxyl group, a cyano group, a halogen atom, a $C_{1-6}$ alkyl group, a $C_{3-8}$ cycloalkyl group, a $C_{2-6}$ alkenyl group, a $C_{2-6}$ alkynyl group, a $C_{6-10}$ aryl group, a 5 to 10-membered heteroaryl group, a 4 to 8-membered heterocyclic group, a $C_{1-6}$ alkoxy group, a $C_{1-6}$ alkylthio group, and a group represented by the formula —CO—$R^B$—$R^{B2}$ (where $R^B$ represents a single bond, an oxygen atom, or a group represented by the formula —$NR^{B3}$—; $R^{B2}$ and $R^{B3}$ each independently represent a hydrogen atom, a $C_{1-6}$ alkyl group, a $C_{3-8}$ cycloalkyl group, a $C_{2-6}$ alkenyl group, a $C_{2-6}$ alkynyl group, a $C_{6-10}$ aryl group, a 5 to 10-membered heteroaryl group, a $C_{6-10}$ aryl $C_{1-6}$ alkyl group, a 5 to 10-membered heteroaryl $C_{1-6}$ alkyl group, a 1-pyrrolidinyl group, 1-morpholinyl group, a 1-piperazinyl group, or a 1-piperidyl group));

DETAILED DESCRIPTION OF THE INVENTION

The present invention is illustrated in detail below.

Herein, a structural formula of a compound sometimes represents a certain isomer for convenience of description. However, compounds of the present invention may include all possible isomers, such as structurally possible geometric isomers, optical isomers generated due to the presence of asymmetric carbons, stereoisomers, tautomers, and mixtures of isomers, and are not limited to formulae being used for the convenience of description, and may be either of two isomers or a mixture of both isomers. Thus, compounds of the present invention may be either optically active compounds having an asymmetric carbon atom in their molecules or their racemates, and are not restricted to either of them but include both. Furthermore, compounds of the present invention may exhibit crystalline polymorphism, but likewise are not restricted to any one of these but may be in any one of these crystal forms or exist as a mixture of two or more crystal forms. Compounds of the present invention also include both anhydrous and hydrated forms. Substances produced through in vivo metabolism of compounds of the invention are also within the scope of claims.

The terms and symbols used herein are defined and the present invention is described in detail below.

As used herein, the phrase "$C_{1-6}$ alkyl group" refers to a linear or branched alkyl group containing 1 to 6 carbon atoms, which is a monovalent group obtained by removal of any one of the hydrogen atoms from an aliphatic hydrocarbon containing 1 to 6 carbons, and specifically, includes, for example, a methyl group, an ethyl group, a 1-propyl group, a 2-propyl group, a 2-methyl-1-propyl group, a 2-methyl-2-propyl group, a 1-butyl group, a 2-butyl group, a 1-pentyl group, a 2-pentyl group, a 3-pentyl group, a 2-methyl-1-butyl group, a 3-methyl-1-butyl group, a 2-methyl-2-butyl group, a 3-methyl-2-butyl group, a 2,2-dimethyl-1-propyl group, a 1-hexyl group, a 2-hexyl group, a 3-hexyl group, a 2-methyl-1-pentyl group, a 3-methyl-1-pentyl group, a 4-methyl-1-pentyl group, a 2-methyl-2-pentyl group, a 3-methyl-2-pentyl group, a 4-methyl-2-pentyl group, a 2-methyl-3-pentyl group, a 3-methyl-3-pentyl group, a 2,3-dimethyl-1-butyl group, a 3,3-dimethyl-1-butyl group, a 2,2-dimethyl-1-butyl group, a 2-ethyl-1-butyl group, a 3,3-dimethyl-2-butyl group, and a 2,3-dimethyl-2-butyl group.

As used herein, the phrase "$C_{2-6}$ alkenyl group" refers to a linear or branched alkenyl group containing 2 to 6 carbons, and specifically includes, for example, a vinyl group, an allyl group, a 1-propenyl group, a 2-propenyl group, a 1-butenyl group, a 2-butenyl group, a 3-butenyl group, a pentenyl group, and a hexenyl group.

As used herein, the phrase "$C_{2-6}$ alkynyl group" refers to a linear or branched alkynyl group containing 2 to 6 carbons, and specifically includes, for example, an ethynyl group, a 1-propynyl group, a 2-propynyl group, a butynyl group, a pentynyl group, and a hexynyl group.

As used herein, the phrase "$C_{3-8}$ cycloalkyl group" refers to a cyclic aliphatic hydrocarbon group containing 3 to 8 carbon atoms, and specifically includes, for example, a cyclopropyl group, a cyclobutyl group, a cyclopentyl group, a cyclohexyl group, a cycloheptyl group, and a cyclooctyl group.

As used herein, the phrase "$C_{1-6}$ alkylene group" refers to a divalent group obtained by removal of another arbitrary hydrogen atom from a "$C_{1-6}$ alkyl group" defined above, and specifically includes, for example, a methylene group, a 1,2-ethylene group, a 1,1-ethylene group, a 1,3-propylene group, a tetramethylene group, a pentamethylene group, and a hexamethylene group.

As used herein, the phrase "$C_{3-8}$ cycloalkylene group" refers to a divalent group obtained by removal of another arbitrary hydrogen atom from a "$C_{3-8}$ cycloalkyl group" defined above.

As used herein, the phrase "$C_{1-6}$ alkoxy group" refers to an oxy group linked to a "$C_{1-6}$ alkyl group" defined above, and specifically includes, for example, a methoxy group, an ethoxy group, a 1-propyloxy group, a 2-propyloxy group, a 2-methyl-1-propyloxy group, a 2-methyl-2-propyloxy group, a 1-butyloxy group, a 2-butyloxy group, a 1-pentyloxy group, a 2-pentyloxy group, a 3-pentyloxy group, a 2-methyl-1-butyloxy group, a 3-methyl-1-butyloxy group, a 2-methyl-2-butyloxy group, a 3-methyl-2-butyloxy group, a 2,2-dimethyl-1-propyloxy group, a 1-hexyloxy group, a 2-hexyloxy group, a 3-hexyloxy group, a 2-methyl-1-pentyloxy group, a 3-methyl-1-pentyloxy group, a 4-methyl-1-pentyloxy group, a 2-methyl-2-pentyloxy group, a 3-methyl-2-pentyloxy group, a 4-methyl-2-pentyloxy group, a 2-methyl-3-pentyloxy group, a 3-methyl-3-pentyloxy group, a 2,3-dimethyl-1-butyloxy group, a 3,3-dimethyl-1-butyloxy group, a 2,2-dimethyl-1-butyloxy group, a 2-ethyl-1-butyloxy group, a 3,3-dimethyl-2-butyloxy group, and a 2,3-dimethyl-2-butyloxy group.

As used herein, the phrase "$C_{1-6}$ alkylthio group" refers to a thio group linked to a "$C_{1-6}$ alkyl group" defined above, and specifically includes, for example, a methylthio group, an ethylthio group, a 1-propylthio group, a 2-propylthio group, a butylthio group, and a pentylthio group.

As used herein, the phrase "$C_{2-7}$ alkoxycarbonyl group" refers to a carbonyl group linked to a "$C_{1-6}$ alkoxy group" defined above, and specifically includes, for example, a methoxycarbonyl group, an ethoxycarbonyl group, a 1-propyloxycarbonyl group, and a 2-propyloxycarbonyl group.

As used herein, the phrase "$C_{2-7}$ alkylcarbonyl group" refers to a carbonyl group linked to a "$C_{1-6}$ alkyl group" defined above, and specifically includes, for example, a methylcarbonyl group, an ethylcarbonyl group, a 1-propylcarbonyl group, and a 2-propylcarbonyl group.

As used herein, the term "halogen atom" refers to a fluorine atom, a chlorine atom, a bromine atom, or an iodine atom.

As used herein, the phrase "$C_{6-10}$ aryl group" refers to an aromatic cyclic hydrocarbon group containing 6 to 10 carbon atoms, and specifically includes, for example, a phenyl group, a 1-naphthyl group, and a 2-naphthyl group.

As used herein, the term "heteroatom" refers to a sulfur atom, an oxygen atom, or a nitrogen atom.

As used herein, the phrase "5 to 10-membered heteroaryl ring" refers to an aromatic 5 to 10-membered ring containing one or more heteroatoms, and specifically includes, for example, a pyridine ring, a thiophene ring, a furan ring, a pyrrole ring, an oxazole ring, an isoxazole ring, a thiazole ring, a thiadiazole ring, an isothiazole ring, an imidazole ring, a triazole ring, a pyrazole ring, a furazan ring, a thiadiazole ring, an oxadiazole ring, a pyridazine ring, a pyrimidine ring, a pyrazine ring, a triazine ring, indole ring, an isoindole ring, an indazole ring, a chromene ring, a quinoline ring, an isoquinoline ring, a cinnoline ring, a quinazoline ring, a quinoxaline ring, a naphthyridine ring, a phthalazine ring, a purine ring, a pteridine ring, a thienofuran ring, an imidazothiazole ring, a benzofuran ring, a benzothiophene ring, a benzoxazole ring, a benzothiazole ring, a benzothiadiazole ring, a benzimidazole ring, an imidazopyridine ring, a pyrrolopyridine ring, a pyrrolopyrimidine ring, and a pyridopyrimidine ring. Preferable "5 to 10-membered heteroaryl rings" include a pyridine ring, a thiophene ring, a furan ring, a pyrrole ring, an imidazole ring, a 1,2,4-triazole ring, a thiazole ring, a thiadiazole ring, a pyrazole ring, a furazan ring, a thiadiazole ring, a pyridazine-ring, a pyrimidine ring, a pyrazine ring, an isoquinoline ring, a benzoxazole ring, a benzothiazole ring, and a benzimidazole ring. The most preferable example is a pyridine ring.

As used herein, the phrase "5 to 10-membered heteroaryl group" refers to a monovalent or divalent group obtained by removal of any one or two hydrogen atoms from a "5 to 10-membered heteroaryl ring" described above.

As used herein, the phrase "4 to 8-membered heterocyclic ring" refers to a non-aromatic ring in which:
(i) the number of atoms constituting the ring is 4 to 8;
(ii) the atoms constituting the ring include 1 to 2 heteroatoms;
(iii) the ring may contain 1 to 2 double bonds;
(iv) the ring may contain 1 to 3 carbonyl groups; and
(v) the ring is monocyclic.

Specifically, the 4 to 8-membered heterocyclic ring includes, for example, an azetidine ring, a pyrrolidine ring, a piperidine ring, an azepan ring, an azocane ring, a tetrahydrofuran ring, a tetrahydropyran ring, a morpholine ring, a thiomorpholine ring, a piperazine ring, a thiazolidine ring, a dioxane ring, an imidazoline ring, a thiazoline ring, and a ring represented by one of the formulae:

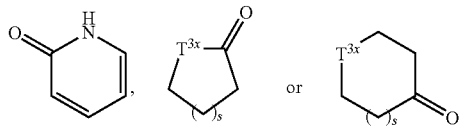

(where s represents an integer from 1 to 3; $T^{3x}$ represents a methylene group, an oxygen atom or a group represented by the formula $-NT^{4x}-$, wherein $T^{4x}$ represents a hydrogen atom or $C_{1-6}$ alkyl group. Preferably the "4- to 8-membered heterocyclic rings" include a pyrrolidine ring, a piperidine ring, an azepan ring, a morpholine ring, a thiomorpholine ring, a piperazine ring, a dihydrofuran-2-one ring, and a thiazolidine ring.

As used herein, the phrase "4 to 8-membered heterocyclic group" refers to a monovalent or divalent group obtained by removal of any one or two hydrogen atoms from a "4 to 8-membered heterocycle" described above. Preferably, the "4 to 8-membered heterocyclic groups" include a piperidin-1-yl group, a pyrrolidin-1-yl group, and a morpholin-4-yl group.

As used herein, the phrase "$C_{6-10}$ aryl $C_{1-6}$ alkyl group" refers to a group obtained by substitution of a "$C_{6-10}$ aryl group" defined above for an arbitrary hydrogen atom in a "$C_{1-6}$ alkyl group" defined above, and specifically includes, for example, a benzyl group, a phenethyl group, and a 3-phenyl-1-propyl group.

As used herein, the phrase "5 to 10-membered heteroaryl $C_{1-6}$ alkyl group" refers to a group obtained by substitution of a "5 to 10-membered heteroaryl group" defined above for an arbitrary hydrogen atom in a "$C_{1-6}$ alkyl group" defined above, and specifically, includes for example, a 2-pyridylmethyl and a 2-thienylmethyl group.

As used herein, the phrase "4 to 8-membered heterocyclic $C_{1-6}$ alkyl group" refers to a group obtained by substitution of a "4 to 8-membered heterocyclic group" defined above for an arbitrary hydrogen atom in a "$C_{1-6}$ alkyl group" defined above.

As used herein, the phrase "monocyclic or bicyclic 4 to 12-membered heterocyclic group containing one or two nitrogen atoms in the ring, that may have one or more substituents" refers to a non-aromatic cyclic group which may have one or more substituents. In the non-aromatic cyclic groups:
(i) the number of atoms constituting the ring of the cyclic group is 4 to 12;
(ii) the atoms constituting the ring of the cyclic group include one or two nitrogen atoms; and
(iii) the group is a monocyclic or bicyclic structure.

Specifically, the group is represented by the formula:

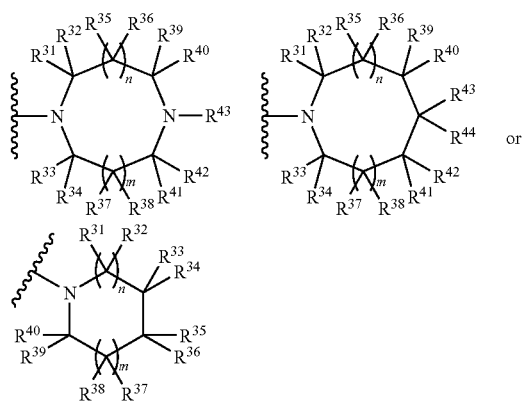

(where n and m each independently represent 0 or 1; $R^{31}$ to $R^{44}$ independently represent a hydrogen atom or a substituent selected from substituents referred to in the phrase "which may have one or more substituents" (the substituent group S defined below); any two of $R^{31}$ to $R^{44}$ may in combination form a $C_{1-6}$ alkylene group).

As used herein, the phrase "which may have one or more substituents" means that a group may have one or more substituents in any combination at replaceable positions. Specifically, such substituents include, for example, a substituent selected from the substituent group S defined below.

<Substituent Group S>
This group consists of:
(1) a halogen atom,
(2) a hydroxyl group,
(3) a mercapto group,
(4) a nitro group,
(5) a cyano group,
(6) a formyl group,
(7) a carboxyl group,
(8) a trifluoromethyl group,
(9) a trifluoromethoxy group,
(10) an amino group,
(11) an oxo group,
(12) an imino group, and
(13) a group represented by the formula $-T^{1x}-T^{2x}$ (where $T^{1x}$ is a single bond, a $C_{1-6}$ alkylene group, an oxygen atom, a group represented by the formula $-CO-$, a group represented by the formula $-S-$, a group represented by the formula $-S(O)-$, a group represented by the formula $-S(O)_2-$, a group represented by the formula $-O-CO-$, a group represented by the formula —CO—O—, a group represented by the formula —NR$^T$—, a group represented by the formula —CO—NR$^T$—, a group represented by the formula —NR$^T$—CO—, a group represented by the formula —SO$_2$—NR$^T$—, a group represented by the formula —NR$^T$—SO$_2$—, a group represented by the formula —NH—CO—NR$^T$ or a group represented by the formula —NH—CS—NR$^T$—;

T$^{2x}$ represents a hydrogen atom, a C$_{1-6}$ alkyl group, a C$_{3-8}$ cycloalkyl group, a C$_{2-6}$ alkenyl group, a C$_{2-6}$ alkynyl group, a phenyl group, a 1-naphthyl group, a 2-naphthyl group, a 5 to 10-membered heteroaryl group or a 4 to 8-membered heterocyclic group;

R$^T$ represents a hydrogen atom, a C$_{1-6}$ alkyl group, a C$_{3-8}$ cycloalkyl group, a C$_{2-6}$ alkenyl group or a C$_{2-6}$ alkynyl group;

provided that T$^{2x}$ and R$^T$ each may independently have 1 to 3 substituents selected from the substituent group T defined below).

<Substituent Group T>

This group consists of: hydroxyl, cyano, a halogen atom, C$_{1-6}$ alkyl, C$_{3-8}$ cycloalkyl, C$_{2-6}$ alkenyl, C$_{2-6}$ alkynyl, phenyl, 1-naphthyl, 2-naphthyl, 5 to 10-membered heteroaryl, 4 to 8-membered heterocyclic ring, C$_{1-6}$ alkoxy, C$_{1-6}$ alkylthio, C$_{2-7}$ alkoxycarbonyl group, etc.

The <substituent group S> preferably consists of:
(1) a halogen atom,
(2) a hydroxyl group,
(3) a cyano group,
(4) a carboxyl group,
(5) a trifluoromethyl group,
(6) a trifluoromethoxy group,
(7) an amino group,
(8) a C$_{1-6}$ alkyl group,
(9) a C$_{3-8}$ cycloalkyl group,
(10) a C$_{2-6}$ alkenyl group,
(11) a C$_{2-6}$ alkynyl group,
(12) a phenyl group, and
(13) a C$_{2-6}$ alkoxy group.

As used herein, the term "group represented by the formula:

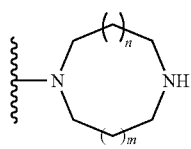

(where n and m each independently represent 0 or 1), which may have one or more substituents" refers to a group represented by the formula:

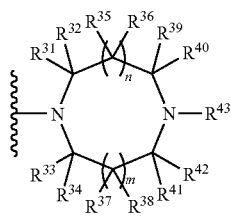

(where R$^{31}$ to R$^{44}$ independently represent a hydrogen atom or a group selected from: substituents referred to in the phrase "which may have one or more substituents" defined above (the substituent group S defined above); n and m each independently represent 0 or 1). The case where m=n=0 is preferred. More preferably, the term refers to a group represented by one of the formulae:

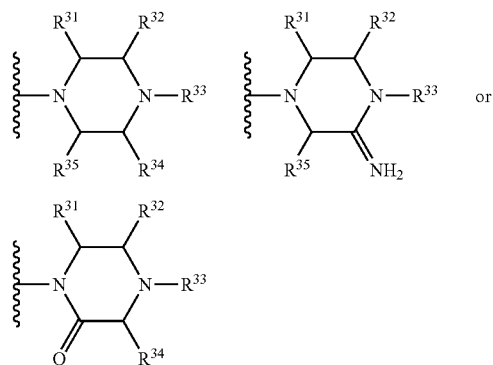

(where R$^{31}$, R$^{32}$, R$^{33}$, R$^{34}$, and R$^{35}$ independently represent a hydrogen atom or a group selected from substituent groups referred to in the phrase "which may have one or more substituents" (the substituent group S defined above)); provided that, at least three of R$^{31}$, R$^{32}$, R$^{33}$, R$^{34}$, and R$^{35}$ are hydrogen atoms Still more preferably, the term refers to a group represented by one of the formulae:

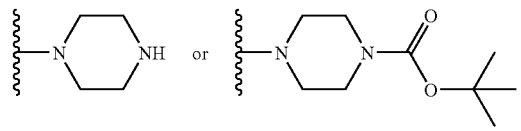

Most preferably, the term refers to a group represented by the formula:

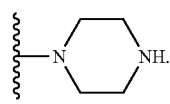

As used herein, the term "group represented by the formula:

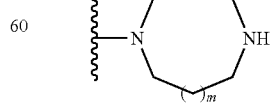

(where n and m each independently represent 0 or 1)" refers to a group represented by one of the formulae:

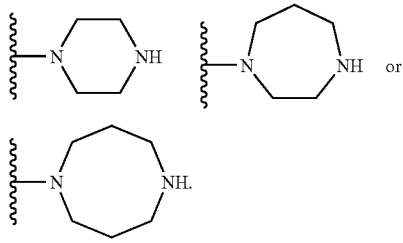

As used herein, the term "piperidin-1-yl group which may have one or more substituents" refers to a "piperidin-1-yl group" which may have one or more substituents selected from the groups referred to in the phrase "which may have one or more substituents" (the substituent group S defined above) at replaceable positions. Preferably, the "piperidin-1-yl group which may have one or more substituents" refers to a group represented by the formula:

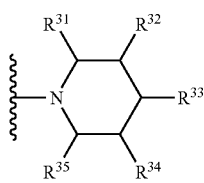

(where $R^{31}$, $R^{32}$, $R^{33}$, $R^{34}$, and $R^{35}$ each independently represent a hydrogen atom or a group selected from the substituents referred to in the phrase "which may have one or more substituents" (the substituent group S defined above)); provided that, at least three of $R^{31}$, $R^{32}$, $R^{33}$, $R^{34}$, and $R^{35}$ are hydrogen atoms. Preferably, the term refers to a group represented by one of the formulae:

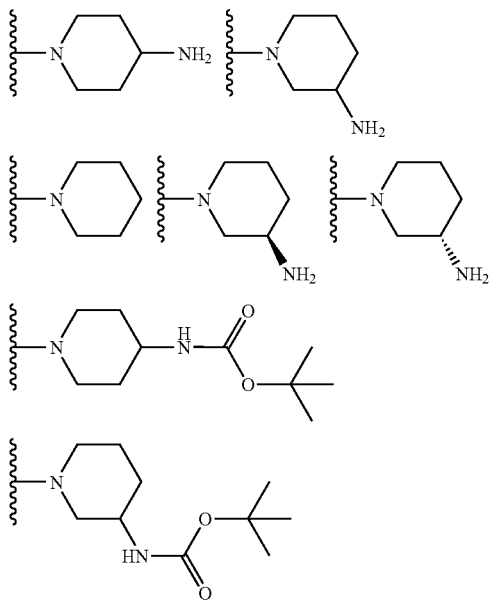

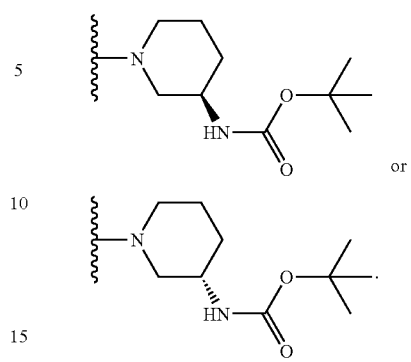

More preferably, the term refers to a group represented by one of the formulae:

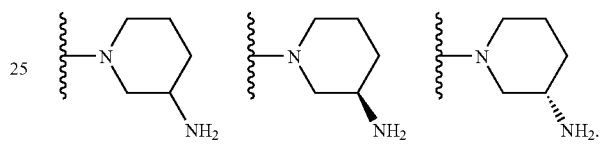

As used herein, the phrase "azetidin-1-yl group may have one or more substituents" refers to an "azetidin-1-yl group" which may have one or more groups selected from the substituents referred to in the phrase "which may have one or more substituents" at replaceable positions.

As used herein, the phrase "pyrrolidin-1-yl group may have one or more substituents" refers to a "pyrrolidin-1-yl group" which may have one or more groups selected from the substituents referred to in the phrase "which may have one or more substituents" at replaceable positions.

As used herein, the phrase "piperidin-1-yl group may have one or more substituents" refers to a "piperidin-1-yl group" which may have one or more groups selected from the substituents referred to in the phrase "which may have one or more substituents" at replaceable positions.

As used herein, the phrase "azepan-1-yl group may have one or more substituents" refers to an "azepan-1-yl group" which may have one or more groups selected from the substituents referred to in the phrase "which may have one or more substituents" at replaceable positions.

As used herein, the phrase "piperidin-1-yl group which may have an amino group" refers to a "piperidin-1-yl group" which may have an amino group at a replaceable position. Specifically, the "piperidin-1-yl group which may have an amino group", for example, refers to the group represented by one of the formulae:

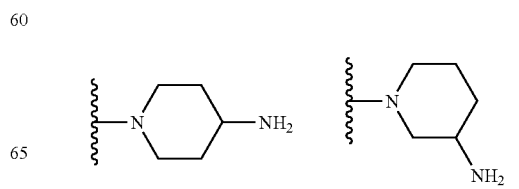

-continued

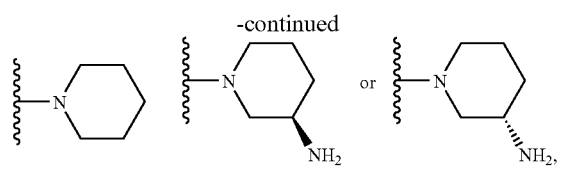

and preferably, to the group represented by one of the formulae:

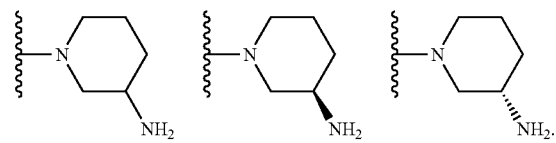

As used herein, the phrase "azetidin-1-yl group which may have an amino group." refers to an "azetidin-1-yl group" which may have an amino group at a replaceable position.

As used herein, the phrase "pyrrolidin-1-yl group which may have an amino group" refers to a "pyrrolidin-1-yl group" which may have an amino group at a replaceable position.

As used herein, the phrase "piperidin-1-yl group which may have an amino group" refers to a "piperidin-1-yl group" which may have an amino group at a replaceable position.

As used herein, the phrase "azepan-1-yl group which may have an amino group" refers to an "azepan-1-yl group" which may have an amino group at a replaceable position.

As used herein, the phrase "$C_{1-6}$ alkyl group which may have one or more substituents" in the substituent group B defined above refers to a "$C_{1-6}$ alkyl group" which may have one or more groups selected from the substituents referred to in the phrase "which may have one or more substituents" at replaceable positions. Preferably, the "$C_{1-6}$ alkyl group which may have one or more substituents" refers to a $C_{1-6}$ alkyl group which may have one or two substituents selected from the group consisting of a cyano group, a carboxyl group, a $C_{2-7}$ alkoxycarbonyl group, a group represented by the formula —$NR^{3T}COR^{4T}$, a group represented by the formula —$CONR^{3T}R^{4T}$ (where $R^{3T}$ and $R^{4T}$ each independently represent a hydrogen atom or a $C_{1-6}$ alkyl group), and a $C_{1-6}$ alkoxy group.

In a compound represented by formula (I) indicated above, $R^1$ and $R^2$ each independently represent a group of the formula -$A^0$-$A^1$-$A^2$ (where $A^0$, $A^1$, and $A^2$ are as defined above); when both $A^0$ and $A^1$ are single bonds, "-$A^0$-$A^1$-" represents a single bond.

In formula (I) indicated above, the phrase "when $Z^2$ represents a group of the formula —$CR^2$=, $R^1$, and $R^2$ may in combination form a 5 to 7-membered ring" means that compounds represented by formula (I) indicated above includes compounds (II) represented by the formula:

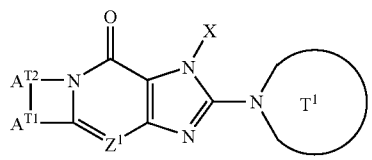

(where $Z^1$, X, and $T^1$ are as defined above; $A^{T1}$ represents an oxygen atom, a sulfur atom, a sulfinyl group, a sulfonyl group, a carbonyl group, a methylene group which may have one or more substituents, or a nitrogen atom which may have one or more substituents; $A^{T2}$ represents a $C_{2-6}$ alkylene group which may have one or more substituents). In formula (II) shown above, $A^T$ preferably represents an oxygen atom, and $A^{T2}$ preferably represents a $C_{2-4}$ alkylene group.

As used herein, the phrase "cyanobenzyl group" refers to a benzyl group having one cyano group, and specifically, includes, for example, a 2-cyanobenzyl group, a 3-cyanobenzyl group, and a 4-cyanobenzyl group.

As used herein, the phrase "fluorocyanobenzyl group" refers to a benzyl group having one fluorine atom and one cyano group, and specifically, includes, for example, a 2-cyano-4-fluorobenzyl group and a 2-cyano-6-fluorobenzyl group.

As used herein, the phrase "carbamoylphenoxy group" refers to a phenoxy group having a group represented by the formula —$CONH_2$, and specifically, includes, for example, a 2-carbamoylphenoxy group, a 3-carbamoylphenoxy group, and a 4-carbamoylphenoxy group.

Herein, there is no limitation on the type of "salts" as long as salts are pharmaceutically acceptable and derived from any compound of the present invention. Such salts include, for example, inorganic acid salts, organic acid salts, inorganic base salts, organic base salts, and acidic or basic amino acid salts.

Examples of preferred inorganic salts include hydrochloride, hydrobromide, sulfate, nitrate, and phosphate. Examples of preferred organic salts include acetate, succinate, fumarate, maleate, tartrate, citrate, lactate, stearate, benzoate, methanesulfonate, and p-toluene sulfonate.

Examples of preferred inorganic base salts include: alkali metal salts such as sodium salts and potassium salts; alkaline earth metal salts such as calcium salts and magnesium salts; aluminum salts; and ammonium salts. Examples of preferred organic base salts include diethylamine salts, diethanolamine salts, meglumine salts, and N,N'-dibenzylethylenediamine salts.

Examples of preferred acidic amino acid salts include aspartate and glutamate. Examples of preferred basic amino acid salts include arginine salts, lysine salts, and ornithine salts.

The present invention provides compounds represented by the following formula (I), or salts or hydrates thereof:

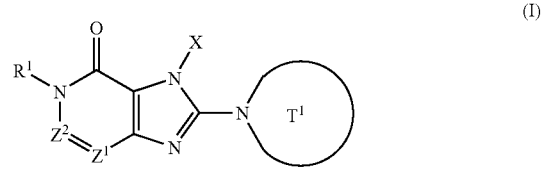

wherein, $T^1$ represents a monocyclic or bicyclic 4 to 12-membered heterocyclic group containing one or two nitrogen atoms in the ring, and may have one or more substituents;

X represents a $C_{1-6}$ alkyl group which may have one or more substituents, a $C_{2-6}$ alkenyl group which may have one or more substituents, a $C_{2-6}$ alkynyl group which may have one or more substituents, a $C_{6-10}$ aryl group which may have one or more substituents, a 5- to 10-membered heteroaryl group which may have one or more substituents, a $C_{6-10}$ aryl $C_{1-6}$ alkyl group which may have one or more substituents, or a 5- to 10-membered heteroaryl $C_{1-6}$ alkyl group which may have one or more substituents;

$Z^1$ and $Z^2$ each independently represent a nitrogen atom or a group represented by the formula —$CR^2$=;

$R^1$ and $R^2$ each independently represent a group of the formula -$A^0$-$A^1$-$A^2$ (where $A^0$ represents a single bond or a $C_{1-6}$ alkylene group which may have 1 to 3 substituents selected from the substituent group B described below;

$A^1$ represents a single bond, an oxygen atom, a sulfur atom, a sulfinyl group, a sulfonyl group, a carbonyl group, a group represented by the formula —O—CO—, a group represented by the formula —CO—O—, a group represented by the formula —$NR^A$—, a group represented by the formula —CO—$NR^A$—, a group represented by the formula —$NR^A$—CO—, a group represented by the formula —$SO_2$—$NR^A$—, or a group represented by the formula —$NR^A$—$SO_2$—;

$A^2$ and $R^A$ each independently represent a hydrogen atom, a halogen atom, a cyano group, a $C_{1-6}$ alkyl group, a $C_{3-8}$ cycloalkyl group, a $C_{2-6}$ alkenyl group, a $C_{2-6}$ alkynyl group, a $C_{6-10}$ aryl group, a 5 to 10-membered heteroaryl group, a 4 to 8-membered heterocyclic group, a 5 to 10-membered heteroaryl $C_{1-6}$ alkyl group, a $C_{6-10}$ aryl $C_{1-6}$ alkyl group, or a $C_{2-7}$ alkylcarbonyl group, provided that, A2 and $R^A$ each may independently have 1 to 3 substituents selected from the substituent group B defined below);

when $Z^2$ represents a group of the formula —$CR^2$=, $R^1$ and $R^2$ may in combination form a 5 to 7-membered ring.

However the cases where: [1] $R^1$ is a hydrogen atom; $Z^1$ is a nitrogen atom; and $Z^2$ is —CH=; and [2] $Z^1$ is a nitrogen atom; and $Z^2$ is —C(OH)= are excluded.

<Substituent B Group>

The substituent group B represents the group consisting of: a hydroxyl group, a mercapto group, a cyano group, a nitro group, a halogen atom, a trifluoromethyl group, a $C_{1-6}$ alkyl group which may have one or more substituents, a $C_{3-8}$ cycloalkyl group, a $C_{2-6}$ alkenyl group, a $C_{2-6}$ alkynyl group, a $C_{6-10}$ aryl group, a 5 to 10-membered heteroaryl group, a 4 to 8-membered heterocyclic group, a $C_{1-6}$ alkoxy group, a $C_{1-6}$ alkylthio group, a group represented by the formula —$SO_2$—$NR^{B1}$—$R^{B2}$, a group represented by the formula —$NR^{B1}$—CO—$R^{B2}$, a group represented by the formula —$NR^{B1}$—$R^{B2}$ (where $R^{B1}$ and $R^{B2}$ each independently represent a hydrogen atom or a $C_{1-6}$ alkyl group), a group represented by the formula —CO—$R^{B3}$ (where $R^{B3}$ represents a 4 to 8-membered heterocyclic group), a group represented by the formula. —CO—$R^{B4}$—$R^{B5}$, and a group represented by the formula —$CH_2$—CO—$R^{B4}$—$R^{B5}$ (where $R^{B4}$ represents a single bond, an oxygen atom or a group represented by the formula —$NR^{B6}$—; $R^{B5}$ and $R^{B6}$ each independently represent a hydrogen atom, a $C_{1-6}$ alkyl group, a $C_{3-8}$ cycloalkyl group, a $C_{2-6}$ alkenyl group, a $C_{2-6}$ alkynyl group, a $C_{6-10}$ aryl group, a 5 to 10-membered heteroaryl group, a 4 to 8-membered heterocyclic $C_{1-6}$ alkyl group, a $C_{6-10}$ aryl $C_{1-6}$ alkyl group, or a 5 to 10-membered heteroaryl $C_{1-6}$ alkyl group).

Preferable compounds represented by the formula (I) include, for example, the following compounds:

(1) compounds in which either but not both of $Z^1$ and $Z^2$ is a nitrogen atom;

(2) compounds in which $Z^1$ is a nitrogen atom; $Z^2$ is a group represented by the formula —$CR^2$= (where $R^2$ has the same definition as $R^2$ defined above);

(3) compounds in which $Z^2$ is a nitrogen atom; $Z^1$ is a group represented by the formula —$CR^2$= (where $R^2$ has the same definition as $R^2$ defined above);

(4) compounds in which $T^1$ is a group which may have one or more substituents and is represented by the formula:

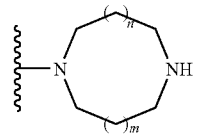

(where n and m each independently represent 0 or 1), an azetidin-1-yl group which may have one or more substituents, a pyrrolidin-1-yl group which may have one or more substituents, a piperidin-1-yl group which may have one or more substituents, or an azepan-1-yl group which may have one or more substituents;

(5) compounds in which $T^1$ is a group represented by the formula:

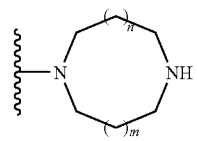

(where n and m each independently represent 0 or 1), an azetidin-1-yl group which may have an amino group, a pyrrolidin-1-yl group which may have an amino group, a piperidin-1-yl group which may have an amino group, or an azepan-1-yl group which may have an amino group;

(6) compounds in which $T^1$ is a piperazin-1-yl group or a 3-amino piperidin-1-yl group;

(7) compounds in which $T^1$ is a piperazin-1-yl group;

(8) compounds in which X is a group represented by the formula —$X^1$—$X^2$ (where $X^1$ represents a single bond or a methylene group which may have one or more substituents; $X^2$ represents a $C_{2-6}$ alkenyl group which may have one or more substituents, a $C_{2-6}$ alkynyl group may have one or more substituents, or a phenyl group which may have one or more substituents);

(9) compounds in which X is a group of the formula —$X^{11}$—$X^{12}$ (where $X^{11}$ represents a single bond or a methylene group; $X^{12}$ represents a $C_{2-6}$ alkenyl group, a $C_{2-6}$ alkynyl group, or a phenyl group which may have one or more substituents);

(10) compounds in which, the phenyl group, which may have one or more substituents, of X represented by the group of the above formula —$X^{11}$—$X^{12}$, is a phenyl group which may have, at the 2 position, a substituent selected from the group consisting of: a hydroxyl group, a fluorine atom, a chlorine atom, a methyl group, a ethyl group, a fluoromethyl group, a vinyl group, a methoxy group, an ethoxy group, an acetyl group, a cyano group, a formyl group, and a $C_{2-7}$ alkoxycarbonyl group;

(11) compounds in which X is a 3-methyl-2-buten-1-yl group, a 2-butyn-1-yl group, a benzyl group, or a 2-chlorophenyl group;

(12) compounds in which X is a 2-butyn-1-yl group;

(13) compounds in which $R^1$ is a hydrogen atom or a group represented by the formula -$A^{10}$-$A^{11}$-$A^{12}$ wherein $A^{10}$ represents a $C_{1-6}$ alkylene group which may have 1 to 3 substituents selected from the substituent group. C described below;

$A^{11}$ represents a single bond, an oxygen atom, a sulfur atom, or a carbonyl group;

$A^{12}$ represents a hydrogen atom, a $C_{6-10}$ aryl group which may have 1 to 3 substituents selected from the substituent group C described below, a 5 to 10-membered heteroaryl group which may have 1 to 3 substituents selected from the substituent group C described below, a 5 to 10-membered heteroaryl $C_{1-6}$ alkyl group which may have 1 to 3 substituents selected from the substituent group C described below, or a $C_{6-10}$ aryl $C_{1-6}$ alkyl group which may have 1 to 3 substituents selected from the substituent group C described below;

<Substituent Group C>

The substituent group C represents the group consisting of: a hydroxyl group, a nitro group, a cyano group, a halogen atom, a $C_{1-6}$ alkyl group, a $C_{1-6}$ alkoxy group, a $C_{1-6}$ alkylthio group, a trifluoromethyl group, a group represented by the formula —$NR^{C1}$—$R^{C2}$, (where each of $R^{C1}$ and $R^{C2}$ independently represent a hydrogen atom or a $C_{1-6}$ alkyl group), a group represented by the formula —CO—$R^{C3}$—$R^{C4}$ and a group represented by the formula —$CH_2$—CO—$R^{C3}$—$R^{C4}$ (where $R^{C3}$ represents a single bond, an oxygen atom or a group represented by the formula —$NR^{C5}$—; $R^{C4}$ and $R^{C5}$ each independently represent a hydrogen atom or a $C_{1-6}$ alkyl group);

(14) compounds in which $R^1$ is a hydrogen atom, a $C_{1-6}$ alkyl group which may have 1 to 3 substituents selected from the substituent group C described below, a 5 to 10-membered heteroaryl $C_{1-6}$ alkyl group which may have 1 to 3 substituents selected from the substituent group C described below, or a $C_{6-10}$ aryl $C_{1-6}$ alkyl group which may have 1 to 3 substituents selected from the substituent group C described below;

<Substituent Group C>

The substituent group C represents the group consisting of: a hydroxyl group, a nitro group, a cyano group, a halogen atom, a $C_{1-6}$ alkyl group, a $C_{1-6}$ alkoxy group, a $C_{1-6}$ alkylthio group, a trifluoromethyl group, a group represented by the formula —$NR^{C1}$—$R^{C2}$ (where $R^{C1}$ and $R^{C2}$ each independently represent a hydrogen atom, or a $C_{1-6}$ alkyl group), a group represented by the formula —CO—$R^{C3}$—$R^{C4}$ and a group represented by the formula —$CH_2$—CO—$R^{C3}$—$R^{C4}$ (where $R^{C3}$ represents a single bond, an oxygen atom, or a group represented by the formula $NR^{C5}$—; $R^{C4}$ and $R^{C5}$ each independently represent a hydrogen atom or a $C_{1-6}$ alkyl group);

(15) compounds in which, the substituent group C defined above for a group of the formula -$A^{10}$-$A^{11}$-$A^{12}$ that is represented by $R^1$, consists of a cyano group, a $C_{1-6}$ alkoxy group, a $C_{2-7}$ alkoxycarbonyl group, and a halogen atom;

(16) compounds in which $R^1$ is a methyl group, a cyanobenzyl group, a fluorocyanobenzyl group, a phenethyl group, a 2-methoxyethyl group or a 4-methoxycarbonyl-pyridin-2-yl group;

(17) compounds in which $R^1$ is a methyl group or a 2-cyanobenzyl group;

(18) compounds in which $R^2$ is a hydrogen atom, a cyano group, or a group represented by the formula -$A^{21}$-$A^{22}$;

wherein $A^{21}$ represents a single bond, an oxygen atom, a sulfur atom, a sulfinyl group, a sulfonyl group, a carbonyl group, a group represented by the formula —O—CO—, a group represented by the formula —CO—O—, a group represented by the formula —$NR^{A2}$—, a group represented by the formula —CO—$NR^{A2}$—, or a group represented by the formula —$NR^{A2}$—CO—;

$A^{22}$ and $R^{A2}$ each independently represent a hydrogen atom, a cyano group, a $C_{1-6}$ alkyl group, a $C_{3-8}$ cycloalkyl group, a $C_{2-6}$ alkenyl group, a $C_{2-6}$ alkynyl group, a $C_{6-10}$ aryl group, a 5 to 10-membered heteroaryl group, a 4 to 8-membered heterocyclic group, a 5 to 10-membered heteroaryl $C_{1-6}$ alkyl group, or a $C_{6-10}$ aryl $C_{1-6}$ alkyl group, provided that, $A^{22}$ and $R^{A2}$ each independently may have 1 to 3 substituents selected from the substituent group D described below;

<Substituent Group D>

The substituent group D represents the group consisting of a hydroxyl group, a cyano group, a nitro group, a halogen atom, a $C_{1-6}$ alkyl group, a $C_{1-6}$ alkoxy group, a $C_{1-6}$ alkylthio group, a trifluoromethyl group, a group represented by the formula —$NR^{D1}$—$R^{D2}$ (where $R^{D1}$ and $R^{D2}$ each independently represent a hydrogen atom or a $C_{1-6}$ alkyl group), a group represented by the formula —CO—$R^{D3}$ (where $R^{D3}$ represents a 4 to 8-membered heterocyclic group), and a group represented by the formula —CO—$R^{D4}$—$R^{D5}$ (where $R^{D4}$ represents a single bond, an oxygen atom, or a group represented by the formula —$NR^{D6}$—; $R^{D5}$ and $R^{D6}$ each independently represent a hydrogen atom, a $C_{3-8}$ cycloalkyl group or a $C_{1-6}$ alkyl group);

(19) a compound in which $R^2$ is a hydrogen atom, a cyano group, a carboxy group, a $C_{2-7}$ alkoxycarbonyl group, a $C_{1-6}$ alkyl group, a group represented by the formula —$CONR^{D7}R^{D8}$ (where $R^{D7}$ and $R^{D8}$ each independently represent a hydrogen atom or a $C_{1-6}$ alkyl group) a group represented by the formula -$A^{23}$-$A^{24}$ (where $A^{23}$ represents an oxygen atom, a sulfur atom, or a group represented by the formula —$NR^{A3}$—; $A^{24}$ and $R^{A3}$ each independently represent a hydrogen atom, a $C_{1-6}$ alkyl group which may have a substituent selected from the substituent group D1 described below, a $C_{3-8}$ cycloalkyl group which may have a substituent selected from the substituent group D1 described below, a $C_{2-6}$ alkenyl group which may have a substituent selected from the substituent group D1 described below, a $C_{2-6}$ alkynyl group which may have a substituent selected from the substituent group D1 described below, a phenyl group which may have a substituent selected from the substituent group D1 described below, or a 5 to 10-membered heteroaryl group which may have a substituent selected from the substituent group D1 described below;

<Substituent Group D1>

The substituent group D1 represents the group consisting of a carboxy group, a $C_{2-7}$ alkoxycarbonyl group, a $C_{1-6}$ alkyl group, a group represented by the formula —$CONR^{D7}R^{D8}$ (where $R^{D7}$ and $R^{D8}$ each independently represent a hydrogen atom or $C_{1-6}$ alkyl group), a pyrrolidin-1-ylcarbonyl group, a $C_{1-6}$ alkyl group, and a $C_{1-6}$ alkoxy group;

(20) compounds in which $R^2$ is a hydrogen atom, a cyano group, a —$C_{1-6}$ alkoxy group, or a group of the formula -$A^{25}$-$A^{26}$ (where: $A^{25}$ represents an oxygen atom, a sulfur atom, or a group represented by the formula —$NR^{A4}$—; $A^{26}$ and $R^{A4}$ each independently represent a hydrogen atom, a $C_{1-6}$ alkyl group having a substituent selected from the substituent group D1 described below, a $C_{3-8}$ cycloalkyl group having a substituent selected from the substituent group D1 described below, or a phenyl group having a substituent selected from the substituent group D1 described below);

<Substituent Group D1>

The substituent group D1 represents the group consisting of a carboxyl group, a $C_{2-7}$ alkoxycarbonyl group, a $C_{1-6}$ alkyl group, a group represented by the formula —$CONR^{D7}R^{D8}$ (where $R^{D7}$ and $R^{D8}$ each independently represent a hydrogen atom or a $C_{1-6}$ alkyl group), a pyrrolidin-1-ylcarbonyl group, a $C_{1-6}$ alkyl group, and a $C_{1-6}$ alkoxy group;

(21) compounds in which $R^2$ is a hydrogen atom, a cyano group, a methoxy group, a carbamoylphenyloxy group, a group represented by one of the formulae:

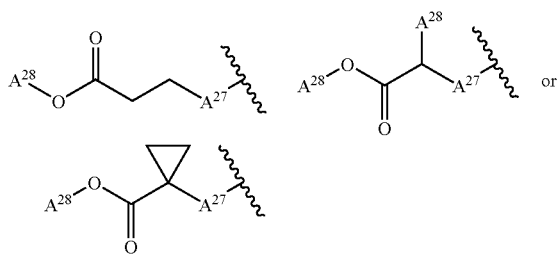

(where $A^{27}$ represents an oxygen atom, a sulfur atom, or a group represented by the formula —NH—;

$A^{28}$ an $A^{29}$ each independently represent a hydrogen atom or a $C_{1-6}$ alkyl group);

(22) compounds in which $R^2$ is a hydrogen atom, a cyano group, or a carbamoylphenyloxy group.

Among the compounds shown above, with respect to $Z^1$ and $Z^2$, the order of preference is (1) to (3) with (3) the most preferable; with respect to $T^1$, the order of preference is (4) to (7) with (7) the most preferable; with respect to X, the order of preference is (8) to (12) with (12) the most preferable; with respect to $R^1$, the order of preference is (13) to (17) with (17) the most preferable; with respect to $R^2$, the order of preference is (18) to (22) with (22) the most preferable.

Furthermore, preferred compounds represented by above formula (I) include compounds defined by any 2 to 5 embodiments selected from the groups consisting of (1)-(3), (4)-(7), (8)-(12), (13)-(17), and (18)-(22).

Preferable compounds include, for example, compounds defined by the following specific combinations of embodiments:

(i) compounds represented by above formula (I), in which $Z^1$ and $Z^2$, $T^1$, X, $R^1$ and $R^2$ represent those in (1), (4), (8), (13), and (18) described above, respectively;

(ii) compounds represented by above formula (I), in which $Z^1$ and $Z^2$, $T^1$, X, $R^1$, and $R^2$ represent those in (2), (6), (11), (16), and (19) described above, respectively;

(iii) compounds represented by above formula (I), in which $Z^1$ and $Z^2$, $T^1$, X, $R^1$, and $R^2$ represent those in (2), (6), (11), (16), and (20) described above, respectively;

(iv) compounds represented by above formula (I), in which $Z^1$ and $Z^2$, $T^1$, X, $R^1$, and $R^2$ represent those in (2), (6), (11), (16), and (21) described above, respectively;

(v) compounds represented by above formula (I), in which $Z^1$ and $Z^2$, $T^1$, X, $R^1$, and $R^2$ represent those in (2), (6), (11), (16), and (22) described above, respectively;

(vi) compounds represented by above formula (I), in which $Z^1$ and $Z^2$, $T^1$, X, $R^1$, and $R^2$ represent those in (2), (6), (12), (17), and (19) described above, respectively;

(vii) compounds represented by above formula (I), in which $Z^1$ and $Z^2$, $T^1$, X, $R^1$, and $R^2$ represent those in (2), (6), (12), (17), and (20) described above, respectively;

(viii) compounds represented by above formula (I), in which $Z^1$ and $Z^2$, $T^1$, X, $R^1$, and $R^2$ represent those in (2), (6), (12), (17), and (21) described above, respectively;

(ix) compounds represented by above formula (I), in which $Z^1$ and $Z^2$, $T^1$, X, $R^1$, and $R^2$ represent those in (2), (6) (12), (17), and (22) described above, respectively;

(x) compounds represented by above formula (I), in which $Z^1$ and $Z^2$, $T^1$, X, $R^1$, and $R^2$ represent those in (3), (6), (11), (16), and (19) described above, respectively;

(xi) compounds represented by above formula (I), in which $Z^1$ and $Z^2$, $T^1$, X, $R^1$, and $R^2$ represent those in (3), (6), (11), (16), and (20) described above, respectively;

(xii) compounds represented by above formula (I), in which $Z^1$ and $Z^2$, T, X, $R^1$ and $R^2$ represent those in (3), (6), (11), (16), and (21) described above, respectively;

(xiii) compounds represented by above formula (I), in which $Z^1$ and $Z^2$, $T^1$, X, $R^1$, and $R^2$ represent those in (3), (6), (11), (16), and (22) described above, respectively;

(xiv) compounds represented by above formula (I), in which $Z^1$ and $Z^2$, $T^1$, X, $R^1$, and $R^2$ represent those in (3), (6), (12), (17), and (19) described above, respectively;

(xv) compounds represented by above formula (I), in which $Z^1$ and $Z^2$, $T^1$, X, $R^1$, and $R^2$ represent those in (3), (6), (12), (17), and (20) described above, respectively;

(xvi) compounds represented by above formula (I), in which $Z^1$ and $Z^2$, $T^1$, X, $R^1$, and $R^2$ represent those in (3), (6), (12), (17) and (21) described above, respectively;

(xvii) compounds represented by above formula (I), in which $Z^1$ and $Z^2$, $T^1$, X, $R^1$, and $R^2$ represent those in (3), (6), (12), (17), and (22) described above, respectively.

Of these, for (ii) to (ix), preference increases in the order (ii) to (ix) while for (x) to (xvii), preference increases in the order (x) to (xvii).

Specific examples of compounds of the formula (I) are listed in the following table, but are not limited thereto.

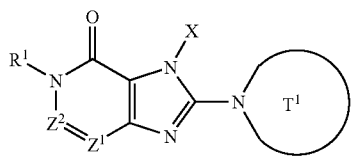

(I)

The abbreviations used in the table have the following meanings:

P1, piperazin-1-yl; P2,3-amino-piperidin-1-yl; 2Btyn, 2-butyn-1-yl; 3Me2Bten, 3-methyl-2-buten-1-yl; Me, methyl; Et, ethyl; 2-CNBen, 2-cyanobenzyl; 6F2CNBen, 6-fluoro-2-cyanobenzyl; Phenethyl, 2-phenylethyl; 2Ph2OxEt, 2-phenyl-2-oxoethyl; —CR2=, —CR²=

| | $Z^1$ | $Z^2$ | $T^1$ | X | $R^1$ | $R^2$ |
|---|---|---|---|---|---|---|
| 1 | N | —CR2= | P1 | 2Btyn | —CH$_3$ | —H |
| 2 | N | —CR2= | P1 | 2Btyn | —CH$_3$ | —CN |
| 3 | N | —CR2= | P1 | 2Btyn | —CH$_3$ | —OMe |
| 4 | N | —CR2= | P1 | 2Btyn | —CH$_3$ | —O-1-C$_2$H$_4$-1-CO$_2$Et |

-continued

|    | Z¹    | Z²    | T¹ | X     | R¹       | R²                                            |
|----|-------|-------|----|-------|----------|-----------------------------------------------|
| 5  | N     | —CR2= | P1 | 2Btyn | —CH₃     | —O—CH₂—CO₂Et                                  |
| 6  | N     | —CR2= | P1 | 2Btyn | —CH₃     | —O-1-cC₃H₄-1-CO₂Et                            |
| 7  | N     | —CR2= | P1 | 2Btyn | —CH₃     | —S—CH₂—CO₂Me                                  |
| 8  | N     | —CR2= | P1 | 2Btyn | —CH₃     | carbamoylphenyloxy                            |
| 9  | N     | —CR2= | P1 | 2Btyn | 2-CNBen  | —H                                            |
| 10 | N     | —CR2= | P1 | 2Btyn | 2-CNBen  | —CN                                           |
| 11 | N     | —CR2= | P1 | 2Btyn | 2-CNBen  | —OMe                                          |
| 12 | N     | —CR2= | P1 | 2Btyn | 2-CNBen  | —O-1-C₂H₄-1-CO₂Et                             |
| 13 | N     | —CR2= | P1 | 2Btyn | 2-CNBen  | —O—CH₂—CO₂Et                                  |
| 14 | N     | —CR2= | P1 | 2Btyn | 2-CNBen  | —O-1-cC₃H₄-1-CO₂Et                            |
| 15 | N     | —CR2= | P1 | 2Btyn | 2-CNBen  | —S—CH₂—CO₂Me                                  |
| 16 | N     | —CR2= | P1 | 2Btyn | 2-CNBen  | carbamoylphenyloxy                            |
| 17 | N     | —CR2= | P1 | 2Btyn | 6F2CNBen | —H                                            |
| 18 | N     | —CR2= | P1 | 2Btyn | 6F2CNBen | —CN                                           |
| 19 | N     | —CR2= | P1 | 2Btyn | 6F2CNBen | —OMe                                          |
| 20 | N     | —CR2= | P1 | 2Btyn | 6F2CNBen | —O-1-C₂H₄-1-CO₂Et                             |
| 21 | N     | —CR2= | P1 | 2Btyn | 6F2CNBen | —O—CH₂—CO₂Et                                  |
| 22 | N     | —CR2= | P1 | 2Btyn | 6F2CNBen | —O-1-cC₃H₄-1-CO₂Et                            |
| 23 | N     | —CR2= | P1 | 2Btyn | 6F2CNBen | —S—CH₂—CO₂Me                                  |
| 24 | N     | —CR2= | P1 | 2Btyn | 6F2CNBen | carbamoylphenyloxy                            |
| 25 | N     | —CR2= | P1 | 2Btyn | Phenethyl| —H                                            |
| 26 | N     | —CR2= | P1 | 2Btyn | Phenethyl| —CN                                           |
| 27 | N     | —CR2= | P1 | 2Btyn | Phenethyl| —OMe                                          |
| 28 | N     | —CR2= | P1 | 2Btyn | Phenethyl| —O-1-C₂H₄-1-CO₂Et                             |
| 29 | N     | —CR2= | P1 | 2Btyn | Phenethyl| —O—CH₂—CO₂Et                                  |
| 30 | N     | —CR2= | P1 | 2Btyn | Phenethyl| —O-1-cC₃H₄-1-CO₂Et                            |
| 31 | N     | —CR2= | P1 | 2Btyn | Phenethyl| —S—CH₂—CO₂Me                                  |
| 32 | N     | —CR2= | P1 | 2Btyn | Phenethyl| carbamoylphenyloxy                            |
| 33 | N     | —CR2= | P1 | 2Btyn | 2Ph2OxEt | —H                                            |
| 34 | N     | —CR2= | P1 | 2Btyn | 2Ph2OxEt | —CN                                           |
| 35 | N     | —CR2= | P1 | 2Btyn | 2Ph2OxEt | —OMe                                          |
| 36 | N     | —CR2= | P1 | 2Btyn | 2Ph2OxEt | —O-1-C₂H₄-1-CO₂Et                             |
| 37 | N     | —CR2= | P1 | 2Btyn | 2Ph2OxEt | —O—CH₂—CO₂Et                                  |
| 38 | N     | —CR2= | P1 | 2Btyn | 2Ph2OxEt | —O-1-cC₃H₄-1-CO₂Et                            |
| 39 | N     | —CR2= | P1 | 2Btyn | 2Ph2OxEt | —S—CH₂—CO₂Me                                  |
| 40 | N     | —CR2= | P1 | 2Btyn | 2Ph2OxEt | carbamoylphenyloxy                            |
| 41 | N     | —CR2= | P2 | 2Btyn | —CH₃     | —H                                            |
| 42 | N     | —CR2= | P2 | 2Btyn | —CH₃     | —CN                                           |
| 43 | N     | —CR2= | P2 | 2Btyn | —CH₃     | —OMe                                          |
| 44 | N     | —CR2= | P2 | 2Btyn | —CH₃     | —O-1-C₂H₄-1-CO₂Et                             |
| 45 | N     | —CR2= | P2 | 2Btyn | —CH₃     | —O—CH₂—CO₂Et                                  |
| 46 | N     | —CR2= | P2 | 2Btyn | —CH₃     | —O-1-cC₃H₄-1-CO₂Et                            |
| 47 | N     | —CR2= | P2 | 2Btyn | —CH₃     | —S—CH₂—CO₂Me                                  |
| 48 | N     | —CR2= | P2 | 2Btyn | —CH₃     | carbamoylphenyloxy                            |
| 49 | N     | —CR2= | P2 | 2Btyn | 2-CNBen  | —H                                            |
| 50 | N     | —CR2= | P2 | 2Btyn | 2-CNBen  | —CN                                           |
| 51 | N     | —CR2= | P2 | 2Btyn | 2-CNBen  | —OMe                                          |
| 52 | N     | —CR2= | P2 | 2Btyn | 2-CNBen  | —O-1-C₂H₄-1-CO₂Et                             |
| 53 | N     | —CR2= | P2 | 2Btyn | 2-CNBen  | —O—CH₂—CO₂Et                                  |
| 54 | N     | —CR2= | P2 | 2Btyn | 2-CNBen  | —O-1-cC₃H₄-1-CO₂Et                            |
| 55 | N     | —CR2= | P2 | 2Btyn | 2-CNBen  | —S—CH₂—CO₂Me                                  |
| 56 | N     | —CR2= | P2 | 2Btyn | 2-CNBen  | carbamoylphenyloxy                            |
| 57 | N     | —CR2= | P2 | 2Btyn | 6F2CNBen | —H                                            |
| 58 | N     | —CR2= | P2 | 2Btyn | 6F2CNBen | —CN                                           |
| 59 | N     | —CR2= | P2 | 2Btyn | 6F2CNBen | —OMe                                          |
| 60 | N     | —CR2= | P2 | 2Btyn | 6F2CNBen | —O-1-C₂H₄-1-CO₂Et                             |
| 61 | N     | —CR2= | P2 | 2Btyn | 6F2CNBen | —O—CH₂—CO₂Et                                  |
| 62 | N     | —CR2= | P2 | 2Btyn | 6F2CNBen | —O-1-cC₃H₄-1-CO₂Et                            |
| 63 | N     | —CR2= | P2 | 2Btyn | 6F2CNBen | —S—CH₂—CO₂Me                                  |
| 64 | N     | —CR2= | P2 | 2Btyn | 6F2CNBen | carbamoylphenyloxy                            |
| 65 | N     | —CR2= | P2 | 2Btyn | Phenethyl| —H                                            |
| 66 | N     | —CR2= | P2 | 2Btyn | Phenethyl| —CN                                           |
| 67 | N     | —CR2= | P2 | 2Btyn | Phenethyl| —OMe                                          |
| 68 | N     | —CR2= | P2 | 2Btyn | Phenethyl| —O-1-C₂H₄-1-CO₂Et                             |
| 69 | N     | —CR2= | P2 | 2Btyn | Phenethyl| —O—CH₂—CO₂Et                                  |
| 70 | N     | —CR2= | P2 | 2Btyn | Phenethyl| —O-1-cC₃H₄-1-CO₂Et                            |
| 71 | N     | —CR2= | P2 | 2Btyn | Phenethyl| —S—CH₂—CO₂Me                                  |
| 72 | N     | —CR2= | P2 | 2Btyn | Phenethyl| carbamoylphenyloxy                            |
| 73 | N     | —CR2= | P2 | 2Btyn | 2Ph2OxEt | —H                                            |
| 74 | N     | —CR2= | P2 | 2Btyn | 2Ph2OxEt | —CN                                           |
| 75 | N     | —CR2= | P2 | 2Btyn | 2Ph2OxEt | —OMe                                          |
| 76 | N     | —CR2= | P2 | 2Btyn | 2Ph2OxEt | —O-1-C₂H₄-1-CO₂Et                             |
| 77 | N     | —CR2= | P2 | 2Btyn | 2Ph2OxEt | —O—CH₂—CO₂Et                                  |
| 78 | N     | —CR2= | P2 | 2Btyn | 2Ph2OxEt | —O-1-cC₃H₄-1-CO₂Et                            |
| 79 | N     | —CR2= | P2 | 2Btyn | 2Ph2OxEt | —S—CH₂—CO₂Me                                  |
| 80 | N     | —CR2= | P2 | 2Btyn | 2Ph2OxEt | carbamoylphenyloxy                            |
| 81 | —CR2= | N     | P1 | 2Btyn | —CH₃     | —H                                            |

-continued

| | Z¹ | Z² | T¹ | X | R¹ | R² |
|---|---|---|---|---|---|---|
| 82 | —CR2= | N | P1 | 2Btyn | —CH₃ | —CN |
| 83 | —CR2= | N | P1 | 2Btyn | —CH₃ | —OMe |
| 84 | —CR2= | N | P1 | 2Btyn | —CH₃ | —CONH₂ |
| 85 | —CR2= | N | P1 | 2Btyn | —CH₃ | —O—CH₂—CO₂Et |
| 86 | —CR2= | N | P1 | 2Btyn | —CH₃ | carbamoylphenyloxy |
| 87 | —CR2= | N | P1 | 2Btyn | 2-CNBen | —H |
| 88 | —CR2= | N | P1 | 2Btyn | 2-CNBen | —CN |
| 89 | —CR2= | N | P1 | 2Btyn | 2-CNBen | —OMe |
| 90 | —CR2= | N | P1 | 2Btyn | 2-CNBen | —CONH₂ |
| 91 | —CR2= | N | P1 | 2Btyn | 2-CNBen | —O—CH₂—CO₂Et |
| 92 | —CR2= | N | P1 | 2Btyn | 2-CNBen | carbamoylphenyloxy |
| 93 | —CR2= | N | P1 | 2Btyn | 6F2CNBen | —H |
| 94 | —CR2= | N | P1 | 2Btyn | 6F2CNBen | —CN |
| 95 | —CR2= | N | P1 | 2Btyn | 6F2CNBen | —OMe |
| 96 | —CR2= | N | P1 | 2Btyn | 6F2CNBen | —CONH₂ |
| 97 | —CR2= | N | P1 | 2Btyn | 6F2CNBen | —O—CH₂—CO₂Et |
| 98 | —CR2= | N | P1 | 2Btyn | 6F2CNBen | carbamoylphenyloxy |
| 99 | —CR2= | N | P1 | 2Btyn | Phenethyl | —H |
| 100 | —CR2= | N | P1 | 2Btyn | Phenethyl | —CN |
| 101 | —CR2= | N | P1 | 2Btyn | Phenethyl | —OMe |
| 102 | —CR2= | N | P1 | 2Btyn | Phenethyl | —CONH₂ |
| 103 | —CR2= | N | P1 | 2Btyn | Phenethyl | —O—CH₂—CO₂Et |
| 104 | —CR2= | N | P1 | 2Btyn | Phenethyl | carbamoylphenyloxy |
| 105 | —CR2= | N | P1 | 2Btyn | 2Ph2OxEt | —H |
| 106 | —CR2= | N | P1 | 2Btyn | 2Ph2OxEt | —CN |
| 107 | —CR2= | N | P1 | 2Btyn | 2Ph2OxEt | —OMe |
| 108 | —CR2= | N | P1 | 2Btyn | 2Ph2OxEt | —CONH₂ |
| 109 | —CR2= | N | P1 | 2Btyn | 2Ph2OxEt | —O—CH₂—CO₂Et |
| 110 | —CR2= | N | P1 | 2Btyn | 2Ph2OxEt | carbamoylphenyloxy |
| 111 | —CR2= | N | P2 | 2Btyn | —CH₃ | —H |
| 112 | —CR2= | N | P2 | 2Btyn | —CH₃ | —CN |
| 113 | —CR2= | N | P2 | 2Btyn | —CH₃ | —OMe |
| 114 | —CR2= | N | P2 | 2Btyn | —CH₃ | —CONH₂ |
| 115 | —CR2= | N | P2 | 2Btyn | —CH₃ | —O—CH₂—CO₂Et |
| 116 | —CR2= | N | P2 | 2Btyn | —CH₃ | carbamoylphenyloxy |
| 117 | —CR2= | N | P2 | 2Btyn | 2-CNBen | —H |
| 118 | —CR2= | N | P2 | 2Btyn | 2-CNBen | —CN |
| 119 | —CR2= | N | P2 | 2Btyn | 2-CNBen | —OMe |
| 120 | —CR2= | N | P2 | 2Btyn | 2-CNBen | —CONH₂ |
| 121 | —CR2= | N | P2 | 2Btyn | 2-CNBen | —O—CH₂—CO₂Et |
| 122 | —CR2= | N | P2 | 2Btyn | 2-CNBen | carbamoylphenyloxy |
| 123 | —CR2= | N | P2 | 2Btyn | 6F2CNBen | —H |
| 124 | —CR2= | N | P2 | 2Btyn | 6F2CNBen | —CN |
| 125 | —CR2= | N | P2 | 2Btyn | 6F2CNBen | —OMe |
| 126 | —CR2= | N | P2 | 2Btyn | 6F2CNBen | —CONH₂ |
| 127 | —CR2= | N | P2 | 2Btyn | 6F2CNBen | —O—CH₂—CO₂Et |
| 128 | —CR2= | N | P2 | 2Btyn | 6F2CNBen | carbamoylphenyloxy |
| 129 | —CR2= | N | P2 | 2Btyn | Phenethyl | —H |
| 130 | —CR2= | N | P2 | 2Btyn | Phenethyl | —CN |
| 131 | —CR2= | N | P2 | 2Btyn | Phenethyl | —OMe |
| 132 | —CR2= | N | P2 | 2Btyn | Phenethyl | —CONH₂ |
| 133 | —CR2= | N | P2 | 2Btyn | Phenethyl | —O—CH₂—CO₂Et |
| 134 | —CR2= | N | P2 | 2Btyn | Phenethyl | carbamoylphenyloxy |
| 135 | —CR2= | N | P2 | 2Btyn | 2Ph2OxEt | —H |
| 136 | —CR2= | N | P2 | 2Btyn | 2Ph2OxEt | —CN |
| 137 | —CR2= | N | P2 | 2Btyn | 2Ph2OxEt | —OMe |
| 138 | —CR2= | N | P2 | 2Btyn | 2Ph2OxEt | —CONH₂ |
| 139 | —CR2= | N | P2 | 2Btyn | 2Ph2OxEt | —O—CH₂—CO₂Et |
| 140 | —CR2= | N | P2 | 2Btyn | 2Ph2OxEt | carbamoylphenyloxy |
| 141 | —CR2= | N | P2 | 3Me2Bten | —CH₃ | —H |
| 142 | —CR2= | N | P2 | 3Me2Bten | —CH₃ | —CN |
| 143 | —CR2= | N | P2 | 3Me2Bten | —CH₃ | —OMe |
| 144 | —CR2= | N | P2 | 3Me2Bten | —CH₃ | —CONH₂ |
| 145 | —CR2= | N | P2 | 3Me2Bten | —CH₃ | —O—CH₂—CO₂Et |
| 146 | —CR2= | N | P2 | 3Me2Bten | —CH₃ | carbamoylphenyloxy |
| 147 | —CR2= | N | P2 | 3Me2Bten | 2-CNBen | —H |
| 148 | —CR2= | N | P2 | 3Me2Bten | 2-CNBen | —CN |
| 149 | —CR2= | N | P2 | 3Me2Bten | 2-CNBen | —OMe |
| 150 | —CR2= | N | P2 | 3Me2Bten | 2-CNBen | —CONH₂ |
| 151 | —CR2= | N | P2 | 3Me2Bten | 2-CNBen | —O—CH₂—CO₂Et |
| 152 | —CR2= | N | P2 | 3Me2Bten | 2-CNBen | carbamoylphenyloxy |
| 153 | —CR2= | N | P2 | 3Me2Bten | 6F2CNBen | —H |
| 154 | —CR2= | N | P2 | 3Me2Bten | 6F2CNBen | —CN |
| 155 | —CR2= | N | P2 | 3Me2Bten | 6F2CNBen | —OMe |
| 156 | —CR2= | N | P2 | 3Me2Bten | 6F2CNBen | —CONH₂ |
| 157 | —CR2= | N | P2 | 3Me2Bten | 6F2CNBen | —O—CH₂—CO₂Et |
| 158 | —CR2= | N | P2 | 3Me2Bten | 6F2CNBen | carbamoylphenyloxy |

-continued

| | $Z^1$ | $Z^2$ | $T^1$ | X | $R^1$ | $R^2$ |
|---|---|---|---|---|---|---|
| 159 | —CR2= | N | P2 | 3Me2Bten | Phenethyl | —H |
| 160 | —CR2= | N | P2 | 3Me2Bten | Phenethyl | —CN |
| 161 | —CR2= | N | P2 | 3Me2Bten | Phenethyl | —OMe |
| 162 | —CR2= | N | P2 | 3Me2Bten | Phenethyl | —CONH$_2$ |
| 163 | —CR2= | N | P2 | 3Me2Bten | Phenethyl | —O—CH$_2$—CO$_2$Et |
| 164 | —CR2= | N | P2 | 3Me2Bten | Phenethyl | carbamoylphenyloxy |
| 165 | —CR2= | N | P2 | 3Me2Bten | 2Ph2OxEt | —H |
| 166 | —CR2= | N | P2 | 3Me2Bten | 2Ph2OxEt | —CN |
| 167 | —CR2= | N | P2 | 3Me2Bten | 2Ph2OxEt | —OMe |
| 168 | —CR2= | N | P2 | 3Me2Bten | 2Ph2OxEt | —CONH$_2$ |
| 169 | —CR2= | N | P2 | 3Me2Bten | 2Ph2OxEt | —O—CH$_2$—CO$_2$Et |
| 170 | —CR2= | N | P2 | 3Me2Bten | 2Ph2OxEt | carbamoylphenyloxy |
| 171 | —CH= | —CR2= | P1 | 2Btyn | —CH$_3$ | —H |
| 172 | —CH= | —CR2= | P1 | 2Btyn | —CH$_3$ | —CN |
| 173 | —CH= | —CR2= | P1 | 2Btyn | —CH$_3$ | —CO$_2$Me |
| 174 | —CH= | —CR2= | P1 | 2Btyn | 2-CNBen | —H |
| 175 | —CH= | —CR2= | P1 | 2Btyn | 2-CNBen | —CN |
| 176 | —CH= | —CR2= | P1 | 2Btyn | 2-CNBen | —CO$_2$Me |
| 177 | —CH= | —CR2= | P1 | 2Btyn | 6F2CNBen | —H |
| 178 | —CH= | —CR2= | P1 | 2Btyn | 6F2CNBen | —CN |
| 179 | —CH= | —CR2= | P1 | 2Btyn | 6F2CNBen | —CO$_2$Me |
| 180 | —CH= | —CR2= | P1 | 2Btyn | Phenethyl | —H |
| 181 | —CH= | —CR2= | P1 | 2Btyn | Phenethyl | —CN |
| 182 | —CH= | —CR2= | P1 | 2Btyn | Phenethyl | —CO$_2$Me |
| 183 | —CH= | —CR2= | P1 | 2Btyn | 2Ph2OxEt | —H |
| 184 | —CH= | —CR2= | P1 | 2Btyn | 2Ph2OxEt | —CN |
| 185 | —CH= | —CR2= | P1 | 2Btyn | 2Ph2OxEt | —CO$_2$Me |
| 186 | —CH= | —CR2= | P1 | 3Me2Bten | —CH$_3$ | —H |
| 187 | —CH= | —CR2= | P1 | 3Me2Bten | —CH$_3$ | —CN |
| 188 | —CH= | —CR2= | P1 | 3Me2Bten | —CH$_3$ | —CO$_2$Me |
| 189 | —CH= | —CR2= | P1 | 3Me2Bten | 2-CNBen | —H |
| 190 | —CH= | —CR2= | P1 | 3Me2Bten | 2-CNBen | —CN |
| 191 | —CH= | —CR2= | P1 | 3Me2Bten | 2-CNBen | —CO$_2$Me |
| 192 | —CH= | —CR2= | P1 | 3Me2Bten | 6F2CNBen | —H |
| 193 | —CH= | —CR2= | P1 | 3Me2Bten | 6F2CNBen | —CN |
| 194 | —CH= | —CR2= | P1 | 3Me2Bten | 6F2CNBen | —CO$_2$Me |
| 195 | —CH= | —CR2= | P1 | 3Me2Bten | Phenethyl | —H |
| 196 | —CH= | —CR2= | P1 | 3Me2Bten | Phenethyl | —CN |
| 197 | —CH= | —CR2= | P1 | 3Me2Bten | Phenethyl | —CO$_2$Me |
| 198 | —CH= | —CR2= | P1 | 3Me2Bten | 2Ph2OxEt | —H |
| 199 | —CH= | —CR2= | P1 | 3Me2Bten | 2Ph2OxEt | —CN |
| 200 | —CH= | —CR2= | P1 | 3Me2Bten | 2Ph2OxEt | —CO$_2$Me |
| 201 | —CH= | —CR2= | P2 | 2Btyn | —CH$_3$ | —H |
| 202 | —CH= | —CR2= | P2 | 2Btyn | —CH$_3$ | —CN |
| 203 | —CH= | —CR2= | P2 | 2Btyn | —CH$_3$ | —CO$_2$Me |
| 204 | —CH= | —CR2= | P2 | 2Btyn | 2-CNBen | —H |
| 205 | —CH= | —CR2= | P2 | 2Btyn | 2-CNBen | —CN |
| 206 | —CH= | —CR2= | P2 | 2Btyn | 2-CNBen | —CO$_2$Me |
| 207 | —CH= | —CR2= | P2 | 2Btyn | 6F2CNBen | —H |
| 208 | —CH= | —CR2= | P2 | 2Btyn | 6F2CNBen | —CN |
| 209 | —CH= | —CR2= | P2 | 2Btyn | 6F2CNBen | —CO$_2$Me |
| 210 | —CH= | —CR2= | P2 | 2Btyn | Phenethyl | —H |
| 211 | —CH= | —CR2= | P2 | 2Btyn | Phenethyl | —CN |
| 212 | —CH= | —CR2= | P2 | 2Btyn | Phenethyl | —CO$_2$Me |
| 213 | —CH= | —CR2= | P2 | 2Btyn | 2Ph2OxEt | —H |
| 214 | —CH= | —CR2= | P2 | 2Btyn | 2Ph2OxEt | —CN |
| 215 | —CH= | —CR2= | P2 | 2Btyn | 2Ph2OxEt | —CO$_2$Me |
| 216 | —CH= | —CR2= | P2 | 3Me2Bten | —CH$_3$ | —H |
| 217 | —CH= | —CR2= | P2 | 3Me2Bten | —CH$_3$ | —CN |
| 218 | —CH= | —CR2= | P2 | 3Me2Bten | —CH$_3$ | —CO$_2$Me |
| 219 | —CH= | —CR2= | P2 | 3Me2Bten | 2-CNBen | —H |
| 220 | —CH= | —CR2= | P2 | 3Me2Bten | 2-CNBen | —CN |
| 221 | —CH= | —CR2= | P2 | 3Me2Bten | 2-CNBen | —CO$_2$Me |
| 222 | —CH= | —CR2= | P2 | 3Me2Bten | 6F2CNBen | —H |
| 223 | —CH= | —CR2= | P2 | 3Me2Bten | 6F2CNBen | —CN |
| 224 | —CH= | —CR2= | P2 | 3Me2Bten | 6F2CNBen | —CO$_2$Me |
| 225 | —CH= | —CR2= | P2 | 3Me2Bten | Phenethyl | —H |
| 226 | —CH= | —CR2= | P2 | 3Me2Bten | Phenethyl | —CN |
| 227 | —CH= | —CR2= | P2 | 3Me2Bten | Phenethyl | —CO$_2$Me |
| 228 | —CH= | —CR2= | P2 | 3Me2Bten | 2Ph2OxEt | —H |
| 229 | —CH= | —CR2= | P2 | 3Me2Bten | 2Ph2OxEt | —CN |
| 230 | —CH= | —CR2= | P2 | 3Me2Bten | 2Ph2OxEt | —CO$_2$Me |

Among the compounds listed above, Nos. 1, 2, 4, 6, 7, 8, 10, 13, 16, 41, 42, 44, 50, 53, 81, 85, 86, 87, 111, 141 and 183 are preferable, and compound Nos. 2, 4, 8, 10, 81, 87 and 111 are more preferable.

[Typical Synthesis Methods]

Representative methods for producing compounds of the present invention, represented by formula (I) above are described below.

Each symbol in the production methods is defined below. $R^{31}$ to $R^{42}$ n, m, $R^1$, $R^2$, X, $A^0$, $A^1$, $A^2$, $R^4$, and $T^1$ are the same as defined above.

$U^1$ and $U^3$ each independently represent a leaving group such as a chlorine atom, a bromine atom, an iodine atom, a methanesulfonyloxy group, or a p-toluenesulfonyloxy group.

$R^{p1}$, $R^{p2}$, and $R^{p3}$ each independently represent an —NH-protecting group such as a pivalyloxymethyl group and a trimethylsilylethoxymethyl group.

$R^{p4}$ represents a hydroxyl group-protecting group such as a t-butyldimethylsilyl group and a t-butyldiphenylsilyl group.

$R^{p5}$ represents an NH-protecting group such as N,N-dimethylsulfamoyl, trityl, benzyl, and t-butoxycarbonyl.

$U^2$ and $U^4$ each independently represent a chlorine atom, a bromine atom, an iodine atom, a methanesulfonyloxy group, a p-toluenesulfonyloxy group, a group represented by the formula —B(OH)$_2$, a 4,4,5,5-tetramethyl-1,3,2-dioxaboran-2-yl group, or a group represented by the formula —Sn(R$^z$)$_3$ (where R$^z$ represents a $C_{1-6}$ alkyl group).

$R^{x2}$ is a group represented by the formula —O-$A^2$, a group represented by the formula —S-$A^2$, a group represented by the formula —N(R$^4$)$A^2$, or a 4- to 8-membered heterocyclic group which may have one or more substituents (for example, 1-pyrrolidinyl, 1-morpholinyl, 1-piperazinyl, or 1-piperidyl), etc.

$R^{x3}$ represents a group of the formula -$A^0$-$A^1$-$A^2$, such as a cyano group, a $C_{1-6}$ alkyl group which may have one or more substituents, a $C_{3-8}$ cycloalkyl group which may have one or more substituents, a $C_{2-6}$ alkenyl group which may have one or more substituents, a $C_{2-6}$ alkynyl group which may have one or more substituents, and a $C_{6-10}$ aryl group which may have one or more substituents.

$A^{2COOR}$ represents a $C_{1-6}$ alkyl group, a $C_{3-8}$ cycloalkyl group, a $C_{2-6}$ alkenyl group, a $C_{2-6}$ alkynyl group, a $C_{6-10}$ aryl group, a 5- to 10-membered heteroaryl group, a 4- to 8-membered heterocyclic group, a 5- to 10-membered heteroaryl $C_{1-6}$ alkyl group, or a $C_{6-10}$ aryl $C_{1-6}$ alkyl group, each of which contains an ester group.

$A^{2COOH}$ represents a $C_{1-6}$ alkyl group, a $C_{3-8}$ cycloalkyl group, a $C_{2-6}$ alkenyl group, a $C_{2-6}$ alkynyl group, $C_{6-10}$ aryl group, a 5- to 10-membered heteroaryl group, a 4- to 8-membered heterocyclic group, a 5- to 10-membered heteroaryl $C_{1-6}$ alkyl group, or a $C_{6-10}$ aryl $C_{1-6}$ alkyl group, each of which contains a carboxylic acid.

$A^{2NO2}$ represents a $C_{1-6}$ alkyl group, a $C_{3-8}$ cycloalkyl group, a $C_{2-6}$ alkenyl group, a $C_{2-6}$ alkynyl group, a $C_{6-10}$ aryl group, a 5- to 10-membered heteroaryl group, a 4- to 8-membered heterocyclic group, a 5- to 10-membered heteroaryl $C_{1-6}$ alkyl group, or a $C_{6-10}$ aryl $C_{1-6}$ alkyl group, each of which contains a nitro group.

$A^{2NH2}$ represents a $C_{1-6}$ alkyl group, a $C_{3-8}$ cycloalkyl group, a $C_{2-6}$ alkenyl group, a $C_{2-6}$ alkynyl group, a $C_{6-10}$ aryl group, a 5- to 10-membered heteroaryl group, a 4- to 8-membered heterocyclic group, a 5- to 10-membered heteroaryl $C_{1-6}$ alkyl group, or a $C_{6-10}$ aryl $C_{1-6}$ alkyl group, each of which contains an amino group.

$A^{2CN}$ represents a $C_{1-6}$ alkyl group, a $C_{3-8}$ cycloalkyl group, a $C_{2-6}$ alkenyl group, a $C_{2-6}$ alkynyl group, a $C_{6-10}$ aryl group, a 5- to 10-membered heteroaryl group, a 4- to 8-membered heterocyclic group, a 5- to 10-membered heteroaryl $C_{1-6}$ alkyl group, or a $C_{6-10}$ aryl $C_{1-6}$ alkyl group, each of which contains a nitrile group.

$A^{CONH2}$ represents a $C_{1-6}$ alkyl group, a $C_{3-8}$ cycloalkyl group, a $C_{2-6}$ alkenyl group, a $C_{2-6}$ alkynyl group, $C_{6-10}$ aryl group, a 5- to 10-membered heteroaryl group, a 4- to 8-membered heterocyclic group, a 5- to 10-membered heteroaryl $C_{1-6}$ alkyl group, or a $C_{6-10}$ aryl $C_{1-6}$ alkyl group, each of which contains a carboxylic amide group.

M represents —MgCl, —MgBr, —Sn(R$^z$)$_3$ (where R$^z$ is as defined above), etc.

The term "room temperature" refers to a temperature of about 20 to about 30° C.

$T^{1a}$ is defined as the group represented by $T^1$, or represents a group of the formula:

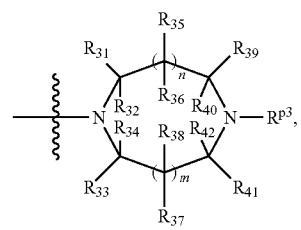

a group represented by the formula:

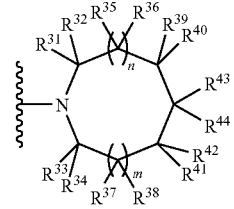

(where $R^{31}$ to $R^{44}$ are as defined above, except that any one of $R^{31}$ to $R^{44}$ represents —NH—$R^{p3}$), or a group represented by the formula:

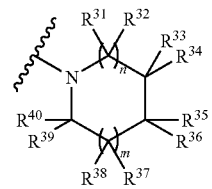

(where $R^{31}$ to $R^{40}$ are as defined above, except that any one of $R^{31}$ to $R^{40}$ represents —NH—$R^{p3}$).

In examples of reactions represented by the following reaction schemes, unless otherwise specified, quantities of reagents, catalysts, and others, to be used (equivalent, weight %, and weight ratio) are represented as ratios to a main compound in each reaction scheme. A main compound refers to a compound represented by a chemical formula in the reaction scheme and having the backbone of compounds of the present invention.

Production Method A
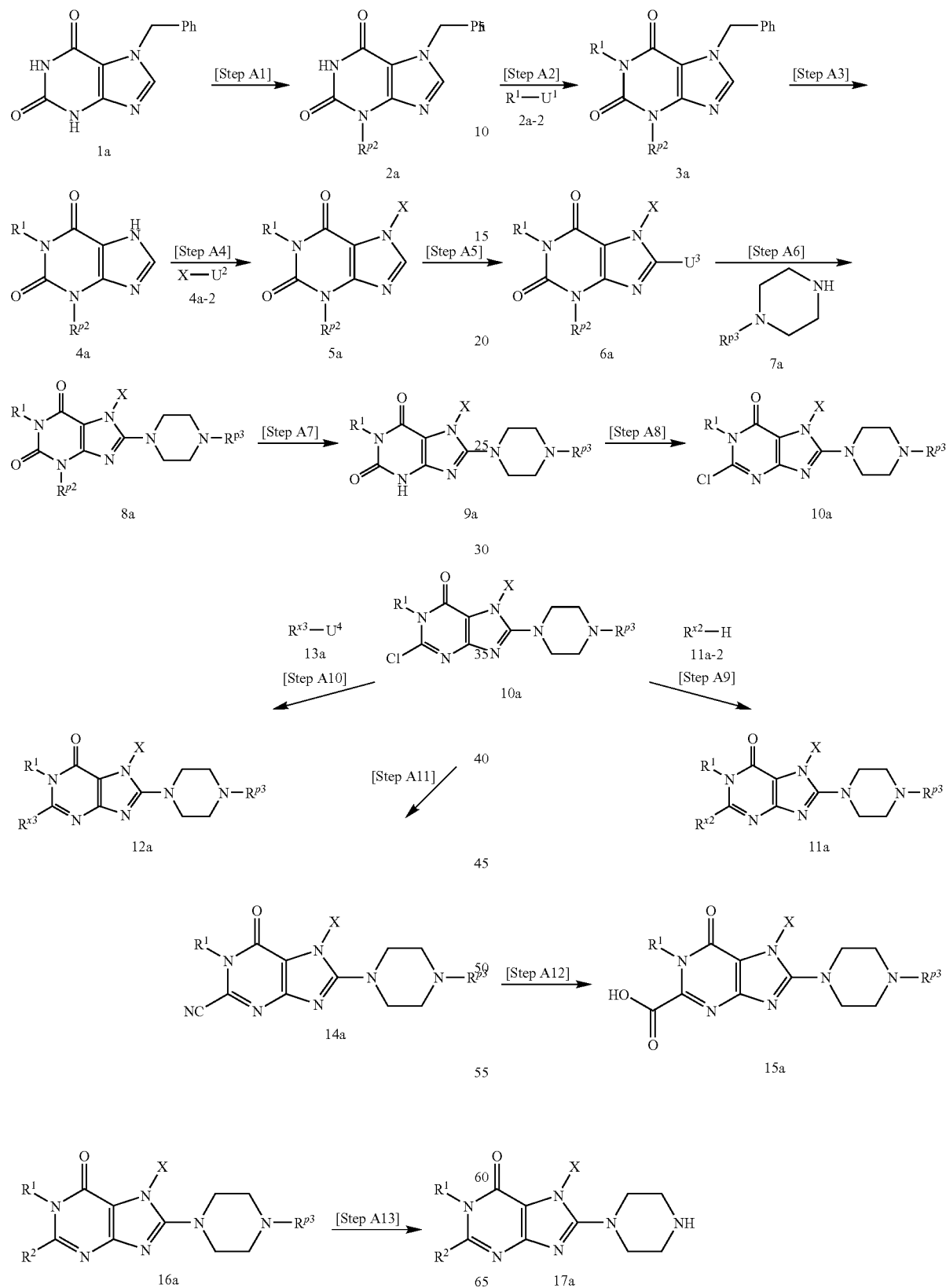

[Step A1]

In this step, an —NH-protecting reagent is reacted with compound (1a) [CAS No. 56160-64-6] to give compound (2a). The reaction conditions are selected depending on the type of —NH-protecting reagent to be used. The reaction may be performed under conditions that are generally used to introduce a protecting group using the reagent.

An —NH-protecting reagent can be a reagent that is generally used to introduce an —NH-protecting group. Specifically, such —NH-protecting reagents include, for example, chloromethyl pivalate. It is preferable to use 1 to 2 equivalents of a protecting reagent. Solvents for the reaction include acetonitrile, N,N-dimethylformamide, N-methylpyrrolidone, 1,4-dioxane, tetrahydrofuran, and dimethoxyethane. N,N-dimethylformamide is preferably used.

The reaction can be achieved in the presence of a base. Examples of bases to be used in the reaction include cesium carbonate, lithium carbonate, sodium carbonate, potassium carbonate, and sodium hydride. Sodium hydride is preferably used. In this case, a base is preferably used in an amount of 1 to 5 equivalents. The reaction can be conducted at a temperature ranging from 0° C. to 150° C. A preferred reaction temperature is room temperature.

[Step A2]

In this step, compound (2a) is reacted with compound (2a-2) to give compound (3a).

Compound (2a-2) can be any compound that is an electrophilic reagent such as an alkyl halide. Specific examples include alkyl halides such as iodomethane, iodoethane, iodopropane, and benzyl bromide; alkenyl halides such as allyl bromide and 1-bromo-3-methyl-2-butene; and alkynyl halides such as propargyl bromide and 1-bromo-2-butyne. One to two equivalents of an electrophilic reagent are preferably used.

Solvents for the reaction include, for example, dimethyl sulfoxide, N,N-dimethylformamide, N-methylpyrrolidone, dioxane, tetrahydrofuran, and toluene.

The reaction can be achieved in the presence or absence of a base. Examples of bases to be used in the reaction include lithium hydroxide, sodium hydroxide, potassium hydroxide, lithium carbonate, sodium carbonate, potassium carbonate, cesium carbonate, lithium hydride, sodium hydride, potassium hydride, butyllithium, methyllithium, lithium bis(trimethylsilyl)amide, sodium bis(trimethylsilyl)amide, and potassium bis(trimethylsilyl)amide. In this case, one to two equivalents of a base are preferably used. The reaction can be conducted at a temperature ranging from 0° C. to 150° C.

[Step A3]

In this step, the benzyl group at the 7-position is removed from compound (3a) to give compound (4a).

Specifically, compound (4a) can be prepared from compound (3a), for example, by catalytic reduction under a hydrogen atmosphere in the presence of a metal catalyst, but the reaction conditions are not limited thereto.

Specific solvents for the reaction include, for example, methanol, ethanol, propanol, acetic acid, dimethyl sulfoxide, N,N-dimethylformamide, N-methylpyrrolidone, dioxane, tetrahydrofuran, and toluene. Examples of metal catalysts include palladium carbon, platinum oxide, and Raney nickel. A metal catalyst is preferably used at 0.5 to 50 weight %. A preferred hydrogen pressure is 1 to 5 atm. The reaction can be conducted at a temperature ranging from 0° C. to 150° C.

[Step A4]

In this step, compound (4a) is reacted with compound (4a-2) to give compound (5a).

Specific examples of compound (4a-2) are: alkyl halides such as iodomethane, iodoethane, iodopropane, and benzyl bromide; alkenyl halides such as allyl bromide and 1-bromo-3-methyl-2-butene; or alkynyl halides such as propargyl bromide and 1-bromo-2-butyne. These halides are preferably used in an amount of one to two equivalents.

Solvents for the reaction include dimethyl sulfoxide, N,N-dimethylformamide, N-methylpyrrolidone, dioxane, tetrahydrofuran, and toluene.

The reaction can be carried out in the presence or absence of a base. Examples of bases to be used in the reaction include lithium hydroxide, sodium hydroxide, potassium hydroxide, lithium carbonate, sodium carbonate, potassium carbonate, cesium carbonate, lithium hydride, sodium hydride, potassium hydride, butyllithium, methyllithium, lithium bis(trimethylsilyl)amide, sodium bis(trimethylsilyl)amide, and potassium bis(trimethylsilyl)amide. In this case, 1 to 4 equivalents of a base are preferably used. The reaction can be conducted at a temperature ranging from 0° C. to 150° C.

Compound (5a) can be obtained by reacting compound (4a) with compound (4a-2) in the presence of a copper catalyst and a base. In this case, it is preferable to use 0.1 to 2 equivalents of a copper catalyst and 1 to 10 equivalents of a base.

In this reaction, compound (4a-2) may be arylboronic acid, heteroarylboronic acid, or such, in which X is a $C_{6-10}$ aryl group which may have one or more substituents or a 5- to 10-membered heteroaryl group which may have one or more substituents, and $U^2$—$B(OH)_2$ or such. One to three equivalents of compound (4a-2) are preferably used.

In this case, reaction solvents include dichloromethane, chloroform, 1,4-dioxane, tetrahydrofuran, toluene, pyridine, N,N-dimethylformamide, and N-methylpyrrolidone.

Bases include triethylamine, diisopropyl ethyl amine, pyridine, and N,N-dimethylaminopyridine. Copper catalysts include copper (II) acetate, copper (II) trifluoroacetate, copper (II) chloride, and copper (II) iodide. The reaction can be conducted at a temperature ranging from 0° C. to 150° C.

[Step A5]

In this step, compound (5a) is reacted with a halogenating agent to give compound (6a).

Specific examples of halogenating agents include, for example, N-chlorosuccinimide, N-bromosuccinimide, and N-iodosuccinimide. A halogenating agent is preferably used in an amount of 1 to 4 equivalents.

Solvents for the reaction include acetonitrile, N,N-dimethylformamide, N-methylpyrrolidone, 1,4-dioxane, tetrahydrofuran, and dimethoxyethane. The reaction can be conducted at a temperature ranging from 0° C. to 150° C.

[Step A6]

In this step, compound (6a) is reacted with compound (7a) to give compound (8a). In this case, 1 to 4 equivalents of compound (7a) are preferably used.

The reaction can be carried out, for example, in a solvent such as tetrahydrofuran, acetonitrile, N,N-dimethylformamide, N-methylpyrrolidone, methanol, ethanol, 1,4-dioxane, toluene, and xylene, or in the absence of a solvent. The reaction can be conducted at a temperature ranging from 0° C. to 200° C. in the presence or absence of a base. Examples of a base include triethylamine, potassium carbonate, and 1,8-diazabicyclo[5,4,0]undecene. In this case, 1 to 4 equivalents of a base are preferably used.

[Step A7]

In this step, the —NH-protecting group at the 3-position of compound (8a) is removed to give compound (9a). The reaction conditions are selected depending on the type of —NH-protecting group to be removed. The deprotection reaction may be preformed under conditions that are generally used for the protecting group.

For example, when $R^{p2}$ is a pivalyloxymethyl group, the reaction can be carried out in methanol, or a mixed solution of methanol and tetrahydrofuran, using a base such as sodium methoxide, sodium hydride, or 1,8-diazabicyclo[5,4,0]-7-undecene at a temperature of 0 to 150° C. In this case, 0.1 to 2 equivalents of a base are preferably used.

Alternatively, when $R^{p2}$ is a trimethylsilylethoxymethyl group, the reaction can be carried out in a solvent such as acetonitrile, N,N-dimethylformamide, N-methylpyrrolidone, 1,4-dioxane, tetrahydrofuran, or dimethoxyethane, using a fluoride reagent such as tetrabutyl ammonium fluoride or cesium fluoride at a temperature of 0 to 150° C. In this case, 1 to 5 equivalents of a fluoride reagent are preferably used.

[Step A8]

In this step, compound (9a) is chlorinated to give compound (10a).

There are no particular limitations on the reaction conditions, and the reaction can be conducted under standard conditions for chlorination. For example, the reaction can be carried out at a temperature ranging from 0 to 150° C. in a solvent such as phosphorus oxychloride. In this case, it is preferable to use a 10 to 200 times amount of halogenating agent by weight.

When $R^{p3}$ is a t-butoxycarbonyl group or such, which is removed under the above-described conditions using phosphorus oxychloride or such, the protecting group should be reintroduced.

There are no particular limitations on the reaction conditions for the protection. In the case of the t-butoxycarbonyl group, the reaction can be carried out using an —NH— protection reagent such as di-t-butyl dicarbonate, in a solvent such as acetonitrile, N,N-dimethylformamide, N-methylpyrrolidone, 1,4-dioxane, tetrahydrofuran, or dimethoxyethane in the presence of a base such as lithium hydroxide, sodium hydroxide, potassium hydroxide, lithium carbonate, sodium carbonate, potassium carbonate, cesium carbonate, potassium bicarbonate, sodium bicarbonate, or triethylamine at 0 to 150° C.

[Step A9]

In this step, compound (10a) is reacted with compound (11a-2) to give compound (11a).

Compound (11a-2) includes alcohol compounds or phenol compounds represented by $A^2$-OH, amine compounds represented by $A^2(R^4)$NH or such, and thiol compounds represented by $A^2$-SH. In this case, compound (11a-2) is preferably used in an amount of 1 to 10 equivalents or 5 to 100 times by weight.

Solvents for the reaction include acetonitrile, N,N-dimethylformamide, N-methylpyrrolidone, 1,4-dioxane, tetrahydrofuran, dimethoxyethane, methanol, and ethanol.

The reaction can be carried out in the presence or absence of a base. Bases to be used in the reaction include lithium hydroxide, sodium hydroxide, potassium hydroxide, lithium carbonate, sodium carbonate, potassium carbonate, cesium carbonate, lithium hydride, sodium hydride, potassium hydride, butyllithium, methyllithium, lithium bis(trimethylsilyl)amide, sodium bis(trimethylsilyl)amide, potassium bis(trimethylsilyl)amide, and triethylamine. In this case, 1 to 10 equivalents of a base is preferably used. The reaction can be conducted at a temperature ranging from 0° C. to 150° C.

[Step A10]

In this step, compound (10a) is reacted with compound (13a) in the presence of a metal catalyst to give compound (12a). In this case, 1 to 50 equivalents of compound (13a) are preferably used.

Solvents for the reaction include acetonitrile, N,N-dimethylformamide, N-methylpyrrolidone, 1,4-dioxane, tetrahydrofuran, dimethoxyethane, methanol, and ethanol.

Metal catalysts include palladium catalyst and copper catalyst. Palladium catalysts include tetrakis triphenylphosphine palladium, palladium acetate, and dibenzylideneacetone palladium. Copper catalyst include copper iodide. It is preferable to use 0.01 to 2 equivalents of a metal catalyst.

The reaction can be conducted in the presence of an organophosphorous ligand. When the reaction is carried out in the presence of an organophosphorous ligand, examples of the ligands include o-tolyl phosphine and diphenylphosphinoferrocene. In this case, it is preferable to use 1 to 5 equivalents of an organophosphorous ligand to the metal catalyst.

The reaction can be carried out in the presence or absence of a base. Bases to be used in the reaction include lithium hydroxide, sodium hydroxide, potassium hydroxide, lithium carbonate, sodium carbonate, potassium carbonate, cesium carbonate, lithium hydride, sodium hydride, potassium hydride, potassium phosphate, lithium bis trimethylsilyl amide, sodium bis trimethylsilyl amide, potassium bis trimethylsilyl amide, and triethylamine. The reaction can be conducted at a temperature ranging from 0° C. to 150° C.

[Step A11]

In this step, compound (10a) is reacted with a cyanidation reagent to give compound (14a).

Specifically, cyanidation reagents include, for example, sodium cyanide and potassium cyanide. It is preferably used in an amount of 1 to 20 equivalents.

Solvents for the reaction include, for example, acetonitrile, N,N-dimethylformamide, N-methylpyrrolidone, 1,4-dioxane, tetrahydrofuran, dimethoxyethane, methanol, and ethanol. The reaction can be conducted at a temperature ranging from 0° C. to 150° C.

[Step A12]

In this step, the cyano group of compound (14a) is hydrolyzed to give compound (15a). There are no particular limitations on the reaction conditions, and the reaction can be carried out under conditions generally used for the conversion of a cyano group to a carbamoyl group by hydrolysis.

Solvents for the reaction include N,N-dimethylformamide, N-methylpyrrolidone, 1,4-dioxane, tetrahydrofuran, dimethoxyethane, methanol, ethanol, and a mixed solvent of tetrahydrofuran and methanol.

The reaction can be carried out in the presence or absence of a base. When a base is used, the reaction can be carried out using an aqueous solution of a base such as potassium hydroxide, sodium hydroxide, lithium hydroxide, or ammonia. The reaction can be achieved after adding an aqueous solution of hydrogen peroxide (preferably an aqueous solution of 30% hydrogen peroxide).

The reaction can be conducted at a temperature ranging from 0° C. to 150° C.

[Step A13]

In this step, $R^{p3}$ of compound (16a) is removed to give compound (17a). Compounds (11a), (12a), (14a), (15a), and others can be used as compound (16a).

The deprotection reaction for $R^{p3}$ can be carried out under standard reaction conditions for removing an —NH-protecting group.

For example, when $R^{p3}$ is a t-butoxycarbonyl group, the reaction can be carried out in the presence of an acid such as an anhydrous methanol solution of hydrogen chloride, an anhydrous ethanol solution of hydrogen chloride, an anhydrous dioxane solution of hydrogen chloride, trifluoroacetic acid, or formic acid.

An alternative method for producing compound (10a) is described below.

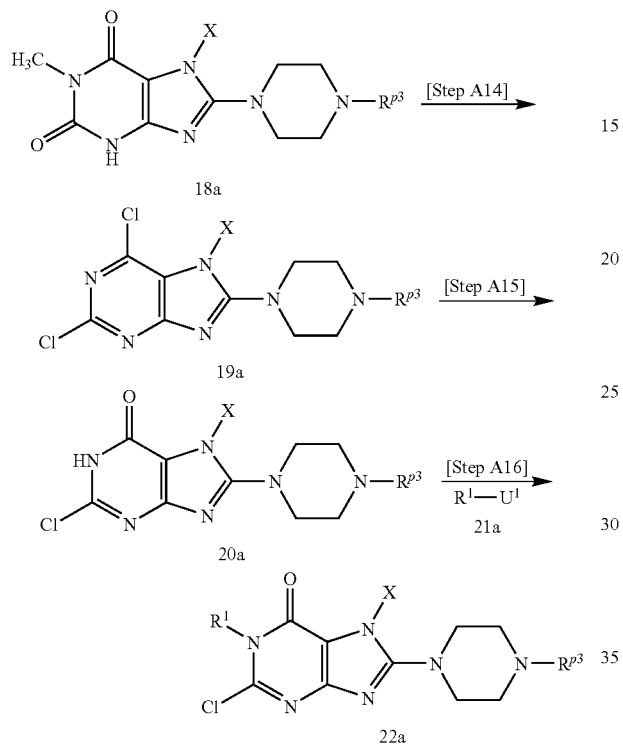

[Step A14]

In this step, compound (18a) is chlorinated to give compound (19a). There are no particular limitations on the reaction conditions, and the reaction can be conducted under standard conditions for chlorination. For example, the reaction can be carried out in a solvent such as phosphorus oxychloride at a temperature ranging from 0 to 150° C. Preferably 10 to 200 times by weight of chlorination reagent is used.

When $R^{p3}$ is a t-butoxycarbonyl group or such, which is removed under the above-described condition using phosphorus oxychloride or such, the protecting group should be reintroduced.

There are no particular limitations on the reaction conditions for the protection, and when $R^{p3}$ is a t-butoxycarbonyl group, the reaction can be carried out using an —NH— protection reagent such as di-t-butyl dicarbonate, in a solvent such as acetonitrile, N,N-dimethylformamide, N-methylpyrrolidone, 1,4-dioxane, tetrahydrofuran, and dimethoxyethane, in the presence of a base such as lithium hydroxide, sodium hydroxide, potassium hydroxide, lithium carbonate, sodium carbonate, potassium carbonate, cesium carbonate, potassium bicarbonate, sodium bicarbonate, or triethylamine at a temperature ranging from 0 to 150° C.

[Step A15]

In this step, compound (19a) is partially hydrolyzed to give compound (20a). The reaction is carried out in the presence of a base such as sodium acetate, potassium carbonate, or sodium hydroxide. One to ten equivalents of a base are preferably used. Solvents for the reaction include dimethyl sulfoxide, N-methylpyrrolidone, tetrahydrofuran, water, and mixtures thereof. The reaction can be conducted at a temperature ranging from 0° C. to 100° C.

[Step A16]

In this step, compound (20a) is reacted with compound (21a) to give compound (22a). The reaction can be conducted under the same conditions as used in [Step A2] of production method A.

An alternative method for producing compound (19a) is described below.

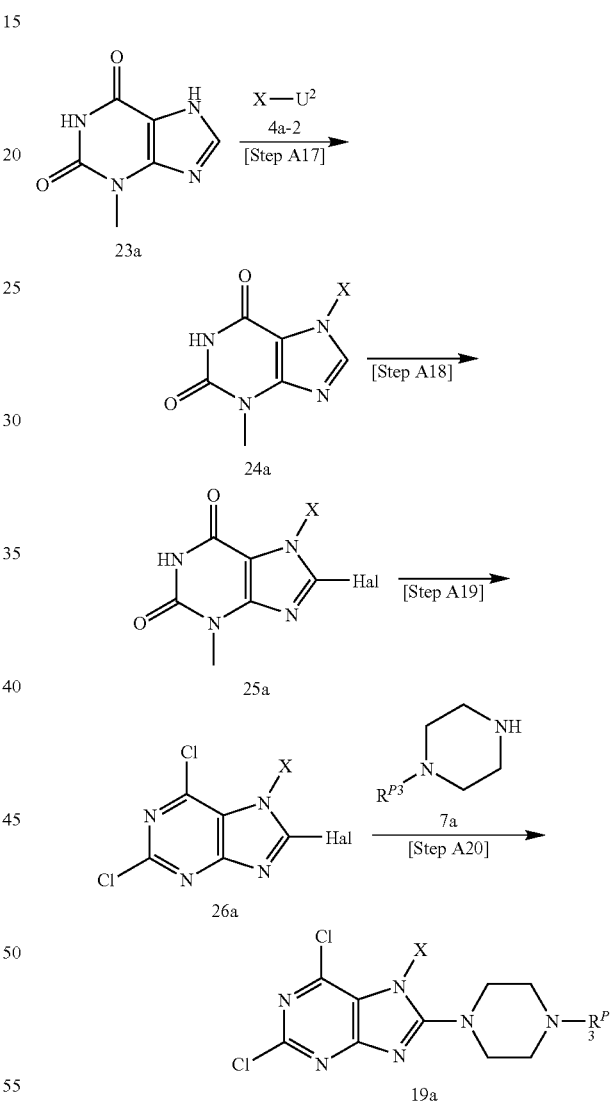

[Step A17]

In this step, a substitution reaction is carried out using compound (23a) [CAS No. 1076-22-8] and compound (4a-2) to give compound (24a).

The reaction can be conducted under the same conditions as used in [Step A4] of production method A.

[Step A18]

In this step, compound (24a) is reacted with a halogenating agent to give compound (25a).

The reaction can be conducted under the same conditions as used in [Step A5] of production method A.

[Step A19]

In this step, compound (25a) is chlorinated to give compound (26a).

There are no particular limitations on the reaction conditions, and compound (25a) can be reacted with phosphorus oxychloride, phosphorus pentachloride, or a mixture thereof in a solvent or in the absence of a solvent at a temperature of 0 to 150° C. Solvents include, for example, toluene, acetonitrile, and dichloroethane.

[Step A20]

In this step, compound (26a) is reacted with compound (7a) to give compound (19a).

The reaction can be conducted under the same conditions as used in [Step A6] of production method A.

Production Method B

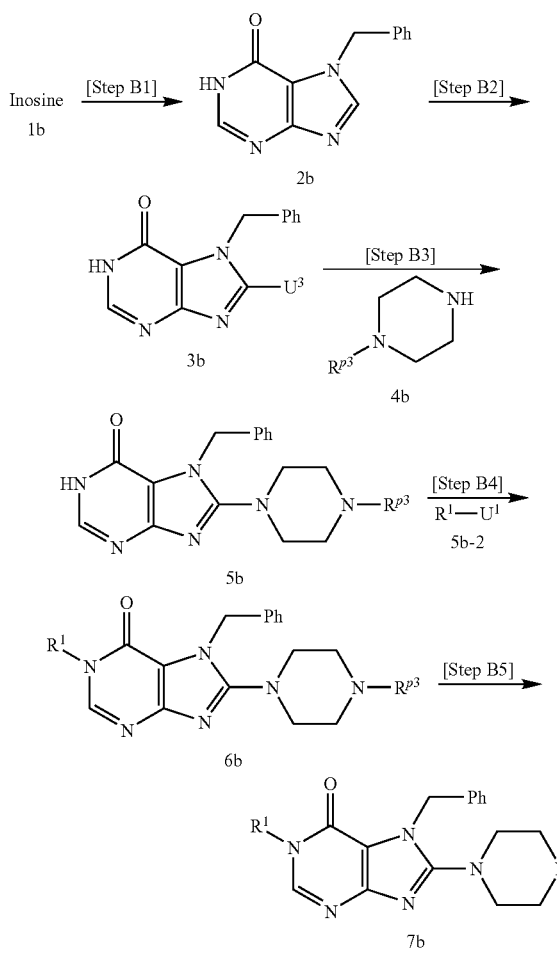

[Step B1]

In this step, compound (1b) is benzylated and the sugar chain is cleaved to give compound (2b).

There are no particular limitations on the reaction conditions. Compound (2b) can be obtained by reacting compound (1b) with benzyl bromide in a solvent such as acetonitrile, N,N-dimethylformamide, N-methylpyrrolidone, dimethyl sulfoxide, 1,4-dioxane, tetrahydrofuran, dimethoxyethane, methanol, or ethanol, at a temperature of 0 to 150° C., adding 3 to 10 equivalents of hydrochloric acid, and incubating the mixture at a temperature of 0 to 150° C. to cleave the sugar moiety. It is preferable to use 1 to 3 equivalents of benzyl bromide.

[Step B2]

In this step, compound (2b) is reacted with a halogenating agent to give compound (3b). The halogenation reaction can be conducted under the same conditions as used in [Step A5] of production method A.

[Step B3]

In this step, compound (3b) is reacted with compound (4b) to give compound (5b). The reaction can be conducted under the same conditions as used in [Step A6] of production method A.

[Step B4]

In this step, compound (5b) is reacted with compound (5b-2) to give compound (6b). The reaction can be conducted under the same condition as used in [Step A2] of production method A.

[Step B5]

In this step, $R^{p3}$ of compound (6b) is removed to give compound (7b). The reaction can be conducted under the same conditions as used in [Step A13] of production method A.

Production Method B-2

Compound (9b) represented by the formula:

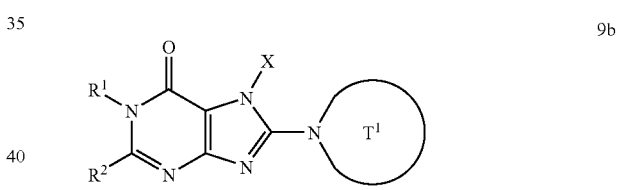

can be obtained by using compound (8b) represented by H-$T^{1a}$, instead of compound (7a) in [Step A6] of production method A described above under the same reaction conditions as used in [Step A6], and then appropriately applying [Step A7] to [Step A13] described above.

Compound (10b) represented by the formula:

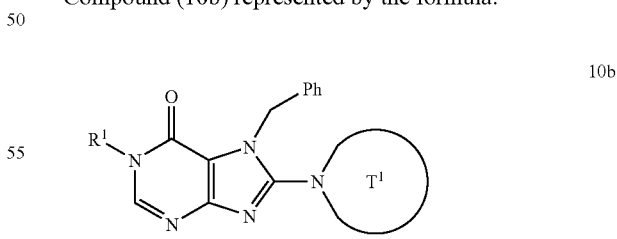

can be obtained by using compound (8b) represented by H-$T^{1a}$, instead of compound (3b) in [Step B3] of production method B described above under the same reaction conditions as used in [Step B3] and then appropriately applying [Step B4] to [Step B6] described above. Preferable examples of compound (8b) include piperidin-3-yl carbamic acid t-butyl ester.

Production Method C
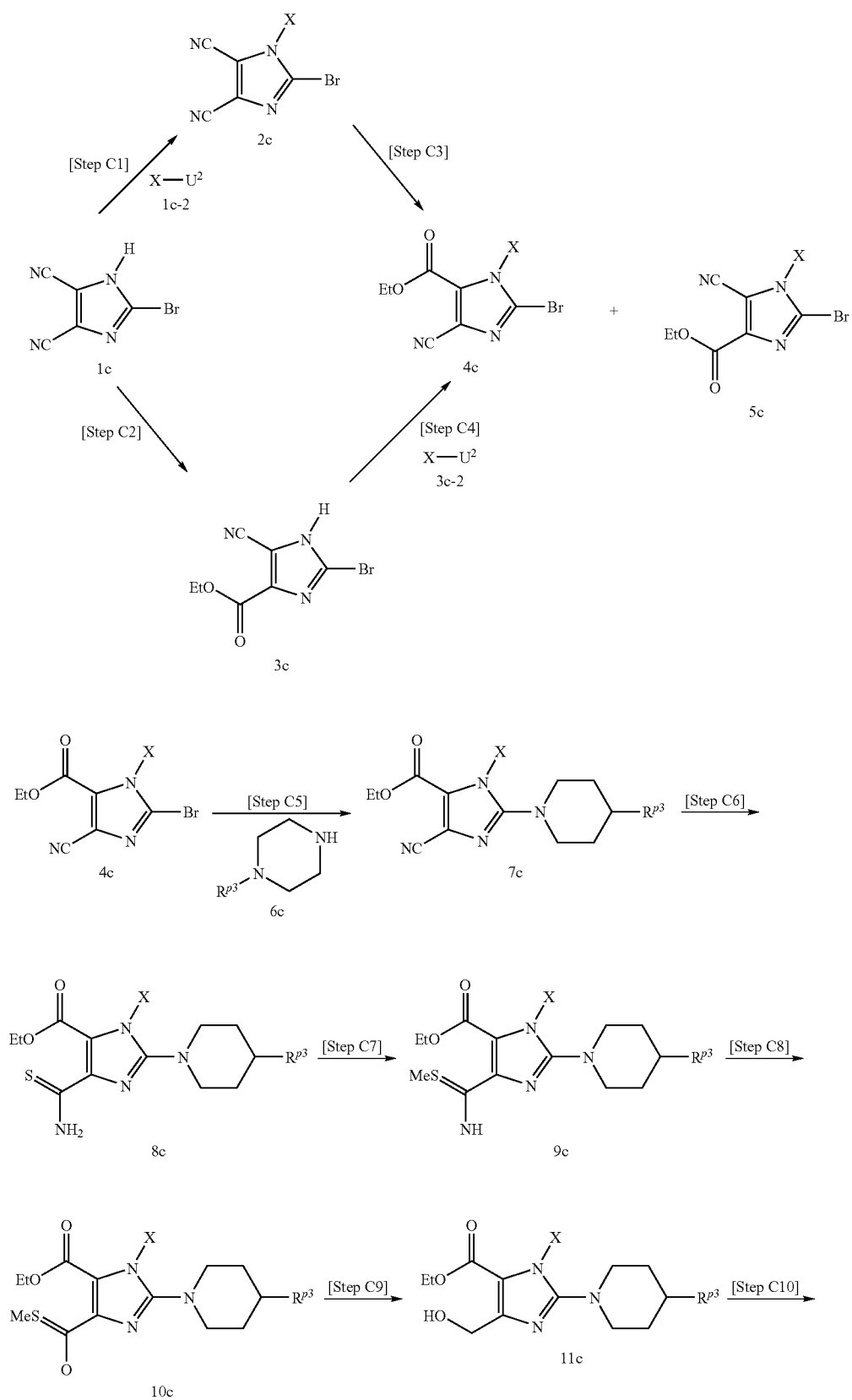

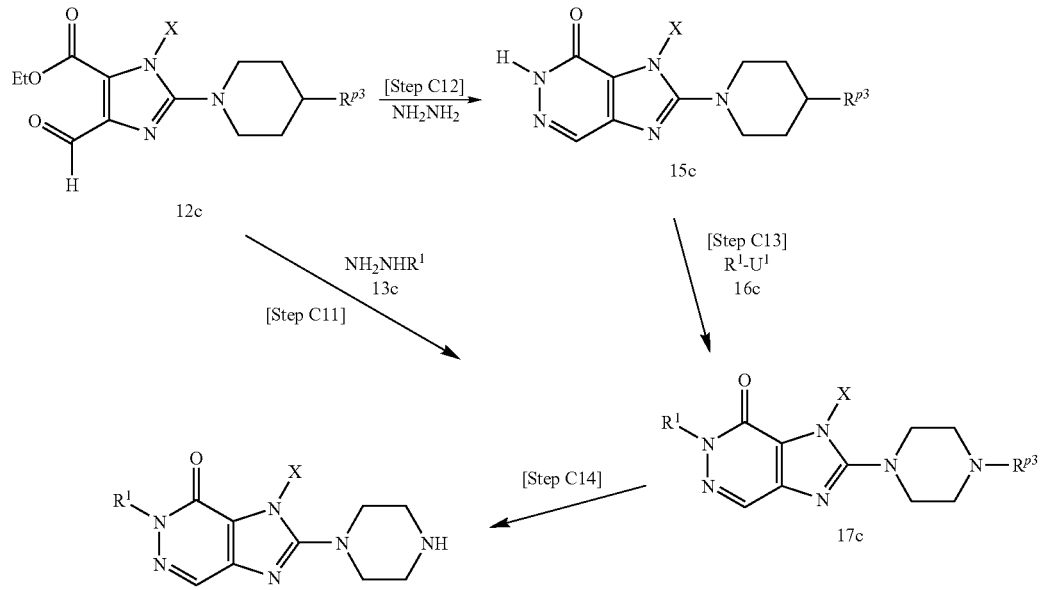
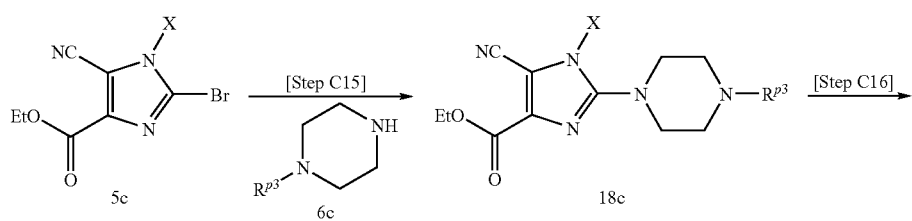
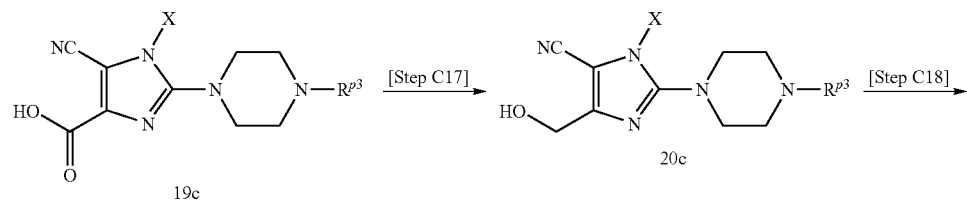
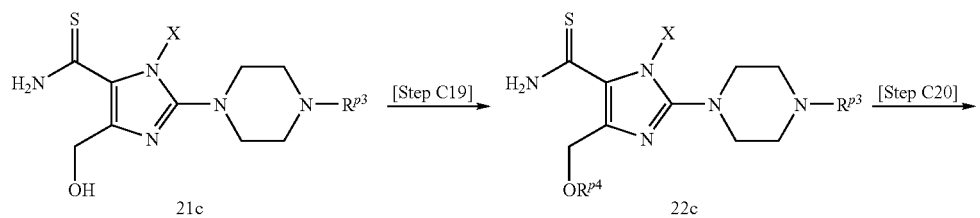
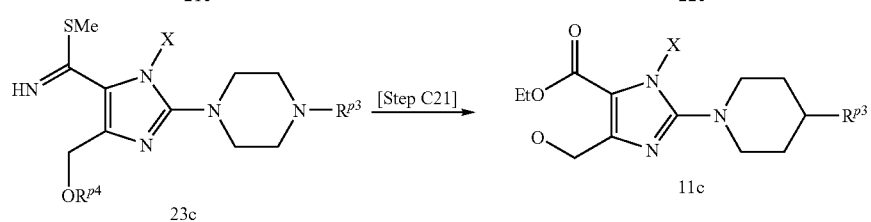

[Step C1]

In this step, compound (1c) is reacted with compound (1c-2) to give compound (2c). The reaction can be conducted under the same conditions as used in [Step A4] of production method A.

[Step C2]

In this step, compound (1c) is reacted with ethanol to give compound (3c).

Compound (3c) can be obtained, for example, by heating an ethanol solution of compound (2c) under reflux in the presence of an acid such as sulfuric acid or hydrochloric acid. However, the reaction conditions are not limited thereto. In this reaction, it is preferable to use one to two equivalents of an acid.

[Step C3]

In this step, compound (2c) is reacted with ethanol to give compounds (4c) and (5c). The reaction can be conducted under the same conditions as used in [Step C2] of production method C.

[Step C4]

In this step, compound (3c) is reacted with compound (3c-2) to give compounds (4c) and (5c). The reaction can be conducted under the same conditions as used in [Step A4] of production method A.

[Step C5]

In this step, compound (4c) is reacted with compound (6c) to give compound (7c). The reaction can be conducted under the same conditions as used in [Step A6] of production method A.

[Step C6]

In this step, compound (7c) is thioamidated to give compound (8c). Solvents for the reaction include methanol, ethanol, N,N-dimethylformamide, N-methylpyrrolidone, 1,4-dioxane, tetrahydrofuran, and dimethoxyethane. Thioamidation reagents include ammonium sulfide, sodium sulfide, and hydrogen sulfide. It is preferable to use 2 to 10 equivalents of a thioamidation reagent. When hydrogen sulfide is used as the thioamidation reagent, the reaction is carried out in the presence of a base such as triethylamine or N,N-diisopropylethylamine. The reaction can be conducted at a temperature ranging from 0° C. to 150° C.

[Step C7]

In this step, compound (8c) is reacted with a methylating reagent to give compound (9c). Methylating reagents include trimethyl oxonium tetrafluoroborate, methyl sulfate, methyl iodide, and trimethylphosphite. It is preferable to use 1.0 to 1.5 equivalent of the methylating reagent.

When trimethyl oxonium tetrafluoroborate is used as the methylating reagent, compound (9c) can be obtained by carrying out the reaction in a halogenated solvent such as dichloromethane at a temperature ranging from 0° C. to 50° C.

When methyl sulfate, methyl iodide, or trimethyl phosphite is used as the methylating reagent, compound (9c) can be obtained by carrying out the reaction in the presence of a base such as potassium carbonate, triethylamine, or N,N-diisopropylethylamine. In this case, it is preferable to use 1.0 to 1.5 equivalent of a base. Solvents for the reaction include acetone, N,N-dimethylformamide, N-methylpyrrolidone, 1,4-dioxane, tetrahydrofuran, and dimethoxyethane. The reaction can be performed at a temperature ranging from 0° C. to 100° C.

[Step C8]

In this step, compound (9c) is hydrolyzed to give compound (10c).

There are no particular limitations on the reaction conditions for the hydrolysis. The reaction can be carried out in a mixed solvent of ethanol and water in the presence of an acid such as sulfuric acid, hydrochloric acid, or p-toluenesulfonic acid, at a temperature ranging from 0° C. to 80° C. In this case, it is preferable to use 5 to 50 equivalents of the acid.

When $R^{p3}$ is a group, such as a t-butoxycarbonyl group, which is removed under the above-described condition, the protecting group should be reintroduced. There are no particular limitations on the reaction conditions for the introduction of this protecting group. When $R^{p3}$ is a t-butoxycarbonyl group, the reaction can be carried out using a reagent such as t-butyl dicarbonate in a solvent such as dichloromethane, chloroform, N,N-dimethylformamide, or tetrahydrofuran, in the presence of a base such as pyridine, 4-aminopyridine, triethylamine, and N,N-diisopropylethylamine, at a temperature ranging from 0 to 80° C. In this case, it is preferable to use 2 to 3 equivalents of a base.

[Step C9]

In this step, compound (10c) is reacted with a reducing agent to give compound (11c).

There are no particular limitations on the reaction conditions for the reduction. The reaction can be achieved by reacting compound (10c) with hydrogen in the presence of Raney nickel in a solvent such as benzene, ethanol, 2-propanol, or acetone, at a temperature ranging from 0° C. to 50° C., or alternatively reacting compound (10c) with a reducing agent such as sodium borohydride, in a solvent such as methanol, ethanol, or 2-methyl-2-propanol, or in a mixed solvent of water and tetrahydrofuran at a temperature ranging from 0° C. to 50° C., or alternatively reacting compound (10c) with a reducing agent such as sodium borohydride, in the presence of 1 to 5 equivalents of a mercury salt such as mercuric acetate in a solvent such as methanol, ethanol, or 2-methyl-2-propanol at a temperature ranging from 0° C. to 50° C. It is preferable to use two to three equivalents of a reducing agent.

[Step C10]

In this step, compound (11c) is subjected to an oxidation reaction to give compound (12c).

When an oxidant such as manganese dioxide, pyridinium chlorochromate, or pyridinium dichromate is used in the oxidation reaction, compound (12c) can be obtained by carrying out the reaction in a solvent such as dichloromethane or chloroform, at a temperature ranging from 20° C. to 80° C. Alternatively, compound (12c) can also be obtained by carrying out the reaction under standard conditions for the oxidation of a primary alcohol to aldehyde, such as Swern oxidation. It is preferable to use 5 to 20 equivalents of an oxidant.

[Step C11]

In this step, compound (12c) is reacted with compound (13c) to give compound (17c). In this case, it is preferable to use 2 to 10 equivalents of compound (13c).

Compound (17c) can be obtained, for example, by combining compounds (12c) and (13c) in a solvent such as methanol, ethanol, 1-methyl-2-pyrrolidone, 1,4-dioxane, tetrahydrofuran, or dimethoxyethane, or in the absence of solvent, and reacting the mixture at a temperature of 20 to 150° C. However, the reaction conditions are not limited thereto.

[Step C12]

In this step, compound (12c) is reacted with hydrazine to give compound (15c). The reaction can be conducted under the same conditions as used in [Step C11] of production method C. It is preferable to use 2 to 10 equivalents of hydrazine.

[Step C13]

In this step, a substitution reaction is carried out using compound (15c) and compound (16c) to give compound (17c). The reaction can be conducted under the same conditions as used in [Step A2] of production method A. It is preferable to use 1 to 3 equivalents of compound (16c).

[Step C14]

In this step, $R^{p3}$ of compound (17c) is removed to give compound (14c). The reaction can be conducted under the same conditions as used in [Step A13] of production method A.

[Step C15]

In this step, compound (5d) is reacted with compound (6c) to give compound (18c). The reaction can be conducted under the same conditions as used in [Step A6] of production method A.

[Step C16]

In this step, compound (18c) is hydrolyzed to give compound (19c).

There are no particular limitations on the reaction conditions for the hydrolysis. For example, compound (19c) can be obtained by incubating compound (18c) in the presence of a base at a temperature ranging from 0° C. to 100° C.

Solvents for the reaction include methanol, ethanol, tetrahydrofuran, water, or mixtures thereof. Bases include lithium hydroxide, sodium hydroxide, and potassium hydroxide. It is preferable to use 1 to 2 equivalents of a base.

[Step C17]

In this step, compound (19c) is reacted with a reducing agent to give compound (20c). The reduction can be achieved under a standard condition for the reduction of carboxylic acid to methyl alcohol.

Reducing agents include borane derivatives such as borane-tetrahydrofuran complex and borane-methyl sulfide complex, and sodium borohydride. It is preferable to use 5 to 30 equivalents of a reducing agent.

When a borane derivative is used as a reducing agent, compound (20c) can be obtained by carrying out the reaction using a solvent such as 1,4-dioxane, tetrahydrofuran, or dimethoxyethane at a temperature ranging from −78° C. to 35° C.

Alternatively, when sodium borohydride is used as a reducing agent, first, compound (19c) is reacted with an activator such as isobutyl chloroformate, at a temperature ranging from −78° C. to 20° C., then reacted with a reducing agent such as sodium borohydride at a temperature ranging from −78° C. to 35° C., to obtain compound (20c). Solvents for the reaction include 1,4-dioxane, tetrahydrofuran, and dimethoxyethane.

[Step C18]

In this step, compound (20c) is thioamidated to give compound (21c). The reaction can be conducted under the same conditions as used in [Step C6] of production method C.

[Step C19]

In this step, compound (21c) is reacted with a silylating agent in the presence of a base to give compound (22c).

Solvents for the reaction include dichloromethane, N,N-dimethylformamide, 1,4-dioxane, tetrahydrofuran, and dimethoxyethane. Bases include imidazole, pyridine, 4-dimethylaminopyridine, triethylamine, and N,N-diisopropylethylamine. Silylating agents include t-butyldimethylchlorosilane, and t-butylchlorodiphenylsilane. It is preferable to use 1.0 to 1.5 equivalent of a base and 1.0 to 1.5 equivalent of a silylating agent. The reaction can be conducted at a temperature ranging from 0° C. to 80° C.

[Step C20]

In this step, compound (22c) is methylated to give compound (23c).

The reaction can be conducted under the same condition as used in [Step C7] of production method C.

[Step C21]

In this step, compound (23c) is hydrolyzed to give compound (24c).

There are no particular limitations on the reaction conditions for the hydrolysis. Compound (24c) can be obtained by carrying out the reaction in a mixed solvent of ethanol and water in the presence of an acid such as sulfuric acid, hydrochloric acid, or p-toluenesulfonic acid, at a temperature ranging from 50° C. to 100° C.

When such a reaction results in removal of —$R^{p3}$, —NH— is re-protected through a protection reaction. Specifically, for example, when $R^{p3}$ is a t-butoxycarbonyl group, the reaction can be carried out using a reagent such as t-butyl dicarbonate, in a solvent such as dichloromethane, chloroform, N,N-dimethylformamide, or tetrahydrofuran, in the presence of a base such as pyridine, 4-aminopyridine, triethylamine, or N,N-diisopropyl ethylamine, at a temperature ranging from 0 to 80° C. However, the reaction is not limited thereto.

Production Method D

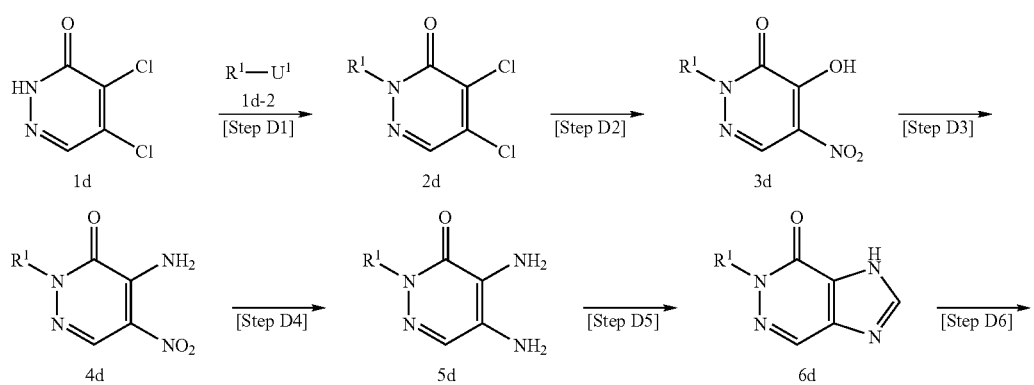

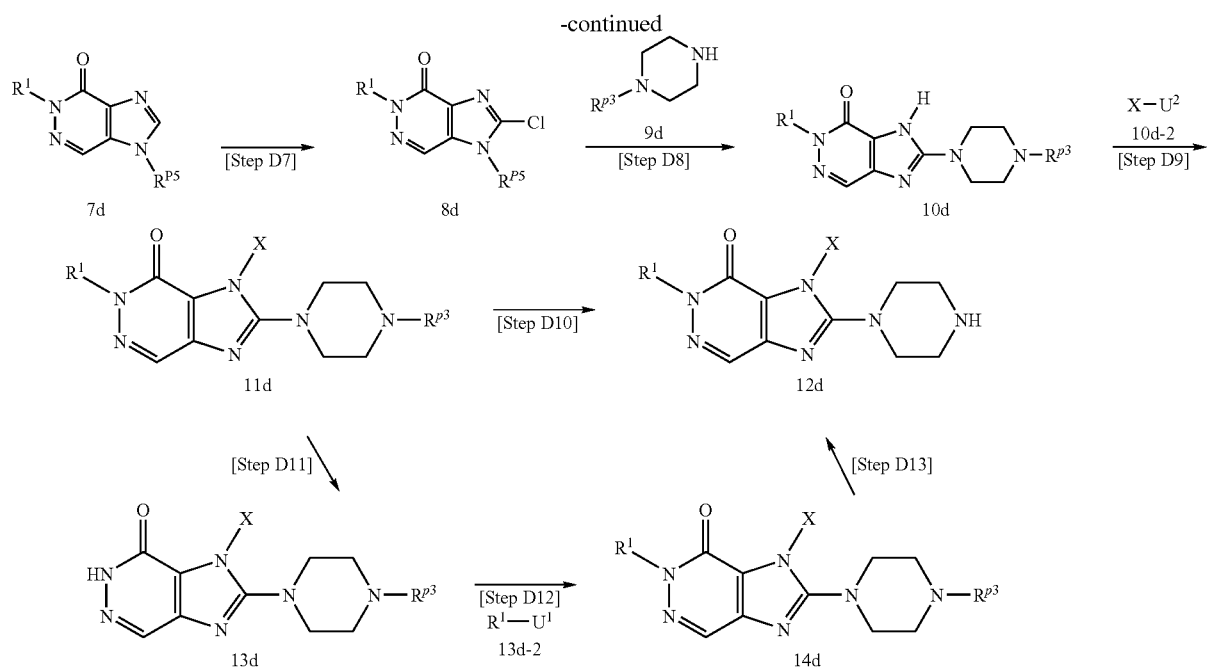

[Step D1]

In this step, compound (1d) is reacted with compound (1d-2) to give compound (2d).

Specifically, compound (1d-2) includes, for example, alkyl halides such as iodomethane, iodoethane, iodopropane, benzyl bromide, 2-bromoacetophenone, chloromethyl benzyl ether, and bromoacetonitrile; alkenyl halides such as allyl bromide and 1-bromo-3-methyl-2-butene; and alkynyl halides such as propargyl bromide and 1-bromo-2-butyne. It is preferable to use 1 to 1.5 equivalent of compound (1d-2).

Solvents for the reaction include N,N-dimethylformamide, N-methylpyrrolidone, tetrahydrofuran, 1,2-dimethoxyethane, 1,4-dioxane, and dichloromethane. The reaction can be carried out in the presence or absence of a base. Bases to be used in the reaction include 1,8-diazabicyclo[5,4,0]undecene, triethylamine, N,N-diisopropylethylamine, and sodium hydride. In this case, it is preferable to use 1 to 1.5 equivalent of the base. The reaction can be conducted at a temperature ranging from 0° C. to 150° C.

[Step D2]

In this step, compound (2d) is reacted with a nitrite salt to give compound (3d).

Solvents for the reaction include a mixed solvent of water and a solvent from N,N-dimethylformamide, N-methylpyrrolidone, tetrahydrofuran, 1,2-dimethoxyethane, and 1,4-dioxane. Nitrite salts include sodium nitrite and potassium nitrite. It is preferable to use 3 to 5 equivalents of a nitrite. The reaction can be conducted at a temperature ranging from 20° C. to 120° C.

[Step D3]

In this step, compound (3d) is reacted with ammonia to give compound (4d). It is preferable to use 10 to 20 equivalents of ammonia.

The reaction can be carried out in a solvent such as methanol, ethanol, or 1,4-dioxane at a temperature ranging from 20° C. to 200° C.

[Step D4]

In this step, compound (4d) is subjected to catalytic reduction under hydrogen atmosphere or in the presence of 2 to 3 equivalents of hydrazine using a metal catalyst to give compound (5d).

Solvents for the reaction include methanol, ethanol, N,N-dimethylformamide, tetrahydrofuran, 1,2-dimethoxyethane, 1,4-dioxane, water, or a mixed solvent thereof. Metal catalysts include palladium carbon, platinum oxide, and Raney nickel. It is preferable to use a metal catalyst in the amount of 0.5 to 10% by weight. The reaction can be conducted at a temperature ranging from 0° C. to 150° C.

[Step D5]

In this step, compound (5d) is reacted with an orthoformate ester to give compound (6d).

The reaction is carried out in the presence of a carboxylic anhydride such as acetic anhydride. Orthoformate esters include methyl orthoformate, and ethyl orthoformate. It is preferable to use 1 to 20 times as much orthoformate ester by weight and 3 to 10 equivalents of carboxylic anhydride. The reaction can be conducted at a temperature ranging from 20° C. to 200° C.

[Step D6]

In this step, the NH group at the 1-position of compound (6d) is protected to give compound (7d).

Protecting reagents include N,N-dimethylsulfamoyl chloride, trityl chloride, di-t-butyl dicarbonate, and benzyl bromide. It is preferable to use 1 to 1.5 equivalent of a protecting reagent. Solvents for the reaction include dichloromethane, chloroform, carbon tetrachloride, toluene, N,N-dimethylformamide, and tetrahydrofuran. Bases include pyridine, 4-dimethylaminopyridine, 1,8-diazabicyclo[5,4,0]undecene, triethylamine, and N,N-diisopropylethylamine. In typical cases, it is preferable to use 1.2 equivalents of a base. However, when the protecting reagent is di-t-butyl dicarbonate, 0.005 to 0.1 equivalent of 4-dimethylaminopyridine is used preferably. The reaction can be conducted at a temperature ranging from 20° C. to 200° C.

[Step D7]

In this step, compound (7d) is chlorinated to give compound (8d).

There are no particular limitations on the reaction conditions. For example, the reaction is carried out as follows. Compound (7d) is reacted with a base at a temperature ranging from −100° C. to 20° C., and then a chlorinating reagent is reacted thereto. This reaction produces compound (8d). Compound (8d) can also be obtained by reacting compound (7d) with a base in the presence of a chlorination reagent. Solvents for the reaction include, for example, diethyl ether, tetrahydrofuran, 1,2-dimethoxyethane, and 1,4-dioxane. Bases include n-butyllithium, t-butyllithium, lithium diisopropylamide, lithium bis(trimethylsilyl)amide, and magnesium diisopropylamide. It is preferable to use 1 to 1.5 equivalent of a base. Chlorinating reagents include hexachloroethane, and N-chloro succinimide. It is preferable to use 1 to 3 equivalents of a chlorination reagent.

[Step D8]

In this step, compound (8d) is reacted with compound (9d) to give compound (10d). The reaction can be conducted under the same conditions as used in [Step A6] of production method A.

[Step D9]

In this step, a substitution reaction is carried out using compound (10d) and compound (10d-2) to give compound (11d). The reaction can be conducted under the same conditions as used in [Step A4] of production method A.

[Step D10]

In this step, $R^{P3}$ of compound (11d) is removed to give compound (12d). The reaction can be conducted under the same condition as used in [Step A13] of production method A.

[Step D11]

In this step, the group at the 5-position of compound (11d) is obtained by dealkylation to give compound (13d). There are no particular limitations on the reaction conditions for the dealkylation. For example, such a reaction can be achieved as follows:

When $R^1$ is a benzyloxymethyl group, compound (11d) is reacted with 3 to 10 equivalents of boron tribromide, boron trichloride, or such in a solution such as dichloromethane at a temperature ranging from −100° C. to 20° C. This reaction produces compound (13d).

When such a reaction results in removal of $R^{P3}$, —NH— is re-protected through a protection reaction. Specifically, for example, when $R^{P3}$ is a t-butoxycarbonyl group, the reaction can be carried out using a reagent such as di-t-butyl dicarbonate, in a solvent such as dichloromethane, chloroform, N,N-dimethylformamide, or tetrahydrofuran, in the presence of a base such as pyridine, 4-aminopyridine, triethylamine, or N,N-diisopropylethylamine, at a temperature ranging from 0 to 80° C. However, the reaction is not limited thereto.

[Step D12]

In this step, compound (13d) is reacted with compound (13d-2) to give compound (14d). The reaction can be conducted under the same conditions as used in [Step D1] of production method D.

[Step D13]

In this step, $R^{P3}$ of compound (14d) is removed to give compound (12d). The reaction can be conducted under the same conditions as used in [Step A13] of production method A.

An alternative method for producing compound (11d) is described below.

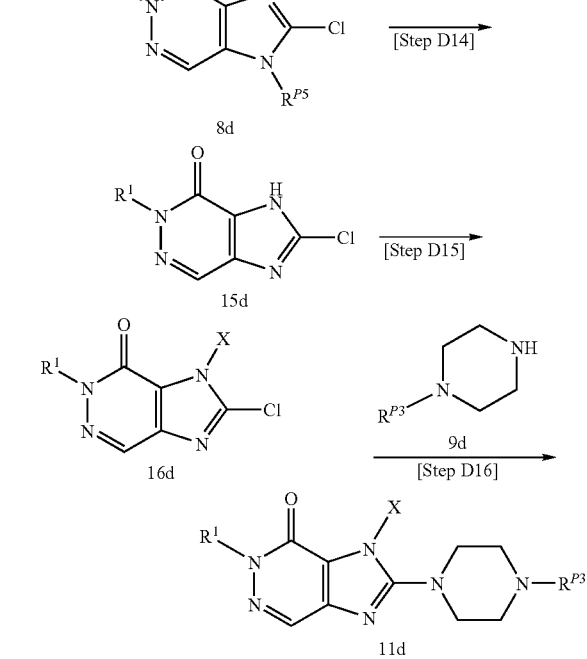

[Step D14]

In this step, compound (8d) is deprotected to give compound (15d).

The deprotection can be achieved under standard reaction conditions depending on the type of protecting group. For example, in the case of a t-butoxycarbonyl group, the deprotection can be achieved by carrying out the reaction using a base such as sodium hydroxide, potassium carbonate, and ammonia, in tetrahydrofuran, N,N-dimethylformamide, methanol, ethanol, water, or a mixed solvent thereof at a temperature ranging from 0° C. to 100° C. When a solvent and a base are added after chlorination in the previous step, the deprotection can be achieved without isolating compound (8d).

[Step D15]

In this step, X is introduced into compound (15d) to give compound (16d). The reaction can be conducted using X—$U^2$ under the same conditions as used in [Step A4] of production method A.

An alcohol (X—OH) can be introduced using Mitsunobu's reaction. Specifically, compound (16d) can be obtained by reacting an alcohol (X—OH) with an azodicarboxylic acid dialkyl ester and triphenylphosphine in a solvent such as tetrahydrofuran, at a temperature ranging from −70° C. to 50° C.

[Step D16]

In this step, compound (16d) is reacted with compound (9d) to give compound (11d).

The reaction can be conducted under the same conditions as used in [Step A6] of production method A.

Production Method E

Compound (1e) represented by the formula:

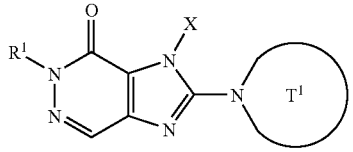

1e can be obtained by using compound (8b) represented by H-T$^{1a}$, instead of compound (6c), in [Step C5] or [Step C15] of production method C described above under the same reaction conditions as used in [Step C5], and then appropriately applying [Step C6] to [Step C21] described above.

Compound (1e) represented by the formula:

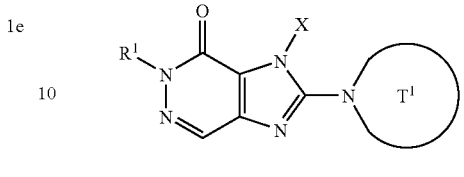

1e can be obtained by using compound (8b) represented by H-T$^{1a}$, instead of compound (9d) in [Step D8] of production method D described above under the same reaction conditions as used in [Step D8], and then appropriately applying [Step D9] to [Step D13] described above.

Production Method F

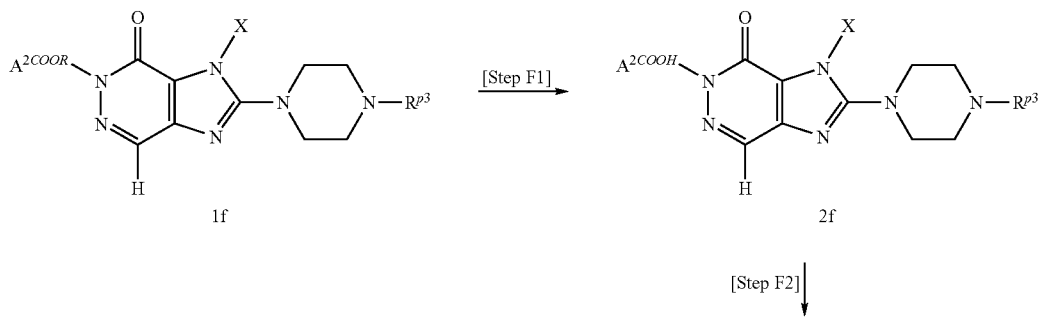

[Step F2]

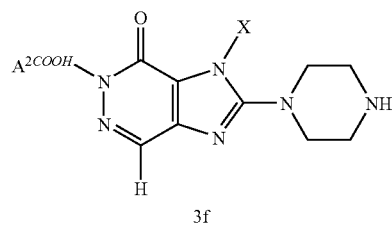

[Step F1]

In this step, the ester group of compound (1f) is hydrolyzed to give compound (2f). The reaction can be conducted under the same conditions as used in [Step C16] of production method C.

[Step F2]

In this step, $R^{p3}$ of compound (2f) is removed to give compound (3f). The reaction can be conducted under the same conditions as used in [Step A13] of production method A.

Production Method G

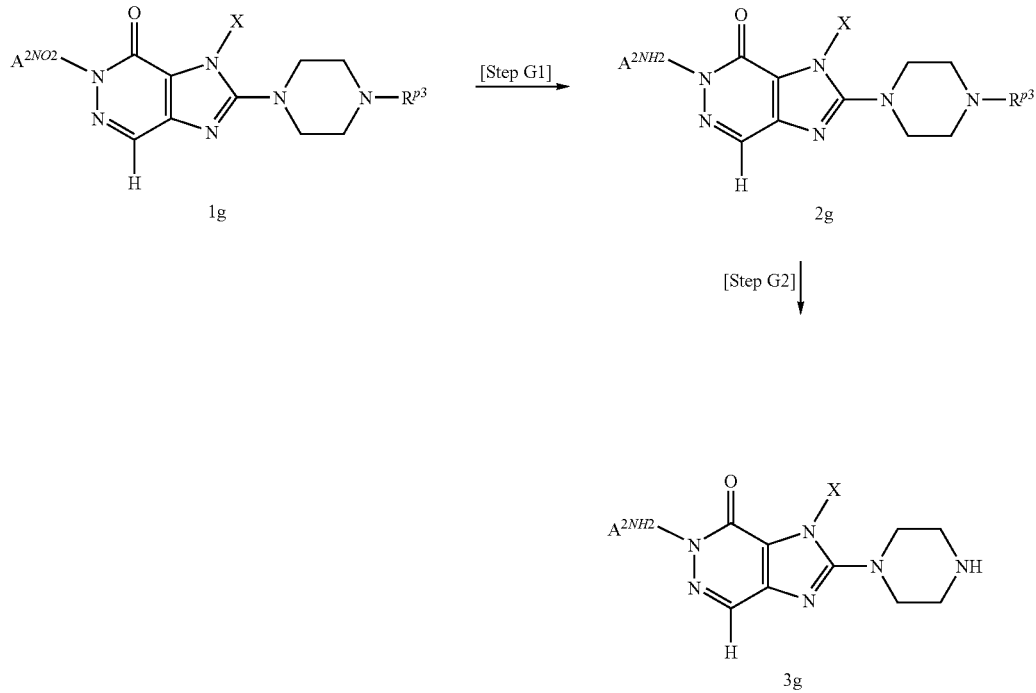

[Step G1]

In this step, the nitro group of compound (1g) is reduced to give compound (2g).

Solvents for the reaction include methanol, ethanol, tetrahydrofuran, water, or mixtures thereof. Reducing agents includes, iron, tin, and zinc. Catalysts include hydrochloric acid and ammonium salts such as ammonium chloride. The reaction can be conducted at a temperature ranging from 20° C. to 120° C.

[Step G2]

In this step, $R^{p3}$ of compound (2g) is removed to give compound (3g). The reaction can be conducted under the same conditions as used in [Step A13] of production method A.

Production Method H

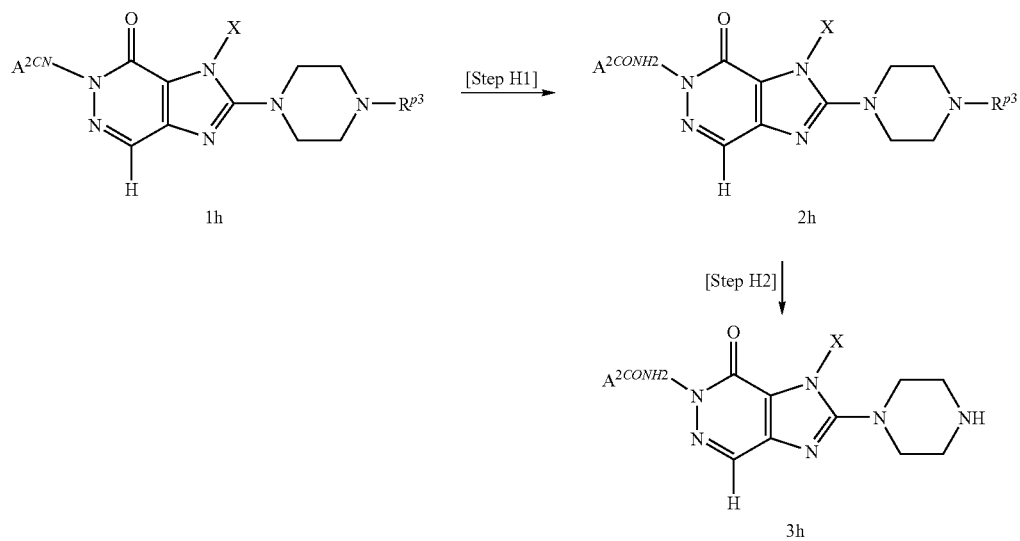

[Step H1]

In this step, the nitrile group of compound (1 h) is hydrolyzed to give compound (2h).

There are no particular limitations on the reaction conditions. For example, the reaction is carried out as follows. Compound (2h) can be obtained by reacting compound (1 h) with hydrogen peroxide in the presence of a base at a temperature ranging from −20° C. to 50° C. Solvents include methanol, ethanol, tetrahydrofuran, water, or a solvent mixture thereof. Bases include ammonia and alkyl amines such as triethylamine.

[Step H2]

In this step, $R^{p3}$ of compound (2h) is removed to give compound (3h). The reaction can be conducted under the same conditions as used in [Step A13] of production method A.

Production method I

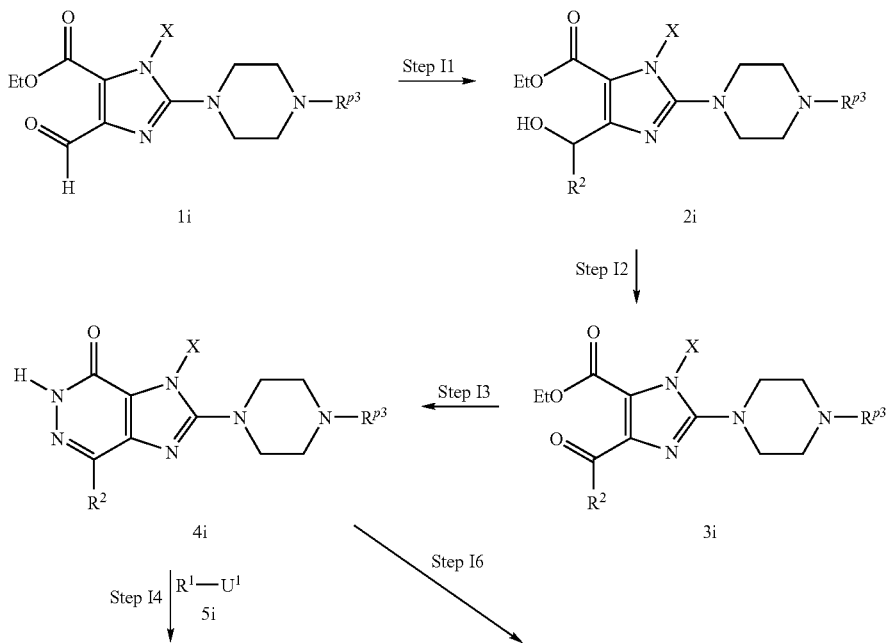

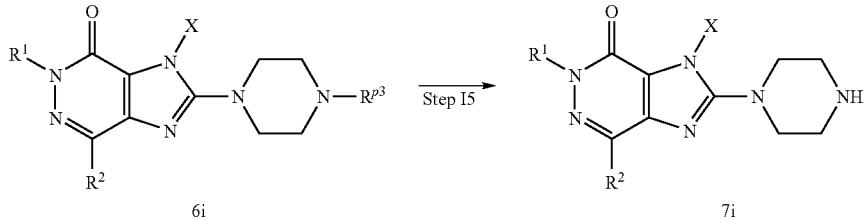

[Step I1]

In this step, compound (1i) is reacted with an alkyl metal agent or an aryl metal agent to give compound (2i).

There are no particular limitations on the reaction conditions. For example, the reaction is carried out as follows. Compound (1i) may be reacted with an agent such as alkyllithium, aryllithium, alkyl Grignard reagent, or aryl Grignard reagent, in a solvent such as diethyl ether or tetrahydrofuran, at a temperature ranging from −100° C. to 100° C. Alternatively, the compound may be reacted with alkylzinc or arylzinc in a solvent such as N,N-dimethylformamide or 1-methyl-2-pyrrolidone, at a temperature ranging from 0° C. to 50° C.

[Step I2]

In this step, compound (2i) is oxidized to give compound (3i). A typical reagent that is generally used in the oxidation of an alcohol can be used as the oxidant. Specifically, for example, manganese dioxide can be used as the oxidant in a solvent such as dichloromethane or chloroform, at a temperature within the range of 20 to 100° C. Alternatively, sulfur trioxide pyridine can be used as the oxidant in a solvent such as dimethyl sulfoxide, at a temperature within the range of 20 to 100° C. Alternatively, Dess-Martin periodinane may be used in a solvent such as dichloromethane or chloroform, at a temperature within the range of −50 to 50° C.

[Step I3]

In this step, compound (3i) is reacted with hydrazine to give compound (4i). The reaction can be conducted under the same conditions as used in [Step C12] of production method C.

[Step I4]

In this step, a substitution reaction is carried out using compound (4i) and compound (5i) to give compound (6i). The reaction can be conducted under the same conditions as used in [Step A2] of production method A.

[Step I5]

In this step, $R^{p3}$ of compound (6i) is removed to give compound (7i). The reaction can be conducted under the same conditions as used in [Step A13] of production method A.

[Step I6]

In this step, $R^{p3}$ of compound (4i) is removed to give compound (7i) when $R^1$ of compound (7i) is H. The reaction can be conducted under the same conditions as used in [Step A13] of production method A.

Production Method J

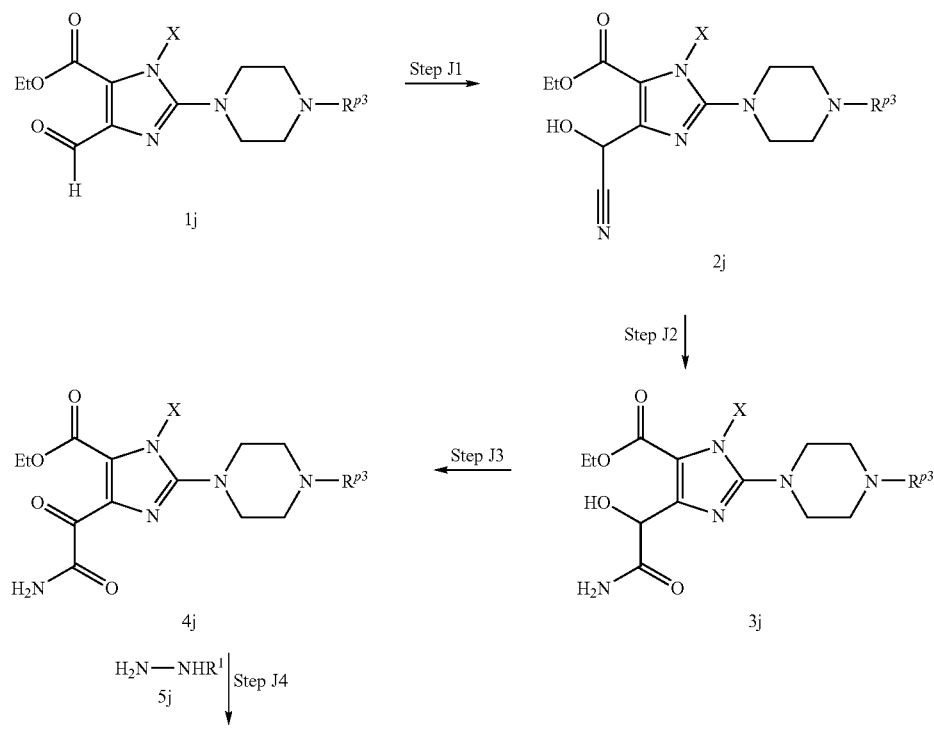

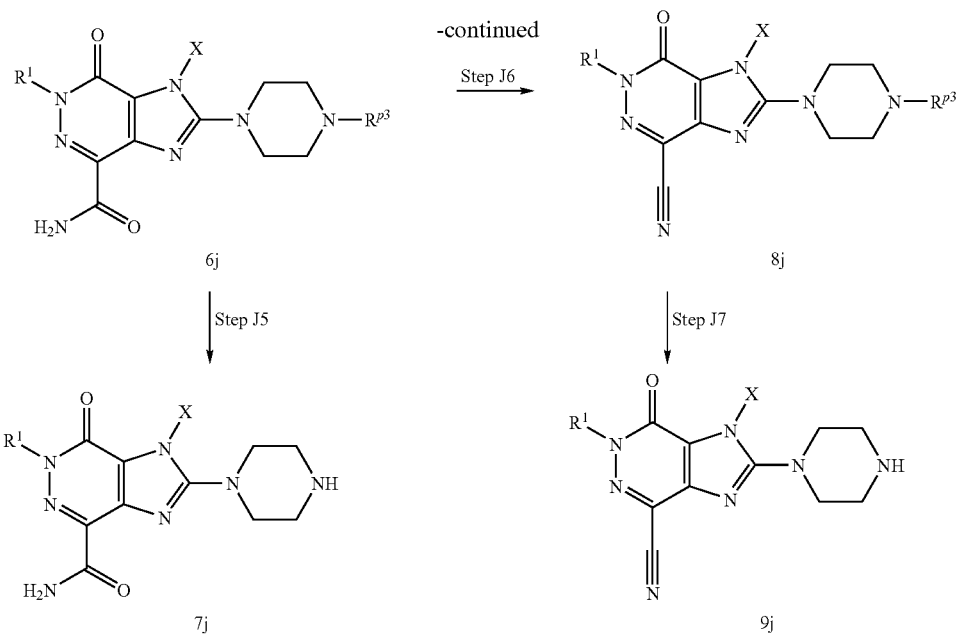

[Step J1]
In this step, compound (1j) is reacted with a cyanidation agent in the presence of a catalyst to give compound (2j).

Cyanidation agents include sodium cyanide, and potassium cyanide. Catalysts include acetic acid. Solvents include, for example, acetonitrile. The reaction can be conducted at a temperature ranging from 0° C. to 100° C.

[Step J2]
In this step, the nitrile group of compound (2j) is hydrolyzed to give compound (3j). The reaction can be conducted under the same conditions as used in [Step H1] of production method H.

[Step J3]
In this step, the hydroxyl group of compound (3j) is oxidized to give compound (4j). The reaction can be conducted under the same conditions as used in [Step I2] of production method I.

[Step J4]
In this step, compound (4j) is reacted with compound (5j) to give compound (6j). The reaction can be conducted under the same conditions as used in [Step C11] of production method C.

[Step J5]
In this step, $R^{p3}$ of compound (6j) is removed to give compound (7j). The reaction can be conducted under the same conditions as used in [Step A13] of production method A.

[Step J6]
In this step, the carbamoyl group of compound (6j) is dehydrated in the presence of a base to give compound (8j).

Dehydrating agents include, for example, phosphorus oxychloride. Bases include alkyl amines such as triethylamine. Solvents include dichloromethane, and chloroform. Alternatively, the reaction can be carried out in the absence of solvent. The reaction can be conducted at a temperature ranging from 0° C. to 100° C.

[Step J7]
In this step, $R^{p3}$ of compound (8j) is removed to give compound (9j). The reaction can be conducted under the same conditions as used in [Step A13] of production method A.

Production Method K

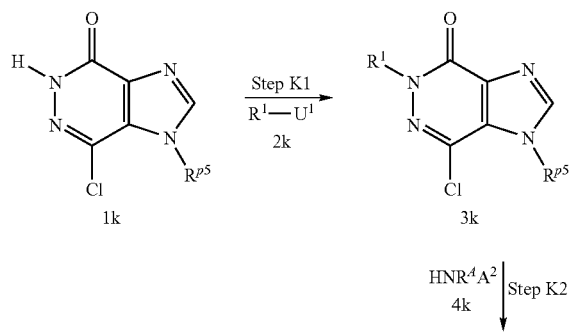

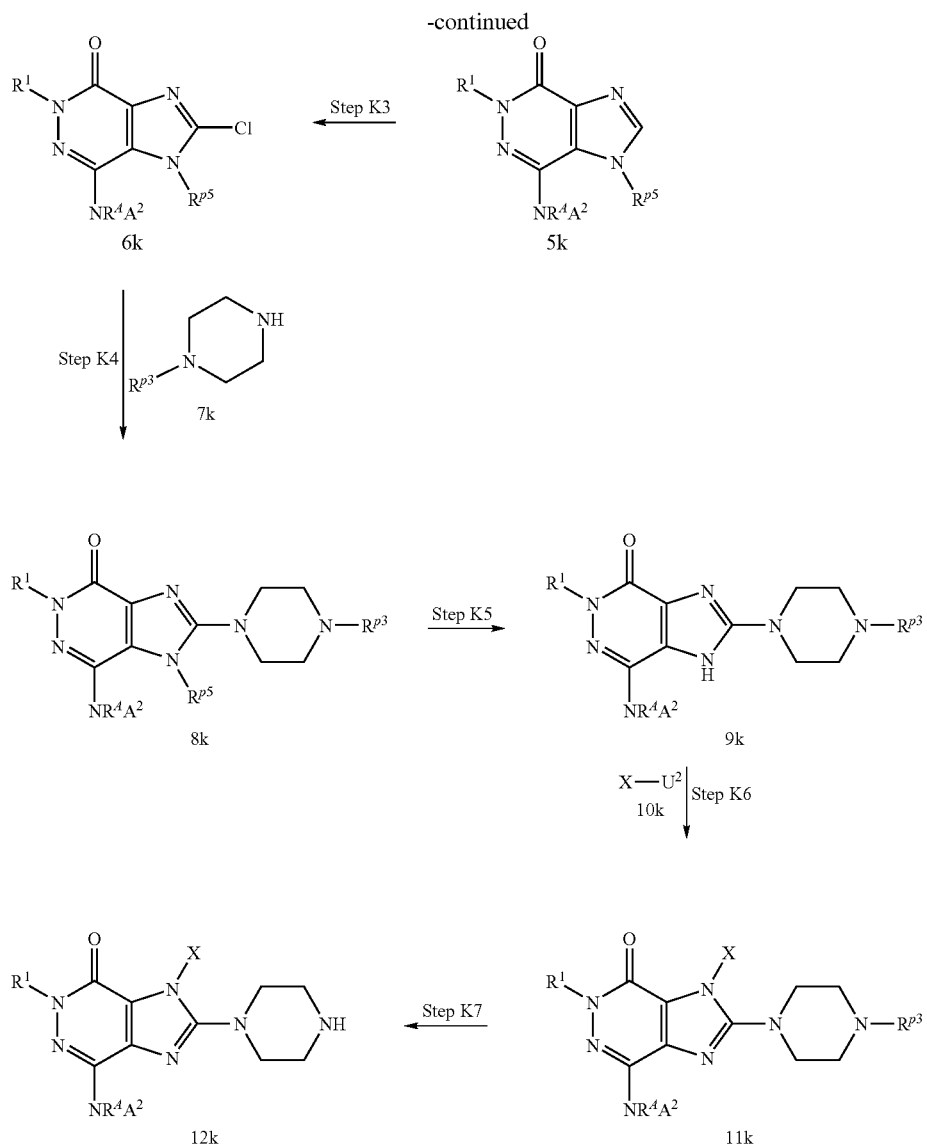

[Step K1]

In this step, a substitution reaction using compound (1k) and compound (2k) is carried out to give compound (3k). The reaction can be conducted under the same conditions as used in [Step A2] of production method A.

[Step K2]

In this step, a substitution reaction using compound (3k) and compound (4k) is carried out to give compound (5k).

Compound (5k) can be obtained, for example, by reacting a mixture of compounds (3k) and (4k) in a solvent such as methanol, ethanol, 1-methyl-2-pyrrolidone, 1,4-dioxane, tetrahydrofuran, or dimethoxyethane, or in the absence of solvent at a temperature ranging from 20° C. to 200° C. However, the reaction conditions are not limited thereto.

[Step K3]

In this step, compound (5k) is chlorinated to give compound (6k). The reaction can be conducted under the same conditions as used in [Step D7] of production method D.

[Step K4]

In this step, compound (6k) is reacted with compound (7k) to give compound (8k). The reaction can be conducted under the same conditions as used in [Step A6] of production method. A.

[Step K5]

In this step, $R^{p5}$ of compound (8k) is removed to give compound (9k).

The deprotection reaction for $R^{p5}$ can be carried out under standard reaction conditions for removing an —NH-protecting group. For example, when $R^{p5}$ is a benzyl group, the reaction can be achieved using a metal such as lithium or sodium in liquid ammonia at a temperature within the range of −78° C. to −30° C.

[Step K6]

In this step, a substitution reaction using compound (9k) and compound (10k) is carried out to give compound (11k). The reaction can be conducted under the same conditions as used in [Step A4] of production method A.

[Step K7]

In this step, $R^{p3}$ of compound (11k) is removed to give compound (12k). The reaction can be conducted under the same conditions as used in [Step A13] of production method A.

Production Method L can be carried out using a reagent such as di-t-butyl dicarbonate, in a solvent such as dichloromethane, chloroform, N,N-dimethylformamide, or tetrahydrofuran, in the presence of a base such as pyridine, 4-aminopyridine, triethylamine, or N,N-diisopropylethylamine, at a temperature ranging from 0 to 80° C. However, the reaction is not limited thereto.

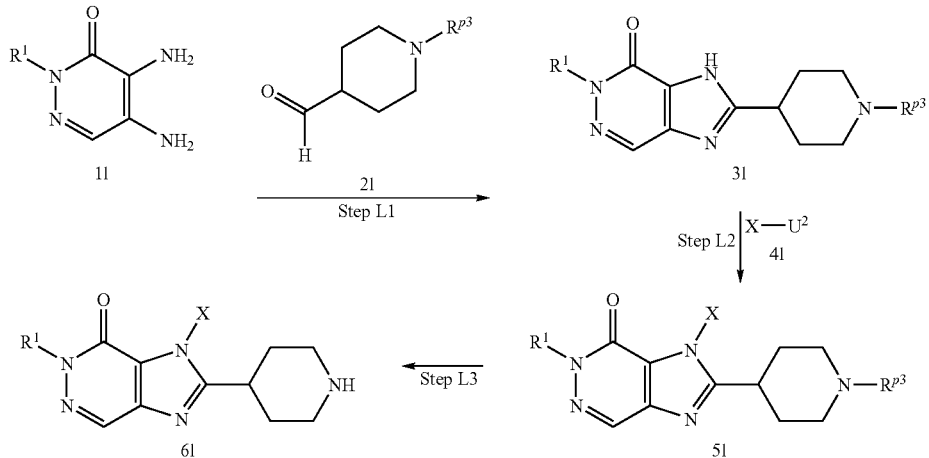

[Step L1]

In this step, compound (1l) is reacted with compound (2l) in the presence of an oxidant to give compound (3l).

Oxidants include salts such as iron (III) chloride. Solvents include methanol, ethanol, and water. The reaction can be conducted at a temperature ranging from 20° C. to 100° C.

When such a reaction results in removal of —$R^{p3}$, —NH— is re-protected through a protection reaction. Specifically, for example, when Pro3 is a t-butoxycarbonyl group, the reaction

[Step L2]

In this step, compound (3l) is reacted with compound (4l) to give compound (5l). The reaction can be conducted under the same conditions as used in [Step A4] of production method A

[Step L3]

In this step, $R^{p3}$ of compound (5l) is removed to give compound (6l). The reaction can be conducted under the same conditions as used in [Step A13] of production method A.

Production Method M

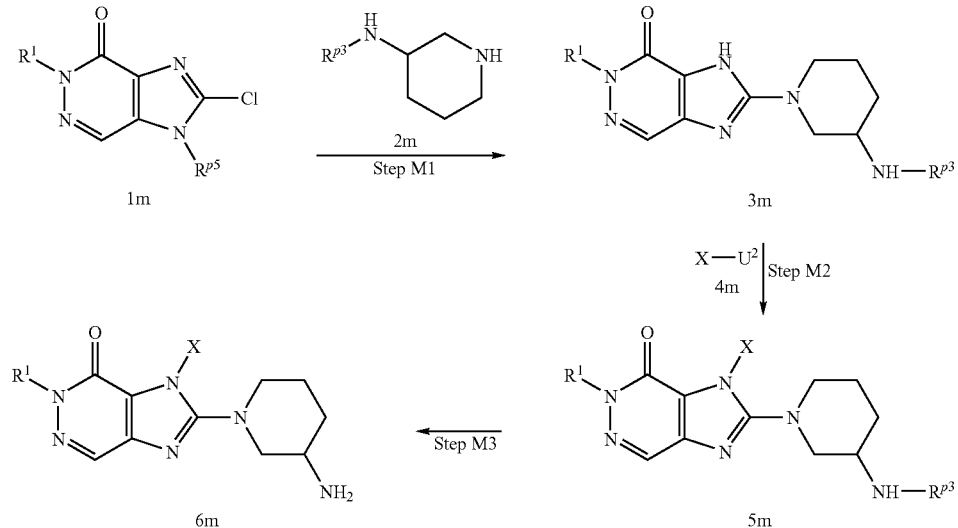

[Step M1]

In this step, compound (1m) is reacted with compound (2m) to give compound (3m). The reaction can be conducted under the same conditions as used in [Step A6] of production method A.

[Step M2]

In this step, compound (3m) is reacted with compound (4m) to give compound (5m). The reaction can be conducted under the same conditions as used in [Step A4] of production method A.

[Step M3]

In this step, $R^{p3}$ of compound (5m) is removed to give compound (6m). The reaction can be conducted under the same conditions as used in [Step A13] of production method A.

Production Method N

[Step N1]

In this step, compound (1n) is reacted with allylamine to give compound (2n).

The reaction can be conducted at a temperature ranging from 20° C. to 150° C. Solvents for the reaction include methanol, ethanol, water, and a mixed solvent thereof.

[Step N2].

In this step, compound (2n) is reduced while being chlorinated to give compound (3n).

Reducing agents include tin salts such as tin chloride. Solvents include concentrated hydrochloric acid. The reaction can be conducted at a temperature ranging from 20° C. to 150° C.

[Step N3]

In this step, compound (3n) is reacted with N,N'-disuccinimidyl carbonate to give compound (4n).

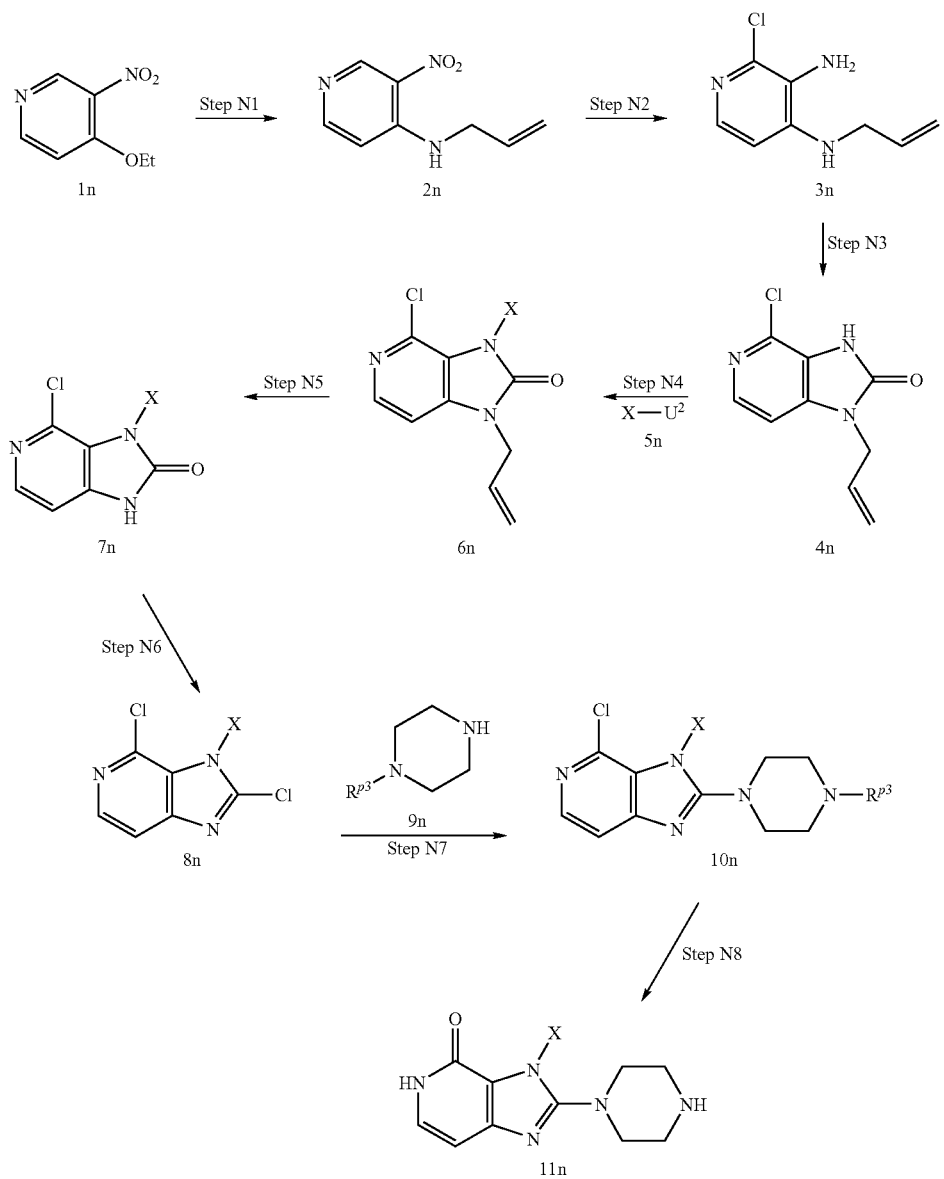

75

The reaction can be achieved using a solvent such as acetonitrile or tetrahydrofuran. The reaction can be conducted at a temperature ranging from 20° C. to 100° C.

[Step N4]

In this step, compound (4n) is reacted with compound (5n) to give compound (6n). The reaction can be conducted under the same conditions as used in [Step A4] of production method A.

[Step N5]

In this step, the allyl group is removed from compound (6n) to give compound (7n).

Compound (7n) can be obtained, for example, by reacting compound (6n) with osmic acid and sodium periodate in a solvent such as tetrahydrofuran, 1,4-dioxane, 1,2-dimethoxyethane, or water at a temperature ranging from 20° C. to 100° C. However, the reaction conditions are not limited to this example.

76

[Step N6]

In this step, compound (7n) is chlorinated to give compound (8n).

There are no particular limitations on the reaction conditions. The reaction can be conducted under standard reaction conditions to be used for chlorination. Compound (8n) can be obtained, for example, by using a reagent such as phosphorus pentachloride in a solvent such as phosphorus oxychloride, at a temperature of 0 to 150° C.

[Step N7]

In this step, compound (8n) is reacted with compound (9n) to give compound (10n). The reaction can be conducted under the same conditions as used in [Step A6] of production method A.

[Step N8]

In this step, $R^{p3}$ of compound (10n) is removed to give compound (11n). The reaction can be conducted under the same conditions as used in [Step A13] of production method A.

Production Method O

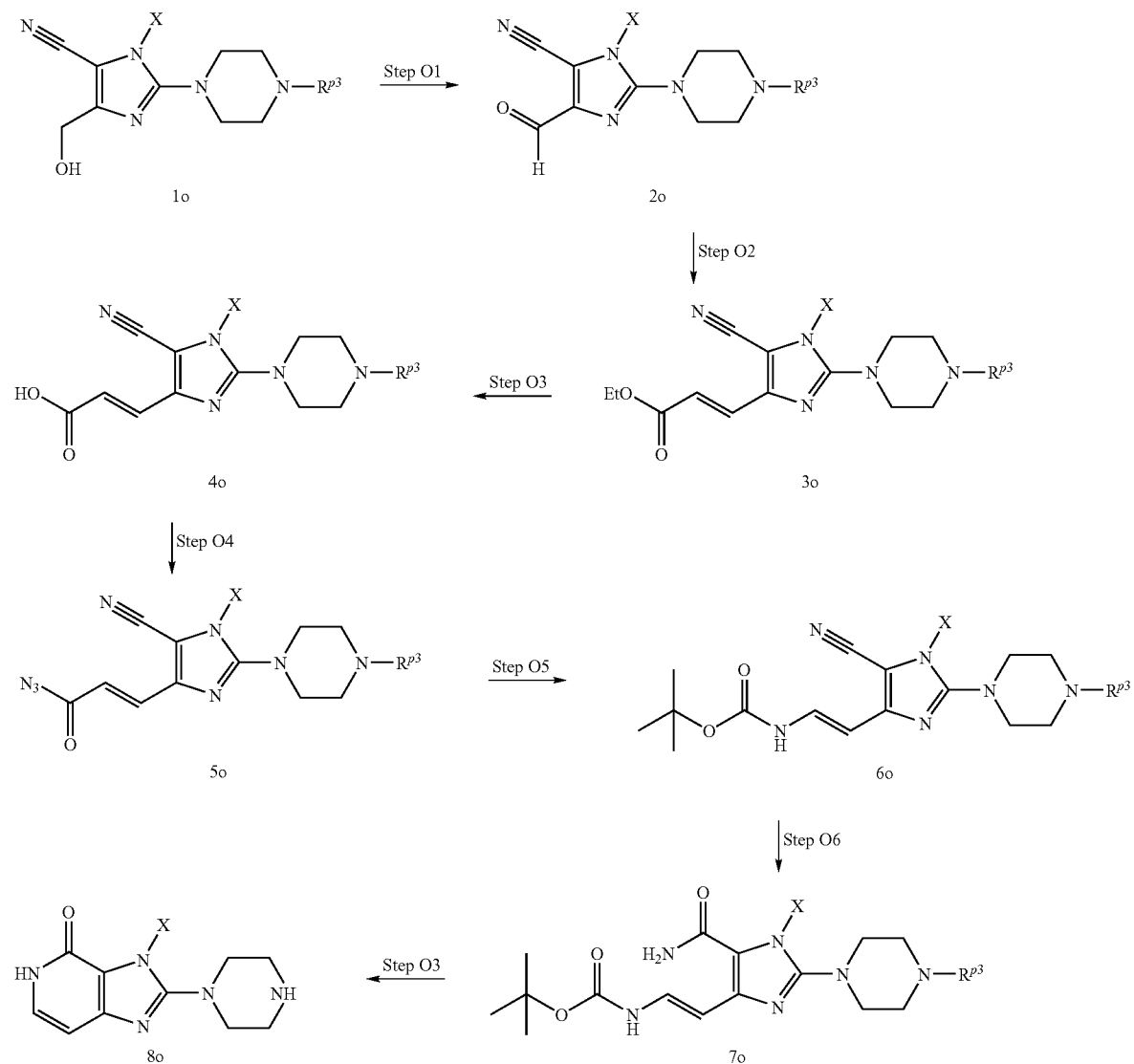

[Step O1]

In this step, the hydroxyl group of compound (1o) is oxidized to give compound (2o). The reaction can be conducted under the same conditions as used in [Step I2] of production method I.

[Step O2]

In this step, compound (2o) is reacted with ethyl diethylphosphonoacetate in the presence of a base to give compound (3o).

Bases include sodium hydride and lithium diisopropylamide. Solvents include, for example, tetrahydrofuran and N,N-diformamide. The reaction can be conducted at a temperature ranging from 0° C. to 100° C.

[Step O3]

In this step, the ester of compound (3o) is hydrolyzed to give compound (4o). The reaction can be conducted under the same condition as used in [Step C16] of production method C.

[Step O4]

In this step, compound (4o) is reacted with diphenylphosphoryl azide in the presence of a base to give compound (5o).

Solvents for the reaction include toluene, t-butanol, tetrahydrofuran, and dichloromethane. Bases include tertiary amines such as triethylamine and diisopropylethylamine. The reaction can be conducted at a temperature ranging from −50° C. to 50° C.

[Step O5]

In this step, compound (5o) is rearranged to give compound (6o).

The reaction can be achieved in t-butanol at a temperature ranging from 50° C. to 100° C.

[Step O6]

In this step, the nitrile group of compound (6o) is hydrolyzed to give compound (7o). The reaction can be conducted under the same conditions as used in [Step H1] of production method H.

[Step O7]

In this step, compound (7o) is reacted with an acid to give compound (8o).

Acids include hydrochloric acid, sulfuric acid, and trifluoroacetic acid. Solvents include methanol, ethanol, 1,4-dioxane, water, and mixtures thereof. The reaction can be conducted at a temperature ranging from 0° C. to 50° C.

Production Method P

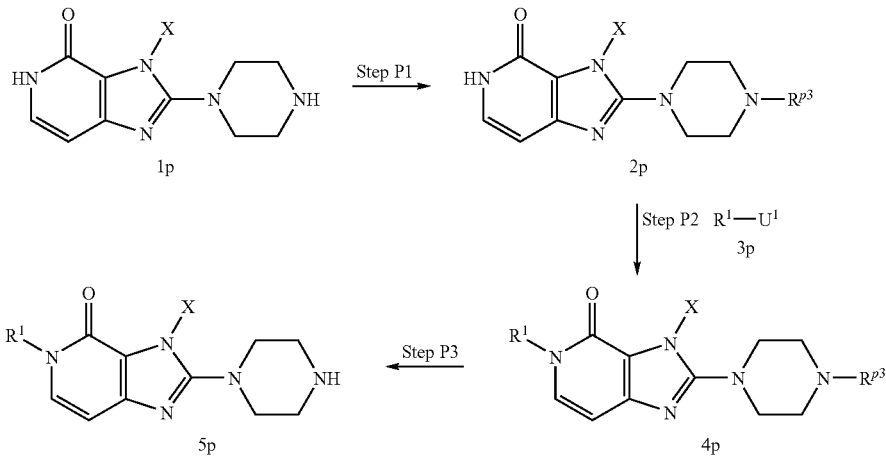

[Step P1]

In this step, compound (1p) is protected to give compound (2p).

A typical NH group-protecting reagent that is generally used in protecting NH groups can be used as an NH group-protecting reagent. For example, when $R^{p3}$ is a t-butoxycarbonyl group, the reaction can be achieved at a temperature ranging from 0 to 80° C. using a reagent such as di-t-butyl dicarbonate, in a solvent such as dichloromethane, chloroform, N,N-dimethylformamide, and tetrahydrofuran, in the presence of a base such as pyridine, 4-aminopyridine, triethylamine, and N,N-diisopropylethylamine.

[Step P2]

In this step, compound (2p) is reacted with compound (3p) to give compound (4p). The reaction can be conducted under the same conditions as used in [Step A2] of production method A.

[Step P3]
In this step, $R^{p3}$ of compound (4p) is removed to give compound (5p). The reaction can be conducted under the same conditions as used in [Step A13] of production method A.
Production Method Q
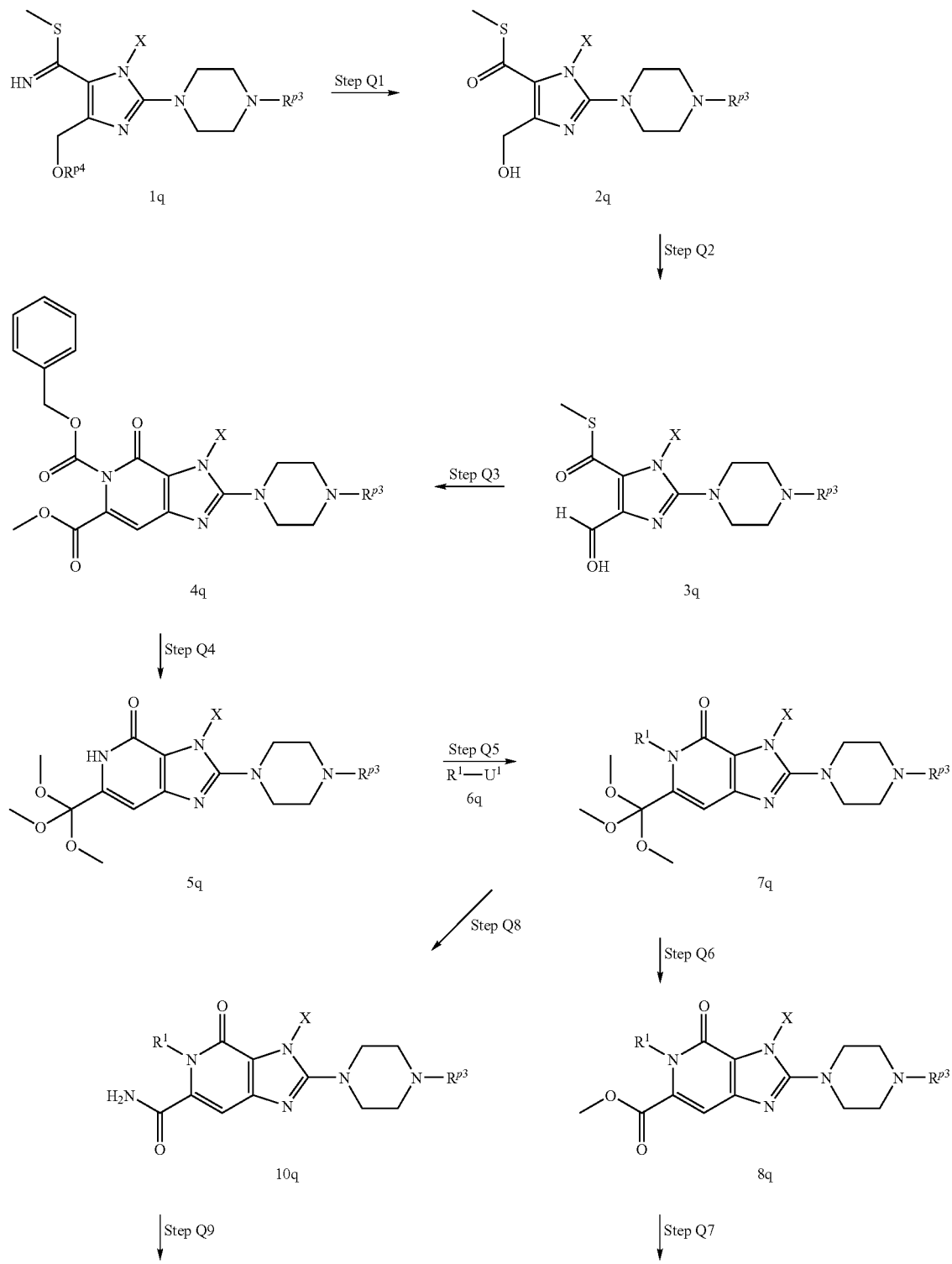

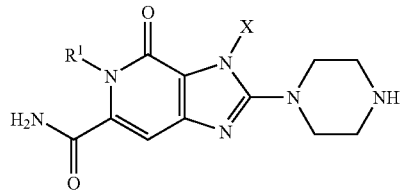

11q

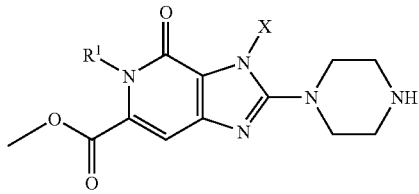

9q

[Step Q1]

In this step, compound (1q) is hydrolyzed to give compound (2q).

Reaction solvents include tetrahydrofuran, methanol, and ethanol. Acids include inorganic acids such as hydrochloric acid and sulfuric acid. The reaction can be conducted at a temperature ranging from 0° C. to 100° C.

[Step Q2]

In this step, the hydroxyl group of compound (2q) is oxidized to give compound (3q). The reaction can be conducted under the same conditions as used in [Step I2] of production method I.

[Step Q3]

In this step, compound (3q) is reacted with methyl benzyloxycarbonylamino(dimethoxyphosphoryl)acetate in the presence of a base to give compound (4q).

Bases include sodium hydride, potassium t-butoxide, and 8-diazabicyclo[5.4.0]-7-undecene. Solvents include dichloromethane, tetrahydrofuran, and N,N-dimethylformamide. The reaction can be conducted at a temperature ranging from 0° C. to 100° C.

[Step Q4]

In this step, compound (4q) is reacted with sodium methoxide to give compound (5q).

Methanol can be used as solvent. The reaction can be conducted at a temperature ranging from 0° C. to 80° C.

[Step Q5]

In this step, compound (5q) is reacted with compound (6q) to give compound (7q). The reaction can be conducted under the same conditions as used in [Step A2] of production method A.

[Step Q6]

In this step, compound (7q) is reacted with an acid to give compound (8q). The reaction can be conducted under the same conditions as used in [Step O7] of production method O.

[Step Q7]

In this step, $R^{p3}$ of compound (8q) is removed to give compound (9q). The reaction can be conducted under the same conditions as used in [Step A13] of production method A.

[Step Q8]

In this step, compound (7q) is reacted with ammonia to give compound (10q).

Reaction solvents include methanol, ethanol, and water. The reaction can be conducted at a temperature ranging from 20° C. to 150° C.

[Step Q9]

In this step, $R^{p3}$ of compound (10q) is removed to give compound (11q). The reaction can be conducted under the same conditions as used in [Step A13] of production method A.

The compounds indicated below, salts thereof, or hydrates thereof, are exceedingly useful as intermediates in the synthesis of compound (I) of the present invention.

Compounds, or salts thereof, or hydrates thereof, represented by the formula:

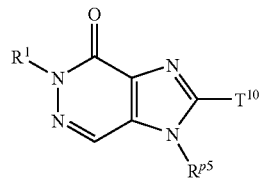

[where $R^1$ is defined as in [1] above;

$R^{p5}$ represents a t-butoxycarbonyloxy group, a trityl group, or a group represented by the formula $-SO_2NH_2$;

$T^{10}$ represents a halogen atom or a hydrogen atom];

Compounds, or salts thereof, or hydrates thereof, represented by the formula:

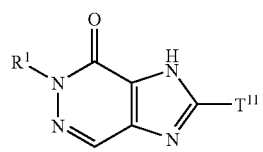

[where $R^1$ is defined as in [1] above;

$T^{11}$ represents a halogen atom or a group represented by the formula:

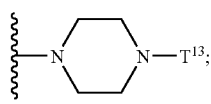

$T^{13}$ represents a t-butoxycarbonyl group, a benzyloxycarbonyl group, or a formyl group];

Compounds, or salts thereof, or hydrates thereof, represented by the formula:

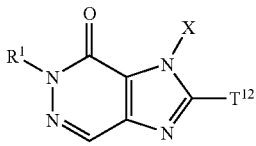

[where $R^1$ and X are defined as in [1] above;

$T^{12}$ represents a halogen atom];

Compounds, or salts thereof, or hydrates thereof, represented by the formula:

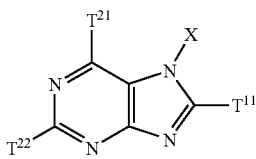

[where X is defined as in [1] above, but excluding the case where X is a benzyl group;

$T^{21}$ and $T^{22}$ each independently represent a halogen atom;

$T^{11}$ represents a halogen atom or a group represented by the formula:

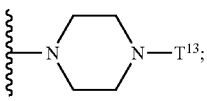

$T^{13}$ represents a t-butoxycarbonyl group, a benzyloxycarbonyl group, or a formyl group];

Compounds, or salts thereof, or hydrates thereof, represented by the formula:

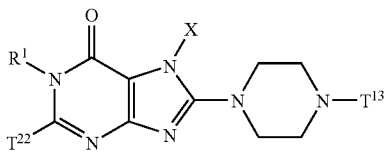

[where X and $R^1$ are defined as in [1] above;

$T^{22}$ represents a halogen atom;

$T^{13}$ represents a t-butoxycarbonyl group, a benzyloxycarbonyl group, or a formyl group].

The methods indicated above are representative methods for producing compound (I) of the present invention. The starting compounds and various reagents to be used in the methods for producing compounds of the present invention may be salts or hydrates, or solvates depending on the type of starting materials, solvents to be used, or such, and are not limited as long as they do not inhibit the reactions. The type of solvents to be used depends on the types of starting compounds, reagents to be used, or such, and is not limited as long as it does not inhibit the reactions and dissolves starting materials to some extent. When compound (I) of the present invention is obtained in a free form, such a compound can be converted to a salt or a hydrate, which is a possible form of compound (I) described above, according to a conventional method.

When compound (I) of the present invention is obtained as a salt or a hydrate, such a product can be converted to a free form of compound (I) described above according to a conventional method.

In addition, various isomers of compound (I) of the present invention (for example, geometric isomers, enantiomers on the basis of asymmetric carbon, rotamers, stereoisomers, and tautomers) can be purified and isolated by typical isolation means, for example, including recrystallization, diastereomer salt method, enzyme-based separation, and various chromatographic methods (for example, thin layer chromatography, column chromatography, and gas chromatography).

Compounds of the present invention, salts thereof, or hydrates thereof, can be formulated into tablets, powders, particles, granules, coated tablets, capsules, syrups, troches, inhalants, suppositories, injections, ointments, eye ointments, eye drops, nasal drops, ear drops, epithem, lotions, etc. by conventional methods. Such formulation can be achieved by using typical diluting agents, binders, lubricants, colorants, flavoring agents, and if required, stabilizers, emulsifiers, absorbefacients, surfactants, pH modulators, preservatives, antioxidants, etc., and materials commonly used as ingredients of pharmaceutical preparations according to conventional methods. For example, an oral preparation can be produced by combining a compound of the present invention or a pharmaceutically acceptable salt thereof with a diluting agent, and if required, a binder, a disintegrating agent, a lubricant, a colorant, a flavoring agent, or such, and formulating the mixture into powders, particles, granules, tablets, coated tablets, capsules, or the like according to conventional methods. Examples of the materials include, for example, animal and vegetable oils such as soya bean oil, beef tallow, and synthetic glyceride; hydrocarbons such as liquid paraffin, squalane, and solid paraffin; ester oils such as octyldodecyl myristate and isopropyl myristate; higher alcohols such as cetostearyl alcohol and behenyl alcohol; silicon resins; silicone oils; surfactants such as polyoxyethylene fatty acid ester, sorbitan fatty acid ester, glycerol fatty acid ester, polyoxyethylene sorbitan fatty acid ester, polyoxyethylene hydrogenated castor oil, and polyoxyethylene polyoxypropylene block co-polymer; water-soluble polymers such as hydroxyethyl cellulose, poly-acrylic acid, carboxyvinyl polymer, polyethylene glycol, polyvinylpyrrolidone, and methyl cellulose; lower alcohols such as ethanol and isopropanol; polyhydric alcohols such as glycerol, propylene glycol, dipropylene glycol, and sorbitol; sugars such as glucose and sucrose; inorganic powder such as anhydrous silicic acid, magnesium aluminum silicate, and aluminum silicate; and pure water. Diluting agents include, for example, lactose, corn starch, white sugar, glucose, mannitol, sorbitol, crystal cellulose, and silicon dioxide. Binders include, for example, polyvinyl alcohol, polyvinyl ether, methyl cellulose, ethyl cellulose, gum arabic, tragacanth, gelatin, shellac, hydroxypropyl methyl cellulose, hydroxypropyl cellulose, polyvinylpyrrolidone, polypropylene glycol-polyoxyethylene block co-polymer, and meglumine. Disintegrating agents include, for example, starch, agar, gelatin powder, crystalline cellulose, calcium carbonate, sodium bicarbonate, calcium citrate, dextrin, pectin, and calcium carboxymethyl cellulose. Lubricants include, for example, magnesium stearate, talc, polyethylene glycol, silica, and hydrogenated vegetable oil. Colorants include those pharmaceutically acceptable. Flavoring agents include cocoa powder, peppermint camphor, aromatic powder peppermint oil, Borneo camphor, and cinnamon powder. Tablets and granules may be coated with sugar, or if required, other appropriate coatings can be made. Solution, such as syrups or injectable preparations, to be administered can be formulated by combining a compound of the present invention or a pharmaceutically acceptable salt thereof with a pH modulator, a solubilizing agent, an isotonizing agent, or such, and if required, with an auxiliary solubilizing agent, a stabilizer, or the like, according to conventional methods. Methods for producing an external preparation are not limited and such preparations can be produced by conventional methods. Specifically, various materials typically used for producing pharmaceuticals, quasi drugs, cosmetics, and such can be used as base materials for the external formulation. Specifically, base materials to be used include, for example, animal and vegetable oils, mineral oils, ester oil, wax, higher alcohols, fatty acids, silicone oil, surfactants, phospholipids, alcohols, polyhydric alcohols, water-soluble polymers, clay minerals, and pure water. Furthermore, external preparations of the present invention can contain, as required, pH modulators, antioxidants, chelating agents, antibacterial/antifungal agents, coloring matters, odoriferous substances, etc. But this does not limit the type of base materials that are to be used in an external preparation of the present invention. If required, the preparation may contain differentiation inducers, blood flow improving agents, antimicrobial agents, antiphlogistics, cell activators, vitamins, amino acids, humectants, keratolytic agents, etc. The amount of base materials listed above is adjusted within a concentration range used for producing typical external preparations.

When a compound of the present invention, or a salt thereof, or a hydrate thereof is administered, the forms of a compound are not limited and a compound can be given orally or parenterally by a conventional method. For example, a compound can be administered as a dosage form such as tablets, powders, granules, capsules, syrups, troches, inhalants, suppositories, injections, ointments, eye ointments, eye drops, nasal drops, ear drops, epithems, and lotions. The dose of a pharmaceutical of the present invention can be selected appropriately based on symptom severity, age, sex, weight, forms of compounds, type of salts, specific type of diseases, etc.

The dose varies depending on the patient's disease, symptom severity, age and sex, drug susceptibility, etc. A pharmaceutical agent of this invention is administered once or several times at a dose of approx. 0.03 to approx. 1000 mg/adult/day, preferably 0.1 to 500 mg/adult/day, more preferably 0.1 to 100 mg/adult/day. An injection can be given at a dose of approx. 1 to approx. 3000 µg/kg, preferably approx. 3 to approx. 1000 µg/kg.

Compounds of the present invention can be produced, for example, by the methods described in Examples below. However, the compounds of the present invention are under no circumstances to be construed as being limited to specific examples described below.

All patents and publications mentioned herein are incorporated by reference.

PRODUCTION EXAMPLE

Production Example 1 t-Butyl 4-[1-(2-butynyl)-6-methyl-7-oxo-6,7-dihydro-1H-imidazo[4,5-d]pyridazin-2-yl]piperazin-1-carboxylate (a) t-Butyl 5-methyl-4-oxo-4,5-dihydroimidazo[4,5-d]pyridazine-1-carboxylate A mixture consisting of 1.0 g of 5-methyl-3,5-dihydroimidazo[4,5-d]pyridazin-4-one, 16 mg of 4-dimethylaminopyridine, 1.6 g of di-t-butyl dicarbonate, and 5 ml of tetrahydrofuran was stirred at room temperature overnight. Then, a 0.5-ml tetrahydrofuran solution containing 300 mg of di-t-butyl dicarbonate was added to the solution, and the resulting mixture was stirred at room temperature for three hours. 5 ml of t-butyl methyl ether was added to the reaction mixture, and the mixture was cooled with ice. The resulting crystals were collected by filtration to give 1.63 g of the title compound.

$^1$H-NMR (CDCl$_3$)

δ 1.72 (s, 9H) 3.93 (s, 3H) 8.38 (s, 1H) 8.54 (s, 1H)

(b) 2-Chloro-5-methyl-1,5-dihydroimidazo[4,5-d]pyridazin-4-one 8.4 ml of lithium hexamethyldisilazide (1.0 M tetrahydrofuran solution) was added dropwise over one hour to a 300-ml tetrahydrofuran solution containing 1.68 g of t-butyl 5-methyl-4-oxo-4,5-dihydroimidazo[4,5-d]pyridazine-1-carboxylate and 4.15 g of hexachloroethane under a nitrogen atmosphere at 0° C. The resulting mixture was stirred for 30 minutes. 2N ammonia water was added to the solution, and the mixture was stirred for three hours. Then, the reaction solution was concentrated to 50 ml, and washed with 20 ml of t-butyl methyl ether. The solution was acidified with concentrated hydrochloric acid. The resulting precipitate was collected by filtration, and washed successively with 10 ml of water and 10 ml of t-butyl methyl ether. Thus, 1.03 g of the title compound was obtained.

$^1$H-NMR (DMSO-d6)

δ 1.45 (s, 9H) 3.72 (s, 3H) 8.33 (s, 1H)

(c) 3-(2-Butynyl)-2-chloro-5-methyl-3,5-dihydroimidazo[4,5-d]pyridazin-4-one 7.72 g of 2-chloro-5 methyl-1,5-dihydroimidazo[4,5-d]-pyridazin-4-one was suspended in 400 ml of tetrahydrofuran under a nitrogen atmosphere, and 14.22 g of triphenylphosphine and 3.85 g of 2-butyn-1-ol were added thereto. The resulting mixture was cooled to 0° C. A 100-ml tetrahydrofuran solution containing 12.55 g of azodicarboxylic acid di-t-butyl ester was added dropwise, and the reaction mixture was stirred for three hours. The reaction mixture was concentrated under reduced pressure. 50 ml of dichloromethane and 50 ml of trifluoroacetic acid were added to the residue, and the mixture was stirred for 15 hours. The reaction mixture was concentrated under reduced pressure. The resulting residue was dissolved in 400 ml of ethyl acetate, and washed with a 200 ml of a 5N aqueous sodium hydroxide solution. The aqueous layer was extracted with 100 ml of ethyl acetate. The organic layers were combined together, dried over magnesium sulfate, and concentrated under reduced pressure. The resulting residue was purified by silica gel column chromatography. Thus, 8.78 g of the title compound was obtained from the fraction eluted with hexane-ethyl acetate (4:1).

$^1$H-NMR (CDCl$_3$)

δ 1.82 (t, J=2.3 Hz, 3H) 3.87 (s, 3H) 5.32 (q, J=2.3 Hz, 2H) 8.19 (s, 1H)

(d) t-Butyl 4-[1-(2-butynyl)-6-methyl-7-oxo-6,7-dihydro-1H-imidazo[4,5-d]pyridazin-2-yl]piperazine-1-carboxylate 5 ml of 1-methyl-2-pyrrolidone was added to a mixture consisting of 1.183 g of 3-(2-butynyl)-2-chloro-5-methyl-3,5-dihydroimidazo[4,5-d]pyridazin-4-one, 0.829 g of potassium carbonate, and 1.395 g of t-butyl piperazine-1-carboxylate under a nitrogen atmosphere. The resulting mixture was heated at 130° C. for 6 hours. The reaction mixture was cooled, and 50 ml of water was added thereto. Then, the mixture was extracted with 100 ml of ethyl acetate. The organic layer was washed twice with 50 ml of water and then with 50 ml of an aqueous solution saturated with sodium chloride. The organic layer was dried over magnesium sulfate, and concentrated under reduced pressure. The resulting residue was purified by silica gel column chromatography. Thus, 1.916 g of the title compound was obtained from the fraction eluted with hexane-ethyl acetate (1:4).

$^1$H-NMR (CDCl$_3$)

δ 1.52 (s, 9H) 1.83 (t, J=2.3 Hz, 3H) 3.38-3.42 (m, 4H) 3.61-3.64 (m, 4H) 3.85 (s, 3H) 5.09 (q, J=2.3 Hz, 2H) 8.13 (s, 1H)

Production Example 2 t-Butyl 4-[7-(2-butynyl)-2,6-dichloro-7H-purin-8-yl]piperazine-1-carboxylate (a) 7-(2-Butynyl)-3-methyl-3,7-dihydropurine-2,6-dione 55.3 ml of 1-bromo-2-butyne and 84.9 g of anhydrous potassium carbonate were added to a mixture of 100 g of 3-methyl xanthine [CAS No. 1076-22-8] and 1000 ml of N,N-dimethylformamide. The resulting mixture was stirred at room temperature for 18 hours. 1000 ml of water was added to the reaction solution, and the mixture was stirred at room temperature for 1 hour. The resulting white precipitate was collected by filtration. The white solid was washed with water and then t-butyl methyl ether. Thus, 112 g of the title compound was obtained.

$^1$H-NMR (DMSO-d6)

δ 1.82 (t, J=2.2 Hz, 3H) 3.34 (s, 3H) 5.06 (q, J=2.2 Hz, 2H) 8.12 (s, 1H) 11.16 (br.s, 1H).

(b) 7-(2-Butynyl)-8-chloro-3-methyl-3,7-dihydropurine-2,6-dione 112 g of 7-(2-butynyl)-3-methyl-3,7-dihydropurine-2,6-dione was dissolved in 2200 ml of N,N-dimethylformamide, and 75.3 g of N-chlorosuccinimide was added thereto. The resulting mixture was stirred at room temperature for five hours. 2200 ml of water was added to the reaction solution, and the mixture was stirred at room temperature for 1.5 hour. The white precipitate was collected by filtration, and the white solid was washed with water and, with t-butyl methyl ether. Thus, 117 g of the title compound was obtained.

$^1$H-NMR (DMSO-d6)

δ 1.78 (t, J=2.0 Hz, 3H) 3.30 (s, 3H) 5.06 (q, J=2.0 Hz, 2H) 11.34 (br.s, 1H)

(c) 7-(2-Butynyl)-2,6,8-trichloro-7H-purine

A mixture of 2.52 g of 7-(2-butynyl)-8-chloro-3-methyl-3,7-dihydropurine-2,6-dione and 100 ml of phosphorus oxychloride was stirred at 120° C. for 14 hours. After the reaction mixture had been cooled, 4.15 g of phosphorus pentachloride was added to the solution. The resulting mixture was stirred at 120° C. for 24 hours. After the reaction solution had been cooled to room temperature, the solvent was evaporated under reduced pressure. The residue was dissolved in tetrahydrofuran. The solution was poured into a saturated sodium bicarbonate solution, and the mixture was extracted with ethyl acetate. The resulting organic layer was washed with water, then saturated brine, and was then concentrated under reduced pressure. The residue was purified by silica gel column chromatography (ethyl acetate:hexane=1:3) to give 2.40 g of the title compound.

$^1$H-NMR (CDCl$_3$)

δ 1.82 (t, J=2.4 Hz, 3H) 5.21 (q, J=2.4 Hz, 2H)

(d) t-Butyl 4-[7-(2-butynyl)-2,6-dichloro-7H-purin-8-yl]piperazine-1-carboxylate A mixture of 2.4 g of 7-(2-butynyl)-2,6,8-trichloro-7H-purine, 1.46 g of sodium bicarbonate, 2.43 g of t-butyl piperazine-1-carboxylate, and 45 ml of acetonitrile was stirred at room temperature for 2 hours and 20 minutes. Then, 0.73 g of sodium bicarbonate and 1.21 g of t-butyl piperazine-1-carboxylate were added, and the resulting mixture was stirred at room temperature for 1 hour. The reaction mixture was extracted with ethyl acetate-water, and the organic layer was washed with 1N hydrochloric acid, dried over anhydrous magnesium sulfate, and then concentrated under reduced pressure. The residue was triturated with diethyl ether. The crystals were collected by filtration, and washed with diethyl ether. Thus, 3.0 g of the title compound was obtained as a white solid.

$^1$H-NMR (DMSO-d6)

δ 1.42 (s, 9H) 1.83 (t, J=2 Hz, 3H) 3.48-3.55 (m, 4H) 3.57-3.63 (m, 4H) 4.89 (q, J=2 Hz, 2H)

EXAMPLE

Example 1

Ethyl [7-(2-chlorophenyl)-1-methyl-6-oxo-8-(piperazin-1-yl)-6,7-dihydro-1H-purin-2-yloxy]acetate trifluoroacetate (a) [7-Benzyl-2,6-dioxo-1,2,6,7-tetrahydropurin-3-yl]methyl 2,2-dimethylpropionate 8.66 g of 7-benzylxanthine was dissolved in 300 ml of N,N-dimethylformamide, and 1.57 g of sodium hydride and 7.7 ml of chloromethyl pivalate were added thereto. The resulting mixture was stirred at room temperature overnight. The reaction solution was diluted with ethyl acetate, and washed with water and 1N hydrochloric acid. The organic layer was dried over anhydrous magnesium sulfate, then filtered. The solvent was evaporated under reduced pressure. The residue was purified by silica gel column chromatography. Thus, 2.66 g of the title compound was obtained from the fraction eluted with hexane-ethyl acetate (1:1).

$^1$H-NMR (CDCl$_3$)

δ 1.18 (s, 9H) 5.45 (s, 2H) 6.06 (s, 2H) 7.34-7.39 (m, 5H) 7.58 (s, 1H) 8.18 (s, 1H)

(b) [7-Benzyl-1-methyl-2,6-dioxo-1,2,6,7-tetrahydropurin-3-yl]methyl 2,2-dimethylpropionate 2.66 g of [7-benzyl-2,6-dioxo-1,2,6,7-tetrahydropurin-3-yl]methyl 2,2-dimethylpropionate was dissolved in 30 ml of N,N-dimethylformamide, and 1.6 g of potassium carbonate and 1 ml of methyl iodide were added thereto. The mixture was stirred at room temperature overnight. The reaction mixture was diluted with ethyl acetate, and washed with water and 1N hydrochloric acid. The organic layer was dried over anhydrous magnesium sulfate, then filtered. The solvent was evaporated under reduced pressure. The residue was triturated with toluene. Thus, 2.16 g of the title compound was obtained.

$^1$H-NMR (CDCl$_3$)

δ 1.18 (s, 9H) 3.41 (s, 3H) 5.49 (s, 2H) 6.11 (s, 2H) 7.26-7.39 (m, 5H) 7.57 (s, 1H)

(c) [1-Methyl-2,6-dioxo-1,2,6,7-tetrahydropurin-3-yl]methyl 2,2-dimethylpropionate 2.349 g of [7-benzyl-1-methyl-2,6-dioxo-1,2,6,7-tetrahydropurin-3-yl]methyl 2,2-dimethylpropionate was dissolved in 100 ml of acetic acid, and 1 g of 10% palladium carbon was added thereto. The mixture was stirred under a hydrogen atmosphere at room temperature overnight. The reaction mixture was filtered and concentrated to give 1.871 g of the title compound.

$^1$H-NMR (CDCl$_3$)

δ 1.19 (s, 9H) 3.48 (s, 3H) 6.17 (s, 2H) 7.83 (s, 1H).

(d) [7-(2-Chlorophenyl)-1-methyl-2,6-dioxo-1,2,6,7-tetrahydropurin-3-yl]methyl 2,2-dimethylopropionate 1.60 g of [1-methyl-2,6-dioxo-1,2,6,7-tetrahydropurin-3-yl]methyl 2,2-dimethylpropionate, 1.83 g of 2-chlorophenylboronic acid, and 1.5 g of copper (II) acetate were suspended in 30 ml of N,N-dimethylformamide, and 3 ml of pyridine was added thereto. The mixture was stirred at room temperature for 3 days. The reaction mixture was filtered through a short column filled with silica gel, and the filtrate was diluted with ethyl acetate. The organic layer was washed with 1N hydrochloric acid, water, and saturated saline, and dried over anhydrous magnesium sulfate, then filtered. The filtrate was concentrated. The residue was suspended in ether, and the suspension was filtered. The filtrate was purified by silica gel column chromatography. Thus, 724 mg of the title compound was obtained from the fraction eluted with hexane-ethyl acetate (3:2).

(e) t-Butyl 4-[7-(2-chlorophenyl)-3-(2,2-dimethylpropionyloxymethyl)-1-methyl-2,6-dioxo-2,3,6,7-tetrahydro-1H-purin-8-yl]piperazine-1-carboxylate 724 mg of [7-(2-chlorophenyl)-1-methyl-2,6-dioxo-1,2,6,7-tetrahydropurin-3-yl]methyl 2,2-dimethylpropionate was suspended in 15 ml of N,N-dimethylformamide, and 760 mg of N-chlorosuccinimide was added thereto. The reaction solution was stirred overnight, and then diluted with ethyl acetate. The solution was washed with water and 1N hydrochloric acid, and dried over anhydrous magnesium sulfate, then filtered. The filtrate was concentrated. Thus, 764 mg of [8-chloro-7-(2-chlorophenyl)-1-methyl-2,6-dioxo-1,2,6,7-tetrahydropurin-3-yl]methyl 2,2-dimethylpropionate was obtained. This compound was mixed with 4 g of t-butyl piperazine-1-carboxylate. The mixture was heated at 150° C., and stirred for three hours. Ethyl acetate and water were added to the reaction mixture, and the mixture was separated. The organic layer was washed with 1N hydrochloric acid, and dried over anhydrous magnesium sulfate, then filtered. The filtrate was concentrated. The residue was purified by silica gel column chromatography. Thus, 724 mg of the title compound was obtained from the fraction eluted with hexane-ethyl acetate (3:2).

(f) t-Butyl 4-[7-(2-chlorophenyl)-1-methyl-2,6-dioxo-2,3,6,7-tetrahydro-1H-purin-8-yl]piperazine-1-carboxylate t-Butyl 4-[7-(2-chlorophenyl)-3-(2,2-dimethylpropionyloxy methyl)-1-methyl-2,6-dioxo-2,3,6,7-tetrahydro-1H-purin-8-yl]piperazine-1-carboxylate was dissolved in a mixture of 10 ml of methanol and 20 ml of tetrahydrofuran, and 200 mg of sodium hydride was added thereto. The resulting mixture was stirred at room temperature overnight. 1N hydrochloric acid was added to the reaction solution, and the mixture was extracted with ethyl acetate. The organic layer was dried over anhydrous magnesium sulfate, then filtered. The filtrate was concentrated. The residue was suspended in ether and the mixture was filtered. Thus, 450 mg of the title compound was obtained.

$^1$H-NMR (DMSO-d$^6$)

δ 1.35 (s, 9H) 3.04 (s, 3H) 3.06-3.12 (m, 4H) 3.17-3.22 (m, 4H) 7.48 (dt, J=1.6, 7.6 Hz, 1H) 7.53 (dt, J=2.0, 7.6 Hz, 1H) 7.63 (dd, J=2.0, 8.0 Hz, 1H) 7.65 (dd, J=1.6, 8.0 Hz, 1H).

(g) t-Butyl 4-[2-chloro-7-(2-chlorophenyl)-1-methyl-6-oxo-6,7-dihydro-1H-purin-8-yl]piperazine-1-carboxylate (g-1), and t-butyl 4-[2,6-dichloro-7-(2-chlorophenyl)-7H-purin-8-yl]piperazine-1-carboxylate (g-2)

78 mg of t-butyl 4-[7-(2-chlorophenyl)-1-methyl-2,6-dioxo-2,3,6,7-tetrahydro-1H-purin-8-yl]piperazine-1-carboxylate was dissolved in 3 ml of phosphorus oxychloride, and the mixture was stirred at 120° C. overnight. The reaction solution was concentrated, and the residue was dissolved in 1 ml of tetrahydrofuran. This solution was poured into a suspension consisting of 50 mg of di-t-butyl dicarbonate, 1 ml of tetrahydrofuran, and 0.5 ml of water containing 100 mg of sodium bicarbonate. The resulting mixture was stirred at room temperature for three hours. The reaction mixture was diluted with ethyl acetate and washed with water. The organic layer was dried over anhydrous magnesium sulfate, then filtered. The filtrate was concentrated, and the residue was purified by silica gel column chromatography. Thus, 16 mg of t-butyl 4-[2,6-dichloro-7-(2-chlorophenyl)-7H-purin-8-yl]piperazine-1-carboxylate was obtained from the fraction eluted with hexane-ethyl acetate (3:2), and 10 mg of t-butyl 4-[2-chloro-7-(2-chlorophenyl)-1-methyl-6-oxo-6,7-dihydro-1H-purin-8-yl]piperazine-1-carboxylate was obtained from the fraction eluted with hexane-ethyl acetate (1:9).

(h) Ethyl [7-(2-chlorophenyl)-1-methyl-6-oxo-8-(piperazin-1-yl)-6,7-dihydro-1H-purin-2-yloxy]acetate trifluoroacetate 10 mg of t-butyl 4-[2-chloro-7-(2-chlorophenyl)-1-methyl-6-oxo-6,7-dihydro-1H-purin-8-yl]piperazine-1-carboxylate and 10 mg of ethyl glycolate were dissolved in 0.2 ml of N-methylpyrrolidone, and 10 mg of sodium hydride was added thereto. The mixture was stirred at room temperature for 2 hours. The reaction solution was dissolved in ethyl acetate, and the mixture was washed with 1N hydrochloric acid. Thus, 24 mg of t-butyl 4-[7-(2-chlorophenyl)-2-ethoxycarbonylmethoxy-1-methyl-6-oxo-6,7-dihydro-1H-purin-8-yl]piperazine-1-carboxylate was obtained. 8 mg of this compound was dissolved in trifluoroacetic acid, and the mixture was concentrated. The residue was purified by reverse-phase high performance liquid chromatography (using an acetonitrile-water mobile phase (containing 0.1% trifluoroacetic acid)) to give 2.11 mg of the title compound.

MS m/e (ESI) 447 (MH$^+$-CF$_3$COOH)

Example 2

[7-(2-chlorophenyl)-1-methyl-6-oxo-8-(piperazin-1-yl)-6,7-dihydro-1H-purin-2-yloxy]acetic acid trifluoroacetate 16 mg of t-butyl 4-[7-(2-chlorophenyl)-2-ethoxycarbonylmethoxy-1-methyl-6-oxo-6,7-dihydro-1H-purin-8-yl]piperazine-1-carboxylate was combined with 0.4 ml of methanol and 0.1 ml of a 5N aqueous sodium hydroxide solution, and the mixture was allowed to stand at room temperature for two hours. 1N hydrochloric acid was added to the reaction solution. The acidified solution was extracted with ethyl acetate. The organic layer was concentrated, and the residue was dissolved in trifluoroacetic acid. The mixture was concentrated, and the residue was purified by reverse-phase high performance liquid chromatography (using an acetonitrile-water mobile phase (containing 0.1% trifluoroacetic acid)) to give 2.45 mg of the title compound.

MS m/e (ESI) 419 (MH$^+$-CF$_3$COOH)

Example 3

7-(2-Chlorophenyl)-2-cyclobutyloxy-8-(piperazin-1-yl)-1,7-dihydropurin-6-one (a) [7-Benzyl-3-(2,2-dimethylpropionyloxymethyl)-2,6-dioxo-2,3,6,7-tetrahydropurin-1-yl]methyl 2,2-dimethylpropionate 9.54 g of 7-benzylxanthine was dissolved in 250 ml of N,N-dimethylformamide, and 17 g of potassium carbonate and 14.2 ml of chloromethyl pivalate were added thereto. The mixture was stirred at 50° C. overnight. The reaction mixture was diluted with ethyl acetate, and washed with water and 1N hydrochloric acid. The organic layer was dried over anhydrous magnesium sulfate, then filtered. The solvent was evaporated under reduced pressure, and the residue was purified by silica gel column chromatography. Thus, 12.8 g of the title compound was obtained from the fraction eluted with hexane-ethyl acetate (3:2).

(b) [3-(2,2-Dimethylpropionyloxymethyl)-2,6-dioxo-2,3,6,7-tetrahydro purin-1-yl]methyl 2,2-dimethylpropionate The title compound was obtained by treating [7-benzyl-3-(2,2-dimethylpropionyloxy methyl)-2,6-dioxo-2,3,6,7-tetrahydropurin-1-yl]methyl 2,2-dimethylpropionate by the same method as used in Example (1c).

(c) [7-(2-Chlorophenyl)-3-(2,2-dimethylpropionyloxymethyl)-2,6-dioxo-2,3,6,7-tetrahydropurin-1-yl]methyl 2,2-dimethylpropionate The title compound was obtained by treating [3-(2-2-dimethyl propionyloxymethyl)-2-6-dioxo-2,3,6,7-tetrahydropurin-1-yl]methyl 2,2-dimethylpropionate by the same method as used in Example (1d).

$^1$H-NMR (CDCl$_3$)

δ 1.16 (s, 9H) 1.22 (s, 9H) 5.99 (s, 2H) 6.19 (s, 2H) 7.42-7.52 (m, 3H) 7.58-7.61 (m, 1H) 7.73 (s, 1H)

(d) t-Butyl 4-[7-(2-chlorophenyl)-1,3-bis-(2,2-dimethylpropionyloxymethyl)-2,6-dioxo-2,3,6,7-tetrahydro-1H-purin-8-yl]piperazine-1-carboxylate The title compound was obtained by treating [7-(2-chlorophenyl)-3-(2,2-dimethylpropionyloxymethyl)-2,6-dioxo-2,3,6,7-tetrahydropurin-1-yl]methyl 2,2-dimethylpropionate by the same method as used in Example (1e).

$^1$H-NMR (CDCl$_3$)

δ 1.16 (s, 9H) 1.23 (s, 9H) 1.44 (s, 9H) 3.20-3.35 (m, 4H) 3.32-3.37 (m, 4H) 5.92 (s, 2H) 6.09 (s, 2H) 7.41-7.49 (m, 2H) 7.52-7.57 (m, 2H)

(e) t-Butyl 4-[7-(2-chlorophenyl)-1-(2,2-dimethylpropionyloxymethyl)-2,6-dioxo-2,3,6,7-tetrahydro-1H-purin-8-yl]piperazine-1-carboxylate 2.227 g of t-butyl 4-[7-(2-chlorophenyl)-1,3-bis-(2,2-dimethylpropionyloxymethyl)-2,6-dioxo-2,3,6,7-tetrahydro-1H-purin-8-yl]piperazine-1-carboxylate was dissolved in a mixture of 10 ml of tetrahydrofuran and 20 ml of methanol, and 0.518 ml of 1,8-diazabicyclo[5,4,0]undec-7-ene was added thereto. The mixture was stirred at room temperature overnight. 1N hydrochloric acid was added to the mixture, and the precipitated solid was collected by filtration. The solid was dried to give 1.025 g of the title compound.

$^1$H-NMR (CDCl$_3$)

δ 1.16 (s, 9H) 1.44 (s, 9H) 3.22-3.24 (m, 4H) 3.33-3.35 (m, 4H) 5.90 (s, 2H) 7.43-7.47 (m, 2H) 7.51-7.57 (m, 2H) 8.71 (br, 1H)

(f) 7-(2-Chlorophenyl)-2-cyclobutyloxy-8-(piperazin-1-yl)-1,7-dihydropurin-6-one 8 mg of t-butyl 4-[7-(2-chlorophenyl)-1-(2,2-dimethylpropionyloxymethyl)-2,6-dioxo-2,3,6,7-tetrahydro-1H-purin-8-yl]piperazine-1-carboxylate was dissolved in 0.3 ml of N,N-dimethylformamide, and 0.05 ml of bromocyclobutane and 20 mg of potassium carbonate were added thereto. The mixture was stirred at 50° C. overnight. Ethyl acetate was added to the reaction mixture, and the mixture was washed with water. The organic layer was concentrated. The residue was dissolved in methanol, and 5 mg of sodium hydride was added to the solution. The mixture was stirred at room temperature for three hours. The reaction mixture was neutralized with 1N hydrochloric acid, and extracted with ethyl acetate. The solvent was concentrated, and the residue was dissolved in trifluoroacetic acid. The mixture was concentrated, and the residue was purified by reverse-phase high performance liquid chromatography (using an acetonitrile-water mobile phase (containing 0.1% trifluoroacetic acid)) to give 1.89 mg of the title compound.

MS m/e (ESI) 375 (MH$^+$-CF$_3$COOH)

Example 4

Methyl 2-[7-(2-butynyl)-1-methyl-6-oxo-8-(piperazin-1-yl)-6,7-dihydro-1H-purin-2-yloxy]phenylacetate trifluoroacetate (a) [7-(2-Butynyl)-1-methyl-2,6-dioxo-1,2,6,7-tetrahydropurin-3-yl]methyl 2,2-dimethylpropionate 1.871 g of [1-methyl-2,6-dioxo-1,2,6,7-tetrahydropurin-3-yl]methyl 2,2-dimethylpropionate was dissolved in 30 ml of N,N-dimethylformamide, and 1.5 g of potassium carbonate and 0.7 ml of 2-butynyl bromide were added thereto. The mixture was stirred at room temperature overnight. The reaction mixture was diluted with ethyl acetate, and washed with water and 1N hydrochloric acid. The organic layer was dried over anhydrous magnesium sulfate, then filtered. The solvent was evaporated under reduced pressure, and the residue was purified by silica gel column chromatography. Thus, 2.12 g of the title compound was obtained from the fraction eluted with hexane-ethyl acetate (3:2).

(b) 7-(2-Butynyl)-1-methyl-3,7-dihydropurine-2,6-dione

The title compound was obtained by treating [7-(2-butynyl)-1-methyl-2,6-dioxo-1,2,6,7-tetrahydropurin-3-yl]methyl 2,2-dimethylpropionate by the same method as used in Example (1f).

$^1$H-NMR (CDCl$_3$)
δ 1.91 (t, J=2.4 Hz, 3H) 3.39 (s, 3H) 5.10 (s, 2H) 7.93 (s, 1H) 10.62 (s, 1H).

(c) t-Butyl 4-[7-(2-butynyl)-1-methyl-2,6-dioxo-2,3,6,7-tetrahydro-1H-purin-8-yl]piperazine-1-carboxylate The title compound was obtained by treating 7-(2-butynyl)-1-methyl-3,7-dihydropurine-2,6-dione by the same method as used in Example (1e).

$^1$H-NMR (CDCl$_3$)
δ 1.48 (s, 9H) 1.83 (t, J=2.4 Hz, 3H) 3.37 (s, 3H) 3.37-3.39 (m, 4H) 3.58-3.60 (m, 4H) 4.87 (s, 2H) 9.68 (s, 1H).

(d) Methyl 2-[7-(2-butynyl)-1-methyl-6-oxo-8-(piperazin-1-yl)-6,7-dihydro-1H-purin-2-yloxy]phenylacetate trifluoroacetate 8 mg of t-butyl 4-[(7-(2-butynyl)-1-methyl-2,6-dioxo-2,3,6,7-tetrahydro-1H-purin-8-yl]piperazine-1-carboxylate and 10 mg of methyl 2-bromophenylacetate were dissolved in 0.2 ml of N,N-dimethylformamide, and 10 mg of potassium carbonate was added thereto. The mixture was stirred at 50° C. overnight. Ethyl acetate was added to the reaction solution, and the mixture was washed with water and 1N hydrochloric acid. The organic layer was concentrated. The residue was dissolved in trifluoroacetic acid, and the mixture was concentrated. The residue was purified by reverse-phase high performance liquid chromatography (using an acetonitrile-water mobile phase (containing 0.1% trifluoroacetic acid)) to give 1.07 mg of the title compound.
MS m/e (ESI) 451 (MH$^+$-CF$_3$COOH)

Example 5

7-(2-Butynyl)-2-cyclohexyloxy-1-methyl-8-(piperazin-1-yl)-1,7-dihydropurin-6-one trifluoroacetate Using iodocyclohexane instead of methyl 2-bromophenylacetate in Example (4d), the title compound was obtained by the same method as used in Example 4.
MS m/e (ESI) 385 (MH$^+$-CF$_3$COOH)

Example 6

7-(2-Butynyl)-2-(2-butoxy)-1-methyl-8-(piperazin-1-yl)-1,7-dihydropurin-6-one trifluoroacetate Using 2-bromobutane instead of methyl 2-bromophenylacetate in Example (4d), the title compound was obtained by the same method as used in Example 4.
MS m/e (ESI) 359 (MH$^+$-CF$_3$COOH)

Example 7

7-(2-Butynyl)-2-cyclopentyloxy-1-methyl-8-(piperazin-1-yl)-1,7-dihydropurin-6-one trifluoroacetate Using bromocyclopentane instead of methyl 2-bromophenylacetate in Example (4d), the title compound was obtained by the same method as used in Example 4.

MS m/e (ESI) 371 (MH$^+$-CF$_3$COOH)

Example 8

Ethyl 2-[7-(2-butynyl)-1-methyl-6-oxo-8-(piperazin-1-yl)-6,7-dihydro-1H-purin-2-yloxy]butanoate trifluoroacetate Using 2-bromobutanoic acid ethyl ester instead of methyl 2-bromophenylacetate in Example (4d), the title compound was obtained by the same method as used in Example 4.
MS m/e (ESI) 417 (MH$^+$-CF$_3$COOH)

Example 9

Ethyl 2-[7-(2-butynyl)-1-methyl-6-oxo-8-(piperazin-1-yl)-6,7-dihydro-1H-purin-2-yloxy]propionate Using ethyl 2-bromopropionate instead of methyl 2-bromophenylacetate in Example (4d), trifluoroacetate of the title compound was obtained by the same method as used in Example 4. The compound was purified by chromatography using NH-silica gel (silica gel whose surface had been modified with amino groups: Fuji Silysia Chemical Ltd. NH-DM 2035). Thus, the title compound was obtained from the fraction eluted with ethyl acetate-methanol (20:1).
MS m/e (ESI) 404 (MH$^+$)

Example 10

2-[7-(2-Butynyl)-1-methyl-6-oxo-8-(piperazin-1-yl)-6,7-dihydro-1H-purin-2-yloxy]propionic acid trifluoroacetate 8 mg of t-butyl 4-[7-(2-butynyl)-1-methyl-2,6-dioxo-2,3,6,7-tetrahydro-1H-purin-8-yl]piperazine-1-carboxylate and 10 mg of ethyl 2-bromopropionate were dissolved in 0.2 ml of N,N-dimethylformamide, and 10 mg of potassium carbonate was added thereto. The mixture was stirred at 50° C. overnight. Ethyl acetate was added to the reaction solution, and the mixture was washed with water and 1N hydrochloric acid. The organic layer was concentrated to give t-butyl 4-[7-(2-butynyl)-2-(1-carboxyethoxy)-1-methyl-6-oxo-6,7-dihydro-1H-purin-8-yl]piperazine-1-carboxylate. This compound was dissolved in 0.4 ml of ethanol, and 0.1 ml of a 5N aqueous sodium hydroxide solution was added thereto. The mixture was stirred at room temperature for 3 hours. 1N-hydrochloric acid was added to the solution, and the mixture was extracted with ethyl acetate. The organic layer was concentrated, and the residue was dissolved in trifluoroacetic acid. The mixture was concentrated, and the residue was purified by reverse-phase high performance liquid chromatography (using an acetonitrile-water mobile phase (containing 0.1% trifluoroacetic acid)) to give 3.37 mg of the title compound.
MS m/e (ESI) 375 (MH$^+$-CF$_3$COOH)

Example 11

7-(2-Butynyl)-2-methoxy-1-methyl-8-(piperazin-1-yl)-1,7-dihydropurin-6-one trifluoroacetate (a) t-Butyl 4-[7-(2-butynyl)-2-chloro-1-methyl-6-oxo-6,7-dihydro-1H-purin-8-yl]piperazine-1-carboxylate (a-1), and t-butyl 4-[7-(2-butynyl)-2,6-dichloro-7H-purin-8-yl]piperazine-1-carboxylate (a-2)

5.127 g of t-butyl 4-[7-(2-butynyl)-1-methyl-2,6-dioxo-2,3,6,7-tetrahydro-1H-purin-8-yl]piperazine-1-carboxylate was dissolved in 75 ml of phosphorus oxychloride, and then the mixture was stirred at 120° C. overnight. The reaction solution was concentrated, and the residue was dissolved in 50 ml of tetrahydrofuran. This solution was poured into a suspension consisting of 7 g of di-t-butyl dicarbonate, 50 ml of tetrahydrofuran, 100 g of sodium bicarbonate, and 200 ml of water, and the mixture was stirred at room temperature for one hour. The reaction mixture was diluted with ethyl acetate, and the mixture was washed with water. The organic layer was dried over anhydrous magnesium sulfate, then filtered. The filtrate was concentrated, and the residue was purified by silica gel column chromatography. Thus, 1.348 g of t-butyl 4-[7-(2-butynyl)-2,6-dichloro-7H-purin-8-yl]piperazine-1-carboxylate [$^1$H-NMR (CDCl$_3$) δ 1.50 (s, 9H) 1.87 (t, J=2.4 Hz, 3H) 3.64 (m, 8H) 4.81 (q, J=2.4 Hz, 2H)] was obtained from the fraction eluted with hexane-ethyl acetate (1:1), and 1.238 g of t-butyl 4-[7-(2-butynyl)-2-chloro-1-methyl-6-oxo-6,7-dihydro-1H-purin-8-yl]piperazine-1-carboxylate [$^1$H-NMR (CDCl$_3$) δ 1.49 (s, 9H) 1.83 (t, J=2.4 Hz, 3H) 3.42-3.44 (m, 4H) 3.59-3.62 (m, 4H) 3.73 (s, 3H) 4.93 (q, J=2.4 Hz, 2H)] was obtained from the fraction eluted with hexane-ethyl acetate (1:9).

(b) 7-(2-Butynyl)-2-methoxy-1-methyl-8-(piperazin-1-yl)-1,7-dihydropurin-6-one trifluoroacetate 8 mg of t-butyl 4-[7-(2-butynyl)-2-chloro-1-methyl-6-oxo-6,7-dihydro-1H-purin-8-yl]piperazine-1-carboxylate was dissolved in 0.2 ml of methanol, and 10 mg of sodium hydride was added thereto. The mixture was stirred at room temperature for one hour. 1N hydrochloric acid was added to the reaction solution, and the mixture was extracted with ethyl acetate. The organic layer was concentrated, and the residue was dissolved in trifluoroacetic acid. The mixture was concentrated, and the residue was purified by reverse-phase high performance liquid chromatography (using an acetonitrile-water mobile phase (containing 0.1% trifluoroacetic acid)) to give 1.72 mg of the title compound.
MS m/e (ESI) 317 (MH$^+$-CF$_3$COOH)

Example 12

7-(2-Butynyl)-2-ethoxy-1-methyl-8-(piperazin-1-yl)-1,7-dihydropurin-6-one

Using ethanol instead of methanol in Example (11b), the trifluoroacetate of the title compound was obtained by the same method as used in Example 11. This compound was purified by chromatography using NH-silica gel. Thus, the title compound was obtained from the fraction eluted with ethyl acetate-methanol (20:1).
$^1$H-NMR (CDCl$_3$)
δ 1.42 (t, J=7.2 Hz, 3H) 1.82 (t, J=2.4 Hz, 3H) 3.02-3.06 (m, 4H) 3.40-3.42 (m, 4H) 3.46 (s, 3H) 4.51 (q, J=7.2 Hz, 2H) 4.90 (q, J=2.4 Hz, 2H).
MS m/e (ESI) 331 (MH$^+$)

Example 13

Ethyl [7-(2-butynyl)-1-methyl-6-oxo-8-(piperazin-1-yl)-6,7-dihydro-1H-purin-2-yloxy]acetate Example 14

[7-(2-Butynyl)-1-methyl-6-oxo-8-(piperazin-1-yl)-6,7-dihydro-1H-purin-2-yloxy]acetic acid Ethyl [7-(2-butynyl)-1-methyl-6-oxo-8-(piperazin-1-yl)-6,7-dihydro-1H-purin-2-yloxy]acetate trifluoroacetate and [7-(2-butynyl)-1-methyl-6-oxo-8-(piperazin-1-yl)-6,7-dihydro-1H-purin-2-yloxy]acetic acid trifluoroacetate [MS m/e (ESI) 361 (MH$^+$-CF$_3$COOH)] were obtained by treating t-butyl 4-[7-(2-butynyl)-2-chloro-1-methyl-6-oxo-6,7-dihydro-1H-purin-8-yl]piperazine-1-carboxylate using ethyl 2-hydroxyacetate, instead of ethanol, by the same method as used in Example 11. Ethyl [7-(2-butynyl)-1-methyl-6-oxo-8-(piperazin-1-yl)-6,7-dihydro-1H-purin-2-yloxy]acetate trifluoroacetate was purified by chromatography using NH-silica gel. Thus, ethyl [7-(2-butynyl)-1-methyl-6-oxo-8-(piperazin-1-yl)-6,7-dihydro-1H-purin-2-yloxy]acetate [$^1$H-NMR (CDCl$_3$) δ 1.29 (t, J=7.22 Hz, 3H) 1.83 (t, J=2.4 Hz, 3H) 3.02-3.06 (m, 4H) 3.38-3.41 (m, 4H) 3.55 (s, 3H) 4.22 (q, J=7.2 Hz, 2H) 4.90 (q, J=2.4 Hz, 2H) 5.03 (s, 2H); MS m/e (ESI) 389 (MH$^+$)] was obtained from the fraction eluted with ethyl acetate-methanol (20:1)

Example 15

7-(2-Butynyl)-2-(2-methoxyethoxy)-1-methyl-8-(piperazin-1-yl)-1,7-dihydropurin-6-one trifluoroacetate Using 2-methoxy ethanol instead of ethyl 2-hydroxyacetate in Example 13, the title compound was obtained by the same method as used in Example 13.
MS m/e (ESI) 361 (MH$^+$-CF$_3$COOH)

Example 16

Ethyl 1-[7-(2-butynyl)-1-methyl-6-oxo-8-(piperazin-1-yl)-6,7-dihydro-1H-purin-2-yloxy]cyclopropanecarboxylate Using ethyl 1-hydroxycyclopropanecarboxylate instead of ethyl 2-hydroxyacetate in Example 13, the trifluoroacetate of the title compound was obtained by the same method as used in Example 13. The compound was purified by chromatography using NH-silica gel. Thus, the title compound was obtained from the fraction eluted with ethyl acetate-methanol (20:1).
$^1$H-NMR (CDCl$_3$)
δ 1.19 (t, J=7.2 Hz, 3H) 1.39-1.42 (m, 2H) 1.67-1.71 (m, 2H) 1.83 (t, J=2.4 Hz, 3H) 3.02-3.05 (m, 4H) 3.37-3.40 (m, 4H) 3.49 (s, 3H) 4.14 (q, J=7.2 Hz, 2H) 4.90 (q, J=2.4 Hz, 2H)
MS m/e (ESI) 415 (MH$^+$)

Example 17

1-[7-(2-Butynyl)-1-methyl-6-oxo-8-(piperazin-1-yl)-6,7-dihydro-1-H-purin-2-yloxy]cyclopropanecarboxylic acid trifluoroacetate 20 mg of t-butyl 4-[7-(2-butynyl)-2-chloro-1-methyl-6-oxo-6,7-dihydro-1H-purin-8-yl]piperazine-1-carboxylate and 20 mg of ethyl 1-hydroxycyclopropanecarboxylate were dissolved in 0.2 ml of N-methylpyrrolidone, and 10 mg of sodium hydride was added thereto. The mixture was stirred at room temperature overnight. 1N hydrochloric acid was added to the reaction solution, and the mixture was extracted with ethyl acetate. The organic layer was concentrated to give 63 mg of t-butyl 4-[7-(2-butynyl)-2-(1-ethoxycarbonylcyclopropyloxy)-1-methyl-6-oxo-6,7-dihydro-1H-purin-8-yl]piperazine-1-carboxylate. This compound was dissolved in a solution consisting of 0.4 ml of ethanol and 0.1 ml of a 5N aqueous sodium hydroxide solution, and the mixture was stirred at 50° C. overnight. 1N hydrochloric acid solution was added to the reaction solution, and the mixture was extracted with ethyl acetate. The organic layer was concentrated to give 22 mg of t-butyl 4-[7-(2-butynyl)-2-(1-carboxycyclopropyloxy)-1-methyl-6-oxo-6,7-dihydro-1H-purin-8-yl]piperazine-1-carboxylate. 11 mg of this compound was dissolved in trifluoroacetic acid, and the mixture was concentrated. The residue was purified by reverse-phase high performance liquid chromatography (using an acetonitrile-water mobile phase (containing 0.1% trifluoroacetic acid)) to give 1.64 mg of the title compound.

MS m/e (ESI) 387 (MH$^+$-CF$_3$COOH)

Example 18

1-[7-(2-Butynyl)-1-methyl-6-oxo-8-(piperazin-1-yl)-6,7-dihydro-1H-purin-2-yloxy]cyclopropanecarboxylic amide trifluoroacetate 11 mg of t-butyl 4-[7-(2-butynyl)-2-(1-carboxycyclopropyloxy)-1-methyl-6-oxo-6,7-dihydro-1H-purin-8-yl]piperazine-1-carboxylate was dissolved in 1 ml of tetrahydrofuran, and 0.05 ml of triethylamine and 0.05 ml of ethyl chlorocarbonate were added thereto. The mixture was stirred at room temperature for 15 minutes. 0.1 ml of 20% ammonia water was added to the solution, and the mixture was stirred at room temperature for 15 minutes. Water was added to the reaction solution, and the mixture was extracted with ethyl acetate. The organic layer was concentrated, and the residue was dissolved in trifluoroacetic acid. The mixture was concentrated, and the residue was purified by reverse-phase high performance liquid chromatography (using an acetonitrile-water mobile phase (containing 0.1% trifluoroacetic acid)) to give 1.18 mg of the title compound.

MS m/e (ESI) 386 (MH$^+$-CF$_3$COOH)

Example 19

7-(2-Butynyl)-1-methyl-2-(2-oxotetrahydrofuran-3-yloxy)-8-(piperazin-1-yl)-1,7-dihydropurin-6-one trifluoroacetate Using 3-hydroxydihydrofuran-2-one instead of ethyl 2-hydroxyacetate in Example 13, the title compound was obtained by the same method as used in Example 13.

MS m/e (ESI) 387 (MH$^+$-CF$_3$COOH)

Example 20

7-(2-Butynyl)-1-methyl-2-phenoxy-8-(piperazin-1-yl)-1,7-dihydropurin-6-one trifluoroacetate Using phenol instead of ethyl 2-hydroxyacetate in Example 13, the title compound was obtained by the same method as used in Example 13.

MS m/e (ESI) 379 (MH$^+$-CF$_3$COOH)

Example 21

Ethyl [7-(2-butynyl)-1-methyl-6-oxo-8-(piperazin-1-yl)-6,7-dihydro-1H-purin-2-yl]acetate trifluoroacetate Using ethyl 2-(t-butoxycarbonyl)acetate instead of ethyl 2-hydroxyacetate in Example 13, the title compound was obtained by the same method as used in Example 13.

MS m/e (ESI) 373 (MH$^+$-CF$_3$COOH)

Example 22

7-(2-Butynyl)-1,2-dimethyl-8-(piperazin-1-yl)-1,7-dihydropurin-6-one trifluoroacetate 8 mg of t-butyl 4-[7-(2-butynyl)-2-chloro-1-methyl-6-oxo-6,7-dihydro-1H-purin-8-yl]piperazine-1-carboxylate and 2 mg of tetrakis(triphenylphosphine)palladium were dissolved in 0.2 ml of dioxane, and 0.2 ml of methylzinc chloride (1.5 M tetrahydrofuran solution) was added thereto. The mixture was stirred at 50° C. for 0.5 hour. The reaction solution was concentrated, and the residue was dissolved in trifluoroacetic acid. The mixture was concentrated, and the residue was purified by reverse-phase high performance liquid chromatography (using an acetonitrile-water mobile phase (containing 0.1% trifluoroacetic acid)) to give 4.56 mg of the title compound.

MS m/e (ESI) 301 (MH$^+$-CF$_3$COOH)

Example 23

7-(2-Butynyl)-1-methyl-2-butyl-8-(piperazin-1-yl)-1,7-dihydropurin-6-one trifluoroacetate 8 mg of t-butyl 4-[7-(2-butynyl)-2-chloro-1-methyl-6-oxo-6,7-dihydro-1H-purin-8-yl]piperazine-1-carboxylate and 2 mg of tetrakis(triphenylphosphine)palladium were dissolved in 0.2 ml of dioxane, and 0.3 ml of a mixed solution consisting of 0.5 ml of butylmagnesium chloride (2.0 M diethyl ether solution) and 2 ml of zinc chloride (0.5 M tetrahydrofuran solution) was added thereto. The resulting mixture was stirred at 50° C. for five hours. The reaction solution was concentrated, and the residue was dissolved in trifluoroacetic acid. The mixture was concentrated, and the residue was purified by reverse-phase high performance liquid chromatography (using an acetonitrile-water mobile phase (containing 0.1% trifluoroacetic acid)) to give 3.38 mg of the title compound.

MS m/e (ESI) 343 (MH$^+$-CF$_3$COOH)

Example 24

7-(2-Butynyl)-1-methyl-2-benzyl-8-(piperazin-1-yl)-1,7-dihydropurin-6-one trifluoroacetate The title compound was obtained using a mixed solution consisting of 0.5 ml of benzylmagnesium chloride (2.0 M diethyl ether solution) and 2 ml of zinc chloride (0.5 M tetrahydrofuran solution) by the same method as used in Example 23.

MS m/e (ESI) 377 (MH$^+$-CF$_3$COOH)

Example 25

7-(2-Butynyl)-1-methyl-2-(2-phenylethyl)-8-(piperazin-1-yl)-1,7-dihydropurin-6-one trifluoroacetate The title compound was obtained using a mixed solution consisting of 0.5 ml of phenethylmagnesium chloride (2.0 M diethyl ether solution) and 2 ml of zinc chloride (0.5 M tetrahydrofuran solution) by the same method as used in Example 23.

MS m/e (ESI) 391 (MH$^+$-CF$_3$COOH)

Example 26

7-(2-Butynyl)-1-methyl-2-phenyl-8-(piperazin-1-yl)-1,7-dihydropurin-6-one trifluoroacetate 10 mg of t-butyl 4-[7-(2-butynyl)-2-chloro-1-methyl-6-oxo-6,7-dihydro-1H-purin-8-yl]piperazine-1-carboxylate and 2 mg of tetrakis(triphenylphosphine)palladium and 20 mg of phenyltributyltin were dissolved in 0.2 ml of dioxane, and the mixture was stirred at 80° C. for 5 hours. The reaction solution was concentrated, and the residue was dissolved in trifluoroacetic acid. The mixture was concentrated, and the residue was purified by reverse-phase high performance liquid chromatography (using an acetonitrile-water mobile phase (containing 0.1% trifluoroacetic acid)) to give 4.62 mg of the title compound.
MS m/e (ESI) 363 (MH$^+$-CF$_3$COOH)

Example 27

7-(2-Butynyl)-1-methyl-2-amino-8-(piperazin-1-yl)-1,7-dihydropurin-6-one trifluoroacetate 8 mg of t-butyl 4-[7-(2-butynyl)-2-chloro-1-methyl-6-oxo-6,7-dihydro-1H-purin-8-yl]piperazine-1-carboxylate was dissolved in 0.2 ml of 20% aqueous ammonia solution, and the mixture was stirred at 80° C. for 5 hours. The reaction solution was concentrated, and the residue was dissolved in trifluoroacetic acid. The mixture was concentrated, and the residue was purified by reverse-phase high performance liquid chromatography (using an acetonitrile-water mobile phase (containing 0.1% trifluoroacetic acid)) to give 3.82 mg of the title compound.
MS m/e (ESI) 302 (MH$^+$-CF$_3$COOH)

Example 28

7-(2-Butynyl)-1-methyl-2-methylamino-(8-piperazin-1-yl)-1,7-dihydropurin-6-one trifluoroacetate 8 mg of t-butyl 4-[7-(2-butynyl)-2-chloro-1-methyl-6-oxo-6,7-dihydro-1H-purin-8-yl]piperazine-1-carboxylate was dissolved in 0.2 ml of an aqueous solution of 40% methyl amine, and the mixture was stirred at 80° C. for 5 hours. The reaction solution was concentrated, and the residue was dissolved in trifluoroacetic acid. The mixture was concentrated, and the residue was purified by reverse-phase high performance liquid chromatography (using an acetonitrile-water mobile phase (containing 0.1% trifluoroacetic acid)) to give 6.95 mg of the title compound.
MS m/e (ESI) 316 (MH$^+$-CF$_3$COOH)

Example 29

7-(2-Butynyl)-1-methyl-2-dimethylamino-8-(piperazin-1-yl)-1,7-dihydropurin-6-one trifluoroacetate 8 mg of t-butyl 4-[7-(2-butynyl)-2-chloro-1-methyl-6-oxo-6,7-dihydro-1H-purin-8-yl]piperazine-1-carboxylate was dissolved in 0.2 ml of an aqueous solution of 40% dimethylamine, and the mixture was stirred at 80° C. for 5 hours. The reaction solution was concentrated, and the residue was dissolved in trifluoroacetic acid. The mixture was concentrated, and the residue was purified by reverse-phase high performance liquid chromatography (using an acetonitrile-water mobile phase (containing 0.1% trifluoroacetic acid)) to give 6.95 mg of the title compound.

$^1$H-NMR (CDCl$_3$)
δ 1.82 (t, J=2.4 Hz, 3H) 2.83 (s, 6H) 3.02-3.05 (m, 4H) 3.39-3.42 (m, 4H) 3.56 (s, 3H) 4.90 (d, J=2.4 Hz, 2H)
MS m/e (ESI) 330 (MH$^+$-CF$_3$COOH)

Example 30

Ethyl [7-(2-butynyl)-1-methyl-6-oxo-8-(piperazin-1-yl)-6,7-dihydro-1H-purin-2-ylamino]acetate trifluoroacetate 10 mg of t-butyl 4-[7-(2-butynyl)-2-chloro-1-methyl-6-oxo-6,7-dihydro-1H-purin-8-yl]piperazine-1-carboxylate was dissolved in 0.15 ml of 1-methyl-2-pyrrolidone, and 15 mg of glycine ethyl ester hydrochloride and 50 μl of triethylamine were added thereto. The mixture was stirred at 80° C. for 12 hours. Then, the reaction solution was concentrated by flushing with nitrogen gas. The residue was dissolved in 0.40 ml of trifluoroacetic acid, and the solution was concentrated by flushing with nitrogen gas. The residue was purified by reverse-phase high performance liquid chromatography (using an acetonitrile-water mobile phase (containing 0.1% trifluoroacetic acid)) to give 7.60 mg of the title compound.
MS m/e (ESI) 388 (MH$^+$-CF$_3$COOH)

Example 31

[7-(2-butynyl)-1-methyl-6-oxo-8-(piperazin-1-yl)-6,7-dihydro-1H-purin-2-ylamino]acetic acid trifluoroacetate 6 mg of t-butyl 4-[7-(2-butynyl)-2-chloro-1-methyl-6-oxo-6,7-dihydro-1H-purin-8-yl]piperazine-1-carboxylate was dissolved in 0.15 ml of 1-methyl-2-pyrrolidone, and 15 mg of glycine t-butyl ester hydrochloride and 50 μl of triethylamine were added thereto. After the mixture had been stirred at 80° C. for 12 hours, the reaction solution was concentrated by flushing with nitrogen gas. The resulting residue was dissolved in 0.40 ml of trifluoroacetic acid, and the solution was concentrated by flushing with nitrogen gas. The residue was purified by reverse-phase high performance liquid chromatography (using an acetonitrile-water mobile phase (containing 0.1% trifluoroacetic acid)) to give 2.36 mg of the title compound.
MS m/e (ESI) 360 (MH$^+$-CF$_3$COOH)

Example 32

Ethyl [N-[7-(2-butynyl)-1-methyl-6-oxo-8-(piperazin-1-yl)-6,7-dihydro-1H-purin-2-yl]methylamino] acetic acid trifluoroacetate Using N-methyl glycine ethyl ester hydrochloride instead of glycine ethyl ester hydrochloride in Example 30, 2.06 mg of the title compound was obtained by the same method as used in Example 30.
MS m/e (ESI) 402 (MH$^+$-CF$_3$COOH)

Example 33

Methyl (S)-1-[7-(2-butynyl)-1-methyl-6-oxo-8-(piperazin-1-yl)-6,7-dihydro-1H-purin-2-yl]pyrrolidine-2-carboxylate trifluoroacetate Using L-proline methyl ester hydrochloride instead of glycine ethyl ester hydrochloride in Example 30, 1.35 mg of the title compound was obtained by the same method as used in Example 30.
MS m/e (ESI) 414 (MH$^+$-CF$_3$COOH)

Example 34

[N-[7-(2-butynyl)-1-methyl-6-oxo-8-(piperazin-1-yl)-6,7-dihydro-1H-purin-2-yl]methylamino]acetic acid trifluoroacetate Using N-methyl glycine t-butyl ester hydrochloride instead of glycine ethyl ester hydrochloride in Example 30, 3.16 mg of the title compound was obtained by the same method as used in Example 30.

MS m/e (ESI) 374 ($MH^+$-$CF_3COOH$)

Example 35

Methyl (R)-1-[7-(2-butynyl)-1-methyl-6-oxo-8-(piperazin-1-yl)-6,7-dihydro-1H-purin-2-yl]pyrrolidine-2-carboxylate trifluoroacetate Using D-proline methyl ester hydrochloride instead of glycine ethyl ester hydrochloride in Example 30, 0.74 mg of the title compound was obtained by the same method as used in Example 30.

MS m/e (ESI) 414 ($MH^+$-$CF_3COOH$)

Example 36

Methyl 2-[7-(2-butynyl)-1-methyl-6-oxo-8-(piperazin-1-yl)-6,7-dihydro-1 H-purin-2-ylamino]propionate trifluoroacetate Using DL-alanine methyl ester hydrochloride instead of glycine ethyl ester hydrochloride in Example 30, 1.20 mg of the title compound was obtained by the same method as used in Example 30.

MS m/e (ESI) 388 ($MH^+$-$CF_3COOH$).

Example 37

Methyl 2-[7-(2-butynyl)-1-methyl-6-oxo-8-(piperazin-1-yl)-6,7-dihydro-1H-purin-2-ylamino]-2-methylpropionate trifluoroacetate Using methyl 2-aminoisobutylate hydrochloride instead of glycine ethyl ester hydrochloride in Example 30, 1.18 mg of the title compound was obtained by the same method as used in Example 30.

MS m/e (ESI) 402 ($MH^+$-$CF_3COOH$)

Example 38

Ethyl (S)-2-[7-(2-butynyl)-1-methyl-6-oxo-8-(piperazin-1-yl)-6,7-dihydro-1H-purin-2-ylamino]propionate trifluoroacetate Using L-alanine ethyl ester hydrochloride instead of glycine ethyl ester hydrochloride in Example 30, 2.38 mg of the title compound was obtained by the same method as used in Example 30.

MS m/e (ESI) 402 ($MH^+$-$CF_3COOH$)

Example 39

(S)-2-[7-(2-butynyl)-1-methyl-6-oxo-8-(piperazin-1-yl)-6,7-dihydro-1H-purin-2-ylamino]propionic acid trifluoroacetate Using L-alanine t-butyl ester hydrochloride instead of glycine ethyl ester hydrochloride in Example 30, 0.76 mg of the title compound was obtained by the same method as used in Example 30.

MS m/e (ESI) 374 ($MH^+$-$CF_3COOH$)

Example 40

Ethyl 3-[7-(2-butynyl)-1-methyl-6-oxo-8-(piperazin-1-yl)-6,7-dihydro-1 H-purin-2-ylamino]propionate trifluoroacetate Using β-alanine ethyl ester hydrochloride instead of glycine ethyl ester hydrochloride in Example 30, 0.8.5 mg of the title compound was obtained by the same method as used in Example 30.

MS m/e (ESI) 402 ($MH^+$-$CF_3COOH$).

Example 41

7-(2-Butynyl)-2-(2-ethoxyethylamino)-1-methyl-8-(piperazin-1-yl)-1,7-dihydro-purin-6-one trifluoroacetate 10 mg of t-butyl 4-[7-(2-butynyl)-2-chloro-1-methyl-6-oxo-6,7-dihydro-1H-purin-8-yl]piperazine-1-carboxylate was dissolved in 0.15 ml of 1-methyl-2-pyrrolidone, and 20 μl of 2-ethoxyethylamine was added thereto. After the mixture had been stirred at 80° C. for 12 hours, the reaction solution was concentrated by flushing with nitrogen. The resulting residue was dissolved in 0.40 ml of trifluoroacetic acid, and the mixture was concentrated by flushing with nitrogen gas. The residue was purified by reverse-phase high performance liquid chromatography (using an acetonitrile-water mobile phase (containing 0.1% trifluoroacetic acid)) to give 6.95 mg of the title compound.

MS m/e (ESI) 374 ($MH^+$-$CF_3COOH$)

Example 42

7-(2-Butynyl)-1-methyl-2-(morpholin-4-yl)-8-(piperazin-1-yl)-1,7-dihydropurin-6-one trifluoroacetate Using morpholine instead of 2-ethoxyethylamine in Example 41, 7.31 mg of the title compound was obtained by the same method as used in Example 41.

MS m/e (ESI) 372 ($MH^+$-$CF_3COOH$)

Example 43

2-Benzylamino-7-(2-butynyl)-1-methyl-8-(piperazin-1-yl)-1,7-dihydropurin-6-one trifluoroacetate Using benzylamine instead of 2-ethoxyethylamine in Example 41, 8.40 mg of the title compound was obtained by the same method as used in Example 41.

MS m/e (ESI) 392 ($MH^+$-$CF_3COOH$)

Example 44

Ethyl 1-[7-(2-butynyl)-1-methyl-6-oxo-8-(piperazin-1-yl)-6,7-dihydro-1H-purin-2-yl]piperidine-4-carboxylate trifluoroacetate Using ethyl isonipecotate instead of 2-ethoxyethylamine in Example 41, 7.43 mg of the title compound was obtained by the same method as used in Example 41.
MS m/e (ESI) 442 (MH$^+$-CF$_3$COOH)

Example 45

2-(N-benzylmethylamino)-7-(2-butynyl)-1-methyl-8-(piperazin-1-yl)-1,7-dihydropurin-6-one trifluoroacetate Using N-methylbenzylamine instead of 2-ethoxyethylamine in Example 41, 2.38 mg of the title compound was obtained by the same method as used in Example 41.
MS m/e (ESI) 406 (MH$^+$-CF$_3$COOH)

Example 46

7-(2-Butynyl)-2-(4-chlorobenzylamino)-1-methyl-8-(piperazin-1-yl)-1,7-dihydropurin-6-one trifluoroacetate Using 4-chlorobenzylamine instead of 2-ethoxyethylamine in Example 41, 2.84 mg of the title compound was obtained by the same method as used in Example 41.
MS m/e (ESI) 426 (MH$^+$-CF$_3$COOH)

Example 47

7-(2-Butynyl)-2-(4-methoxybenzylamino)-1-methyl-8-(piperazin-1-yl)-1,7-dihydropurin-6-one trifluoroacetate Using 4-methoxybenzylamine, 3.77 mg of the title compound was obtained by the same method as used in Example 41.
MS m/e (ESI) 422 (MH$^+$-CF$_3$COOH)

Example 48

7-(2-Butynyl)-1-methyl-2-(2-phenylethylamino)-8-(piperazin-1-yl)-1,7-dihydropurin-6-one trifluoroacetate Using phenethylamine instead of 2-ethoxyethylamine in Example 41, 2.70 mg of the title compound was obtained by the same method as used in Example 41.
MS m/e (ESI) 406 (MH$^+$-CF$_3$COOH).

Example 49

7-(2-Butynyl)-1-methyl-2-[N-(2-phenylethyl)methylamino]-8-(piperazin-1-yl)-1,7-dihydropurin-6-one trifluoroacetate Using N-methylphenethylamine instead of 2-ethoxyethylamine in Example 41, 2.17 mg of the title compound was obtained by the same method as used in Example 41.
MS m/e (ESI) 420 (MH$^+$-CF$_3$COOH)

Example 50

Ethyl 1-[7-(2-butynyl)-1-methyl-6-oxo-8-(piperazin-1-yl)-6,7-dihydro-1H-purin-2-yl]piperidine-3-carboxylate trifluoroacetate Using ethyl nipecotate instead of 2-ethoxyethylamine in Example 41, 2.93 mg of the title compound was obtained by the same method as used in Example 41.
MS m/e (ESI) 442 (MH$^+$-CF$_3$COOH)

Example 51

7-(2-Butynyl)-1-methyl-8-(piperazin-1-yl)-2-(pyridin-2-ylmethylamino)-1,7-dihydropurin-6-one trifluoroacetate Using 2-aminomethylpyridine instead of 2-ethoxyethylamine in Example 41, 1.62 mg of the title compound was obtained by the same method as used in Example 41.
MS m/e (ESI) 393 (MH$^+$-CF$_3$COOH)

Example 52

Ethyl 1-[7-(2-butynyl)-1-methyl-6-oxo-8-(piperazin-1-yl)-6,7-dihydro-1H-purin-2-yl]piperidine-2-carboxylate trifluoroacetate Using ethyl pipecolate instead of 2-ethoxyethylamine in Example 41, 0.97 mg of the title compound was obtained by the same method as used in Example 41.
MS m/e (ESI) 442 (MH$^+$-CF$_3$COOH)

Example 53

(S)-1-[7-(2-Butynyl)-1-methyl-6-oxo-8-(piperazin-1-yl)-6,7-dihydro-1H-purin-2-yl]pyrrolidine-2-carboxylic acid trifluoroacetate Using L-proline t-butyl ester instead of 2-ethoxyethylamine in Example 41, 4.07 mg of the title compound was obtained by the same method as used in Example 41.
MS m/e (ESI) 400 (MH$^+$-CF$_3$COOH)

Example 54

7-(2-Butynyl)-2-diethylamino-1-methyl-8-(piperazin-1-yl)-1,7-dihydropurin-6-one trifluoroacetate Using diethylamine instead of 2-ethoxyethylamine in Example 41, 2.24 mg of the title compound was obtained by the same method as used in Example 41.
MS m/e (ESI) 358 (MH$^+$-CF$_3$COOH)

Example 55

7-(2-Butynyl)-2-(N-ethylmethylamino)-1-methyl-8-(piperazin-1-yl)-1,7-dihydropurin-6-one trifluoroacetate Using N-ethylmethylamine instead of 2-ethoxyethylamine in Example 41, 3.27 mg of the title compound was obtained by the same method as used in Example 41.
MS m/e (ESI) 344 (MH$^+$-CF$_3$COOH)

Example 56

Ethyl (R)-1-[7-(2-butynyl)-1-methyl-6-oxo-8-(piperazin-1-yl)-6,7-dihydro-1H-purin-2-yl]piperidine-3-carboxylate trifluoroacetate Using ethyl (R)-nipecotate instead of 2-ethoxyethylamine in Example 41, 0.87 mg of the title compound was obtained by the same method as used in Example 41.
MS m/e (ESI) 442 (MH$^+$-CF$_3$COOH)

Example 57

Ethyl (S)-1-[7-(2-butynyl)-1-methyl-6-oxo-8-(piperazin-1-yl)-6,7-dihydro-1H-purin-2-yl]piperidine-3-carboxylate trifluoroacetate Using ethyl (L)-nipecotate instead of 2-ethoxyethylamine in Example 41, 2.94 mg of the title compound was obtained by the same method as used in Example 41.
MS m/e (ESI) 442 (MH$^+$-CF$_3$COOH)

Example 58

[N-[7-(2-Butynyl)-1-methyl-6-oxo-8-(piperazin-1-yl)-6,7-dihydro-1H-purin-2-yl]methylamino]acetonitrile trifluoroacetate Using methylaminoacetonitrile instead of 2-ethoxyethylamine in Example 41, 1.00 mg of the title compound was obtained by the same method as used in Example 41.
MS m/e (ESI) 355 (MH$^+$-CF$_3$COOH)

Example 59

7-(2-Butynyl)-2-isopropylamino-1-methyl-8-(piperazin-1-yl)-1,7-dihydropurin-6-one trifluoroacetate 6 mg of t-butyl 4-[7-(2-butynyl)-2-chloro-1-methyl-6-oxo-6,7-dihydro-1H-purin-8-yl]piperazine-1-carboxylate was dissolved in 0.15 ml of 1-methyl-2-pyrrolidone, and 5.0 µl of isopropylamine was added thereto. The mixture was stirred at 60° C. for five hours, and then concentrated by flushing with nitrogen gas. The residue was dissolved in 0.40 ml of trifluoroacetic acid, and the mixture was concentrated by flushing with nitrogen gas. The residue was purified by reverse-phase high performance liquid chromatography (using an acetonitrile-water mobile phase (containing 0.1% trifluoroacetic acid)) to give 2.28 mg of the title compound.
MS m/e (ESI) 344 (MH$^+$-CF$_3$COOH)

Example 60

7-(2-Butynyl)-1-methyl-8-(piperazin-1-yl)-2-(pyridin-2-ylamino)-1,7-dihydropurin-6-one trifluoroacetate 6 mg of t-butyl 4-[7-(2-butynyl)-2-chloro-1-methyl-6-oxo-6,7-dihydro-1H-purin-8-yl]piperazine-1-carboxylate was dissolved in 0.15 ml of 1-methyl-2-pyrrolidone, and 50 µl of 2-aminopyridine was added thereto. The mixture was stirred at 110° C. for 12 hours, and then the reaction solution was concentrated by flushing with nitrogen gas. The residue was dissolved in 0.40 ml of trifluoroacetic acid, and the mixture was concentrated by flushing with nitrogen gas. The residue was purified by reverse-phase high performance liquid chromatography (using an acetonitrile-water mobile phase (containing 0.1% trifluoroacetic acid)) to give 0.10 mg of the title compound.
MS m/e (ESI) 379 (MH$^+$-CF$_3$COOH)

Example 61

7-(2-Butynyl)-1-methyl-2-phenylamino-8-(piperazin-1-yl)-1,7-dihydropurin-6-one trifluoroacetate 6 mg of t-butyl 4-[7-(2-butynyl)-2-chloro-1-methyl-6-oxo-6,7-dihydro-1H-purin-8-yl]piperazine-1-carboxylate was dissolved in 0.15 ml of 1-methyl-2-pyrrolidone, and 100 µl of aniline was added thereto. The mixture was stirred at 110° C. for 12 hours, and then concentrated by flushing with nitrogen gas. The residue was dissolved in 0.40 ml of trifluoroacetic acid, and the mixture was concentrated by flushing with nitrogen gas. The residue was purified by reverse-phase high performance liquid chromatography (using an acetonitrile-water mobile phase (containing 0.1% trifluoroacetic acid)) to give 3.23 mg of the title compound.
MS m/e (ESI) 378 (MH$^+$-CF$_3$COOH)

Example 62

1-[7-(2-Butynyl)-1-methyl-6-oxo-8-(piperazin-1-yl)-6,7-dihydro-1H-purin-2-yl]piperidine-3-carboxylic acid trifluoroacetate 6 mg of t-butyl 4-[7-(2-butynyl)-2-chloro-1-methyl-6-oxo-6,7-dihydro-1H-purin-8-yl]piperazine-1-carboxylate was dissolved in 0.15 ml of 1-methyl-2-pyrrolidone, and 20 µl of ethyl nipecotate was added thereto. The mixture was stirred at 80° C. for 12 hours, and then concentrated by flushing with nitrogen gas. The residue was dissolved in a solution consisting of 0.20 ml of ethanol and 0.20 ml of a 5N aqueous sodium hydroxide solution. The mixture was stirred at room temperature for five hours, and then concentrated by flushing with nitrogen gas. The residue was dissolved in 0.40 ml of trifluoroacetic acid, and the mixture was concentrated by flushing with nitrogen gas. The residue was purified by reverse-phase high performance liquid chromatography (using an acetonitrile-water mobile phase (containing 0.1% trifluoroacetic acid)) to give 1.92 mg of the title compound.
MS m/e (ESI) 414 (MH$^+$-CF$_3$COOH)

Example 63

(R)-1-[7-(2-Butynyl)-1-methyl-6-oxo-8-(piperazin-1-yl)-6,7-dihydro-1H-purin-2-yl]pyrrolidine-2-carboxylic acid trifluoroacetate 6 mg of t-butyl 4-[7-(2-butynyl)-2-chloro-1-methyl-6-oxo-6,7-dihydro-1H-purin-8-yl]piperazine-1-carboxylate was dissolved in 0.15 ml of 1-methyl-2-pyrrolidone, and 15 mg of D-proline methyl ester hydrochloride and 50 µl of triethylamine were added thereto. After the resulting mixture had been stirred at 80° C. for 12 hours, the reaction solution was concentrated by flushing with nitrogen gas. The residue was dissolved in a solution consisting of 0.20 ml of ethanol and 0.20 ml of a 5N aqueous sodium hydroxide solution. The mixture was stirred at room temperature for five hours, and then concentrated by flushing with nitrogen gas. The residue was dissolved in 0.40 ml of trifluoroacetic acid, and the mixture was concentrated by flushing with nitrogen gas. The residue was purified by reverse-phase high performance liquid chromatography (using an acetonitrile-water mobile phase (containing 0.1% trifluoroacetic acid)) to give 3.42 mg of the title compound.
MS m/e (ESI) 400 (MH$^+$-CF$_3$COOH)

Example 64

2-[7-(2-Butynyl)-1-methyl-6-oxo-8-(piperazin-1-yl)-6,7-dihydro-1H-purin-2-ylamino]propionic acid trifluoroacetate Using DL-alanine methyl ester hydrochloride instead of D-proline methyl ester hydrochloride in Example 63, 1.12 mg of the title compound was obtained by the same method as used in Example 63.
MS m/e (ESI) 374 (MH$^+$-CF$_3$COOH)

Example 65

7-(2-Butynyl)-1-methyl-8-(piperazin-1-yl)-2-(pyridin-2-yl-methyl oxy)-1,7-dihydropurin-6-one trifluoroacetate 6 mg of t-butyl 4-[7-(2-butynyl)-2-chloro-1-methyl-6-oxo-6,7-dihydro-1H-purin-8-yl]piperazine-1-carboxylate was dissolved in 0.15 ml of 1-methyl-2-pyrrolidone, and 25 µl of pyridin-2-ylmethanol and 5 mg of sodium hydride were added thereto. The mixture was stirred at room temperature for five hours, and then concentrated by flushing with nitrogen gas. The residue was dissolved in 0.40 ml of trifluoroacetic acid, and the mixture was concentrated by flushing with nitrogen gas. The residue was purified by reverse-phase high performance liquid chromatography (using an acetonitrile-water mobile phase (containing 0.1% trifluoroacetic acid)) to give 0.58 mg of the title compound.
MS m/e (ESI) 394 (MH$^+$-CF$_3$COOH)

Example 66

7-(2-Butynyl)-2-isopropoxy-1-methyl-8-(piperazin-1-yl)-1,7-dihydropurin-6-one trifluoroacetate 6 mg of t-butyl 4-[7-(2-butynyl)-2-chloro-1-methyl-6-oxo-6,7-dihydro-1H-purin-8-yl]piperazine-1-carboxylate was dissolved in 0.15 ml of 1-methyl-2-pyrrolidone, and 0.10 ml of isopropanol and 5 mg of sodium hydride were added thereto. After the mixture was stirred at room temperature for five hours, an aqueous solution saturated with ammonium chloride was added to the reaction solution. The resulting mixture was extracted with ethyl acetate. The organic layer was concentrated. The residue was dissolved in 0.40 ml of trifluoroacetic acid, and the mixture was concentrated by flushing with nitrogen gas. The residue was purified by reverse-phase high performance liquid chromatography (using an acetonitrile-water mobile phase (containing 0.1% trifluoroacetic acid)) to give 2.68 mg of the title compound.
MS m/e (ESI) 345 (MH$^+$-CF$_3$COOH)

Example 67

7-(2-Butynyl)-2-(2-butynyloxy)-1-methyl-8-(piperazin-1-yl)-1,7-dihydropurin-6-one trifluoroacetate Using 2-butyn-1-ol instead of isopropanol in Example 66, 3.40 mg of the title compound was obtained by the same method as used in Example 66.
MS m/e (ESI) 355 (MH$^+$-CF$_3$COOH)

Example 68

Methyl [7-(2-butynyl)-1-methyl-6-oxo-8-(piperazin-1-yl)-6,7-dihydro-1H-purin-2-ylsulfanyl]acetate trifluoroacetate 6 mg of t-butyl 4-[7-(2-butynyl)-2-chloro-1-methyl-6-oxo-6,7-dihydro-1H-purin-8-yl]piperazine-1-carboxylate was dissolved in 0.15 ml of 1-methyl-2-pyrrolidone, and 20 µl of methyl mercaptoacetate and 6 mg of potassium carbonate were added thereto. The mixture was stirred at room temperature for five hours. An aqueous solution saturated with ammonium chloride was added to the reaction solution, and the mixture was extracted with ethyl acetate. The organic layer was concentrated, and the residue was dissolved in 0.40 ml of trifluoroacetic acid. The solution was concentrated by flushing with nitrogen gas. The residue was purified by reverse-phase high performance liquid chromatography (using an acetonitrile-water mobile phase (containing 0.1% trifluoroacetic acid)) to give 4.83 mg of the title compound.
MS m/e (ESI) 391 (MH$^+$-CF$_3$COOH)

Example 69

Ethyl 2-[7-(2-butynyl)-1-methyl-6-oxo-8-(piperazin-1-yl)-6,7-dihydro-1H-purin-2-ylsulfanyl]propionate trifluoroacetate Using ethyl 2-mercaptopropionate instead of methyl mercaptoacetate in Example 68, 4.30 mg of the title compound was obtained by the same method as used in Example 68.
MS m/e (ESI) 419 (MH$^+$-CF$_3$COOH)

Example 70

Ethyl 3-[7-(2-butynyl)-1-methyl-6-oxo-8-(piperazin-1-yl)-6,7-dihydro-1H-purin-2-ylsulfanyl]propionate trifluoroacetate Using ethyl 3-mercaptopropionate instead of methyl mercaptoacetate in Example 68, 3.75 mg of the title compound was obtained by the same method as used in Example 68.
MS m/e (ESI) 419 (MH$^+$-CF$_3$COOH)

Example 71

7-(2-Butynyl)-2-ethylsulfanyl-1-methyl-8-(piperazin-1-yl)-1,7-dihydropurin-6-one trifluoracetate Using ethanethiol instead of methyl mercaptoacetate in Example 68, 4.70 mg of the title compound was obtained by the same method as used in Example 68.
MS m/e (ESI) 347 (MH$^+$-CF$_3$COOH)

Example 72

7-(2-Butynyl)-2-(2-hydroxyethylsulfanyl)-1-methyl-8-(piperazin-1-yl)-1,7-dihydropurin-6-one trifluoroacetate Using 2-mercaptoethanol instead of methyl mercaptoacetate in Example 68, 3.57 mg of the title compound was obtained by the same method as used in Example 68.
MS m/e (ESI) 363 (MH$^+$-CF$_3$COOH)

Example 73

7-(2-Butynyl)-1-methyl-8-(piperazin-1-yl)-2-(pyridin-2-ylsulfanyl)-1,7-dihydropurin-6-one trifluoroacetate Using 2-mercaptopyridine instead of methyl mercaptoacetate in Example 68, 4.66 mg of the title compound was obtained by the same method as used in Example 68.

MS m/e (ESI) 396 (MH$^+$-CF$_3$COOH)

Example 74

7-(2-Butynyl)-1-methyl-2-methylsulfanyl-8-(piperazin-1-yl)-1,7-dihydropurin-6-one trifluoroacetate Using methyl mercaptan (30%; methanol solution) instead of methyl mercaptoacetate in Example 68, 4.08 mg of the title compound was obtained by the same method as used in Example 68.

MS m/e (ESI) 333 (MH$^+$-CF$_3$COOH)

Example 75

7-(2-Butynyl)-2-cyclohexylsulfanyl-1-methyl-8-(piperazin-1-yl)-1,7-dihydropurin-6-one trifluoroacetate Using cyclohexanethiol instead of methyl mercaptoacetate in Example 68, 4.13 mg of the title compound was obtained by the same method as used in Example 68.

MS m/e (ESI) 401 (MH$^+$-CF$_3$COOH)

Example 76

7-(2-Butynyl)-2-isopropylsulfanyl-1-methyl-8-(piperazin-1-yl)-1,7-dihydropurin-6-one trifluoroacetate 6 mg of t-butyl 4-[7-(2-butynyl)-2-chloro-1-methyl-6-oxo-6,7-dihydro-1H-purin-8-yl]piperazine-1-carboxylate was dissolved in 0.15 ml of 1-methyl-2-pyrrolidone, and 15 mg of the sodium salt of propane-2-thiol was added thereto. The mixture was stirred at room temperature for five hours. A saturated ammonium chloride solution was added to the reaction solution, and the mixture was extracted with ethyl acetate. The organic layer was concentrated, and the residue was dissolved in 0.40 ml of trifluoroacetic acid. The solution was concentrated by flushing with nitrogen gas. The residue was purified by reverse-phase high performance liquid chromatography (using an acetonitrile-water mobile phase (containing 0.1% trifluoroacetic acid)) to give 4.56 mg of the title compound.

MS m/e (ESI) 361 (MH$^+$-CF$_3$COOH)

Example 77

2-t-Butylsulfanyl-7-(2-butynyl)-1-methyl-8-(piperazin-1-yl)-1,7-dihydropurin-6-one trifluoroacetate Using the sodium salt of 2-methyl-2-propanethiol instead of the sodium salt of propane-2-thiol in Example 76, 2.58 mg of the title compound was obtained by the same method as used in Example 76.

MS m/e (ESI) 375 (MH$^+$-CF$_3$COOH)

Example 78

7-(2-Butynyl)-2-mercapto-1-methyl-8-(piperazin-1-yl)-1,7-dihydro purin-6-one trifluoroacetate

Example 79

[7-(2-Butynyl)-1-methyl-6-oxo-8-(piperazin-1-yl)-6,7-dihydro-1H-purin-2-ylsulfanyl]acetic acid trifluoroacetate 6 mg of t-butyl 4-[7-(2-butynyl)-2-chloro-1-methyl-6-oxo-6,7-dihydro-1H-purin-8-yl]piperazine-1-carboxylate was dissolved in 0.15 ml of N-methylpyrrolidone, and 20 μl of methyl mercaptoacetate and 6 mg of potassium carbonate were added thereto. After the mixture had been stirred at room temperature for five hours, an aqueous solution saturated with ammonium chloride was added to the reaction solution. The mixture was extracted with ethyl acetate. The organic layer was concentrated. The resulting residue was dissolved in a solution consisting of 0.20 ml of ethanol and 0.20 ml of a 5N aqueous sodium hydroxide solution. The mixture was stirred at room temperature overnight, and then concentrated by flushing with nitrogen gas. The residue was dissolved in 0.40 ml of trifluoroacetic acid, and the solution was concentrated by flushing with nitrogen gas. The residue was purified by reverse-phase high performance liquid chromatography (using an acetonitrile-water mobile phase (containing 0.1% trifluoroacetic acid)) to give 0.96 mg of 7-(2-butynyl)-2-mercapto-1-methyl-8-(piperazin-1-yl)-1,7-dihydro purin-6-one trifluoroacetate [MS m/e (ESI) 319 (MH$^+$-CF$_3$COOH)] and 0.61 mg of [7-(2-butynyl)-1-methyl-6-oxo-8-(piperazin-1-yl)-6,7-dihydro-1H-purin-2-ylsulfanyl]acetic acid trifluoroacetate [MS m/e (ESI) 377 (MH$^+$-CF$_3$COOH)].

Example 80

7-(2-Butynyl)-2-ethanesulfinyl-1-methyl-8-(piperazin-1-yl)-1,7-dihydropurin-6-one trifluoroacetate 6 mg of t-butyl 4-[7-(2-butynyl)-2-chloro-1-methyl-6-oxo-6,7-dihydro-1H-purin-8-yl]piperazine-1-carboxylate was dissolved in 0.15 ml of 1-methyl-2-pyrrolidone, and 20 μl of ethanethiol and 6 mg of potassium carbonate were added thereto. The mixture was stirred at room temperature for 5 hours. A saturated ammonium chloride solution was added to the reaction solution, and the mixture was extracted with ethyl acetate. The organic layer was concentrated. The residue was dissolved in 0.30 ml of dichloromethane, and the mixture was cooled to −78° C. 5 mg of m-chloroperbenzoic acid was added to the solution, and the mixture was stirred at −78° C. for 15 minutes. An aqueous solution saturated with sodium sulfite was added to the reaction solution, and the mixture was extracted with dichloromethane. The organic layer was concentrated. The residue was dissolved in 0.40 ml of trifluoroacetic acid, and the solution was concentrated by flushing with nitrogen gas. The residue was purified by reverse-phase high performance liquid chromatography (using an acetonitrile-water mobile phase (containing 0.1% trifluoroacetic acid)) to give 3.21 mg of the title compound.

MS m/e (ESI) 363 (MH$^+$-CF$_3$COOH)

Example 81

7-(2-Butynyl)-2-ethanesulfonyl-1-methyl-8-(piperazin-1-yl)-1,7-dihydropurin-6-one trifluoroacetate 6 mg of t-butyl 4-[7-(2-butynyl)-2-chloro-1-methyl-6-oxo-6,7-dihydro-1H-purin-8-yl]piperazine-1-carboxylate was dissolved in 0.15 ml of 1-methyl-2-pyrrolidone, and 20 µl of ethanethiol and 6 mg of potassium carbonate were added thereto. The mixture was stirred at room temperature for 5 hours. A saturated ammonium chloride solution was added to the reaction solution, and the mixture was extracted with ethyl acetate. The organic layer was concentrated. The residue was dissolved in 0.3 ml of dichloromethane, and the solution was cooled to −78° C. 10 mg of m-chloroperbenzoic acid was added to the solution. The mixture was stirred at −78° C. for 15 minutes and then at 0° C. for 15 minutes. An aqueous solution saturated with sodium sulfite was added to the reaction solution, and the mixture was extracted with dichloromethane. The organic layer was concentrated. The residue was dissolved in trifluoroacetic acid, and the solution was concentrated. The residue was purified by reverse-phase high performance liquid chromatography (using an acetonitrile-water mobile phase (containing 0.1% trifluoroacetic acid)) to give 1.19 mg of the title compound.

MS m/e (ESI) 379 ($MH^+$-$CF_3COOH$)

Example 82

7-(2-Butynyl)-2-cyano-1-methyl-8-(piperazin-1-yl)-1,7-dihydropurin-6-one trifluoroacetate 8 mg of t-butyl 4-[7-(2-butynyl)-2-chloro-1-methyl-6-oxo-6,7-dihydro-1H-purin-8-yl]piperazine-1-carboxylate was dissolved in 0.2 ml of N-methylpyrrolidone, and 10 mg of sodium cyanide was added thereto. The mixture was stirred at 50° C. for 1 hour. Water was added to the reaction mixture, and the mixture was extracted with ethyl acetate. The organic layer was concentrated to give 14 mg of t-butyl 4-[7-(2-butynyl)-2-cyano-1-methyl-6-oxo-6,7-dihydro-1H-purin-8-yl]piperazine-1-carboxylate. 5 mg of this compound was dissolved in trifluoroacetic acid, and the solution was concentrated. The residue was purified by reverse-phase high performance liquid chromatography (using an acetonitrile-water mobile phase (containing 0.1% trifluoroacetic acid)) to give 4.12 mg of the title compound.

MS m/e (ESI) 312 ($MH^+$-$CF_3COOH$)

Example 83

7-(2-Butynyl)-1-methyl-6-oxo-8-(piperazin-1-yl)-6,7-dihydro-1H-purine-2-carboxamide (a) t-Butyl 4-[7-(2-butynyl)-2-carbamoyl-1-methyl-6-oxo-6,7-dihydro-1H-purin-8-yl]piperazine-1-carboxylate 176 mg of t-butyl 4-[7-(2-butynyl)-2-chloro-1-methyl-6-oxo-6,7-dihydro-1H-purin-8-yl]piperazine-1-carboxylate was dissolved in 2 ml of N-methylpyrrolidone, and 100 mg of sodium cyanide was added thereto. The mixture was stirred at 50° C. for 0.5 hour. Water was added to the reaction mixture, and the mixture was extracted with ethyl acetate. The organic layer was concentrated to give 170 mg of t-butyl 4-[7-(2-butynyl)-2-cyano-1-methyl-6-oxo-6,7-dihydro-1H-purin-8-yl]piperazine-1-carboxylate. 98 mg of this compound was dissolved in a mixture of 3 ml of tetrahydrofuran and 2 ml of methanol, and 0.5 ml of an aqueous solution of 20% ammonia and 0.5 ml of an aqueous solution of 30% hydrogen peroxide were added thereto. The mixture was stirred at room temperature overnight. Ethyl acetate was added to the reaction solution, and the mixture was washed with water. The organic layer was dried over anhydrous magnesium sulfate, then filtered. The solvent was evaporated under reduced pressure. The residue was purified by silica gel column chromatography. Thus, 77 mg of the title compound was obtained from the fraction eluted with ethyl acetate-methanol.

$^1$H-NMR ($CDCl_3$)

δ 1.49 (s, 9H) 1.83 (t, J=1.2 Hz, 3H) 3.42-3.49 (m, 4H) 3.58-3.65 (m, 4H) 3.95 (s, 3H) 5.01 (d, J=2.4 Hz, 2H) 5.54 (br, 1H) 7.61 (br, 1H)

(b) 7-(2-Butynyl)-1-methyl-6-oxo-8-(piperazin-1-yl)-6,7-dihydro-1H-purine-2-carboxamide 77 mg of t-butyl 4-[7-(2-butynyl)-2-carbamoyl-1-methyl-6-oxo-6,7-dihydro-1H-purin-8-yl]piperazine-1-carboxylate was dissolved in 1 ml of trifluoroacetic acid, and the solution was concentrated. The residue was purified by chromatography using NH-silica gel. Thus, 49 mg of the title compound was obtained from the fraction eluted with ethyl acetate-methanol (5:1)

$^1$H-NMR ($CDCl_3$)

δ 1.83 (t, J=2.4 Hz, 3H) 3.05-3.07 (m, 4H) 3.45-3.48 (m, 4H) 3.94 (s, 3H) 4.98 (s, 2H) 5.57 (br, 1H) 7.65 (br, 1H)

Example 84

7-(2-Butynyl)-2-carboxy-1-methyl-8-(piperazin-1-yl)-1,7-dihydropurin-6-one trifluoroacetate

Example 85

7-(2-Butynyl)-1-methyl-8-(piperazin-1-yl)-1,7-dihydropurin-6-one trifluoroacetate 12.5 mg of t-butyl 4-[7-(2-butynyl)-2-carbamoyl-1-methyl-6-oxo-6,7-dihydro-1H-purin-8-yl]piperazine-1-carboxylate was dissolved in 0.3 ml of tetrahydrofuran and 0.2 ml of methanol, and 0.05 ml of 2N sodium hydroxide was added thereto. The mixture was stirred at 50° C. for 2 hours. The reaction solution was concentrated, and the residue was dissolved in trifluoroacetic acid. The mixture was concentrated. The residue was purified by reverse-phase high performance liquid chromatography (using an acetonitrile-water mobile phase (containing 0.1% trifluoroacetic acid)) to give 0.44 mg of 7-(2-butynyl)-2-carboxy-1-methyl-8-(piperazin-1-yl)-1,7-dihydropurin-6-one trifluoroacetate [MS m/e (ESI) 331 ($MH^+$-$CF_3COOH$)] and 6.4 mg of 7-(2-butynyl)-1-methyl-8-(piperazin-1-yl)-1,7-dihydropurin-6-one trifluoroacetate [$^1$H-NMR ($CDCl_3$) δ 1.81 (t, J=2.4 Hz, 3H) 3.54 (br, 4H) 3.63 (s, 3H) 3.83 (br, 4H) 5.02 (s, 2H) 8.20 (s, 1H); MS m/e (ESI) 287 ($MH^+$-$CF_3COOH$)].

Example 86

7-(2-Butynyl)-2-methoxy-1-(2-phenylethyl)-8-(piperazin-1-yl)-1,7-dihydropurin-6-one hydrochloride (a) [7-Benzyl-2,6-dioxo-1-(2-phenylethyl)-1,2,6,7-tetrahydropurin-yl]methyl 2,2-dimethylpropionate A mixture consisting of 5.00 mg of [7-benzyl-2,6-dioxo-1,2,6,7-tetrahydropurin-3-yl]methyl 2,2-dimethylpropionate, 0.38 ml of 2-bromoethyl benzene, 390 mg of anhydrous potassium carbonate, and 5 ml of N,N-dimethylformamide was stirred in an oil bath at 50° C. for two hours. The reaction mixture was extracted with ethyl acetate and water, and the organic layer was washed with water and then with saturated saline. The organic liquid was dried over anhydrous magnesium sulfate, and then concentrated under reduced pressure. The residue was crystallized with ethyl acetate-hexane to give 540 mg of the title compound.

$^1$H-NMR (CDCl$_3$)

δ 1.19 (s, 9H) 2.92-2.98 (m, 2H) 4.19-4.25 (m, 2H) 5.48 (s, 2H) 6.11 (s, 2H) 7.17-7.40 (m, 10H) 7.54 (s, 1H)

(b)[7-(2-Butynyl)-8-chloro-2,6-dioxo-1-(2-phenylethyl)-1,2,6,7-tetrahydropurin-3-yl]methyl 2,2-dimethyl propionate A mixture consisting of 540 mg of [7-benzyl-2,6-dioxo-1-(2-phenylethyl)-1,2,6,7-tetrahydropurin-3-yl]methyl 2,2-dimethylpropionate, 50 mg of 10% palladium carbon, and 8 ml of acetic acid was stirred under a hydrogen atmosphere at room temperature overnight. The reaction mixture was filtered and then concentrated under reduced pressure to give 410 mg of residue.

The entire residue was combined with 0.15 ml of 1-bromo-2-butyne, 300 mg of anhydrous potassium carbonate, and 5 ml of N,N-dimethylformamide. The mixture was stirred at room temperature for 2 hours. The reaction solution was extracted with ethyl acetate and water. The organic layer was washed with water and then with saturated brine. The organic liquid was dried over anhydrous magnesium sulfate and concentrated under reduced pressure to give 470 mg of residue.

The entire residue was combined with 180 mg of N-chlorosuccinimide and 5 ml of N,N-dimethylformamide. The mixture was stirred at room temperature for 2 hours. After 0.5 ml of an aqueous solution of 1M sodium thiosulfate had been added to the reaction solution, the mixture was extracted with ethyl acetate and water. The organic layer was washed with water and then with saturated brine. The organic liquid was dried over anhydrous magnesium sulfate, and then concentrated under reduced pressure. 380 mg of the title compound was obtained by crystallization using ethyl acetate-hexane.

$^1$H-NMR (CDCl$_3$)

δ 1.21 (s, 9H) 1.83 (t, J=2 Hz, 3H) 2.92-2.98 (m, 2H) 4.19-4.25 (m, 2H) 5.11 (q, J=2 Hz, 2H) 6.05 (s, 2H) 7.18-7.32 (m, 5H)

(c) t-Butyl 4-[7-(2-butynyl)-2,6-dioxo-1-(2-phenylethyl)-2,3,6,7-tetrahydro-1H-purin-8-yl]piperazine-1-carboxylate A mixture consisting of 380 mg of [7-(2-butynyl)-8-chloro-2,6-dioxo-1-(2-phenylethyl)-1,2,6,7-tetrahydropurin-3-yl]methyl 2,2-dimethyl propionate, 460 mg of t-butyl piperazine-1-carboxylate, and 0.5 ml of N-methylpyrrolidone was stirred in an oil bath at 150° C. for 15 minutes. The reaction mixture was extracted with ethyl acetate and water, and the organic layer was washed with water and then with saturated brine. The organic layer was dried over anhydrous magnesium sulfate, and then concentrated under reduced pressure. The residue was dissolved in ethyl acetate/hexane (1/1). The solution was filtered through a small amount of silica gel, and then washed with ethyl acetate/hexane (1/1). The filtrate was combined with the washing solution. The mixed solution was concentrated under reduced pressure to give 570 mg of residue.

The entire residue was combined with 5 ml of tetrahydrofuran and 2.5 ml of methanol. 33 mg of sodium hydride was added to the mixture, and the resulting mixture was stirred at room temperature for 30 minutes. 1 ml of 1 N hydrochloric acid was added to the reaction solution, and then the mixture was extracted with ethyl acetate and water, then was washed with water and then with saturated brine. The organic liquid was dried over anhydrous magnesium sulfate, and concentrated under reduced pressure to give 350 mg of the title compound.

$^1$H-NMR (CDCl$_3$)

δ 1.50 (s, 9H) 1.85 (t, J=2 Hz, 3H) 2.91-2.98 (m, 2H) 3.37 (br.s, 4H) 3.56-3.62 (m, 4H) 4.15-4.22 (m, 2H) 4.87 (q, J=2 Hz, 2H) 7.18-7.35 (m, 5H)

(d) t-Butyl 4-[7-(2-butynyl)-2-chloro-6-oxo-1-(2-phenylethyl)-6,7-dihydro-1H-purin-8-yl]piperazine-1-carboxylate A mixture consisting of 290 mg of t-butyl 4-[7-(2-butynyl)-2,6-dioxo-1-(2-phenylethyl)-2,3,6,7-tetrahydro-1H-purin-8-yl]piperazine-1-carboxylate and 4 ml of phosphorus oxychloride was heated and stirred in an oil bath at 120° C. for 8 hours. The reaction solution was concentrated under reduced pressure, and the residue was dissolved in 5 ml of tetrahydrofuran. This solution was added dropwise to a mixture consisting of 250 mg of di-t-butyl dicarbonate, 10 ml of a saturated sodium bicarbonate solution, and 10 ml of tetrahydrofuran while the mixture was being stirred and cooled with ice. The mixture was incubated at room temperature for 4 hours, and then extracted with ethyl acetate. The organic layer was washed with water then with saturated brine, dried over anhydrous magnesium sulfate, and then concentrated under reduce pressure. The residue was purified by silica gel column chromatography using 30 to 50% ethyl acetate/hexane. Then, the material was further purified by reverse-phase column chromatography using 50 to 100% methanol/water to give 60 mg of the title compound.

$^1$H-NMR (CDCl$_3$)

δ 1.49 (s, 9H) 1.84 (t, J=2 Hz, 3H) 3.10-3.16 (m, 2H) 3.40-3.46 (m, 2H) 3.57-3.63 (m, 4H) 4.42-4.49 (m, 4H) 4.94 (q, J=2 Hz, 2H) 7.21-7.34 (m, 5H)

(e) 7-(2-Butynyl)-2-methoxy-1-(2-phenylethyl)-8-(piperazin-1-yl)-1,7-dihydropurin-6-one hydrochloride 10 mg of sodium hydride (60%; oily) was added to a mixture consisting of 7 mg of t-butyl 4-[7-(2-butynyl)-2-chloro-6-oxo-1-(2-phenylethyl)-6,7-dihydro-1H-purin-8-yl]piperazine-1-carboxylate and 0.5 ml of methanol. The mixture was stirred at room temperature for 20 minutes. Water was added to the reaction solution. The mixture was extracted with ethyl acetate. The organic layer was washed with water and then with saturated brine, and concentrated. 0.5 ml of trifluoroacetic acid was added to the residue. The mixture was stirred at room temperature for 30 minutes, and then concentrated. The residue was purified by reverse-phase column chromatography using 20 to 80% methanol/water (containing 0.1% concentrated hydrochloric acid) to give 4.3 mg of the title compound.

¹H-NMR (DMSO-d6)

δ 1.80 (br.s, 3H) 2.85 (t, J=7 Hz, 2H) 3.28 (br.s, 4H) 3.48-3.54 (m, 4H) 3.83 (s, 3H) 4.15 (t, J=7 Hz, 2H) 4.97 (br.s, 2H) 7.16-7.24 (m, 3H) 7.29 (t, J=8 Hz, 2H) 9.08 (br.s, 2H)

Example 87

7-(2-Butynyl)-2-ethoxy-1-(2-phenylethyl)-8-(piperazin-1-yl)-1,7-dihydropurin-6-one hydrochloride Using ethanol instead of methanol in Example 86 (e), the title compound was synthesized by the same method as used in Example 86 (e).

¹H-NMR (DMSO-d6)

δ 1.28 (t, J=7 Hz, 3H) 1.80 (s, 3H) 2.86 (t, J=7 Hz, 2H) 3.27 (br.s, 4H) 3.46-3.53 (m, 4H) 4.15 (t, J=7 Hz, 2H) 4.25 (q, J=7 Hz, 2H) 4.97 (s, 2H) 7.17 (d, J=7 Hz, 2H) 7.22 (t, J=7 Hz, 1H) 7.29 (t, J=7 Hz, 2H) 9.04 (br.s, 2H)

Example 88

Methyl [7-(2-butynyl)-6-oxo-1-(2-phenylethyl)-8-(piperazin-1-yl)-6,7-dihydro-1H-purin-2-ylsulfanyl]acetate hydrochloride Using methyl thioglycolate instead of methanol and using potassium carbonate as a base in Example 86 (e), the title compound was synthesized by the same method as used in Example 86.

¹H-NMR (DMSO-d6)

δ 1.80 (s, 3H) 2.96 (t, J=8 Hz, 2H) 3.29 (br.s, 4H) 3.50-3.56 (m, 4H) 3.68 (s, 3H) 4.16 (s, 2H) 4.23 (t, J=8 Hz, 2H) 4.99 (s, 2H) 7.24-7.38 (m, 5H) 8.96 (br.s, 2H)

Example 89

Ethyl [7-(2-butynyl)-6-oxo-1-(2-phenylethyl)-8-(piperazin-1-yl)-6,7-dihydro-1H-purin-2-ylamino]acetate hydrochloride Using glycine ethyl ester hydrochloride instead of methanol and using potassium carbonate as a base in Example 86(e), the title compound was synthesized by the same method as used in Example 86.

¹H-NMR (DMSO-d6)

δ 1.22 (t, J=7 Hz, 3H) 1.78 (s, 3H) 2.87 (t, J=8 Hz, 2H) 3.26 (br.s, 4H) 3.47 (br.s, 4H) 4.05 (d, J=6 Hz, 2H) 4.12 (q, J=7 Hz, 2H) 4.21 (t, J=8 Hz, 2H) 4.89 (br.s, 2H) 7.17-7.35 (m, 5H) 7.51 (t, J=6 Hz, 1H) 8.93 (br.s, 2H)

Example 90

2-[7-(2-Butynyl)-6-oxo-1-(2-phenylethyl)-8-(piperazin-1-yl)-6,7dihydro-1H-purin-2-ylamino]acetamide hydrochloride Using glycine amide hydrochloride instead of methanol and using potassium carbonate as a base in Example 86 (e), the title compound was synthesized by the same method as used in Example 86.

¹H-NMR (DMSO-d6)

δ 1.79 (s, 3H) 2.87 (t, J=8 Hz, 2H) 3.26 (br.s, 4H) 3.52 (br.s, 4H) 3.84 (d, J=5 Hz, 2H) 4.19 (t, J=8 Hz, 2H) 4.91 (s, 2H) 7.02 (s, 1H) 7.16-7.40 (m, 7H) 9.08 (br.s, 2H)

Example 91

Ethyl N-[7-(2-butynyl)-6-oxo-1-(2-phenylethyl)-8-(piperazin-1-yl)-6,7-dihydro-1H-purin-2-yl]-N-methylaminoacetate hydrochloride Using N-methylglycine ethyl ester hydrochloride instead of methanol and using potassium carbonate as a base in Example 86 (e) the title compound was synthesized by the same method as used in Example 86.

¹H-NMR (DMSO-d6)

δ 1.17 (t, J=7 Hz, 3H) 1.80 (s, 3H) 2.76 (s, 3H) 2.96 (t, J=8 Hz, 2H) 3.28 (br.s, 4H) 3.46-3.52 (m, 4H) 3.88 (s, 2H) 4.09 (q, J=7 Hz, 2H) 4.27 (t, J=8 Hz, 2H) 4.98 (s, 2H) 7.15-7.30 (m, 5H) 8.95 (br.s, 2H)

Example 92

Methyl [7-(2-butynyl)-6-oxo-1-(2-phenylethyl)-8-(piperazin-1-yl)-6,7-dihydro-1H-purin-2-yloxy]acetate hydrochloride Using methyl glycolate instead of methanol in Example 86(e), the title compound was synthesized by the same method as used in Example 86.

¹H-NMR (DMSO-d6)

δ 1.80 (s, 3H) 2.93 (t, J=8 Hz, 2H) 3.28 (br.s, 4H) 3.49 (br.s, 4H) 3.72 (s, 3H) 4.20 (t, J=8 Hz, 2H) 4.96 (s, 2H) 5.02 (s, 2H) 7.20-7.34 (m, 5H) 8.87 (br.s, 2H)

Example 93

7-(2-Butynyl)-2-(2-hydroxyethoxy)-1-(2-phenylethyl)-8-(piperazin-1-yl)-1,7-dihydropurin-6-one hydrochloride Using ethylene glycol instead of methanol in Example 86 (e), the title compound was synthesized by the same method as used in Example 86.

¹H-NMR (DMSO-d6)

δ 1.80 (s, 3H) 2.88 (t, J=8 Hz, 2H) 3.29 (br.s, 4H) 3.49 (br.s, 4H) 3.71 (t, J=6 Hz, 2H) 4.18 (t, J=8 Hz, 2H) 4.28 (t, J=6 Hz, 2H) 4.97 (s, 2H) 7.16-7.32 (m, 5H) 8.90 (br.s, 2H)

Example 94

7-(2-Butynyl)-2-dimethylamino-1-(2-phenylethyl)-8-(piperazin-1-yl)-1,7-dihydropurin-6-one hydrochloride Using an aqueous solution of 50% dimethylamine instead of methanol in Example 86 (e), the title compound was synthesized by the same method as used in Example 86.

¹H-NMR (DMSO-d6)

δ 1.80 (s, 3H) 2.60 (s, 6H) 2.89 (t, J=8 Hz, 2H) 3.28 (br.s, 4H) 3.49 (br.s, 4H) 4.26 (t, J=8 Hz, 2H) 4.98 (s, 2H) 7.06-7.27 (m, 5H) 8.93 (br.s, 2H)

Example 95

7-(2-Butynyl)-2-chloro-8-(piperazin-1-yl)-1,7-dihydropurin-6-one trifluoroacetate (a) t-Butyl 4-[7-(2-butynyl)-2-chloro-6-oxo-6,7-dihydro-1H-purin-8-yl]piperazine-1-carboxylate A mixture consisting of 1.0 g of t-butyl 4-[7-(2-butynyl)-2,16-dichloro-7H-purin-8-yl]piperazine-1-carboxylate, 580 mg of sodium acetate, and 10 ml of dimethyl sulfoxide was stirred in an oil bath at 80° C. for 24 hours. The reaction solution was extracted with ethyl acetate and water. The organic layer was washed with water and then with saturated brine, then was dried over anhydrous magnesium sulfate, and concentrated under reduced pressure. The residue was purified by silica gel column chromatography using 50 to 70% ethyl acetate/hexane and crystallized with ethyl acetate-hexane to give 800 mg of the title compound.

$^1$H-NMR (CDCl$_3$)

δ 1.49 (s, 9H) 1.83 (t, J=2 Hz, 3H) 3.44 (br.s, 4H) 3.56-3.63 (m, 4H) 4.94 (q, J=2 Hz, 2H)

(b) 7-(2-Butynyl)-2-chloro-8-(piperazin-1-yl)-1,7-dihydropurin-6-one trifluoroacetate 8 mg of t-butyl 4-[7-(2-butynyl)-2-chloro-6-oxo-6,7-dihydro-1H-purin-8-yl]piperazine-1-carboxylate was dissolved in trifluoroacetic acid, and the solution was concentrated. The residue was purified by reverse-phase high performance liquid chromatography (using an acetonitrile-water mobile phase (containing 0.1% trifluoroacetic acid)) to give 3.45 mg of the title compound.

MS m/e (ESI) 307 (MH$^+$-CF$_3$COOH)

Example 96

2-[7-(2-Butynyl)-2-dimethylamino-6-oxo-8-(piperazin-1-yl)-6,7-dihydropurin-1-ylmethyl]benzonitrile hydrochloride (a) t-Butyl 4-[7-(2-butynyl)-2-chloro-1-(2-cyanobenzyl)-6-oxo-6,7-dihydro-1H-purin-8-yl]piperazine-1-carboxylate A mixture consisting of 100 mg of t-butyl 4-[7-(2-butynyl)-2-chloro-6-oxo-6,7-dihydro-1H-purin-8-yl]piperazine-1-carboxylate, 60 mg of 2-cyanobenzyl bromide, 68 mg of anhydrous potassium carbonate, and 1 ml of N,N-dimethylformamide was stirred at room temperature for 4 hours. Ethyl acetate/hexane (1/1) and water were added to the reaction solution. The insoluble material was removed by filtration. The filtrate was extracted with ethyl acetate. The organic layer was washed with water and then with saturated brine, dried over anhydrous magnesium sulfate, and then concentrated under reduced pressure. The residue was purified by silica gel column chromatography using 30 to 50% ethyl acetate/hexane to give 50 mg of the title compound.

$^1$H-NMR (CDCl$_3$)

δ 1.49 (s, 9H) 1.83 (t, J=2 Hz, 3H) 3.43-3.49 (m, 4H) 3.58-3.64 (m, 4H) 4.95 (q, J=2 Hz, 2H) 5.72 (s, 2H) 7.06 (d, J=8 Hz, 1H) 7.39 (t, J=8 Hz, 1H) 7.51 (t, J=8 Hz, 1H) 7.71 (d, J=8 Hz, 1H)

(b) t-Butyl 4-[7-(2-butynyl)-1-(2-cyanobenzyl)-2-dimethylamino-6-oxo-6,7-dihydro-1H-purin-8-yl]piperazine-1-carboxylate A mixture consisting of 8 mg of t-butyl 4-[7-(2-butynyl)-2-chloro-1-(2-cyano benzyl)-6-oxo-6,7-dihydro-1H-purin-8-yl]piperazine-1-carboxylate, 20 μl of an aqueous solution of 50% dimethylamine, and 0.2 ml of N,N-dimethylformamide was stirred at room temperature for 2 hours. The reaction solution was extracted with ethyl acetate and water. The organic layer was washed with water and with saturated brine, and concentrated. The residue was separated by silica gel thin-layer chromatography using 70% ethyl acetate/hexane to give 6.5 mg of the title compound.

$^1$H-NMR (CDCl$_3$)

δ 1.50 (s, 9H) 1.81 (t, J=2 Hz, 3H) 2.73 (s, 6H) 3.38-3.45 (m, 4H) 3.56-3.64 (m, 4H) 4.91, (q, J=2 Hz, 2H) 5.55 (s, 2H) 7.07 (d, J=8 Hz, 1H) 7.32 (t, J=8 Hz, 1H) 7.46, (t, J=8 Hz, 1H) 7.65 (d, J=8 Hz, 1H)

(c) 2-[7-(2-Butynyl)-2-dimethylamino-6-oxo-8-(piperazin-1-yl)-6,7-dihydropurin-1-ylmethyl]benzonitrile hydrochloride 6.5 mg of t-butyl 4-[7-(2-butynyl)-1-(2-cyanobenzyl)-2-dimethylamino-6-oxo-6,7-dihydro-1H-purin-8-yl]piperazine-1-carboxylate was dissolved in 0.5 ml of trifluoroacetic acid, and the mixture was allowed to stand at room temperature for 20 minutes. The reaction solution was concentrated, and the residue was purified by reverse-phase column chromatography using 20 to 80% methanol/water (containing 0.1% concentrated hydrochloric acid) to give 6.4 mg of the title compound.

$^1$H-NMR (DMSO-d6)

δ 1.76 (s, 3H) 2.69 (s, 6H) 3.28 (br.s, 4H) 3.51 (br.s, 4H) 4.91 (s, 2H) 5.40 (s, 2H) 7.04 (d, J=8 Hz, 1H) 7.43 (t, J=8 Hz, 1H) 7.60 (t, J=8 Hz, 1H) 7.83 (d, J=8 Hz, 1H) 8.90 (br.s, 2H)

Example 97

Methyl [7-(2-butynyl)-1-(2-cyanobenzyl)-6-oxo-8-(piperazin-1-yl)-6,7-dihydro-1H-purin-2-ylsulfanyl]acetate hydrochloride Using methyl thioglycolate instead of dimethylamine and using anhydrous potassium carbonate as a base in Example 96 (b), the title compound was synthesized by the same method as used in Example 96.

$^1$H-NMR (DMSO-d6)

δ 1.79 (s, 3H) 3.29 (br.s, 4H) 3.56 (br.s, 4H) 3.65 (s, 3H) 4.12 (s, 2H) 4.99 (s, 2H) 5.48 (s, 2H) 7.10 (d, J=8 Hz, 1H) 7.50 (t, J=8 Hz, 1H) 7.65 (t, J=8 Hz, 1H) 7.92 (d, J=8 Hz, 1H) 8.95 (br.s, 2H)

Example 98

2-[7-(2-Butynyl)-2-methoxy-6-oxo-8-(piperazin-1-yl)-6,7-dihydropurin-1-ylmethyl]benzonitrile hydrochloride Using methanol instead of dimethylamine and using anhydrous potassium carbonate as a base in Example 96(b), the title compound was synthesized by the same method as used in Example 96.

$^1$H-NMR (DMSO-d6)

δ 1.79 (s, 3H) 3.28 (br.s, 4H) 3.48-3.56 (m, 4H) 3.91 (s, 3H) 4.97 (s, 2H) 5.32 (s, 2H) 7.19 (d, J=8 Hz, 1H) 7.48 (t, J=8 Hz, 1H) 7.63 (t, J=8 Hz, 1H) 7.87 (d, J=8 Hz, 1H) 9.05 (br.s, 2H)

Example 99

Methyl [7-(2-butynyl)-1-cyanomethyl-6-oxo-8-(piperazin-1-yl)-6,7-dihydro-1H-purin-2-ylsulfanyl]acetate hydrochloride (a) t-Butyl 4-[7-(2-butynyl)-2-chloro-1-cyanomethyl-6-oxo-6,7-dihydro-1H-purin-8-yl]piperazine-1-carboxylate Using bromoacetonitrile instead of dimethylamine in Example 96(b), the title compound was synthesized by the same method as used in Example 96(a).

¹H-NMR (CDCl₃)

δ 1.49 (s, 9H) 1.84 (t, J=2 Hz, 3H) 3.43-3.49 (m, 4H) 3.58-3.63 (m, 4H) 4.91 (q, J=2 Hz, 2H) 5.18 (s, 2H)

(b) Methyl [7-(2-butynyl)-1-cyanomethyl-6-oxo-8-(piperazin-1-yl)-6,7-dihydro-1H-purin-2-ylsulfanyl]acetate hydrochloride Using the compound obtained in Example 99(a) described above instead of the compound obtained in Example 96 (a) in Example 97, the title compound was synthesized by the same method as used in Example 97.

¹H-NMR (DMSO-d6)

δ 1.80 (s, 3H) 3.29 (br.s, 4H) 3.55 (br.s, 4H) 3.68 (s, 3H) 4.22 (s, 2H) 4.98 (s, 2H) 5.21 (s, 2H) 8.93 (br.s, 2H)

Example 100

Methyl [1,7-bis(2-butynyl)-6-oxo-8-(piperazin-1-yl)-6,7-dihydro-1H-purin-2-ylsulfanyl]acetate hydrochloride (a) t-Butyl 4-[1,7-bis(2-butynyl)-2-chloro-6-oxo-6,7-dihydro-1H-purin-8-yl]piperazine-1-carboxylate Using 1-bromo-2-butyne instead of 2-cyanobenzyl bromide in Example 96 (a), the title compound was synthesized by the same method as used in Example 96(a).

¹H-NMR (CDCl₃)

δ 1.49 (s, 9H) 1.80 (t, J=2 Hz, 3H) 1.83 (t, J=2 Hz, 3H) 3.40-3.45 (m, 4H) 3.57-3.62 (m, 4H) 4.93 (q, J=2 Hz, 2H) 4.98 (q, J=2 Hz, 2H)

(b) Methyl [1,7-bis(2-butynyl)-6-oxo-8-(piperazin-1-yl)-6,7-dihydro-1H-purin-2-ylsulfanyl]acetate hydrochloride Using the compound obtained in Example 100(a) described above instead of the compound obtained in Example 96(a) in Example 97, the title compound was synthesized by the same method as used in Example 97.

¹H-NMR (DMSO-d6)

δ 1.79 (s, 6H) 3.28 (br.s, 4H) 3.53 (br.s, 4H) 3.67 (s, 3H) 4.15 (s, 2H) 4.83 (s, 2H) 4.98 (s, 2H) 9.02 (br.s, 2H)

Example 101

1,7-Bis(2-butynyl)-6-oxo-8-(piperazin-1-yl)-6,7-dihydro-1H-purine-2-carbonitrile hydrochloride Using sodium cyanide instead of methyl thioglycolate in Example 100, the title compound was synthesized by the same method as used in Example 100.

¹H-NMR (DMSO-d6)

δ 1.81 (s, 3H) 1.82 (s, 3H) 3.28 (br.s, 4H) 3.56-3.63 (m, 4H) 4.95 (q, J=2 Hz, 2H) 5.07 (q, J=2 Hz, 2H) 9.04 (br.s, 2H)

Example 102

1,7-Bis(2-butynyl)-2-methoxy-8-(piperazin-1-yl)-1,7-dihydropurin-6-one hydrochloride Using methanol instead of methyl thioglycolate and using sodium hydride as the base in Example 100, the title compound was synthesized by the same method as used in Example 100.

¹H-NMR (DMSO-d6)

δ 1.75 (s, 3H) 1.80 (s, 3H) 3.28 (br.s, 4H) 3.47-3.55 (m, 4H) 3.98 (s, 3H) 4.66 (s, 2H) 4.96 (s, 2H) 9.01 (br.s, 2H)

Example 103

Methyl [1-allyl-7-(2-butynyl)-6-oxo-8-(piperazin-1-yl)-6,7-dihydro-1H-purin-2-ylsulfanyl]acetate hydrochloride (a) t-Butyl 4-[1-allyl-7-(2-butynyl)-2-chloro-6-oxo-6,7-dihydro-1H-purin-8-yl]piperazine-1-carboxylate Using allyl bromide instead of 2-cyanobenzyl bromide in Example 96 (a), the title compound was synthesized by the same method as used in Example 96(a).

¹H-NMR (CDCl₃)

δ 1.49 (s, 9H) 1.83 (t, J=2 Hz, 3H) 3.38-3.45 (m, 4H) 3.55-3.63 (m, 4H) 4.90 (d, J=5 Hz, 2H) 4.93 (q, J=2 Hz, 2H) 5.19-5.29 (m, 2H) 5.93 (ddt, J=10, 17, 5 Hz, 1H)

(b) Methyl [1-allyl-7-(2-butynyl)-6-oxo-8-(piperazin-1-yl)-6,7-dihydro-1H-purin-2-ylsulfanyl]acetate hydrochloride Using the compound obtained in Example 103(a) described above instead of the compound obtained in Example 96 (a) in Example 97, the title compound was synthesized by the same method as used in Example 97.

¹H-NMR (DMSO-d6)

δ 1.79 (s, 3H) 3.27 (br.s, 4H) 3.48-3.56 (m, 4H) 3.66 (s, 3H) 4.12 (s, 2H) 4.70 (d, J=5 Hz, 2H) 4.98 (br.s, 2H) 5.07 (d, J=17 Hz, 1H) 5.21 (d, J=10 Hz, 1H) 5.89 (ddt, J=10, 17, 5 Hz, 1H) 9.07 (br.s, 2H)

Example 104

1-Allyl-7-(2-butynyl)-6-oxo-8-(piperazin-1-yl)-6,7-dihydro-1H-purine-2-carbonitrile hydrochloride The title compound was synthesized by using sodium cyanide, instead of allyl bromide by the same method as used in Example 103.

¹H-NMR (DMSO-d6)

δ 1.81 (t, J=2 Hz, 3H) 3.29 (br.s, 4H) 3.57-3.64 (m, 4H) 4.81 (d, J=5 Hz, 2H) 5.04-5.10 (m, 3H) 5.26 (d, J=10 Hz, 1H) 6.00 (ddt, J=10, 17, 5 Hz, 1H) 9.12 (br.s, 2H)

Example 105

1-Allyl-7-(2-butynyl)-2-methoxy-8-(piperazin-1-yl)-1,7-dihydropurin-6-one hydrochloride Using methanol instead of methyl thioglycolate and using sodium hydride as a base in Example 103, the title compound was synthesized by the same method as used in Example 103.

¹H-NMR (DMSO-d6)

δ 1.79 (t, J=2 Hz, 3H) 3.27 (br.s, 4H) 3.48-3.56 (m, 4H) 3.93 (s, 3H) 4.55 (d, J=5 Hz, 2H) 4.94-5.02 (m, 3H) 5.12 (d, J=10 Hz, 1H) 5.87 (ddt, J=10, 17, 5 Hz, 1H) 9.04 (br.s, 2H)

Example 106

Methyl [7-(2-butynyl)-1-(2-methoxyethyl)-6-oxo-8-(piperazin-1-yl)-6,7-dihydro-1H-purine-2-ylsulfanyl] acetate hydrochloride (a) t-Butyl 4-[7-(2-butynyl)-1-(2-methoxyethyl)-2-chloro-6-oxo-6,7-dihydro-1H-purin-8-yl]piperazine-1-carboxylate Using 2-bromoethyl methyl ether instead of 2-cyanobenzyl bromide in Example 96 (a), the title compound was synthesized by the same method as used in Example 96(a).

$^1$H-NMR (CDCl$_3$)
δ 1.49 (s, 9H) 1.83 (t, J=2 Hz, 3H) 3.36 (s, 3H) 3.39-3.45 (m, 4H) 3.56-3.61 (m, 4H) 3.69 (t, J=6 Hz, 2H) 4.50 (t, J=6 Hz, 2H) 4.92 (q, J=2 Hz, 2H)

(b) Methyl [7-(2-butynyl)-1-(2-methoxyethyl)-6-oxo-8-(piperazin-1-yl)-6,7-dihydro-1H-purine-2-ylsulfanyl]acetate hydrochloride Using the compound obtained in Example 106 (a) described above instead of the compound obtained in Example 96 (a) in Example 97, the title compound was synthesized by the same method as used in Example 97.

$^1$H-NMR (DMSO-d6)
δ 1.80 (s, 3H) 3.25-3.32 (m, 7H) 3.50-3.55 (m, 4H) 3.61 (t, J=6 Hz, 2H) 3.67 (s, 3H) 4.14 (s, 2H) 4.25 (t, J=6 Hz, 2H) 4.98 (s, 2H) 9.00 (br.s, 2H)

Example 107

7-(2-Butynyl)-1-(2-methoxyethyl)-6-oxo-8-(piperazin-1-yl)-6,7-dihydro-1H-purine-2-carbonitrile hydrochloride Using sodium cyanide instead of methyl thioglycolate in Example 106, the title compound was synthesized by the same method as used in Example 106.

$^1$H-NMR (DMSO-d6)
δ 1.81 (s, 3H) 3.25 (s, 3H) 3.29 (br.s, 4H) 3.55-3.64 (m, 6H) 4.34 (t, J=5 Hz, 2H) 5.08 (s, 2H) 9.05 (br.s, 2H)

Example 108

7-(2-Butynyl)-1-(2-methoxyethyl)-2-methoxy-8-(piperazin-1-yl)-1,7-dihydropurin-6-one hydrochloride Using methanol instead of methyl thioglycolate and using anhydrous potassium carbonate as the base in Example 106, the title compound was synthesized by the same method as used in Example 106.

$^1$H-NMR (DMSO-d6)
δ 1.79 (s, 3H) 3.23 (s, 3H) 3.27 (br.s, 4H) 3.46-3.55 (m, 6H) 3.94 (s, 3H) 4.13 (t, J=6 Hz, 2H), 4.96 (s, 2H), 9.03 (br.s, 2H)

Example 109

7-Benzyl-1-methyl-8-(piperazin-1-yl)-1,7-dihydropurin-6-one trifluoroacetate (a) 7-Benzyl-1,7-dihydropurin-6-one 18.23 g of inosine was dissolved in 90 ml of dimethyl sulfoxide, and 16 ml of benzyl bromide was added thereto. The mixture was stirred at room temperature overnight. The reaction solution was poured into 3 L of ethyl acetate. The resulting supernatant was removed and the precipitated oil was dissolved in 10% hydrochloric acid (135 ml). The solution was heated at 70° C. with stirring for 4 hours. The solution was cooled to room temperature, and then neutralized to pH 7 using a 5N aqueous sodium hydroxide solution. The precipitated solid was collected by filtration, and dried to give 12.748 g of the title compound.

(b) t-Butyl 4-(7-benzyl-6-oxo-6,7-dihydro-1H-purin-8-yl)piperazine-1-carboxy late 12.748 g of 7-benzyl-1,7-dihydropurin-6-one was dissolved in 150 ml of N,N-dimethylformamide, and 7.9 g of N-chlorosuccinimide was added thereto. The reaction solution was stirred overnight, and then diluted with ethyl acetate. The solution was washed with water and 1N hydrochloric acid, and dried over anhydrous magnesium sulfate. The solution was filtered, and the filtrate was concentrated to give 6.103 g of 7-benzyl-8-chloro-1,7-dihydropurin-6-one. This compound was combined with 20 g of t-butyl piperazine-1-carboxylate, and the mixture was heated at 150° C. After being stirred for one hour, the reaction mixture was combined with ethyl acetate and water, and partitioned. The organic layer was washed with 1N hydrochloric acid, and dried over anhydrous magnesium sulfate. After filtration, the filtrate was concentrated. The residue was purified by silica gel column chromatography. Thus, 1.539 g of the title compound was obtained from the fraction eluted with ethyl acetate-methanol (10:1).

$^1$H-NMR (CDCl$_3$)
δ 1.39 (s, 9H) 3.07-3.10 (m, 4H) 3.35-3.39 (m, 4H) 5.44 (s, 2H) 7.16-7.18 (m, 2H) 7.22-7.32 (m, 3H) 7.91 (s, 1H) 12.18 (s, 1H)

(c) 7-Benzyl-1-methyl-8-(piperazin-1-yl)-1,7-dihydropurin-6-one trifluoroacetate 15 mg of t-butyl 4-(7-benzyl-6-oxo-6,7-dihydro-1H-purin-8-yl)piperazine-1-carboxy late was dissolved in 1 ml of N,N-dimethylformamide, and 10 mg of sodium hydride and 10 µl of methyl iodide were added thereto. The mixture was stirred at room temperature for 3 days then ethyl acetate and water were added and the layers separated. The organic layer was concentrated, and the residue was dissolved in trifluoroacetic acid. The solution was concentrated. The residue was purified by reverse-phase high performance liquid chromatography (using an acetonitrile-water mobile phase (containing 0.1% trifluoroacetic acid)) to give 4.31 mg of the title compound.

MS m/e (ESI) 325 (MH$^+$-CF$_3$COOH)

Example 110

7-Benzyl-1-ethyl-8-(piperazin-1-yl)-1,7-dihydropurin-6-one trifluoroacetate

The title compound was obtained by using iodoethane, instead of methyl iodide, by the same method as used in Example 109.

MS m/e (ESI) 339 (MH$^+$-CF$_3$COOH)

Example 111

Ethyl [7-benzyl-6-oxo-8-(piperazin-1-yl)-6,7-dihydropurin-1-yl]acetate trifluoroacetate The title compound was obtained by using ethyl bromoacetate, instead of methyl iodide, by the same method as used in Example 109.
MS m/e (ESI) 397 (MH$^+$-CF$_3$COOH)

Example 112

7-Benzyl-1-(2-methoxyethyl)-8-(piperazin-1-yl)-1,7-dihydropurin-6-one trifluoroacetate The title compound was obtained by using 2-methoxyethyl bromide, instead of methyl iodide, by the same method as used in Example 109.
MS m/e (ESI) 369 (MH$^+$-CF$_3$COOH)

Example 113

7-Benzyl-1-(2-propynyl)-8-(piperazin-1-yl)-1,7-dihydropurin-6-one trifluoroacetate The title compound was obtained by using propargyl bromide, instead of methyl iodide, by the same method as used in Example 109.
MS m/e (ESI) 349 (MH$^+$-CF$_3$COOH)

Example 114

7-Benzyl-1-cyanomethyl-8-(piperazin-1-yl)-1,7-dihydropurin-6-one trifluoroacetate The title compound was obtained by using bromoacetonitrile, instead of methyl iodide, by the same method as used in Example 109.
MS m/e (ESI) 350 (MH$^+$-CF$_3$COOH)

Example 115

3-(2-Butynyl)-5-methyl-2-(piperazin-1-yl)-3,5-dihydroimidazo[4,5-d]pyridazin-4-one trifluoroacetate (a) Ethyl 2-bromo-3-(2-butynyl)-5-cyano-3H-imidazole-4-carboxylate 4.56 ml of sulfuric acid was added to 170 ml of ethanol containing 16.80 g of 2-bromo-1H-imidazole-4,5-dicarbonitrile [CAS No. 50847-09-1], and the mixture was heated under reflux for 48 hours. The solution was cooled, and then 500 ml of ethyl acetate and 200 ml of water were added thereto. The organic layer was dried over anhydrous magnesium sulfate, filtered, and concentrated under reduced pressure. The residue was dissolved in N,N-dimethylformamide, and 14.1 g of potassium carbonate and 8.6 ml of 2-butynyl bromide were added thereto. The mixture was stirred at room temperature for 18 hours. 500 ml of ethyl acetate was added to the solution, and the mixture was washed three times with 300 ml of water, and then with 300 ml of a saturated sodium chloride solution. Then, the solution was dried over anhydrous magnesium sulfate, and filtered. The filtrate was concentrated under reduced pressure. The residue was purified by silica gel column chromatography. Thus, 4.09 g of the title compound was obtained from the fraction eluted with hexane-ethyl acetate (9:1).

$^1$H-NMR (CDCl$_3$)
δ 1.43 (t, J=7.2 Hz, 3H) 1.81 (s, 3H) 4.47 (q, J=7.2 Hz, 2H) 5.16 (s, 2H)

(b) t-Butyl 4-[1-(2-butynyl)-4-cyano-5-ethoxycarboxyl-1H-imidazol-2-yl]piperazine-1-carboxylate 4.09 g of ethyl 2-bromo-3-(2-butynyl)-5-cyano-3H-imidazole-4-carboxylate was combined with 7.70 g of t-butyl piperazine-1-carboxylate, and the mixture was heated to 150° C. with stirring for 50 minutes. The reaction mixture was dissolved in toluene. The mixture was purified by silica gel column chromatography. Thus, 4.47 g of the title compound was obtained from the fraction eluted with hexane-ethyl acetate (2:1).

$^1$H-NMR (CDCl$_3$)
δ 1.43 (t, J=7.2 Hz, 3H) 1.47 (s, 9H) 1.82 (t, J=2.3 Hz, 3H) 3.08-3.13 (m, 4H) 3.57-3.61 (m, 4H) 4.44 (q, J=7.2 Hz, 2H) 4.89 (q, J=2.3 Hz, 2H)

(c) t-Butyl 4-[1-(2-butynyl)-5-ethoxycarbonyl-4-thiocarbamoyl-1H-imidazol-2-yl]piperazine-1-carboxylate 5 ml of an aqueous solution of 50% ammonium sulfide was added to a 20-ml ethanol solution containing 0.80 g of t-butyl 4-[1-(2-butynyl)-4-cyano-5-ethoxycarbonyl-1H-imidazol-2-yl]piperazine-1-carboxylate, and the mixture was heated at 60° C. for 14 hours. 100 ml of ethyl acetate and 50 ml of water were added to the mixture, and the organic layer was washed successively with 50 ml of water and 50 ml of a saturated sodium chloride solution. The reaction solution was dried over anhydrous magnesium sulfate, then filtered. The filtrate was concentrated under reduced pressure. The residue was purified by silica gel column chromatography. Thus, 0.58 g of the title compound was obtained from the fraction eluted with hexane-ethyl acetate (3:2).

$^1$H-NMR (CDCl$_3$)
δ 1.43 (t, J=7.2 Hz, 3H) 1.48 (s, 9H) 82 (t, J=2.3 Hz, 3H) 3.12-3.16 (m, 4H) 3.54-3.59 (m, 4H) 4.44 (q, J=7.2 Hz, 2H) 4.89 (q, J=2.3 Hz, 2H) 7.41 (br.s, 1H) 8.88 (br.s, 1H)

(d) t-Butyl 4-[1-(2-butynyl)-5-ethoxycarbonyl-4-methylsulfanylcarbonimidoyl-1H-imidazol-2-yl]piperazine-1-carboxylate 0.235 of trimethyl oxonium tetrafluoroborate was added to a 20-ml dichloromethane solution of 0.58 g of t-butyl 4-[1-(2-butynyl)-5-ethoxycarbonyl-4-thiocarbamoyl-1H-imidazol-2-yl]piperazine-1-carboxylate, and the mixture was stirred at room temperature for 18 hours. 50 ml of dichloromethane was added to the solution, and the mixture was washed with 20 ml of a saturated sodium bicarbonate solution. The mixture was dried over anhydrous magnesium sulfate, and concentrated under reduced pressure to give 0.55 g of the title compound.

$^1$H-NMR (CDCl$_3$)
δ 1.41 (t, J=7.2 Hz, 3H) 1.47 (s, 9H) 1.81 (t, J=2.3 Hz, 3H) 2.39 (s, 3H) 3.12-3.16 (m, 4H) 3.56-3.59 (m, 4H) 4.42 (q, J=7.2 Hz, 2H) 4.80 (q, J=2.3 Hz, 2H)

(e) t-Butyl 4-[1-(2-butynyl)-5-ethoxycarbonyl-4-methylsulfanylcarbonyl-1H-imidazol-2-yl]piperazine-1-carboxylate 5 ml of a 2N aqueous solution of hydrochloric acid was added to a 30-ml ethanol solution of 0.55 g of t-butyl 4-[1-

(2-butynyl)-5-ethoxycarbonyl-4-methyl sulfanylcarbonimidoyl-1H-imidazol-2-yl]piperazine-1-carboxylate, and the mixture was heated at 60° C. for 5 hours. After the reaction solution had been concentrated under reduced pressure, 25 ml of ethyl acetate and 1N sodium hydroxide solution were added thereto. The aqueous layer was extracted with 25 ml of ethyl acetate, and the organic layers were combined together. The mixture was washed with 10 ml of a saturated sodium chloride solution containing 1 ml of 1N sodium hydroxide solution, and dried over anhydrous magnesium sulfate. The solution was filtered, and the filtrate was concentrated under reduced pressure. The residue was dissolved in 10 ml of dichloromethane, and 0.10 ml of triethylamine and 0.256 g of di-t-butyl dicarbonate were added thereto. The mixture was stirred at room temperature for 15 hours, and then 25 ml of ethyl acetate was added thereto. The mixture was washed successively with 10 ml of 0.1N hydrochloric acid, 10 ml of a saturated sodium bicarbonate solution, and 10 ml of a saturated sodium chloride solution, and then dried over anhydrous magnesium sulfate. The solution was concentrated under reduced pressure. The residue was purified by silica gel column chromatography. Thus, 0.15 g of the title compound was obtained from the fraction eluted with hexane-ethyl acetate (4:1).

$^1$H-NMR (CDCl$_3$)

δ 1.43 (t, J=7.1 Hz, 3H) 1.48 (s, 9H) 1.81 (t, J=2.3 Hz, 3H) 2.40 (s, 3H) 3.16-3.20 (m, 4H) 3.55-3.59 (m, 4H) 4.35 (q, J=7.1 Hz, 2H) 4.80 (q, J=2.3 Hz, 2H)

(f) t-Butyl 4-[1-(2-butynyl)-5-ethoxycarbonyl-4-hydroxymethyl-1H-imidazol-2-yl]piperazine-1-carboxylate 0.187 g of mercury (II) acetate and 0.090 of sodium borohydride were added to 8 ml of an ethanol solution containing 0.265 g of t-butyl 4-[1-(2-butynyl)-5-ethoxycarbonyl-4-methylsulfanyl carbonyl-1H-imidazol-2-yl]piperazine-1-carboxylate at 0° C., and the mixture was stirred at room temperature for 4 hours. After 0.187 g of mercury (II) acetate and 0.090 of sodium borohydride had been added to the solution, the mixture was stirred at room temperature for 15 hours. 100 ml of ethyl acetate and 50 ml of 0.5N hydrochloric acid were added to the solution, and the organic layer was washed successively with 50 ml of water and 50 ml of a saturated sodium chloride solution. The mixture was dried over anhydrous magnesium sulfate, and concentrated under reduced pressure. The residue was purified by silica gel column chromatography. 0.172 g of the starting material was collected from the fraction eluted with hexane-ethyl acetate (4:1). Then, 0.061 g of the title compound was obtained from the fraction eluted with hexane-ethyl acetate (1:4).

$^1$H-NMR (CDCl$_3$)

δ 1.42 (t, J=7.1 Hz, 3H) 1.48 (s, 9H) 1.81 (t, J=2.3 Hz, 3H) 3.17-3.21 (m, 4H) 3.41 (t, J=4.8 Hz, 1H) 3.56-3.60 (m, 4H) 4.36 (q, J=7.1 Hz, 2H) 4.75 (d, J=4.8 Hz, 2H) 4.81 (q, J=2.3 Hz, 2H)

(g) t-Butyl 4-[1-(2-butynyl)-5-ethoxycarbonyl-4-formyl-1H-imidazol-2-yl]piperazine-1-carboxylate 0.120 g of manganese dioxide was added to a 2-ml dichloromethane solution of 0.061 g of t-butyl 4-[1-(2-butynyl)-5-ethoxycarbonyl-4-hydroxymethyl-1H-imidazol-2-yl]piperazine-1-carboxylate, and the reaction was stirred at room temperature for 15 hours. The reaction solution was filtered through celite, and the filtrate was concentrated under reduced pressure. The residue was purified by silica gel column chromatography. Thus, 0.055 g of the title compound was obtained from the fraction eluted with hexane-ethyl acetate (7:3).

$^1$H-NMR (CDCl$_3$)

δ 1.42 (t, J=7.1 Hz, 3H) 1.48 (s, 9H) 1.82 (t, J=2.3 Hz, 3H) 3.23-3.26 (m, 4H) 3.55-3.59 (m, 4H) 4.45 (q, J=7.1 Hz, 2H) 4.89 (q, J=2.3 Hz, 2H) 10.36 (s, 1H)

(h) t-Butyl 4-[1-(2-butynyl)-6-methyl-7-oxo-6,7-dihydro-1H-imidazo[4,5-d]pyridazin-2-yl]piperazine-1-carboxylate 0.05 ml of methylhydrazine was added to a 2.5-ml ethanol solution of 0.055 g of t-butyl 4-[1-(2-butynyl)-5-ethoxycarbonyl-4-formyl-1H-imidazol-2-yl]piperazine-1-carboxylate. The mixture was stirred at 80° C. for 15 hours, and then heated at 130° C. for 14 hours. The reaction solution was concentrated under reduced pressure. Then, the residue was purified by silica gel column chromatography. Thus, 0.035 g of the title compound was obtained from the fraction eluted with hexane-ethyl acetate (1:1).

$^1$H-NMR (CDCl$_3$)

δ 1.52 (s, 9H) 1.83 (t, J=2.3 Hz, 3H) 3.38-3.42 (m, 4H) 3.61-3.64 (m, 4H) 3.85 (s, 3H) 5.09 (q, J=2.3 Hz, 2H) 8.13 (s, 1H)

MS m/e (ESI) 387.4 (MH$^+$)

(i) 3-(2-Butynyl)-5-methyl-2-(piperazin-1-yl)-3,5-dihydroimidazo[4,5-d]pyridazin-4-one trifluoroacetate 0.4 ml of trifluoroacetic acid was added to a 0.4-ml dichloromethane solution of 0.0351 g of t-butyl 4-[1-(2-butynyl)-6-methyl-7-oxo-6,7-dihydro-1H-imidazo[4,5-d]pyridazin-2-yl]piperazine-1-carboxylate, and the mixture was stirred at room temperature for one hour. The solvent was concentrated. The residue was purified by reverse-phase high performance liquid chromatography (using an acetonitrile-water mobile phase (containing 0.1% trifluoroacetic acid)) to give 0.0295 g of the title compound.

$^1$H-NMR (CD$_3$OD)

δ 1.83 (t, J=2.3 Hz, 3H) 3.45-3.49 (m, 4H) 3.65-3.69 (m, 4H) 3.83 (s, 3H) 5.15 (q, J=2.3 Hz, 2H) 8.20 (s, 1H)

MS m/e (ESI) 287.09 (MH$^+$-CF$_3$COOH)

Example 116

5-Benzyloxymethyl-3-(2-butynyl)-2-(piperazin-1-yl)-3,5-dihydro-imidazo[4,5-d]pyridazin-4-one trifluoroacetate (a) 5-Benzyloxymethyl-4-oxo-4,5-dihydroimidazo[4,5-d]pyridazine-1-sulfonic acid dimethylamide 2.08 g of triethylamine, 2.80 g of N,N-dimethyl sulfamoyl chloride, and 0.22 g of 4-dimethylaminopyridine were added to 50 ml of a dichloromethane solution of 3.04 g of 5-benzyloxymethylimidazo[4,5-d]pyridazin-4-one [CAS NO. 82137-50-6] (R. Paul Gagnier, Michael J. Halat, and Brian A. Otter Journal of Heterocyclic Chemistry, 21, p 481, 1984), and the mixture was heated under reflux for 4 hours. 250 ml of ethyl acetate was added to the solution, and the mixture was washed successively with 50 ml of an aqueous solution of 1N hydrochloric acid, 50 ml of a saturated sodium bicarbonate solution, and 50 ml of a saturated sodium chloride solution. The mixture was dried over anhydrous magnesium sulfate, and concentrated under reduced pressure. The residue was purified by silica gel column chromatography. Thus, 2.86 g of the title compound was obtained from the fraction eluted with hexane-ethyl acetate (2:3).

$^1$H-NMR (CDCl$_3$)

δ 2.98 (s, 6H) 4.77 (s, 2H) 5.74 (s, 2H) 7.30-7.39 (m, 5H) 8.21 (s, 1H) 8.46 (s, 1H)

(b) 5-Benzyloxymethyl-2-chloro-4-oxo-4,5-dihydroimidazo[4,5-d]pyridazine-1-sulfonic acid dimethylamide 5.3 ml of n-butyl lithium (2.0 M cyclohexane solution) was added to a 150-ml tetrahydrofuran solution of 3.34 g of 5-benzyloxymethyl-4-oxo-4,5-dihydroimidazo[4,5-d]pyridazine-1-sulfonic acid dimethylamide under a nitrogen atmosphere at −78° C., and the mixture was stirred at −78° C. for one hour. Then, 20 ml of a tetrahydrofuran solution of 3.26 g of hexachloroethane was added to this solution. The mixture was allowed to warm to room temperature. 25 ml of a 5% aqueous solution of ammonium chloride was added to the solution, and the mixture was extracted with 50 ml of ethyl acetate. The organic layer was washed successively with 25 ml of water and 25 ml of a saturated sodium chloride solution, and then dried over anhydrous magnesium sulfate. The organic liquid was concentrated under reduced pressure. The residue was purified by silica gel column chromatography. Thus, 2.31 g of the title compound was obtained from the fraction eluted with hexane-ethyl acetate (2:3).

$^1$H-NMR (CDCl$_3$)

δ 3.12 (s, 6H) 4.77 (s, 2H) 5.70 (s, 2H) 7.30-7.39 (m, 5H) 8.48 (s, 1H)

(c) t-Butyl 4-(6-benzyloxymethyl-7-oxo-6,7-dihydro-1H-imidazo[4,5-d]pyridazin-2-yl)piperazine-1-carboxylate A mixture consisting of 2.31 g of 5-benzyloxymethyl-2-chloro-4-oxo-4,5-dihydroimidazo[4,5-d]pyridazine-1-sulfonic acid dimethylamide and 4.49 g of t-butyl piperazine-1-carboxylate was heated at 150° C. under nitrogen atmosphere for 2.5 hours. The residue was purified by silica gel column chromatography. Thus, 1.94 g of the title compound was obtained from the fraction eluted with ethyl acetate.

$^1$H-NMR (CDCl$_3$)

δ 3.54-3.58 (m, 4H) 3.71-3.75 (m, 4H) 4.68 (s, 2H) 5.65 (s, 2H) 7.25-7.35 (m, 5H) 8.21 (s, 1H) 12.58 (br.s, 1H)

(d) t-Butyl 4-[6-benzyloxymethyl-1-(2-butynyl)-7-oxo-6,7-dihydro-1H-imidazo[4,5-d]pyridazin-2-yl]piperazine-1-carboxylate 0.74 g of potassium carbonate and 0.078 g of 2-butynyl bromide were added to a 20-ml N,N-dimethylformamide solution of 0.216 g of t-butyl 4-(6-benzyloxymethyl-7-oxo-6,7-dihydro-1H-imidazo[4,5-d]pyridazin-2-yl)piperazine-1-carboxylate and the mixture was stirred at room temperature for 16 hours. Then, 50 ml of ethyl acetate was added to the solution. The organic layer was washed three times with 20 ml of water, and then with 10 ml of a saturated sodium chloride solution. The solution was dried over anhydrous magnesium sulfate, and then concentrated under reduced pressure. The residue was purified by silica gel column chromatography. Thus, 0.139 g of the title compound was obtained from the fraction eluted with hexane-ethyl acetate (3:2).

$^1$H-NMR (CDCl$_3$)

δ 1.50 (s, 9H) 1.86 (t, J=2.3 Hz, 3H) 3.38-3.44 (m, 4H) 3.61-3.66 (m, 4H) 4.72 (s, 2H) 5.10 (q, J=2.3 Hz, 2H) 5.65 (s, 2H) 7.25-7.38 (m, 5H) 8.18 (s, 1H)

(e) 5-Benzyloxymethyl-3-(2-butynyl)-2-(piperazin-1-yl)-3,5-dihydroimidazo[4,5-d]pyridazin-4-one trifluoroacetate 0.0043 g of the title compound was obtained by treating 0.0073 g of t-butyl 4-[6-benzyloxymethyl-1-(2-butynyl)-7-oxo-6,7-dihydro-1H-imidazo[4,5-d]pyridazin-2-yl]piperazine-1-carboxylate and purifying the product by the same method as used in Example 115(i).

$^1$H-NMR (CD$_3$OD)

δ 1.83 (t, J=2.3 Hz, 2H) 3.45-3.49 (m, 4H) 3.65-3.69 (m, 4H) 4.69 (s, 2H) 5.15 (q, J=2.3 Hz, 2H) 5.64 (s, 2H) 7.17-7.32 (m, 5H) 8.20 (s, 1H)

MS m/e (ESI) 393.28 (MH$^+$-CF$_3$COOH)

Example 117

3-(2-Butynyl)-2-(piperazin-1-yl)-3,5-dihydroimidazo[4,5-d]pyridazin-4-one trifluoroacetate 8 ml of a dichloromethane solution of 0.123 g of t-butyl 4-[6-benzyloxymethyl-1-(2-butynyl)-7-oxo-6,7-dihydro-1H-imidazo[4,5-d]pyridazin-2-yl]piperazine-1-carboxylate was cooled to −78° C. under a nitrogen atmosphere, and 1.9 ml of boron trichloride (1.0 M dichloromethane solution) was added thereto. The mixture was stirred at −78° C. for five hours, and 10 ml of a 1:1 mixed solvent of dichloromethane-methanol was added thereto. The mixture was stirred at −78° C. for two hours, and then allowed to warm to room temperature. The solvent was concentrated under reduced pressure, and 10 ml of methanol was added thereto. Then, the solution was again concentrated under reduced pressure. The residue was dissolved in 3 ml of pyridine, and the mixture was heated under reflux for two hours. 0.3 ml of this solution was concentrated under reduced pressure. The residue was purified by reverse-phase high performance liquid chromatography (using an acetonitrile-water mobile phase (containing 0.1% trifluoroacetic acid)) to give 0.005 g of the title compound.

$^1$H-NMR (CD$_3$OD)

δ 1.83 (t, J=2.3 Hz, 3H) 3.45-3.49 (m, 4H) 3.65-3.69 (m, 4H) 5.16 (q, J=2.3 Hz, 2H) 8.21 (s, 1H)

MS m/e (ESI) 273.16 (MH$^+$-CF$_3$COOH)

Example 118

2-[7-(2-Butynyl)-1-methyl-6-oxo-8-(piperazin-1-yl)-6,7-dihydro-1H-purin-2-yloxy]benzamide hydrochloride (a) t-Butyl 4-[7-(2-butynyl)-2-(2-carbamoylphenoxy)-1-methyl-6-oxo-6,7-dihydro-1H-purin-8-yl]piperazine-1-carboxylate 200 mg of t-butyl 4-[7-(2-butynyl)-2-chloro-1-methyl-6-oxo-6,7-dihydro-1H-purin-8-yl]piperazine-1-carboxylate was dissolved in 2.0 ml of 1-methyl-2-pyrrolidone, and 85 mg of salicylamide and 129 mg of potassium carbonate were added thereto. The mixture was stirred at 100° C. for 2 hours. After the reaction mixture had been cooled to room temperature, 5.0 ml of water was added thereto. After the mixture had been stirred at room temperature for 1 hour, the white precipitate was collected by filtration. The resulting white solid was washed with water and ether to give of 221 mg of the title compound (89%).

$^1$H-NMR (DMSO-d6)

δ 1.43 (s, 9H) 1.79 (t, J=2.5 Hz, 3H) 3.23-3.27 (m, 4H) 3.36 (s, 3H) 3.48-3.52 (m, 4H) 4.95 (q, 2.5 Hz, 2H) 6.59 (td, J=8.0, 1.0 Hz, 1H) 6.63 (dd, J=8.0, 1.0 Hz, 1H) 7.14 (ddd, J=8.0, 7.5, 2.0 Hz, 1H) 7.80 (dd, J=7.5, 2.0 Hz, 1H)

MS m/e (ESI) 522 (MH$^+$)

(b) 2-[7-(2-Butynyl)-1-methyl-6-oxo-8-(piperazin-1-yl)-6,7-dihydro-1H-purin-2-yloxy]benzamide hydrochloride 210 mg of t-butyl 4-[7-(2-butynyl)-2-(2-carbamoylphenoxy)-1-methyl-6-oxo-6,7-dihydro-1H-purin-8-yl]piperazine-1-carboxylate was combined with 3.5 ml of methanol and 2.1 ml of 4N hydrochloric acid-ethyl acetate solution. After the mixture had been stirred at room temperature for 4 hours, the reaction solution was concentrated by flushing with nitrogen gas. The resulting residue was washed with ethanol and ethyl acetate to give 177 mg of the title compound (96%).

$^1$H-NMR (DMSO-d6)

δ 1.82 (t, J=2.3 Hz, 3H) 3.28-3.32 (m, 4H) 3.48 (s, 3H) 3.54-3.58 (m, 4H) 5.04 (q, 2.3 Hz, 2H) 6.96 (br.t, J=7.0 Hz, 1H) 6.99 (br.d, J=8.0 Hz, 1H) 7.46 (ddd, J=8.0, 7.0, 1.5 Hz, 1H) 7.93 (br.d, J=8.0 Hz, 1H)

MS m/e (ESI) 422 (MH$^+$-HCl)

Example 119

3-(2-Butynyl)-5-methyl-2-(piperazin-1-yl)-3,5-dihydroimidazo[4,5-d]pyridazin-4-one (a) 5-Methyl-1-trityl-1,5-dihydroimidazo[4,5-d]pyridazin-4-one 78.8 g of 5-methyl-1,5-dihydroimidazo[4,5-d]pyridazin-4-one [CAS No. 76756-58-6] (Shih-Fong Chen and Raymond P. Panzica, Journal of Organic Chemistry 46, p 2467, 1981) was suspended in 2.5 L of dichloromethane at room temperature, and 78.8 of triethylamine was added thereto. 176 g of trityl chloride was added to the mixture, which was then stirred for three hours. 7.5 L of ethyl acetate was added to the mixture. After being washed successively with 3 L of water and 3 L of a saturated sodium chloride solution, the mixture was dried over anhydrous magnesium sulfate and concentrated under reduced pressure. The residue was purified by silica gel column chromatography. Thus, 136.5 g of the title compound was obtained from the fraction eluted with hexane-ethyl acetate (20:80 to 0:100).

$^1$H-NMR (CDCl$_3$)

δ 3.79 (s, 3H) 6.92 (s, 1H) 7.07-7.13 (m, 6H) 7.32-7.40 (m, 9H) 7.87 (s, 1H)

(b) 2-Chloro-5-methyl-1-trityl-1,5-dihydroimidazo[4,5-d]pyridazin-4-one 220 ml of lithium hexamethyldisilazide (1.0 M tetrahydrofuran solution) was added to a 4-L tetrahydrofuran solution of 68.3 g of 5-methyl-1-trityl-1,5-dihydroimidazo[4,5-d]pyridazin-4-one at −75° C. under a nitrogen atmosphere, and the mixture was stirred at −75° C. for 1 hour. Then, 200 ml of a tetrahydrofuran solution of 82.3 g of hexachloroethane was added to the solution. The mixture was allowed to warm to −20° C. 5 L of 5% aqueous ammonium chloride was added, and the mixture was extracted with 4 L of ethyl acetate. The organic layer was washed successively with 5 L of water and 5 L of a saturated sodium chloride solution. The solution was dried over anhydrous magnesium sulfate, and concentrated under reduced pressure. The residue was suspended in 150 ml of t-butyl methyl ether, and then collected by filtration. The solid was washed twice with 100 ml of t-butyl methyl ether to give 69.7 g of the title compound.

$^1$H-NMR (CDCl$_3$)

δ 3.78 (s, 3H) 5.81 (s, 1H) 7.25-7.27 (m, 6H) 7.28-7.38 (m, 9H)

(c) t-Butyl 4-(6-methyl-7-oxo-6,7-dihydro-1H-imidazo[4,5-d]pyridazin-2-yl)piperazine-1-carboxylate 69.7 g of 2-chloro-5-methyl-1-trityl-1,5-dihydroimidazo[4,5-d]pyridazin-4-one was combined with 153.4 g of t-butyl piperazine-1-carboxylate, and the mixture was stirred and heated to 100° C. under nitrogen atmosphere. When the reaction mixture became easily stirrable, the temperature was raised to 150° C. The mixture was kept at this temperature for one hour. The reaction solution allowed to cool and then suspended in 250 ml of t-butyl methyl ether. The suspended material was collected by filtration. The solid was washed twice with 200 ml of t-butyl methyl ether and three times with 200 ml of water. The solid was again washed twice with 200 ml of t-butyl methyl ether, and dried to give 50.3 g of the title compound.

$^1$H-NMR (CDCl$_3$)

δ 1.50 (s, 9H) 3.56-3.62 (m, 4H) 3.73-3.80 (m, 4H) 3.87 (s, 3H) 8.16 (s, 1H) 12.65 (br.s, 1H)

(d) t-Butyl 4-[1-(2-butynyl)-6-methyl-7-oxo-6,7-dihydro-1H-imidazo[4,5-d]pyridazin-2-yl]piperazine-1-carboxylate 43.9 g of potassium carbonate and 27.8 ml of 2-butynyl bromide were successively added to a 5.5-L N,N-dimethylformamide solution of 88.4 g of t-butyl 4-(6-methyl-7-oxo-6,7-dihydro-1H-imidazo[4,5-d]pyridazin-2-yl)piperazine-1-carboxylate at 15° C. under a nitrogen atmosphere. The reaction solution was stirred at room temperature for 22 hours, and then poured into 10 L of water. The mixture was extracted with 5 L of ethyl acetate. The organic layer was successively washed twice with 5 L of water, and with 5 L of a saturated sodium chloride solution. The aqueous layer was extracted twice with 3 L of ethyl acetate. The organic layers were combined together, and then dried over anhydrous magnesium sulfate. The organic layer was concentrated under reduced pressure. The residue was purified by silica gel column chromatography. Thus, 54.3 g of the title compound was obtained from the fraction eluted with hexane-ethyl acetate (3:2 to 3:7).

$^1$H-NMR (CDCl$_3$)

δ 1.52 (s, 9H) 1.83 (t, J=2.33 Hz, 3H) 3.38-3.42 (m, 4H) 3.61-3.64 (m, 4H) 3.85 (s, 3H) 5.09 (q, J=2.3 Hz, 2H) 8.13 (s, 1H)

(e) 3-(2-Butynyl)-5-methyl-2-(piperazin-1-yl)-3,5-dihydroimidazo[4,5-d]pyridazin-4-one 200 ml of trifluoroacetic acid was added to 200 ml of a dichloromethane solution containing 54.3 g of t-butyl 4-[1-(2-butynyl)-6-methyl-7-oxo-6,7-dihydro-1H-imidazo[4,5-d]pyridazin-2-yl]piperazine-1-carboxylate, and the mixture was stirred at room temperature for 1 hour. The mixture was concentrated under reduced pressure, the residue was dis-

Example 119-2

3-(2-Butynyl)-5-methyl-2-(piperazin-1-yl)-3,5-dihydroimidazo[4,5-d]pyridazin-4-one toluene-4-sulfonate 98.7 mg of 3-(2-butynyl)-5-methyl-2-(piperazin-1-yl)-3,5-dihydroimidazo[4,5-d]pyridazin-4-one was dissolved in 1 ml of ethanol, and then 1 ml of an ethanol solution of 101 mg of p-toluenesulfonic acid monohydrate was added thereto while the solution was being stirred. The mixture was cooled with ice for two hours while being stirred. The precipitate was collected by filtration, and then dried under reduced pressure at 50° C. for one hour to give 153.2 mg of the title compound.

$^1$H-NMR (DMSO-d6)

δ 1.79 (t, J=2 Hz, 3H) 2.27 (s, 3H) 3.25-3.35 (m, 4H) 3.50-3.54 (m, 4H) 3.70 (s, 3H) 5.13 (d, J=2 Hz, 2H) 7.10 (d, J=8 Hz, 2H) 7.47 (d, J=8 Hz, 2H) 8.25 (s, 1H) 8.79 (br.s, 2H)

Furthermore, 107.95 mg of the title compound was recrystallized from acetone, yielding 84.9 mg of crystalline product.

Example 120

2-(3-Aminopiperidin-1-yl)-3-(2-butynyl)-5-methyl-3,5-dihydroimidazo[4,5-d]pyridazin-4-one trifluoroacetate

(a) 9H-fluoren-9-ylmethyl 3-t-butoxycarbonylaminopiperidine-1-carboxylate 1.84 g of diisopropylethylamine and 4.71 g of diphenylphosphorylazide were added to 10 ml of a t-butanol solution of 5.01 g of 9H-fluoren-9-ylmethyl 3-carboxypiperidine-1-carboxylate, and the mixture was heated at 60° C. under a nitrogen atmosphere for 18 hours. The reaction solution was cooled, and 150 ml of ethyl acetate was added thereto. The organic layer was washed successively with 100 ml of 5% aqueous sulfuric acid, 100 ml of 5% aqueous sodium bicarbonate solution, 100 ml of water, and 100 ml of a saturated sodium chloride solution, and then dried over anhydrous magnesium sulfate. The organic layer was concentrated under reduced pressure. The residue was purified by silica gel column chromatography. Thus, 1.88 g of the title compound was obtained from the fraction eluted with hexane-ethyl acetate (4:1).

$^1$H-NMR (CDCl$_3$)

δ 1.45 (s, 9H) 1.45-1.72 (m, 3H) 1.82-1.87 (br.s, 1H) 3.09-3.30 (br.s, 2H) 3.58 (br.s, 2H) 3.82-3.98 (br.s, 1H) 4.24 (t, J=7.2 Hz, 1H) 4.27-4.48 (br.s, 2H) 4.52-4.59 (br.s, 1H) 7.32 (dd, J=10.3, 10.0 Hz, 2H) 7.39 (t, J=10.0 Hz, 2H) 7.59 (d, J=10.0 Hz, 2H) 7.75 (d, J=10.3 Hz, 2H)

(b) t-Butyl piperidin-3-ylcarbamate 25 ml of diethylamine was added to 250 ml of an ethanol solution of 1.88 g of 9H-fluoren-9-ylmethyl 3-t-butoxycarbonylaminopiperidine-1-carboxylate, and the mixture was stirred at room temperature for 18 hours. After the solution had been concentrated under reduced pressure, the residue was dissolved in a mixture consisting of 150 ml of toluene and 100 ml of 10% aqueous citric acid solution. The aqueous layer was made alkaline with a 5N aqueous sodium hydroxide solution, and then extracted twice with 100 ml of dichloromethane. The organic layers were combined together, dried over anhydrous magnesium sulfate, and concentrated under reduced pressure to give 0.79 g of the title compound.

$^1$H-NMR (CDCl$_3$)

δ 1.45 (s, 9H) 1.41-1.53 (m, 2H) 1.65-1.72 (m, 1H) 1.79-1.86 (m, 1H) 2.48-2.56 (m, 1H) 2.64-2.70 (m, 1H) 2.78-2.86 (m, 1H) 3.06 (dd, J=12.0, 4.0 Hz, 1H) 3.48-3.62 (br.s, 1H) 4.71-4.88 (br.s, 1H)

(c) 2-(3-Aminopiperidin-1-yl)-3-(2-butynyl)-5-methyl-3,5-dihydroimidazo[4,5-d]pyridazin-4-one trifluoroacetate 0.020 g of 2-chloro-5-methyl-1-trityl-1,5-dihydroimidazo[4,5-d]pyridazine-4-one and 0.040 g of t-butyl piperidin-3-ylcarbamate were combined together, and the mixture was heated under a nitrogen atmosphere at 150° C. for 1 hour. The reaction mixture was purified by silica gel column chromatography. Thus, 0.016 g of t-butyl [1-(6-methyl-7-oxo-6,7-dihydro-1H-imidazo[4,5-d]pyridazin-2-yl)piperidin-3-yl] carbamate was obtained from the fraction eluted with ethyl acetate. 0.0080 g of this compound was dissolved in 0.6 ml of N,N-dimethylformamide, and then 0.0038 g of potassium carbonate and 0.003 ml of 2-butynyl bromide were added thereto. The mixture was stirred at room temperature for 18 hours. The reaction mixture was partitioned between 1 ml of ethyl acetate and 1 ml of water, and the organic layer was concentrated. The residue was dissolved in 0.5 ml of dichloromethane, and then 0.5 ml of trifluoroacetic acid was added thereto. After 1 hour, the reaction solution was concentrated. The residue was purified by reverse-phase high performance liquid chromatography (using an acetonitrile-water mobile phase (containing 0.1% trifluoroacetic acid)) to give 0.0046 g of the title compound.

$^1$H-NMR (CDCl$_3$)

δ 1.74-1.80 (br.s, 1H) 1.82 (br.s, 3H) 1.96-2.19 (br.m, 3H) 3.43-3.79 (br.m, 5H) 3.86 (s, 3H) 5.05 (br.d, J=16.0 Hz, 1H) 5.23 (br.d, J=16.0 Hz, 1H) 8.15 (s, 1H)

Example 121

2-(3-Aminopiperidin-1-yl)-5-methyl-3-(3-methyl-2-butenyl)-3,5-dihydroimidazo[4,5-d]pyridazin-4-one trifluoroacetate 0.0034 g of the title compound was obtained using 0.0080 g of t-butyl [1-(6-methyl-7-oxo-6,7-dihydro-1H-imidazo[4,5-d]pyridazin-2-yl)piperidin-3-yl]-carbamate and 0.004 ml of 4-bromo-2-methyl-2-butene by the same method as used in Example 120.

$^1$H-NMR (CDCl$_3$)

δ 1.66-1.74 (br.s, 1H) 1.76 (s, 3H) 1.80 (s, 3H) 1.96-2.20 (br.m, 3H) 3.20-3.79 (br.m, 5H) 3.85 (s, 3H) 4.90-5.05 (m, 2H) 5.37-5.42 (m, 1H) 8.15 (s, 1H)

Example 122

2-[7-(2-Butynyl)-1-methyl-6-oxo-8-(piperazin-1-yl)-6,7-dihydro-1H-purin-2-yloxy]benzamide 53.0 g of t-butyl 4-[7-(2-butynyl)-2-(2-carbamoylphenoxy)-1-methyl-6-oxo-6,7-dihydro-1H-purin-8-yl]piperazine-1-carboxylate was dissolved in 160 ml of trifluoroacetic acid, and the mixture was stirred at room temperature for one hour. 1250 ml of a 2 M aqueous sodium hydroxide solution was added drop wise to the reaction solution, and the mixture was stirred at room temperature for one hour and 50 minutes. The resulting white precipitate was collected by filtration. The white solid was washed with water and then with ethanol, and dried at 60° C. overnight to give 42.8 g of the title compound.

$^1$H-NMR (DMSO-d6)

δ 1.78 (t, J=2.4 Hz, 3H) 2.82-2.86 (m, 4H) 3.18-3.22 (m, 4H) 3.36 (s, 3H) 4.91 (q, 2.4 Hz, 2H) 6.58 (td, J=8.4, 1.2 Hz, 1H) 6.63 (dd, J=8.0, 0.8 Hz, 1H) 7.14 (ddd, J=8.0, 7.2, 2.0 Hz, 1H) 7.80 (dd, J=7.6, 2.0 Hz, 1H)

MS m/e (ESI) 422 (MH$^+$)

Example 123

7-(2-Butynyl)-2-(3-hydroxypropylsulfanyl)-1-methyl-8-(piperazin-1-yl)-1,7-dihydropurin-6-one trifluoroacetate 7 mg of t-butyl 4-[7-(2-butynyl)-2-chloro-1-methyl-6-oxo-6,7-dihydro-1H-purin-8-yl]piperazine-1-carboxylate was dissolved in 0.15 ml of 1-methyl-2-pyrrolidone, and then 20 μl of 3-mercapto-1-propanol and 6 mg of potassium carbonate were added thereto. The mixture was stirred at room temperature for five hours. A saturated ammonium chloride solution was added to the reaction solution, and the mixture was extracted with ethyl acetate. The organic layer was concentrated, and 0.5 ml of 5N aqueous hydrochloric acid was added to the residue. The mixture was concentrated by flushing with nitrogen gas. The residue was purified by reverse-phase high performance liquid chromatography (using an acetonitrile-water mobile phase (containing 0.1% trifluoroacetic acid)) to give 3.15 mg of the title compound.

MS m/e (ESI) 377 (MH$^+$-CF$_3$COOH)

Example 124

7-(2-Butynyl)-2-(2-hydroxypropylsulfanyl)-1-methyl-8-(piperazin-1-yl)-1,7-dihydropurin-6-one trifluoroacetate 1.70 mg of the title compound was obtained by using 1-mercapto-2-propanol, instead of 3-mercapto-1-propanol, by the same method as used in Example 123.

MS m/e (ESI) 377 (MH$^+$-CF$_3$COOH)

Example 125

7-(2-Butynyl)-2-(2,3-dihydroxypropylsulfanyl)-1-methyl-8-(piperazin-1-yl)-1,7-dihydropurin-6-one trifluoroacetate 2.63 mg of the title compound was obtained by using 3-mercapto-1,2-propanediol, instead of 3-mercapto-1-propanol, by the same method as used in Example 123.

MS m/e (ESI) 393 (MH$^+$-CF$_3$COOH)

Example 126

3-[7-(2-Butynyl)-1-methyl-6-oxo-8-(piperazin-1-yl)-6,7-dihydro-1H-purin-2-ylsulfanyl]propionic acid trifluoroacetate 7 mg of t-butyl 4-[7-(2-butynyl)-2-chloro-1-methyl-6-oxo-6,7-dihydro-1H-purin-8-yl]piperazine-1-carboxylate was dissolved in 0.15 ml of 1-methyl-2-pyrrolidone, and then 20 μl of 3-mercaptopropionic acid and 6 mg of potassium carbonate were added thereto. The mixture was stirred at room temperature for five hours. A saturated ammonium chloride solution was added to the reaction solution, and the mixture was extracted with ethyl acetate. The organic layer was concentrated, and the residue was dissolved in 0.40 ml of trifluoroacetic acid. The solution was concentrated by flushing with nitrogen gas. The residue was purified by reverse-phase high performance liquid chromatography (using an acetonitrile-water mobile phase (containing 0.1% trifluoroacetic acid)) to give 4.60 mg of the title compound.

MS m/e (ESI) 391 (MH$^+$-CF$_3$COOH)

Example 127

2-[7-(2-Butynyl)-1-methyl-6-oxo-8-(piperazin-1-yl)-6,7-dihydro-1H-purin-2-ylsulfanyl]propionic acid trifluoroacetate 6.10 mg of the title compound was obtained by using 2-mercaptopropionic acid, instead of 3-mercaptopropionic acid, by the same method as used in Example 126.

MS m/e (ESI) 391 (MH$^+$-CF$_3$COOH)

Example 128

2-s-Butylsulfanyl-7-(2-butynyl)-1-methyl-8-(piperazin-1-yl)-1,7-dihydropurin-6-one trifluoroacetate 4.68 mg of the title compound was obtained by using butane-2-thiol, instead of 3-mercaptopropionic acid, by the same method as used in Example 126.

MS m/e (ESI) 375 (MH$^+$-CF$_3$COOH)

Example 129

7-(2-Butynyl)-1-methyl-8-(piperazin-1-yl)-2-propylsulfanyl-1,7-dihydropurin-6-one trifluoroacetate 4.61 mg of the title compound was obtained by using propane-1-thiol, instead of 3-mercaptopropionic acid, by the same method as used in

Example 126

MS m/e (ESI) 361 (MH$^+$-CF$_3$COOH)

Example 130

7-(2-Butynyl)-1-methyl-2-cyclopentylsulfanyl-8-(piperazin-1-yl)-1,7-dihydropurin-6-one trifluoroacetate 5.15 mg of the title compound was obtained by using cyclopentanethiol, instead of 3-mercaptopropionic acid, by the same method as used in Example 126.

MS m/e (ESI) 387 (MH$^+$-CF$_3$COOH)

Example 131

7-(2-Butynyl)-2-dodecylsulfanyl-1-methyl-8-(piperazin-1-yl)-1,7-dihydropurin-6-one trifluoroacetate 4.96 mg of the title compound was obtained by using dodecane-1-thiol, instead of 3-mercaptopropionic acid, by the same method as used in Example 126.
MS m/e (ESI) 487 (MH$^+$-CF$_3$COOH)

Example 132

2-(2-Aminoethylsulfanyl)-7-(2-butynyl)-1-methyl-8-(piperazin-1-yl)-1,7-dihydropurin-6-one trifluoroacetate 3.98 mg of the title compound was obtained by using 2-aminoethanethiol, instead of 3-mercaptopropionic acid, by the same method as used in Example 126.
MS m/e (ESI) 362 (MH$^+$-CF$_3$COOH)

Example 133

7-(2-Butynyl)-1-methyl-8-(piperazin-1-yl)-2-(thiophen-2-ylsulfanyl)-1,7-dihydropurin-6-one trifluoroacetate 5.11 mg of the title compound was obtained by using thiophene-2-thiol, instead of 3-mercaptopropionic acid, by the same method as used in Example 126.
MS m/e (ESI) 401 (MH$^+$-CF$_3$COOH)

Example 134

7-(2-Butynyl)-1-methyl-8-(piperazin-1-yl)-2-(1H-[1,2,4]triazol-3-ylsulfanyl)-1,7-dihydropurin-6-one trifluoroacetate 2.54 mg of the title compound was obtained by using 1H-[1,2,4]-triazole-3-thiol, instead of 3-mercaptopropionic acid, by the same method as used in Example 126.
MS m/e (ESI) 386 (MH$^+$-CF$_3$COOH)

Example 135

7-(2-Butynyl)-1-methyl-8-(piperazin-1-yl)-2-(pyridin-4-ylsulfanyl)-1,7-dihydropurin-6-one trifluoroacetate 0.77 mg of the title compound was obtained by using pyridine-4-thiol, instead of 3-mercaptopropionic acid, by the same method as used in Example 126.
MS m/e (ESI) 396 (MH$^+$-CF$_3$COOH)

Example 136

7-(2-Butynyl)-1-methyl-2-phenylsulfanyl-8-(piperazin-1-yl)-1,7-dihydropurin-6-one trifluoroacetate 1.44 mg of the title compound was obtained by using benzene thiol, instead of 3-mercaptopropionic acid, by the same method as used in Example 126.
MS m/e (ESI) 395 (MH$^+$-CF$_3$COOH)

Example 137

(R)-2-Amino-3-[7-(2-butynyl)-1-methyl-6-oxo-8-(piperazin-1-yl)-6,7-dihydro-1H-purin-2-ylsulfanyl] propionic acid trifluoroacetate 4.38 mg of the title compound was obtained by using L-cystine, instead of 3-mercaptopropionic acid, by the same method as used in Example 126.
MS m/e (ESI) 406 (MH$^+$-CF$_3$COOH)

Example 138

7-(2-Butynyl)-2-(2-methylpropylsulfanyl)-1-methyl-8-(piperazin-1-yl)-1,7-dihydropurin-6-one trifluoroacetate 4.52 mg of the title compound was obtained by using 2-methylpropane-1-thiol, instead of 3-mercaptopropionic acid, by the same method as used in Example 126.
MS m/e (ESI) 375 (MH$^+$-CF$_3$COOH)

Example 139

7-(2-Butynyl)-2-(1,2-dimethyl propylsulfanyl)-1-methyl-8-(piperazin-1-yl)-1,7-dihydropurin-6-one trifluoroacetate 3.03 mg of the title compound was obtained by using 3-methylbutane-2-thiol, instead of 3-mercaptopropionic acid, by the same method as used in Example 126.
MS m/e (ESI) 389 (MH$^+$-CF$_3$COOH)

Example 140

7-(2-Butynyl)-1-methyl-8-(piperazin-1-yl)-2-(pyrimidin-2-ylsulfanyl)-1,7-dihydropurin-6-one trifluoroacetate 3.60 mg of the title compound was obtained by using pyrimidine-2-thiol, instead of 3-mercaptopropionic acid, by the same method as used in Example 126.
MS m/e (ESI) 397 (MH$^+$-CF$_3$COOH)

Example 141

7-(2-Butynyl)-2-(1H-imidazol-2-ylsulfanyl)-1-methyl-8-(piperazin-1-yl)-1,7-dihydropurin-6-one trifluoroacetate 5.75 mg of the title compound was obtained by using 1H-imidazole-2-thiol, instead of 3-mercaptopropionic acid, by the same method as used in Example 126.
MS m/e (ESI) 385 (MH$^+$-CF$_3$COOH)

Example 142

7-(2-Butynyl)-1-methyl-8-(piperazin-1-yl)-2-(thiazol-2-ylsulfanyl)-1,7-dihydropurin-6-one trifluoroacetate 3.86 mg of the title compound was obtained by using thiazole-2-thiol, instead of 3-mercaptopropionic acid, by the same method as used in Example 126.
MS m/e (ESI) 402 (MH$^+$-CF$_3$COOH)

Example 143

7-(2-Butynyl)-2-(furan-2-ylmethylsulfanyl)-1-methyl-8-(piperazin-1-yl)-1,7-dihydropurin-6-one trifluoroacetate 4.84 mg of the title compound was obtained by using (furan-2-yl)methanethiol, instead of 3-mercaptopropionic acid, by the same method as used in Example 126.
MS m/e (ESI) 399 (MH$^+$-CF$_3$COOH)

Example 144

2-[7-(2-Butynyl)-1-methyl-6-oxo-8-(piperazin-1-yl)-6,7-dihydro-1H-purin-2-ylsulfanyl]acetamide trifluoroacetate 1.86 mg of the title compound was obtained by using 2-mercaptoacetamide, instead of 3-mercaptopropionic acid, by the same method as used in Example 126.
MS m/e (ESI) 376 (MH$^+$-CF$_3$COOH)

Example 145

7-(2-Butynyl)-1-methyl-8-(piperazin-1-yl)-2-(thiophen-2-ylmethyl sulfanyl)-1,7-dihydropurin-6-one trifluoroacetate 3.35 mg of the title compound was obtained by using (thiophen-2-yl)methanethiol, instead of 3-mercaptopropionic acid, by the same method as used in Example 126.
MS m/e (ESI) 415 (MH$^+$-CF$_3$COOH)

Example 146

7-(2-Butynyl)-1-methyl-8-(piperazin-1-yl)-2-[1-(thiophen-2-yl)ethylsulfanyl]-1,7-dihydropurin-6-one trifluoroacetate 0.51 mg of the title compound was obtained by using 1-(thiophen-2-yl)ethanethiol, instead of 3-mercaptopropionic acid, by the same method as used in Example 126.
MS m/e (ESI) 429 (MH$^+$-CF$_3$COOH)

Example 147

7-(2-Butynyl)-1-methyl-2-(1-methyl-1H-imidazol-2-ylsulfanyl)-8-(piperazin-1-yl)-1,7-dihydropurin-6-one trifluoroacetate 5 mg of t-butyl 4-[7-(2-butynyl)-2-chloro-1-methyl-6-oxo-6,7-dihydro-1H-purin-8-yl]piperazine-1-carboxylate was dissolved in 0.15 ml of 1-methyl-2-pyrrolidone, and then 10 mg of 1-methyl-1H-imidazole-2-thiol and 8 mg of potassium carbonate were added thereto. The mixture was stirred at room temperature for five hours. A saturated ammonium chloride solution was added to the reaction solution, and the mixture was extracted with ethyl acetate. The organic layer was concentrated, and the residue was dissolved in 0.40 ml of trifluoroacetic acid. The solution was concentrated by flushing with nitrogen gas. The residue was purified by reverse-phase high performance liquid chromatography (using an acetonitrile-water mobile phase (containing 0.1% trifluoroacetic acid)) to give 3.75 mg of the title compound.
MS m/e (ESI) 399 (MH$^+$-CF$_3$COOH)

Example 148

7-(2-Butynyl)-1-methyl-2-(4-methylpyrimidin-2-ylsulfanyl)-8-(piperazin-1-yl)-1,7-dihydropurin-6-one trifluoroacetate 4.00 mg of the title compound was obtained by using 4-methylpyrimidine-2-thiol, instead of 1-methyl-1H-imidazole-2-thiol, by the same method as used in Example 147.
MS m/e (ESI) 411 (MH$^+$-CF$_3$COOH)

Example 149

7-(2-Butynyl)-1-methyl-8-(piperazin-1-yl)-2-(pyrazin-2-ylsulfanyl)-1,7-dihydropurin-6-one trifluoroacetate 4.00 mg of the title compound was obtained by using pyrazine-2-thiol, instead of 1-methyl-1H-imidazole-2-thiol, by the same method as used in Example 147.
MS m/e (ESI) 411 (MH$^+$-CF$_3$COOH)

Example 150

2-(Benzothiazol-2-ylsulfanyl)-7-(2-butynyl)-1-methyl-8-(piperazin-1-yl)-1,7-dihydropurin-6-one trifluoroacetate 0.07 mg of the title compound was obtained by using benzothiazole-2-thiol, instead of 1-methyl-1H-imidazole-2-thiol, by the same method as used in Example 147.
MS m/e (ESI) 452 (MH$^+$-CF$_3$COOH)

Example 151

2-(1H-benzimidazol-2-ylsulfanyl)-7-(2-butynyl)-1-methyl-8-(piperazin-1-yl)-1,7-dihydropurin-6-one trifluoroacetate 3.18 mg of the title compound was obtained by using 1H-benzimidazole-2-thiol, instead of 1-methyl-1H-imidazole-2-thiol, by the same method as used in Example 147.
MS m/e (ESI) 435 (MH$^+$-CF$_3$COOH)

Example 152

2-(5-Amino-[1,3,4]thiadiazol-2-ylsulfanyl)-7-(2-butynyl)-1-methyl-8-(piperazin-1-yl)-1,7-dihydropurin-6-one trifluoroacetate 3.62 mg of the title compound was obtained by using 5-amino-[1,3,4]thiadiazole-2-thiol, instead of 1-methyl-1H-imidazole-2-thiol, by the same method as used in Example 147.
MS m/e (ESI) 418 (MH$^+$-CF$_3$COOH)

Example 153

6-[7-(2-Butynyl)-1-methyl-6-oxo-8-(piperazin-1-yl)-6,7-dihydro-1H-purin-2-ylsulfanyl]nicotinic acid trifluoroacetate 1.01 mg of the title compound was obtained by using 6-mercaptonicotinic acid, instead of 1-methyl-1H-imidazole-2-thiol, by the same method as used in Example 147.
MS m/e (ESI) 440 (MH$^+$-CF$_3$COOH)

Example 154

7-(2-Butynyl)-2-(4-methoxyphenylsulfanyl)-1-methyl-8-(piperazin-1-yl)-1,7-dihydropurin-6-one trifluoroacetate 4.14 mg of the title compound was obtained by using 4-methoxybenzenethiol, instead of 1-methyl-1H-imidazole-2-thiol, by the same method as used in Example 147.
MS m/e (ESI) 425 (MH$^+$-CF$_3$COOH)

Example 155

7-(2-Butynyl)-1-methyl-2-(4-nitrophenylsulfanyl)-8-(piperazin-1-yl)-1,7-dihydropurin-6-one trifluoroacetate 1.52 mg of the title compound was obtained by using 4-nitrobenzenethiol, instead of 1-methyl-1H-imidazole-2-thiol, by the same method as used in Example 147.
MS m/e (ESI) 440 (MH$^+$-CF$_3$COOH)

Example 156

N-[2-[7-(2-butynyl)-1-methyl-6-oxo-8-(piperazin-1-yl)-6,7-dihydro-1H-purin-2-ylsulfanyl]ethyl]acetamide trifluoroacetate 2.39 mg of the title compound was obtained by using N-(2-mercaptoethyl)acetamide, instead of 1-methyl-1H-imidazole-2-thiol, by the same method as used in Example 147.
MS m/e (ESI) 404 (MH$^+$-CF$_3$COOH)

Example 157

7-(2-Butynyl)-1-methyl-2-(5-methyl-[1,3,4]thiadiazol-2-ylsulfanyl)-8-(piperazin-1-yl)-1,7-dihydropurin-6-one trifluoroacetate 1.24 mg of the title compound was obtained by using 5-methyl-[1,3,4]thiadiazole-2-thiol, instead of 1-methyl-1H-imidazole-2-thiol, by the same method as used in Example 147.
MS m/e (ESI) 417 (MH$^+$-CF$_3$COOH)

Example 158

7-(2-Butynyl)-2-(4,6-dimethylpyrimidin-2-ylsulfanyl)-1-methyl-8-(piperazin-1-yl)-1,7-dihydropurin-6-one trifluoroacetate 3.11 mg of the title compound was obtained by using 4,6-dimethylpyrimidine-2-thiol, instead of 1-methyl-1H-imidazole-2-thiol, by the same method as used in Example 147.
MS m/e (ESI) 425 (MH$^+$-CF$_3$COOH)

Example 159

7-(2-Butynyl)-1-methyl-2-(4-methylthiazol-2-ylsulfanyl)-8-(piperazin-1-yl)-1,7-dihydropurin-6-one trifluoroacetate 4.01 mg of the title compound was obtained by using 4-methylthiazol-2-thiol, instead of 1-methyl-1H-imidazole-2-thiol, by the same method as used in Example 147.
MS m/e (ESI) 416 (MH$^+$-CF$_3$COOH)

Example 160

2-(Benzoxazol-2-ylsulfanyl)-7-(2-butynyl)-1-methyl-8-(piperazin-1-yl)-1,7-dihydropurin-6-one trifluoroacetate 0.84 mg of the title compound was obtained by using benzoxazole-2-thiol, instead of 1-methyl-1H-imidazole-2-thiol, by the same method as used in Example 147.
MS m/e (ESI) 436 (MH$^+$-CF$_3$COOH)

Example 161

7-(2-Butynyl)-1-methyl-8-(piperazin-1-yl)-2-([1,3,4]thiadiazol-2-ylsulfanyl)-1,7-dihydropurin-6-one trifluoroacetate 1.95 mg of the title compound was obtained by using [1,3,4]thiadiazole-2-thiol, instead of 1-methyl-1H-imidazole-2-thiol, by the same method as used in Example 147.
MS m/e (ESI) 403 (MH$^+$-CF$_3$COOH)

Example 162

2-Allylsulfanyl-7-(2-butynyl)-1-methyl-8-(piperazin-1-yl)-1,7-dihydropurin-6-one trifluoroacetate 2.85 mg of the title compound was obtained by using allyl mercaptan, instead of 1-methyl-1H-imidazole-2-thiol, by the same method as used in Example 147.
MS m/e (ESI) 359 (MH$^+$-CF$_3$COOH)

Example 163

7-(2-Butynyl)-1-methyl-2-(3-methylsulfanylphenylamino)-8-(piperazin-1-yl)-1,7-dihydropurin-6-one trifluoroacetate 1.32 mg of the title compound was obtained by using 3-methylsulfanylphenylamine, instead of 1-methyl-1H-imidazole-2-thiol, by the same method as used in Example 147.
MS m/e (ESI) 424 (MH$^+$-CF$_3$COOH)

Example 164

7-(2-Butynyl)-1-methyl-8-(piperazin-1-yl)-2-(thiomorpholin-4-yl)-1,7-dihydropurin-6-one trifluoroacetate 5.33 mg of the title compound was obtained by using thiomorpholine, instead of 1-methyl-1H-imidazole-2-thiol, by the same method as used in Example 147.
MS m/e (ESI) 388 (MH$^+$-CF$_3$COOH)

Example 165

2-[7-(2-Butynyl)-1-methyl-6-oxo-8-(piperazin-1-yl)-6,7-dihydro-1H-purin-2-ylsulfanyl]-2-methylpropionic acid trifluoroacetate 1.63 mg of the title compound was obtained by using 2-mercapto-2-methylpropionic acid, instead of 1-methyl-1H-imidazole-2-thiol, by the same method as used in Example 147.
MS m/e (ESI) 405 (MH$^+$-CF$_3$COOH)

Example 166

7-(2-Butynyl)-2-(N-isopropylmethylamino)-1-methyl-8-(piperazin-1-yl)-1,7-dihydropurin-6-one trifluoroacetate

6 mg of t-butyl 4-[(7-(2-butynyl)-2-chloro-1-methyl-6-oxo-6,7-dihydro-1H-purin-8-yl]piperazine-1-carboxylate was dissolved in 0.15 ml of 1-methyl-2-pyrrolidone, and then 30 μl of N-isopropylmethylamine was added thereto. After the mixture was stirred at 80° C. for 12 hours, the reaction solution was concentrated by flushing with nitrogen gas. The resulting residue was dissolved in 0.60 ml of trifluoroacetic acid. The solution was concentrated by flushing with nitrogen gas. The residue was purified by reverse-phase high performance liquid chromatography (using an acetonitrile-water mobile phase (containing 0.1% trifluoroacetic acid)) to give 1.66 mg of the title compound.

MS m/e (ESI) 358 (MH$^+$-CF$_3$COOH)

Example 167

3-[7-(2-Butynyl)-1-methyl-6-oxo-8-(piperazin-1-yl)-6,7-dihydro-1H-purin-2-yloxy]benzonitrile trifluoroacetate

5 mg of t-butyl 4-[7-(2-butynyl)-2-chloro-1-methyl-6-oxo-6,7-dihydro-1H-purin-8-yl]piperazine-1-carboxylate was dissolved in 0.2 ml of 1-methyl-2-pyrrolidone, and then 5 mg of 3-cyanophenol and 8 mg of sodium hydride were added thereto. The mixture was stirred at 90° C. for three hours. 1N hydrochloric acid was added to the reaction solution, and the mixture was extracted with ethyl acetate. The organic layer was concentrated, and the residue was dissolved in trifluoroacetic acid. The solution was concentrated, and the residue was purified by reverse-phase high performance liquid chromatography (using an acetonitrile-water mobile phase (containing 0.1% trifluoroacetic acid)) to give 1.02 mg of the title compound.

MS m/e (ESI) 404 (MH$^+$-CF$_3$COOH)

Example 168

4-[7-(2-butynyl)-1-methyl-6-oxo-8-(piperazin-1-yl)-6,7-dihydro-1H-purin-2-yloxy]benzonitrile trifluoroacetate

2.76 mg of the title compound was obtained by using 4-cyanophenol, instead of 3-cyanophenol, by the same method as used in Example 167.

MS m/e (ESI) 404 (MH$^+$-CF$_3$COOH)

Example 169

7-(2-Butynyl)-1-methyl-8-(piperazin-1-yl)-2-(3-tolyloxy)-1,7-dihydropurin-6-one trifluoroacetate

3.14 mg of the title compound was obtained by using 3-methylphenol, instead of 3-cyanophenol, by the same method as used in Example 167.

MS m/e (ESI) 393 (MH$^+$-CF$_3$COOH)

Example 170

7-(2-Butynyl)-1-methyl-2-(2-methylsulfanylphenoxy)-8-(piperazin-1-yl)-1,7-dihydropurin-6-one trifluoroacetate

3.50 mg of the title compound was obtained by using 2-methylsulfanylphenol, instead of 3-cyanophenol, by the same method as used in Example 167.

MS m/e (ESI) 425 (MH$^+$-CF$_3$COOH)

Example 171

3-[7-(2-Butynyl)-1-methyl-6-oxo-8-(piperazin-1-yl)-6,7-dihydro-1H-purin-2-yloxy]benzoic acid trifluoroacetate

5 mg of t-butyl 4-[7-(2-butynyl)-2-chloro-1-methyl-6-oxo-6,7-dihydro-1H-purin-8-yl]piperazine-1-carboxylate and 10 mg of ethyl 3-hydroxybenzoate were dissolved in 0.2 ml of N-methylpyrrolidone and then 8 mg of sodium hydride was added thereto. The mixture was stirred at 90° C. for 3 hours. 1N hydrochloric acid was added to the reaction solution, and the mixture was extracted with ethyl acetate. The organic layer was concentrated, and the residue was dissolved in a mixture consisting of 0.4 ml of ethanol and 0.1 ml of a 5N aqueous sodium hydroxide solution. The mixture was stirred at 50° C. overnight. 1N hydrochloric acid was added to the reaction solution, and the mixture was extracted with ethyl acetate. The organic layer was concentrated, and the residue was dissolved in trifluoroacetic acid. The solution was concentrated, and the residue was purified by reverse-phase high performance liquid chromatography (using an acetonitrile-water mobile phase (containing 0.1% trifluoroacetic acid)) to give 1.09 mg of the title compound.

MS m/e (ESI) 423 (MH$^+$-CF$_3$COOH)

Example 172

4-[7-(2-Butynyl)-1-methyl-6-oxo-8-(piperazin-1-yl)-6,7-dihydro-1H-purin-2-yloxy]benzoic acid trifluoroacetate

1.55 mg of the title compound was obtained by using ethyl 4-hydroxybenzoate, instead of 3-hydroxybenzoic acid, by the same method as used in Example 171.

MS m/e (ESI) 423 (MH$^+$-CF$_3$COOH)

Example 173

7-(2-Butynyl)-1-methyl-8-(piperazin-1-yl)-2-(2-tolyloxy)-1,7-dihydropurin-6-one trifluoroacetate

7 mg of t-butyl 4-[7-(2-butynyl)-2-chloro-1-methyl-6-oxo-6,7-dihydro-1H-purin-8-yl]piperazine-1-carboxylate was dissolved in 0.2 ml of 1-methyl-2-pyrrolidone, and then 5 mg of 2-methylphenol and 8 mg of potassium carbonate were added thereto. The mixture was stirred at 90° C. for five hours. 1N hydrochloric acid was added to the reaction solution, and the mixture was extracted with ethyl acetate. The organic layer was concentrated, and the residue was dissolved in trifluoroacetic acid. The solution was concentrated, and the residue was purified by reverse-phase high performance liquid chromatography (using an acetonitrile-water mobile phase (containing 0.1% trifluoroacetic acid)) to give 4.40 mg of the title compound.

MS m/e (ESI) 393 (MH$^+$-CF$_3$COOH)

Example 174

7-(2-Butynyl)-1-methyl-8-(piperazin-1-yl)-2-(4-tolyloxy)-1,7-dihydropurin-6-one trifluoroacetate 3.95 mg of the title compound was obtained by using 4-methylphenol, instead of 2-methylphenol, by the same method as used in Example 173.
MS m/e (ESI) 393 (MH$^+$-CF$_3$COOH)

Example 175

7-(2-Butynyl)-2-(2-methoxyphenoxy)-1-methyl-8-(piperazin-1-yl)-1,7-dihydropurin-6-one trifluoroacetate 5.24 mg of the title compound was obtained by using 2-methoxyphenol, instead of 2-methylphenol, by the same method as used in Example 173.
MS m/e (ESI) 409 (MH$^+$-CF$_3$COOH)

Example 176

7-(2-Butynyl)-2-(3-methoxyphenoxy)-1-methyl-8-(piperazin-1-yl)-1,7-dihydropurin-6-one trifluoroacetate 2.84 mg of the title compound was obtained by using 3-methoxyphenol, instead of 2-methylphenol, by the same method as used in Example 173.
MS m/e (ESI) 409 (MH$^+$-CF$_3$COOH)

Example 177

7-(2-Butynyl)-2-(4-methoxyphenoxy)-1-methyl-8-(piperazin-1-yl)-1,7-dihydropurin-6-one trifluoroacetate 5.61 mg of the title compound was obtained by using 4-methoxyphenol, instead of 2-methylphenol, by the same method as used in Example 173.
MS m/e (ESI) 409 (MH$^+$-CF$_3$COOH)

Example 178

4-[7-(2-Butynyl)-1-methyl-6-oxo-8-(piperazin-1-yl)-6,7-dihydro-1H-purin-2-yloxy]benzenesulfonamide trifluoroacetate 4.21 mg of the title compound was obtained by using 4-hydroxybenzenesulfonamide, instead of 2-methylphenol, by the same method as used in Example 173.
MS m/e (ESI) 458 (MH$^+$-CF$_3$COOH)

Example 179

4-[7-(2-Butynyl)-1-methyl-6-oxo-8-(piperazin-1-yl)-6,7-dihydro-1H-purin-2-yloxy]-3-methoxybenzonitrile trifluoroacetate 4.24 mg of the title compound was obtained by using 4-hydroxy-3-methoxybenzonitrile, instead of 2-methylphenol, by the same method as used in Example 173.
MS m/e (ESI) 434 (MH$^+$-CF$_3$COOH)

Example 180

2-[7-(2-Butynyl)-1-methyl-6-oxo-8-(piperazin-1-yl)-6,7-dihydro-1H-purin-2-yloxy]benzonitrile trifluoroacetate 5.26 mg of the title compound was obtained by using 2-cyanophenol, instead of 2-methylphenol, by the same method as used in Example 173.
MS m/e (ESI) 404 (MH$^+$-CF$_3$COOH)

Example 181

4-[7-(2-Butynyl)-1-methyl-6-oxo-8-(piperazin-1-yl)-6,7-dihydro-1H-purin-2-yloxy]benzamide trifluoroacetate 4.80 mg of the title compound was obtained by using 4-hydroxybenzamide, instead of 2-methylphenol, by the same method as used in Example 173.
MS m/e (ESI) 422 (MH$^+$-CF$_3$COOH)

Example 182

Ethyl 2-[7-(2-butynyl)-1-methyl-6-oxo-8-(piperazin-1-yl)-6,7-dihydro-1H-purin-2-yloxy]benzoate trifluoroacetate 4.38 mg of the title compound was obtained by using ethyl 2-hydroxybenzoate, instead of 2-methylphenol, by the same method as used in Example 173.
MS m/e (ESI) 451 (MH$^+$-CF$_3$COOH)

Example 183

7-(2-Butynyl)-1-methyl-8-(piperazin-1-yl)-2-(pyrimidin-2-yloxy)-1,7-dihydropurin-6-one trifluoroacetate 1.12 mg of the title compound was obtained by using pyrimidin-2-ol, instead of 2-methylphenol, by the same method as used in Example 173.
MS m/e (ESI) 381 (MH$^+$-CF$_3$COOH)

Example 184

7-(2-Butynyl)-2-(4,6-dimethylpyrimidin-2-yloxy)-1-methyl-8-(piperazin-1-yl)-1,7-dihydropurin-6-one trifluoroacetate 0.66 mg of the title compound was obtained by using 4,6-dimethylpyrimidin-2-ol, instead of 2-methylphenol, by the same method as used in Example 173.
MS m/e (ESI) 409 (MH$^+$-CF$_3$COOH)

Example 185

3-[7-(2-Butynyl)-1-methyl-6-oxo-8-(piperazin-1-yl)-6,7-dihydro-1H-purin-2-yloxy]benzamide trifluoroacetate 6 mg of t-butyl 4-[7-(2-butynyl)-2-chloro-1-methyl-6-oxo-6,7-dihydro-1H-purin-8-yl]piperazine-1-carboxylate and 10 mg of ethyl 3-hydroxybenzoate were dissolved in 0.2 ml of N-methylpyrrolidone, and then 10 mg of potassium carbonate was added thereto. The mixture was stirred at 90° C. for 3 hours. 1N hydrochloric acid was added to the reaction solution, and the mixture was extracted with ethyl acetate. The organic layer was concentrated, and the residue was dissolved in 1.0 ml of ammonia (7N methanol solution). The mixture was stirred at 50° C. overnight. The reaction solution was concentrated, and the residue was dissolved in trifluoroacetic acid. The solution was concentrated, and the residue was purified by reverse-phase high performance liquid chromatography (using an acetonitrile-water mobile phase (containing 0.1% trifluoroacetic acid)) to give 1.91 mg of the title compound.

MS m/e (ESI) 422 (MH$^+$-CF$_3$COOH)

Example 186

4-[7-(2-Butynyl)-1-methyl-6-oxo-8-(piperazin-1-yl)-6,7-dihydro-1H-purin-2-yloxy]-3,5-dimethylbenzoic acid trifluoroacetate 7 mg of t-butyl 4-[7-(2-butynyl)-2-chloro-1-methyl-6-oxo-6,7-dihydro-1H-purin-8-yl]piperazine-1-carboxylate was dissolved in 0.2 ml of 1-methyl-2-pyrrolidone, and then 8 mg of 4-hydroxy-3,5-dimethylbenzoic acid and 8 mg of potassium carbonate were added thereto. The mixture was stirred at 100° C. for 2 hours. 1N hydrochloric acid was added to the reaction solution, and the mixture was extracted with ethyl acetate. The organic layer was concentrated, and the residue was dissolved in trifluoroacetic acid. The solution was concentrated, and the residue was purified by reverse-phase high performance liquid chromatography (using an acetonitrile-water mobile phase (containing 0.1% trifluoroacetic acid)) to give 2.71 mg of the title compound.

MS m/e (ESI) 451 (MH$^+$-CF$_3$COOH)

Example 187

4-[7-(2-Butynyl)-1-methyl-6-oxo-8-(piperazin-1-yl)-6,7-dihydro-1H-purin-2-yloxy]-3-fluorobenzoic acid trifluoroacetate 3.49 mg of the title compound was obtained by using 3-fluoro-4-hydroxybenzoic acid, instead of 4-hydroxy-3,5-dimethylbenzoic acid, by the same method as used in Example 186.

MS m/e (ESI) 441 (MH$^+$-CF$_3$COOH)

Example 188

[4-[7-(2-Butynyl)-1-methyl-6-oxo-8-(piperazin-1-yl)-6,7-dihydro-1H-purin-2-yloxy]phenyl]acetic acid trifluoroacetate 3.45 mg of the title compound was obtained by using (4-hydroxyphenyl)acetic acid, instead of 4-hydroxy-3,5-dimethylbenzoic acid, by the same method as used in Example 186.

MS m/e (ESI) 437 (MH$^+$-CF$_3$COOH)

Example 189

[2-[7-(2-Butynyl)-1-methyl-6-oxo-8-(piperazin-1-yl)-6,7-dihydro-1H-purin-2-yloxy]phenyl]acetic acid trifluoroacetate 1.34 mg of the title compound was obtained by using (2-hydroxyphenyl)acetic acid, instead of 4-hydroxy-3,5-dimethylbenzoic acid, by the same method as used in Example 186.

MS m/e (ESI) 437 (MH$^+$-CF$_3$COOH)

Example 190

2-(2-Acetylphenoxy)-7-(2-butynyl)-1-methyl-8-(piperazin-1-yl)-1,7-dihydropurin-6-one trifluoroacetate 1.99 mg of the title compound was obtained by using 1-(2-hydroxyphenyl)ethanone, instead of 4-hydroxy-3,5-dimethylbenzoic acid, by the same method as used in Example 186.

MS m/e (ESI) 421 (MH$^+$-CF$_3$COOH)

Example 191

7-(2-Butynyl)-2-(2,6-difluorophenoxy)-1-methyl-8-(piperazin-1-yl)-1,7-dihydropurin-6-one trifluoroacetate 5.26 mg of the title compound was obtained by using 2,6-difluorophenol, instead of 4-hydroxy-3,5-dimethylbenzoic acid, by the same method as used in Example 186.

MS m/e (ESI) 415 (MH$^+$-CF$_3$COOH)

Example 192

7-(2-Butynyl)-1-methyl-2-pentafluorophenoxy-8-(piperazin-1-yl)-1,7-dihydropurin-6-one trifluoroacetate 5.61 mg of the title compound was obtained by using 2,3,4,5,6-pentafluorophenol, instead of 4-hydroxy-3,5-dimethylbenzoic acid, by the same method as used in Example 186.

MS m/e (ESI) 469 (MH$^+$-CF$_3$COOH)

Example 193

7-(2-Butynyl)-1-methyl-8-(piperazin-1-yl)-2-[4-(pyrrolidine-1-carbonyl)phenoxy]-1,7-dihydropurin-6-one trifluoroacetate 30 mg of t-butyl 4-[7-(2-butynyl)-2-chloro-1-methyl-6-oxo-6,7-dihydro-1H-purin-8-yl]piperazine-1-carboxylate was dissolved in 1 ml of 1-methyl-2-pyrrolidone, and then 15 mg of 1-(4-hydroxybenzoyl) pyrrolidine and 11 mg of potassium carbonate were added thereto. The mixture was stirred at 100° C. for 2.5 hours. Water was added to the reaction solution, and the mixture was extracted with ethyl acetate. The organic layer was concentrated, and the residue was dissolved in trifluoroacetic acid. The solution was concentrated, and the residue was purified by reverse-phase high performance liquid chromatography (using an acetonitrile-water mobile phase (containing 0.1% trifluoroacetic acid)) to give 23.7 mg of the title compound.

MS m/e (ESI) 476 (MH$^+$-CF$_3$COOH)

Example 194

2-[7-(2-Butynyl)-1-methyl-6-oxo-8-(piperazin-1-yl)-6,7-dihydro-1H-purin-2-yloxy]-N-[2-(piperidin-1-yl)ethyl]benzamide trifluoroacetate 3.05 mg of the title compound was obtained by using 2-hydroxy-N-[2-(piperidin-1-yl)ethyl]benzamide by the same method as used in Example 193.

MS m/e (ESI) 533 (MH$^+$-CF$_3$COOH)

Example 195

5-Acetyl-2-[7-(2-butynyl)-1-methyl-6-oxo-8-(piperazin-1-yl)-6,7-dihydro-1H-purin-2-yloxy]benzamide trifluoroacetate 0.82 mg of the title compound was obtained by using 5-acetyl salicylamide, instead of 1-(4-hydroxybenzoyl)pyrrolidine, by the same method as used in Example 193.
MS m/e (ESI) 464 (MH$^+$-CF$_3$COOH)

Example 196

2-[7-(2-Butynyl)-1-methyl-6-oxo-8-(piperazin-1-yl)-6,7-dihydro-1H-purin-2-ylsulfanyl]benzoic acid trifluoroacetate 0.70 mg of the title compound was obtained by using thiosalicylic acid, instead of 1-(4-hydroxybenzoyl)pyrrolidine, by the same method as used in Example 193.
MS m/e (ESI) 439 (MH$^+$-CF$_3$COOH)

Example 197

6-[7-(2-Butynyl)-1-methyl-6-oxo-8-(piperazin-1-yl)-6,7-dihydro-1H-purin-2-ylamino]nicotinamide trifluoroacetate 1.43 mg of the title compound was obtained by using 6-amino-nicotinamide, instead of 1-(4-hydroxybenzoyl)pyrrolidine, by the same method as used in Example 193.
MS m/e (ESI) 422 (MH$^+$-CF$_3$COOH)

Example 198

3-[7-(2-Butynyl)-1-methyl-6-oxo-8-(piperazin-1-yl)-6,7-dihydro-1H-purin-2-yloxy]pyridine-2-carboxylic amide trifluoroacetate 1.44 mg of the title compound was obtained by using 3-hydroxypicolinamide, instead of 1-(4-hydroxybenzoyl)pyrrolidine, by the same method as used in Example 193.
MS m/e (ESI) 423 (MH$^+$-CF$_3$COOH)

Example 199

N-t-butyl-2-[7-(2-butynyl)-1-methyl-6-oxo-8-(piperazin-1-yl)-6,7-dihydro-1H-purin-2-ylamino]benzamide trifluoroacetate 0.87 mg of the title compound was obtained by using 2-amino-N-t-butylbenzamide, instead of 1-(4-hydroxybenzoyl)pyrrolidine, by the same method as used in Example 193.
MS m/e (ESI) 477 (MH$^+$-CF$_3$COOH)

Examples 200 and 201

2-[7-(2-Butynyl)-1-methyl-6-oxo-8-(piperazin-1-yl)-6,7-dihydro-1H-purin-2-ylamino]benzamide trifluoroacetate 1.36 mg of the polar compound of the title compound and 0.39 mg of the non-polar compound of the title compound were obtained by using 2-aminobenzamide, instead of 1-(4-hydroxybenzoyl)pyrrolidine, by the same method as used in Example 193.
MS m/e (ESI) 477 (MH$^+$-CF$_3$COOH)

Example 202

N-[3-[7-(2-butynyl)-1-methyl-6-oxo-8-(piperazin-1-yl)-6,7-dihydro-1H-purin-2-yloxy]phenyl]acetamide trifluoroacetate 10.79 mg of the title compound was obtained by using 3-acetamidophenol, instead of 1-(4-hydroxybenzoyl)pyrrolidine, by the same method as used in Example 193.
MS m/e (ESI) 436 (MH$^+$-CF$_3$COOH)

Example 203

N-[4-[7-(2-butynyl)-1-methyl-6-oxo-8-(piperazin-1-yl)-6,7-dihydro-1H-purin-2-yloxy]phenyl]acetamide trifluoroacetate 11.38 mg of the title compound was obtained by using 4-acetamidophenol, instead of 1-(4-hydroxybenzoyl)pyrrolidine, by the same method as used in Example 193.
MS m/e (ESI) 436 (MH$^+$-CF$_3$COOH)

Example 204

2-[N-[7-(2-butynyl)-1-methyl-6-oxo-8-(piperazin-1-yl)-6,7-dihydro-1H-purin-2-yl]methylamino]benzoic acid trifluoroacetate 3.48 mg of the title compound was obtained by using N-methylanthranilic acid, instead of 1-(4-hydroxybenzoyl)pyrrolidine, by the same method as used in Example 193.
MS m/e (ESI) 436 (MH$^+$-CF$_3$COOH)

Example 205

2-[7-(2-butynyl)-1-methyl-6-oxo-8-(piperazin-1-yl)-6,7-dihydro-1H-purin-2-yloxy]benzoic acid trifluoroacetate 25.75 mg of the title compound was obtained by using salicylic acid, instead of 1-(4-hydroxybenzoyl)pyrrolidine, by the same method as used in Example 193.
MS m/e (ESI) 423 (MH$^+$-CF$_3$COOH)

Example 206

2-[7-(2-butynyl)-1-methyl-6-oxo-8-(piperazin-1-yl)-6,7-dihydro-1H-purin-2-ylamino]benzenesulfonamide trifluoroacetate 0.91 mg of the title compound was obtained by using 2-aminobenzenesulfonamide, instead of 1-(4-hydroxybenzoyl)pyrrolidine, by the same method as used in Example 193.
MS m/e (ESI) 457 (MH$^+$-CF$_3$COOH)

Example 207

2-[7-(2-Butynyl)-1-methyl-6-oxo-8-(piperazin-1-yl)-6,7-dihydro-1H-purin-2-yl sulfanyl]benzoic acid ethyl ester trifluoroacetate 0.66 mg of the title compound was obtained by using ethyl thiosalicylate, instead of 1-(4-hydroxybenzoyl)pyrrolidine, by the same method as used in Example 193.
MS m/e (ESI) 467 (MH$^+$-CF$_3$COOH)

Example 208

3-[7-(2-Butynyl)-1-methyl-6-oxo-8-(piperazin-1-yl)-6,7-dihydro-1H-purin-2-yloxy]pyridine-2-carboxylic acid trifluoroacetate 4.36 mg of the title compound was obtained by using 3-hydroxypicolinic acid, instead of 1-(4-hydroxybenzoyl)pyrrolidine, by the same method as used in Example 193.

MS m/e (ESI) 424 (MH$^+$-CF$_3$COOH)

Example 209

N-[2-[7-(2-butynyl)-1-methyl-6-oxo-8-(piperazin-1-yl)-6,7-dihydro-1H-purin-2-yloxy]phenyl]acetamide trifluoroacetate 0.126 mg of the title compound was obtained by using 2-acetamidophenol, instead of 1-(4-hydroxybenzoyl)pyrrolidine, by the same method as used in Example 193.

MS m/e (ESI) 436 (MH$^+$-CF$_3$COOH)

Example 210

2-[7-(2-butynyl)-1-methyl-6-oxo-8-(piperazin-1-yl)-6,7-dihydro-1H-purin-2-yloxy]-N,N-dimethylbenzamide trifluoroacetate 100 mg of salicylic acid and 0.76 ml of a 2 M tetrahydrofuran solution of dimethylamine were dissolved in 1 ml of N,N-dimethylformamide, and then 109 μl of diethyl cyanophosphonate and 250 μl of triethylamine were added thereto. The mixture was stirred at room temperature for 5.5 hours. Water was added to the reaction solution, and the mixture was extracted with ethyl acetate. The organic layer was concentrated, and 20 mg of 4-[7-(2-butynyl)-2-chloro-1-methyl-6-oxo-6,7-dihydro-1H-purin-8-yl]piperazine-1-carboxylic acid t-butyl ester, potassium carbonate and 1 ml of 1-methyl-2-pyrrolidone were added to a one-third aliquot of the residue. The mixture was stirred at 150° C. for 1.5 hours. Water was added to the reaction solution, and the mixture was extracted with ethyl acetate. The organic layer was concentrated, and the residue was dissolved in trifluoroacetic acid. The solution was concentrated, and the residue was purified by reverse-phase high performance liquid chromatography (using an acetonitrile-water mobile phase (containing 0.1% trifluoroacetic acid)) to give 1.06 mg of the title compound.

MS m/e (ESI) 450 (MH$^+$-CF$_3$COOH)

Example 211

7-(2-Butynyl)-1-methyl-8-(piperazin-1-yl)-2-[2-(thiazolidine-3-carbonyl)phenoxy]-1,7-dihydropurin-6-one trifluoroacetate 2.10 mg of the title compound was obtained by using thiazolidine, instead of dimethylamine, by the same method as used in Example 210.

MS m/e (ESI) 494 (MH$^+$-CF$_3$COOH)

Example 212

7-(2-Butynyl)-1-methyl-8-(piperazin-1-yl)-2-[2-(pyrrolidine-1-carbonyl)phenoxy]-1,7-dihydropurin-6-one trifluoroacetate 6.86 mg of the title compound was obtained by using pyrrolidine, instead of dimethylamine, by the same method as used in Example 210.

MS m/e (ESI) 476 (MH$^+$-CF$_3$COOH)

Example 213

7-(2-Butynyl)-1-methyl-2-[2-(morpholine-4-carbonyl)phenoxy]-8-(piperazin-1-yl)-1,7-dihydropurin-6-one trifluoroacetate 3.63 mg of the title compound was obtained by using morpholine, instead of dimethylamine, by the same method as used in Example 210.

MS m/e (ESI) 492 (MH$^+$-CF$_3$COOH)

Example 214

[7-(2-butynyl)-1-methyl-6-oxo-8-(piperazin-1-yl)-6,7-dihydro-1H-purin-2-yl]acetonitrile trifluoroacetate

Example 215

[7-(2-butynyl)-2-cyanomethyl-1-methyl-6-oxo-8-(piperazin-1-yl)-2,3,6,7-tetrahydro-1H-purin-2-yl]acetonitrile trifluoroacetate 8 mg of 4-[7-(2-butynyl)-2-chloro-1-methyl-6-oxo-6,7-dihydro-1H-purin-8-yl]piperazine-1-carboxylic acid t-butyl ester was dissolved in 0.8 ml of acetonitrile, and then 8 mg of sodium hydride was added thereto. The mixture was stirred at 60° C. for three hours. 1N hydrochloric acid was added to the reaction solution, and the mixture was extracted with ethyl acetate. The organic layer was concentrated, and the residue was dissolved in trifluoroacetic acid. The solution was concentrated, and the residue was purified by reverse-phase high performance liquid chromatography (using an acetonitrile-water mobile phase (containing 0.1% trifluoroacetic acid)) to give 1.85 mg and 2.20 mg of the title compounds (Examples 214 and 215), respectively.

(Example 214) MS m/e (ESI) 326 (MH$^+$-CF$_3$COOH)
(Example 215) MS m/e (ESI) 367 (MH$^+$-CF$_3$COOH)

Example 216

7-(2-butynyl)-1-methyl-2-(2-oxopropyl)-8-(piperazin-1-yl)-1,7-dihydropurin-6-one trifluoroacetate 8 mg of t-butyl 4-[7-(2-butynyl)-2-chloro-1-methyl-6-oxo-6,7-dihydro-1H-purin-8-yl]piperazine-1-carboxylate was dissolved in 0.8 ml of acetone, and then 8 mg of sodium hydride was added thereto. The mixture was stirred at 60° C. for three hours. 1N hydrochloric acid was added to the reaction solution, and the mixture was extracted with ethyl acetate. The organic layer was concentrated, and the residue was dissolved in trifluoroacetic acid. The solution was concentrated, and the residue was purified by reverse-phase high performance liquid chromatography (using an acetonitrile-water mobile phase (containing 0.1% trifluoroacetic acid)) to give 1.17 mg of the title compound.

MS m/e (ESI) 343 (MH$^+$-CF$_3$COOH)

Example 217

7-(2-Butynyl)-2-ethynyl-1-methyl-8-(piperazin-1-yl)-1,7-dihydropurin-6-one trifluoroacetate 50 μl of trimethylsilylacetylene was dissolved in 1.0 ml of tetrahydrofuran, and then 0.27 ml of n-butyl lithium (1.56 M hexane solution) was added thereto at −78° C. The mixture was stirred at 0° C. for 15 minutes, and then 1.0 ml of a tetrahydrofuran solution of 10 mg of t-butyl 4-[7-(2-butynyl)-2-chloro-1-methyl-6-oxo-6,7-dihydro-1H-purin-8-yl]piperazine-1-carboxylate was added to the reaction solution. After the mixture had been stirred at room temperature for 30 minutes, a saturated ammonium chloride solution was added to the reaction solution. The mixture was extracted with ethyl acetate. The organic layer was concentrated, and the residue was dissolved in 1.0 ml of methanol. 10 mg of potassium carbonate was added to the solution. After the mixture had been stirred at room temperature for 1 hour, a saturated ammonium chloride solution was added to the reaction solution. The mixture was extracted with ethyl acetate. The organic layer was concentrated, and the residue was dissolved in trifluoroacetic acid. The solution was concentrated, and the residue was purified by reverse-phase high performance liquid chromatography (using an acetonitrile-water mobile phase (containing 0.1% trifluoroacetic acid)) to give 1.06 mg of the title compound.
MS m/e (ESI) 311 (MH$^+$-CF$_3$COOH).

Example 218

7-(2-Butynyl)-1-methyl-8-(piperazin-1-yl)-2-(propane-2-sulfinyl)-1,7-dihydropurin-6-one trifluoroacetate 6 mg of t-butyl 4-[7-(2-butynyl)-2-chloro-1-methyl-6-oxo-6,7-dihydro-1H-purin-8-yl]piperazine-1-carboxylate was dissolved in 0.15 ml of 1-methyl-2-pyrrolidone, and then 20 μl of 2-propanethiol and 6 mg of potassium carbonate were added thereto. The mixture was stirred at room temperature for five hours. A saturated ammonium chloride solution was added to the reaction solution, and the mixture was extracted with ethyl acetate. The organic layer was concentrated, and the residue was dissolved in 0.30 ml of dichloromethane. The mixture was cooled to −78° C. 5 mg of m-chloroperbenzoic acid was added to the mixture, and the resulting mixture was stirred at −78° C. for 15 minutes. A saturated sodium sulfite solution was added to the reaction solution, and the mixture was extracted with dichloromethane. The organic layer was concentrated, and the residue was dissolved in 0.40 ml of trifluoroacetic acid. The solution was concentrated by flushing with nitrogen gas. The residue was purified by reverse-phase high performance liquid chromatography (using an acetonitrile-water mobile phase (containing 0.1% trifluoroacetic acid)) to give 0.89 mg of the title compound.
MS m/e (ESI) 377 (MH$^+$-CF$_3$COOH)

Example 219

N-acetyl-N-[7-(2-butynyl)-1-methyl-6-oxo-8-(piperazin-1-yl)-6,7-dihydro-1H-purin-2-yl]acetamide trifluoroacetate 8 mg of t-butyl 4-[7-(2-butynyl)-2-chloro-1-methyl-6-oxo-6,7-dihydro-1H-purin-8-yl]piperazine-1-carboxylate was dissolved in 0.2 ml of a 20% aqueous ammonia, and the mixture was stirred at 80° C. for 5 hours. The reaction solution was concentrated, and the residue was dissolved in 0.4 ml of pyridine. 0.05 ml of acetic anhydride was added to the mixture. The resulting mixture was stirred at room temperature for 48 hours. The reaction solution was concentrated, and the residue was dissolved in trifluoroacetic acid. The solution was concentrated, and the residue was purified by reverse-phase high performance liquid chromatography (using an acetonitrile-water mobile phase (containing 0.1% trifluoroacetic acid)) to give 1.49 mg of the title compound.
MS m/e (ESI) 386 (MH$^+$-CF$_3$COOH)

Example 220

N-[7-(2-butynyl)-1-methyl-6-oxo-8-(piperazin-1-yl)-6,7-dihydro-1H-purin-2-yl]acetamide trifluoroacetate 8 mg of t-butyl 4-[7-(2-butynyl)-2-chloro-1-methyl-6-oxo-6,7-dihydro-1H-purin-8-yl]piperazine-1-carboxylate was dissolved in 0.2 ml of 20% aqueous ammonia, and the mixture was stirred at 80° C. for 5 hours. The reaction solution was concentrated, and the residue was dissolved in 0.4 ml of pyridine. 0.05 ml of acetic anhydride was added to the solution. The mixture was stirred at room temperature for 48 hours. The reaction solution was concentrated, and the residue was dissolved in methanol. 10 mg of potassium carbonate was added to the solution. The mixture was stirred at room temperature for 6 hours. The reaction solution was concentrated, and the residue was dissolved in trifluoroacetic acid. The solution was concentrated, and the residue was purified by reverse-phase high performance liquid chromatography (using an acetonitrile-water mobile phase (containing 0.1% trifluoroacetic acid)) to give 1.36 mg of the title compound.
MS m/e (ESI) 344 (MH$^+$-CF$_3$COOH)

Example 221

[7-(2-Butynyl)-1-methyl-6-oxo-8-(piperazin-1-yl)-6,7-dihydro-1H-purin-2-yloxy]acetonitrile trifluoroacetate 8 mg of t-butyl 4-[7-(2-butynyl)-2-chloro-1-methyl-6-oxo-6,7-dihydro-1H-purin-8-yl]piperazine-1-carboxylate was dissolved in 0.15 ml of 1-methyl-2-pyrrolidone, and then 50 μl of hydroxy acetonitrile and 5 mg of sodium hydride were added thereto. The mixture was stirred at room temperature for one hour. 1N hydrochloric acid was added to the reaction solution, and the mixture was extracted with ethyl acetate. The organic layer was concentrated, and the residue was dissolved in trifluoroacetic acid. The solution was concentrated, and the residue was purified by reverse-phase high performance liquid chromatography (using an acetonitrile-water mobile phase (containing 0.1% trifluoroacetic acid)) to give 2.12 mg of the title compound.
MS m/e (ESI) 342 (MH$^+$-CF$_3$COOH).

Example 222

N-[7-(2-butynyl)-1-methyl-6-oxo-8-(piperazin-1-yl)-6,7-dihydro-1H-purin-2-yl]guanidine trifluoroacetate 7 mg of t-butyl 4-[7-(2-butynyl)-2-chloro-1-methyl-6-oxo-6,7-dihydro-1H-purin-8-yl]piperazine-1-carboxylate was dissolved in 0.15 ml of 1-methyl-2-pyrrolidone, and then 10 mg of guanidine was added thereto. The mixture was stirred at 90° C. for 12 hours. The reaction solution was concentrated, and the residue was dissolved in 1.0 ml of trifluoroacetic acid. The solution was concentrated by flush-

Example 223

7-(2-Butynyl)-2-methylsulfanyl-8-(piperazin-1-yl)-1,7-dihydropurin-6-one trifluoroacetate (a) t-Butyl 4-[7-(2-butynyl)-2-chloro-6-oxo-1-(2-trimethylsilanylethoxymethyl)-6,7-dihydro-1H-purin-8-yl]piperazine-1-carboxylate 50 mg of t-butyl 4-[7-(2-butynyl)-2-chloro-6-oxo-6,7-dihydro-1H-purin-8-yl]piperazine-1-carboxylate was dissolved in 1.2 ml of N,N-dimethylformamide, and then 44 μl of (2-chloromethoxyethyl)trimethylsilane and 34 mg of potassium carbonate were added thereto. The mixture was stirred at room temperature for 2 hours. A saturated aqueous ammonium chloride solution was added to the reaction mixture, and the mixture was extracted with ethyl acetate. The organic layer was concentrated, and the residue was purified by silica gel chromatography to give 55 mg of the title compound.

$^1$H-NMR (CDCl3)

δ 0.07 (s, 9H) 0.97 (t, J=8.4 Hz, 2H) 1.49 (s, 9H) 1.82 (t, J=2.4 Hz, 3H) 3.40-3.44 (m, 4H) 3.58-3.62 (m, 4H) 3.71 (t, J=8.4 Hz, 2H) 4.92 (q, J=2.4 Hz, 2H) 5.67 (s, 2H)

(b) 7-(2-Butynyl)-2-methylsulfanyl-8-(piperazin-1-yl)-1,7-dihydro purin-6-one trifluoroacetate 6 mg of t-butyl 4-[7-(2-butynyl)-2-chloro-6-oxo-1-(2-trimethylsilanylethoxymethyl)-6,7-dihydro-1H-purin-8-yl]piperazine-1-carboxylate was dissolved in 0.15 ml of 1-methyl-2-pyrrolidone, and then 50 μl of methyl mercaptan (30%; methanol solution) and 10 mg of potassium carbonate were added thereto. The mixture was stirred at room temperature for five hours. A saturated aqueous ammonium chloride solution was added to the reaction solution, and the mixture was extracted with ethyl acetate. The organic layer was concentrated, and the residue was dissolved in 0.60 ml of trifluoroacetic acid. The resulting mixture was stirred at room temperature for 5 hours. Then, the solution was concentrated by flushing with nitrogen gas. The residue was purified by reverse-phase high performance liquid chromatography (using an acetonitrile-water mobile phase (containing 0.1% trifluoroacetic acid)) to give 3.99 mg of the title compound.

MS m/e (ESI) 319 (MH$^+$-CF$_3$COOH)

Example 224

7-(2-Butynyl)-2-isopropylsulfanyl-8-(piperazin-1-yl)-1,7-dihydro purin-6-one trifluoroacetate 2.97 mg of the title compound was obtained by using propane-2-thiol sodium salt, instead of methyl mercaptan, according to the method described in Example 223.

MS m/e (ESI) 347 (MH$^+$-CF$_3$COOH)

Example 225

2-t-Butylsulfanyl-7-(2-butynyl)-8-(piperazin-1-yl)-1,7-dihydropurin-6-one trifluoroacetate 2.99 mg of the title compound was obtained by using 2-methyl-2-propanethiol sodium salt, instead of methyl mercaptan, according to the method described in Example 223.

MS m/e (ESI) 361 (MH$^+$-CF$_3$COOH)

Example 226

7-(2-Butynyl)-6-oxo-8-(piperazin-1-yl)-6,7-dihydro-1H-purine-2-carbonitrile trifluoroacetate 6 mg of t-butyl 4-[7-(2-butynyl)-2-chloro-6-oxo-1-(2-trimethylsilanylethoxymethyl)-6,7-dihydro-1H-purin-8-yl]piperazine-1-carboxylate was dissolved in 0.15 ml of 1-methyl-2-pyrrolidone, and then 8 mg of sodium cyanide and 10 mg of potassium carbonate were added thereto. The mixture was stirred at 50° C. for five hours. A saturated aqueous ammonium chloride solution was added to the reaction solution, and the mixture was extracted with ethyl acetate. The organic layer was concentrated, and the residue was dissolved in 0.60 ml of trifluoroacetic acid. The resulting mixture was stirred at room temperature for 5 hours. Then, the solution was concentrated by flushing with nitrogen gas. The residue was purified by reverse-phase high performance liquid chromatography (using an acetonitrile-water mobile phase (containing 0.1% trifluoroacetic acid)) to give 1.46 mg of the title compound.

MS m/e (ESI) 298 (MH$^+$-CF$_3$COOH)

Example 227

2-[7-(2-Butynyl)-6-oxo-8-(piperazin-1-yl)-6,7-dihydro-1H-purin-2-yloxy]benzamide trifluoroacetate 6 mg of t-butyl 4-[7-(2-butynyl)-2-chloro-6-oxo-1-(2-trimethylsilanylethoxymethyl)-6,7-dihydro-1H-purin-8-yl]piperazine-1-carboxylate was dissolved in 0.15 ml of 1-methyl-2-pyrrolidone, and then 8 mg of salicylamide and 8 mg of potassium carbonate were added thereto. The mixture was stirred at 100° C. for three hours. A saturated ammonium chloride solution was added to the reaction solution, and the mixture was extracted with ethyl acetate. The organic layer was concentrated, and the residue was dissolved in 0.80 ml of trifluoroacetic acid. The mixture was stirred at room temperature for 5 hours. The solution was concentrated by flushing with nitrogen gas. The residue was purified by reverse-phase high performance liquid chromatography (using an acetonitrile-water mobile phase (containing 0.1% trifluoroacetic acid)) to give 2.45 mg of the title compound.

MS m/e (ESI) 408 (MH$^+$-CF$_3$COOH)

Example 228

4-[7-(2-Butynyl)-6-oxo-8-(piperazin-1-yl)-6,7-dihydro-1H-purin-2-yloxy]benzoic acid trifluoroacetate 1.55 mg of the title compound was obtained by using 4-hydroxybenzoic acid, instead of salicylamide, according to the method described in Example 227.

MS m/e (ESI) 409 (MH$^+$-CF$_3$COOH)

Example 229

7-(2-Butynyl)-1-(2-cyanobenzyl)-6-oxo-8-(piperazin-1-yl)-6,7-dihydro-1H-purine-2-carbonitrile hydrochloride (a) t-Butyl 4-[7-(2-butynyl)-2-cyano-1-(2-cyanobenzyl)-6-oxo-6,7-dihydro-1H-purin-8-yl]piperazine-1-carboxylate A mixture consisting of 8 mg of t-butyl 4-[7-(2-butynyl)-2-chloro-1-(2-cyanobenzyl)-6-oxo-6,7-dihydro-1H-purin-8-yl]piperazine-1-carboxylate obtained in Example 96(a), 10 mg of sodium cyanide and 0.3 ml of N,N-dimethylformamide was stirred at room temperature for 4 hours. The reaction mixture was extracted with ethyl acetate-water, and the organic layer was washed with water and then with saturated brine. The organic layer was concentrated. The residue was purified by thin layer chromatography (50% ethyl acetate/hexane) to give 6.1 mg of the title compound.

$^1$H-NMR (CDCl$_3$)

δ 1.50 (s, 9H) 1.83 (s, 3H) 3.50 (s, 4H) 3.58-3.64 (m, 4H) 4.99 (s, 2H) 5.74 (s, 2H) 7.02 (d, J=8 Hz, 1H) 7.44 (t, J=8 Hz, 1H) 7.55 (t, J=8 Hz, 1H) 7.74 (d, J=8 Hz, 1H)

(b) 7-(2-Butynyl)-1-(2-cyanobenzyl)-6-oxo-8-(piperazin-1-yl)-6,7-dihydro-1H-purine-2-carbonitrile hydrochloride A mixture consisting of 6.1 mg of t-butyl 4-[7-(2-butynyl)-2-cyano-1-(2-cyanobenzyl)-6-oxo-6,7-dihydro-1H-purin-8-yl]piperazine-1-carboxylate and 0.2 ml of trifluoroacetic acid was stirred at room temperature for 20 minutes. The reaction solution was concentrated, and the residue was purified by reverse-phase column chromatography using a 20% to 60% methanol/water (0.1% concentrated hydrochloric acid) solvent to give 5.0 mg of the title compound.

$^1$H-NMR (DMSO-d6)

δ 1.80 (s, 3H) 3.30 (s, 4H) 3.60-3.70 (m, 4H) 5.09 (s, 2H) 5.60 (s, 2H) 7.27 (d, J=8 Hz, 1H) 7.54 (t, J=8 Hz, 1H) 7.68 (t, J=8 Hz, 1H) 7.94 (d, J=8 Hz, 1H) 9.36 (br.s, 2H)

Example 230

3-[7-(2-Butynyl)-1-(2-cyanobenzyl)-6-oxo-8-(piperazin-1-yl)-6,7-dihydro-1H-purin-2-yloxy]pyridine-2-carboxylic amide trifluoroacetate 7 mg of t-butyl 4-[7-(2-butynyl)-2-chloro-1-(2-cyanobenzyl)-6-oxo-6,7-dihydro-1H-purin-8-yl]piperazine-1-carboxylate was dissolved in 0.2 ml of 1-methyl-2-pyrrolidone, and then 8 mg of 3-hydroxypyridine-2-carboxylic amide and 8 mg of potassium carbonate were added thereto. The mixture was stirred at 100° C. for 2 hours. 1N hydrochloric acid was added to the reaction mixture, and the mixture was extracted with ethyl acetate. The organic layer was concentrated, and the residue was dissolved in trifluoroacetic acid. The solution was concentrated, and the residue was purified by reverse-phase high performance liquid chromatography (using an acetonitrile-water mobile phase (containing 0.1% trifluoroacetic acid)) to give 2.93 mg of the title compound.

MS m/e (ESI) 524 (MH$^+$-CF$_3$COOH)

Example 231

4-[7-(2-Butynyl)-1-(2-cyanobenzyl)-6-oxo-8-(piperazin-1-yl)-6,7-dihydro-1H-purin-2-yloxy]benzenesulfonamide trifluoroacetate 1.90 mg of the title compound was obtained by using 4-hydroxybenzenesulfonamide, instead of 3-hydroxypyridine-2-carboxylic amide, according to the method described in Example 230.

M m/e (ESI) 559 (MH$^+$-CF$_3$COOH)

Example 232

2-[7-(2-Butynyl)-1-(2-cyanobenzyl)-6-oxo-8-(piperazin-1-yl)-6,7-dihydro-1H-purin-2-yloxy]benzonitrile trifluoroacetate 2.15 mg of the title compound was obtained by using 2-cyanophenol, instead of 3-hydroxypyridine-2-carboxylic amide, according to the method described in Example 230.

MS m/e (ESI) 505 (MH$^+$-CF$_3$COOH)

Example 233

4-[7-(2-Butynyl)-1-(2-cyanobenzyl)-6-oxo-8-(piperazin-1-yl)-6,7-dihydro-1H-purin-2-yloxy]benzoic acid trifluoroacetate 3.74 mg of the title compound was obtained by using 4-hydroxybenzoic acid, instead of 3-hydroxypyridine-2-carboxylic amide, according to the method described in Example 230.

MS m/e (ESI) 524 (MH$^+$-CF$_3$COOH)

Example 234

2-[7-(2-Butynyl)-1-(2-cyanobenzyl)-6-oxo-8-(piperazin-1-yl)-6,7-dihydro-1H-purin-2-yloxy]benzamide trifluoroacetate 3.74 mg of the title compound was obtained by using salicylamide, instead of 3-hydroxypyridine-2-carboxylic amide, according to the method described in Example 230.

MS m/e (ESI) 523 (MH$^+$-CF$_3$COOH)

Example 235

2-[7-(2-Butynyl)-1-(4-cyanobenzyl)-6-oxo-8-(piperazin-1-yl)-6,7-dihydro-1H-purin-2-yloxy]benzamide trifluoroacetate (a) t-Butyl 4-[7-(2-Butynyl)-2-chloro-1-(4-cyanobenzyl)-6-oxo-6,7-dihydro-1H-purin-8-yl]piperazine-1-carboxylate 100 mg of t-butyl 4-[7-(2-butynyl)-2-chloro-6-oxo-6,7-dihydro-1H-purin-8'-yl]piperazine-1-carboxylate was dissolved in 1.2 ml of N,N-dimethylformamide, and then 97 mg of 4-cyanobenzyl bromide and 68 mg of potassium carbonate were added thereto. The mixture was stirred at room temperature for 4 hours. A saturated aqueous ammonium chloride solution was added to the reaction mixture, and the mixture was extracted with ethyl acetate. The organic layer was concentrated, and the residue was purified by silica-gel chromatography to give 71 mg of the title compound.

$^1$H-NMR (CDCl$_3$)

δ 1.49 (s, 9H) 1.84 (t, J=2.5 Hz, 3H) 3.43-3.47 (m, 4H) 3.59-3.63 (m, 4H) 4.94 (q, 2.5 Hz, 2H) 5.53 (s, 2H) 7.42 (d, J=8.0 Hz, 2H) 7.62 (d, J=8.0 Hz, 2H)

(b) 2-[7-(2-Butynyl)-1-(4-cyanobenzyl)-6-oxo-8-(piperazin-1-yl)-6,7-dihydro-1H-purin-2-yloxy]benzamide trifluoroacetate 12 mg of t-butyl 4-[7-(2-butynyl)-2-chloro-1-(4-cyanobenzyl)-6-oxo-6,7-dihydro-1H-purin-8-yl]piperazine-1-carboxylate was dissolved in 0.3 ml of 1-methyl-2-pyrrolidone, and then 10 mg of salicylamide and 10 mg of potassium carbonate were added thereto. The mixture was stirred at 100° C. for 12 hours. 1N hydrochloric acid was added to the reaction solution, and the mixture was extracted with ethyl acetate. The organic layer was concentrated, and the residue was dissolved in trifluoroacetic acid. The solution was concentrated, and the residue was purified by reverse-phase high performance liquid chromatography (using an acetonitrile-water mobile phase (containing 0.1% trifluoroacetic acid)) to give 6.69 mg of the title compound.

MS m/e (ESI) 523 (MH$^+$-CF$_3$COOH)

Example 236

7-(2-Butynyl)-1-(4-cyanobenzyl)-6-oxo-8-(piperazin-1-yl)-6,7-dihydro-1H-purine-2-carbonitrile trifluoroacetate 12 mg of t-butyl 4-[7-(2-butynyl)-2-chloro-1-(4-cyanobenzyl)-6-oxo-6,7-dihydro-1H-purin-8-yl]piperazine-1-carboxylate was dissolved in 0.3 ml of 1-methyl-2-pyrrolidone, and then 10 mg of sodium cyanide was added thereto. The mixture was stirred at 50° C. for 2 hours. 1N hydrochloric acid was added to the reaction solution, and the mixture was extracted with ethyl acetate. The organic layer was concentrated, and the residue was dissolved in trifluoroacetic acid. The solution was concentrated, and the residue was purified by reverse-phase high performance liquid chromatography (using an acetonitrile-water mobile phase (containing 0.1% trifluoroacetic acid)) to give 3.87 mg of the title compound.

MS m/e (ESI) 413 (MH$^+$-CF$_3$COOH)

Example 237

4-[7-(2-Butynyl)-2-methylsulfanyl-6-oxo-8-(piperazin-1-yl)-6,7-dihydropurin-1-ylmethyl]benzonitrile trifluoroacetate 12 mg of t-butyl 4-[7-(2-butynyl)-2-chloro-1-(4-cyanobenzyl)-6-oxo-6,7-dihydro-1H-purin-8-yl]piperazine-1-carboxylate was dissolved in 0.3 ml of 1-methyl-2-pyrrolidone, and then 20 µl of methyl mercaptan (30%; methanol solution) and 10 mg of potassium carbonate were added thereto. The mixture was stirred at 50° C. for 2 hours. 1N hydrochloric acid was added to the reaction solution, and the mixture was extracted with ethyl acetate. The organic layer was concentrated, and the residue was dissolved in trifluoroacetic acid. The solution was concentrated, and the residue was purified by reverse-phase high performance liquid chromatography (using an acetonitrile-water mobile phase (containing 0.1% trifluoroacetic acid)) to give 6.69 mg of the title compound.

MS m/e (ESI) 434 (MH$^+$-CF$_3$COOH)

Example 238

2-[7-(2-Butynyl)-1-(3-cyanobenzyl)-6-oxo-8-(piperazin-1-yl)-6,7-dihydro-1H-purin-2-yloxy]benzamide trifluoroacetate (a) t-Butyl 4-[7-(2-butynyl)-2-chloro-1-(3-cyanobenzyl)-6-oxo-6,7-dihydro-1H-purin-8-yl]piperazine-1-carboxylate 100 mg of t-butyl 4-[7-(2-butynyl)-2-chloro-6-oxo-6,7-dihydro-1H-purin-8-yl]piperazine-1-carboxylate was dissolved in 1.2 ml of N,N-dimethylformamide, and then 97 mg of 3-cyanobenzyl bromide and 68 mg of potassium carbonate were added thereto. The mixture was stirred at room temperature for 12 hours. Then, a saturated ammonium chloride solution was added to the reaction solution, and the mixture was extracted with ethyl acetate. The organic layer was concentrated, and the residue was purified by silica gel chromatography to give 71 mg of the title compound.

$^1$H-NMR (CDCl$_3$)

δ 1.49 (s, 9H) 1.84 (t, J=2.5 Hz, 3H) 3.43-3.47 (m, 4H) 3.59-3.63 (m, 4H) 4.94 (q, 2.5 Hz, 2H) 5.53 (s, 2H) 7.42 (d, J=8.0 Hz, 2H) 7.62 (d, J=8.0 Hz, 2H)

(b) 2-[7-(2-Butynyl)-1-(3-cyanobenzyl)-6-oxo-8-(piperazin-1-yl)-6,7-dihydro-1H-purin-2-yloxy]benzamide trifluoroacetate 12 mg of t-butyl 4-[7-(2-butynyl)-2-chloro-1-(3-cyanobenzyl)-6-oxo-6,7-dihydro-1H-purin-8-yl]piperazine-1-carboxylate was dissolved in 0.3 ml of 1-methyl-2-pyrrolidone, and then 10 mg of salicylamide and 10 mg of potassium carbonate were added thereto. The mixture was stirred at 100° C. for five hours. 1N hydrochloric acid was added to the reaction solution, and the mixture was extracted with ethyl acetate. The organic layer was concentrated, and the residue was dissolved in trifluoroacetic acid. The solution was concentrated, and the residue was purified by reverse-phase high performance liquid chromatography (using an acetonitrile-water mobile phase (containing 0.1% trifluoroacetic acid)) to give 8.76 mg of the title compound.

MS m/e (ESI) 523 (MH$^+$-CF$_3$COOH)

Example 239

7-(2-Butynyl)-1-(3-cyanobenzyl)-6-oxo-8-(piperazin-1-yl)-6,7-dihydro-1H-purine-2-carbonitrile trifluoroacetate 12 mg of t-butyl 4-[7-(2-butynyl)-2-chloro-1-(3-cyanobenzyl)-6-oxo-6,7-dihydro-1H-purin-8-yl]piperazine-1-carboxylate was dissolved in 0.3 ml of 1-methyl-2-pyrrolidone, and then 10 mg of sodium cyanide was added thereto. The mixture was stirred at 50° C. for 1 hour. 1N hydrochloric acid was added to the reaction solution, and the mixture was extracted with ethyl acetate. The organic layer was concentrated, and the residue was dissolved in trifluoroacetic acid. The solution was concentrated, and the residue was purified by reverse-phase high performance liquid chromatography (using an acetonitrile-water mobile phase (containing 0.1% trifluoroacetic acid)) to give 4.96 mg of the title compound.

MS m/e (ESI) 413 (MH$^+$-CF$_3$COOH)

Example 240

1-(2-Butynyl)-2-(piperazin-1-yl)-7,8-dihydro-1H, 6H-5-oxa-1,3,4,8a-tetraazacyclopenta[b]naphthalen-9-one hydrochloride

(a) t-Butyl 4-[7-(2-butynyl)-2-chloro-6-oxo-1-[3-(tetrahydropyran-2-yloxy)propyl]-6,7-dihydro-1H-purin-8-yl]piperazine-1-carboxylate A mixture consisting of 20 mg of t-butyl 4-[7-(2-butynyl)-2-chloro-6-oxo-6,7-dihydro-1H-purin-8-yl]piperazine-1-carboxylate obtained in Example 95 (a), 20 μl of 2-(3-bromopropoxy)tetrahydropyran, 20 mg of anhydrous potassium carbonate and 0.2 ml of N,N-dimethylformamide was stirred at room temperature overnight. The reaction solution was extracted with ethyl acetate-water, and the organic layer was washed with water and then with saturated brine. The organic layer was then concentrated, and the residue was purified by thin layer chromatography (70% ethyl acetate/hexane) to give 8 mg of the title compound.

$^1$H-NMR (CDCl$_3$)

δ 1.49 (s, 9H) 1.50-1.81 (m, 6H) 1.83 (t, J=2 Hz, 3H) 2.06 (quint, J=7 Hz, 2H) 3.38-3.62 (m, 10H) 3.80-3.90 (m, 2H) 4.34-4.47 (m, 2H) 4.59 (t, J=3 Hz, 1H) 4.92 (q, J=2 Hz, 2H)

(b) t-Butyl 4-[1-(2-butynyl)-9-oxo-1,7,8,9-tetraazacyclopenta[b]naphthalen-2-yl]piperazine-1-carboxylate A mixture consisting of 8 mg of t-butyl 4-[7-(2-butynyl)-2-chloro-6-oxo-1-[3-(tetrahydropyran-2-yloxy)propyl]-6,7-dihydro-1H-purin-8-yl]piperazine-1-carboxylate, 0.2 ml of ethanol and a catalytic amount of para-toluenesulfonic-acid monohydrate was stirred at room temperature for 4 hours, and then 40 mg of anhydrous potassium carbonate was added thereto. The mixture was further stirred overnight. The reaction solution was extracted with ethyl acetate-water, and the organic layer was washed with water and then with saturated brine. The organic layer was then concentrated, and the residue was purified by thin layer chromatography (20% methanol/ethyl acetate) to give 3 mg of the title compound.

$^1$H-NMR (CDCl$_3$)

δ 1.48 (s, 9H) 1.82 (t, J=2 Hz 3H) 2.18-2.26 (m, 2H) 3.37-3.43 (m, 4H) 3.56-3.62 (m, 4H) 4.07 (t, J=6 Hz, 2H) 4.43 (t, J=5 Hz, 2H) 4.88 (q, J=2 Hz, 2H)

(c) 1-(2-Butynyl)-2-(piperazin-1-yl)-7,8-dihydro-1H, 6H-5-oxa-1,3,4,8a-tetraazacyclopenta[b]naphthalen-9-one hydrochloride A mixture consisting of 3 mg of t-butyl 4-[1-(2-butynyl)-9-oxo-1,7,8,9-tetraazacyclopenta[b]naphthalen-2-yl]piperazine-1-carboxylate and 0.5 ml of trifluoroacetic acid was stirred at room temperature for 20 minutes. Then, the solution was concentrated, and the residue was purified by reverse-phase column chromatography using 20% to 50% methanol/water (0.1% concentrated hydrochloric acid) solvent to give 2.1 mg of the title compound.

$^1$H-NMR (DMSO-d6)

δ 1.79 (s, 3H) 2.08-2.16 (m, 2H) 3.27 (br.s, 4H) 3.44-3.54 (m, 4H) 3.90 (t, J=6 Hz, 2H) 4.38 (t, J=5 Hz, 2H) 4.94 (s, 2H) 9.02 (br.s, 2H)

Example 241

1-(2-Butynyl)-2-(piperazin-1-yl)-6,7-dihydro-1H-5-oxa-1,3,4,7a-tetraaza-s-indacen-8-one hydrochloride In Example 240, the title compound was obtained by using 2-(2-bromoethoxy)tetrahydropyran, instead of 2-(3-bromopropoxy)tetrahydropyran, according to the method described in Example 240.

$^1$H-NMR (DMSO-d6)

δ 1.80 (s, 3H) 3.27 (br.s, 4H) 4.19 (t, J=8 Hz, 2H) 4.70 (t, J=8 Hz, 2H) 4.94 (s, 2H) 9.06 (br.s, 2H)

Example 242

8-(3-aminopiperidin-1-yl)-7-(2-butynyl)-1-(2-cyanobenzyl)-6-oxo-6,7-dihydro-1H-purine-2-carbonitrile hydrochloride

(a) Benzyl 3-t-butoxycarbonylaminopiperidine-1-carboxylate 88 g of benzyl chloroformate (30% toluene solution) was added dropwise to a mixture consisting of 24.3 g of ethyl piperidine-3-carboxylate, 26 ml of triethylamine and 300 ml of ethyl acetate over 30 minutes while the mixture was being cooled with ice. The reaction mixture was filtered to remove insoluble material. The filtrate was again filtered through a small amount of silica gel. The filtrate was concentrated.

200 ml of ethanol and 40 ml of a 5 M aqueous sodium hydroxide solution were added to the residue. The mixture was stirred at room temperature overnight. The reaction solution was concentrated, and 200 ml of water was added to the residue. The mixture was extracted with t-butyl methyl ether. 5 M aqueous hydrochloric acid was added to the aqueous layer, and the mixture was extracted with ethyl acetate. The organic layer was washed with water and then with saturated brine. The organic layer was dried over anhydrous magnesium sulfate, and then concentrated to give an oily residue (30.9 g).

A mixture consisting of 30 g of this residue, 24.5 ml of diphenyl phosphoryl azide, 15.9 ml of triethylamine and 250 ml of t-butanol was stirred at room temperature for 1.5 hours. The mixture was further stirred in an oil bath at 100° C. for 20 hours. The reaction solution was concentrated, and the residue was extracted with ethyl acetate-water. The organic layer was washed with dilute aqueous sodium bicarbonate solution and then with saturated brine. The organic layer was dried over anhydrous magnesium sulfate, and then concentrated. The residue was purified by silica gel column chromatography using 10% to 20% ethyl acetate/hexane, followed by recrystallization from ethyl acetate-hexane to give 21.4 g of the title compound.

$^1$H-NMR (CDCl$_3$)

δ 1.43 (s, 9H) 1.48-1.92 (m, 4H) 3.20-3.80 (m, 5H) 4.58 (br.s, 1H) 5.13 (s, 2H) 7.26-7.40 (m, 5H)

(b) t-Butyl piperidin-3-ylcarbamate

A mixture consisting of 10 g of benzyl 3-t-butoxycarbonylaminopiperidine-1-carboxylate, 500 mg of 10% palladium carbon and 100 ml of ethanol was stirred at room temperature under a hydrogen atmosphere overnight. The catalyst was removed by filtration. The filtrate was concentrated and dried to give 6.0 g of the title compound.

$^1$H-NMR (CDCl$_3$)

δ 1.44 (s, 9H) 1.47-1.80 (m, 4H) 2.45-2.60 (m, 1H) 2.60-2.75 (m, 1H) 2.75-2.90 (m, 1H) 3.05 (dd, J=3 Hz, 1.2 Hz, 1H) 3.57 (br.s, 1H) 4.83 (br.s, 1H)

(c) t-Butyl

[1-[7-(2-butynyl)-2,6-dichloro-7H-purin-8-yl]piperidin-3-yl]carbamate

A mixture consisting of 1.25 g of 7-(2-butynyl)-2,6,8-trichloro-7H-purine, 1.0 g of t-butyl piperidin-3-ylcarbamate and 10 ml of acetonitrile was stirred at room temperature for 10 minutes. 0.63 ml of triethylamine was added dropwise over 10 minutes, and then the mixture was continuously stirred at room temperature for 30 minutes. The reaction solution was partitioned between ethyl acetate and water, and the organic layer was washed with saturated brine. The organic layer was dried over anhydrous magnesium sulfate, and then concentrated. The residue was crystallized with t-butyl methyl ether-hexane to give 1.79 g of the title compound.

$^1$H-NMR (CDCl$_3$)

δ 1.43 (s, 9H) 1.60-2.02 (m, 4H) 1.83 (t, J=2 Hz, 3H) 3.32-3.41 (m, 1H) 3.42-3.52 (m, 1H) 3.67-3.76 (m, 1H) 3.80-3.91 (m, 1H) 4.76-4.90 (m, 3H)

(d) t-Butyl [1-[7-(2-butynyl)-2-chloro-6-oxo-6,7-dihydro-1H-purin-8-yl]piperidin-3-yl]carbamate A mixture consisting of 1.79 g of t-butyl [1-[7-(2-butynyl)-2,6-dichloro-7H-purin-8-yl]piperidin-3-yl]carbamate, 1.0 g of sodium acetate and 18 ml of dimethyl sulfoxide was stirred in an oil bath at 120° C. for three hours. The mixture was removed from the oil bath, and 18 ml of water was added to the reaction solution. The mixture was cooled to room temperature. The crystals were collected by filtration, and washed with water and then with t-butyl methyl ether. The crystals were then dried to give 1.59 g of the title compound.

$^1$H-NMR (DMSO-d6)

δ 1.39 (s, 9H) 1.34-1.88 (m, 4H) 1.78 (s, 3H) 2.81 (t, J=11 Hz, 1H) 2.95 (t, J=11 Hz, 1H) 3.48-3.60 (m, 2H) 3.64 (d, J=6 Hz, 1H) 4.90 (s, 2H) 6.94 (d, J=8 Hz, 1H)

(e) t-Butyl [1-[7-(2-butynyl)-2-chloro-1-(2-cyanobenzyl)-6-oxo-6,7-dihydro-1H-purin-8-yl]piperidin-3-yl]carbamate A mixture consisting of 100 mg of t-butyl [1-[7-(2-butynyl)-2-chloro-6-oxo-6,7-dihydro-1H-purin-8-yl]piperidin-3-yl]carbamate, 66 mg of anhydrous potassium carbonate, 70 mg of 2-cyanobenzyl bromide and 1 ml of N,N-dimethylformamide was stirred at room temperature for five hours. The reaction solution was partitioned between ethyl acetate and water, and the organic layer was washed with water and then with saturated brine. The organic layer was dried over anhydrous magnesium sulfate, and then concentrated. The residue was purified by silica gel column chromatography using 50% ethyl acetate/hexane to give 44.7 mg of the title compound.

$^1$H-NMR (CDCl$_3$)

δ 1.44 (s, 9H) 1.59-1.81 (m, 2H) 1.83 (t, J=2 Hz, 3H) 1.86-1.94 (m, 2H) 3.20-3.50 (m, 3H) 3.66 (d, J=7 Hz, 1H) 3.86 (br.s, 1H) 4.88-5.06 (m, 3H) 5.72 (s, 2H) 7.06 (d, J=8 Hz, 1H) 7.38 (t, J=8 Hz, 1H) 7.51 (t, J=8 Hz, 1H) 7.70 (d, J=8 Hz, 1H)

(f) t-Butyl [1-[7-(2-butynyl)-2-cyano-1-(2-cyanobenzyl)-6-oxo-6,7-dihydro-1-purin-8-yl]piperidin-3-yl] carbamate A mixture consisting of 15 mg of t-butyl [1-[7-(2-butynyl)-2-chloro-1-(2-cyanobenzyl)-6-oxo-6,7-dihydro-1H-purin-8-yl]piperidin-3-yl]carbamate, 20 mg of sodium cyanide and 0.2 ml of N,N-dimethylformamide was stirred at room temperature for three hours. The reaction solution was partitioned between ethyl acetate and water, and the organic layer was washed with water and then with saturated brine. Then, the organic layer was concentrated, and the residue was purified by thin layer chromatography using 50% ethyl acetate/hexane solvent (developed three times) to give 10.3 mg of the title compound.

$^1$H-NMR (CDCl$_3$)

δ 1.44 (s, 9H) 1.52-1.98 (m, 4H) 1.81 (t, J=2 Hz 3H) 3.24 (dd, J=7 Hz, 12 Hz, 1H) 3.30-3.40 (m, 1H) 3.46-3.56 (m, 1H) 3.72 (d, J=12 Hz, 1H) 3.86 (br.s, 1H) 4.86-5.10 (m, 3H) 5.73 (s, 2H) 7.00 (d, J=8 Hz, 1H) 7.42 (t, J=8 Hz, 1H) 7.54 (dt, J=2 Hz, 8 Hz, 1H) 7.73 (dd, J=2 Hz, 8 Hz, 1H)

(g) 8-(3-Aminopiperidin-1-yl)-7-(2-butynyl)-1-(2-cyanobenzyl)-6-oxo-6,7-dihydro-1H-purine-2-carbonitrile hydrochloride A mixture consisting of 10.3 mg of t-butyl [1-[7-(2-butynyl)-2-cyano-1-(2-cyanobenzyl)-6-oxo-6,7-dihydro-1H-purin-8-yl]piperidin-3-yl]carbamate and 0.2 ml of trifluoroacetic acid was stirred for 20 minutes. The reaction solution was concentrated, and the residue was purified by reverse-phase column chromatography using 20% to 80% methanol/water (0.1% concentrated hydrochloric acid) solvent to give 8.0 mg of the title compound.

$^1$H-NMR (DMSO-d6)

δ 1.60-1.74 (m, 2H) 1.79 (t, J=2 Hz, 3H) 1.88-2.03 (m, 2H) 3.14-3.28 (m, 2H) 3.42 (br.s, 1H) 3.52-3.82 (m, 2H) 4.98-5.12 (m, 2H) 5.58 (s, 2H) 7.26 (d, J=8 Hz, 1H) 7.53 (t, J=8 Hz, 1H) 7.66 (t, J=8 Hz, 1H) 7.93 (d, J=8 Hz, 1H) 8.16 (br.s, 3H)

Example 243

2-[8-(3-Amino piperidin-1-yl)-7-(2-butynyl)-2-methoxy-6-oxo-6,7-dihydropurin-1-ylmethyl]benzonitrile hydrochloride A mixture consisting of 15 mg of t-butyl [1-[7-(2-butynyl)-2-chloro-1-(2-cyanobenzyl)-6-oxo-6,7-dihydro-1H-purin-8-yl]piperidin-3-yl]carbamate, 20 mg of anhydrous potassium carbonate and 0.2 ml of methanol was stirred for three hours. Subsequent steps were carried out according to the same procedure as used in Examples 242 (f) and (g). Thus, the title compound was synthesized.

$^1$H-NMR (DMSO-d6)

δ 1.58-1.72 (m, 2H) 1.84-1.94 (m, 1H) 1.96-2.04 (m, 1H) 3.08-3.20 (m, 2H) 3.36-3.70 (m, 3H) 3.90 (s, 3H) 4.90-5.02 (m, 2H) 5.32 (s, 2H) 7.20 (d, J=8 Hz, 1H) 7.47 (t, J=8 Hz, 1H) 7.63 (t, J=8 Hz, 1H) 7.87 (d, J=8 Hz, 1H) 8.12 (br.s, 3H)

Example 244

8-(3-Amino piperidin-1-yl)-7-(2-butynyl)-6-oxo-1-(2-phenylethyl)-6,7-dihydro-1H-purine-2-carbonitrile hydrochloride (a) t-Butyl [1-[7-(2-butynyl)-2-chloro-6-oxo-1-(2-phenylethyl)-6,7-dihydro-1H-purin-8-yl]piperidin-3-yl]carbamate The title compound was obtained using 2-bromoethyl benzene, instead of 2-cyanobenzyl bromide, according to the method described in Example 242(e).

$^1$H-NMR (CDCl$_3$)
δ 1.44 (s, 9H) 1.58-1.80 (m, 2H) 1.83 (t, J=2 Hz, 3H) 1.86-1.94 (m, 2H) 3.00-3.06 (m, 2H) 3.20-3.50 (m, 3H) 3.60 (d, J=12 Hz, 1H) 3.85 (b.s, 1H) 4.42-4.48 (m, 2H) 4.88-5.04 (m, 3H) 7.02-7.34 (m, 5H)

(b) 8-(3-Aminopiperidin-1-yl)-7-(2-butynyl)-6-oxo-1-(2-phenylethyl)-6,7-dihydro-1H-purine-2-carbonitrile hydrochloride The title compound was synthesized by using t-butyl [1-[7-(2-butynyl)-2-chloro-6-oxo-1-(2-phenylethyl)-6,7-dihydro-1H-purin-8-yl]piperidin-3-yl]carbamate according to the method described in Example 242 (f) and (g).

$^1$H-NMR (DMSO-d6)
δ 1.60-1.72 (m, 2H) 1.83 (s, 3H) 1.88-2.06 (m, 3H) 3.04 (t, J=7 Hz, 2H) 3.35-3.60 (m, 2H) 3.75 (d, J=12 Hz, 1H) 4.35 (t, J=7 Hz, 2H) 5.09 (s, 2H) 7.18 (d, J=7 Hz, 2H) 7.22-7.34 (m, 3H) 8.16 (br.s, 3H)

Example 245

8-(3-Aminopiperidin-1-yl)-7-(2-butynyl)-2-methoxy-1-(2-phenylethyl)-1,7-dihydropurin-6-one hydrochloride The title compound was synthesized by using t-butyl [1-[7-(2-butynyl)-2-chloro-6-oxo-1-(2-phenylethyl)-6,7-dihydro-1H-purin-8-yl]piperidin-3-yl]carbamate, according to the method described in Example 243.

$^1$H-NMR (DMSO-d6)
δ 1.56-1.72 (m, 2H) 1.80 (t, J=2 Hz, 3H) 1.84-2.04 (m, 2H) 2.85 (t, J=7 Hz, 2H) 3.08-3.18 (m, 2H) 3.34-3.54 (m, 2H) 3.64 (d, J=12 Hz, 1H) 3.83 (s, 3H) 4.15 (t, J=7 Hz, 2H) 4.88-5.02 (m, 2H) 7.16-7.24 (m, 3H) 7.29 (t, J=7 Hz, 2H) 8.09 (br.s, 3H)

Example 246

8-(3-Aminopiperidin-1-yl)-7-(2-butynyl)-1-(4-cyanobenzyl)-6-oxo-6,7-dihydro-1H-purine-2-carbonitrile hydrochloride (a) t-Butyl [1-[7-(2-butynyl)-2-chloro-1-(4-cyanobenzyl)-6-oxo-6,7-dihydro-1H-purin-8-yl]piperidin-3-yl]carbamate The title compound was obtained by using 4-cyanobenzyl bromide, instead of 2-cyanobenzyl bromide, according to the method described in Example 242(e).

$^1$H-NMR (CDCl$_3$)
δ 1.44 (s, 9H) 1.58-1.80 (m, 2H) 1.82 (t, J=2 Hz, 3H), 1.85-1.95 (m, 2H) 3.18-3.26 (m, 1H) 3.29-3.37 (m, 1H) 3.40-3.48 (m, 1H) 3.65 (d, J=12 Hz, 1H) 3.86 (br.s, 1H) 4.86-5.04 (m, 3H) 5.22 (s, 2H) 7.41 (d, J=8 Hz, 2H) 7.62 (d, J=8 Hz, 2H)

(b) 8-(3-Aminopiperidin-1-yl)-7-(2-butynyl)-1-(4-cyanobenzyl)-6-oxo-6,7-dihydro-1H-purine-2-carbonitrile hydrochloride The title compound was synthesized by using t-butyl [1-[7-(2-butynyl)-2-chloro-1-(4-cyanobenzyl)-6-oxo-6,7-dihydro-1H-purin-8-yl]piperidin-3-yl]carbamate according to the method described in Examples 242 (f) and (g).

$^1$H-NMR (DMSO-d6)
δ 1.62-1.72 (m, 2H) 1.80 (s, 3H) 1.88-1.96 (m, 1H) 1.98-2.06 (m, 1H) 3.16-3.26 (m, 2H) 3.41 (br.s, 1H) 3.50-3.80 (m, 2H) 5.07 (s, 2H) 5.49 (s, 2H) 7.49 (d, J=8 Hz, 2H) 7.85 (d, J=8 Hz, 2H) 8.16 (br.s, 3H)

Example 247

4-[8-(3-Aminopiperidin-1-yl)-7-(2-butynyl)-2-methoxy-6-oxo-6,7-dihydropurin-1-ylmethyl]benzonitrile hydrochloride The title compound was synthesized by using t-butyl [1-[7-(2-butynyl)-2-chloro-1-(4-cyanobenzyl)-6-oxo-6,7-dihydro-1H-purin-8-yl]piperidin-3-yl]carbamate according to the method described in Example 243.

$^1$H-NMR (DMSO-d6)
δ 1.58-1.70 (m, 2H) 1.79 (s, 3H) 1.84-2.04 (m, 2H) 3.08-3.20 (m, 2H) 3.36-3.70 (m, 3H) 3.89 (s, 3H) 4.88-5.02 (m, 2H) 5.22 (s, 2H) 7.39 (d, J=8 Hz, 2H) 7.79 (d, J=8 Hz, 2H) 8.14 (br.s, 3H)

Example 248

2-[8-(3-Aminopiperidin-1-yl)-7-(2-butynyl)-1-methyl-6-oxo-6,7-dihydro-1H-purin-2-yloxy]benzamide trifluoroacetic acid salt (a) t-Butyl [1-[7-(2-butynyl)-2-chloro-1-methyl-6-oxo-6,7-dihydro-1H-purin-8-yl]piperidin-3-yl]carbamate 700 mg of t-butyl [1-[7-(2-butynyl)-2-chloro-6-oxo-6,7-dihydro-1H-purin-8-yl]piperidin-3-yl]carbamate was dissolved in 7.0 ml of dimethyl sulfoxide, and then 114 µl of methyl iodide and 299 mg of potassium carbonate were added thereto. The mixture was stirred at room temperature for 30 minutes, and 40 ml of water was added to the reaction solution. The mixture was stirred at room temperature for 30 minutes, and the white precipitate was collected by filtration. The resulting white solid was washed with water and then with hexane to give 540 mg of the title compound.

$^1$H-NMR (CDCl$_3$)
δ 1.44 (s, 9H) 1.72-1.94 (m, 4H) 1.81 (t, J=2.4 Hz, 3H) 3.16-3.92 (m, 5H) 3.72 (s, 3H) 4.91 (dd, J=17.6, 2.4 Hz, 1H) 5.01 (d, J=17.6 Hz, 1H)

(b) 2-[8-(3-Aminopiperidin-1-yl)-7-(2-butynyl)-1-methyl-6-oxo-6,7-dihydro-1H-purin-2-yloxy]benzamide trifluoroacetate 10 mg of t-butyl [1-[7-(2-butynyl)-2-chloro-1-methyl-6-oxo-6,7-dihydro-1H-purin-8-yl]piperidin-3-yl]carbamate was dissolved in 0.3 ml of 1-methyl-2-pyrrolidone, and then 10 mg of salicylamide and 10 mg of potassium carbonate were added thereto. The mixture was stirred at 100° C. for 2 hours. 1N hydrochloric acid was added to the reaction solution, and the mixture was extracted with ethyl acetate. The organic layer was concentrated, and the residue was dissolved in trifluoroacetic acid. The solution was concentrated, and the residue was purified by reverse-phase high performance liquid chromatography (using an acetonitrile-water mobile phase (containing 0.1% trifluoroacetic acid)) to give 5.54 mg of the title compound.

MS m/e (ESI) 436 (MH$^+$-CF$_3$COOH)

Example 249

8-(3-Aminopiperidin-1-yl)-7-(2-butynyl)-1-methyl-6-oxo-6,7-dihydro-1H-purine-2-carbonitrile trifluoroacetate 10 mg of t-butyl [1-[7-(2-butynyl)-2-chloro-1-methyl-6-oxo-6,7-dihydro-1H-purin-8-yl]piperidin-3-yl]carbamate dissolved in 0.3 ml of 1-methyl-2-pyrrolidone, and then 10 mg of sodium cyanide was added thereto. The mixture was stirred at 60° C. for 2 hours. 1N hydrochloric acid was added to the reaction solution, and the mixture was extracted with ethyl acetate. The organic layer was concentrated, and the residue was dissolved in trifluoroacetic acid. The solution was concentrated, and the residue was purified by reverse-phase high performance liquid chromatography (using an acetonitrile-water mobile phase (containing 0.1% trifluoroacetic acid)) to give 3.67 mg of the title compound.

MS m/e (ESI) 326 (MH$^+$-CF$_3$COOH)

Example 250

8-(3-Aminopiperidin-1-yl)-2-t-butylsulfanyl-7-(2-butynyl)-1-methyl-1,7-dihydropurin-6-one trifluoroacetate 10 mg of t-butyl [1-[7-(2-butynyl)-2-chloro-1-methyl-6-oxo-6,7-dihydro-1H-purin-8-yl]piperidin-3-yl]carbamate was dissolved in 0.3 ml of 1-methyl-2-pyrrolidone, and then 10 mg of the sodium salt of 2-methyl-2-propanethiol was added thereto. The mixture was stirred at room temperature for 2 hours. 1N hydrochloric acid was added to the reaction solution, and the mixture was extracted with ethyl acetate. The organic layer was concentrated, and the residue was dissolved in trifluoroacetic acid. The solution was concentrated, and the residue was purified by reverse-phase high performance liquid chromatography (using an acetonitrile-water mobile phase (containing 0.1% trifluoroacetic acid)) to give 5.00 mg of the title compound.

MS m/e (ESI) 389 (MH$^+$-CF$_3$COOH)

Example 251

8-(3-Aminopiperidin-1-yl)-7-(2-butynyl)-2-methoxy-1-methyl-1,7-dihydropurin-6-one trifluoroacetate 10 mg of t-butyl [1-[7-(2-butynyl)-2-chloro-1-methyl-6-oxo-6,7-dihydro-1H-purin-8-yl]piperidin-3-yl]carbamate was dissolved in 0.6 ml of methanol, and then 8 mg of sodium hydride was added thereto. The mixture was stirred at room temperature for one hour. 1N hydrochloric acid was added to the reaction solution, and the mixture was extracted with ethyl acetate. The organic layer was concentrated, and the residue was dissolved in trifluoroacetic acid. The solution was concentrated, and the residue was purified by reverse-phase high performance liquid chromatography (using an acetonitrile-water mobile phase (containing 0.1% trifluoroacetic acid)) to give 2.14 mg of the title compound.

MS m/e (ESI) 331 (MH$^+$-CF$_3$COOH)

Example 252

8-(3-Aminopiperidin-1-yl)-7-(2-butynyl)-2-diethylamino-1-methyl-1,7-dihydropurin-6-one trifluoroacetate 10 mg of t-butyl [1-[7-(2-butynyl)-2-chloro-1-methyl-6-oxo-6,7-dihydro-1H-purin-8-yl]piperidin-3-yl]carbamate was dissolved in 0.3 ml of 1-methyl-2-pyrrolidone, and then 50 μl of diethylamine was added thereto. The mixture was stirred at 60° C. for 4 hours. 1N hydrochloric acid was added to the reaction solution, and the mixture was extracted with ethyl acetate. The organic layer was concentrated, and the resulting residue was dissolved in trifluoroacetic acid. The solution was concentrated, and the residue was purified by reverse-phase high performance liquid chromatography (using an acetonitrile-water mobile phase (containing 0.1% trifluoroacetic acid)) to give 2.17 mg of the title compound.

MS m/e (ESI) 372 (MH$^+$-CF$_3$COOH)

Example 253

8-(3-Aminopiperidin-1-yl)-7-(2-butynyl)-1-methyl-2-(pyrrolidin-1-yl)-1,7-dihydropurin-6-one trifluoroacetate 1.94 mg of the title compound was obtained by using pyrrolidine, instead of diethylamine, according to the method described in Example 252.

MS m/e (ESI) 370 (MH$^+$-CF$_3$COOH)

Example 254

8-(3-Methylaminopiperidin-1-yl)-7-(2-butynyl)-1-methyl-6-oxo-6,7-dihydro-1H-purine-2-carbonitrile hydrochloride (a) t-Butyl N-methyl-N-(piperidin-3-yl)carbamate 0.4 g of sodium hydride (60%; in oil) was added to a mixture consisting of 3.3 g of benzyl 3-t-butoxycarbonylaminopiperidine-1-carboxylate, 0.75 ml of methyl iodide and 20 ml of N,N-dimethylformamide in a water bath at room temperature. The mixture was stirred at room temperature for 4 hours. The reaction solution was partitioned between ethyl acetate and water, and the organic layer was washed with water and then with saturated brine. The organic layer was dried over anhydrous magnesium sulfate, and then concentrated. The residue was purified by silica gel column chromatography using 10% to 20% ethyl acetate/hexane to give an oily material (3.04 g). This whole amount was combined with 20 ml of ethanol and 10% palladium carbon. This mixture was stirred at room temperature under a hydrogen atmosphere for five hours. After the catalyst was removed by filtration, the filtrate was concentrated to give 1.82 g of the title compound.

$^1$H-NMR (CDCl$_3$)

δ 1.46 (s, 9H) 1.48-1.64 (m, 2H) 1.72-1.84 (m, 2H) 2.43 (dt, J=3 Hz, 12 Hz, 1H) 2.60 (t, J=12 Hz, 1H) 2.75 (s, 3H) 2.74-3.02 (m, 2H) 3.86 (br.s, 1H)

(b) t-Butyl N-[1-[7-(2-butynyl)-2,6-dichloro-7H-purin-8-yl]piperidin-3-yl]-N-methylcarbamate The title compound was synthesized by using 7-(2-butynyl)-2,6,8-trichloro-7H-purine and t-butyl piperidin-3-ylcarbamate according to the method described in Example 242 (c).

$^1$H-NMR (CDCl$_3$)

δ 1.48 (s, 9H) 1.70-2.02 (m, 7H) 2.83 (s, 3H) 3.00 (t, J=12 Hz, 1H) 3.14 (t, J=12 Hz, 1H) 3.96-4.25 (m, 3H) 4.80 (s, 2H)

(c) t-Butyl N-[1-[7-(2-butynyl)-2-chloro-1-methyl-6-oxo-6,7-dihydro-1H-purin-8-yl]piperidin-3-yl]-N-methylcarbamate A mixture consisting of 580 mg of t-butyl N-[1-[7-(2-butynyl)-2,6-dichloro-7H-purin-8-yl]piperidin-3-yl]-N-methylcarbamate, 315 mg of sodium acetate and 6 ml of dimethyl sulfoxide was stirred in an oil bath at 120° C. for 7 hours. The reaction solution was partitioned between ethyl acetate and water, and the organic layer was washed with water and then with saturated brine. The organic layer was dried over anhydrous magnesium sulfate, was filtered through a small amount of silica gel. The filtrate was concentrated, and the residue was crystallized with ethyl acetate-hexane to give 420 mg of t-butyl N-[1-[7-(2-butynyl)-2-chloro-6-oxo-6,7-dihydro-1H-purin-8-yl]piperidin-3-yl]-N-methylcarbamate. A mixture consisting of an 100 mg aliquot of the compound obtained above, 0.17 ml of methyl iodide, 48 mg of anhydrous potassium carbonate and 0.5 ml of N,N-dimethylformamide was stirred at room temperature for 4 hours. The reaction solution was partitioned between ethyl acetate and water, and the organic layer was washed with water and then with saturated brine. Then, the organic layer was concentrated, and the residue was purified by silica gel column chromatography using 50% ethyl acetate/hexane to give 104 mg of the title compound.

$^1$H-NMR (CDCl$_3$)

δ 1.47 (s, 9H) 1.62-1.74 (m, 1H) 1.81 (t, J=2 Hz, 3H) 1.82-1.96 (m, 3H) 2.82 (s, 3H) 2.86 (t, J=12 Hz, 1H) 3.02 (t, J=12 Hz, 1H) 3.68-3.82 (m, 2H) 3.72 (s, 3H) 4.20 (br. s, 1H) 4.90 (s, 2H)

(d) 7-(2-Butynyl)-1-methyl-8-(3-methylaminopiperidin-1-yl)-6-oxo-6,7-dihydro-1H-purine-2-carbonitrile hydrochloride The title compound was synthesized by using t-butyl N-[1-[7-(2-butynyl)-2-chloro-1-methyl-6-oxo-6,7-dihydro-1H-purin-8-yl]piperidin-3-yl]-N-methylcarbamate according to the method described in Example 242 (f) and (g).

$^1$H-NMR (DMSO-d6)

δ 1.60-1.77 (m, 2H) 1.81 (s, 3H) 1.84-2.00 (m, 1H) 2.02-2.12 (m, 1H) 2.60 (t, J=5 Hz, 3H) 3.17-3.40 (m, 3H) 3.46-3.56 (m, 1H) 3.79 (d, J=12 Hz, 1H) 5.00-5.15 (m, 2H) 9.01 (br.s, 2H)

Example 255

2-[7-(2-Butynyl)-1-methyl-8-(3-methylaminopiperidin-1-yl)-6-oxo-6,7-dihydro-1H-purin-2-yloxy]benzamide hydrochloride A mixture consisting of 20 mg of t-butyl N-[1-[7-(2-butynyl)-2-chloro-1-methyl-6-oxo-6,7-dihydro-1H-purin-8-yl]piperidin-3-yl]-N-methylcarbamate, 20 mg of 2-hydroxybenzamide, 20 mg of anhydrous potassium carbonate, and 0.3 ml of N-methyl-2-pyrrolidone was stirred in an oil bath at 80° C. for 4 hours. Subsequent synthesis steps were carried out according to the same procedure as used in Examples 242(f) and (g) to give the title compound.

$^1$H-NMR (DMSO-d6)

δ 1.69 (br.s, 2H) 1.82 (s, 3H) 1.92 (br.s, 1H) 2.07 (br.s, 1H) 2.62 (s, 3H) 3.10-3.40 (m, 4H) 3.48 (s, 3H) 3.76 (br.s, 1H) 5.02 (br.s, 2H) 6.96 (br.s, 2H) 7.44 (br.s, 1H) 7.91 (br.s, 1H) 8.81 (br.s, 2H)

Example 256

8-(3-Aminopyrrolidin-1-yl)-7-(2-butynyl)-1-methyl-6-oxo-6,7-dihydro-1H-purine-2-carbonitrile hydrochloride In Example 254, the title compound was synthesized by using t-butyl pyrrolidin-3-ylcarbamate, instead of t-butyl N-methyl-N-(piperidin-3-yl)carbamate, according to the method described in Examples 254(b), (c), and (d).

$^1$H-NMR (DMSO-d6)

δ 1.81 (s, 3H) 2.13 (br.s, 1H) 2.32 (br.s, 1H) 3.64 (s, 3H) 3.74-3.86 (m, 2H) 3.93 (br.s, 3H) 5.19 (d, J=18 Hz, 1H) 5.28 (d, J=18 Hz, 1H) 8.32 (br.s, 3H)

Example 257

2-[8-(3-Aminopyrrolidin-1-yl)-7-(2-butynyl)-1-methyl-6-oxo-6,7-dihydro-1H-purin-2-yloxy]benzamide hydrochloride The title compound was synthesized by using 2-hydroxybenzamide according to the method described in Examples 255 and 256.

$^1$H-NMR (DMSO-d6)

δ 1.82 (s, 3H) 2.11 (br.s, 1H) 2.32 (br.s, 1H) 3.46 (s, 3H) 3.72-4.00 (m, 5H) 5.15 (d, J=19 Hz, 1H) 5.23 (d, J=19 Hz, 1H) 6.90-7.02 (m, 2H) 7.42-7.50 (m, 1H) 7.90-7.99 (m, 1H) 8.22 (br.s, 3H)

Example 258

3-(2-Butynyl)-2-(piperazin-1-yl)-5-(2-propynyl)-3,5-dihydroimidazo[4,5-d]pyridazin-4-one trifluoroacetate

(a) t-Butyl 4-[1-(2-butynyl)-7-oxo-6,7-dihydro-1H-imidazo[4,5-d]pyridazin-2-yl]piperazine-1-carboxylate 0.299 g of triethylamine, 0.023 g of 4-dimethylaminopyridine and 0.645 g of di-t-butyl dicarbonate were added to 20 ml of an N,N-dimethylformamide solution of 0.448 g of 3-(2-butynyl)-2-(piperazin-1-yl)-3,5-dihydroimidazo[4,5-d]pyridazin-4-one trifluoroacetate at room temperature, and the mixture was stirred for five hours. Then, 2 ml of a 5N aqueous sodium hydroxide solution was added to this solution, and the mixture was stirred for one hour. The reaction solution was poured into a mixture of 200 ml of ethyl acetate and 100 ml of a saturated aqueous ammonium chloride solution. The organic layer was washed twice with 100 ml of water and then with 100 ml of a saturated sodium chloride solution. The organic liquid was dried over magnesium sulfate, and concentrated under reduced pressure. The residue was purified by silica gel column chromatography. Thus, 0.298 g of the title compound was obtained from the fraction eluted with ethyl acetate.

¹H-NMR (CDCl₃)

δ 1.50 (s, 9H) 1.84 (t, J=2.3 Hz, 3H) 3.41 (m, 4H) 3.63 (m, 4H) 5.06 (q, J=2.3 Hz, 2H) 8.17 (s, 1H) 9.92 (br.s, 1H)

(b) 3-(2-Butynyl)-2-(piperazin-1-yl)-5-(2-propynyl)-3,5-dihydroimidazo[4,5-d]pyridazin-4-one trifluoroacetate 0.005 g of potassium carbonate and 0.003 ml of 3-bromo-1-propyne were added to 0.5 ml of an N,N-dimethylformamide solution of 0.010 g of t-butyl 4-[1-(2-butynyl)-7-oxo-6,7-dihydro-1H-imidazo[4,5-d]pyridazin-2-yl]piperazine-1-carboxylate, and the mixture was stirred at room temperature for 10 hours. 1 ml of ethyl acetate and 1 ml of water were added to the reaction solution, and the layers were separated. The organic layer was concentrated, and the resulting residue was dissolved in a mixture consisting of 0.5 ml of dichloromethane and 0.5 ml of trifluoroacetic acid. The mixture was stirred for 1 hour, and then concentrated. The residue was purified by reverse-phase high performance liquid chromatography (using an acetonitrile-water mobile phase (containing 0.1% trifluoroacetic acid)) to give 0.011 g of the title compound.

MS m/e (ESI) 311.29 (MH⁺-CF₃COOH)

Example 259

[3-(2-Butynyl)-4-oxo-2-(piperazin-1-yl)-3,4-dihydroimidazo[4,5-d ]pyridazin-5-yl]acetonitrile trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and bromoacetonitrile according to the method described in Example 258(b).

MS m/e (ESI) 312.28 (MH⁺-CF₃COOH)

Example 260

3-(2-Butynyl)-5-(2-hydroxyethyl)-2-(piperazin-1-yl)-3,5-dihydroimidazo[4,5-d]pyridazin-4-one trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and 2-bromoethanol according to the method described in Example 258(b).

MS m/e (ESI) 317.30 (MH⁺-CF₃COOH)

Example 261

3-(2-Butynyl)-5-(2-methoxyethyl)-2-(piperazin-1-yl)-3,5-dihydroimidazo[4,5-d]pyridazin-4-one trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and bromoethyl methyl ether according to the method described in Example 258(b).

MS m/e (ESI) 331.32 (MH⁺-CF₃COOH)

Example 262

Ethyl [3-(2-butynyl)-4-oxo-2-(piperazin-1-yl)-3,4-dihydroimidazo[4,5-d]pyridazin-5-yl]acetate trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and ethyl bromoacetate according to the method described in Example 258(b).

MS m/e (ESI) 359.13 (MH⁺-CF₃COOH)

Example 263

3-(2-Butynyl)-5-(2-phenylethyl)-2-(piperazin-1-yl)-3,5-dihydroimidazo[4,5-d]pyridazin-4-one trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and (2-bromoethyl)benzene according to the method described in Example 258(b).

MS m/e (ESI) 377.34 (MH⁺-CF₃COOH)

Example 264

3-(2-Butynyl)-5-(2-phenoxyethyl)-2-(piperazin-1-yl)-3,5-dihydroimidazo[4,5-d]pyridazin-4-one trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and 2-bromoethyl phenyl ether according to the method described in Example 258(b).

MS m/e (ESI) 393.32 (MH⁺-CF₃COOH)

Example 265

3-(2-Butynyl)-5-(2-oxo-2-phenylethyl)-2-(piperazin-1-yl)-3,5-dihydroimidazo[4,5-d]pyridazin-4-one trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and 2-bromoacetophenone according to the method described in Example 258(b).

MS m/e (ESI) 391.32 (MH⁺-CF₃COOH)

Example 266

3-(2-Butynyl)-5-[2-(3-methoxyphenyl)-2-oxoethyl]-2-(piperazin-1-yl)-3,5-dihydroimidazo[4,5-d]pyridazin-4-one trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and 2-bromo-3'-methoxy acetophenone according to the method described in Example 258(b).

MS m/e (ESI) 421.33 (MH⁺-CF₃COOH)

Example 267

2-[3-(2-Butynyl)-4-oxo-2-(piperazin-1-yl)-3,4-dihydroimidazo[4,5-d]pyridazin-5-ylmethyl]benzonitrile trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and 2-bromomethylbenzonitrile according to the method described in Example 258(b).

$^1$H-NMR (CD$_3$OD)

δ 1.81 (t, J=2.5 Hz, 3H) 3.45-3.49 (m, 4H) 3.66-3.70 (m, 4H) 5.15 (q, J=2.5 Hz, 2H) 5.62 (s, 2H) 7.34 (dd, J=7.6, 1.5 Hz, 1H) 7.45 (td, J=7.6, 1.5 Hz, 1H) 7.59 (td, J=7.6, 1.7 Hz, 1H) 7.75 (dd, J=7.6, 1.7 Hz, 1H) 8.25 (s, 1H)

MS m/e (ESI) 388.32 (MH$^+$-CF$_3$COOH)

Example 268

3-(2-Butynyl)-2-(piperazin-1-yl)-5-(2-trifluoromethylbenzyl)-3,5-dihydroimidazo[4,5-d]pyridazin-4-one trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and 2-(trifluoromethyl)benzyl bromide according to the method described in Example 258 (b).

MS m/e (ESI) 431.21 (MH$^+$-CF$_3$COOH)

Example 269

3-(2-Butynyl)-2-(piperazin-1-yl)-5-(3-trifluoromethylbenzyl)-3,5-dihydroimidazo[4,5-d]pyridazin-4-one trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and 3-(trifluoromethyl)benzyl bromide according to the method described in Example 258 (b).

MS m/e (ESI) 431.23 (MH$^+$-CF$_3$COOH)

Example 270

3-(2-Butynyl)-5-(2-nitrobenzyl)-2-(piperazin-1-yl)-3,5-dihydroimidazo[4,5-d]pyridazin-4-one trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and 2-nitrobenzyl bromide according to the method described in Example 258(b).

MS m/e (ESI) 408.25 (MH$^+$-CF$_3$COOH)

Example 271

3-[3-(2-Butynyl)-4-oxo-2-(piperazin-1-yl)-3,4-dihydroimidazo[4,5-d]pyridazin-5-ylmethyl]benzonitrile trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and 3-bromomethylbenzonitrile according to the method described in Example 258(b).

MS m/e (ESI) 388.27 (MH$^+$-CF$_3$COOH)

Example 272

4-[3-(2-Butynyl)-4-oxo-2-(piperazin-1-yl)-3,4-dihydroimidazo[4,5-d]pyridazin-5-ylmethyl]benzonitrile trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and 4-bromomethylbenzonitrile according to the method described in Example 258(b).

MS m/e (ESI) 388.29 (MH$^+$-CF$_3$COOH)

Example 273

Methyl 3-[3-(2-butynyl)-4-oxo-2-(piperazin-1-yl)-3,4-dihydroimidazo[4,5-d]pyridazin-5-ylmethyl]benzoate trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and methyl 3-(bromomethyl)benzoate according to the method described in Example 258 (b).

MS m/e (ESI) 421.29 (MH$^+$-CF$_3$COOH)

Example 274

Methyl 4-[3-(2-butynyl)-4-oxo-2-(piperazin-1-yl)-3,4-dihydroimidazo[4,5-d]pyridazin-5-ylmethyl]benzoate trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and methyl 4-(bromomethyl)benzoate according to the method described in Example 258 (b).

MS m/e (ESI) 421.31 (MH$^+$-CF$_3$COOH)

Example 275

Ethyl 5-[3-(2-butynyl)-4-oxo-2-(piperazin-1-yl)-3,4-dihydroimidazo[4,5-d]pyridazin-5-ylmethyl]furan-2-carboxylate trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and ethyl 5-(bromomethyl)furan-2-carboxylate according to the method described in Example 258(b).

MS m/e (ESI) 425.30 (MH$^+$-CF$_3$COOH)

Example 276

3-(2-Butynyl)-5-[2-(2-nitrophenyl)-2-oxoethyl]-2-(piperazin-1-yl)-3,5-dihydroimidazo[4,5-d]pyridazin-4-one trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and 2-bromo-2'-nitroacetophenone according to the method described in Example 258(b).

MS m/e (ESI) 436.28 (MH$^+$-CF$_3$COOH)

Example 277

4-[2-[3-(2-Butynyl)-4-oxo-2-(piperazin-1-yl)-3,4-dihydroimidazo[4,5-d]pyridazin-5-yl]acetyl]benzonitrile trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and 2-bromo-4'-cyanoacetophenone according to the method described in Example 258(b).

MS m/e (ESI) 416.31 (MH$^+$-CF$_3$COOH)

Example 278

3-(2-Butynyl)-5-[2-(4-methoxyphenyl)-2-oxoethyl]-2-(piperazin-1-yl)-3,5-dihydroimidazo[4,5-d]pyridazin-4-one trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and 2-bromo-4'-methoxyacetophenone according to the method described in Example 258(b).

MS m/e (ESI) 421.32 (MH$^+$-CF$_3$COOH)

Example 279

3-(2-Butynyl)-5-[2-(2-methoxyphenyl)-2-oxoethyl]-2-(piperazin-1-yl)-3,5-dihydroimidazo[4,5-d]pyridazin-4-one trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and 2-bromo-2'-methoxyacetophenone according to the method described in Example 258(b).

MS m/e (ESI) 421.33 (MH$^+$-CF$_3$COOH)

Example 280

4-[2-[3-(2-Butynyl)-4-oxo-2-(piperazin-1-yl)-3,4-dihydroimidazo[4,5-d]pyridazin-5-yl]ethyl]benzoic acid trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and t-butyl 4-(2-bromoethyl)benzoate according to the method described in Example 258 (b).

MS m/e (ESI) 421.33 (MH$^+$-CF$_3$COOH)

Example 281

3-(2-Butynyl)-2-(piperazin-1-yl)-5-(pyridin-2-ylmethyl)-3,5-dihydroimidazo[4,5-d]pyridazin-4-one bis trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and 2-(chloromethyl)pyridine hydrochloride according to the method described in Example 258 (b).

MS m/e (ESI) 364.24 (MH$^+$-2CF$_3$COOH)

Example 282

3-(2-Butynyl)-2-(piperazin-1-yl)-5-(pyridin-3-ylmethyl)-3,5-dihydroimidazo[4,5-d]pyridazin-4-one bis trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and 3-(chloromethyl)pyridine hydrochloride according to the method described in Example 258(b).

MS m/e (ESI) 364.30 (MH$^+$-2CF$_3$COOH)

Example 283

3-(2-Butynyl)-2-(piperazin-1-yl)-5-(pyridin-4-ylmethyl)-5-dihydroimidazo[4,5-d]pyridazin-4-one bis trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and 4-(chloromethyl)pyridine hydrochloride according to the method described in Example 258 (b).

MS m/e (ESI) 364.26 (MH$^+$-2CF$_3$COOH)

Example 284

3-(2-Butynyl)-5-[2-oxo-2-(pyridin-2-yl)ethyl]-2-(piperazin-1-yl)-3,5-dihydroimidazo[4,5-d]pyridazin-4-one bis trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and 2-(2-bromoacetyl)pyridine hydrobromide according to the method described in Example 258(b).

MS m/e (ESI) 392.27 (MH$^+$-2CF$_3$COOH)

Example 285

3-(2-Butynyl)-5-[2-oxo-2-(pyridin-3-yl)ethyl]-2-(piperazin-1-yl)-3,5-dihydroimidazo[4,5-d]pyridazin-4-one bis trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and 3-(2-bromoacetyl)pyridine hydrobromide according to the method described in Example 258(b).

MS m/e (ESI) 392.27 (MH$^+$-2CF$_3$COOH)

Example 286

3-(2-Butynyl)-5-[2-oxo-2-(pyridin-4-yl)ethyl]-2-oxoethyl]]-2-(piperazin-1-yl)-3,5-dihydroimidazo[4,5-d]pyridazin-4-one bis trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and 4-(2-bromoacetyl)pyridine hydrobromide according to the method described in Example 258(b).

MS m/e (ESI) 392.28 (MH$^+$-2CF$_3$COOH)

Example 287

3-(2-Butynyl)-5-(2-methoxypyridin-3-ylmethyl)-2-(piperazin-1-yl)-3,5-dihydroimidazo[4,5-d]pyridazin-4-one trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and 3-(chloromethyl)-2-methoxypyridine according to the method described in Example 258(b).

MS m/e (ESI) 394.30 (MH$^+$-CF$_3$COOH)

Example 288

Methyl 6-[3-(2-butynyl)-4-oxo-2-(piperazin-1-yl)-3,4-dihydroimidazo[4,5-d]pyridazin-5-ylmethyl]nicotinate bis trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and methyl 6-(chloromethyl)nicotinate according to the method described in Example 258(b).

MS m/e (ESI) 422.31 (MH$^+$-CF$_3$COOH)

Example 289

5-(6-Aminopyridin-3-ylmethyl)-3-(2-butynyl)-2-(piperazin-1-yl)-3,5-dihydroimidazo[4,5-d]pyridazin-4-one trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and 2-(t-butoxycarbonylamino)-5-(bromomethyl)pyridine according to the method described in Example 258(b).

MS m/e (ESI) 379.31 (MH$^+$-CF$_3$COOH)

Example 290

4-[3-(2-Butynyl)-4-oxo-2-(piperazin-1-yl)-3,4-dihydroimidazo[4,5-d]pyridazin-5-ylmethyl]-3-cyano-5-ethoxy-N-methylbenzamide trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and 4-bromomethyl-3-cyano-5-ethoxy-N-methylbenzamide according to the method described in Example 258(b).

MS m/e (ESI) 489.35 (MH$^+$-CF$_3$COOH)

Example 291

4-[3-(2-Butynyl)-4-oxo-2-(piperazin-1-yl)-3,4-dihydroimidazo[4,5-d]pyridazin-5-ylmethyl]-3,5-dicyano-N-methylbenzamide trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and 4-bromomethyl-3,5-dicyano-N-methylbenzamide according to the method described in Example 258(b).

MS m/e (ESI) 470.33 (MH$^+$-CF$_3$COOH)

Example 292

4-[3-(2-Butynyl)-4-oxo-2-(piperazin-1-yl)-3,4-dihydroimidazo[4,5-d]pyridazin-5-ylmethyl]-3-cyano-5-fluoro-N-methylbenzamide trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and 4-bromomethyl-3-cyano-5-fluoro-N-methylbenzamide according to the method described in Example 258(b).

MS m/e (ESI) 463.33 (MH$^+$-CF$_3$COOH)

Example 293

4-[3-(2-Butynyl)-4-oxo-2-(piperazin-1-yl)-3,4-dihydroimidazo[4,5-d]pyridazin-5-ylmethyl]-5-cyano-2-ethoxy-N-methylbenzamide trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and 4-bromomethyl-5-cyano-2-ethoxy-N-methylbenzamide according to the method described in Example 258(b).

MS m/e (ESI) 489.35 (MH$^+$-CF$_3$COOH)

Example 294

5-[3-(2-Butynyl)-4-oxo-2-(piperazin-1-yl)-3,4-dihydroimidazo[4,5-d]pyridazin-5-ylmethyl]-2-fluorobenzonitrile trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and 5-bromomethyl-2-fluorobenzonitrile according to the method described in Example 258(b).

MS m/e (ESI) 406.15 (MH$^+$-CF$_3$COOH)

Example 295

2-[3-(2-Butynyl)-4-oxo-2-(piperazin-1-yl)-3,4-dihydroimidazo[4,5-d]pyridazin-5-ylmethyl]-5-fluorobenzonitrile trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and 2-bromomethyl-5-fluorobenzonitrile according to the method described in Example 258(b).

MS m/e (ESI) 406.16 (MH$^+$-CF$_3$COOH)

Example 296

4-[3-(2-Butynyl)-4-oxo-2-(piperazin-1-yl)-3,4-dihydroimidazo[4,5-d]pyridazin-5-ylmethyl]-3-fluorobenzonitrile trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and 4-bromomethyl-3-fluorobenzonitrile according to the method described in Example 258(b).

MS m/e (ESI) 406.23 (MH$^+$-CF$_3$COOH)

Example 297

2-[3-(2-Butynyl)-4-oxo-2-(piperazin-1-yl)-3,4-dihydroimidazo[4,5-d]pyridazin-5-ylmethyl]-3-fluorobenzonitrile trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and 2-bromomethyl-3-fluorobenzonitrile according to the method described in Example 258(b).

MS m/e (ESI) 406.25 (MH$^+$-CF$_3$COOH)

Example 298

3-(2-Butynyl)-5-(isoquinolin-1-ylmethyl)-2-(piperazin-1-yl)-3,5-dihydroimidazo[4,5-d]pyridazin-4-one trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and 1-bromomethylisoquinoline according to the method described in Example 258(b).

$^1$H-NMR (CDCl$_3$)

δ 1.80 (t, J=2.4 Hz, 3H) 3.46 (m, 4H) 3.68 (m, 4H) 5.17 (q, J=2.4 Hz, 2H) 6.22 (s, 2H) 7.94 (dd, J=8.2, 8.0 Hz, 1H) 8.08 (t, J=8.2 Hz, 1H) 8.21 (d, J=8.0 Hz, 1H) 8.24 (d, J=6.4 Hz, 1) 8.27 (s, 1H) 8.46 (d, J=6.4 Hz, 1H) 8.68 (d, J=8.2 Hz, 1H)

MS m/e (ESI) 414.32 (MH$^+$-CF$_3$COOH)

Example 299

3-(2-Butynyl)-5-(2-fluoropyridin-3-ylmethyl)-2-(piperazin-1-yl)-3,5-dihydroimidazo[4,5-d]pyridazin-4-one trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and 3-(bromomethyl)-2-fluoropyridine hydrochloride according to the method described in Example 258(b).

MS m/e (ESI) 384.22 (MH$^+$-CF$_3$COOH)

Example 300

3-(2-Butynyl)-5-(2-fluoropyridin-4-ylmethyl)-2-(piperazin-1-yl)-3,5-dihydroimidazo[4,5-d]pyridazin-4-one trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and 4-(bromomethyl)-2-fluoropyridine hydrochloride according to the method described in Example 258 (b).

MS m/e (ESI) 384.20 (MH$^+$-CF$_3$COOH)

Example 301

3-(2-Butynyl)-5-(6-fluoropyridin-2-ylmethyl)-2-(piperazin-1-yl)-3,5-dihydroimidazo[4,5-d]pyridazin-4-one trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and 2-(bromomethyl)-6-fluoropyridine hydrochloride according to the method described in Example 258 (b).

MS m/e (ESI) 384.22 (MH$^+$-CF$_3$COOH)

Example 302

2-[3-(2-Butynyl)-4-oxo-2-(piperazin-1-yl)-3,4-dihydroimidazo[4,5-d]pyridazin-5-ylmethyl]benzamide trifluoroacetate 0.005 g of potassium carbonate and 0.007 g of 2-bromomethylbenzonitrile were added to a 0.5 ml N,N-dimethylformamide solution containing 0.010 g of t-butyl 4-[1-(2-butynyl)-7-oxo-6,7-dihydro-1H-imidazo[4,5-d]pyridazin-2-yl] piperazine-1-carboxylate, and the mixture was stirred at room temperature for 20 hours. 1 ml of ethyl acetate and 1 ml of water were added to the reaction solution, and the layers were separated. The organic layer was concentrated, and the residue was dissolved in 1.0 ml of methanol. 0.2 ml of aqueous ammonia solution and 0.2 ml of 31% aqueous hydrogen peroxide were added to the solution, and the mixture was stirred at 5° C. for 20 hours. 1 ml of ethyl acetate and 1 ml of water were added to the reaction solution, and the layers were separated. The organic layer was concentrated, and the resulting residue was dissolved in a mixture consisting of 0.5 ml of dichloromethane and 0.5 ml of trifluoroacetic acid. The mixture was stirred for 1 hour, and then concentrated. The residue was purified by reverse-phase high performance liquid chromatography (using an acetonitrile-water mobile phase (containing 0.1% trifluoroacetic acid)) to give 0.009 g the title compound.

MS m/e (ESI) 406.28 (MH$^+$-CF$_3$COOH)

Example 303

3-[3-(2-Butynyl)-4-oxo-2-(piperazin-1-yl)-3,4-dihydroimidazo[4,5-d]pyridazin-5-ylmethyl]benzamide trifluoroacetate The title compound was obtained by using t-butyl 4 [1-(2-butynyl)-7-oxo-6,7-dihydro-1H-imidazo[4,5-d]pyridazin-2-yl]piperazine-1-carboxylate and 3-bromomethylbenzonitrile according to the method described in Example 302.

MS m/e (ESI) 406.30 (MH$^+$-CF$_3$COOH)

Example 304

4-[3-(2-Butynyl)-4-oxo-2-(piperazin-1-yl)-3,4-dihydroimidazo[4,5-d]pyridazin-5-ylmethyl]benzamide trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and 4-bromomethylbenzonitrile according to the method described in Example 302.

MS m/e (ESI) 406.31 (MH$^+$-CF$_3$COOH)

Example 305

3-[3-(2-Butynyl)-4-oxo-2-(piperazin-1-yl)-3,4-dihydroimidazo[4,5-d]pyridazin-5-ylmethyl]benzoic acid trifluoroacetate 0.005 g of potassium carbonate and 0.008 g of methyl 3-(bromomethyl)benzoate were added to a 0.5 ml N,N-dimethylformamide solution of 0.010 g of t-butyl 4-[1-(2-butynyl)-7-oxo-6,7-dihydro-1H-imidazo[4,5-d]pyridazin-2-yl] piperazine-1-carboxylate, and the mixture was stirred at room temperature for 20 hours. 1 ml of ethyl acetate and 1 ml of water were added to the reaction mixture, and the layers were separated. The organic layer was concentrated, and the residue was dissolved in 1.0 ml of methanol. 0.1 ml of a 5N aqueous sodium hydroxide solution was added to this solution, and the mixture was stirred at room temperature for 20 hours. 1 ml of ethyl acetate and 1 ml of water were added to the reaction solution. The solution was acidified using concentrated hydrochloric acid, and the layers were separated. The organic layer was concentrated, and the residue was dissolved in a mixture consisting of 0.5 ml of dichloromethane and 0.5 ml of trifluoroacetic acid. The mixture was stirred for one hour and then concentrated. The residue was purified by reverse-phase high performance liquid chromatography (using an acetonitrile-water mobile phase (containing 0.1% trifluoroacetic acid)) to give 0.008 g of the title compound.

MS m/e (ESI) 407.29 (MH$^+$-CF$_3$COOH)

Example 306

4-[3-(2-Butynyl)-4-oxo-2-(piperazin-1-yl)-3,4-dihydroimidazo[4,5-d]pyridazin-5-ylmethyl]benzoic acid trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and methyl 4-(bromomethyl)benzoate according to the method described in Example 305.

MS m/e (ESI) 407.30 (MH$^+$-CF$_3$COOH)

Example 307

5-[3-(2-Butynyl)-4-oxo-2-(piperazin-1-yl)-3,4-dihydroimidazo[4,5-d]pyridazin-5-ylmethyl]furan-2-carboxylic acid trifluoroacetate The title compound was obtained by using t-butyl 4-[1-(2-butynyl)-7-oxo-6,7-dihydro-1H-imidazo[4,5-d]pyridazin-2-yl]piperazine-1-carboxylate and ethyl 5-(bromomethyl)furan-2-carboxylate according to the method described in Example 305.

MS m/e (ESI) 397.28 (MH$^+$-CF$_3$COOH)

Example 308

3-Benzyl-2-(piperazin-1-yl)-3,5-dihydroimidazo[4,5-d]pyridazin-4-one trifluoroacetate (a) t-Butyl 4-(1-benzyl-6-benzyloxymethyl-7-oxo-6,7-dihydro-1H-imidazo[4,5-d]pyridazin-2-yl)piperazine-1-carboxylate The title compound was obtained by using t-butyl 4-(6-benzyloxymethyl-7-oxo-6,7-dihydro-1H-imidazo[4,5-d]pyridazin-2-yl)piperazine-1-carboxylate and benzyl bromide according to the method described in Example 116(d).

$^1$H-NMR (CDCl$_3$)

δ 1.48 (s, 9H) 3.13-3.18 (m, 4H) 3.50-3.54 (m, 4H) 4.72 (s, 2H) 5.61 (s, 2H) 5.65 (s, 2H) 7.20-7.35 (m, 10H) 8.22 (s, 1H)

(b) 3-Benzyl-2-(piperazin-1-yl)-3,5-dihydroimidazo[4,5-d]pyridazin-4-one trifluoroacetate The title compound was obtained by treating t-butyl 4-(1-benzyl-6-benzyloxymethyl-7-oxo-6,7-dihydro-1H-imidazo[4,5-d]pyridazin-2-yl)piperazine-1-carboxylate according to the method described in Example 117.

$^1$H-NMR (CD$_3$OD)

δ 3.31-3.37 (m, 4H) 3.40-3.46 (m, 4H) 5.68 (s, 2H) 7.22-7.36 (m, 5H) 8.25 (s, 1H)

MS m/e (ESI) 311.24 (MH$^+$-CF$_3$COOH)

Example 309

3-Benzyl-5-methyl-2-(piperazin-1-yl)-3,5-dihydroimidazo[4,5-d]pyridazin-4-one trifluoroacetate (a) t-Butyl 4-(1-benzyl-7-oxo-6,7-dihydro-1H-imidazo[4,5-d]pyridazin-2-yl)piperazine-1-carboxylate The title compound was obtained by using 3-benzyl-2-(piperazin-1-yl)-3,5-dihydroimidazo[4,5-d]pyridazin-4-one trifluoroacetate according to the method described in Example 258(a).

$^1$H-NMR (CDCl$_3$)

δ 1.47 (s, 9H) 3.12-3.16 (m, 4H) 3.47-3.52 (m, 4H) 5.58 (s, 2H) 7.20-7.34 (m, 5H) 8.20 (s, 1H) 10.04 (br.s, 1H)

(b) 3-Benzyl-5-methyl-2-(piperazin-1-yl)-3,5-dihydroimidazo[4,5-d]pyridazin-4-one trifluoroacetate The title compound was obtained by using t-butyl 4-(1-benzyl-7-oxo-6,7-dihydro-1H-imidazo[4,5-d]pyridazin-2-yl)piperazine-1-carboxylate and methyl iodide according to the method described in Example 258(b).

$^1$H-NMR (CD$_3$OD)

δ 3.29-3.35 (m, 4H) 3.36-3.41 (m, 4H) 3.83 (s, 3H) 5.68 (s, 2H) 7.21-7.34 (m, 5H) 8.20 (s, 1H)

MS m/e (ESI) 325.01 (MH$^+$-CF$_3$COOH)

Example 310

3-Benzyl-5-(2-oxo-2-phenylethyl)-2-(piperazin-1-yl)-3,5-dihydroimidazo[4,5-d]pyridazin-4-one trifluoroacetate The title compound was obtained by using t-butyl 4-[1-benzyl-7-oxo-6,7-dihydro-1H-imidazo[4,5-d]pyridazin-2-yl]piperazine-1-carboxylate and 2-bromoacetophenone according to the method described in Example 258(b).

$^1$H-NMR (CD$_3$OD)

δ 3.31-3.36 (m, 4H) 3.44-3.49 (m, 4H) 5.69 (s, 2H) 5.77 (s, 2H) 7.22-7.52 (m, 8H) 8.06 (d, J=9.3 Hz, 2H) 8.32 (s, 1H)

MS m/e (ESI) 429.39 (MH$^+$-CF$_3$COOH)

Example 311

3-Benzyl-5-(2-phenylethyl)-2-(piperazin-1-yl)-3,5-dihydroimidazo[4,5-d]pyridazin-4-one trifluoroacetate The title compound was obtained by using t-butyl 4-[1-benzyl-7-oxo-6,7-dihydro-1H-imidazo[4,5-d]pyridazin-2-yl]piperazine-1-carboxylate and (2-bromoethyl)benzene according to the method described in Example 258(b).

$^1$H-NMR (CDCl$_3$)

δ 3.11 (t, J=8.1 Hz, 2H) 3.24-3.29 (m, 4H) 3.37-3.42 (m, 4H) 4.46 (t, J=8.1 Hz, 2H) 5.58 (s, 2H) 7.09-7.34 (m, 10H) 8.20 (s, 1H)

MS m/e (ESI) 415.54 (MH$^+$-CF$_3$COOH)

Example 312

3-Benzyl-5-(2-phenoxyethyl)-2-(piperazin-1-yl)-3,5-dihydroimidazo[4,5-d]pyridazin-4-one trifluoroacetate The title compound was obtained by using t-butyl 4-[1-benzyl-7-oxo-6,7-dihydro-1H-imidazo[4,5-d]pyridazin-2-yl]piperazine-1-carboxylate and 2-bromoethyl phenyl ether according to the method described in Example 258(b).
$^1$H-NMR (CDCl$_3$)
δ 3.21-3.24 (m, 4H) 3.37-3.42 (m, 4H) 4.37 (t, J=5.8 Hz, 2H) 4.64 (t, J=5.8 Hz, 2H) 5.58 (s, 2H) 6.86-6.94 (m, 3H) 7.07-7.34 (m, 7H) 8.21 (s, 1H)
MS m/e (ESI) 431.57 (MH$^+$-CF$_3$COOH)

Example 313

3-benzyl-2-(piperazin-1-yl)-5-(2-propynyl)-3,5-dihydroimidazo[4,5-d]pyridazin-4-one trifluoroacetate The title compound was obtained by using t-butyl 4-[1-benzyl-7-oxo-6,7-dihydro-1H-imidazo[4,5-d]pyridazin-2-yl]piperazine-1-carboxylate and 3-bromo-1-propyne according to the method described in Example 258(b).
MS m/e (ESI) 349.31 (MH$^+$-CF$_3$COOH)

Example 314

[3-Benzyl-4-oxo-2-(piperazin-1-yl)-3,4-dihydroimidazo[4,5-d]pyridazin-5-yl]acetonitrile trifluoroacetate The title compound was obtained by using t-butyl 4-[1-benzyl-7-oxo-6,7-dihydro-1H-imidazo[4,5-d]pyridazin-2-yl]piperazine-1-carboxylate and bromoacetonitrile according to the method described in Example 258(b).
MS m/e (ESI) 350.30 (MH$^+$-CF$_3$COOH)

Example 315

3-Benzyl-5-(2-hydroxyethyl)-2-(piperazin-1-yl)-3,5-dihydroimidazo[4,5-d]pyridazin-4-one trifluoroacetate The title compound was obtained by using t-butyl 4-[1-benzyl-7-oxo-6,7-dihydro-1H-imidazo[4,5-d]pyridazin-2-yl]piperazine-1-carboxylate and 2-bromoethanol according to the method described in Example 258(b).
MS m/e (ESI) 355.32 (MH$^+$-CF$_3$COOH)

Example 316

3-Benzyl-5-(2-methoxyethyl)-2-(piperazin-1-yl)-3,5-dihydroimidazo[4,5-d]pyridazin-4-one trifluoroacetate The title compound was obtained by using t-butyl 4-[1-benzyl-7-oxo-6,7-dihydro-1H-imidazo[4,5-d]pyridazin-2-yl]piperazine-1-carboxylate and bromoethyl methyl ether according to the method described in Example 258(b).
MS m/e (ESI) 369.35 (MH$^+$-CF$_3$COOH)

Example 317

Ethyl [3-benzyl-4-oxo-2-(piperazin-1-yl)-3,4-dihydroimidazo[4,5-d]pyridazin-5-yl]acetate trifluoroacetate The title compound was obtained by using t-butyl 4-[1-benzyl-7-oxo-6,7-dihydro-1H-imidazo[4,5-d]pyridazin-2-yl]piperazine-1-carboxylate and ethyl bromoacetate according to the method described in Example 258(b).
MS m/e (ESI) 397.33 (MH$^+$-CF$_3$COOH)

Example 318

3-Benzyl-5-[2-(3-methoxyphenyl)-2-oxoethyl]-2-(piperazin-1-yl)-3,5-dihydroimidazo[4,5-d]pyridazin-4-one trifluoroacetate The title compound was obtained by using t-butyl 4-[1-benzyl-7-oxo-6,7-dihydro-1H-imidazo[4,5-d]pyridazin-2-yl]piperazine-1-carboxylate and 2-bromo-3'-methoxyacetophenone according to the method described in Example 258(b).
MS m/e (ESI) 459.34 (MH$^+$-CF$_3$COOH)

Example 319

2-[3-Benzyl-4-oxo-2-(piperazin-1-yl)-3,4-dihydroimidazo[4,5-d]pyridazin-5-ylmethyl]benzonitrile trifluoroacetate The title compound was obtained by using t-butyl 4-[1-benzyl-7-oxo-6,7-dihydro-1H-imidazo[4,5-d]pyridazin-2-yl]piperazine-1-carboxylate and 2-bromomethylbenzonitrile according to the method described in Example 258(b).
MS m/e (ESI) 326.33 (MH$^+$-CF$_3$COOH)

Example 320

5-Methyl-2-(piperazin-1-yl)-3-(2-propynyl)-3,5-dihydroimidazo[4,5-d]pyridazin-4-one trifluoroacetate The title compound was obtained by using t-butyl 4-(6-methyl-7-oxo-6,7-dihydro-1H-imidazo[4,5-d]pyridazin-2-yl)piperazine-1-carboxylate and 3-bromo-1-propyne according to the method described in Example 258(b).
$^1$H-NMR (CD$_3$OD)
δ 2.99 (t, J=3.3 Hz, 1H) 3.45-3.49 (m, 4H) 3.65-3.69 (m, 4H) 3.83 (s, 3H) 5.75 (d, J=3.3 Hz, 2H) 8.20 (s, 1H)
MS m/e (ESI) 273.1 (MH$^+$-CF$_3$COOH)

Example 321

3-(2-Butenyl)-5-methyl-2-(piperazin-1-yl)-3,5-dihydroimidazo[4,5-d]pyridazin-4-one trifluoroacetate The title compound was obtained by using t-butyl 4-(6-methyl-7-oxo-6,7-dihydro-1H-imidazo[4,5-d]pyridazin-2-yl)piperazine-1-carboxylate and 1-bromo-2-butene according to the method described in Example 258(b).
$^1$H-NMR (CD$_3$OD)
δ 1.69 and 1.84 (dd, J=6.3, 1.3 Hz and dd, J=6.3, 1.3 Hz, 3H) 3.43-3.48 (m, 4H) 3.54-3.58 (m, 4H) 3.82 and 3.84 (s, 3H) 4.94 and 5.07 (d, J=6.5 Hz and d, J=6.5 Hz, 2H) 5.63-5.80 and 6.11-6.20 (m, 2H) 8.19 and 8.22 (s, 1H)
MS m/e (ESI) 289.2 (MH$^+$-CF$_3$COOH)

Example 322

5-Methyl-3-(2-pentenyl)-2-(piperazin-1-yl)-3,5-dihydroimidazo[4,5-d]pyridazin-4-one trifluoroacetate The title compound was obtained by using t-butyl 4-(6-methyl-7-oxo-6,7-dihydro-1H-imidazo[4,5-d]pyridazin-2-yl)piperazine-1-carboxylate and 1-bromo-2-pentene according to the method described in Example 258(b).

$^1$H-NMR (CD$_3$OD)
δ 0.97 and 1.08 (t, J=7.7 Hz and t, J=7.7 Hz, 3H) 2.04-2.27 (m, 2H) 3.42-3.46 (m, 4H) 3.54-3.58 (m, 4H) 3.81 and 3.84 (s, 3H) 4.91-4.96 (m, 2H) 5.59-5.81 and 6.14-6.22 (m, 2H) 8.19 and 8.22 (s, 1H)
MS m/e (ESI) 303.25 (MH$^+$-CF$_3$COOH)

Example 323

5-Methyl-3-(3-methyl-2-butenyl)-2-(piperazin-1-yl)-3,5-dihydroimidazo[4,5-d]pyridazin-4-one trifluoroacetate The title compound was obtained by using t-butyl 4-(6-methyl-7-oxo-6,7-dihydro-1H-imidazo[4,5-d]pyridazin-2-yl)piperazine-1-carboxylate and 1-bromo-3-methyl-2-butene according to the method described in Example 258(b).

$^1$H-NMR (CD$_3$OD)
δ 1.75 (s, 3H) 1.83 (s, 3H) 3.43-3.47 (m, 4H) 3.52-3.57 (m, 4H) 3.84 (s, 3H) 5.00 (d, J=6.8 Hz, 2H) 5.40-5.45 (m, 1H) 8.17 (s, 1H)
MS m/e (ESI) 303.27 (MH$^+$-CF$_3$COOH)

Example 324

3-Cyclopropylmethyl-5-methyl-2-(piperazin-1-yl)-3,15-dihydroimidazo[4,5-d]pyridazin-4-one trifluoroacetate The title compound was obtained by using t-butyl 4-(6-methyl-7-oxo-6,7-dihydro-1H-imidazo[4,5-d]pyridazin-2-yl)piperazine-1-carboxylate and cyclopropylmethyl bromide according to the method described in Example 258(b).

$^1$H-NMR (CD$_3$OD)
δ 0.44-0.55 (m, 4H) 0.81-0.85 (m, 1H) 3.42-3.46 (m, 4H) 3.54-3.58 (m, 4H) 3.83 (s, 3H) 4.39 (d, J=6.6 Hz, 2H) 8.21 (s, 1H)
MS m/e (ESI) 289.25 (MH$^+$-CF$_3$COOH)

Example 325

5-[2-(2-Aminophenyl)-2-oxoethyl]-3-(2-butynyl)-2-(piperazin-1-yl)-3,5-dihydroimidazo[4,5-d]pyridazin-4-one bistrifluoracetate (a) t-Butyl 4-[1-(2-butynyl)-6-[2-(2-nitrophenyl)-2-oxoethyl]-7-oxo-6,7-dihydro-1H-imidazo[4,5-d]pyridazin-2-yl]piperazine-1-carboxylate The title compound was obtained by using t-butyl 4-[1-(2-butynyl)-7-oxo-6,7-dihydro-1H-imidazo[4,5-d]pyridazin-2-yl]piperazine-1-carboxylate and 2-bromo-2'-nitroacetophenone according to the method described in Example 258(b).

$^1$H-NMR (CDCl$_3$)
δ 1.49 (s, 9H) 1.83 (t, J=2.3 Hz, 3H) 3.37-3.44 (m, 4H) 3.50-3.55 (m, 4H) 5.04 (q, J=2.3 Hz, 2H) 5.44 (s, 2H) 7.62 (m, 1H) 7.71-7.74 (m, 2H) 8.13 (d, J=7.9 Hz, 1H) 8.21 (s, 1H)

(b) 5-[2-(2-Aminophenyl)-2-oxoethyl]-3-(2-butynyl)-2-(piperazin-1-yl)-3,5-dihydroimidazo[4,5-d]pyridazin-4-one bistrifluoracetate 2 ml of water, 0.070 g of iron and 0.007 g of ammonium chloride were added to a 5 ml ethanol solution of 0.058 g of t-butyl 4-[1-(2-butynyl)-6-[2-(2-nitrophenyl)-2-oxoethyl]-7-oxo-6,7-dihydro-1H-imidazo[4,5-d]pyridazin-2-yl]piperazine-1-carboxylate, and the mixture was heated under reflux for three hours. The reaction mixture was filtered, and the filtrate was concentrated under reduced pressure. The residue was dissolved in 4 ml of dichloromethane, and 4 ml of trifluoroacetic acid was added thereto. After the mixture had been stirred for two hours, the solvent was concentrated under reduced pressure. The residue was purified by reverse-phase high performance liquid chromatography (using an acetonitrile-water mobile phase (containing 0.1% trifluoroacetic acid)) to give 0.051 g of the title compound.

$^1$H-NMR (CD$_3$OD)
δ 1.82 (t, J=2.3 Hz, 3H) 3.45-3.50 (m, 4H) 3.68-3.72 (m, 4H) 5.16 (q, J=2.3 Hz, 2H) 5.68 (s, 2H) 6.56 (t, J=7.2 Hz, 1H) 6.67 (d, J=7.2 Hz, 1H) 7.30 (t, J=7.2 Hz, 1H) 7.85 (d, J=7.2 Hz, 1H) 8.25 (s, 1H)
MS m/e (ESI) 406.22 (MH$^+$-2CF$_3$COOH)

Example 326

3-(2-Butynyl)-5,7-dimethyl-2-(piperazin-1-yl)-3,5-dihydroimidazo[4,5-d]pyridazin-4-one trifluoroacetate (a) t-Butyl 4-[1-(2-butynyl)-5-ethoxycarbonyl-4-(1-hydroxyethyl)-1H-imidazol-2-yl]piperazine-1-carboxylate 0.5 ml of a 0.3 M tetrahydrofuran solution of methyl magnesium bromide was added to a 3 ml tetrahydrofuran solution of 0.050 g of t-butyl 4-[1-(2-butynyl)-5-ethoxycarbonyl-4-formyl-1H-imidazol-2-yl]piperazine-1-carboxylate at −70° C. under a nitrogen atmosphere, and the mixture was allowed to warm to room temperature. 10 ml of a 5% aqueous ammonium chloride solution was added to this solution, and the mixture was extracted with 30 ml of ethyl acetate. The organic layer was washed successively with 10 ml of water and 10 ml of a saturated sodium chloride solution, and then dried over magnesium sulfate. The organic layer was concentrated under reduced pressure. The residue was purified by silica gel column chromatography. Thus, 0.049 g of the title compound was obtained from the fraction eluted with ethyl acetate-hexane (1:1).

$^1$H-NMR (CDCl$_3$)
δ 1.37 (t, J=7.1 Hz, 3H) 1.47 (d, J=6.9 Hz, 3H) 1.48 (s, 9H) 1.81 (t, J=2.3 Hz, 3H) 3.17-3.22 (m, 4H) 3.55-3.59 (m, 4H) 3.84 (d, J=6.9 Hz, 1H) 4.38 (q, J=7.1 Hz, 2H) 4.78 (q, J=2.3 Hz, 2H) 5.12 (quint, J=6.9 Hz, 1H)

(b) t-Butyl 4-[4-acetyl-1-(2-butynyl)-5-ethoxycarbonyl-1H-imidazol-2-yl]piperazine-1-carboxylate The title compound was obtained by using t-butyl 4-[1-(2-butynyl)-5-ethoxycarbonyl-4-(1-hydroxyethyl)-1H-imidazol-2-yl]piperazine-1-carboxylate according to the method described in Example 115(g).

$^1$H-NMR (CDCl$_3$)
δ 1.38 (t, J=7.1 Hz, 3H) 1.48 (s, 9H) 1.79 (t, J=2.3 Hz, 3H) 2.53 (s, 3H) 3.14-3.18 (m, 4H) 3.56-3.60 (m, 4H) 4.38 (q, J=7.1 Hz, 2H) 4.77 (q, J=2.3 Hz, 2H)

(c) 3-(2-Butynyl)-5,7-dimethyl-2-(piperazin-1-yl)-3,5-dihydroimidazo[4,5-d]pyridazin-4-one trifluoroacetate 0.15 ml of methylhydrazine was added to a 3 ml ethanol solution of 0.019 g of t-butyl 4-[4-acetyl-1-(2-butynyl)-5-ethoxycarbonyl-1H-imidazol-2-yl]piperazine-1-carboxylate, and the mixture was heated at 110° C. for 25 hours. The solvent was concentrated under reduced pressure. The residue was dissolved in 0.5 ml of dichloromethane, and 0.5 ml of trifluoroacetic acid was added thereto. The solvent was concentrated under reduced pressure. The residue was purified by reverse-phase high performance liquid chromatography (using an acetonitrile-water mobile phase (containing 0.1% trifluoroacetic acid)) to give 0.017 g of the title compound.
MS m/e (ESI) 301.33 (MH$^+$-CF$_3$COOH)

Example 327

3-(2-Butynyl)-7-phenyl-2-(piperazin-1-yl)-3,5-dihydroimidazo[4,5-d]pyridazin-4-one trifluoroacetate

(a) t-Butyl 4-[1-(2-butynyl)-5-ethoxycarbonyl-4-(1-hydroxyphenylmethyl)-1H-imidazol-2-yl]piperazine-1-carboxylate The title compound was obtained by using t-butyl 4-[1-(2-butynyl)-5-ethoxycarbonyl-4-formyl-1H-imidazol-2-yl]piperazine-1-carboxylate and phenylmagnesium bromide according to the method described in Example 326(a).
$^1$H-NMR (CDCl$_3$)
δ 1.33 (t, J=7.3 Hz, 3H) 1.48 (s, 9H) 1.81 (t, J=2.2 Hz, 3H) 3.16-3.27 (m, 4H) 3.55-3.59 (m, 4H) 4.24-4.34 (m, 2H) 4.39 (d, J=8.3 Hz, 1H) 4.78 (q, J=2.2 Hz, 2H) 6.09 (d, J=8.3 Hz, 1H) 7.22 (t, J=8.0 Hz, 1H) 7.30 (t, J=8.0 Hz, 2H) 7.41 (d, J=8.0 Hz, 2H)

(b) t-Butyl 4-[4-benzoyl-1-(2-butynyl)-5-ethoxycarbonyl-1H-imidazol-2-yl]piperazine-1-carboxylate The title compound was obtained by using t-butyl 4-[1-(2-butynyl)-5-ethoxycarbonyl-4-(1-hydroxyphenylmethyl)-1H-imidazol-2-yl]piperazine-1-carboxylate according to the method described in Example 115(g).
$^1$H-NMR (CDCl$_3$)
δ 0.92 (t, J=7.1 Hz, 3H) 1.48 (s, 9H) 1.83 (t, J=2.3 Hz, 3H) 3.22-3.28 (m, 4H) 3.57-3.62 (m, 4H) 4.03 (q, J=7.1 Hz, 2H) 4.88 (q, J=2.3 Hz, 2H) 7.43 (t, J=8.1 Hz, 2H) 7.55 (t, J=8.1 Hz, 1H) 7.92 (d, J=8.1 Hz, 2H)

(c) t-Butyl 4-[1-(2-butynyl)-7-oxo-4-phenyl-6,7-dihydro-1H-imidazo[4,5-d]pyridazin-2-yl]piperazine-1-carboxylate The title compound was obtained by using t-butyl 4-[1-(2-butynyl)-5-ethoxycarbonyl-4-(1-hydroxyphenylmethyl)-1H-imidazol-2-yl]piperazine-1-carboxylate and hydrazine according to the method described in Example 115(h).
$^1$H-NMR (CDCl$_3$)
δ 1.50 (s, 9H) 1.83 (t, J=2.3 Hz, 3H) 3.44-3.48 (m, 4H) 3.63-3.67 (m, 4H) 5.15 (q, J=2.3 Hz, 2H) 7.40-7.50 (m, 3H) 8.34 (d, J=8.1 Hz, 2H) 10.70 (s, 1H)

(d) 3-(2-Butynyl)-7-phenyl-2-(piperazin-1-yl)-3,5-dihydroimidazo[4,5-d]pyridazin-4-one trifluoroacetate The title compound was obtained by using t-butyl 4-[1-(2-butynyl)-7-oxo-4-phenyl-6,7-dihydro-1H-imidazo[4,5-d]pyridazin-2-yl]piperazine-1-carboxylate according to the method described in Example 115(i).
MS m/e (ESI) 349.30 (MH$^+$-CF$_3$COOH)

Example 328

3-(2-Butynyl)-5-methyl-7-phenyl-2-(piperazin-1-yl)-3,5-dihydroimidazo[4,5-d]pyridazin-4-one trifluoroacetate The title compound was obtained by using t-butyl 4-[1-(2-butynyl)-7-oxo-4-phenyl-6,7-dihydro-1H-imidazo[4,5-d]pyridazin-2-yl]piperazine-1-carboxylate and methyl iodide according to the method described in Example 258(b).
$^1$H-NMR (CD$_3$OD)
δ 1.83 (t, J=2.4 Hz, 3H) 3.47-3.51 (m, 4H) 3.71-3.75 (m, 4H) 3.92 (s, 3H) 5.22 (q, J=2.4 Hz, 2H) 7.43-7.48 (m, 3H) 8.35 (d, J=8.1 Hz, 2H)
MS m/e (ESI) 363.31 (MH$^+$-CF$_3$COOH)

Example 329

[3-(2-Butynyl)-4-oxo-7-phenyl-2-(piperazin-1-yl)-3,4-dihydroimidazo[4,5-d]pyridazin-5-yl]acetic acid trifluoroacetate The title compound was obtained by using t-butyl 4-[1-(2-butynyl)-7-oxo-4-phenyl-6,7-dihydro-1H-imidazo[4,5-d]pyridazin-2-yl]piperazine-1-carboxylate and t-butyl bromoacetate according to the method described in Example 258(b).
MS m/e (ESI) 407.29 (MH$^+$-CF$_3$COOH)

Example 330

2-[3-(2-Butynyl)-4-oxo-7-phenyl-2-(piperazin-1-yl)-3,4-dihydroimidazo[4,5-d]pyridazin-5-ylmethyl]benzonitrile trifluoroacetate The title compound was obtained by using t-butyl 4-[1-(2-butynyl)-7-oxo-4-phenyl-6,7-dihydro-1H-imidazo[4,5-d]pyridazin-2-yl]piperazine-1-carboxylate and 2-bromomethylbenzonitrile according to the method described in Example 258(b).
MS m/e (ESI) 464.33 (MH$^+$-CF$_3$COOH)

Example 331

3-(2-Butynyl)-5-methyl-2-(piperazin-1-yl)-7-trifluoromethyl-3,5-dihydroimidazo[4,5-d]pyridazin-4-one trifluoroacetate

(a) t-Butyl 4-[1-(2-butynyl)-5-ethoxycarbonyl-4-(2,2,2-trifluoro-1-hydroxyethyl)-1H-imidazol-2-yl]piperazine-1-carboxylate 0.065 g of zinc and a 2 ml N,N-dimethylformamide solution of 0.200 g of trifluoromethyl iodide were added to a 3 ml N,N-dimethylformamide solution of 0.155 g of t-butyl 4-[1-(2-butynyl)-5-ethoxycarbonyl-4-formyl-1H-imidazol-2-yl]piperazine-1-carboxylate under a nitrogen atmosphere, and the mixture was stirred under sonication for 30 minutes. 30 ml of ethyl acetate and 30 ml of a 5% ammonium chloride solution were added to the mixture. The organic layer was washed twice with 20 ml of water and then with 20 ml of a saturated sodium chloride solution, and dried over magnesium sulfate. The organic liquid was concentrated under reduced pressure. The residue was purified by silica gel column chromatography. Thus, 0.013 g of the title compound was obtained from the fraction eluted with ethyl acetate-hexane (1:9).

$^1$H-NMR (CDCl$_3$)

δ 1.39 (t, J=6.9 Hz, 3H) 1.48 (s, 9H) 1.83 (t, J=2.4 Hz, 3H) 3.15-3.26 (m, 4H) 3.55-3.60 (m, 4H) 4.34 (qq, J=10.2, 6.9 Hz, 2H) 4.53-4.64 (br.s, 1H) 4.83 (qq, J=17.6, 2.4 Hz, 2H) 5.39-5.47 (br.s, 1H)

(b) 3-(2-Butynyl)-5-methyl-2-(piperazin-1-yl)-7-trifluoromethyl-3,5-dihydroimidazo[4,5-d]pyridazin-4-one trifluoroacetate 0.060 g of Dess-Martin reagent was added to a 4 ml dichloromethane solution of 0.013 g of t-butyl 4-[1-(2-butynyl)-5-ethoxycarbonyl-4-(2,2-trifluoro-1-hydroxyethyl)-1H-imidazol-2-yl]piperazine-1-carboxylate, and the mixture was stirred at room temperature for 15 hours. 5 ml of dichloromethane, 10 ml of a saturated aqueous sodium bicarbonate solution and 0.100 g of sodium hydrogen sulfite were added to the solution. The organic layer was dried over magnesium sulfate, and concentrated under reduced pressure. The residue was dissolved in 4 ml of ethanol, and 0.2 ml of methylhydrazine was added to the solution. The mixture was heated at 110° C. for 20 hours. The solvent was concentrated under reduced pressure. The residue was dissolved in 0.5 ml of dichloromethane, and 0.5 ml of trifluoroacetic acid was added thereto. The solvent was concentrated under reduced pressure. The residue was purified by reverse-phase high performance liquid chromatography (using an acetonitrile-water mobile phase (containing 0.1% trifluoroacetic acid)) to give 0.008 g of the title compound.

$^1$H-NMR (CD$_3$OD)

δ 1.83 (t, J=2.3 Hz, 3H) 3.45-3.49 (m, 4H) 3.71-3.75 (m, 4H) 3.87 (s, 3H) 5.18 (q, J=2.3 Hz, 2H)

MS m/e (ESI) 355.16 (MH$^+$-CF$_3$COOH)

Example 332

1-(2-Butynyl)-6-methyl-7-oxo-2-(piperazin-1-yl)-6,7-dihydroimidazo[4,5-d]pyridazine-4-carboxamide trifluoroacetate (a) t-Butyl 4-[1-(2-butynyl)-4-(cyano-hydroxymethyl)-5-methoxycarbonyl-1H-imidazol-2-yl]piperazine-1-carboxylate 0.200 g of sodium cyanide and 0.010 ml of acetic acid were added to a 15 ml acetonitrile solution of t-butyl 4-[1-(2-butynyl)-5-methoxycarbonyl-4-formyl-1H-imidazol-2-yl]piperazine-1-carboxylate, and the mixture was stirred at room temperature for 16 hours. 100 ml of ethyl acetate was added to the solution, and the mixture was washed twice with 50 ml of water and then with 50 ml of a saturated sodium chloride solution. The organic layer was dried over magnesium sulfate, and the solvent was concentrated under reduced pressure. The residue was purified by silica gel column chromatography. Thus, 0.274 g of the title compound was obtained from the fraction eluted with ethyl acetate-hexane (2:3).

$^1$H-NMR (CDCl$_3$)

δ 1.49 (s, 9H) 1.83 (t, J=2.5 Hz, 3H) 3.19-3.23 (m, 4H) 3.56-3.60 (m, 4H) 3.95 (s, 3H) 4.68 (d, J=9.0 Hz, 1H) 4.82 (q, J=2.5 Hz, 2H) 5.72 (d, J=9.0 Hz, 1H)

(b) t-Butyl 4-[1-(2-butynyl)-4-(carbamoyl-hydroxymethyl)-5-methoxycarbonyl-1H-imidazol-2-yl] piperazine-1-carboxylate 3.2 ml of 30% aqueous hydrogen peroxide and 3.2 ml of 28% aqueous ammonia solution were added to an 8 ml methanol solution of 0.274 g of t-butyl 4-[1-(2-butynyl)-4-(cyano-hydroxymethyl)-5-methoxycarbonyl-1H-imidazol-2-yl]piperazine-1-carboxylate at 5° C., and the mixture was stirred for 15 hours. 100 ml of a saturated sodium hydrogen sulfite solution was added to the solution, and the mixture was extracted twice with 100 ml of ethyl acetate. The organic layers were combined together. The combined organic layers were dried over magnesium sulfate, and concentrated under reduced pressure. The residue was purified by silica gel column chromatography. Thus, 0.039 g of the title compound was obtained from the fraction eluted with methanol-ethyl acetate (1:9).

$^1$H-NMR (CDCl$_3$)

δ 1.48 (s, 9H) 1.83 (t, J=2.5 Hz, 3H) 3.13-3.25 (m, 4H) 3.54-3.57 (m, 4H) 3.91 (s, 3H) 4.33-4.37 (br.s, 1H) 4.77 (q, J=2.5 Hz, 2H) 5.54 (s, 1H) 5.63 (s, 1H) 6.82 (s, 1H)

(c) t-Butyl 4-[4-aminooxalyl-1-(2-butynyl)-5-methoxycarbonyl-1H-imidazol-2-yl]piperazine-1-carboxylate 0.051 ml of triethylamine and a 1 ml dimethyl sulfoxide solution of 0.058 g of sulfur trioxide pyridine were added to a 2 ml dichloromethane solution of 0.038 g of t-butyl 4-[1-(2-butynyl)-4-(carbamoyl-hydroxymethyl)-5-methoxycarbonyl-1H-imidazol-2-yl]piperazine-1-carboxylate at 0° C., and the mixture was stirred at room temperature for 15 hours. Then, 0.102 ml of triethylamine and a 1 ml dimethyl sulfoxide solution of 0.116 g of sulfur trioxide pyridine were added, and the mixture was stirred at room temperature for 8 hours. 50 ml of ethyl acetate was added to the solution, and the organic layer was washed successively with 20 ml of an aqueous solution of 1%-sulfuric acid, 20 ml of a saturated sodium bicarbonate solution, and 20 ml of a saturated sodium chloride solution. The organic layer was dried over magnesium sulfate, and concentrated under reduced pressure. The residue was purified by silica gel column chromatography. Thus, 0.021 g of the title compound was obtained from the fraction eluted with ethyl acetate-hexane (2:1).

$^1$H-NMR (CDCl$_3$)

δ 1.48 (s, 9H) 1.82 (t, J=2.5 Hz, 3H) 3.19-3.23 (m, 4H) 3.56-3.59 (m, 4H) 3.84 (s, 3H) 4.84 (q, J=2.5 Hz, 2H) 5.62 (br.s, 1H) 7.02 (br., 1H)

(d) t-Butyl 4-[1-(2-butynyl)-4-carbamoyl-6-methyl-7-oxo-6,7-dihydro-1H-dihydroimidazo[4,5-d]pyridazin-2-yl]piperazine-1-carboxylate The title compound was obtained by using t-butyl 4-[4-aminooxalyl-1-(2-butynyl)-5-methoxycarbonyl-1H-imidazol-2-yl]piperazine-1-carboxylate according to the method described in Example 115 (h).

$^1$H-NMR (CDCl$_3$)

δ 1.50 (s, 9H) 1.84 (t, J=2.3 Hz, 3H) 3.46-3.50 (m, 4H) 3.63-3.66 (m, 4H) 3.99 (s, 3H) 5.12 (q, J=2.3 Hz, 2H) 6.16 (s, 1H) 8.85 (s, 1H)

(e) 1-(2-Butynyl)-6-methyl-7-oxo-2-(piperazin-1-yl)-6,7-dihydroimidazo[4,5-d]pyridazine-4-carboxamide trifluoroacetate The title compound was obtained by using t-butyl 4-[1-(2-butynyl)-4-carbamoyl-6-methyl-7-oxo-6,7-dihydro-1H-dihydroimidazo[4,5-d]pyridazin-2-yl]piperazine-1-carboxylate according to the method described in Example 115(i).
MS m/e (ESI) 330.18 (MH$^+$-CF$_3$COOH)

Example 333

1-(2-Butynyl)-6-methyl-7-oxo-2-(piperazin-1-yl)-6,7-dihydroimidazo[4,5-d]pyridazine-4-carbonitrile trifluoroacetate 0.030 ml of triethylamine and 0.015 ml of phosphorus oxychloride were added to a 1 ml dichloromethane solution of 0.015 g of t-butyl 4-[1-(2-butynyl)-4-carbamoyl-6-methyl-7-oxo-6,7-dihydro-1H-dihydroimidazo[4,5-d]pyridazin-2-yl]piperazine-1-carboxylate, and the mixture was stirred at room temperature for 15 hours. 1 ml of dichloromethane and 1 ml of trifluoroacetic acid were added to the solution. After one hour, the solvent was concentrated under reduced pressure. The residue was purified by reverse-phase high performance liquid chromatography (using an acetonitrile-water mobile phase (containing 0.1% trifluoroacetic acid)) to give 0.001 g of the title compound.
$^1$H-NMR (CD$_3$OD)
δ 1.83 (t, J=2.3 Hz, 3H) 3.45-3.49 (m, 4H) 3.74-3.78 (m, 4H) 3.88 (s, 3H) 5.18 (q, J=2.3 Hz, 2H)
MS m/e (ESI) 312.25 (MH$^+$-CF$_3$COOH)

Example 334

3-(2-Butynyl)-7-dimethylamino-5-methyl-2-(piperazin-1-yl)-3,5-dihydroimidazo[4,5-d]pyridazin-4-one trifluoroacetate (a) 1-Benzyl-7-chloro-5-methyl-1,5-dihydroimidazo[4,5-d]pyridazin-4-one 0.604 g of potassium carbonate and 0.297 ml of methyl iodide were added to a 30 ml N,N-dimethylformamide solution of 1.035 g of 1-benzyl-7-chloro-1,5-dihydroimidazo[4,5-d]pyridazin-4-one (J. A. Carbon Journal of the American Chemical Society, 80, pp. 6083, 1958), and the mixture was stirred at room temperature for 15 hours. 300 ml of ethyl acetate and 100 ml of water were added to the solution, and the organic layer was washed twice with 100 ml of water and then with 100 ml of a saturated sodium chloride solution. The organic layer was dried over magnesium sulfate, and concentrated under reduced pressure. The residue was purified by silica gel column chromatography. Thus, 0.280 g of the title compound was obtained from the fraction eluted with ethyl acetate.
$^1$H-NMR (CDCl$_3$)
δ 3.86 (s, 3H) 5.64 (s, 2H) 7.11-7.16 (m, 2H) 7.35-7.43 (m, 3H) 7.90 (s, 1H)

(b) 1-Benzyl-7-dimethylamino-5-methyl-1,5-dihydroimidazo[4,5-d]pyridazin-4-one

A 2 ml aqueous solution of 50% dimethylamine was added to a 2 ml ethanol solution of 0.138 g of 1-benzyl-7-chloro-5-methyl-1,5-dihydroimidazo[4,5-d]pyridazin-4-one, and the mixture was heated at 130° C. for 72 hours. The reaction solution was cooled to room temperature, and concentrated under reduced pressure. The residue was purified by silica gel column chromatography. Thus, 0.139 g of the title compound was obtained from the fraction eluted with methanol-ethyl acetate (1:19).
$^1$H-NMR (CDCl$_3$)
δ 2.73 (s, 6H) 3.79 (s, 3H) 5.59 (s, 2H) 7.12-7.16 (m, 2H) 7.30-7.39 (m, 3H) 7.79 (s, 1H)

(c) 1-Benzyl-2-chloro-7-dimethylamino-5-methyl-1,5-dihydroimidazo[4,5-d]pyridazin-4-one 1.15 ml of a 1 M tetrahydrofuran solution of dibutylmagnesium was added to a 2 ml tetrahydrofuran solution of 0.320 ml of diisopropylamine at room temperature under a nitrogen atmosphere, and the mixture was stirred for 8 hours. This solution was added to a 4 ml tetrahydrofuran solution of 0.162 g of 1-benzyl-7-dimethylamino-5-methyl-1,5-dihydroimidazo[4,5-d]pyridazin-4-one at room temperature under a nitrogen atmosphere, and the mixture was stirred at room temperature for 15 hours. Then, a 5 ml tetrahydrofuran solution of 0.540 g of hexachloroethane was added dropwise to the solution. After the mixture had been stirred for 4 hours, 30 ml of a 5% aqueous ammonium chloride solution was added thereto. The mixture was extracted with 100 ml of ethyl acetate. The organic layer was washed successively with 30 ml of water and 30 ml of a saturated sodium chloride solution, and dried over magnesium sulfate. The organic layer was concentrated under reduced pressure. The residue was purified by silica gel column chromatography. Thus, 0.094 g of the title compound was obtained from the fraction eluted with ethyl acetate-hexane (2:1).
$^1$H-NMR (CDCl$_3$)
δ 2.68 (s, 6H) 3.78 (s, 3H) 5.60 (s, 2H) 7.05-7.08 (m, 2H) 7.29-7.37 (m, 3H)

(d) t-Butyl 4-[1-benzyl-7-dimethylamino-5-methyl-4-oxo-4,5-dihydro-1H-imidazo[4,5-d]pyridazin-2-yl]piperazine-1-carboxylate The title compound was obtained by using 1-benzyl-2-chloro-7-dimethylamino-5-methyl-1,5-dihydroimidazo[4,5-d]pyridazin-4-one according to the method described in Example 116(c).
$^1$H-NMR (CDCl$_3$)
δ 1.47 (s, 9H) 2.68 (s, 6H) 3.19-3.22 (m, 4H) 3.41-3.46 (m, 4H) 3.76 (s, 3H) 5.40 (s, 2H) 6.88 (m, 2H) 7.20-7.25 (m, 3H)

(e) t-Butyl 4-[7-dimethylamino-5-methyl-4-oxo-4,5-dihydro-1H-imidazo[4,5-d]pyridazin-2-yl]piperazine-1-carboxylate A 5 ml tetrahydrofuran solution of 0.117 g of t-butyl 4-[1-benzyl-7-dimethylamino-5-methyl-4-oxo-4,5-dihydro-1H-imidazo[4,5-d]pyridazin-2-yl]piperazine-1-carboxylate was added to 15 ml of liquid ammonia, and 0.009 g of lithium was added to the mixture under reflux. 1 ml of a 5% aqueous ammonium chloride solution was added to the solution, and the solvent was evaporated off. The residue was purified by reverse-phase high performance liquid chromatography (using an acetonitrile-water mobile phase (containing 0.1% trifluoroacetic acid)) to give 0.007 g of the title compound.
$^1$H-NMR (CD$_3$OD)
δ 1.48 (s, 9H) 3.11 (s, 6H) 3.55-3.58 (m, 8H) 3.69 (s, 3H)

(f) 3-(2-Butynyl)-7-dimethylamino-5-methyl-2-(piperazin-1-yl)-3,5-dihydroimidazo[4,5-d]pyridazin-4-one trifluoroacetate The title compound was obtained by using t-butyl 4-[7-dimethylamino-5-methyl-4-oxo-4,5-dihydro-1H-imidazo[4,5-d]pyridazin-2-yl]piperazine-1-carboxylate and 1-bromo-2-butyne according to the method described in Example 258 (b).

$^1$H-NMR (CD$_3$OD)

δ 1.80 (t, J=2.3 Hz, 3H) 2.75 (s, 6H) 3.44-3.48 (m, 4H) 3.62-3.65 (m, 4H) 3.68 (s, 3H) 5.16 (q, J=2.3 Hz, 2H)

MS m/e (ESI) 330.16 (MH$^+$-CF$_3$COOH)

Example 335

3-(2-Butynyl)-5-methyl-2-(piperidin-4-yl)-3,5-dihydroimidazo[4,5-d]pyridazin-4-one trifluoroacetate (a) 5-Methyl-2-(piperidin-4-yl)-3,5-dihydroimidazo[4,5-d]pyridazin-4-one trifluoroacetate 2.71 g of iron (III) chloride was added to a 16 ml ethanol solution of 0.292 g of 4,5-diamino-2-methyl-2H-pyridazin-3-one [CAS No. 4725-76-2] (Martine Beljean-Leymarie, Michel Pays and Jean-Claude Richer, Canadian Journal of Chemistry 61, pp. 2563, 1983) and 0.426 g of t-butyl 4-formylpiperidine-1-carboxylate, and the mixture was heated under reflux for 6 hours. The reaction solution was cooled to room temperature. The solution was filtered, and concentrated under reduced pressure. The residue was purified by reverse-phase high performance liquid chromatography (using an acetonitrile-water mobile phase (containing 0.1% trifluoroacetic acid)) to give 0.061 g of the title compound.

$^1$H-NMR (CD$_3$OD)

δ 2.06-2.17 (m, 2H) 2.28-2.35 (m, 2H) 3.15-3.24 (m, 2H) 3.29-3.35 (m, 1H) 3.50-3.56 (m, 2H) 3.85 (s, 3H) 8.28 (s, 1H)

(b) t-Butyl 4-(6-methyl-7-oxo-6,7-dihydro-1H-imidazo[4,5-d]pyridazin-2-yl)piperidine-1-carboxylate The title compound was obtained by using 5-methyl-2-(piperidin-4-yl)-3,5-dihydroimidazo[4,5-d]pyridazin-4-one trifluoroacetate according to the method described in Example 258(a).

$^1$H-NMR (CDCl$_3$)

δ 1.50 (s, 9H) 2.00-2.16 (m, 4H) 2.85-2.99 (br.s, 2H) 3.23 (tt, J=11.9, 4.0 Hz, 1H) 3.95 (s, 3H) 4.11-4.40 (br.s, 2H) 8.39 (s, 1H) 13.90 (s, 1H)

(c) t-Butyl 4-[1-(2-butynyl)-6-methyl-7-oxo-6,7-dihydro-1H-imidazo[4,5-d]pyridazin-2-yl]piperidine-1-carboxylate The title compound was obtained by using t-butyl 4-(6-methyl-7-oxo-6,7-dihydro-1H-imidazo[4,5-d]pyridazin-2-yl)piperidine-1-carboxylate according to the method described in Example 119(d).

$^1$H-NMR (CDCl$_3$)

δ 1.48 (s, 9H) 1.81 (t, J=2.3 Hz, 3H) 1.93-2.00 (m, 4H) 2.85-2.96 (br.s, 2H) 3.14 (quint, J=7.9 Hz, 1H) 3.85 (s, 3H) 4.16-4.37 (br.s, 2H) 5.39 (q, J=2.3 Hz, 2H) 8.24 (s, 1H)

(d) 3-(2-Butynyl)-5-methyl-2-(piperidin-4-yl)-3,5-dihydroimidazo[4,5-d]pyridazin-4-one trifluoroacetate The title compound was obtained by using t-butyl 4-[1-(2-butynyl)-6-methyl-7-oxo-6,7-dihydro-1H-imidazo[4,5-d]pyridazin-2-yl]piperidine-1-carboxylate according to the method described in Example 115(i).

$^1$H-NMR (CD$_3$OD)

δ 1.80 (t, J=2.3 Hz, 3H) 2.10-2.11 (m, 2H) 2.25-2.32 (m, 2H) 3.18-3.41 (m, 3H) 3.56-3.61 (m, 2H) 3.83 (s, 3H) 5.47 (t, J=2.3 Hz, 2H) 8.27 (s, 1H)

MS m/e (ESI) 286.27 (MH$^+$-CF$_3$COOH)

Example 336

3-(2-Butynyl)-5-methyl-2-(piperazin-1-yl)-3,5-dihydroimidazo[4,5-c]pyridin-4-one trifluoroacetate (a) 3-(2-Butynyl)-4-chloro-3H-imidazo[4,5-c]pyridine 2.0 μg of 4-chloro-1H-imidazo[4,5-c]pyridine, 1.37 ml of 1-bromo-2-butyne, and 1.98 g of potassium carbonate were suspended in 15 ml of N,N-dimethylformamide, and the suspension was stirred at room temperature for 18 hours. The reaction solution was diluted with ethyl acetate, and washed with water. The organic layer was dried over anhydrous magnesium sulfate, then filtered. The filtrate was concentrated under reduced pressure. The residue was purified by silica gel column chromatography. Thus, 1.79 g of a 1:1 mixture consisting of the title compound and the compound alkylated at the 1-position was obtained from the fraction eluted with hexane-ethyl acetate (1:2).

(b) 3-(2-Butynyl)-2,4-dichloro-3H-imidazo[4,5-c]pyridine 2.22 ml of a tetrahydrofuran solution of lithium diisopropylamide was added dropwise to a 5 ml tetrahydrofuran solution of 490 mg of 3-(2-butynyl)-4-chloro-3H-imidazo[4,5-c]pyridine in a dry ice-methanol bath, and the mixture was stirred below −66° C. for 20 minutes. The resulting reaction mixture was added dropwise to a 2 ml tetrahydrofuran solution of 1.13 g of hexachloroethane while the temperature of the mixture was controlled to be −63° C. or lower. The mixture was stirred for one hour and 40 minutes in the same bath, and then a saturated aqueous ammonium chloride solution was added thereto. The resulting mixture was extracted twice with ethyl acetate, and the organic layer was dried over anhydrous magnesium sulfate, then filtered. The filtrate was concentrated under reduced pressure. Then, the resulting residue was purified by silica gel column chromatography. Thus, 120 mg of brown oily material was obtained from the fraction eluted with hexane-ethyl acetate (2:1).

$^1$H-NMR (d6-DMSO)

δ 1.78 (s, 3H) 5.29 (s, 2H) 7.70 (d, J=5.6 Hz, 1H) 8.21 (d, J=5.6 Hz, 1H)

(c) t-Butyl 4-[3-(2-butynyl)-4-chloro-3H-imidazo[4,5-c]pyridin-2-yl]piperazine-1-carboxylate 211 mg of t-butyl 3-(2-butynyl)-2,4-dichloro-3H-imidazo[4,5-c]pyridine, 197 mg of piperazine-1-carboxylate, and 222 mg of sodium bicarbonate were dissolved in ethanol, and the mixture was stirred at 80° C. for 30 minutes and then at room temperature for three hours and 20 minutes. The reaction solution was diluted with ethyl acetate, and the solution was washed with water. The organic layer was dried over anhydrous magnesium sulfate, then filtered. The filtrate was concentrated under reduced pressure. The residue was purified by silica gel column chromatography. Thus, 244 mg of the title compound was obtained from the fraction eluted with hexane-ethyl acetate (3:1).

$^1$H-NMR (CDCl$_3$)

δ: 1.52 (s, 9H) 1.87 (s, 3H) 3.47-3.49 (m, 4H) 3.65-3.68 (m, 4H) 4.94 (s, 2H) 7.41 (d, J=5.2 Hz, 1H) 8.15 (d, J=5.2 Hz, 1H)

(d) 3-(2-Butynyl)-5-methyl-2-(piperazin-1-yl)-3,5-dihydroimidazo[4,5-c]pyridin-4-one trifluoroacetate 98 mg of sodium acetate was dissolved in 2 ml of dimethyl sulfoxide containing 0.3 mmol of t-butyl 4-[3-(2-butynyl)-4-chloro-3H-imidazo[4,5-c]pyridin-2-yl]piperazine-1-carboxylate, and the mixture was stirred at 120° C. for 4 hours. Then, 100 mg of potassium carbonate and 1 ml of methyl iodide were added to the reaction solution. The mixture was stirred at room temperature. The reaction solution was diluted with ethyl acetate, and the solution was washed with water. The organic layer was dried over anhydrous magnesium sulfate, then filtered. The filtrate was concentrated under reduced pressure. The residue was purified by silica gel column chromatography. 5 mg of the product obtained from the fraction eluted with methanol-ethyl acetate (1:10) was dissolved in 0.5 ml of trifluoroacetic acid, and the mixture was concentrated. The residue was purified by reverse-phase high performance liquid chromatography (using an acetonitrile-water mobile phase (containing 0.1% trifluoroacetic acid)) to give 0.55 mg of the title compound.

MS m/e (ESI) 286 (MH$^+$-CF$_3$COOH)

Example 337

3-Benzyl-2-(piperazin-1-yl)-3,5-dihydroimidazo[4,5-c]pyridin-4-one trifluoroacetate (a) Allyl-(3-nitropyridin-4-yl)amine 40 ml of allylamine was added to a 400 ml ethanol solution of 18.0 g of 4-ethoxy-3-nitropyridine hydrochloride, and the mixture was heated under reflux for 8 hours. The reaction solution was concentrated under reduced pressure. The residue was purified by silica gel column chromatography. Thus, 13.6 g of the title compound was obtained from the fraction eluted with ethyl acetate-hexane (1:1).

$^1$H-NMR (CDCl$_3$)

δ 4.00 (m, 2H) 5.29-5.35 (m, 2H) 5.87-5.98 (m, 1H) 6.63 (d, J=6.5 Hz, 1H) 8.30 (d, J=6.5 Hz, 1H) 8.31 (br.s, 1H) 9.23 (s, 1H)

(b) N*4*-allyl-2-chloropyridine-3,4-diamine 55 ml of 35% hydrochloric acid was added to 3.02 g of allyl-(3-nitropyridin-4-yl)amine, and the mixture was heated to 90° C. 19.1 g of tin chloride was added to the solution, and the mixture was kept at 90° C. for 30 minutes. The reaction solution was cooled in an ice-water bath, and then 250 ml ice/water was added thereto. The reaction solution was concentrated under reduced pressure, and then 250 ml of ammonia-saturated methanol was added thereto. The mixture was stirred for 20 hours. 750 ml of ethyl acetate was added to the solution, and the mixture was filtered through celite. The filtrate was concentrated under reduced pressure. The residue was purified by silica gel column chromatography. Thus, 2.88 g of the title compound was obtained from the fraction eluted with ethyl acetate-hexane (1:1).

$^1$H-NMR (CDCl$_3$)

δ 3.29-3.58 (br.s, 2H) 3.84 (d, J=6.3 Hz, 2H) 4.26-4.37 (br.s, 1H) 5.24 (d, J=11.0 Hz, 1H) 5.29 (d, J=16.0 Hz, 1H) 5.85-5.98 (ddt, J=16.0, 11.0, 6.5 Hz, 1H) 6.43 (d, J=6.5 Hz, 1H) 7.66 (d, J=6.5 Hz, 1H)

(c) 1-Allyl-4-chloro-1,3-dihydroimidazo[4,5-c]pyridin-2-one

A 400 ml acetonitrile solution of 4.46 g of N,N'-disuccinimidyl carbonate was added to an acetonitrile solution containing 2.88 g of N*4*-allyl-2-chloropyridine-3,4-diamine, and the mixture was heated under reflux for 70 hours. The solvent was concentrated under reduced pressure, and the residue was dissolved in a mixture consisting of 500 ml of ethyl acetate and 300 ml of water. The organic layer was washed twice with 100 ml of 1N hydrochloric acid and then with 100 ml of a saturated sodium chloride solution. The organic layer was dried over magnesium sulfate, and concentrated under reduced pressure. The residue was purified by silica gel column chromatography. Thus, 2.30 g of the title compound was obtained from the fraction eluted with ethyl acetate-dichloromethane (1:1).

$^1$H-NMR (CDCl$_3$)

δ 4.51 (d, J=5.7 Hz, 1H) 5.25 (d, J=16.0 Hz, 1H) 5.30 (d, J=10.9 Hz, 1H) 5.85-5.95 (ddt, J=16.0, 10.9, 5.7 Hz, 1H) 6.91 (d, J=6.9 Hz, 1H) 8.10 (d, J=6.9 Hz, 1H) 8.99 (br.s, 1H)

(d) 1-Allyl-3-benzyl-4-chloro-1,3-dihydroimidazo[4,5-c]pyridin-2-one 0.76 g of potassium carbonate and 0.94 g of benzyl bromide were added to a 50 ml N,N-dimethylformamide solution of 1.05 g of 1-allyl-4-chloro-1,3-dihydroimidazo[4,5-c]pyridin-2-one, and the mixture was stirred at room temperature for 14 hours. 300 ml of water and 300 ml of ethyl acetate were added to the solution, and the organic layer was washed three times with 100 ml of water and then with 100 ml of a saturated sodium chloride solution. The organic layer was dried over magnesium sulfate, and concentrated under reduced pressure to give 1.57 g of the title compound.

$^1$H-NMR (CDCl$_3$)

δ 4.56 (d, J=5.7 Hz, 1H) 5.23 (d, J=16.0 Hz, 1H) 5.30 (d, J=10.9 Hz, 1H) 5.44 (s, 2H) 5.85-5.95 (ddt, J=16.0, 10.9, 5.7 Hz, 1H) 6.91 (d, J=6.9 Hz, 1H) 7.25-7.34 (m, 5H) 8.08 (d, J=6.9 Hz, 1H) 8.99 (br.s, 1H)

(e) 3-Benzyl-4-chloro-1,3-dihydroimidazo[4,5-c]pyridin-2-one 1.5 ml of water, 1.06 g of 4-methyl morpholine N-oxide, 3 ml of an aqueous solution of 2% osmic acid, and a 6 ml aqueous solution of 1.94 g of sodium periodate were added to a 15 ml 1,4-dioxane solution of 0.75 g of 1-allyl-3-benzyl-4-chloro-1,3-dihydroimidazo[4,5-c]pyridin-2-one, and the mixture was heated at 60° C. for 18 hours. 200 ml of water was added to the solution, and the mixture was extracted with 100 ml of ethyl acetate. The organic layer was washed twice with 50 ml of water and then washed with 50 ml of a saturated sodium chloride solution. The organic layer was dried over magnesium sulfate, and concentrated under reduced pressure. The residue was purified by silica gel column chromatography. Thus, 0.38 g of the title compound was obtained from the fraction eluted with ethyl acetate-hexane (1:1).

$^1$H-NMR (CDCl$_3$)

δ 5.44 (s, 2H) 7.01 (d, J=6.5 Hz, 1H) 7.30-7.38 (m, 5H) 8.08 (d, J=6.5 Hz, 1H) 9.18 (s, 1H)

(f) 3-Benzyl-2,4-dichloro-1,3-dihydroimidazo[4,5-c]pyridine 5 ml of phosphorus oxychloride and 0.338 g of phosphorus pentachloride were added to 0.383 g of 3-benzyl-4-chloro-1,3-dihydroimidazo[4,5-c]pyridin-2-one, and the mixture was heated under reflux for 24 hours. The solvent was concentrated under reduced pressure, and the residue was poured into 50 g of ice/water. The mixture was extracted with 100 ml of ethyl acetate. The organic layer was dried over magnesium sulfate, and concentrated under reduced pressure. The residue was purified by silica gel column chromatography. Thus, 0.13 g of the title compound was obtained from the fraction eluted with ethyl acetate-hexane (2:1).

$^1$H-NMR (CDCl$_3$)

δ 5.43 (s, 2H) 7.12 (d, J=6.5 Hz, 1H) 7.30-7.38 (m, 5H) 8.18 (d, J=6.5 Hz, 1H)

(g) t-Butyl 4-(3-benzyl-4-chloro-3H-imidazo[4,5-c]pyridin-2-yl)piperazine-1-carboxylate 0.094 g of t-butyl piperazine-1-carboxylate was added to a 1 ml N,N-dimethylformamide solution of 0.127 g of 3-benzyl-2,4-dichloro-1,3-dihydroimidazo[4,5-c]pyridine, and the mixture was heated at 150° C. for two hours. 25 ml of ethyl acetate was added to the mixture, and the organic layer was washed three times with 10 ml of water and then with 10 ml of an aqueous solution saturated with sodium chloride. The organic liquid was dried over magnesium sulfate, and concentrated under reduced pressure. The residue was purified by silica gel column chromatography. Thus, 0.029 g of the title compound was obtained from the fraction eluted with ethyl acetate-hexane (3:2).

$^1$H-NMR (CDCl$_3$)

δ 1.44 (s, 9H) 3.21-3.25 (m, 4H) 3.49-3.53 (m, 4H) 5.53 (s, 2H) 7.0.8 (d, J=6.5 Hz, 1H) 7.30-7.38 (m, 5H) 8.14 (d, J=6.5 Hz, 1H)

(h) 3-Benzyl-2-(piperazin-1-yl)-3,5-dihydroimidazo[4,5-c]pyridin-4-one trifluoroacetate 1 ml of water and 1 ml of 35% hydrochloric acid were added to a 2 ml N,N-dimethylformamide solution of 0.029 g of t-butyl 4-(3-benzyl-4-chloro-3H-imidazo[4,5-c]pyridin-2-yl)piperazine-1-carboxylate, and the mixture was heated under reflux for 36 hours. The solvent was concentrated under reduced pressure. The residue was purified by reverse-phase high performance liquid chromatography (using an acetonitrile-water mobile phase (containing 0.1% trifluoroacetic acid)) to give 0.006 g of the title compound.

MS m/e (ESI) 310.29 (MH$^+$-CF$_3$COOH)

Example 338

3-(2-Butynyl)-2-(piperazin-1-yl)-3,5-dihydroimidazo[4,5-c]pyridin-4-one trifluoroacetate (a) 2-bromo-1-(2-butynyl)-1H-imidazole-4,5-dicarbonitrile 69.8 g of potassium carbonate and 50 ml N,N-dimethylformamide solution of 74 ml of 1-bromo-2-butyne were added to a 520 ml N,N-dimethylformamide solution of 90.6 g of 2-bromo-1H-imidazole-4,5-dicarbonitrile [CAS No 50847-09-1], and the mixture was heated at 50° C. for 8 hours. 1 L of ethyl acetate and 500 ml of water were added to the solution, and the organic layer was washed twice with 500 ml of water and then with 500 ml of a saturated sodium chloride solution. The organic layer was dried over magnesium sulfate, and concentrated under reduced pressure. The residue was purified by silica gel column chromatography. Thus, 48.0 g of the title compound was obtained from the fraction eluted with ethyl acetate-hexane (1:4).

$^1$H-NMR (CDCl$_3$)

δ 1.87 (t, J=2.3 Hz, 3H) 4.85 (q, J=2.3 Hz, 2H)

(b) Ethyl 2-bromo-1-(2-butynyl)-5-cyano-1H-imidazole-4-carboxylate 25 ml of concentrated sulfuric acid was added to a 500 ml ethanol solution of 48.0 g of 2-bromo-1-(2-butynyl)-1H-imidazole-4,5-dicarbonitrile, and the mixture was heated under reflux for 110 hours. The reaction solution was cooled to room temperature, and then concentrated under reduced pressure. The residue was dissolved in a mixture consisting of 500 ml of ethyl acetate and 500 ml of water, and the pH of the solution was adjusted to 8 using potassium hydroxide. The aqueous layer was extracted with 500 ml of ethyl acetate, and the organic layers were combined together. The organic layer was dried over magnesium sulfate, and concentrated under reduced pressure. The residue was purified by silica gel column chromatography. Thus, 21.7 g of the title compound was obtained from the fraction eluted with ethyl acetate-hexane (1:3).

$^1$H-NMR (CDCl$_3$)

δ 1.43 (t, J=7.0 Hz, 3H) 1.87 (t, J=2.3 Hz, 3H) 4.46 (q, J=-7.0 Hz, 2H) 4.85 (q, J=2.3 Hz, 2H)

(c) t-Butyl 4-[1-(2-butynyl)-5-cyano-4-ethoxycarbonyl-1H-imidazol-2-yl]piperazine-1-carboxylate 25.1 g of the title compound was obtained by using 21.7 g of ethyl 2-bromo-1-(2-butynyl)-5-cyano-1H-imidazole-4-carboxylate according to the method described in Example 115(b).

$^1$H-NMR (CDCl$_3$)

δ 1.43 (t, J=7.0 Hz, 3H) 1.49 (s, 9H) 1.87 (t, J=2.3 Hz, 3H) 3.22-3.26 (m, 4H) 3.56-3.61 (m, 4H) 4.44 (q, J=7.0 Hz, 2H) 4.68 (q, J=2.3 Hz, 2H)

(d) t-Butyl 4-[1-(2-butynyl)-4-carboxy-5-cyano-1H-imidazol-2-yl]piperazine-1-carboxylate 16 ml of a 5N aqueous sodium hydroxide solution was added to a 500 ml ethanol solution of 25.1 g of t-butyl 4-[1-(2-butynyl)-5-cyano-4-ethoxycarbonyl-1H-imidazol-2-yl] piper azine-1-carboxylate, and the mixture was stirred at room temperature for two hours. Then, the solvent was concentrated under reduced pressure. The residue was dissolved in a mixture consisting of 1 L of ethyl acetate and 500 ml of water. 50 ml of 2N hydrochloric acid was added to the solution. The organic layer was washed with 200 ml of a saturated sodium chloride solution, and dried over magnesium sulfate. The organic liquid was concentrated under reduced pressure to give 23.2 g of the title compound.

$^1$H-NMR (CDCl$_3$)

δ 1.49 (s, 9H) 1.87 (t, J=2.3 Hz, 3H) 3.22-3.26 (m, 4H) 3.56-3.61 (m, 4H) 4.68 (q, J=2.3 Hz, 2H)

(e) t-Butyl 4-[1-(2-butynyl)-5-cyano-4-hydroxymethyl-1H-imidazol-2-yl]piperazine-1-carboxylate 6.9 g of triethylamine and then 100 ml tetrahydrofuran solution of 10.19 g of isobutyl chloroformate were added dropwise to 600 ml of tetrahydrofuran containing 22.9 g of t-butyl 4-[1-(2-butynyl)-4-carboxy-5-cyano-1H-imidazol-2-yl]piperazine-1-carboxylate at −10° C. After the precipitate had been removed by filtration, the solution was again cooled to −10° C. A 100 ml aqueous solution of 9.45 g of sodium borohydride was added dropwise to the solution. After one hour, 500 ml of ethyl acetate and 500 ml of water were added to the solution. The pH of the solution was adjusted to 5 using 1 N hydrochloric acid, and then adjusted to 10 using a saturated sodium bicarbonate solution. The organic layer was washed successively with 500 ml of water and 500 ml of a saturated sodium chloride solution. The organic layer was dried over magnesium sulfate, and concentrated under reduced pressure. The residue was purified by silica gel column chromatography. Thus, 19.1 g of the title compound was obtained from the fraction eluted with ethyl acetate-hexane (4:1).

$^1$H-NMR (CDCl$_3$)

δ 1.48 (s, 9H) 1.84 (t, J=2.3 Hz, 3H) 2.26 (t, J=6.3 Hz, 1H) 3.13-3.17 (m, 4H) 3.53-3.57 (m, 4H) 4.58 (q, J=2.3 Hz, 2H) 4.64 (d, J=6.3 Hz, 2H)

(f) t-Butyl 4-[1-(2-butynyl)-5-cyano-4-formyl-1H-imidazol-2-yl]piperazine-1-carboxylate 3.28 g of manganese dioxide was added to a 5 ml dichloromethane solution of 1.35 g of t-butyl 4-[1-(2-butynyl)-5-cyano-4-hydroxymethyl-1H-imidazol-2-yl]piperazine-1-carboxylate. The reaction solution was stirred at room temperature for 15 hours, then stirred and heated under reflux for five hours. The solution was filtered, and then concentrated under reduced pressure. The residue was purified by silica gel column chromatography. Thus, 1.11 g of the title compound was obtained from the fraction eluted with ethyl acetate-hexane (2:3).

$^1$H-NMR (CDCl$_3$)

δ 1.50 (s, 9H) 1.88 (t, J=2.3 Hz, 3H) 3.24-3.28 (m, 4H) 3.59-3.63 (m, 4H) 4.70 (q, J=2.3 Hz, 2H) 9.87 (s, 1H)

(g) t-Butyl 4-[1-(2-butynyl)-5-cyano-4-(2-ethoxycarbonylvinyl)-1H-imidazol-2-yl]piperazine-1-carboxylate 0.038 g of sodium hydride was added to a 5 ml tetrahydrofuran solution of 0.243 g of ethyl diethylphosphonoacetate at 5° C. under a nitrogen atmosphere. 0.310 g of t-butyl 4-[1-(2-butynyl)-5-cyano-4-formyl-1H-imidazol-2-yl]piperazine-1-carboxylate dissolved in 5 ml of tetrahydrofuran was added, and the mixture was stirred for 30 minutes. 50 ml of ethyl acetate and 25 ml of 0.1N sodium hydroxide were added to the solution. The organic layer was dried over magnesium sulfate, and concentrated under reduced pressure. The residue was purified by silica gel column chromatography. Thus, 0.380 g of the title compound was obtained from the fraction eluted with ethyl acetate-hexane (3:7).

$^1$H-NMR (CDCl$_3$)

δ 1.33 (t, J=7.4 Hz, 3H) 1.50 (s, 9H) 1.8.6 (t, J=2.3 Hz, 3H) 3.19-3.23 (m, 4H) 3.55-3.59 (m, 4H) 4.25 (q, J=7.4 Hz, 2H) 4.59 (q, J=2.3 Hz, 2H) 6.70 (d, J=15.8 Hz, 1H) 7.50 (d, J=15.8 Hz, 1H)

(h) t-Butyl 4-[1-(2-butynyl)-5-cyano-4-(2-carboxyvinyl)-1H-imidazol-2-yl]piperazine-1-carboxylate The title compound was obtained by using t-butyl 4-[1-(2-butynyl)-5-cyano-4-(2-ethoxycarbonylvinyl)-1H-imidazol-2-yl]piperazine-1-carboxylate according to the method described in Example 338(d).

$^1$H-NMR (CDCl$_3$)

δ 1.50 (s, 9H) 1.86 (t, J=2.3 Hz, 3H) 3.19-3.23 (m, 4H) 3.55-3.59 (m, 4H) 4.59 (q, J=2.3 Hz, 2H) 6.70 (d, J=15.8 Hz, 1H) 7.50 (d, J=15.8 Hz, 1H)

(i) t-Butyl 4-[1-(2-butynyl)-5-cyano-4-(2-azidecarbonylvinyl)-1H-imidazol-2-yl]piperazine-1-carboxylate A mixture consisting of 0.200 g of t-butyl 4-[1-(2-butynyl)-5-cyano-4-(2-carboxyvinyl)-1H-imidazol-2-yl]piperazine-1-carboxylate, 0.073 ml of triethylamine, and a 2 ml t-butanol solution of 0.108 ml of diphenylphosphoryl azide was heated at 50° C. under a nitrogen atmosphere for 4 hours. 50 ml of ethyl acetate was added to the solution, and the mixture was washed with 20 ml of water. The organic layer was dried over magnesium sulfate, and concentrated under reduced pressure. The residue was purified by silica gel column chromatography. Thus, 0.178 g of the title compound was obtained from the fraction eluted with ethyl acetate-hexane (2:3).

$^1$H-NMR (CDCl$_3$)

δ 1.48 (s, 9H) 1.86 (t, J=2.2 Hz, 3H) 3.19-3.23 (m, 4H) 3.55-3.59 (m, 4H) 4.59 (q, J=2.2 Hz, 2H) 6.67 (d, J=15.4 Hz, 1H) 7.56 (d, J=15.4 Hz, 1H)

(j) t-Butyl 4-[4-(2-t-butoxycarbonylaminovinyl)-1-(2-butynyl)-5-cyano-1H-imidazol-2-yl]piperazine-1-carboxylate A 10 ml t-butanol solution of 0.178 g of t-butyl 4-[1-(2-butynyl)-5-cyano-4-(2-azidecarbonylvinyl)-1H-imidazol-2-yl]piperazine-1-carboxylate was heated under reflux under a nitrogen atmosphere for 15 hours. The solvent was concentrated under reduced pressure. The residue was purified by silica gel column chromatography. Thus, 0.169 g of the title compound was obtained from the fraction eluted with ethyl acetate-hexane (9:11).

$^1$H-NMR (CDCl$_3$)

δ 1.48 (s, 9H) 1.84 (t, J=2.2 Hz, 3H) 3.16-3.19 (m, 4H) 3.54-3.58 (m, 4H) 4.51 (q, J=2.2 Hz, 2H) 5.83 (d, J=15.0 Hz, 1H) 6.43-6.53 (m, 1H) 7.55-7.66 (m, 1H)

(k) t-Butyl 4-[4-(2-t-butoxycarbonylaminovinyl)-1-(2-butynyl)-5 carbamoyl-1H-imidazol-2-yl]piperazine-1'-carboxylate The title compound was obtained by using t-butyl 4-[4-(2-t-butoxycarbonylaminovinyl)-1-(2-butynyl)-5-cyano-1H-imidazol-2-yl]piperazine-1-carboxylate according to the method described in Example 332(b).

$^1$H-NMR (CDCl$_3$)

δ 1.48 (s, 9H) 1.84 (t, J=2.2 Hz, 3H) 3.21-3.25 (m, 4H) 3.54-3.58 (m, 4H) 4.68 (q, J=2.2 Hz, 2H) 5.90 (br.s, 1H) 6.36 (br.d, J=14.8 Hz, 1H) 6.92 (br.d, J=8.4 Hz, 1H) 7.45 (br.s, 1H) 7.52 (m, 1H)

(l) 3-(2-Butynyl)-2-(piperazin-1-yl)-3,5-dihydroimidazo[4,5-c]pyridin-4-one trifluoroacetate 0.1 ml of 5N hydrochloric acid was added to a 0.3 ml ethanol solution of 0.0075 g of t-butyl 4-[4-(2-t-butoxycarbonylaminovinyl)-1-(2-butynyl)-5-carbamoyl-1H-imidazol-2-yl]piperazine-1-carboxylate, and the mixture was stirred at room temperature for 15 hours. The solvent was concentrated under reduced pressure. The residue was purified by reverse-phase high performance liquid chromatography (using an acetonitrile-water mobile phase (containing 0.1% trifluoroacetic acid)) to give 0.0043 g of the title compound.

¹H-NMR (CD₃OD)
δ 1.81 (t, J=2.4 Hz, 3H) 3.45-3.48 (m, 4H) 3.62-3.65 (m, 4H) 5.15 (q, J=2.4 Hz, 2H) 6.60 (d, J=7.1 Hz, 1H) 7.18 (d, J=7.1 Hz, 1H)

MS m/e (ESI) 272.32 (MH⁺-CF₃COOH)

Example 339

3-(2-Butynyl)-5-(2-phenylethyl)-2-(piperazin-1-yl)-3,5-dihydroimidazo[4,5-c]pyridin-4-one trifluoroacetate (a) t-Butyl-4-[3-(2-butynyl)-4-oxo-4,5-dihydro-3H-imidazo[4,5-c]pyridin-2-yl]piperazine-1-carboxylate The title compound was obtained by using 3-(2-butynyl)-2-(piperazin-1-yl)-3,5-dihydroimidazo[4,5-c]pyridin-4-one trifluoroacetate according to the method described in Example 258(a).

¹H-NMR (CDCl₃)
δ 1.49 (s, 9H) 1.83 (t, J=2.3 Hz, 3H) 3.35-3.39 (m, 4H) 3.60-3.64 (m, 4H) 5.07 (q, J=2.3 Hz, 2H) 6.55 (d, J=7.1 Hz, 1H) 6.97 (d, J=7.1 Hz, 1H)

(b) 3-(2-Butynyl)-5-(2-phenylethyl)-2-(piperazin-1-yl)-3,5-dihydroimidazo[4,5-c]pyridin-4-one trifluoroacetate The title compound was obtained by using t-butyl 4-[3-(2-butynyl)-4-oxo-4,5-dihydro-3H-imidazo[4,5-c]pyridin-2-yl]piperazine-1-carboxylate and (2-bromoethyl)benzene according to the method described in Example 258(b).

¹H-NMR (CD₃OD)
δ 1.83 (t, J=2.4 Hz, 3H) 3.05 (t, J=7.3 Hz, 2H) 3.45-3.48 (m, 4H) 3.62-3.65 (m, 4H) 4.26 (t, J=7.3 Hz, 2H) 5.18 (q, J=2.4 Hz, 2H) 6.46 (d, J=7.3 Hz, 1H) 7.15 (d, J=7.3 Hz, 1H) 7.16-7.30 (m, 5H)

MS m/e (ESI) 376.36 (MH⁺-CF₃COOH)

Example 340

3-(2-Butynyl)-5-(2-phenoxyethyl)-2-(piperazin-1-yl)-3,5-dihydroimidazo[4,5-c]pyridin-4-one trifluoroacetate The title compound was obtained by using t-butyl 4-[3-(2-butynyl)-4-oxo-4,5-dihydro-3H-imidazo[4,5-c]pyridin-2-yl]piperazine-1-carboxylate and 2-bromoethyl phenyl ether according to the method described in Example 258(b).

¹H-NMR (CD₃OD)
δ 1.80 (t, J=2.4 Hz, 3H) 3.45-3.48 (m, 4H) 3.62-3.65 (m, 4H) 4.30 (t, J=5.5 Hz, 2H) 4.44 (t, J=5.5 Hz, 2H) 5.16 (q, J=2.4 Hz, 2H) 6.59 (d, J=6.1 Hz, 1H) 6.87-6.91 (m, 3H) 7.20-7.24 (m, 2H) 7.50 (d, J=6.1 Hz, 1H)

MS m/e (ESI) 392.34 (MH⁺-CF₃COOH)

Example 341

3-(2-Butynyl)-5-(2-oxo-2-phenylethyl)-2-(piperazin-1-yl)-3,5-dihydroimidazo[4,5-c]pyridin-4-one trifluoroacetate The title compound was obtained by using t-butyl 4-[3-(2-butynyl)-4-oxo-4,5-dihydro-3H-imidazo[4,5-c]pyridin-2-yl]piperazine-1-carboxylate and 2-bromoacetophenone according to the method described in Example 258(b).

¹H-NMR (CD₃OD)
δ 1.79 (t, J=2.3 Hz, 3H) 3.46-3.50 (m, 4H) 3.64-3.68 (m, 4H) 5.16 (q, J=2.3 Hz, 2H) 5.61 (s, 2H) 6.65 (d, J=7.3 Hz, 1H) 7.37 (d, J=7.3 Hz, 1H) 7.57 (t, J=8.0 Hz, 2H) 7.69 (t, J=8.0 Hz, 1H) 8.10 (d, J=8.0 Hz, 2H)

MS m/e (ESI) 392.34 (MH⁺-CF₃COOH)

Example 342

2-[3-(2-Butynyl)-4-oxo-2-(piperazin-1-yl)-3,4-dihydroimidazo[4,5-c]pyridin-5-ylmethyl]benzonitrile trifluoroacetate The title compound was obtained by using t-butyl 4-[1-(2-butynyl)-7-oxo-6,7-dihydro-1H-imidazo[4,5-d]pyridin-2-yl]piperazine-1-carboxylate and 2-bromomethylbenzonitrile according to the method described in Example 258(b).

¹H-NMR (CD₃OD)
δ 1.78 (t, J=2.3 Hz, 3H) 3.45-3.49 (m, 4H) 3.64-3.67 (m, 4H) 5.14 (q, J=2.3 Hz, 2H) 5.47 (s, 2H) 6.67 (d, J=7.0 Hz, 1H) 7.20 (dd, J=7.2, 1.0 Hz, 1H) 7.46 (td, J=7.2, 1.0 Hz, 1H) 7.50 (d, J=7.0 Hz, 1H) 7.60 (td, J=7.2, 1.0 Hz, 1H) 7.80 (dd, J=7.2, 1.0 Hz, 1H)

MS m/e (ESI) 387.34 (MH⁺-CF₃COOH)

Example 343

Methyl 3-(2-butynyl)-4-oxo-2-(piperazin-1-yl)-4,5-dihydroimidazo[4,5-c]pyridine-6-carboxylate trifluoroacetate (a) t-Butyl 4-[1-(2-butynyl)-4-hydroxymethyl-5-thiocarbamoyl-1H-imidazol-2-yl]piperazine-1-carboxylate 10 ml of a 50% aqueous solution of ammonium sulfide was added to a 50 ml ethanol solution of 3.596 g of t-butyl 4-[1-(2-butynyl)-5-cyano-4-hydroxymethyl-1H-imidazol-2-yl]piperazine-1-carboxylate, and the mixture was stirred at room temperature for 16 hours. 400 ml of ethyl acetate was added to the solution, and the mixture was washed three times with 100 ml of water and then with 100 ml of a saturated sodium chloride solution. The organic layer was dried over magnesium sulfate, and concentrated under reduced pressure. The residue was purified by silica gel column chromatography. Thus, 3.221 g of the title compound was obtained from the fraction eluted with ethyl acetate-hexane (4:1).

¹H-NMR (CDCl₃)
δ 1.49 (s, 9H) 1.84 (t, J=2.4 Hz, 3H) 3.17-3.21 (m, 4H) 3.54-3.60 (m, 4H) 3.62 (t, J=5.8 Hz, 1H) 4.68 (d, J=5.8 Hz, 2H) 5.05 (q, J=2.4 Hz, 2H) 7.35 (br.s, 1H) 8.46 (br.s, 1H)

(b) t-Butyl 4-[4-(t-butyldiphenylsilanyloxymethyl)-1-(2-butynyl)-5-thiocarbamoyl-1H-imidazol-2-yl]piperazine-1-carboxylate 0.668 g of imidazole and 2.70 g of t-butylchlorodiphenylsilane were added to a 25 ml N,N-dimethylformamide solution of 3.221 g of t-butyl 4-[1-(2-butynyl)-4-hydroxymethyl-5-thiocarbamoyl-1H-imidazol-2-yl]piperazine-1-carboxylate, and the mixture was stirred at room temperature for 16 hours. 300 ml of ethyl acetate was added to the solution, and the organic layer was washed three times with 100 ml of water and then with 100 ml of a saturated sodium chloride solution. The organic layer was dried over magnesium sulfate, and concentrated under reduced pressure. The residue was purified by silica gel column chromatography. Thus, 4.357 g of the title compound was obtained from the fraction eluted with ethyl acetate-hexane (2:3).

$^1$H-NMR (CDCl$_3$)

δ 1.05 (s, 9H) 1.49 (s, 9H) 1.84 (t, J=2.4 Hz, 3H) 3.06-3.11 (m, 4H) 3.53-3.57 (m, 4H) 4.74 (s, 2H) 5.19 (q, J=2.4 Hz, 2H) 7.31 (br.d, J=4.1 Hz, 1H) 7.37 (t, J=7.2 Hz, 4H) 7.44 (d, J=7.2 Hz, 2H) 7.63 (d, J=7.2 Hz, 4H) 9.28 (br.d, J=4.1 Hz, 1H)

(c) t-Butyl 4-[4-(t-butyldiphenylsilanyloxymethyl)-1-(2-butynyl)-5-methylsulfanylcarbonimidoyl-1H-imidazol-2-yl]piperazine-1-carboxylate 1.23 g of trimethyloxonium tetrafluoroborate was added to a 100 ml dichloromethane solution of 4.351 g of t-butyl 4-[4-(t-butyldiphenylsilanyloxymethyl)-1-(2-butynyl)-5-thiocarbamoyl-1H-imidazol-2-yl]piperazine-1-carboxylate, and the mixture was stirred at room temperature for 15 hours. 300 ml of ethyl acetate was added to the solution, and the organic layer was washed successively with 100 ml of a saturated sodium bicarbonate solution and 100 ml a saturated ammonium chloride solution. The organic layer was dried over magnesium sulfate, and concentrated under reduced pressure to give 4.439 g of the title compound.

$^1$H-NMR (CDCl$_3$)

δ 1.05 (s, 9H) 1.49 (s, 9H) 1.84 (br.s, 3H) 2.36 (br.s, 3H) 3.11-3.15 (m, 4H) 3.54-3.58 (m, 4H) 4.63 (br.s, 2H) 4.66 (br.s, 2H) 7.37 (t; J=7.2 Hz, 4H) 7.44 (d, J=7.2 Hz, 2H) 7.63 (d, J=7.2 Hz, 4H)

(d) t-Butyl 4-[1-(2-butynyl)-4-hydroxymethyl-5-methylsulfanylcarbonyl-1H-imidazol-2-yl]piperazine-1-carboxylate 30 ml of 5N hydrochloric acid was added to a 100 ml tetrahydrofuran solution of 5.05 g of t-butyl 4-[4-(t-butyl diphenylsilanyloxymethyl)-1-(2-butynyl)-5-methylsulfanyl-carbonimidoyl-1H-imidazol-2-yl]piperazine-1-carboxylate, and the mixture was stirred at room temperature for 22 hours. The solvent was concentrated under reduced pressure. The residue was dissolved in 100 ml of dichloromethane, and 2.05 g of di-t-butyl dicarbonate was added thereto. The solution was made alkaline with 5N sodium hydroxide, and stirred for 2 hours. The organic layer was dried over magnesium sulfate, and concentrated under reduced pressure. The residue was purified by silica gel column chromatography. Thus, 2.24 g of the title compound was obtained from the fraction eluted with ethyl acetate-hexane (2:3).

$^1$H-NMR (CDCl$_3$)

δ 1.49 (s, 9H) 1.84 (t, J=2.3 Hz, 3H) 2.47 (s, 3H) 3.21-3.25 (m, 4H) 3.27 (t, J=5.6 Hz, 1H) 3.56-3.60 (m, 4H) 4.81 (q, J=2.4 Hz, 2H) 4.89 (d, J=5.6 Hz, 2H)

(e) t-Butyl 4-[1-(2-butynyl)-4-formyl-5-methylsulfanylcarbonyl-1H-imidazol-2-yl]piperazine-1-carboxylate The title compound was obtained by using t-butyl 4-[1-(2-butynyl)-4-hydroxymethyl-5-methylsulfanylcarbonyl-1H-imidazol-2-yl]piperazine-1-carboxylate according to the method described in Example 115(g).

$^1$H-NMR (CDCl$_3$)

δ 1.48 (s, 9H) 1.84 (t, J=2.3 Hz, 3H) 2.58 (s, 3H) 3.22-3.26 (m, 4H) 3.56-3.60 (m, 4H) 4.80 (q, J=2.4 Hz, 2H) 9.88 (s, 1H)

(f) 2-(4-t-Butoxycarbonylpiperazin-1-yl)-3-(2-butynyl)-4-oxo-3,4-dihydroimidazo[4,5-c]pyridine-5,6-dicarboxylic acid 5-benzyl ester 6-methyl ester 0.079 g of 1,8-diazabicyclo[5.4.0]-7-undecene and then 5 ml of dichloromethane containing 0.194 g of t-butyl 4-[1-(2-butynyl)-4-formyl-5-methylsulfanylcarbonyl-1H-imidazol-2-yl]piperazine-1-carboxylate were added to a 2 ml dichloromethane solution of 0.174 g of methyl benzyloxycarbonylamino-(dimethoxyphosphoryl)-acetate, and the mixture was stirred at room temperature for 16 hours. The solvent was concentrated under reduced pressure. The residue was purified by silica gel column chromatography. Thus, 0.147 g of the title compound was obtained from the fraction eluted with ethyl acetate-hexane (3:2).

$^1$H-NMR (CDCl$_3$)

δ 1.49 (s, 9H) 1.83 (t, J=2.3 Hz, 3H) 3.37-3.41 (m, 4H) 3.59-3.64 (m, 4H) 3.83 (s, 3H) 5.04 (q, J=2.3 Hz, 2H) 5.46 (s, 2H) 7.33-7.38 (m, 3H) 7.41 (s, 1H) 7.45-7.48 (m, 2H)

(g) t-Butyl 4-[3-(2-butynyl)-4-oxo-6-trimethoxy methyl-4,5-dihydro-3H-imidazo[4,5-c]pyridin-2-yl]piperazine-1-carboxylate 0.023 g of sodium was added to 2 ml of methanol under a nitrogen atmosphere. After hydrogen generation stopped, a 2 ml methanol solution of 0.147 g of 2-(4-t-butoxycarbonylpiperazin-1-yl)-3-(2-butynyl)-4-oxo-3,4-dihydroimidazo[4,5-c]pyridine-5,67-dicarboxylic acid 5-benzyl ester 6-methyl ester was added to the solution. The mixture was stirred at room temperature for 16 hours. Then, 40 ml of ethyl acetate, 20 ml of 5% aqueous ammonium chloride solution, and 1 ml of 1 N hydrochloric acid were added to the solution. The organic layer was dried over magnesium sulfate, and concentrated under reduced pressure. The residue was purified by silica gel column chromatography. Thus, 0.108 g of the title compound was obtained from the fraction eluted with ethyl acetate.

$^1$H-NMR (CDCl$_3$)

δ 1.50 (s, 9H) 1.83 (t, J=2.3 Hz, 3H) 3.20 (s, 9H) 3.37-3.41 (m, 4H) 3.59-3.64 (m, 4H) 5.07 (q, J=2.3 Hz, 2H) 6.82 (s, 1H) 8.60 (br.s, 1H)

(h) Methyl 3-(2-butynyl)-4-oxo-2-(piperazin-1-yl)-4,5-dihydroimidazo[4,5-c]pyridine-6-carboxylate trifluoroacetate The title compound was obtained by using t-butyl 4-[3-(2-butynyl)-4-oxo-6-trimethoxymethyl-4,5-dihydro-3H-imidazo[4,5-c]pyridin-2-yl]piperazin-1-carboxylate according to the method described in Example 338(l).

$^1$H-NMR (CD$_3$OD)

δ 1.81 (t, J=2.3 Hz, 3H) 3.45-3.49 (m, 4H) 3.64-3.67 (m, 4H) 3.95 (s, 3H) 5.17 (q, J=2.3 Hz, 2H) 7.35 (s, 1H)

MS m/e (ESI) 330.16 (MH$^+$-CF$_3$COOH)

Example 344

Methyl 3-(2-butynyl)-5-methyl-4-oxo-2-(piperazin-1-yl)-4,5-dihydroimidazo[4,5-c]pyridine-6-carboxylate trifluoroacetate 0.024 g of potassium carbonate and 0.027 ml of methyl iodide were added to a 2 ml N,N-dimethylformamide solution of 0.030 g of t-butyl 4-[3-(2-butynyl)-4-oxo-6-trimethoxymethyl-4,5-dihydro-3H-imidazo[4,5-c]pyridin-2-yl]piperazine-1-carboxylate, and the mixture was heated at 50° C. for 48 hours. 2 ml of ethyl acetate and 2 ml of water were added to the solution. The aqueous layer was extracted with 1 ml of ethyl acetate. The organic layers were combined together, and then divided into equal halves. One of the halves was concentrated by flushing with nitrogen gas, and the residue was dissolved in 0.5 ml of methanol. The solution was combined with 0.1 ml of 5N hydrochloric acid, and the mixture was left for 1 hour. The solvent was removed, and the residue was purified by reverse-phase high performance liquid chromatography (using an acetonitrile-water mobile phase (containing 0.1% trifluoroacetic acid)) to give 0.007 g of the title compound.

$^1$H-NMR (CD$_3$OD)

δ 1.81 (t, J=2.4 Hz, 3H) 3.45-3.48 (m, 4H) 3.62-3.65 (m, 4H) 3.74 (s, 3H) 3.94 (s, 3H) 5.17 (q, J=2.4 Hz, 2H) 7.25 (s, 1H)

MS m/e (ESI) 344.30 (MH$^+$-CF$_3$COOH)

Example 345

3-(2-Butynyl)-5-methyl-4-oxo-2-(piperazin-1-yl)-4,5-dihydroimidazo[4,5-c]pyridine-6-carboxylic amide trifluoroacetate The other half of the solution prepared in Example 344 was concentrated by flushing with nitrogen gas. The residue was treated with 1 ml of 28% ammonia water. The solution was heated under reflux in a sealed tube for 48 hours. The solvent was concentrated under reduced pressure. Subsequent synthetic steps were carried out according to the same procedure as used in Example 115(i). Thus, 0.010 g of the title compound was synthesized.

MS m/e (ESI) 329.32 (MH$^+$-CF$_3$COOH)

Example 346

Methyl 3-(2-butynyl)-4-oxo-5-(2-oxo-2-phenylethyl)-2-(piperazin-1-yl)-4,5-dihydroimidazo[4,5-c]pyridine-6-carboxylate trifluoroacetate The title compound was obtained by using t-butyl 4-[3-(2-butynyl)-4-oxo-6-trimethoxymethyl-4,5-dihydro-3H-imidazo[4,5-c]pyridin-2-yl]piperazine-1-carboxylate and 2-bromoacetophenone according to the method described in Example 344.

MS m/e (ESI) 448.31 (MH$^+$-CF$_3$COOH)

Example 347

Methyl 3-(2-butynyl)-5-(2-cyanobenzyl)-4-oxo-2-(piperazin-1-yl)-4,5-dihydroimidazo[4,5-c]pyridine-6-carboxylate trifluoroacetate The title compound was obtained by using t-butyl 4-[3-(2-butynyl)-4-oxo-6-trimethoxy methyl-4,5-dihydro-3H-imidazo[4,5-c]pyridin-2-yl]piperazine-1-carboxylate and 2-bromomethylbenzonitrile according to the method described in Example 344.

MS m/e (ESI) 445.32 (MH$^+$-CF$_3$COOH)

Example 348

3-(2-Butynyl)-5-(2-cyanobenzyl)-4-oxo-2-(piperazin-1-yl)-4,5-dihydroimidazo[4,5-c]pyridine-6-carboxylic amide trifluoroacetate The title compound was obtained by using t-butyl 4-[3-(2-butynyl)-4-oxo-6-trimethoxymethyl-4,5-dihydro-3H-imidazo[4,5-c]pyridin-2-yl]piperazine-1-carboxylate and 2-bromomethylbenzonitrile according to the method described in Example 345.

MS m/e (ESI) 430.34 (MH$^+$-CF$_3$COOH)

Example 349

1-(2-Butynyl)-5-methyl-2-(piperazin-1-yl)-1,5-dihydroimidazo[4,5-d]pyridazin-4-one trifluoroacetate (a)-1 3-(2-butynyl)-2-chloro-5-methyl-3,5-dihydroimidazo[4,5-d]pyridazin-4-one and (a)-2 1-(2-butynyl)-2-chloro-5-methyl-1,5-dihydroimidazo[4,5-d]pyridazin-4-one 0.166 g of potassium carbonate and 0.106 μl of 2-butynyl bromide were added to a 10 ml N,N-dimethylformamide solution of 0.184 g of 2-chloro-5-methyl-1,5-dihydroimidazo[4,5-d]pyridazin-4-one, and the mixture was stirred at room temperature for 18 hours. 50 ml of ethyl acetate was added to the solution, and the mixture was washed three times with 20 ml of water and then with 20 ml of a saturated sodium chloride solution. The organic liquid was dried over magnesium sulfate, and concentrated under reduced pressure. Then, the residue was purified by silica gel column chromatography. Thus, 0.175 g of 3-(2-butynyl)-2-chloro-5-methyl-3,5-dihydroimidazo[4,5-d]pyridazin-4-one was obtained from the fraction eluted with hexane-ethyl acetate (4:1), and 0.033 g of 1-(2-butynyl)-2-chloro-5-methyl-1,5-dihydroimidazo[4,5-d]pyridazin-4-one was obtained from the fraction eluted with hexane-ethyl acetate (2:3).

3-(2-butynyl)-2-chloro-5-methyl-3,5-dihydroimidazo[4,5-d]pyridazin-4-one $^1$H-NMR (CDCl$_3$)

δ 1.82 (t, J=2.3 Hz, 3H) 3.87 (s, 3H) 5.32 (q, J=2.3 Hz, 2H) 8.19 (s, 1H)

1-(2-butynyl)-2-chloro-5-methyl-1,5-dihydroimidazo[4,5-d]pyridazin-4-one $^1$H-NMR (CDCl$_3$)

δ 1.87 (t, J=2.3 Hz, 3H) 3.91 (s, 3H) 4.90 (q, J=2.3 Hz, 2H) 8.20 (s, 1H)

(b) t-Butyl 4-[1-(2-butynyl)-5-methyl-4-oxo-4,5-dihydro-1H-imidazo[4,5-d]pyridazin-2-yl]piperazine-1-carboxylate The title compound was obtained by using 1-(2-butynyl)-2-chloro-5-methyl-1,5-dihydroimidazo[4,5-d]pyridazin-4- one and t-butyl piperazine-1-carboxylate according to the method described in Example 119(c).

¹H-NMR (CDCl₃)

δ 1.50 (s, 9H) 1.87 (t, J=2.3 Hz, 3H) 3.30-3.34 (m, 4H) 3.59-3.63 (m, 4H) 3.90 (s, 3H) 4.70 (q, J=2.3 Hz, 2H) 8.11 (s, 1H)

(c) 1-(2-Butynyl)-5-methyl-2-(piperazin-1-yl)-1,5-dihydroimidazo[4,5-d]pyridazin-4-one trifluoroacetate The title compound was obtained by using t-butyl 4-[5-methyl-1-(2-butynyl)-4-oxo-4,5-dihydro-1H-imidazo[4,5-d]pyridazin-2-yl]piperazine-1-carboxylate according to the method described in Example 115(i).

¹H-NMR (CD₃OD)

δ 1.84 (t, J=2.4 Hz, 3H) 3.44-3.48 (m, 4H) 3.58-3.62 (m, 4H) 3.86 (s, 3H) 4.96 (q, J=2.4 Hz, 2H) 8.39 (s, 1H)

MS m/e (ESI) 287.17 (MH⁺-CF₃COOH)

Example 350

2-[(1R*,2R*)2-aminocyclohexylamino]-3-(2-butynyl)-5-methyl-3,5-dihydroimidazo[4,5-d]pyridazin-4-one trifluoroacetate The title compound was obtained by reacting 3-(2-butynyl)-2-chloro-5-methyl-3,5-dihydroimidazo[4,5-d]pyridazin-4-one and trans-1,2-cyclohexanediamine by the method as used in Example 119(c) and purifying the product by reverse-phase high performance liquid chromatography.

¹H-NMR (CD₃OD)

δ 1.39-1.49 (m, 2H) 1.50-1.61 (m, 2H) 1.80 (t, J=2.3 Hz, 3H) 1.85-1.92 (m, 2H) 2.11-2.18 (m, 2H) 3.19 (td, J=11.0, 4.1 Hz, 1H) 3.80 (s, 3H) 3.93 (td, J=11.0, 4.2 Hz, 1H) 4.91 (dq, J=18.0, 2.3 Hz, 1H) 5.44 (dq, J=18.0, 2.3 Hz, 1H) 8.07 (s, 1H)

MS m/e (ESI) 315.19 (MH⁺-CF₃COOH)

Example 351

2-[(1R*,2S*)2-aminocyclohexylamino]-3-(2-butynyl)-5-methyl-3,5-dihydroimidazo[4,5-d]pyridazin-4-one trifluoroacetate The title compound was obtained by reacting 3-(2-butynyl)-2-chloro-5-methyl-3,5-dihydroimidazo[4,5-d]pyridazin-4-one and cis-1,2-cyclohexanediamine by the method as used in Example 119(c) and purifying the product by reverse-phase high performance liquid chromatography.

¹H-NMR (CD₃OD)

δ 1.54-1.68 (m, 3H) 1.71-1.81 (m, 2H) 1.83 (t, J=2.4 Hz, 3H) 1.85-1.91 (m, 2H) 1.91-2.01 (m, 1H) 3.69 (m, 1H) 3.80 (s, 3H) 4.37 (m, 1H) 5.04 (dq, J=18.3, 2.4 Hz, 1H) 5.55 (dq, J=18.3, 2.4 Hz, 1H) 8.09 (s, 1H)

MS m/e (ESI) 315.27 (MH⁺-CF₃COOH)

Example 352

3-(2-Butynyl)-5-methyl-2-(1,2,3,6-tetrahydropyridin-4-yl)-3,5-dihydroimidazo[4,5-d]pyridazin-4-one trifluoroacetate (a) 5-Methyl-2-(pyridin-4-yl)-1,5-dihydroimidazo[4,5-d]pyridazin-4-one 0.560 g of 4,5-diamino-2-methyl-2H-pyridazin-3-one and 0.535 g of 4-pyridinecarbaldehyde were added to 10 ml of nitrobenzene, and the mixture was heated at 190° C. under a nitrogen atmosphere for three hours. The reaction solution was cooled down, and the precipitate was collected by filtration to give 0.381 g of the title compound.

¹H-NMR (d₆DMSO)

δ 3.78 (s, 3H) 8.14 (d, J=6.0 Hz, 2H) 8.48 (s, 1H) 8.76 (d, J=6.0 Hz, 2H)

MS m/e (ESI) 228.1 (MH⁺)

(b)

3-(2-Butynyl)-5-methyl-2-(pyridin-4-yl)-3,5-dihydroimidazo[4,5-d]pyridazin-4-one The title compound was obtained by using 5-methyl-2-(pyridin-4-yl)-1,5-dihydro-imidazo[4,5-d]pyridazin-4-one and 2-butynyl bromide according to the method described in Example 119(d).

¹H-NMR (CDCl₃)

δ 1.84 (t, J=2.3 Hz, 3H) 3.91 (s, 3H) 5.37 (q, J=2.3 Hz, 2H) 7.89 (d, J=6.1 Hz, 2H) 8.32 (s, 1H) 8.85 (d, J=2.3 Hz, 2H)

(c) 4-[1-(2-Butynyl)-6-methyl-7-oxo-6,7-dihydro-1H-imidazo[4,5-d]pyridazin-2-yl]-1-(4-methoxybenzyl)pyridinium chloride 0.045 g of 3-(2-butynyl)-5-methyl-2-(pyridin-4-yl)-3,5-dihydroimidazo[4,5-d]pyridazin-4-one and 0.060 μl of p-methoxybenzyl chloride were added to 0.100 ml of N,N-dimethylformamide, and the mixture was stirred at 65° C. under a nitrogen atmosphere for 4 hours. The reaction solution was cooled down, and 1 ml of acetone and 1 ml of diethyl ether were added thereto. The precipitate was collected by filtration to give 0.060 g of the title compound.

¹H-NMR (CD₃OD)

δ 1.75 (t, J=2.3 Hz, 3H) 3.74 (s, 3H) 3.77 (s, 3H) 5.64 (q, J=2.3 Hz, 2H) 5.86 (s, 2H) 7.05 (d, J=8.3 Hz, 2H) 7.54 (d, J=8.3 Hz, 2H) 8.43 (s, 1H) 8.70 (d, J=6.3 Hz, 2H) 9.24 (d, J=6.3 Hz, 2H)

(d) 3-(2-Butynyl)-2-[1-(4-methoxybenzyl)-1,2,3,6-tetrahydropyridin-4-yl]-5-methyl-3,5-dihydroimidazo[4,5-d]pyridazin-4-one 0.020 g of sodium borohydride was added to a 5 ml methanol solution of 0.060 g of 4-[1-(2-butynyl)-6-methyl-7-oxo-6,7-dihydro-1H-imidazo[4,5-d]pyridazin-2-yl]-1-(4-methoxybenzyl)pyridinium chloride, and the mixture was stirred for one hour. 15 ml of water and 0.1 ml of 5N hydrochloric acid were added to the solution to quench the reducing agent. Then, the solution was made alkaline with 1 ml of 5N sodium hydroxide, and extracted with 30 ml of ethyl acetate. The organic layer was dried over magnesium sulfate, and concentrated under reduced pressure. The residue was purified by silica gel column chromatography. Thus, 0.033 g of the title compound was obtained from the fraction eluted with methanol-ethyl acetate (1:19).

¹H-NMR (CDCl₃)

δ 1.80 (t, J=2.4 Hz, 3H) 2.71-2.78 (m, 4H) 3.25-3.28 (m, 2H) 3.62 (s, 2H) 3.82 (s, 3H) 3.87 (s, 3H) 5.30 (q, J=2.4 Hz, 2H) 6.61 (m, 1H) 6.89 (d, J=9.1 Hz, 2H) 7.30 (d, J=9.1 Hz, 2H) 8.22 (s, 1H)

(e) 3-(2-Butynyl)-5-methyl-2-(1,2,3,6-tetrahydropyridin-4-yl)-3,5-dihydroimidazo[4,5-d]pyridazin-4-one trifluoroacetate 0.10 ml of 1-chloroethyl chloroformate was added to a 2 ml 1,2-dichloroethane solution of 0.033 g of 3-(2-butynyl)-2-[1-(4-methoxybenzyl)-1,2,3,6-tetrahydropyridin-4-yl]-5-methyl-3,5-dihydroimidazo[4,5-d]pyridazin-4-one, and the mixture was heated under reflux for 90 minutes. 5 ml of methanol was added to the solution, and the mixture was further heated under reflux for 4 hours. The solvent was then concentrated under reduced pressure. The residue was purified by reverse-phase high performance liquid chromatography to give 0.010 g of the title compound.

$^1$H-NMR (CD$_3$OD)

δ 1.81 (t, J=2.4 Hz, 3H) 2.89-2.94 (m, 2H) 3.52 (t, J=6.2 Hz, 2H) 3.84 (s, 3H) 4.01 (q, J=2.8 Hz, 2H) 5.27 (q, J=2.4 Hz, 2H) 6.67 (m, 1H) 8.30 (s, 1H)

MS m/e (ESI) 284.22 (MH$^+$-CF$_3$COOH)

Assay Example 1

DPPIV-inhibiting Activity Assay

Porcine kidney-derived DPP-IV was dissolved in a reaction buffer (50 mM Tris-HCl (pH 7.4)/0.1% BSA) at a concentration of 10 mµ/ml. After 110 µl of this solution had been combined with 15 µl of an agent, the mixture was incubated at room temperature for 20 minutes. 25 µl of 2 mM Gly-Pro-p-nitroanilide was added (to a final concentration of 0.33 mM) to the solution to initiate the enzyme reaction. The reaction time was 20 minutes. 25 µl of 1N phosphoric acid solution was added to the reaction solution to quench the reaction. Absorbance of this solution at 405 nm was determined, and then the inhibition rate for the enzyme reaction was calculated to determine the IC$_{50}$.

TABLE 1

| Example No. | IC$_{50}$ (µM) |
| --- | --- |
| Example 1 | 0.287 |
| Example 4 | 0.211 |
| Example 7 | 0.401 |
| Example 9 | 0.141 |
| Example 12 | 0.183 |
| Example 13 | 0.125 |
| Example 16 | 0.272 |
| Example 20 | 0.152 |
| Example 22 | 0.170 |
| Example 29 | 0.310 |
| Example 53 | 0.0469 |
| Example 64 | 0.126 |
| Example 73 | 0.0334 |
| Example 76 | 0.0865 |
| Example 79 | 0.0357 |
| Example 82 | 0.161 |
| Example 83 | 0.0274 |
| Example 86 | 0.00408 |
| Example 88 | 0.00289 |
| Example 98 | 0.00969 |
| Example 109 | 1.48 |
| Example 119 | 0.154 |
| Example 120 | 0.116 |
| Example 122 | 0.0153 |
| Example 129 | 0.115 |
| Example 142 | 0.0685 |
| Example 146 | 0.0817 |
| Example 159 | 0.0377 |
| Example 229 | 0.00897 |
| Example 230 | 0.000890 |
| Example 234 | 0.00174 |
| Example 235 | 0.00144 |

TABLE 1-continued

| Example No. | IC$_{50}$ (µM) |
| --- | --- |
| Example 238 | 0.00119 |
| Example 243 | 0.00215 |
| Example 248 | 0.00640 |
| Example 266 | 0.00155 |
| Example 267 | 0.00722 |
| Example 297 | 0.00622 |
| Example 311 | 0.0775 |
| Example 341 | 0.00732 |

Assay Example 2

Effect on the Glucose Tolerance of Normal Mice (In Vivo Test)

Animal: male C57BL/6N mice (purchased from Charles River Japan, Inc.)

Method:

[Preparation and Administration of Test Compounds]

Each test compound was suspended in a 0.5% methyl cellulose (MC) solution at the concentration indicated below in Table. The suspension of a test compound, and of NVP DPP728 (U.S. Pat. No. 6,011,155), or a 0.5% MC solution that was used as a medium control group was given orally at a dose of 10 mL/kg. After 30 minutes, a glucose solution was given orally at a dose of 10 mL/kg. The dose of glucose given orally was 2 g/kg.

[Blood Collection and Determination of Blood Glucose Levels]

Immediately before administering the test compound and NVP DPP728, immediately before administering the glucose solution, and 30, 60, and 120 minutes after the administration, without anesthetic the caudal vein was lightly cut with a razor blade to let blood out. 10 µl of blood was collected and immediately combined with 140 µl of 0.6 M perchloric acid. The sample was centrifuged at 1500 g at 4° C. for 10 minutes in a refrigerated centrifuge GS-6KR (Beckman Corp.). The glucose concentration in the resulting supernatant was determined using Glucose CII TEST WAKO (Wako Pure Chemical Industries).

Result:

The area under the blood glucose level time curve (AUC$_{0-120}$; Area Under the Curve) obtained from the curve of time vs. blood glucose level between the start of glucose administration and 120 minutes after administration was determined for each of the 0.5% MC solution-treated group, NVP DPP728-treated group and test compound-treated group. The improvement factor for glucose tolerance of a test compound was determined by taking the AUC$_{0-120}$ of the 0.5% MC solution-treated group as 100% and the AUC$_{0-120}$ of the NVP DPP728 (10 mg/kg)-treated group as 0% according to the formula indicated below.

Improvement factor for glucose tolerance (%)= (AUC$_{0-120}$ of the group treated with a test compound−AUC$_{0-120}$ of the group treated with NVP DPP728 (10 mg/kg))/AUC$_{0-120}$ of the group treated with 0.5% MC solution−AUC$_{0-120}$ of the group treated with NVP DPP728 (10 mg/kg))× 100

The lower the % value, the greater the improvement in the glucose tolerance.

Some of the novel condensed imidazole derivatives of the present invention were found to have significant effects on the glucose tolerance of normal mice through the in vivo experiment described above which comprised oral administration of the compounds at doses of 0.1-10 (mg/kg).

Assay Example 3

Acceptable Timing of Administration in In Vivo Test

A drug for treating postprandial hyperglycemia is ideally required to have comparable effectiveness in treating postprandial hyperglycemia when it is given immediately before meals as well as 1 hour before meals. Thus, an excellent drug exhibiting higher efficacy can be achieved by widening the range of acceptable timing of administration Method:

The respective tests described below were carried out in combination with the in vivo test (administration before 0.5 hour) as described in Assay Example 2:

1. A test compound is administered simultaneously with glucose loading (2 g/kg) (the test compound is suspended in an aqueous solution of 0.5% methyl cellulose; the solution is combined with an equal volume of a glucose solution; and the mixture is administered orally at a dose of 10 ml/kg);

2. A test compound is administered one hour before glucose loading (2 g/kg) (the test compound suspended in an aqueous solution of 0.5% methyl cellulose is administered orally one hour before the oral administration of the glucose solution; each is given orally at a dose of 10 ml/kg).

The improvement factor for glucose tolerance is estimated in each test. The range of acceptable timing of administration can be assessed by estimating whether comparable degrees of improvement are obtained by the two types of administrations, preferably when the dose difference is 3 times or lower, and most preferably estimating whether comparable degrees of improvement are obtained by the two types of administrations when the doses are identical. Such representative compounds of the present invention (in particular, compounds selected from the group consisting of those shown in Examples 82, 119, 120, 122, 229, and 267) were shown to have sufficiently wide ranges of acceptable timing of administration as defined above.

Assay Example 4

Purpose: Effect of a Test Compound on the Blood Glucose Level of Fasted Male Wistar Rats (In Vivo Test)

Animal: male Wistar rats (purchased from Charles River Japan, Inc.)

Method:

[Preparation and Administration of Test Compounds]

A test compound was suspended in 0.5% methyl cellulose (MC) solution and administered orally at a dose of 5 mL/kg. The control group was treated with a 0.5% MC solution. The solution was administered orally at a dose of 5 mL/kg.

[Blood Collection and Determination of Blood Glucose Levels]

Immediately before administering a test compound or 0.5% MC solution, and 0.5, 1, and 3 hours after the administration, without anesthetic the caudal vein was lightly cut with a razor blade to let the blood out. 10 μL of blood was collected and combined with 140 μL of 0.6 M perchloric acid solution. The sample was centrifuged at 3000 g at 4° C. for 10 minutes and the resultant supernatant was assayed with the Glucose CII TEST WAKO (Wako Pure Chemical Industries).

Result:

Some of the novel condensed imidazole derivatives of the present invention (in particular, compounds selected from the group consisting of those shown in Examples 82, 119, 120, 122, 229, and 267) showed no significant change in the blood glucose level in blood samples collected at any sampling time, as compared with the control group treated with the medium alone in the in vivo experiment as described above, where each compound was administered orally at a dose of 10-30 (mg/kg).

Assay Example 5

Effect of a Test Compound on the Glucose Tolerance of Male Zucker fa/fa Rat (Obesity Type II Diabetes Mellitus Model Animal) (In Vivo Test)

Animal: male Zucker fa/fa rats (purchased from Charles River Japan, Inc.)

Method:

[Preparation and Administration of Test Compounds]

The test compound was suspended in 0.5% methyl cellulose (MC) solution. The suspension of the test compound or a 0.5% MC solution that was used as a medium-control group was given orally at a dose of 5 mL/kg. After 0.5 hr, a glucose solution was given orally at a dose of 5 mL/kg. The dose of glucose given orally was 2 g/kg.

[Blood Collection Method and Determination of Blood Glucose, Insulin, and GLP-1 Levels]

Immediately before administering a test compound or 0.5% MC solution, immediately before the glucose loading, and 0.5, 1, 2, and 3 hours after the glucose loading, without anesthetic the caudal vein was slightly cut with a razor blade to let blood out. 250 μl of blood was collected using a heparin-coated capillary, and transferred into a centrifuge tube. The sample was centrifuged at 10000 g at 4° C. for 2 minutes. The levels of insulin and GLP-1 in the resultant supernatant were determined with an insulin assay kit (Morinaga Biochemical Institute) and Active GLP-1 ELISA kit (Linco), respectively. At the same time, 10 μl of blood was collected and combined with 140 μl of 0.6 M perchloric acid solution. The sample was centrifuged at 3000 g at 4° C. for 10 minutes, and the resultant supernatant was assayed with the Glucose CII TEST WAKO (Wako Pure Chemical Industries). Only the blood glucose level was determined three hours after glucose loading.

Result:

The area under the blood glucose level ($AUC_{Glu(0-3h)}$) between the start of glucose administration and 3 hours after administration, the area under insulin level time curve ($AUC_{ins(0-2h)}$), and the area under GLP-1 level time curve ($AUC_{GLP-1(0-2h)}$) were determined for each of the 0.5% MC solution-treated group and each of the test compound-treated groups. The variation in glucose tolerance, variations in the insulin level, and GLP-1 level due to the test compound were determined by taking the AUC of the 0.5% MC solution-treated group as 100% according to the following formula.

The rate of change in glucose tolerance (%)=$AUC_{0-3h}$ of the group treated with a test compound/ ($AUC_{0-3h}$ of the group treated with 0.5% MC solution)×100

The rate of change in insulin and GLP-1 level (%)=$AUC_{0-2h}$ of the group treated with a test compound/($AUC_{0-2h}$ of the group treated with 0.5% MC solution)×100

Some of the novel condensed imidazole derivatives of the present invention (in particular, compounds selected from the group consisting of those shown in Examples 82, 119, 120, 122, 229, and 267) were shown to change the insulin and GLP-1 levels at rates higher than 100% and exhibit glucose tolerance at a rate of change lower than 100% in the in vivo experiment as described above, where each compound was administered orally at a dose of 0.1-10 (mg/kg).

Assay Example 6

<Assessment for Drug-Metabolizing Enzyme (Cytochrome P450)>

The inhibitory activity $IC_{50}$ was determined using an expression system for recombinant P450 and the fluorescent substrates (GENTEST Corp.) indicated in Tables 2 and 3 according to the Assay Procedure (WWW.gentest.com) prepared by GENTEST Corp. P450 molecular species assessed were the five molecular species, CYP1A2, CYP2C9, CYP2C19, CYP2D6, and CYP3A4. The experimental conditions used are shown below. The fluorescence intensity was determined using a plate reader (CYTO FLUOR Multi-Well Plate Reader Series 4000; PerSeptive Biosystems Corp.). The degree of inhibition was determined as a mean value from nine independent assays per second using as an index the intensity fluorescence emitted from the metabolite of the fluorescent substrate.

The substrates, metabolites, inhibitors, excitation wavelengths, and fluorescence wavelengths used in the assay are shown in Table 2.

group of molecules, namely the molecular species, CYP1A2, CYP2C9, CYP2C19, CYP2D6, and CYP3A4.

Assay Example 7

<Suppression of hERG Channel Current>

(1) Activity towards inhibiting the hERG channel current was evaluated according to the report Zhou, Z et al, Biophysical Journal, 74(1), 230-241 (1998).

(2) This experiment was carried out using HEK-293 cells into which the hERG channel gene (subtype 1) had been introduced (the cell line was established by the inventors).

(3) One to several days before the experiment, cells were plated on a poly-lysine-coated glass plate. The cells were cultured until the day of the experiment. At the start of the experiment, the cell-seeded glass plate was transferred into a bath for current measurement. The hERG channel current was measured by the voltage clamp method using the patch clamp technique. The current was measured using a current amplifier (Axon Instruments). The current was recorded and analyzed using pCLAMP software (Axon Instruments)

(4) The hERG channel current was induced by applying to the cells a depolarizing pulse from a holding potential of −80 mV to +20 mV for 5 seconds and to −50 mV for 4 seconds, at 20 second intervals. After the current became stable in a control solution, the cells were perfused with solutions containing various concentrations of test compounds.

TABLE 2

| Molecular species of p450 | Substrate | Metabolite | Inhibitor | Excitation wavelength (nm) | Fluorescence wavelength (nm) |
|---|---|---|---|---|---|
| CYP1A2 | CEC | CHC | α-Naphthoflavone | 409 | 460 |
| CYP2C9 | MFC | HFC | Sulfaphenazole | 409 | 530 |
| CYP2C19 | CEC | CHC | Tranylcypromine | 409 | 460 |
| CYP2D6 | AMMC | AHMC | Quinidine | 390 | 460 |
| CYP3A4 | BFC | HFC | Ketoconazole | 409 | 530 |

The abbreviations for the substrates and metabolites are listed in Table 3.

TABLE 3

| | |
|---|---|
| CEC | 3-Cyano-7-ethoxycoumarin |
| CHC | 3-Cyano-7-hydroxycoumarin |
| MFC | 7-Methoxy-4-trifluoromethylcoumarin |
| HFC | 7-Hydroxy-4-trifluoromethylcoumarin |
| CEC | 7-Ethoxy-3-cyanocoumarin |
| CHC | 7-Hydroxy-3-cyanocoumarin |
| AMMC | 3-[2-(N,N-diethyl-N-methylamino)ethyl]-7-methoxy-4-methylcoumarin |
| AHMC | 3-[2-(N,N-diethylamino)ethyl]-7-hydroxy-4-methylcoumarin |
| BFC | 7-Benzyloxy-4-(trifluoromethyl)-coumarin |
| HFC | 7-hydroxy-4-(trifluoromethyl)-coumarin |

<Assay Result>

The compounds of the present invention were evaluated for their ability to inhibit metabolic reactions due to P450 in Assay Example 6. This experiment showed that representative compounds of the present invention (in particular, compounds selected from the group consisting of those shown in Examples 82, 119, 120, 122, 229, and 267) exhibited 10 μM or higher $IC_{50}$ values with respect to five out of the P450

(5) The amplitude of the hERG channel current was defined as the peak value of the tail current observed upon restoring the potential to −50 mV. The inhibiting effect of a test compound on the hERG channel current ($IC_{50}$) was estimated based on the change in the peak value of tail current upon addition of the test compound at various concentrations. The peak value of tail current recorded for a normal solution was taken as 100%.

<Test Result>

Representative compounds of the present invention (in particular, compounds selected from the group consisting of those shown in Examples 82, 119, 120, 122, 229, and 267) were evaluated for their ability to inhibit the hERG channel current in Assay Example 7. The $IC_{50}$ values of the compounds were 30 μM or higher.

The structural formulae for the compounds in Production examples and Examples described above are shown below.

Production Example 1. a)
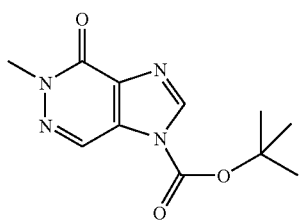
Production Example 1. b)
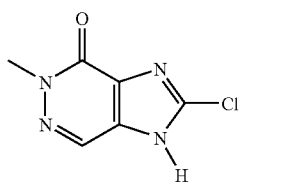
Production Example 1. c)
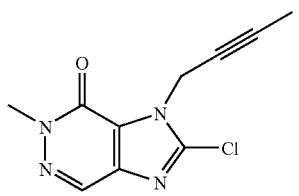
Production Example 1. d)
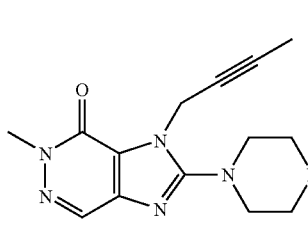
Production Example 2. a)
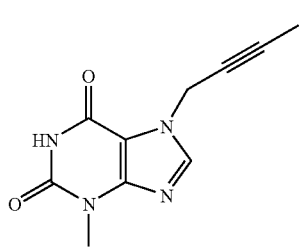
Production Example 2. b)
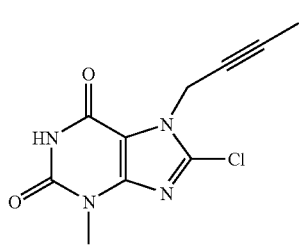
Production Example 2. c)
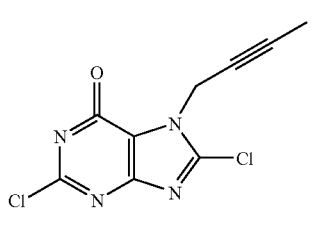
-continued
Production Example 2. d)
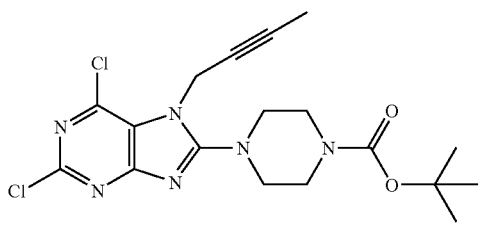
Example 1. a)
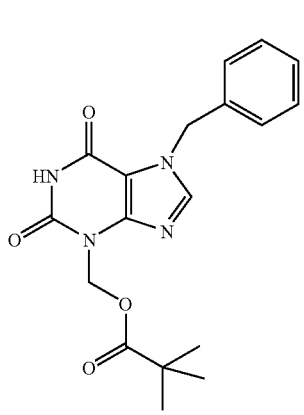
Example 1. b)
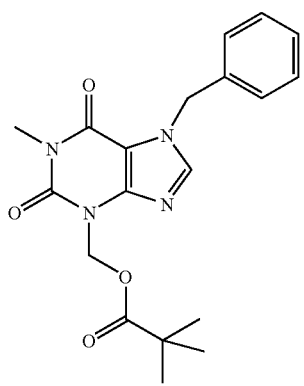
Example 1. c)
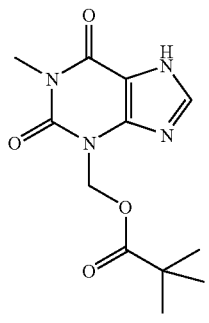

Example 1. d)
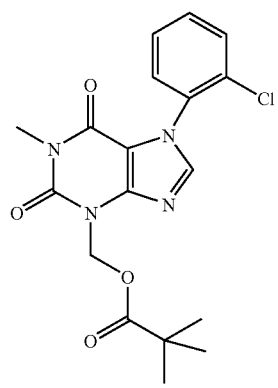
Example 1. e)
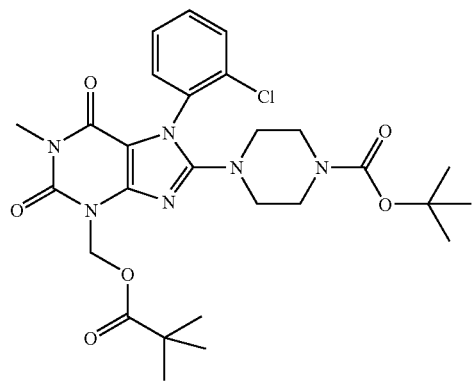
Example 1. f)
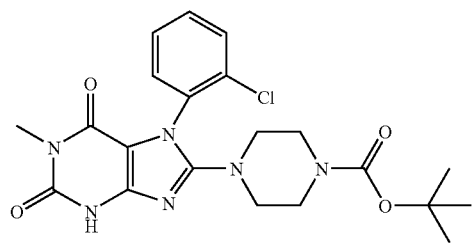
Example 1. g)-1
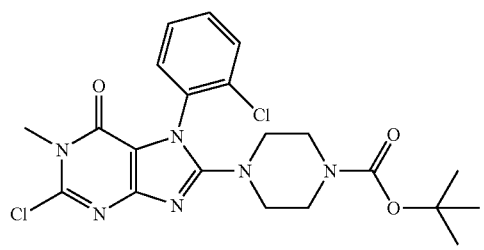
Example 1. g)-2
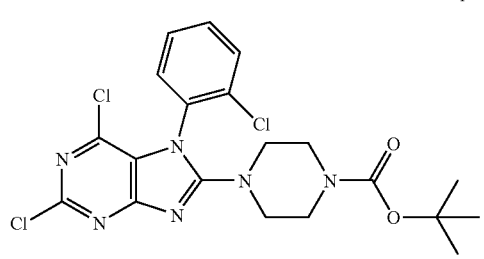
Example 2.
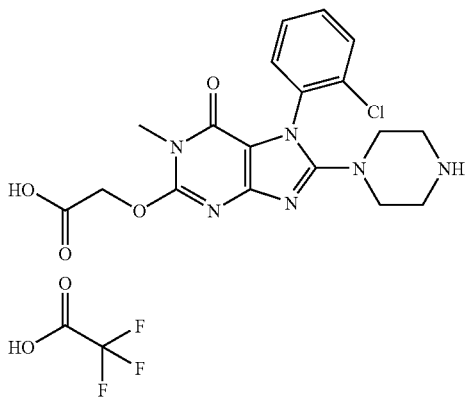
Example 3. a)
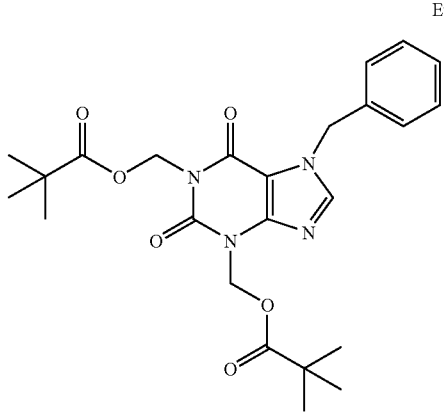
Example 3. b)
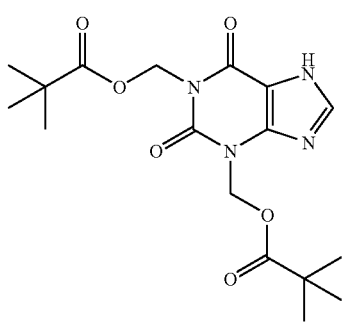
Example 3. c)
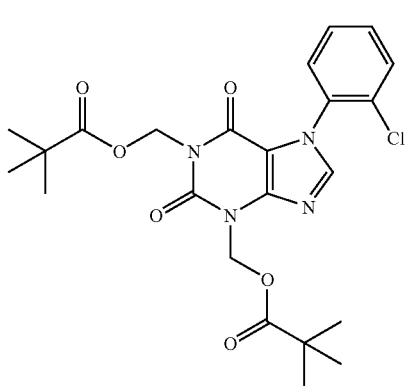

Example 3. d)
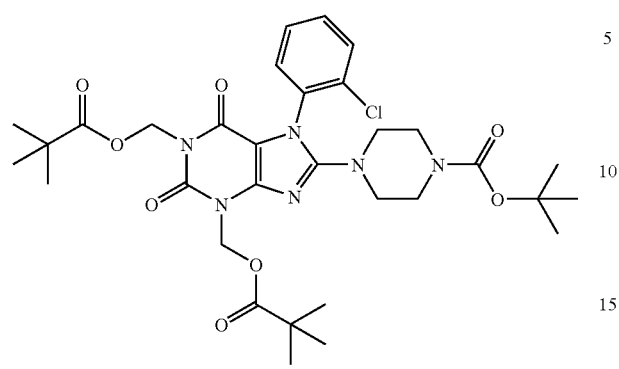
Example 3. e)
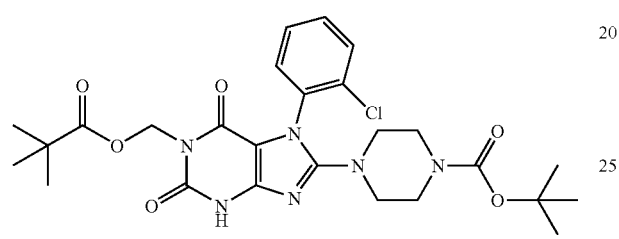
Example 3. f)
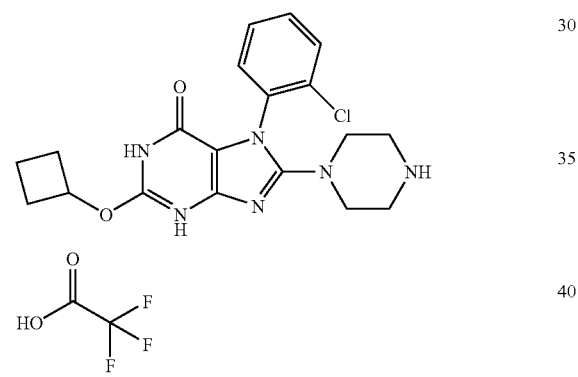
Example 4. a)
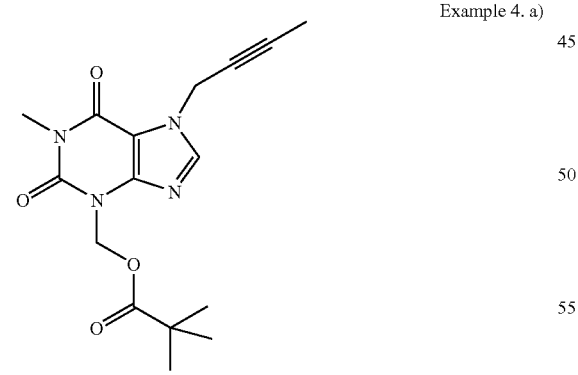
Example 4. b)
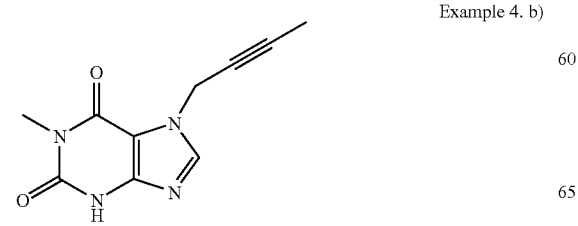
Example 4. c)
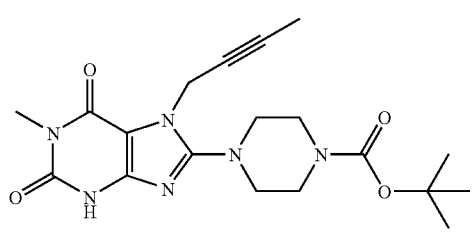
Example 4. d)
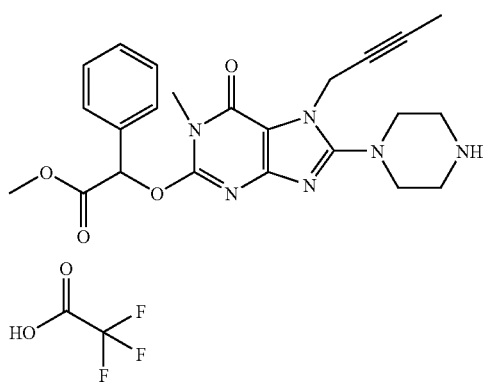
Example 5.
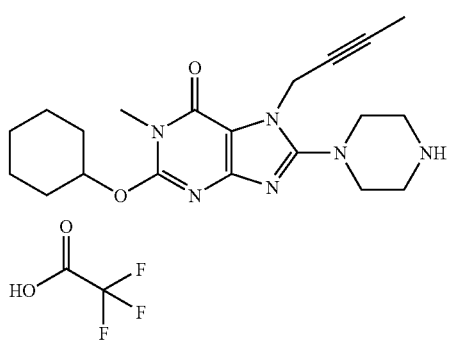
Example 6.
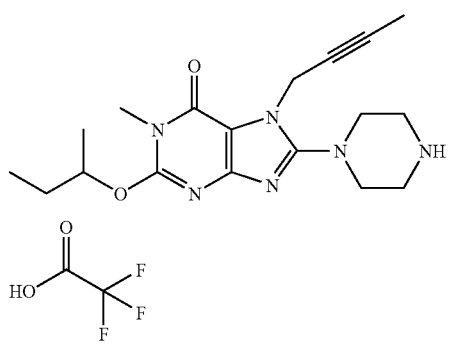
Example 7.
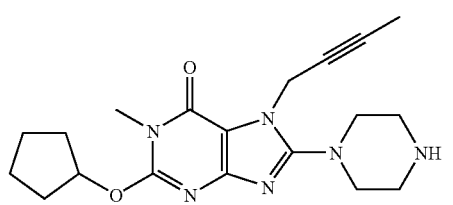

-continued
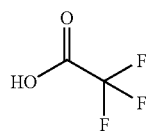
Example 8.
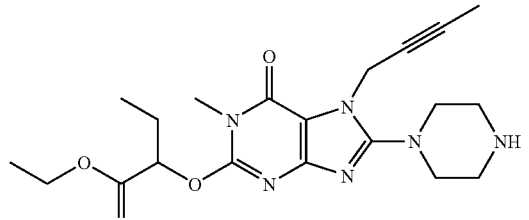
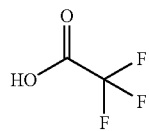
Example 9.
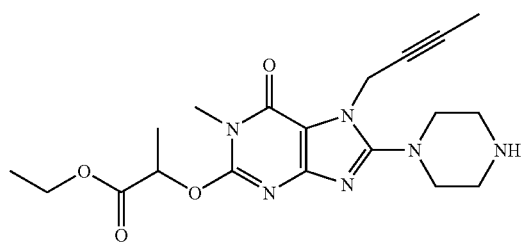
Example 10.
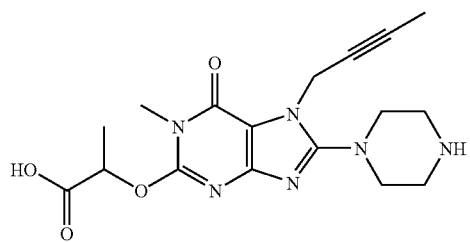
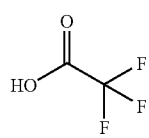
Example 11. a)-1
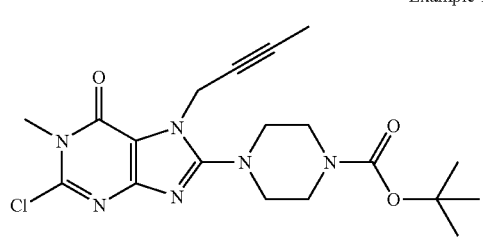
-continued
Example 11. a)-2
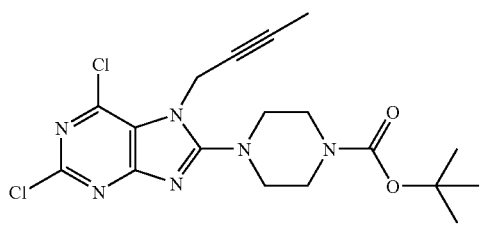
Example 11. b)
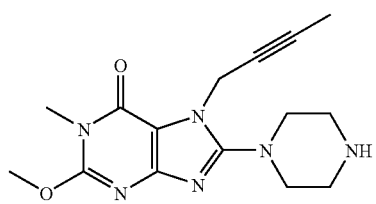
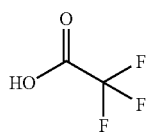
Example 12.
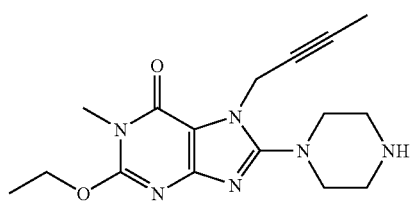
Example 13.
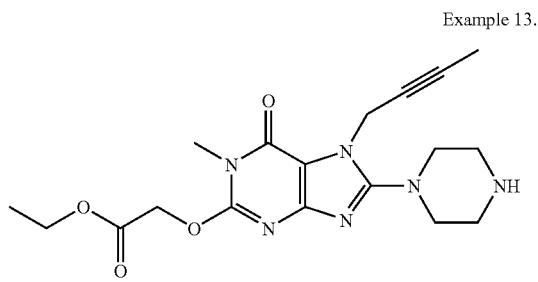
Example 14.
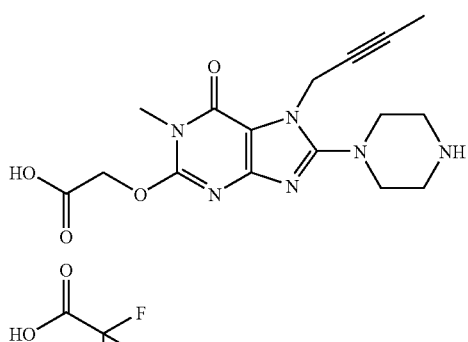

-continued
Example 15.
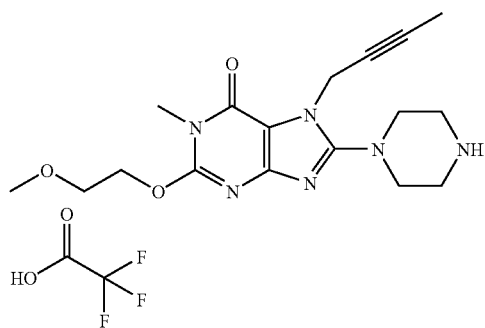
Example 16.
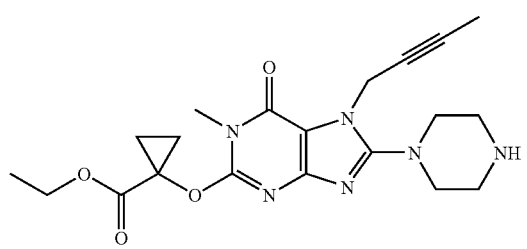
Example 17.
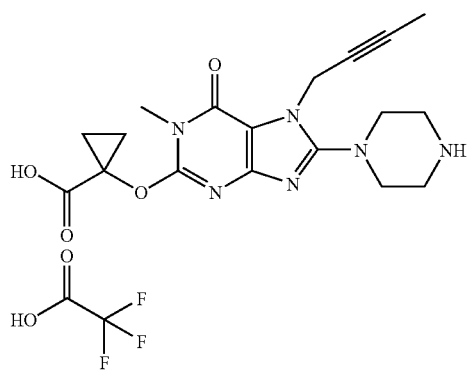
Example 18.
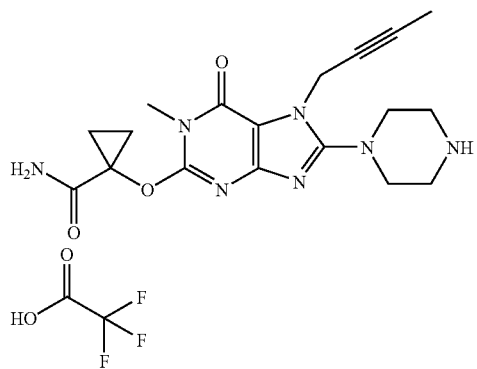
Example 19.
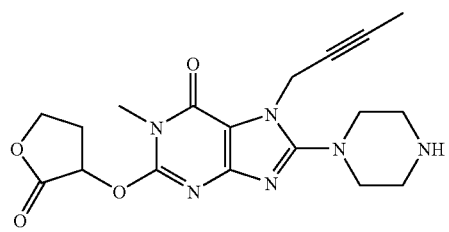
-continued
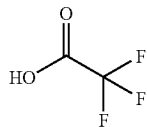
Example 20.
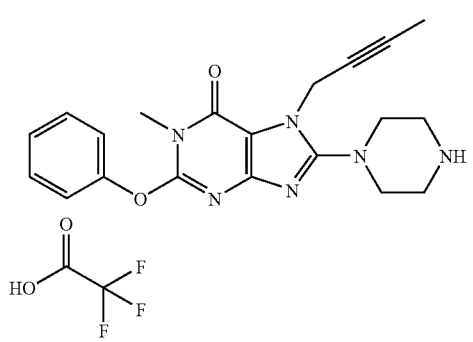
Example 21.
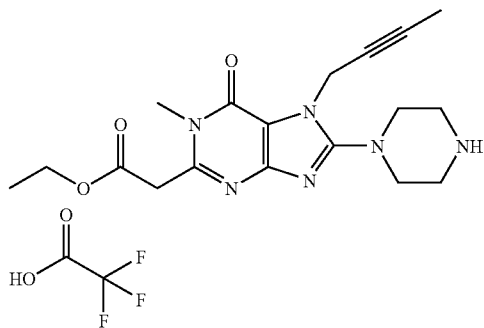
Example 22.
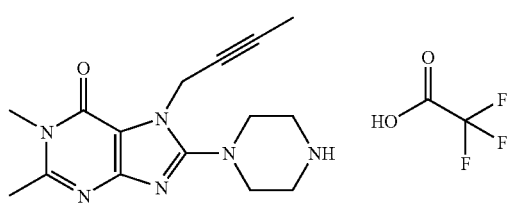
Example 23.
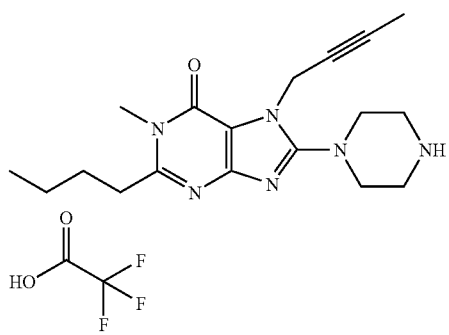
Example 24.
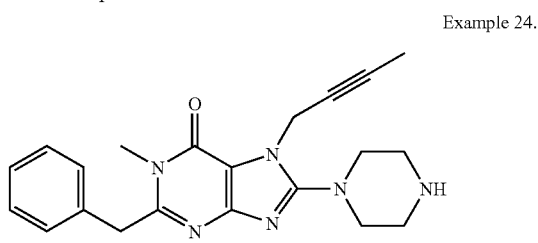

Example 25.
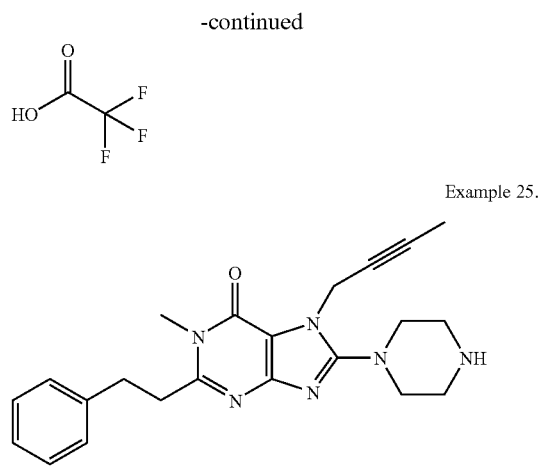
Example 26.
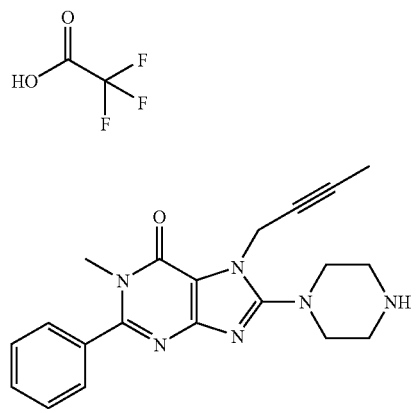
Example 27.
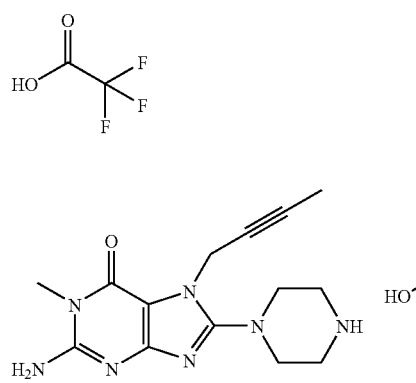
Example 28.
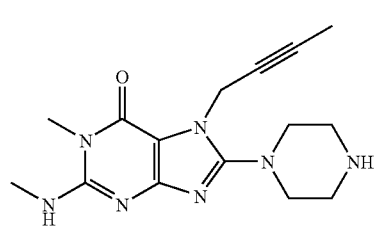
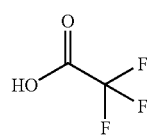
Example 29.
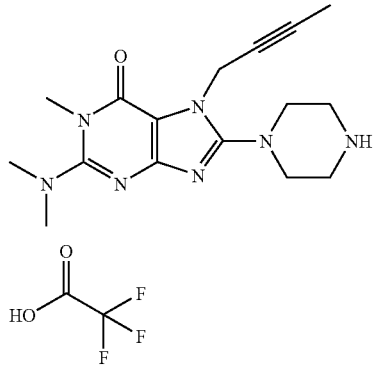
Example 30.
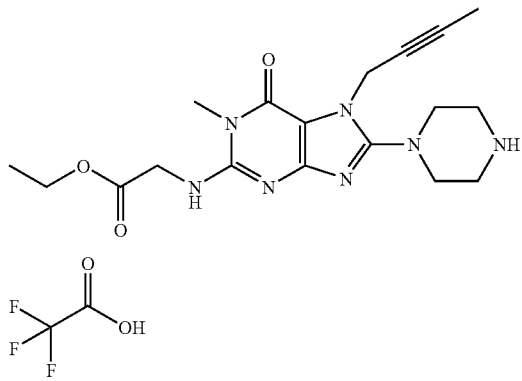
Example 31.
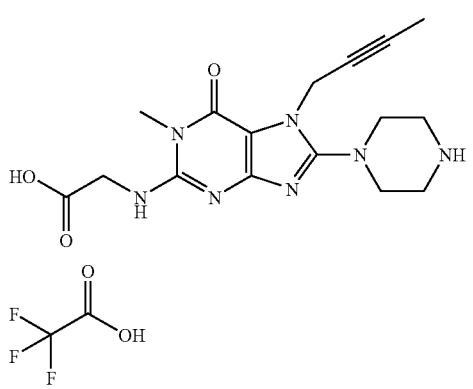
Example 32.
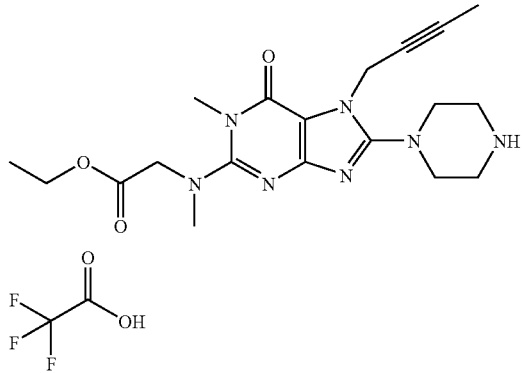

-continued
Example 33.
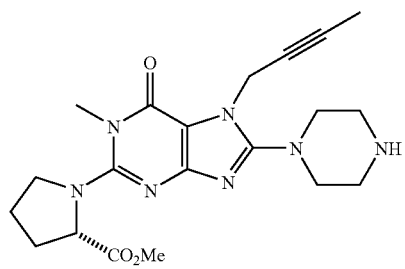
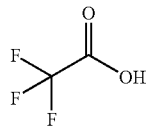
Example 34.
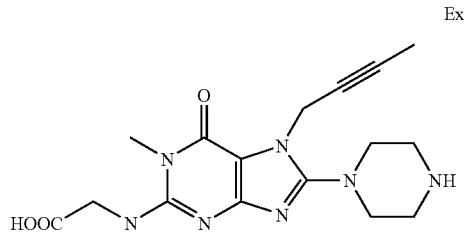
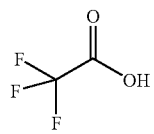
Example 35.
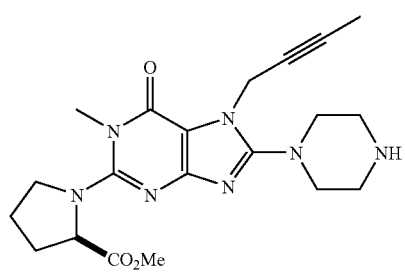
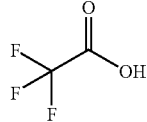
Example 36.
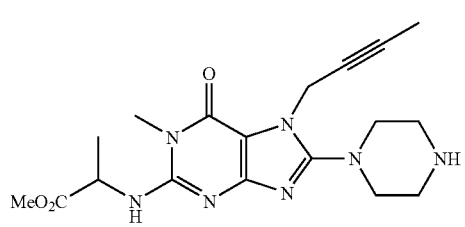
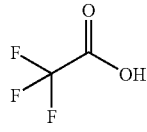
-continued
Example 37.
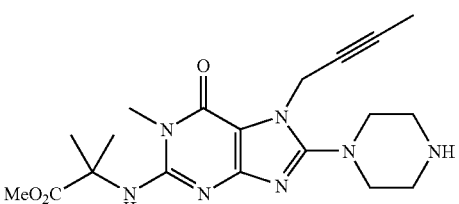
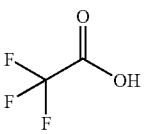
Example 38.
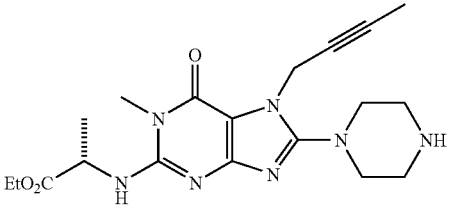
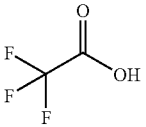
Example 39.
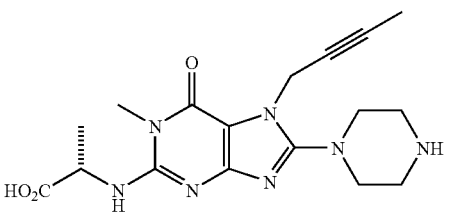
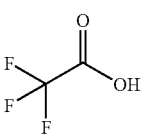
Example 40.

Example 41.
Example 42.
Example 43.
Example 44.
Example 45.
Example 46.
Example 47.
Example 48.

Example 49.
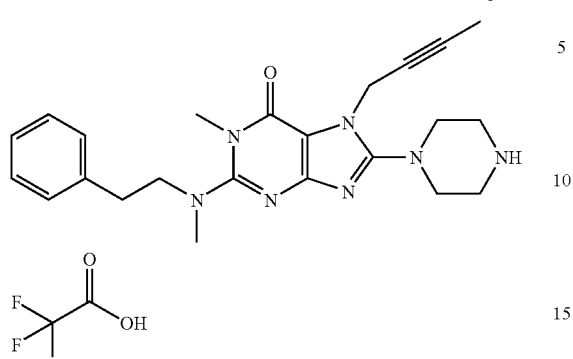
Example 50.
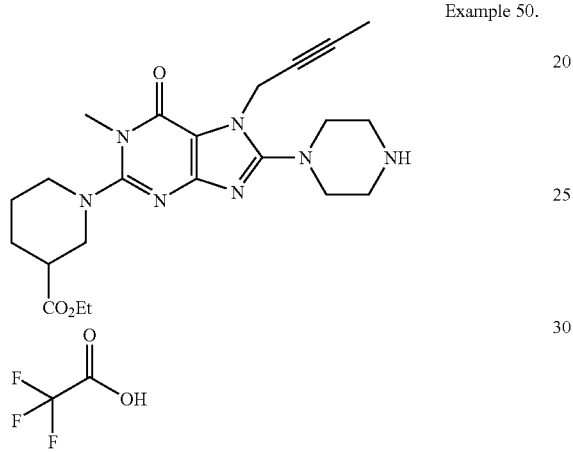
Example 51.
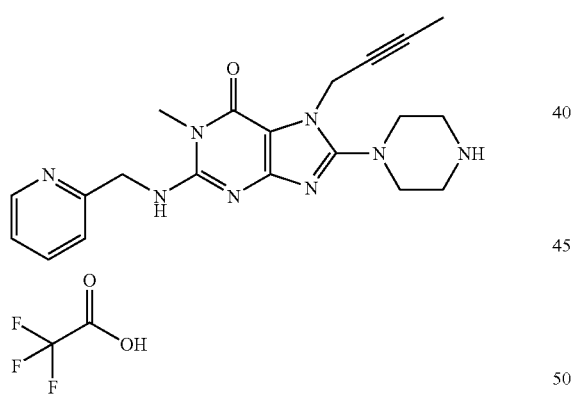
Example 52.
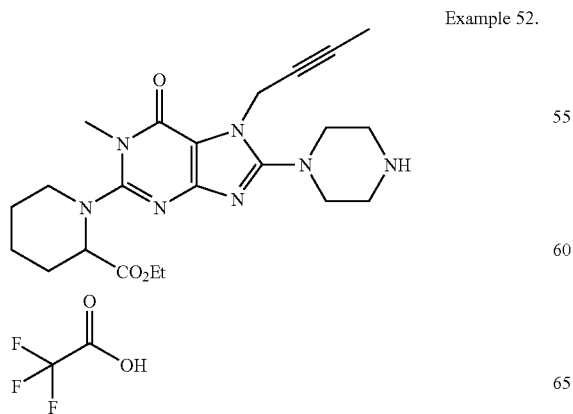
Example 53.
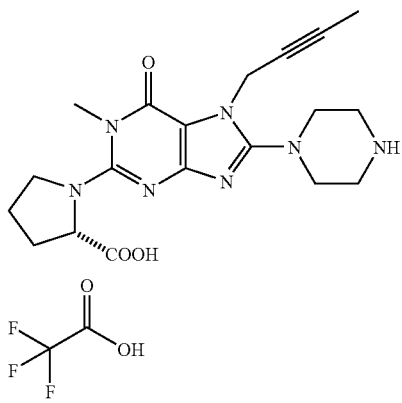
Example 54.
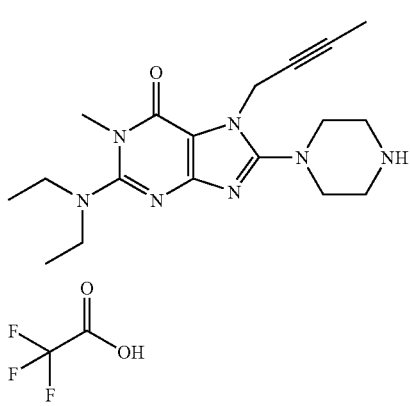
Example 55.
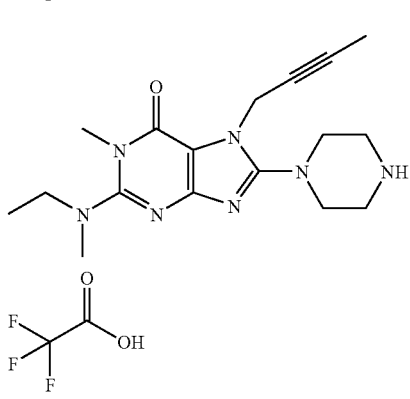
Example 56.
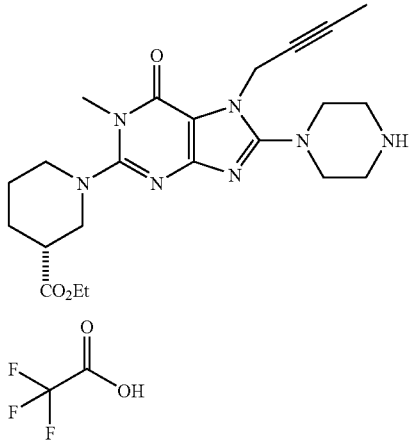

Example 57.
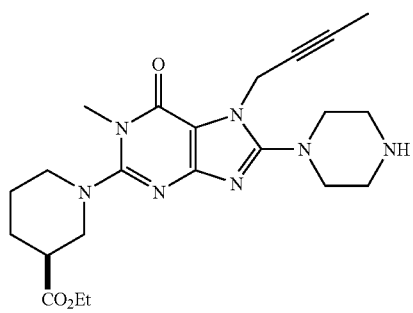
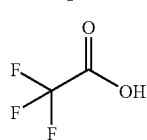
Example 58.
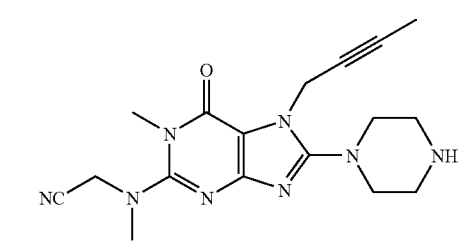
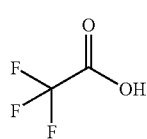
Example 59.
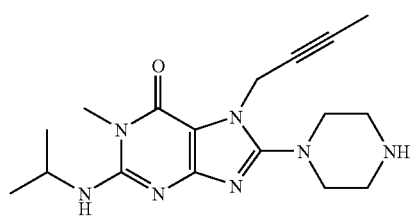
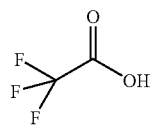
Example 60.
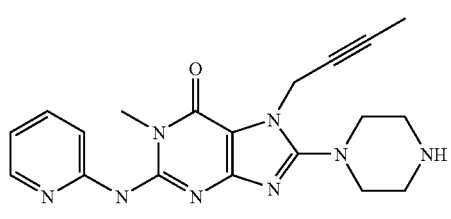
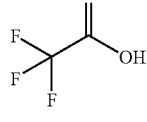
Example 61.
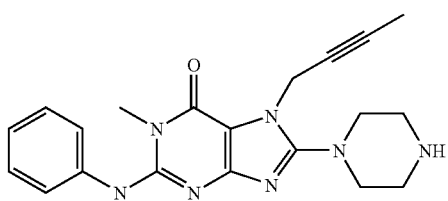
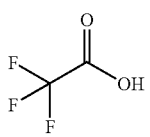
Example 62.
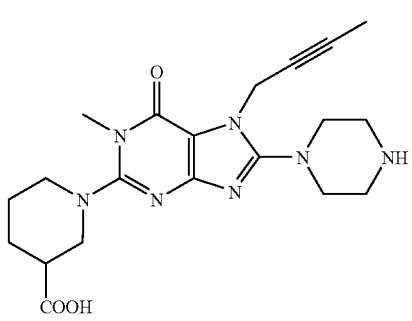
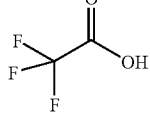
Example 63.
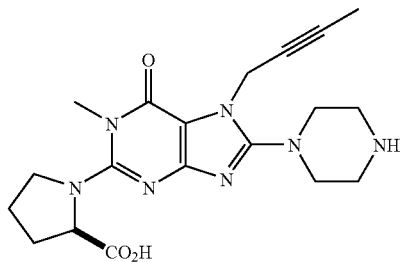
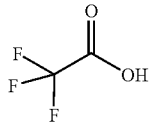
Example 64.
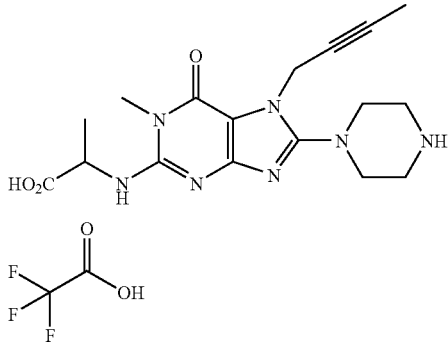
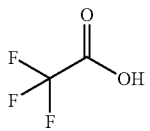

Example 65.
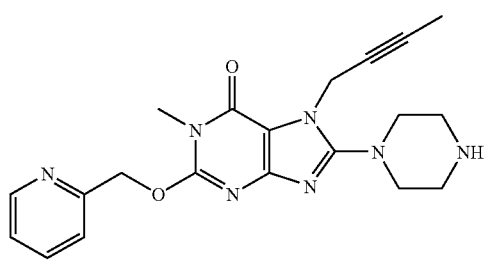
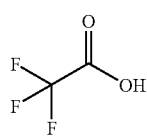
Example 66.
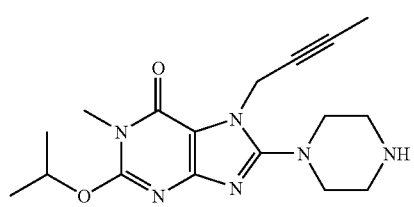
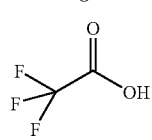
Example 67.
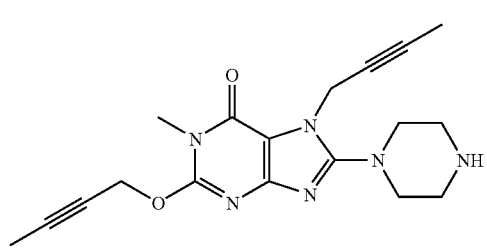
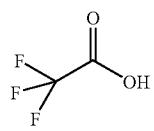
Example 68.
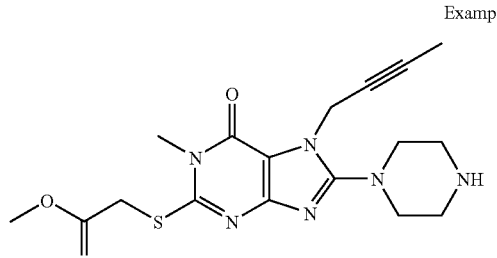
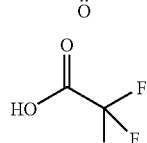
Example 69.
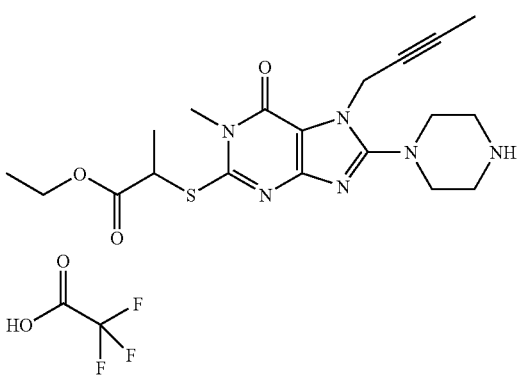
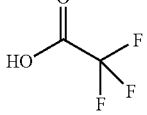
Example 70.
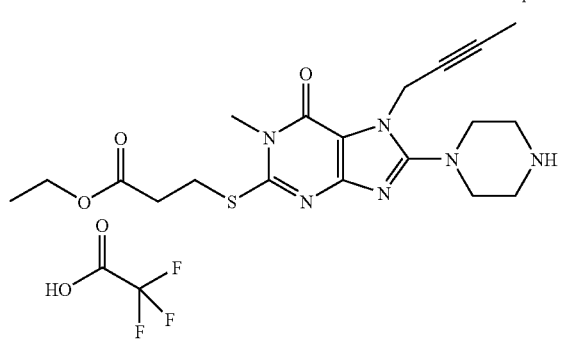
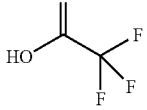
Example 71.
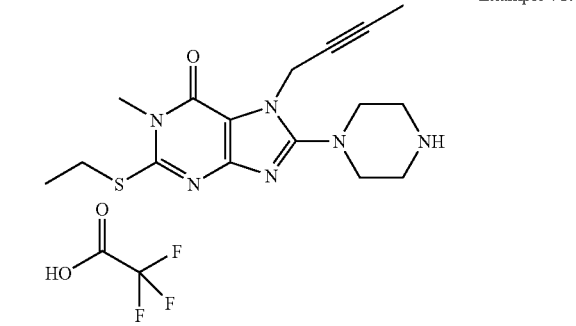
Example 72.
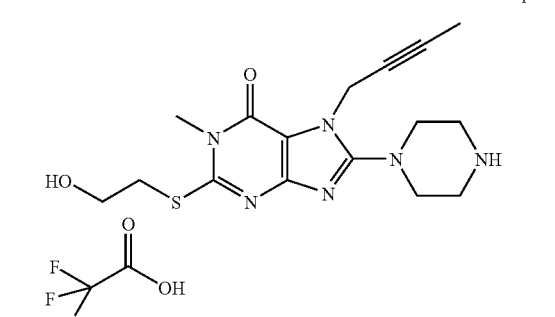
Example 73.
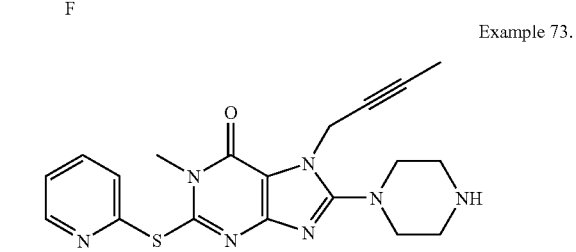
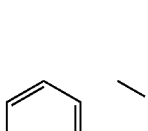

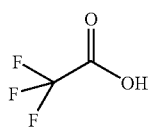
Example 74.
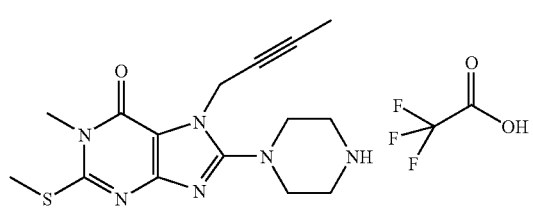
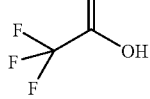
Example 75.
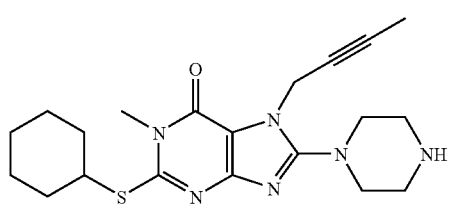
Example 76.
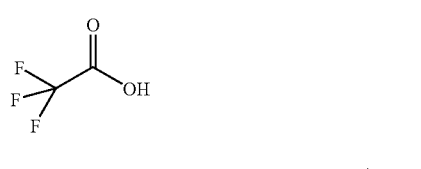
Example 77.
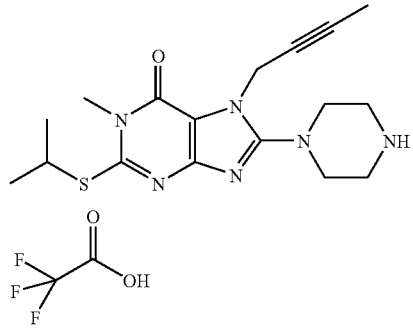
Example 78.
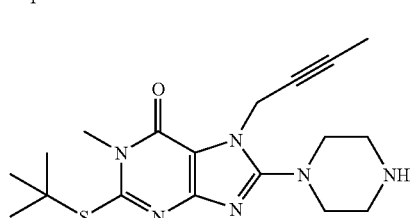
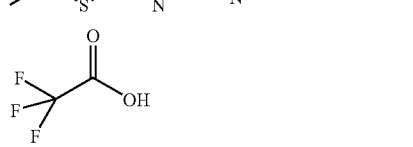
Example 79.
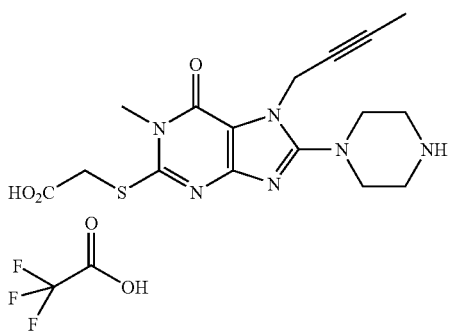
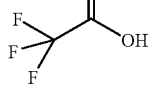
Example 80.
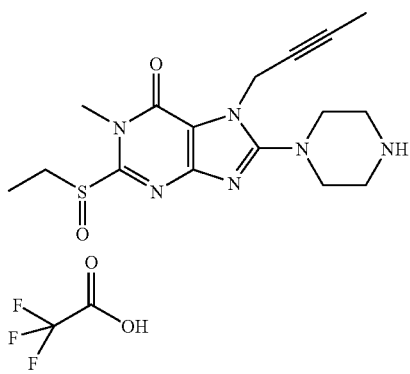
Example 81.
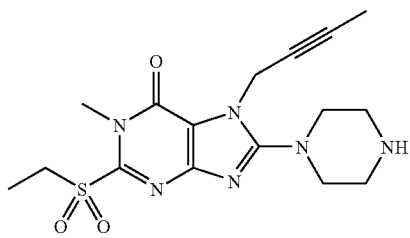
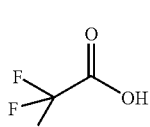
Example 82.
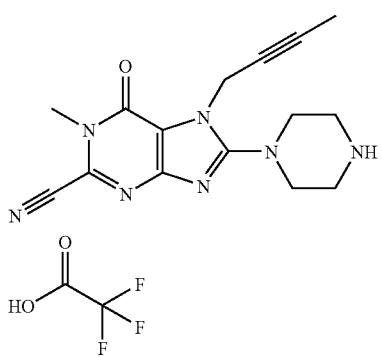
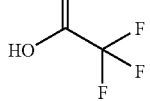

-continued

Example 83. a)

Example 83. b)

Example 84.

Example 85.

Example 86. a)

-continued

Example 86. b)

Example 86. c)

Example 86. d)

Example 86. e)

Example 87.

Example 88.

-continued
Example 89.
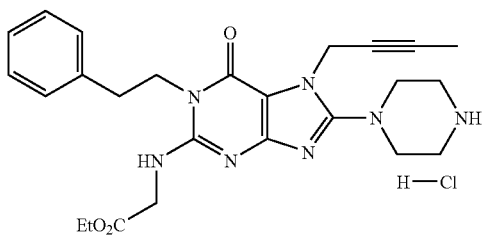
Example 90.
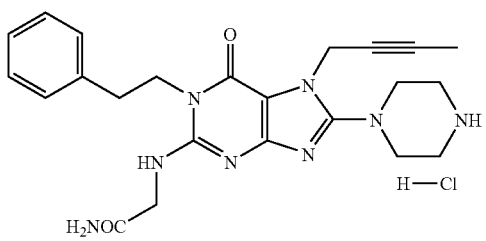
Example 91.
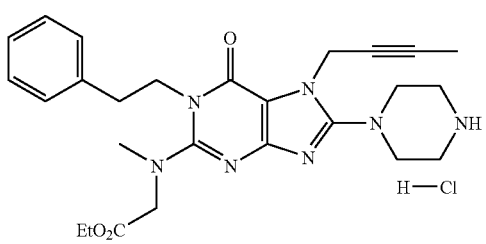
Example 92.
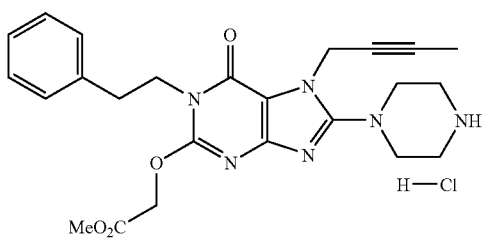
Example 93.
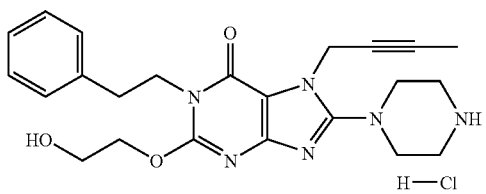
Example 94.
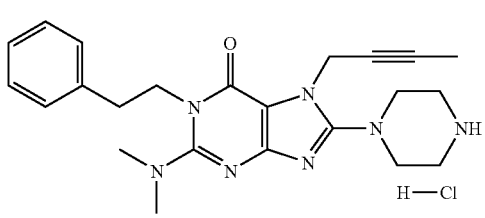
-continued
Example 95. a)
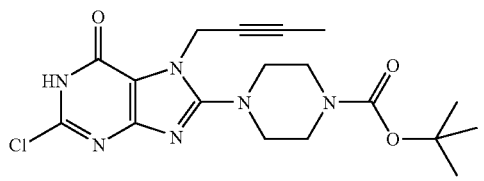
Example 95. b)
Example 96. a)
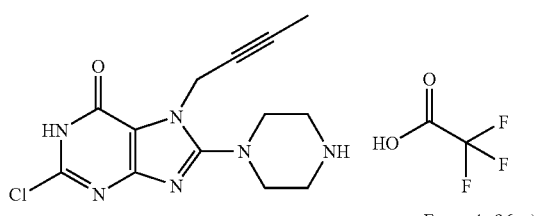
Example 96. b)
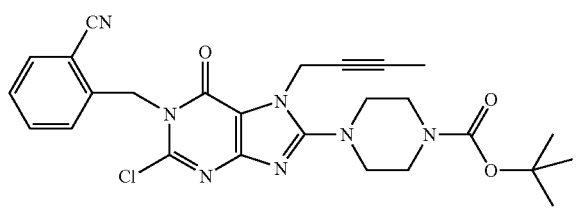
Example 96. c)
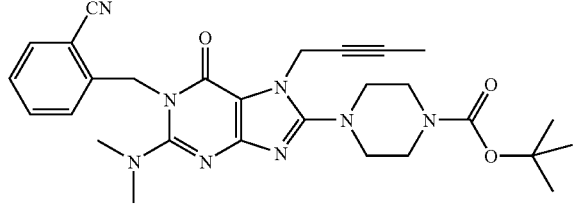
Example 97.
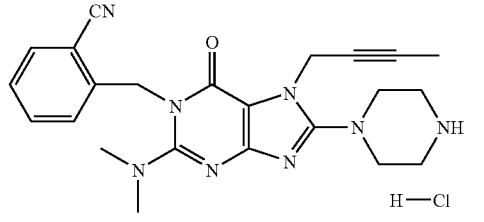
Example 98.
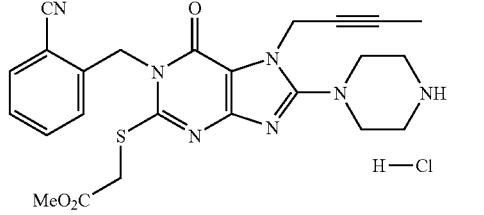

Example 99. a)
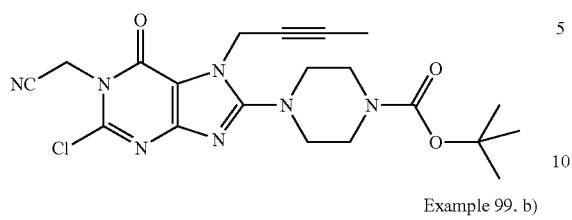
Example 99. b)
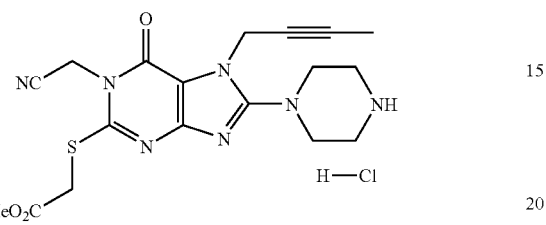
Example 100. a)
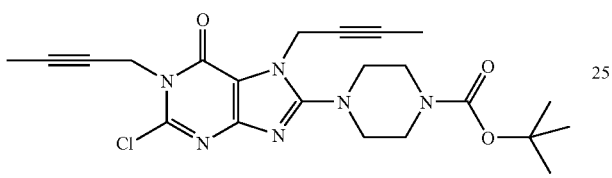
Example 100. b)
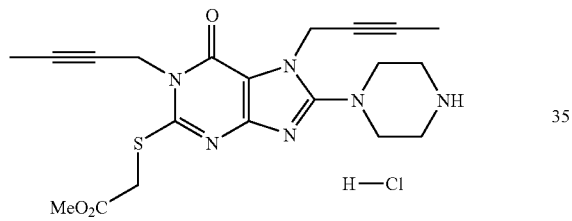
Example 101.
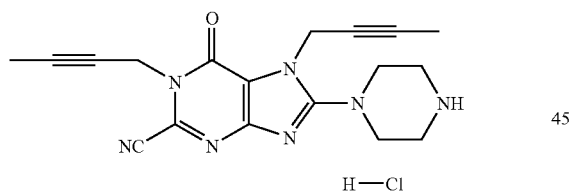
Example 102.
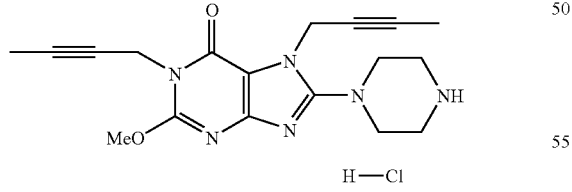
Example 103. a)
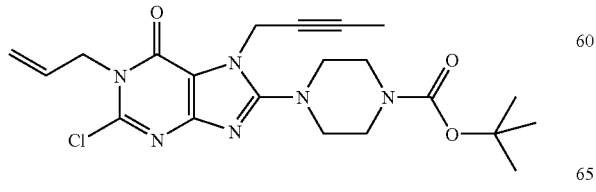
Example 103. b)
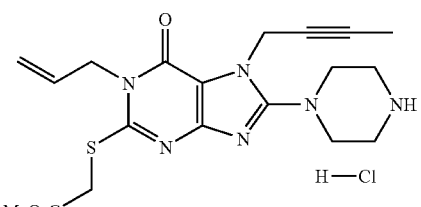
Example 104.
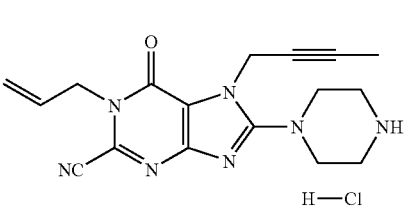
Example 105.
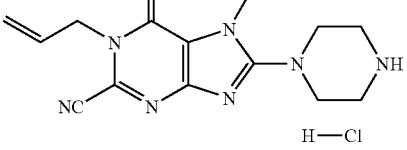
Example 106. a)
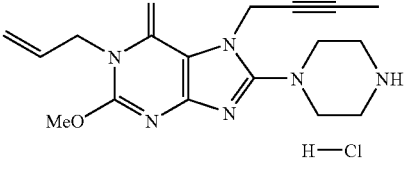
Example 106. b)
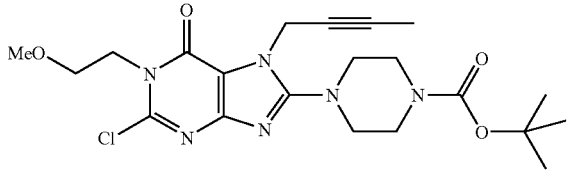
Example 107.
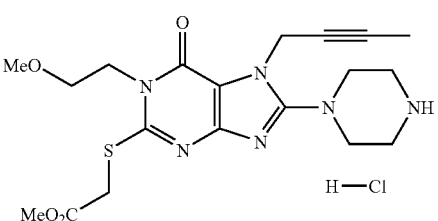
Example 108.
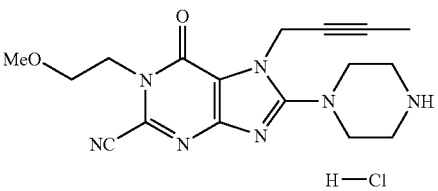

-continued
Example 109. a)
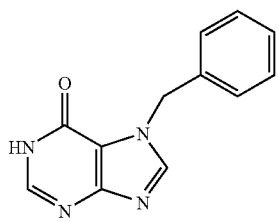
Example 109. b)
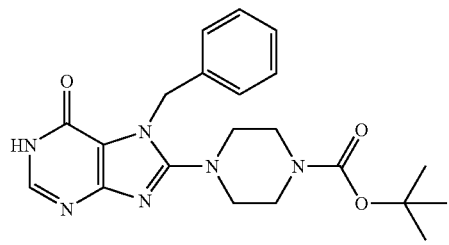
Example 109. c)
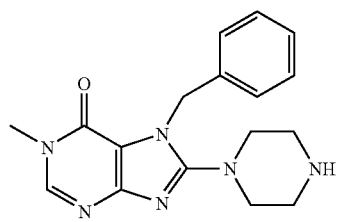 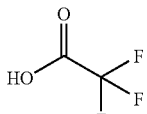
Example 110.
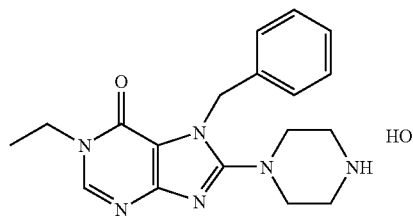 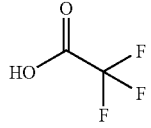
Example 111.
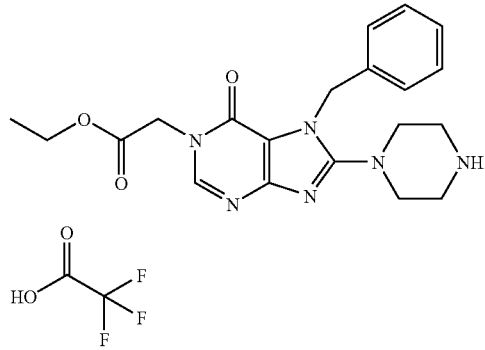
Example 112.
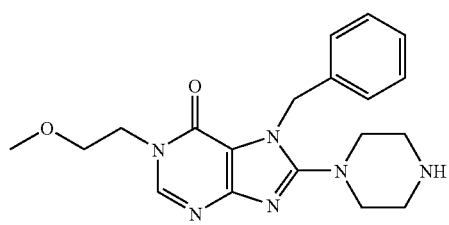
-continued
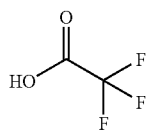
Example 113.
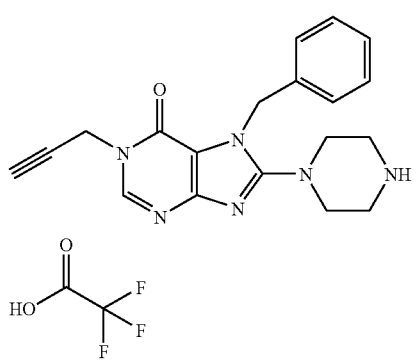
Example 114.
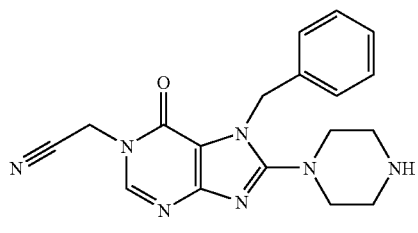
Example 115. a)
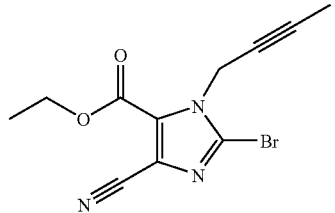
Example 115. b)
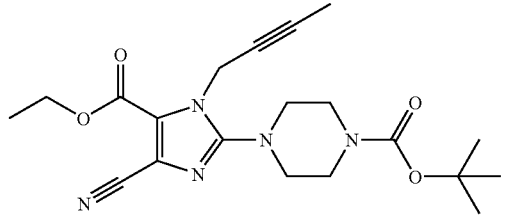
Example 115. c)
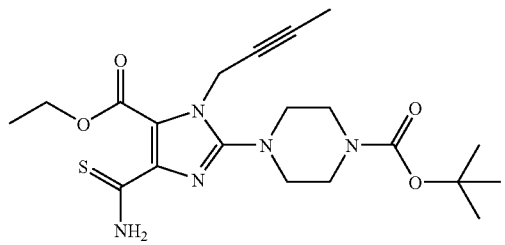

-continued

Example 115. d)
Example 115. e)
Example 115. f)
Example 115. g)
Example 115. h)
Example 115. i)

-continued

Example 116. a)
Example 116. b)
Example 116. c)
Example 116. d)
Example 116. e)
Example 117.

Example 118. a)

Example 118. b)

Example 119. a)

Example 119. b)

Example 119. c)

Example 119. d)

Example 119. e)

Example 120. a)

Example 120. b)

Example 120. c)

Example 121

-continued

Example 122.

Example 123.

Example 124.

Example 125.

Example 126.

-continued

Example 127.

Example 128.

Example 129.

Example 130.

Example 131.

Example 132.

Example 133.

Example 134.

Example 135.

Example 136.

Example 137.

Example 138.

Example 139.

-continued
Example 140.
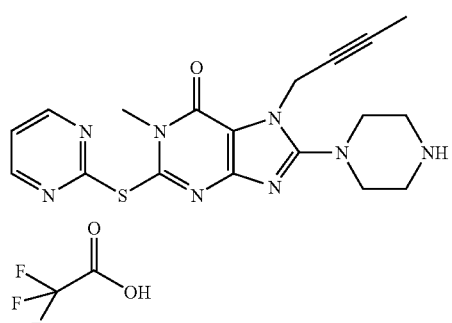
Example 141.
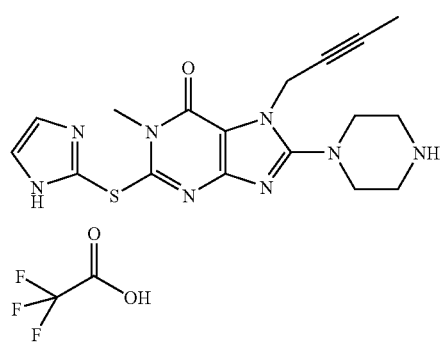
Example 142.
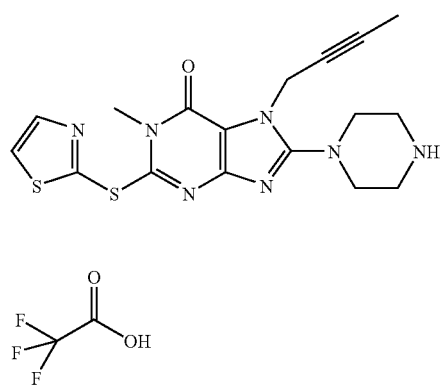
Example 143.
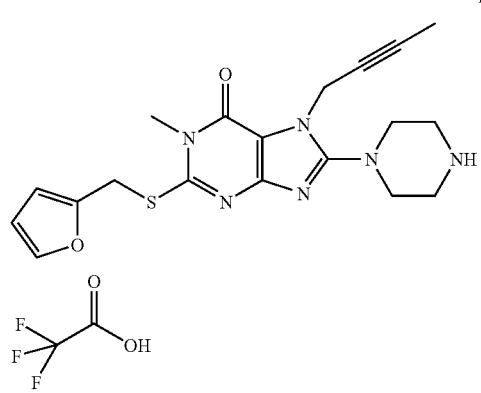
-continued
Example 144.
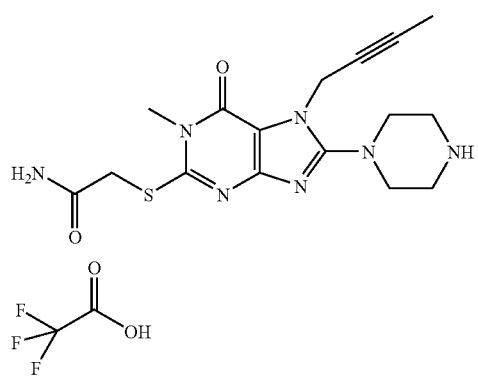
Example 145.
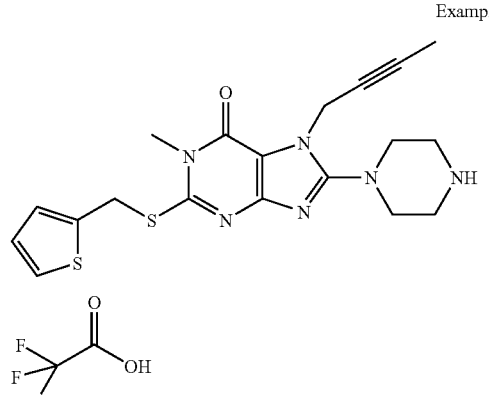
Example 146.
Example 147.
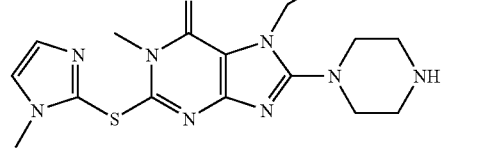

-continued
Example 148.
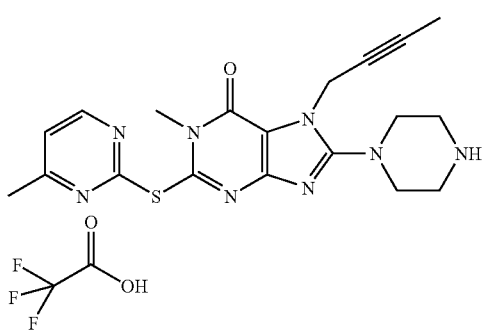
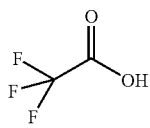
Example 149.
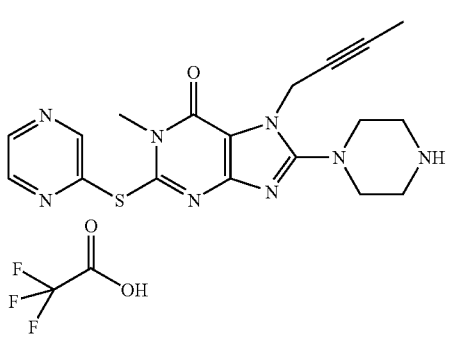
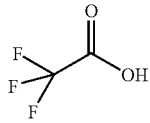
Example 150.
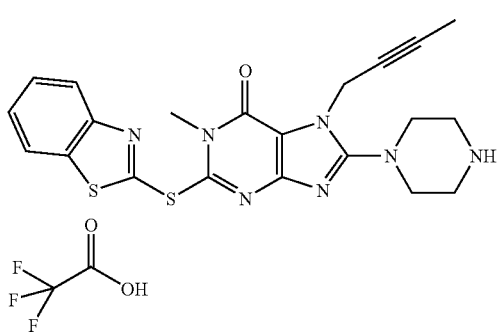
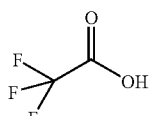
Example 151.
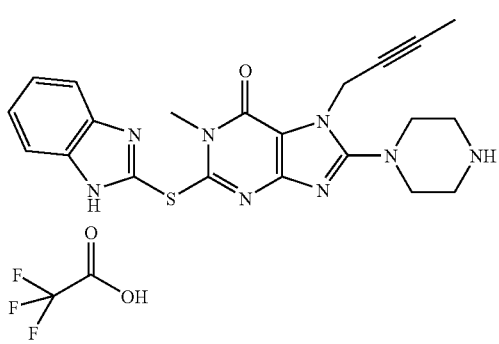
Example 152.
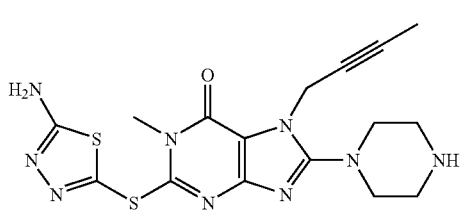
-continued
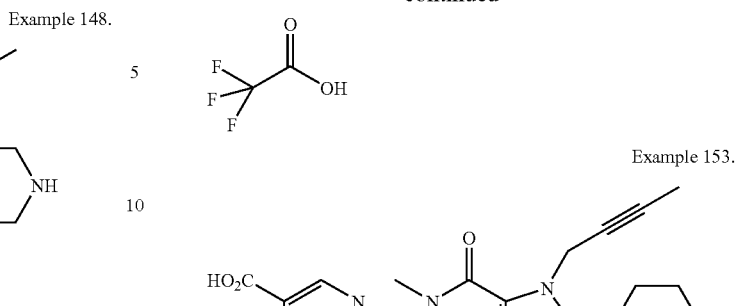
Example 153.
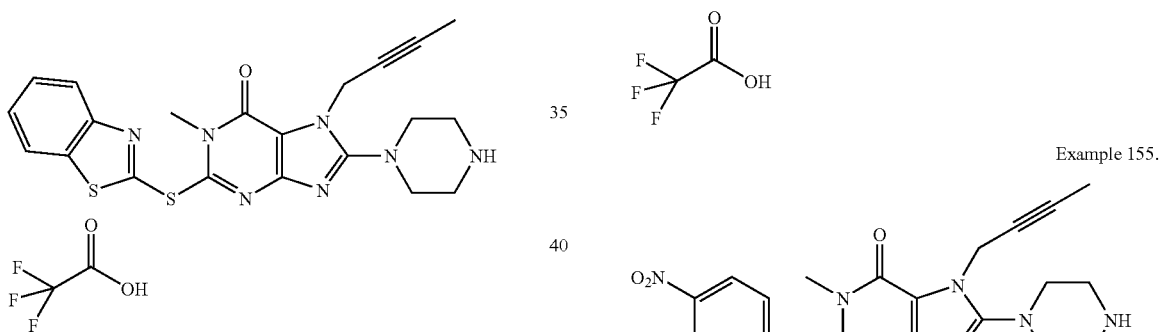
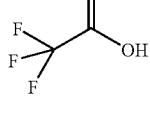
Example 154.
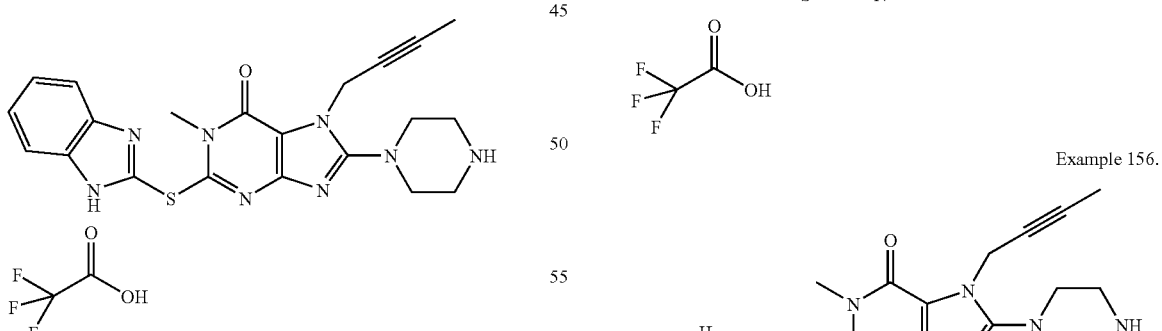
Example 155.
Example 156.
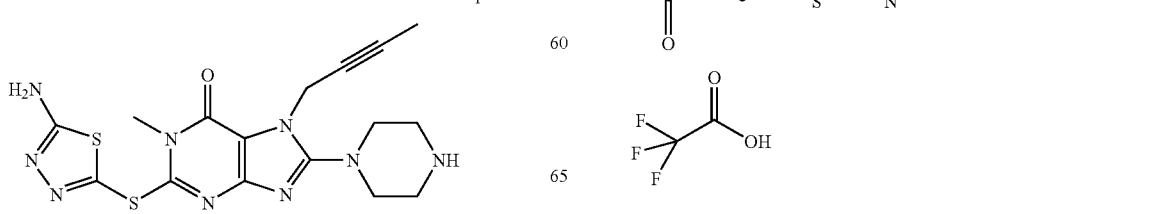

Example 157.
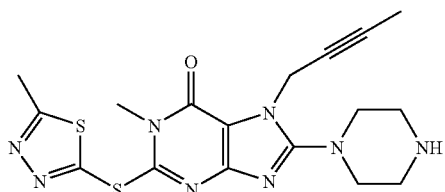
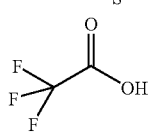
Example 158.
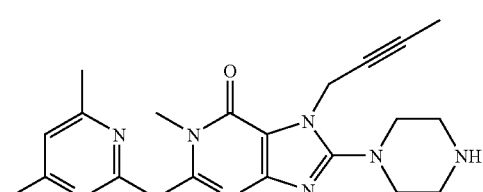
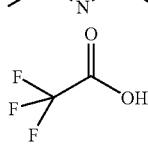
Example 159.
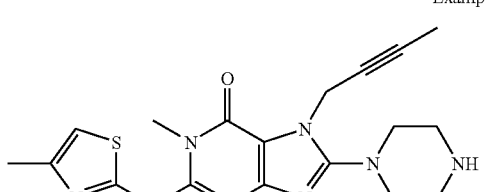
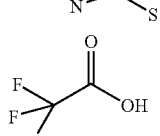
Example 160.
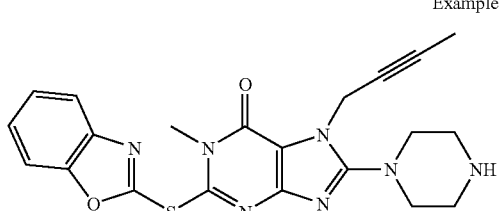
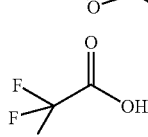
Example 161.
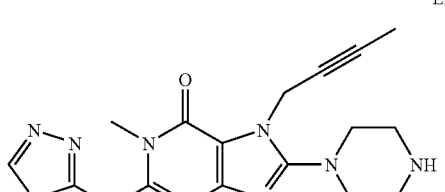
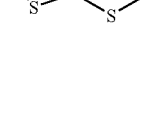
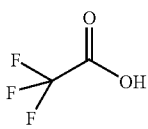
Example 162.
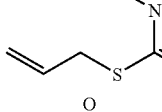
Example 163.
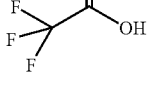
Example 164.
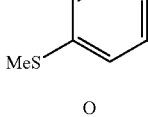
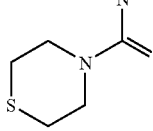
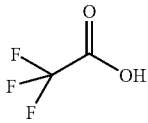
Example 165.
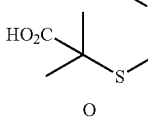
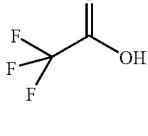

Example 166.
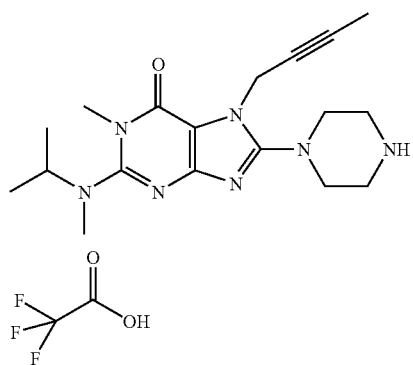
Example 167.
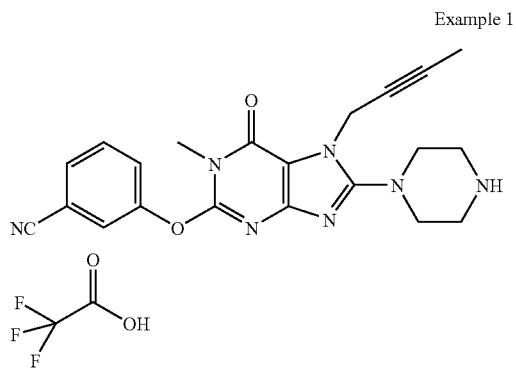
Example 168.
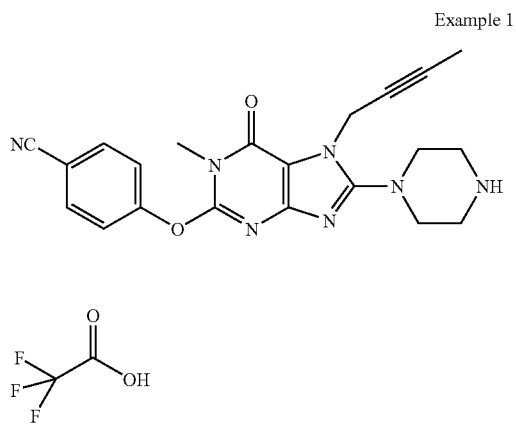
Example 169.
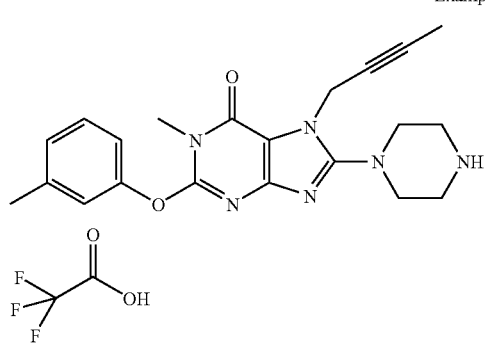
Example 170.
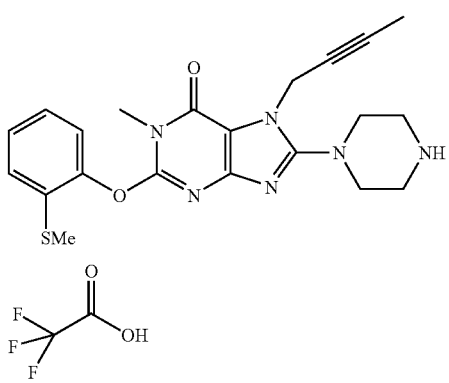
Example 171.
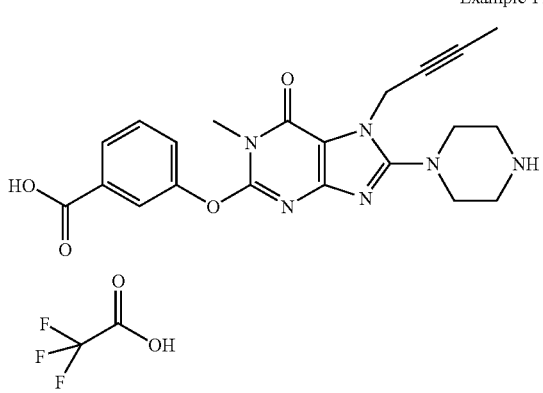
Example 172.
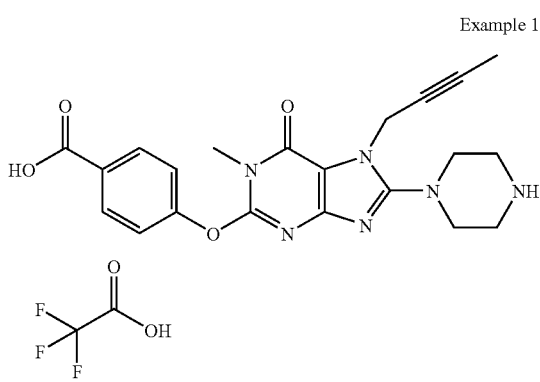
Example 173.
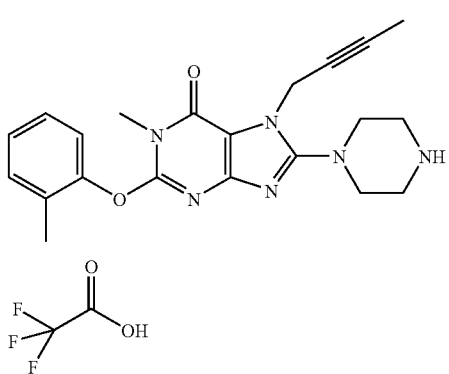

-continued
Example 174.
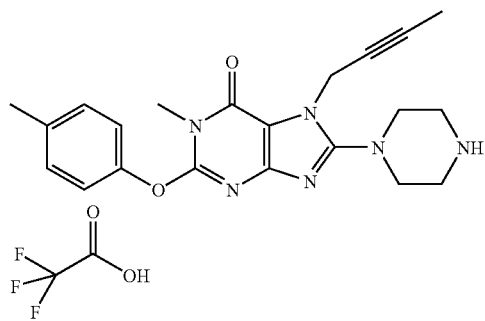
Example 175.
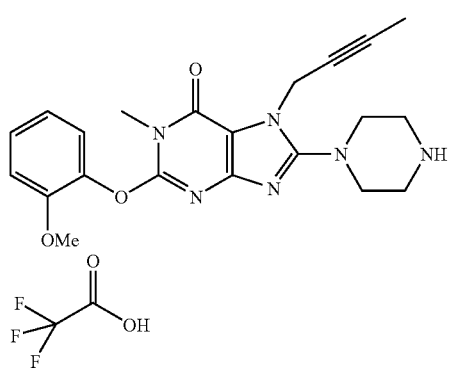
Example 176.
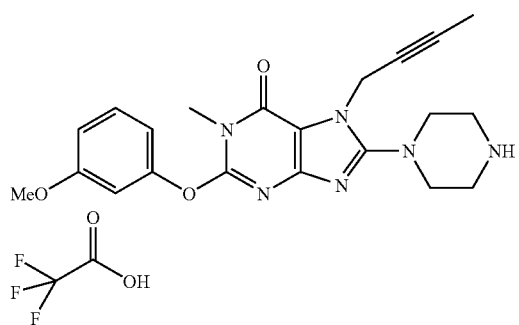
Example 177.
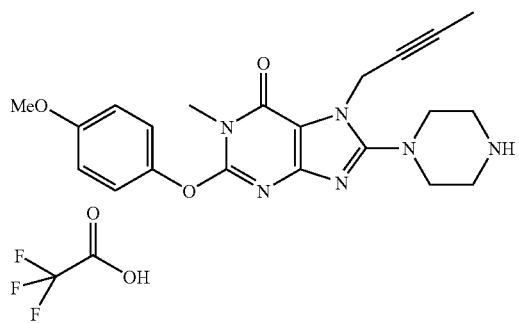
Example 178.
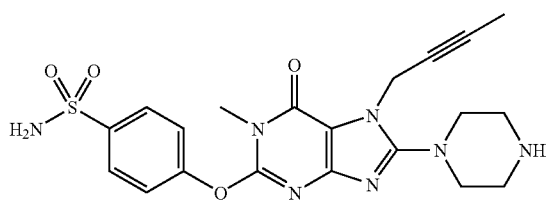
-continued
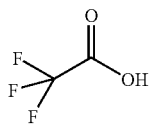
Example 179.
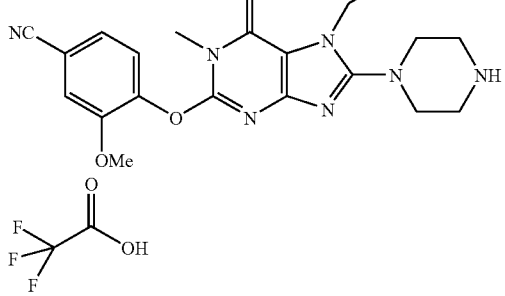
Example 180.
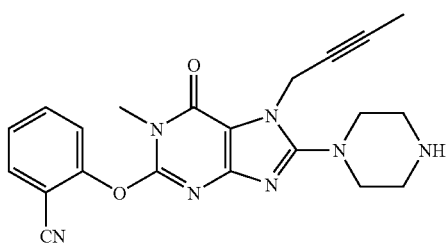
Example 181.
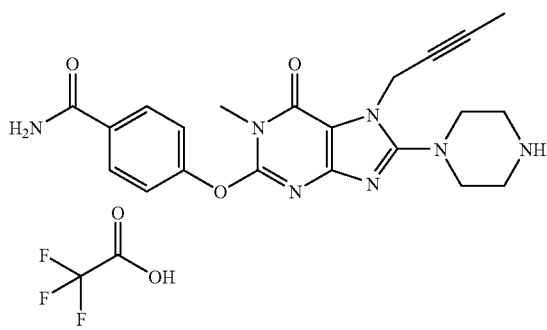
Example 182.
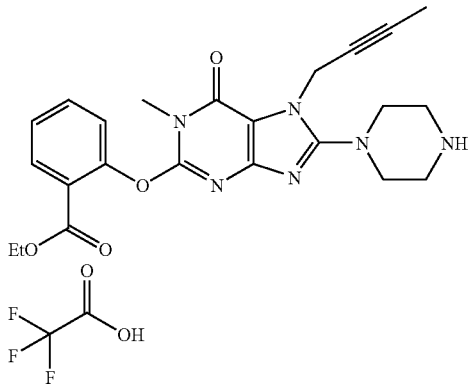

-continued
Example 183.
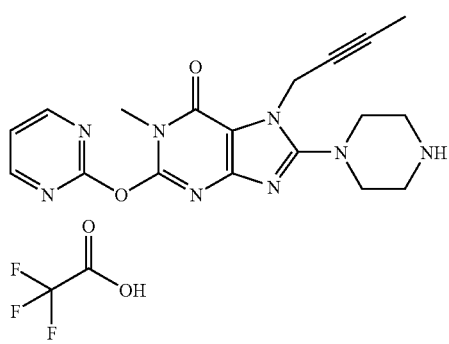
Example 184.
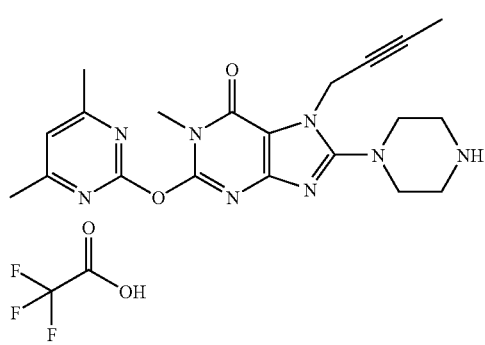
Example 185.
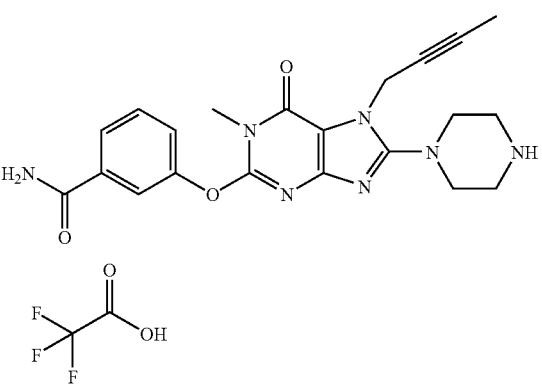
Example 186.
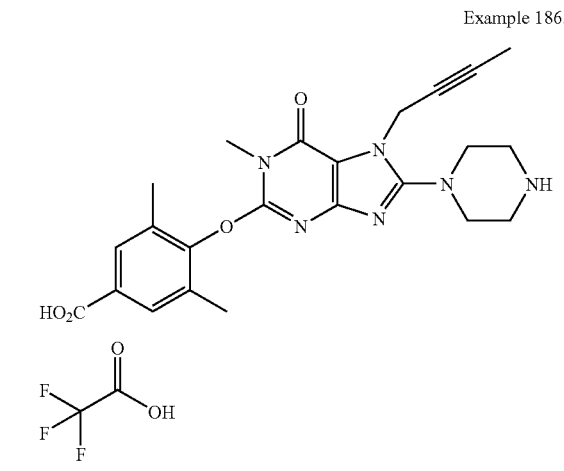
-continued
Example 187.
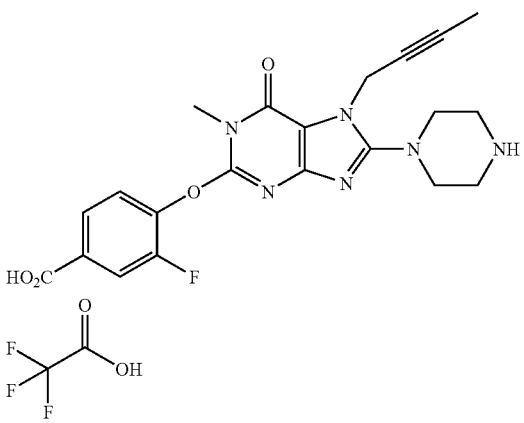
Example 188.
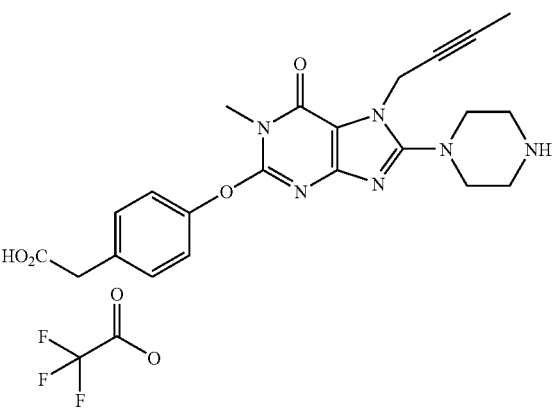
Example 189.
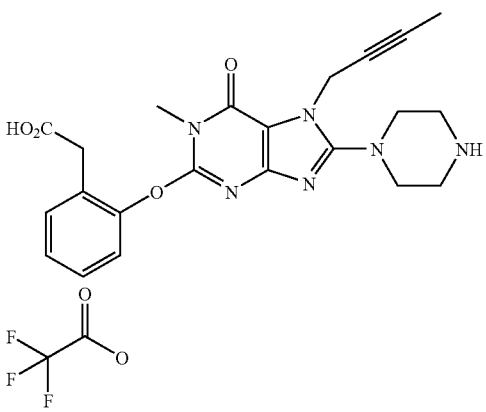
Example 190.
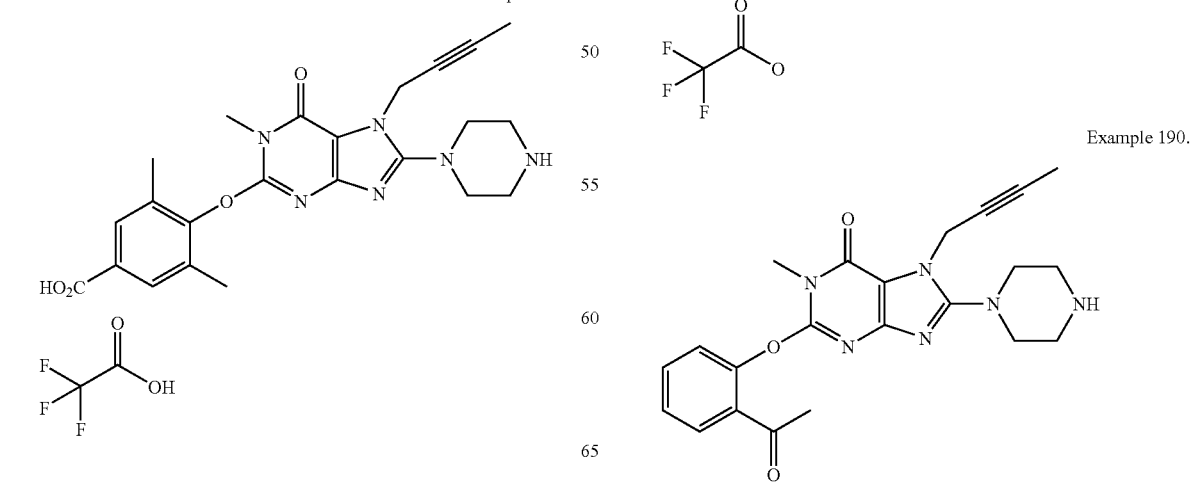

-continued
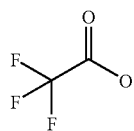
Example 191.
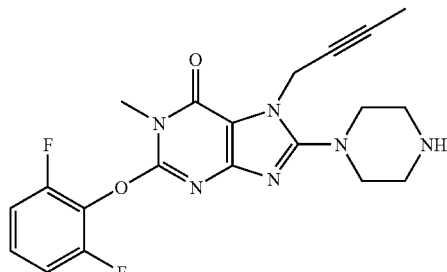
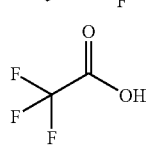
Example 192.
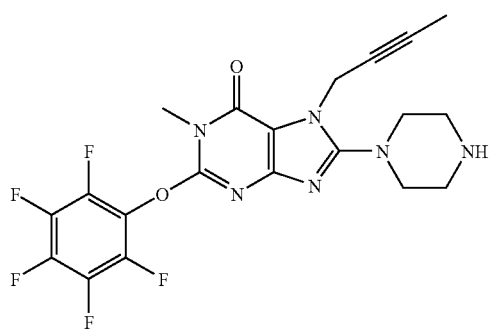
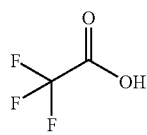
Example 193.
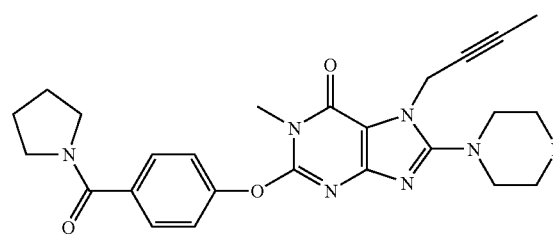
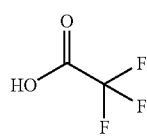
-continued
Example 194.
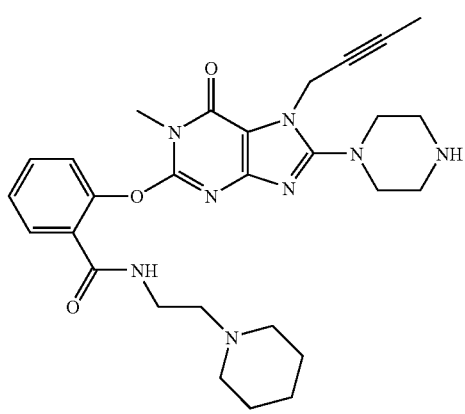
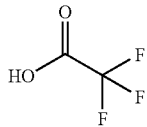
Example 195.
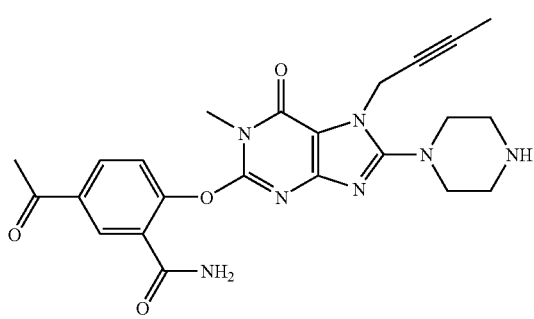
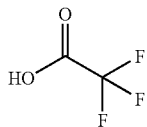
Example 196.
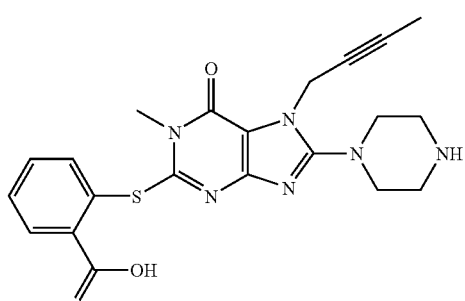
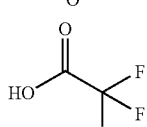

-continued
Example 197.
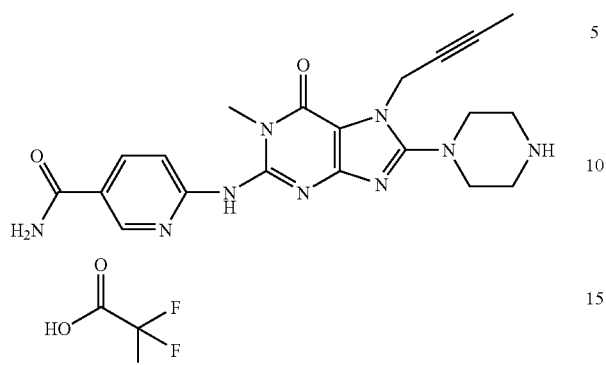
Example 198.
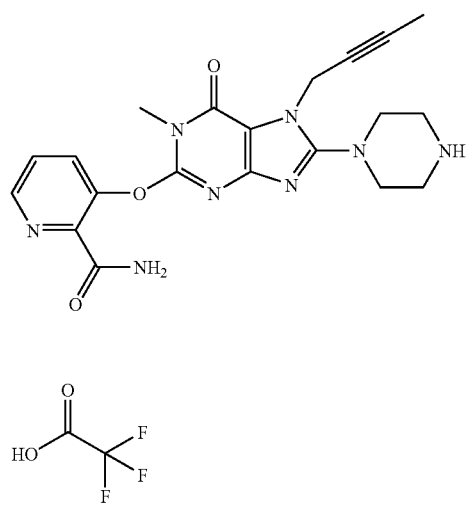
Example 199.
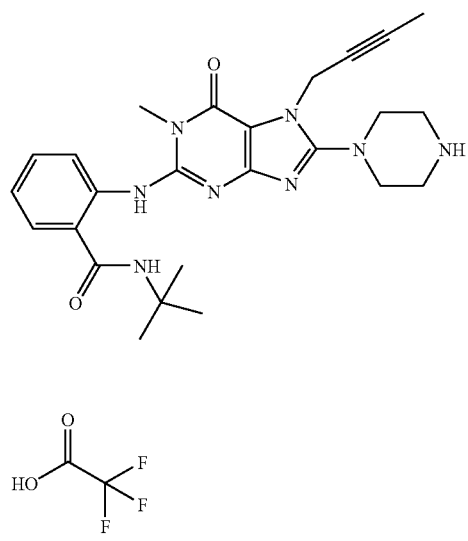
-continued
Example 200, 201.
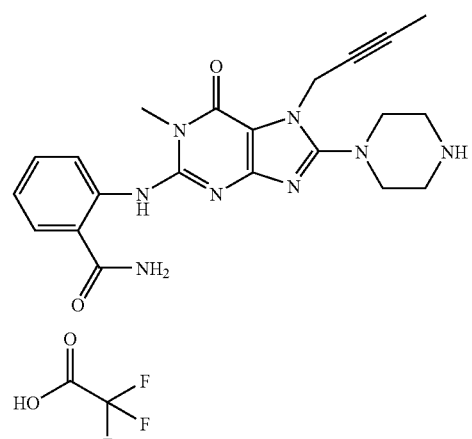
Example 202.
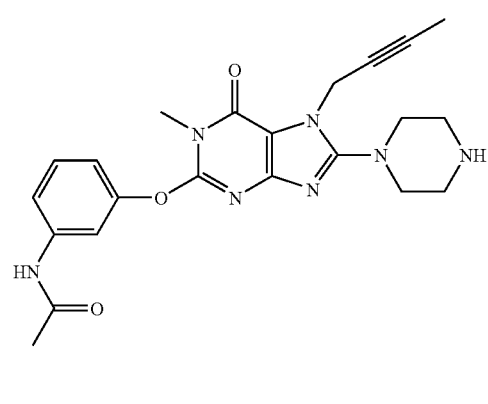
Example 203.
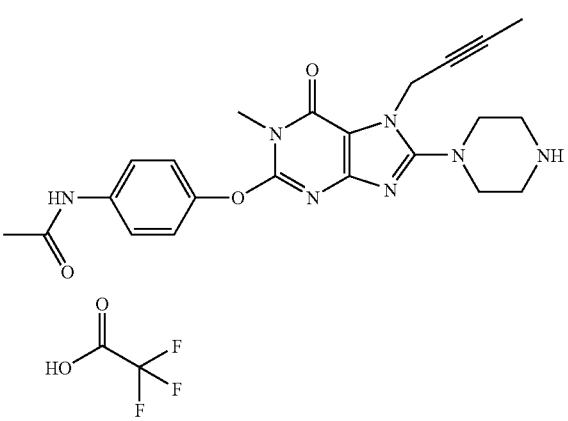

Example 204.
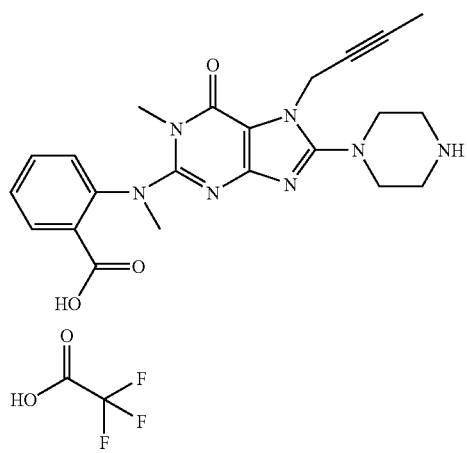
Example 207.
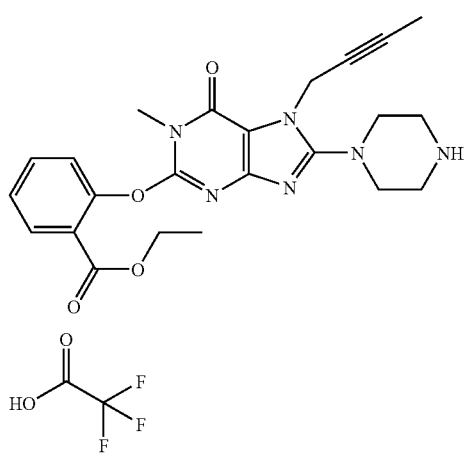
Example 205.
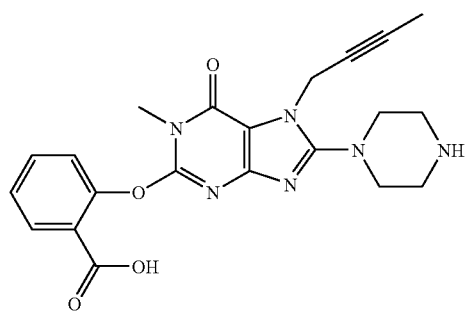
Example 208.
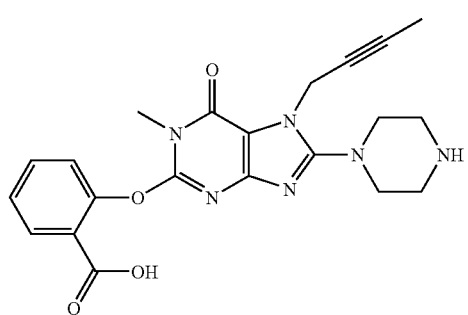
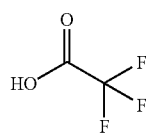
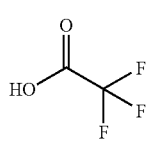
Example 206.
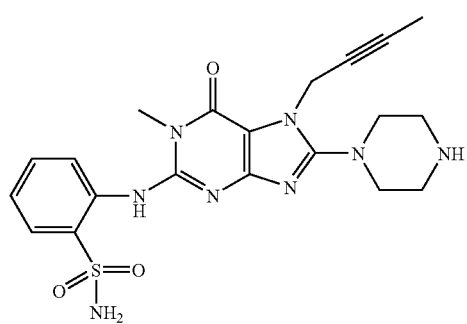
Example 209.
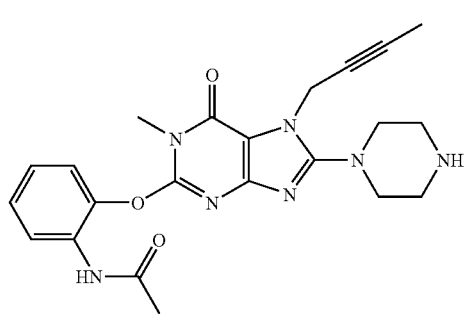
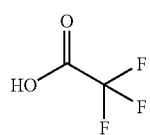
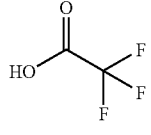

Example 210.
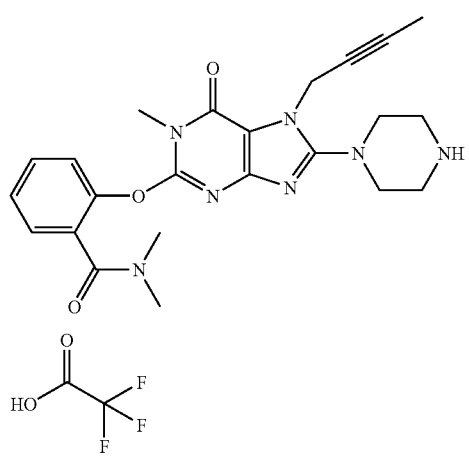
Example 211.
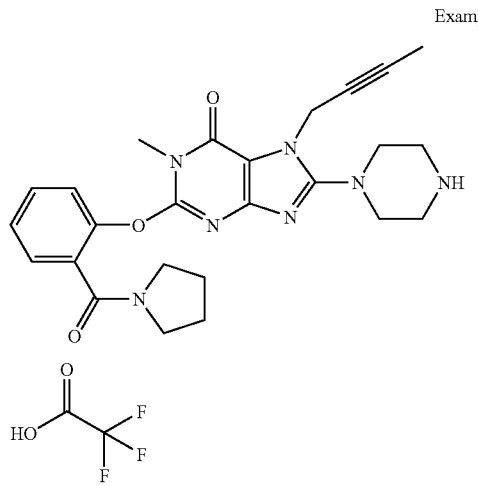
Example 212.
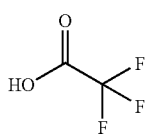
Example 213.
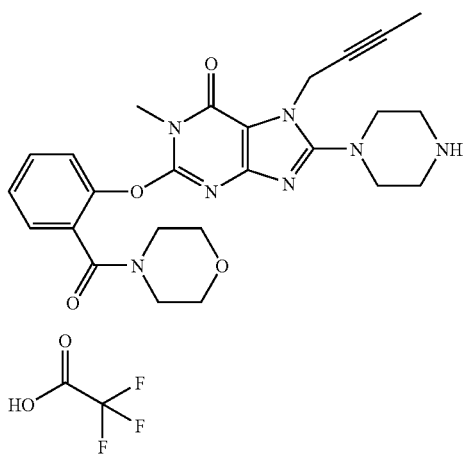
Example 214.
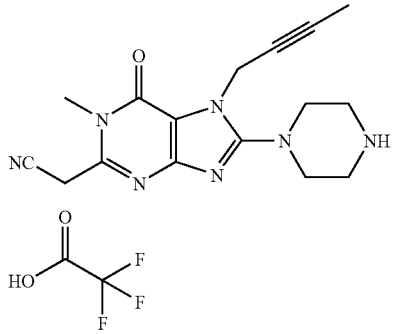
Example 215.
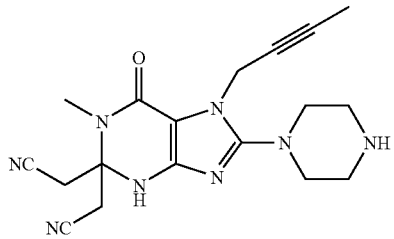
Example 216.
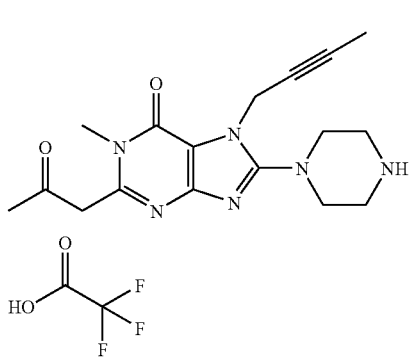

-continued
Example 217.
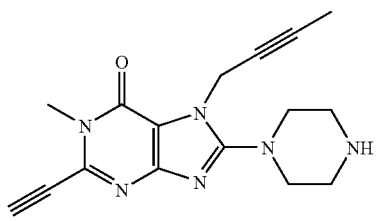
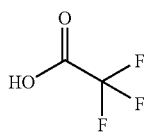
Example 218.
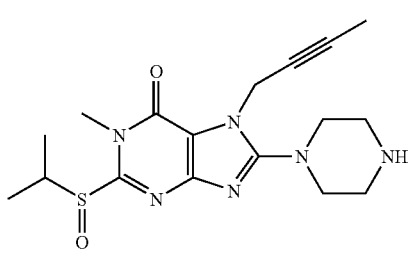
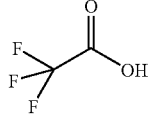
Example 219.
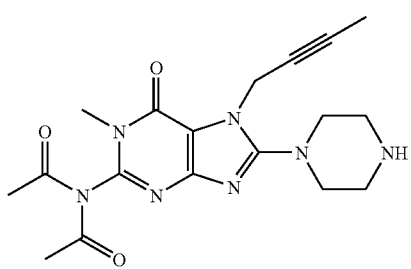
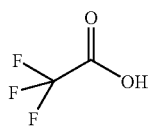
Example 220.
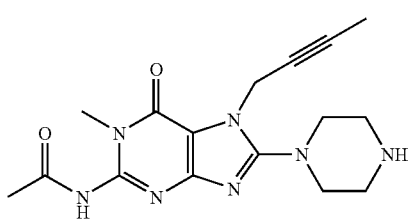
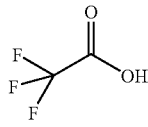
-continued
Example 221.
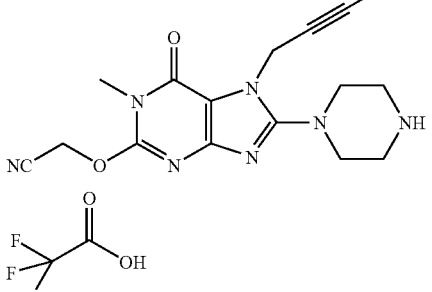
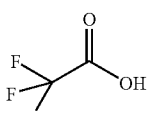
Example 222.
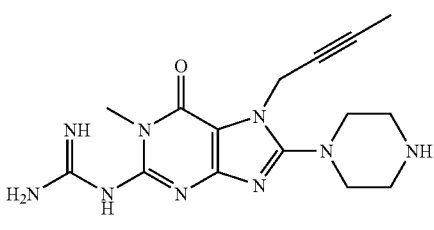
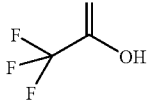
Example 223. a)
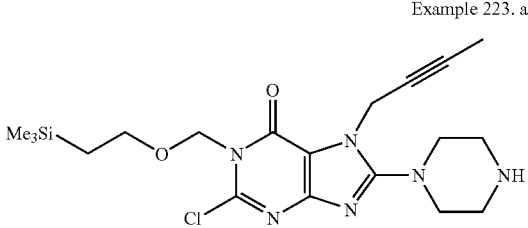
Example 223. b)
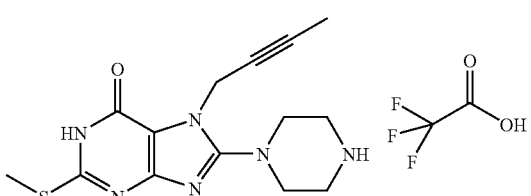
Example 224.
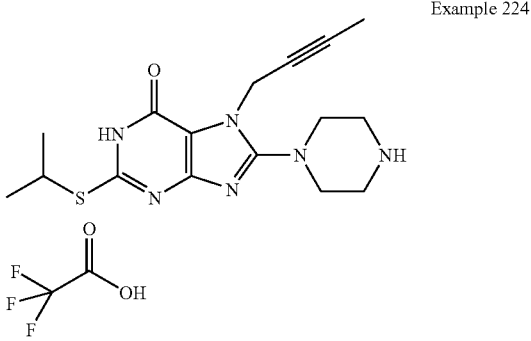

Example 225.
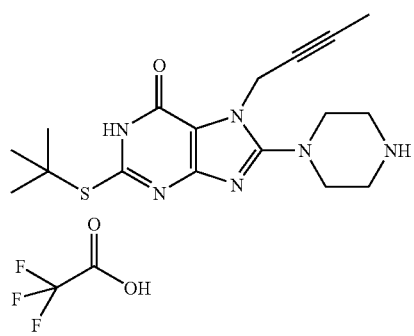
Example 226.
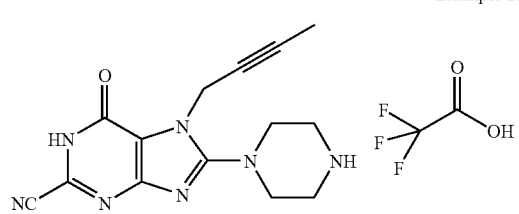
Example 227.
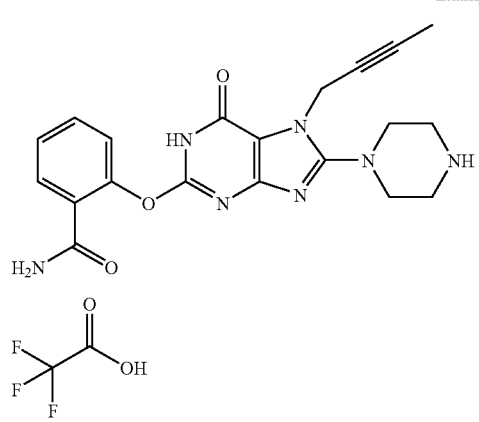
Example 228.
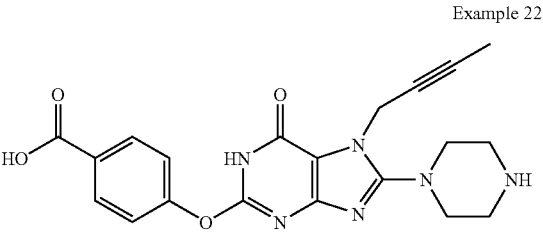
Example 229. a)
Example 229. b)
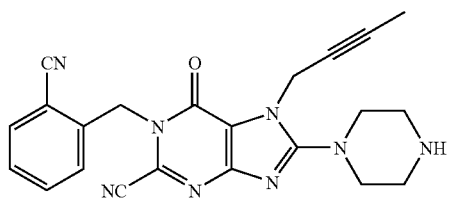
Example 230.
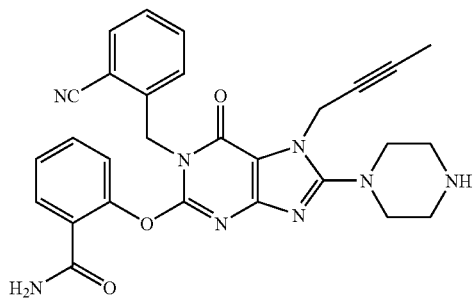
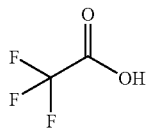
Example 231.
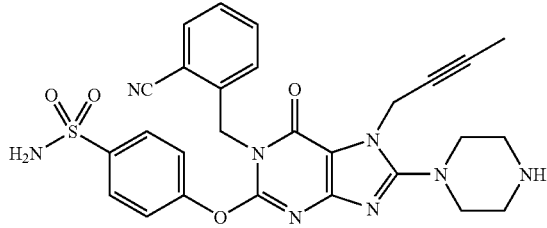
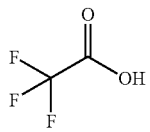
Example 232.
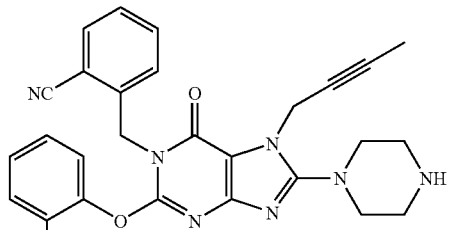
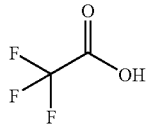

Example 233.
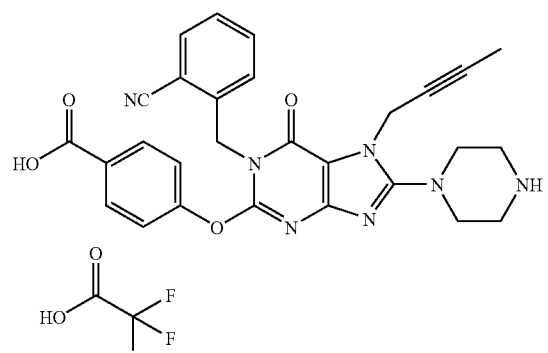
Example 234.
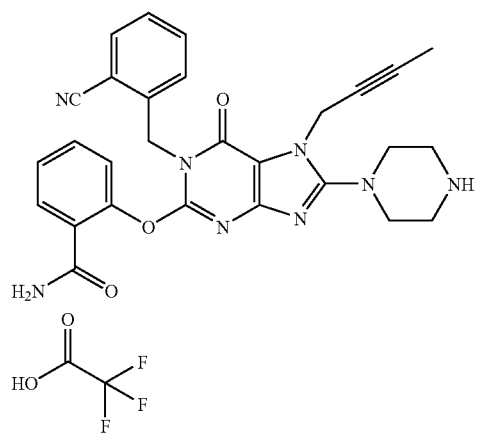
Example 235. a)
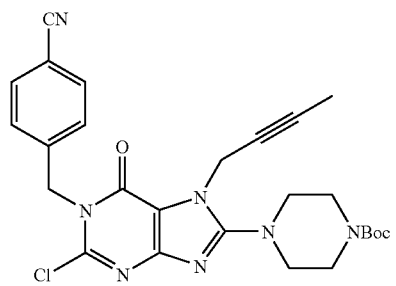
Example 235. b)
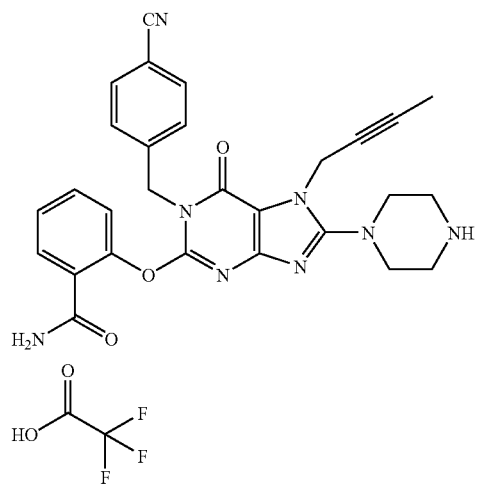
Example 236.
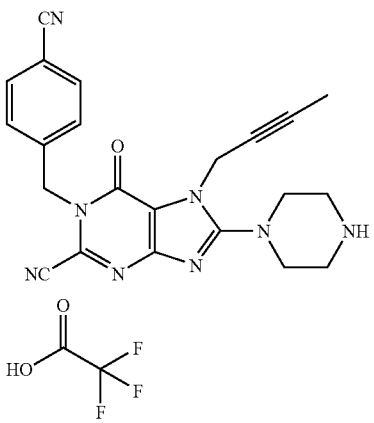
Example 237.
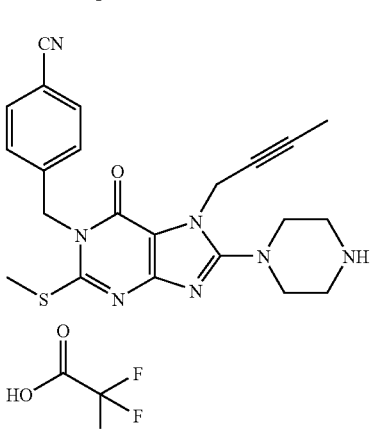
Example 238. a)
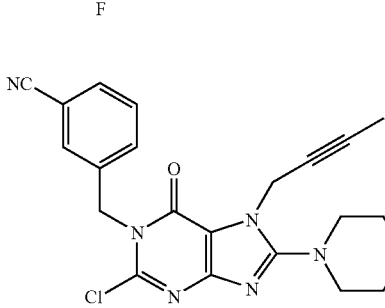
Example 238. b)
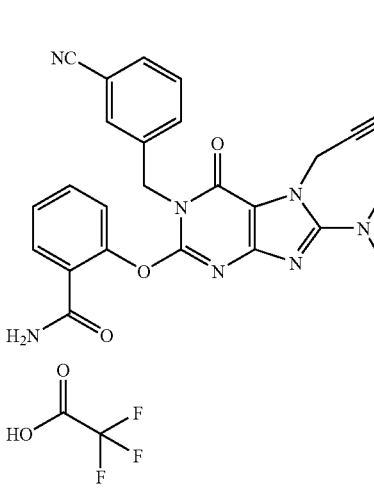

-continued
Example 239.
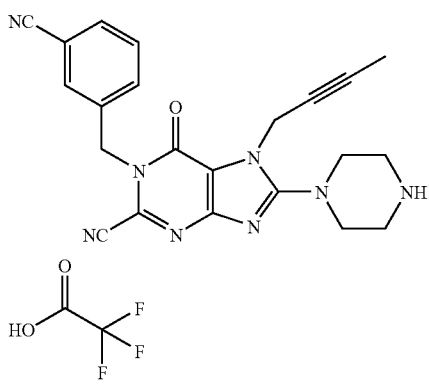
Example 240. a)
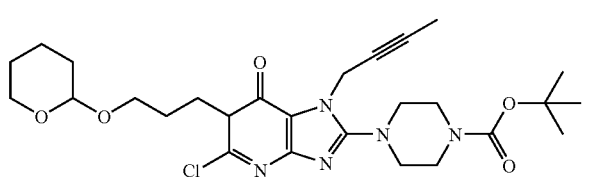
Example 240. b)
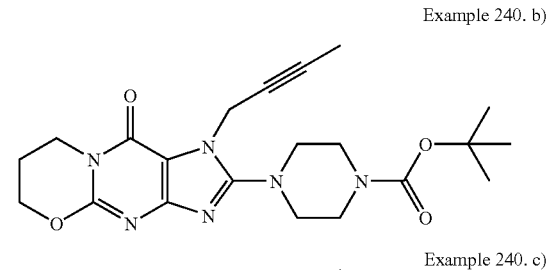
Example 240. c)
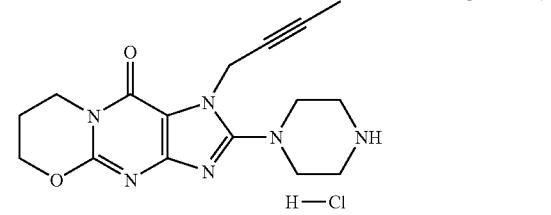
Example 241.
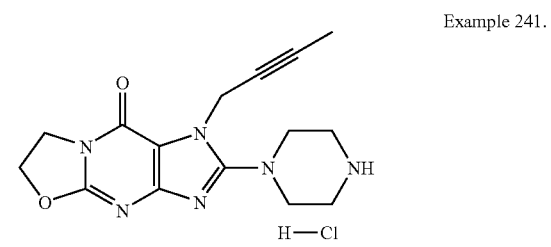
Example 242. a)
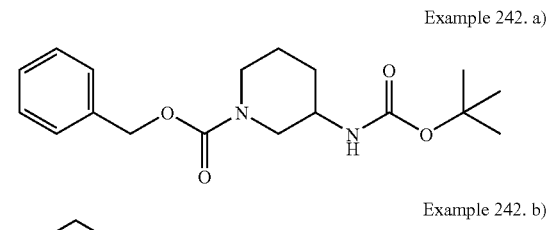
Example 242. b)
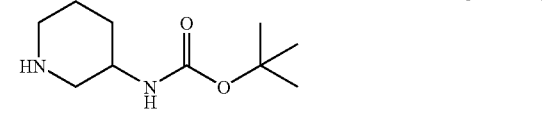
Example 242. c)
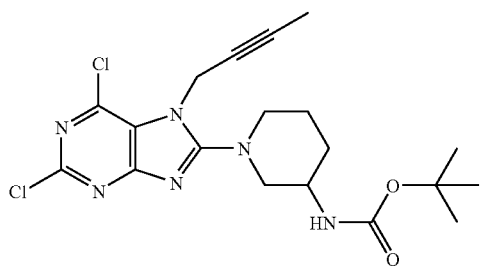
Example 242. d)
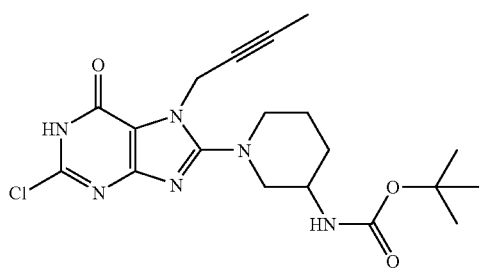
Example 242. e)
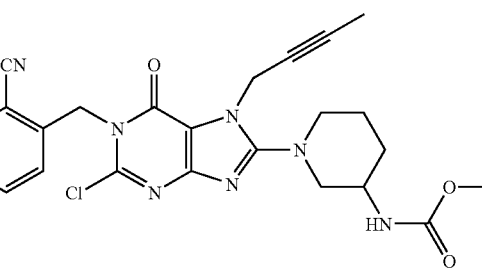
Example 242. f)
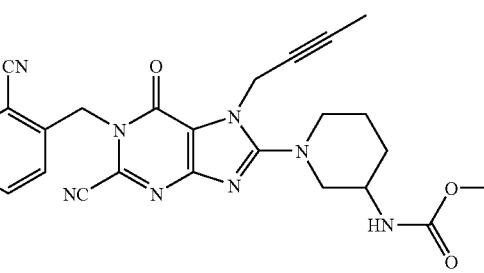
Example 242. g)
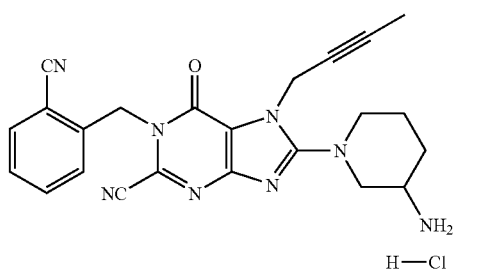

Example 243.
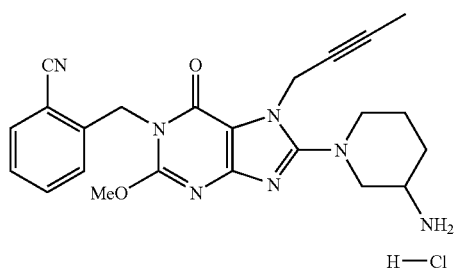
Example 244. a)
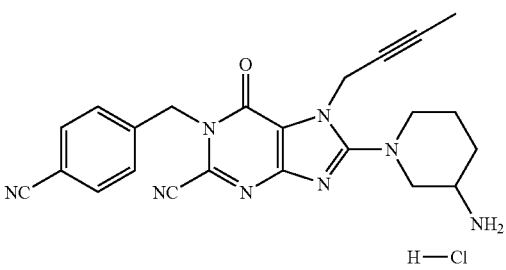
Example 246. b)
Example 244. b)
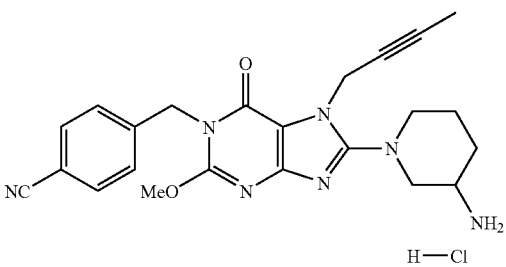
Example 247.
Example 248. a)
Example 245.
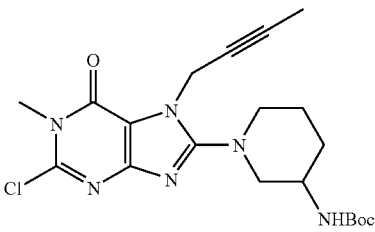
Example 248. b)
Example 249.
Example 246. a)
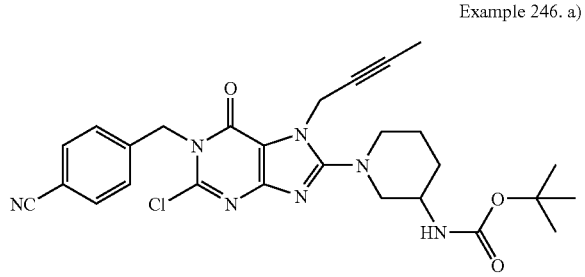
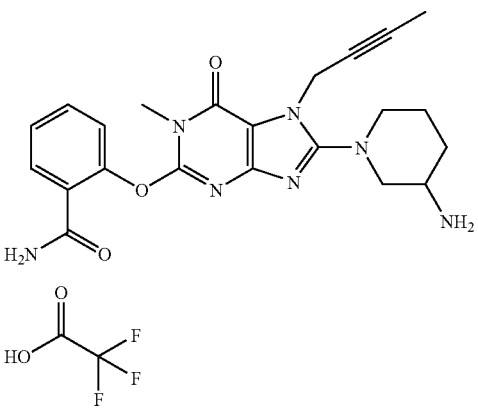
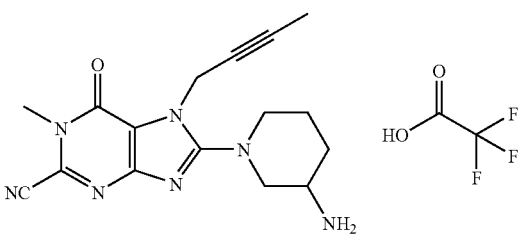

-continued
Example 250.
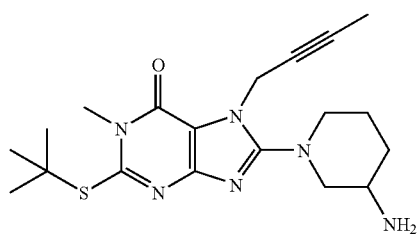
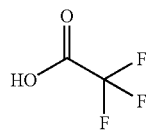
Example 251.
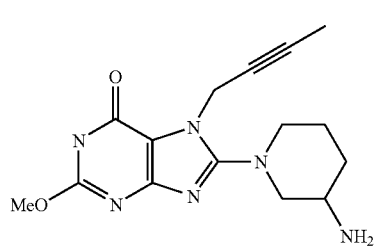
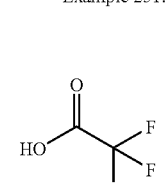
Example 252.
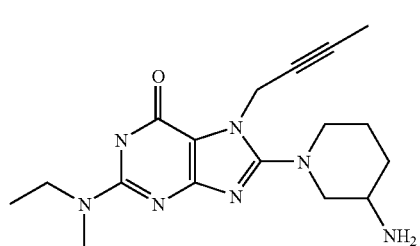
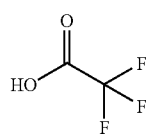
Example 253.
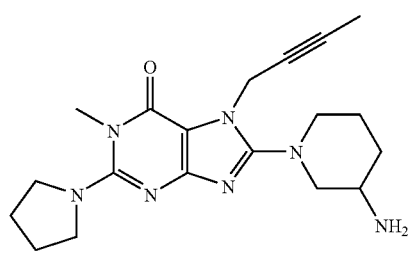
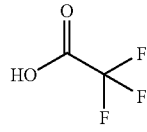
Example 254. a)
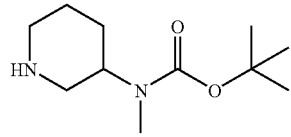
-continued
Example 254. b)
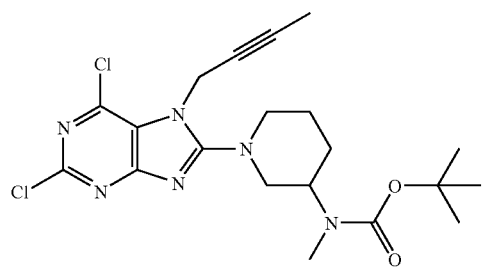
Example 254. c)
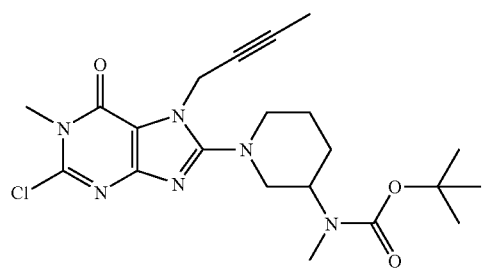
Example 254. d)
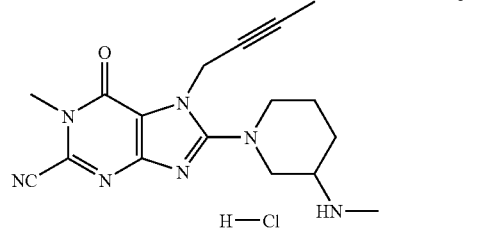
Example 255.
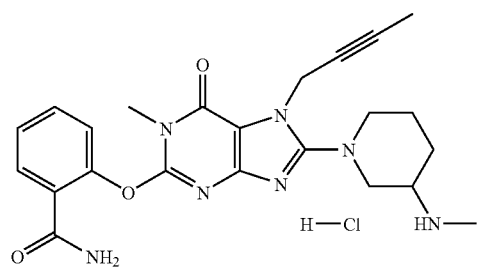
Example 256.
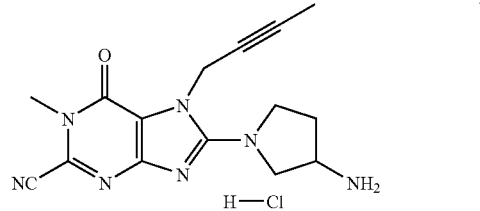
Example 257.
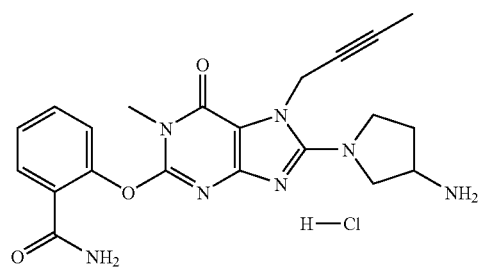

-continued
Example 258. a)
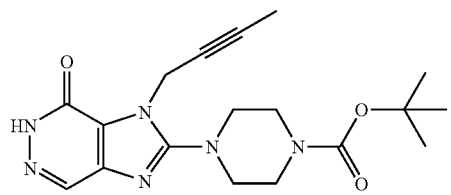
Example 258. b)
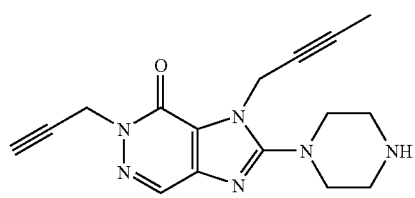
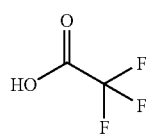
Example 259.
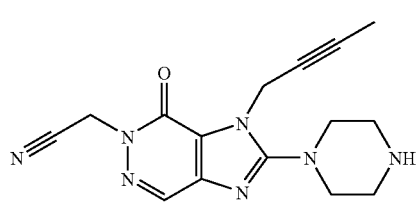
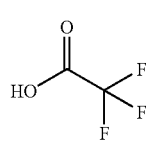
Example 260.
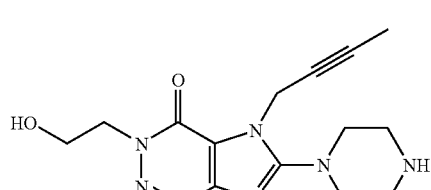
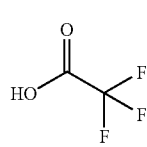
Example 261.
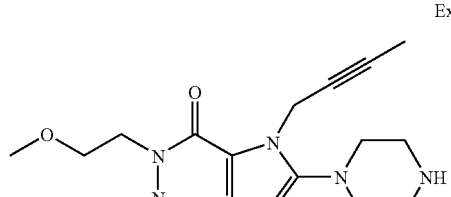
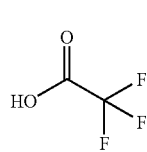
-continued
Example 262.
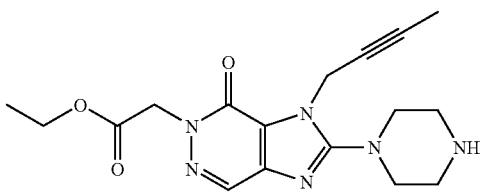
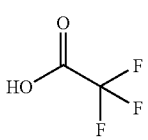
Example 263.
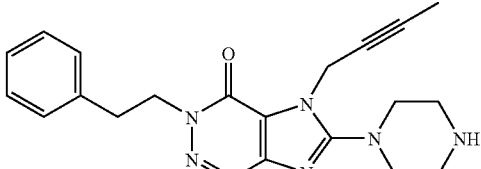
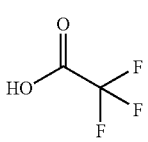
Example 264.
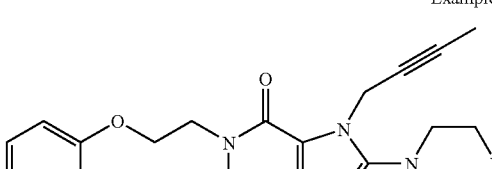
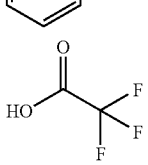
Example 265.
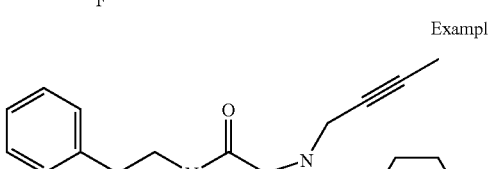
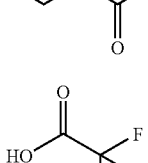
Example 266.
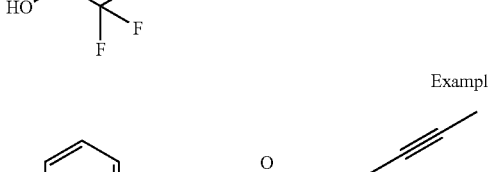
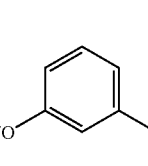

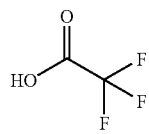
Example 267.
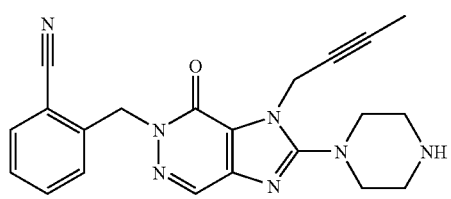
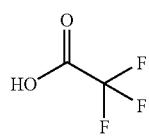
Example 268.
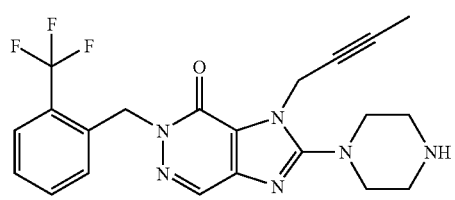
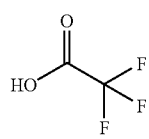
Example 269.
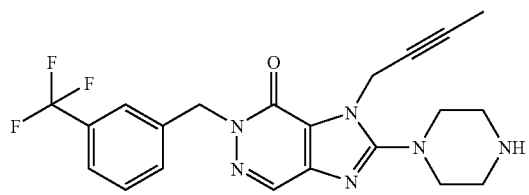
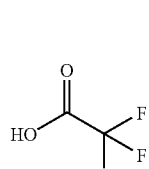
Example 270.
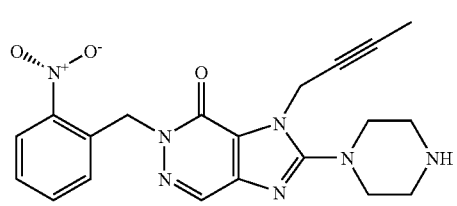
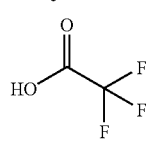
Example 271.
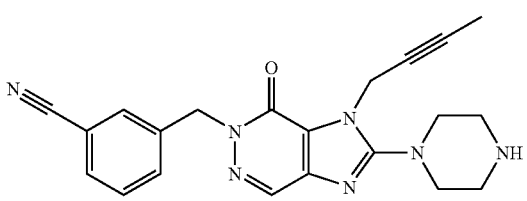
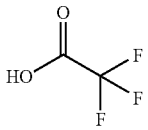
Example 272.
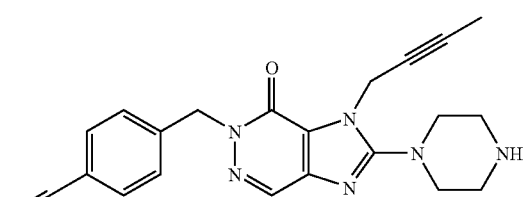
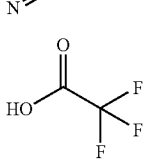
Example 273.
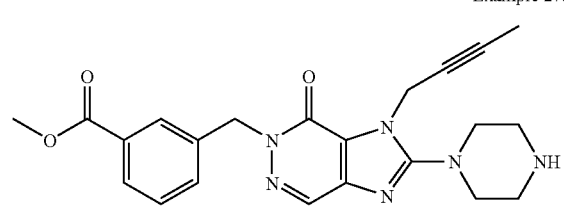
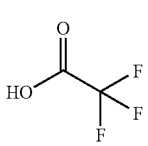
Example 274.
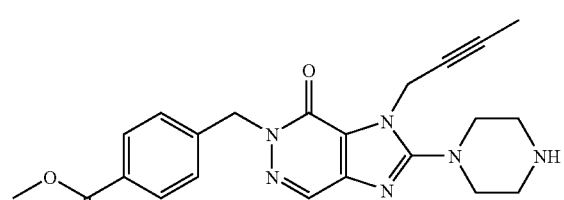
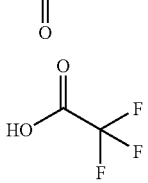

Example 275.
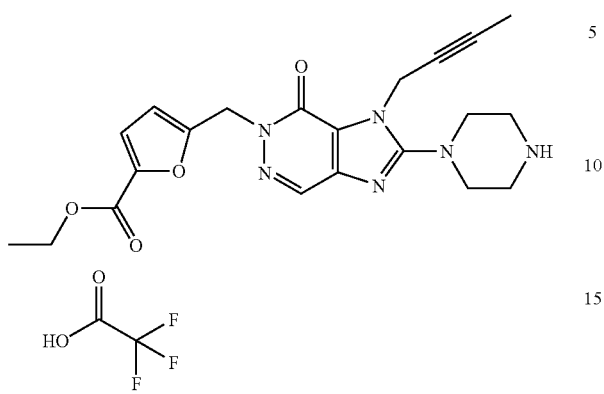
Example 276.
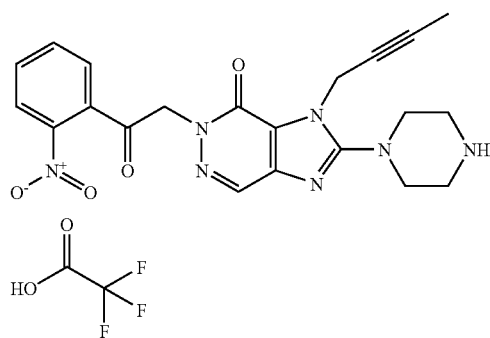
Example 277.
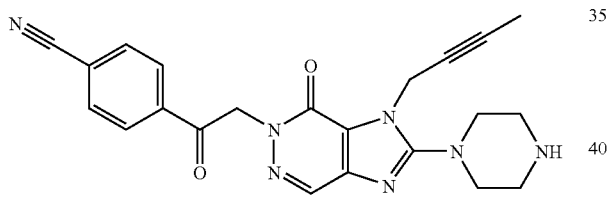
Example 278.
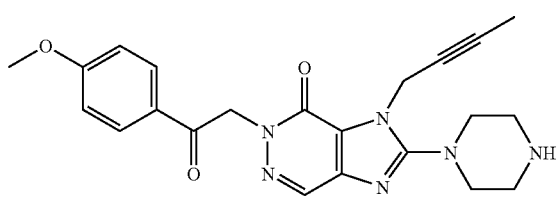
Example 279.
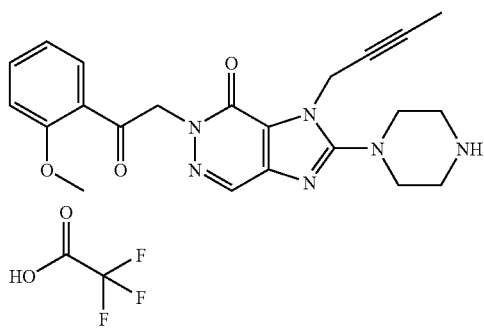
Example 280.
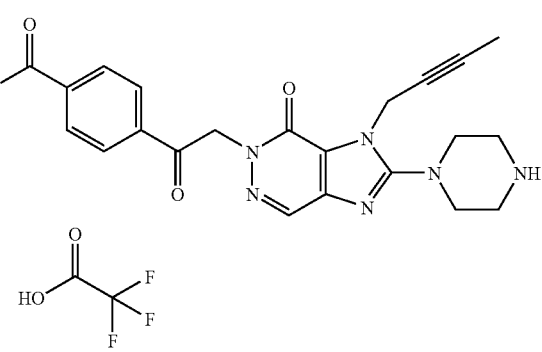
Example 281.
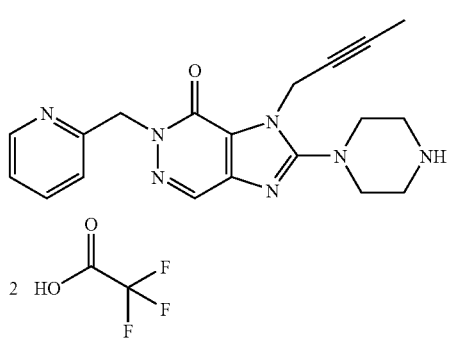
2 
Example 282.
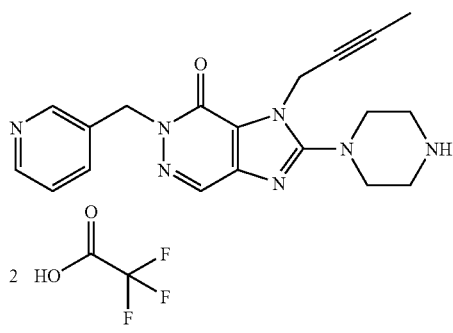
2 
Example 283.
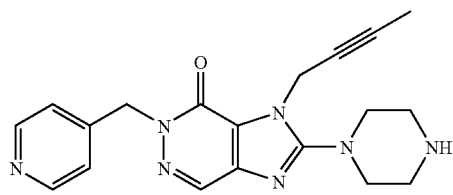

-continued
Example 284.
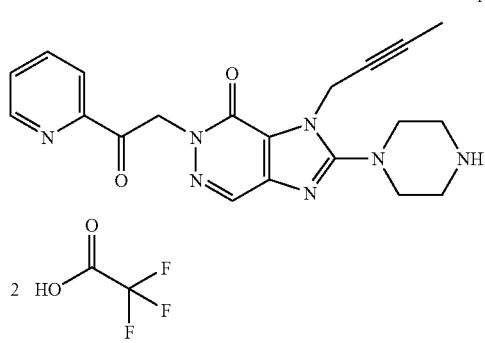
Example 285.
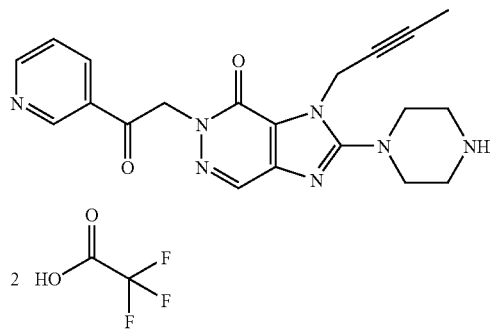
Example 286.
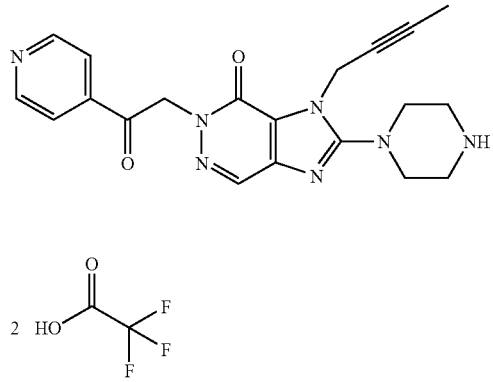
Example 287.
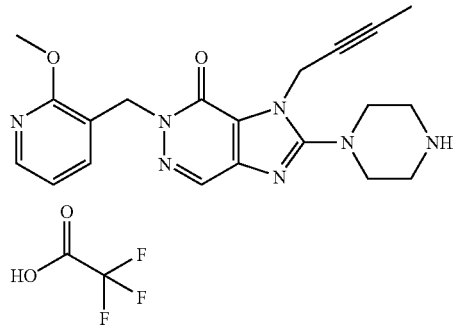
-continued
Example 288.
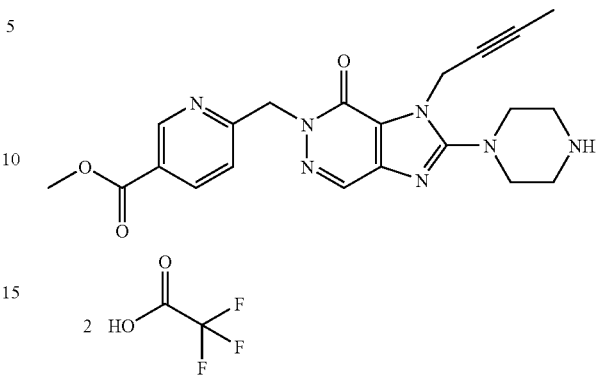
Example 289.
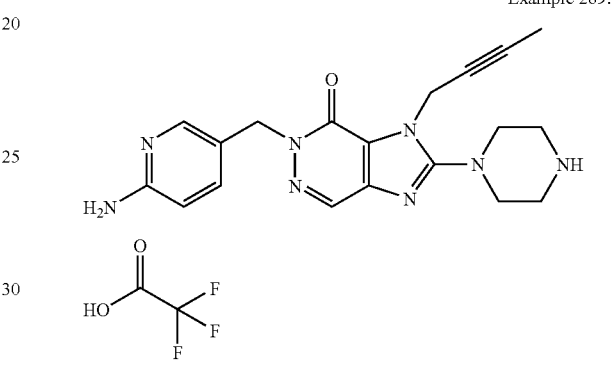
Example 290.
Example 291.

Example 292.
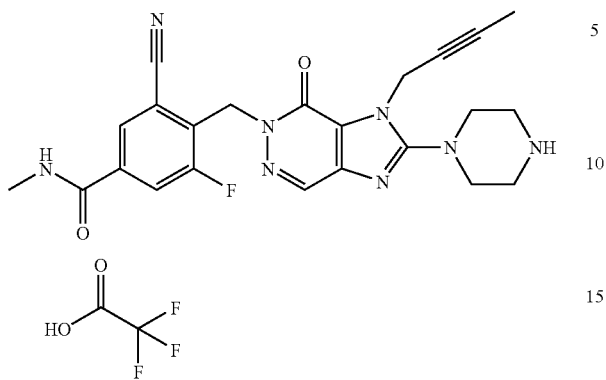
Example 293.
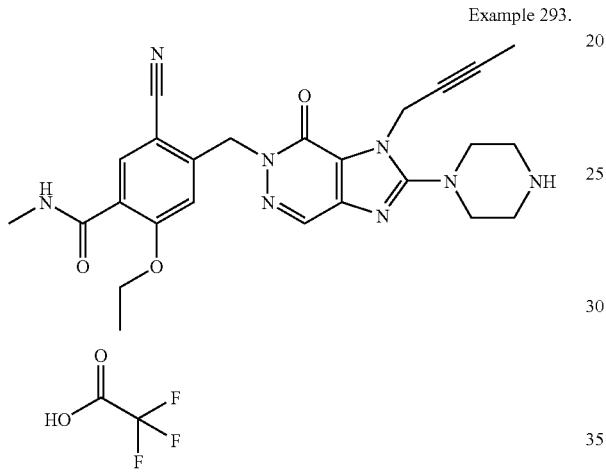
Example 294.
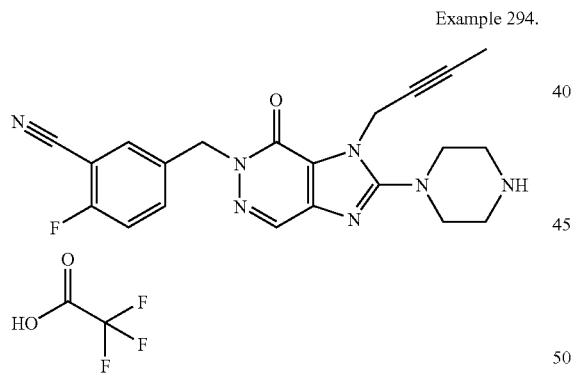
Example 295.
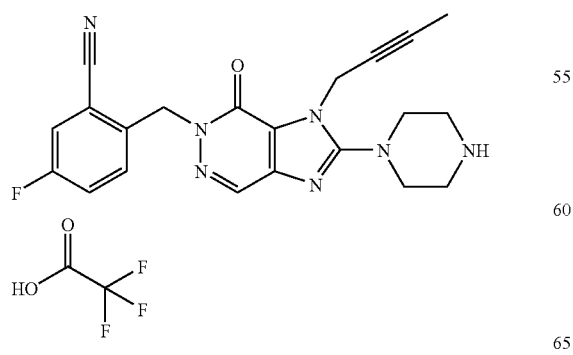
Example 296.
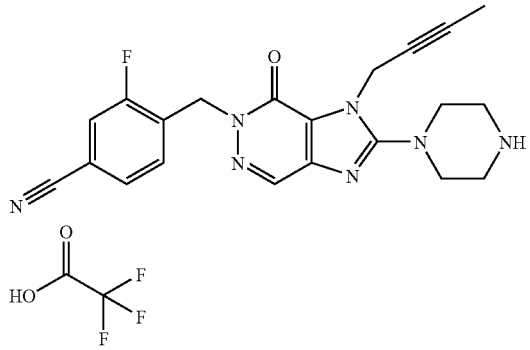
Example 297.
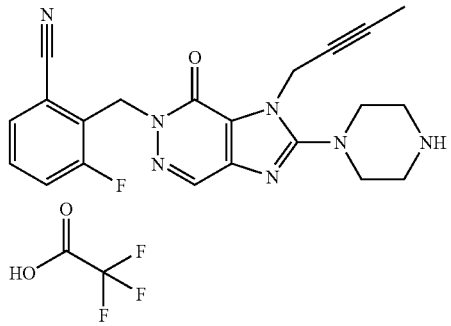
Example 298.
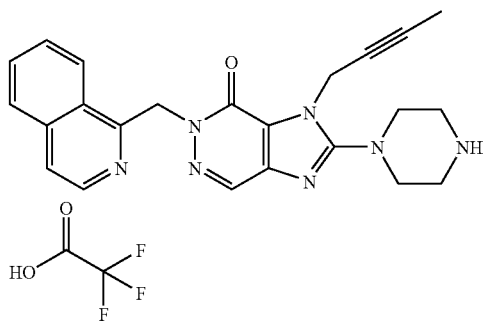
Example 299.
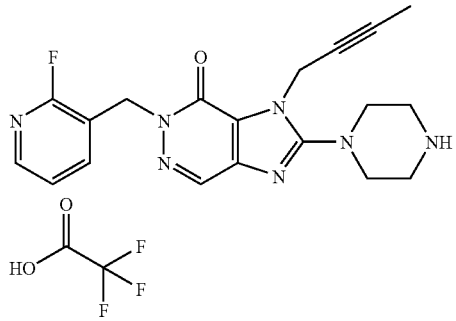
Example 300.
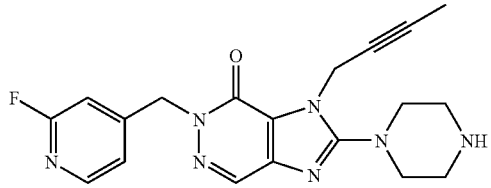

Example 301.
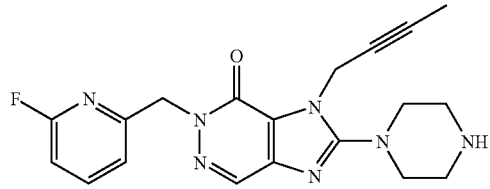
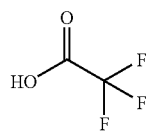
Example 302.
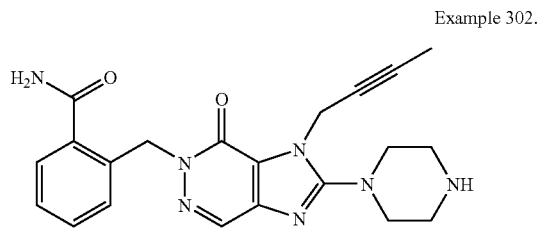
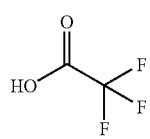
Example 303.
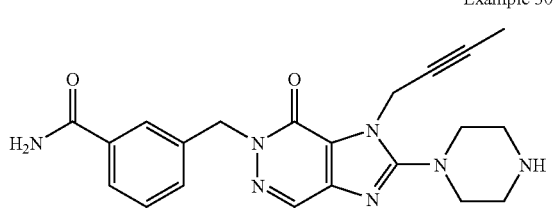
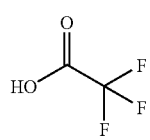
Example 304.
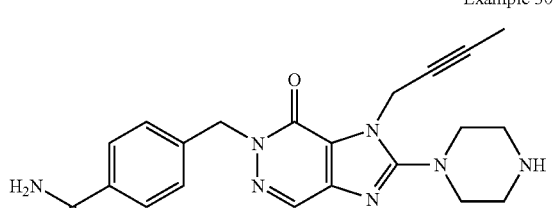
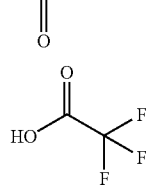
Example 305.
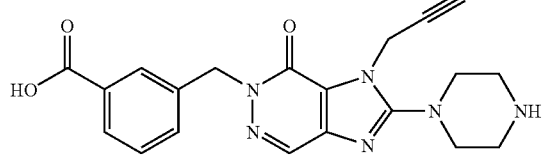
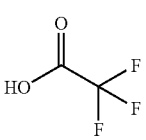
Example 306.
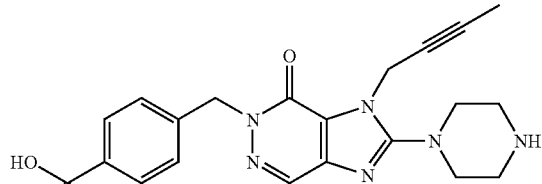
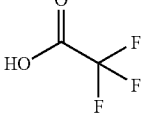
Example 307.
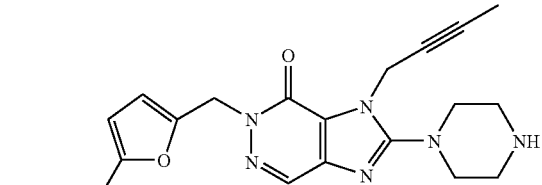
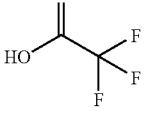
Example 308. a)
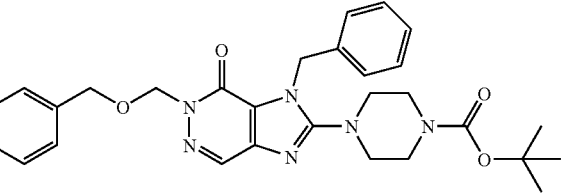
Example 308. b)
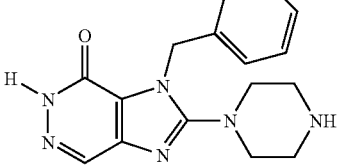

297
-continued
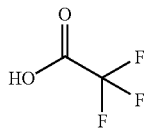
Example 309. a)
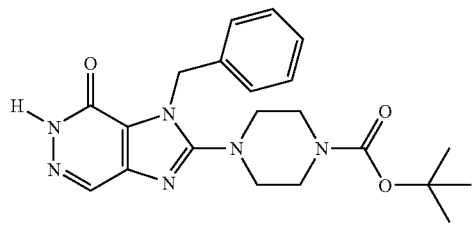
Example 309. b)
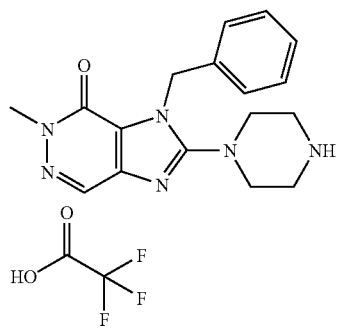
Example 310.
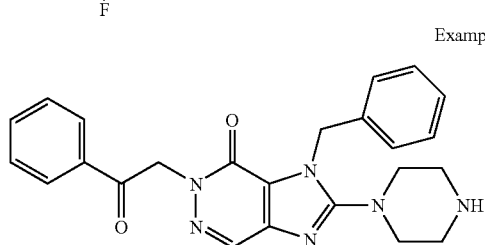
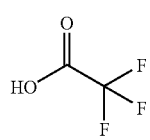
Example 311.
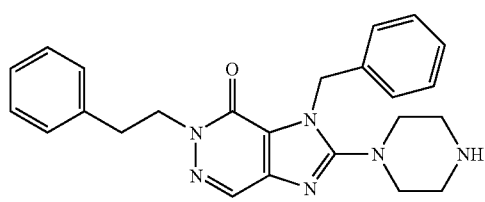
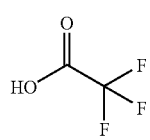
Example 312.
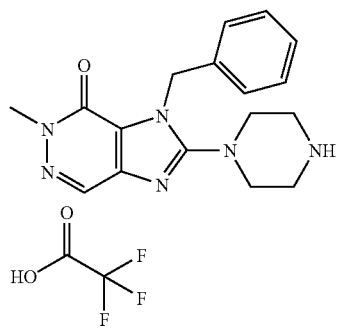
298
-continued
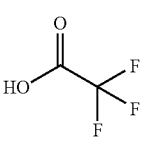
Example 313.
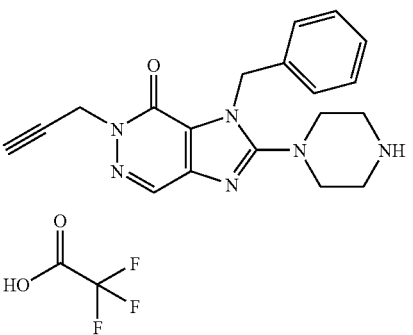
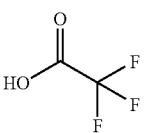
Example 314.
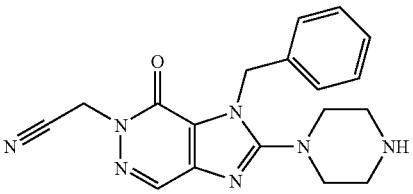
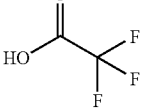
Example 315.
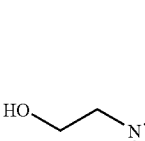
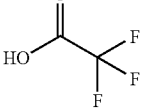
Example 316.
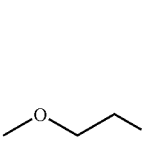
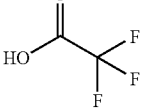

-continued

Example 317.

Example 318.

Example 319.

Example 320.

Example 321.

-continued

Example 322.

Example 323.

Example 324.

Example 325. a)

Example 325. b)

Example 326. a)

Example 326. b)
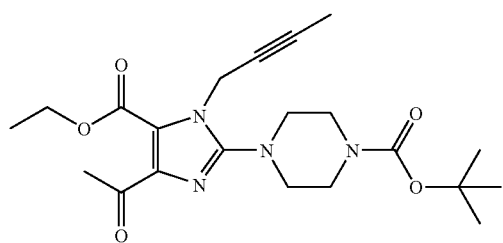
Example 326. c)
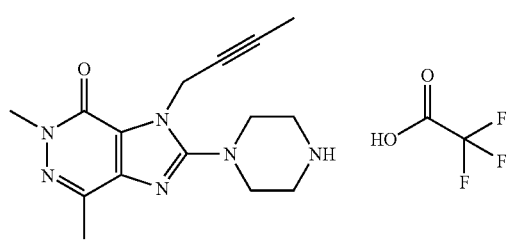
Example 327. a)
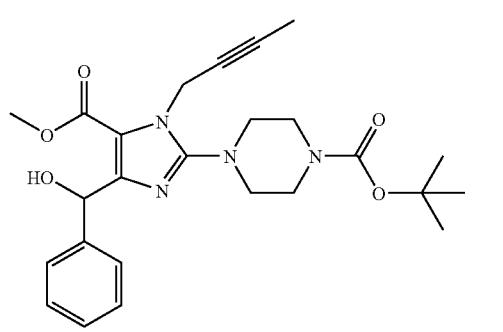
Example 327. b)
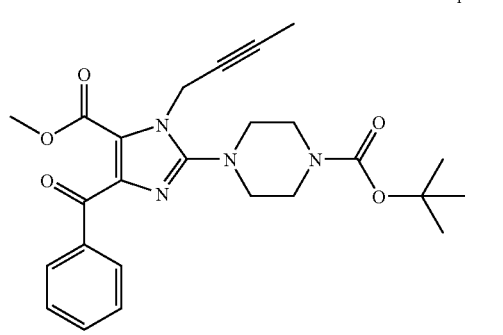
Example 327. c)
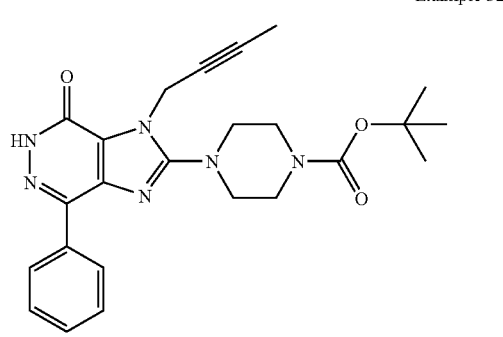
Exampel 327. d)
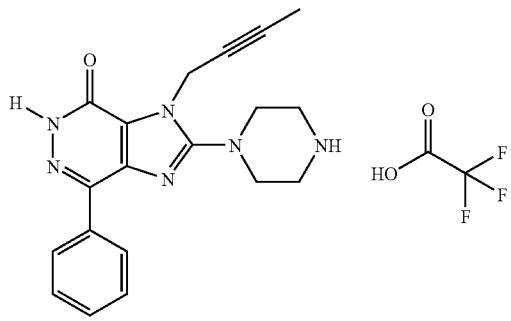
Example 328.
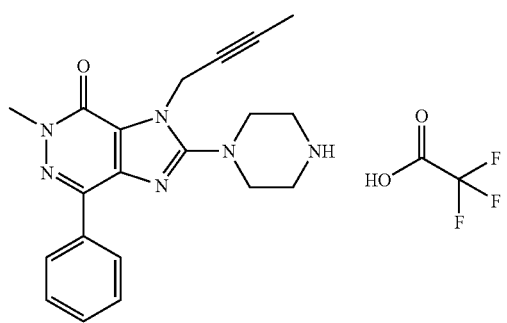
Example 329.
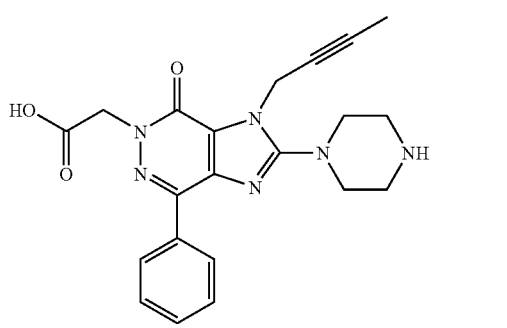
Example 330.
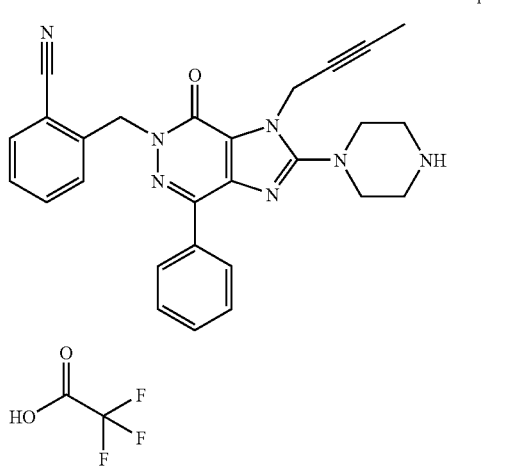

-continued
Example 331. a)
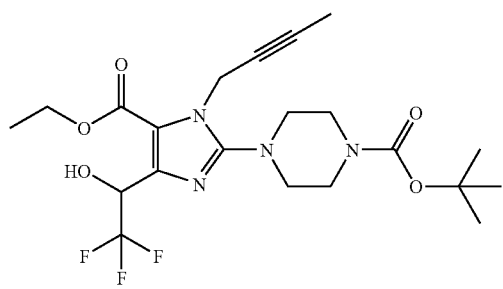
Example 331. b)
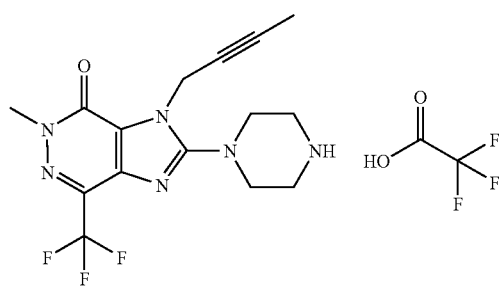
Example 332. a)
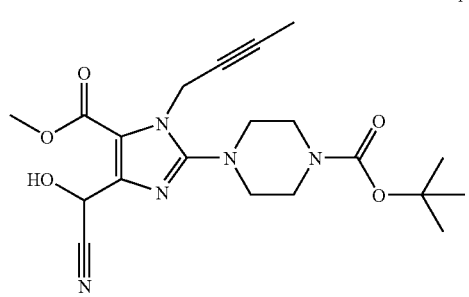
Example 332. b)
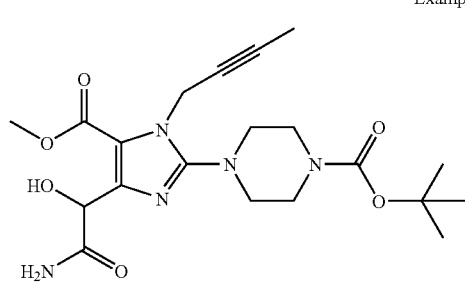
Example 332. c)
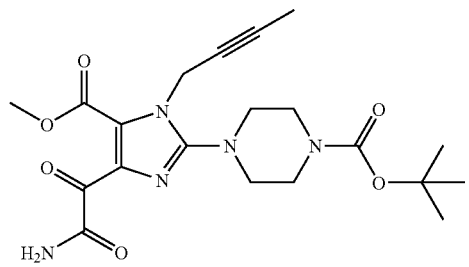
-continued
Example 332. d)
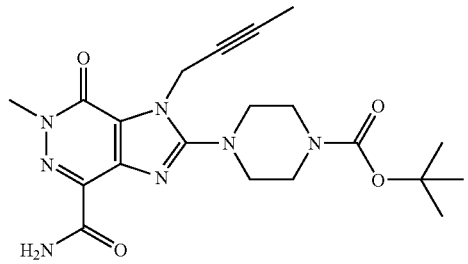
Example 332. e)
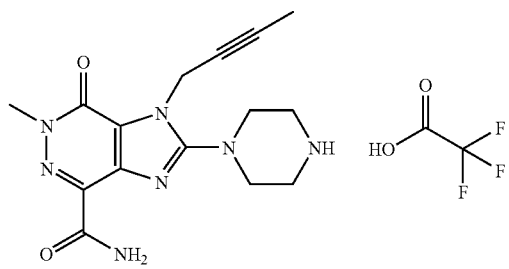
Example 333.
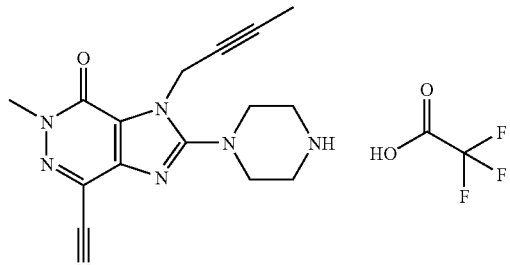
Example 334. a)
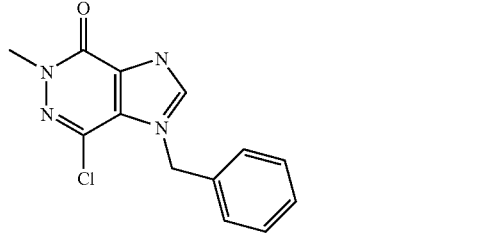
Example 334. b)
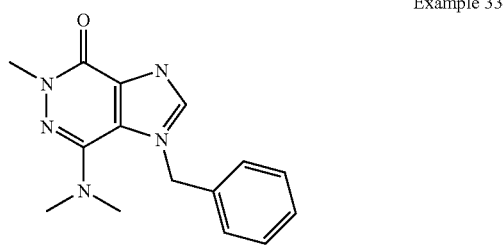
Example 334. c)
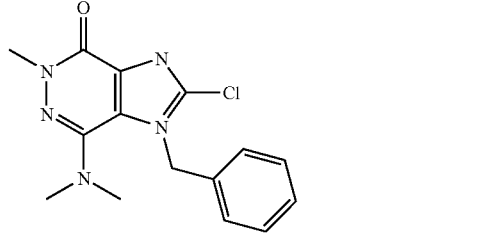

Example 334. d)
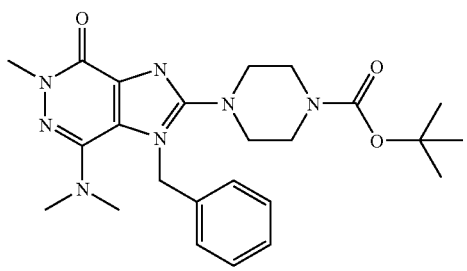
Example 334. e)
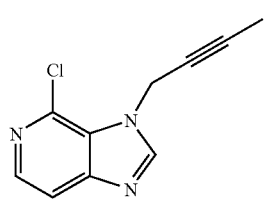
Example 334. f)
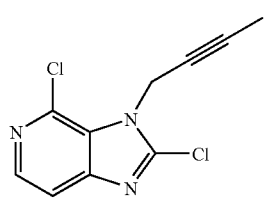
Example 335. a)
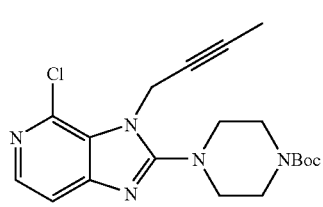
Example 335. b)
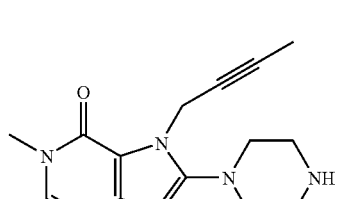
Example 335. c)
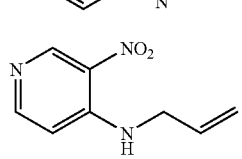
Example 335. d)
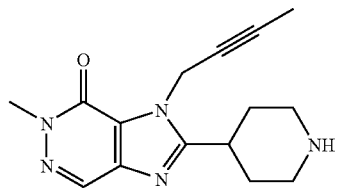 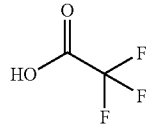
Example 336. a)
Example 336. b)
Example 336. c)
Example 336. d)
Exampel 337. a)
Example 337. b)
Example 337. c)
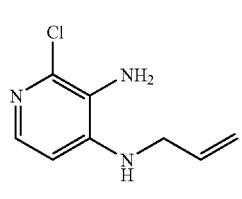
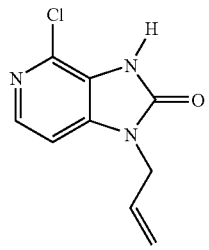

Example 337. d)
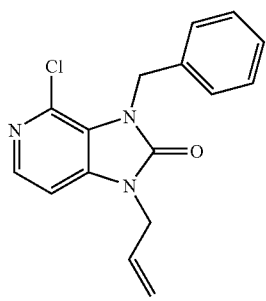
Example 337. e)
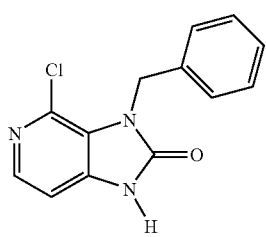
Example 337. f)
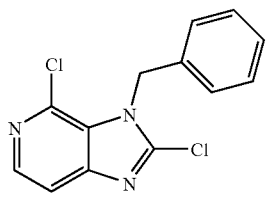
Example 337. g)
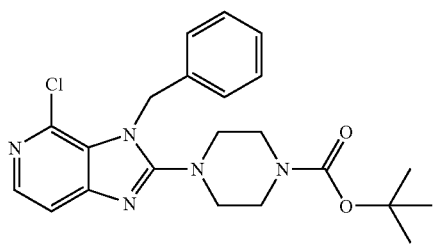
Example 337. h)
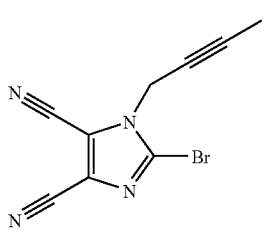 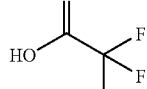
Example 338. a)
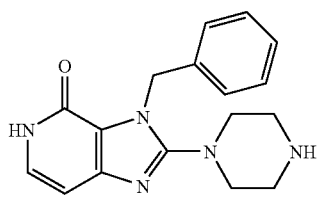
Example 338. b)
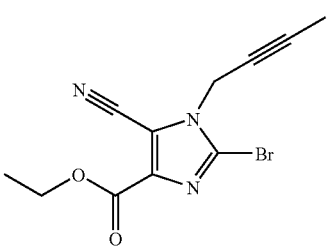
Example 338. c)
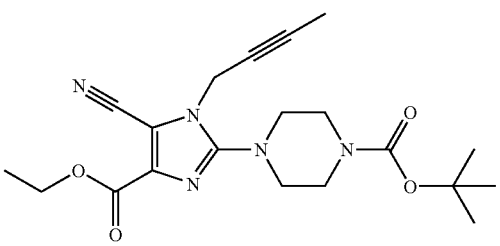
Example 338. d)
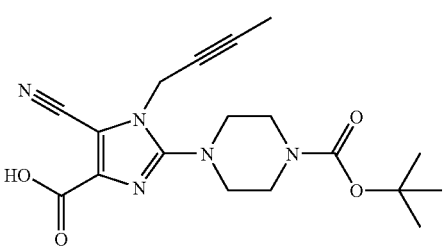
Example 338. e)
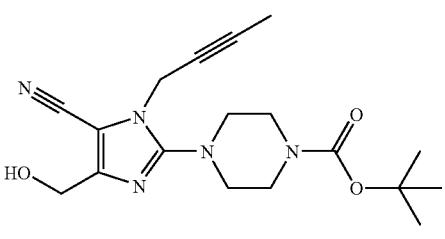
Example 338. f)
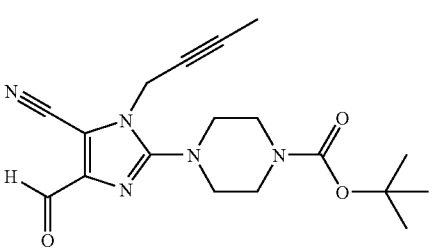
Example 338. g)
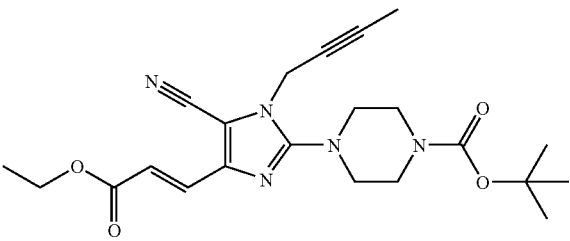

Example 338. h)
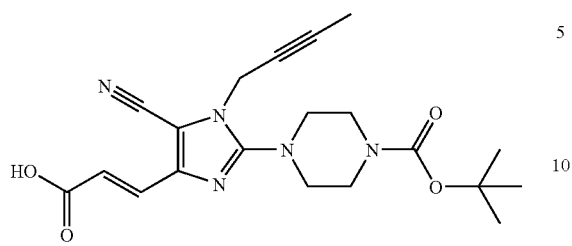
Example 338. i)
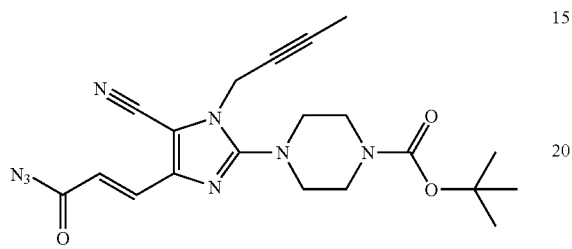
Example 338. j)
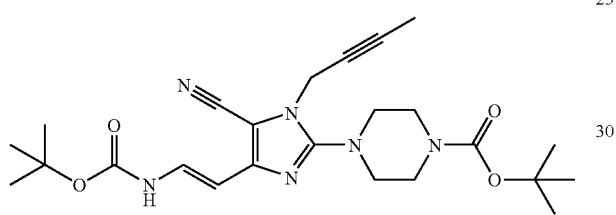
Example 338. k)
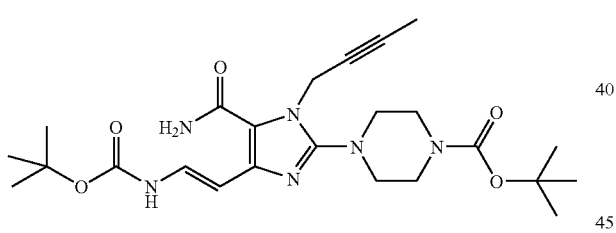
Example 338. l)
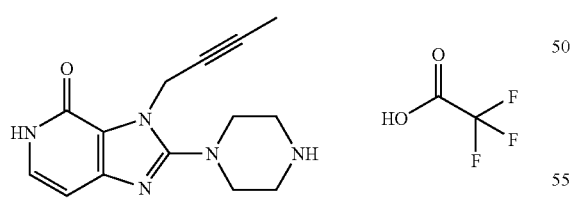
Example 339. a)
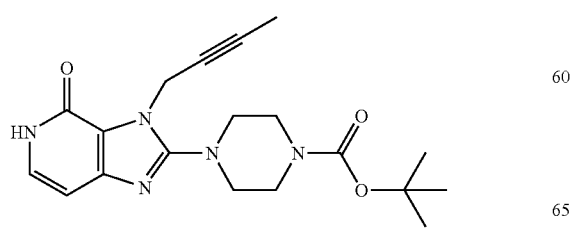
Example 339. b)
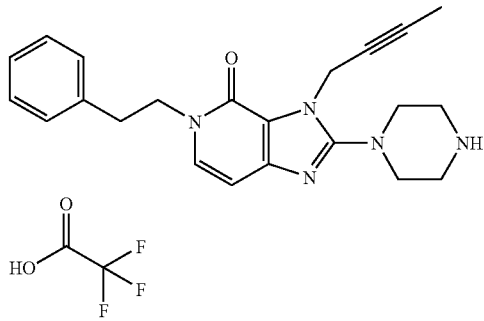
Example 340.
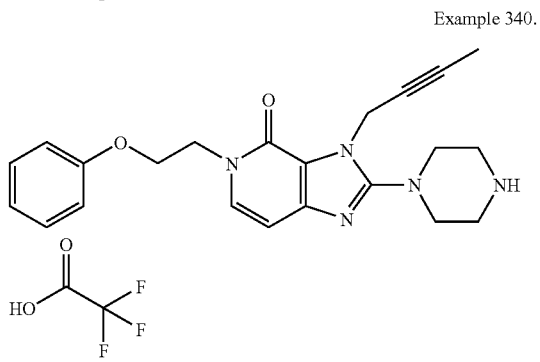
Example 341.
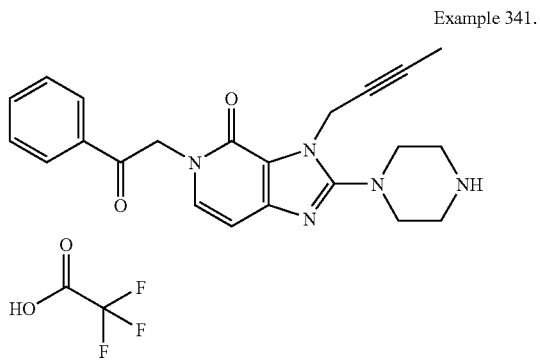
Example 342.
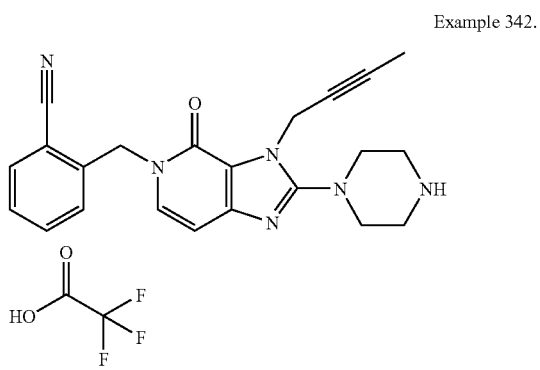
Example 343. a)
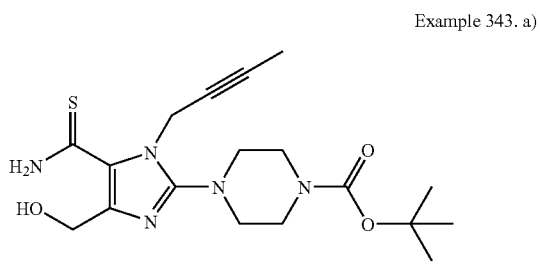

Example 343. b)
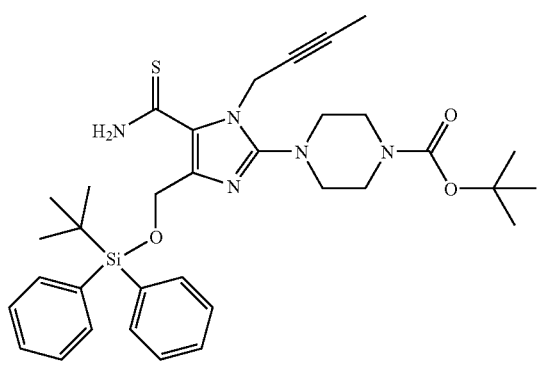
Example 343. c)
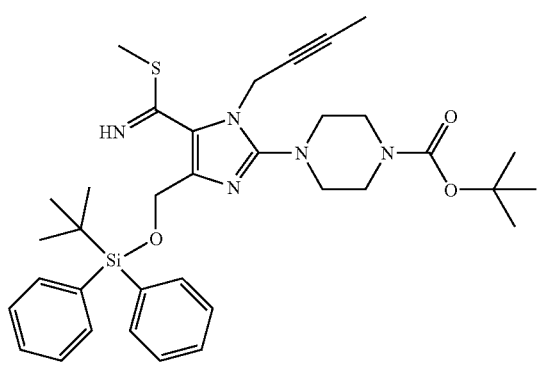
Example 343. d)
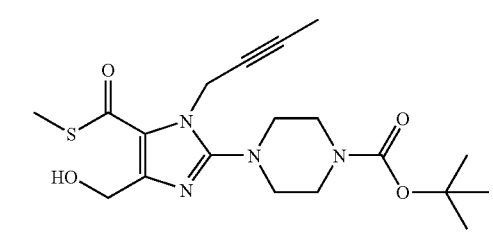
Example 343. e)
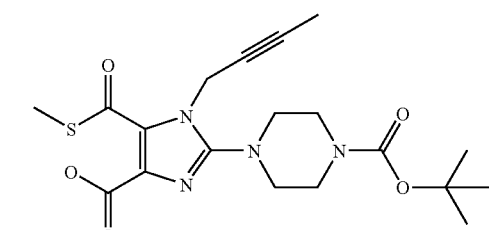
Example 343. f)
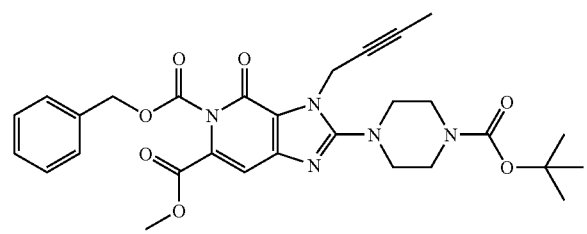
Example 343. g)
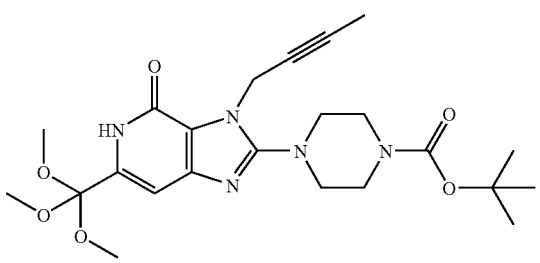
Example 343. h)
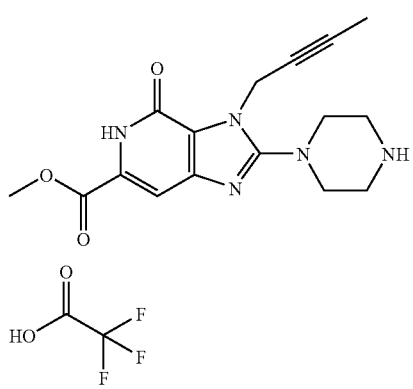
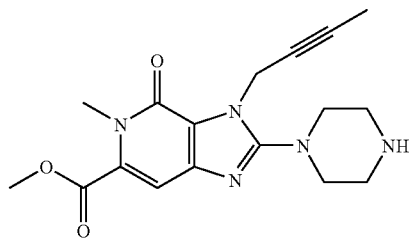
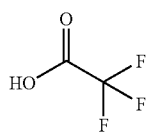
Example 344.
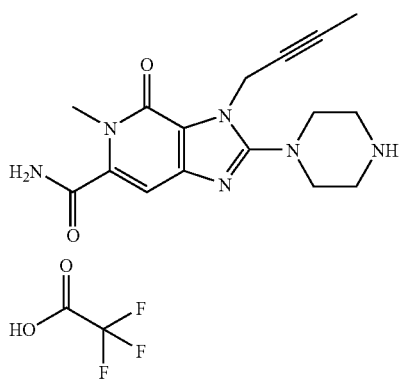
Example 345.

Example 346.
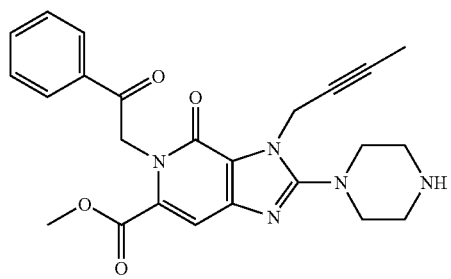
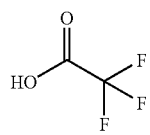
Example 347.
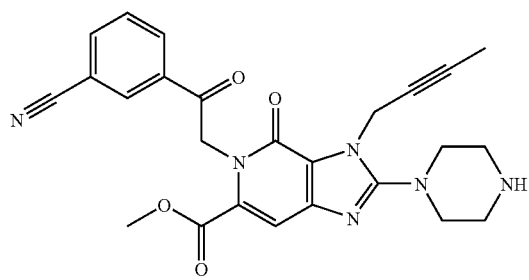
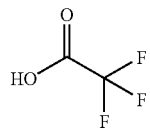
Example 348.
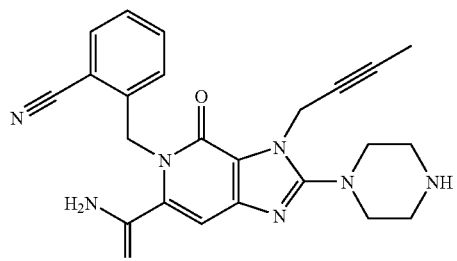
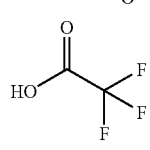
Example 349. a)-1
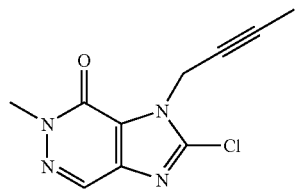
Example 349. a)-2
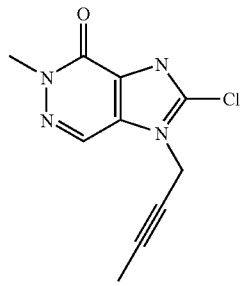
Example 349. b)
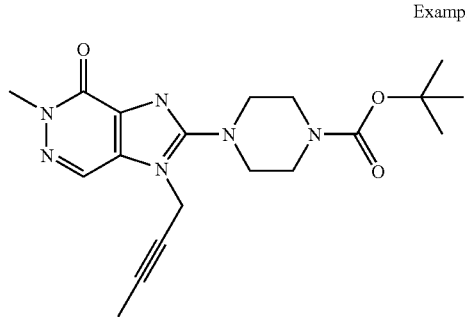
Example 349. c)
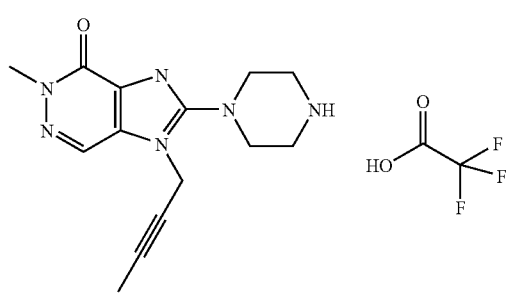
Example 350.
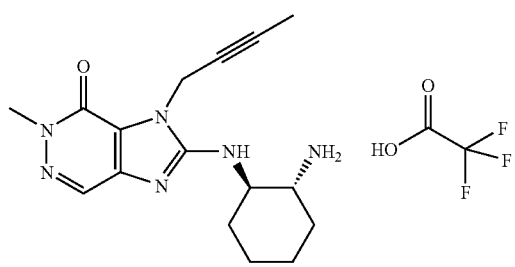
Example 351.
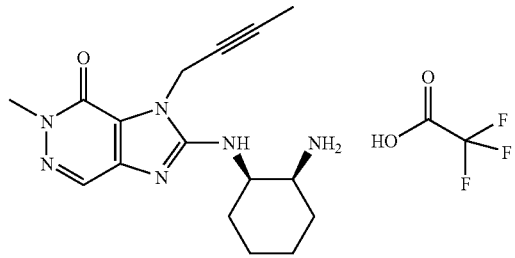

-continued

Example 352. a)
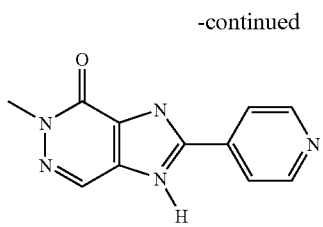

Example 352. b)
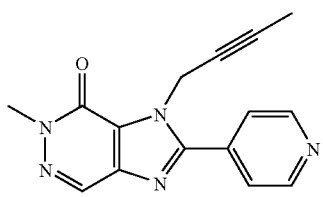

Example 352. c)
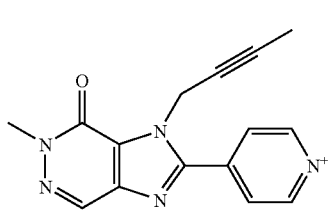
HCl

Example 352. d)
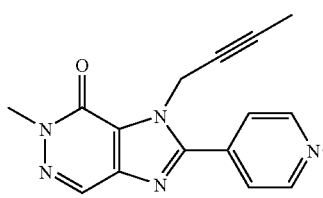

Example 352. e)
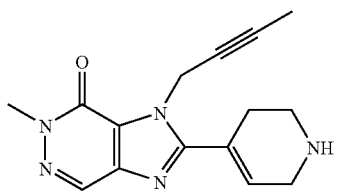

INDUSTRIAL APPLICABILITY

The present invention provides condensed imidazole derivatives having a DPPIV-inhibiting activity.

Accordingly, the condensed imidazole derivatives of the present invention are useful as therapeutic and preventive agents, for example, for diabetes mellitus, obesity, hyperlipidemia, AIDS, osteoporosis, gastrointestinal disorders, angiogenesis, infertility, as anti-inflammatory agents, anti-allergy agents, immunomodulators, hormone regulators, anti-rheumatic drugs, and anti-cancer agents.

Furthermore, using their glucose tolerance improving action as an index, these compounds were tested to assess their efficacy after oral administration. In result, it was confirmed that these compounds were sufficiently effective, thereby demonstrating their usefulness as pharmaceuticals.

The invention claimed is:

1. A compound represented by the following formula, or a salt thereof,

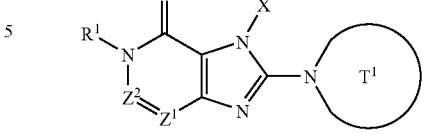

(I)

wherein, $T^1$ is a group represented by the following formula:

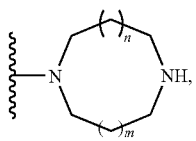

(wherein, n and m each independently represent 0 or 1) which may have one or more substituents selected from the substituent group S described below;

X represents a $C_{2-6}$ alkynyl group or a $C_{6-10}$ aryl $C_{1-6}$ alkyl group;

$Z^1$ and $Z^2$ each represent a group represented by the formula $—CR^2\!=$;

$R^1$ is H;

$R^2$ represents H or a group according to the formula $-A^0$-$A^1$-$A^2$ (wherein $A^0$ represents a single bond;

$A^1$ represents a single bond or a group represented by the formula —CO—O—;

$A^2$ is a $C_{1-6}$ alkyl group;

however, $A^2$ may have 1 to 3 substituents selected from the substituent group B described below:

Substituent group B represents the group consisting of: a hydroxyl group, a $C_{1-6}$ alkoxy group, a $C_{1-6}$ alkylthio group, and a group represented by the formula $—NR^{B1}—R^{B2}$ (where $R^{B1}$ and $R^{B2}$ each independently represent a hydrogen atom or a $C_{1-6}$ alkyl group));

wherein, Substituent group S represents the group consisting of:

a formyl group, a carboxyl group, and a group represented by the formula $-T^{1x}-T^{2x}$ (where $T^{1x}$ is a group represented by the formula —CO—, a group represented by the formula —CO—O—, or a group represented by the formula $—CO—NR^T—$;

$T^{2x}$ represents a hydrogen atom, or a $C_{1-6}$ alkyl group;

$R^T$ represents a hydrogen atom, or a $C_{1-6}$ alkyl group).

2. The compound according to claim 1, or a salt thereof, wherein $T^1$ is a piperazin-1-yl group.

3. The compound according to claim 1, or a salt thereof, wherein X is a 2-butyn-1-yl group, or a benzyl group.

4. The compound according to claim 1, or a salt thereof, wherein X is a 2-butyn-1-yl group.

5. The compound according to claim 1, or a salt thereof, wherein $R^2$ is a hydrogen atom, or a group represented by the formula $-A^{21}-A^{22}$ (where $A^{21}$ represents a single bond, or a group represented by the formula —CO—O—;

$A^{22}$ represents a $C_{1-6}$ alkyl group;

however, $A^{22}$ may have 1- to 3 substituents selected from the substituent group D described below:

Substituent group D represents the group consisting of: a hydroxyl group, a $C_{1-6}$ alkoxy group, a $C_{1-6}$ alkylthio group, and a group represented by the formula —NR$^{D1}$—R$^{D2}$ (where R$^{D1}$ and R$^{D2}$ each independently represent a hydrogen atom or a $C_{1-6}$ alkyl group)).

6. The compound according to claim 1, or a salt thereof, wherein $R^2$ represents a $C_{2-7}$ alkoxycarbonyl group, or a $C_{1-6}$ alkyl group.

7. The compound according to claim 1, wherein the compound is selected from the group consisting of:

* * * * *